United States Patent
Konetzki et al.

(10) Patent No.: US 9,315,490 B2
(45) Date of Patent: Apr. 19, 2016

(54) 2,5-SUBSTITUTED PYRIMIDINES

(71) Applicant: Grünenthal GmbH, Aachen (DE)

(72) Inventors: Ingo Konetzki, Aachen (DE); Tobias Craan, Aachen (DE); Florian Jakob, Aachen (DE); Antonio Nardi, Herzogenrath (DE); Christian Hesslinger, Zoznegg (DE); Andre Welbers, Köln (DE)

(73) Assignee: GRUENENTHAL GMBH, Aachen (DE)

( * ) Notice: Subject to any disclaimer, the term of this patent is extended or adjusted under 35 U.S.C. 154(b) by 0 days.

(21) Appl. No.: 14/800,180

(22) Filed: Jul. 15, 2015

(65) Prior Publication Data

US 2016/0024053 A1 Jan. 28, 2016

(30) Foreign Application Priority Data

Jul. 16, 2014 (EP) .................................... 14002451

(51) Int. Cl.
| | |
|---|---|
| A61K 31/506 | (2006.01) |
| C07D 403/04 | (2006.01) |
| C07D 401/14 | (2006.01) |
| C07D 405/14 | (2006.01) |
| C07D 403/14 | (2006.01) |
| C07D 413/14 | (2006.01) |
| C07D 491/107 | (2006.01) |
| C07D 471/10 | (2006.01) |
| C07D 417/14 | (2006.01) |
| C07D 487/04 | (2006.01) |
| C07D 498/08 | (2006.01) |

(52) U.S. Cl.
CPC ............ *C07D 403/04* (2013.01); *C07D 401/14* (2013.01); *C07D 403/14* (2013.01); *C07D 405/14* (2013.01); *C07D 413/14* (2013.01); *C07D 417/14* (2013.01); *C07D 471/10* (2013.01); *C07D 487/04* (2013.01); *C07D 491/107* (2013.01); *C07D 498/08* (2013.01); *A61K 31/506* (2013.01)

(58) Field of Classification Search
CPC .. C07D 403/04; C07D 401/14; C07D 403/14; C07D 405/14; C07D 413/14; C07D 417/14; C07D 471/10; C07D 487/04; C07D 491/107; C07D 498/08
See application file for complete search history.

(56) References Cited

FOREIGN PATENT DOCUMENTS

| | | |
|---|---|---|
| WO | 9501338 A1 | 1/1995 |
| WO | 0164639 A2 | 9/2001 |
| WO | 03055882 A1 | 7/2003 |
| WO | WO 2007041130 A2 * | 4/2007 ........... C07D 487/04 |
| WO | 2014170020 A1 | 10/2014 |

OTHER PUBLICATIONS

K. Komatsu et al., 4 Nature Communications, 1-13 (2013).*
C.D. Manning et al., 128 British Journal of Pharmacology, 1393-1398 (1999).*
J.A. Siuciak et al., 197 Psychopharmacology, 115-126 (2008).*
J.K. Miller et al., 310 Science, 1187-1195 (2005).*
G. Sebastiani et al., 29 Neurobiology of Aging, 691-701 (2006).*
C. Schudt, et al., "PDE isoenzymes as targets for anti-asthma drugs", Eur Respir J., 1955, 8, 1179-1183.
F. Mori, et al., "The human area postrema and other nuclei related to the emetic reflex express cAMP phosphodiesterases 4B and 4D", 2010, Journal of Chemical Neuroanatomy, 40, 36-42.
K. H. Banner, et al., "2 PDE4 Inhibitors—A Review of the Current Field", 2009, Progress in Medicinal Chemistry , 47, 37-74.
A. Robichaud, et al., "α2-adrenoceptor-mediated anesthesia, a behavioral correlate of emesis", The Journal of Clinical Investigation, Oct. 2002, vol. 110, No. 7, 1045-52.
Ji Hyun Lee, et al., "Dynamic Regulation of Cystic Fibrosis Transmembrane Conductance Regulator by Competitive Interactions of Molecular Adaptors", Journal of Biological Chemistry, Apr. 2007, vol. 282, 10414-22.
Mark A. Giembycz, "4D of not 4D—the emetogenic basis of PDE4 inhibitors uncovered?", Dec. 2002, Trends in Pharmacological Sciences, vol. 23, No. 12.
S. Han, et al., "Recent development of peptide coupling reagents in organic synthesis", Tetrahedron, 2004, 60, 2447-2467.
L.J. Ravin, "Prefomulation", Chapter 76, Gennaro (Ed), Remington's Pharmaceutical Sciences, 17th Ed., 1985.
A.R. Disanto, "Bioavailability and Bioequivalency Testing", Chapter 77, Gennaro (Ed), Remington's Pharmaceutical Sciences, 17th Ed., 1985.
A.M. Knevel, "Separation", Chapter 78, Gennaro (Ed), Remington's Pharmaceutical Sciences, 17th Ed., 1985.
G.B. Phillips, "Sterilization", Chapter 79, Gennaro (Ed), Remington's Pharmaceutical Sciences, 17th Ed., 1985.

(Continued)

*Primary Examiner* — Alexander R Pagano
(74) *Attorney, Agent, or Firm* — Norris McLaughlin & Marcus PA

(57) ABSTRACT

The invention relates to novel substituted condensed pyrimidine compounds of general formula (I)

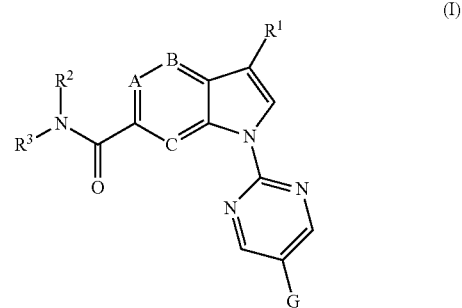

(I)

in which the chemical groupings, substituents and indices are as defined in the description, and to their use as medicaments, in particular as medicaments for the treatment of conditions and diseases that can be treated by inhibition of the PDE4 enzyme.

13 Claims, No Drawings

(56) References Cited

OTHER PUBLICATIONS

F.P. Siegel, "Tonicity, Osmoticity, Osmolality, and Osmolarity", Chapter 80, Gennaro (Ed), Remington's Pharmaceutical Sciences, 17th Ed., 1985.
R.L. Giles, et al., "Plastic Packaging Materials", Chapter 81, Gennaro (Ed), Remington's Pharmaceutical Sciences, 17th Ed., 1985.
C.J. Lintner, "Stability of Pharmaceutical Products", Chapter 82, Gennaro (Ed), Remington's Pharmaceutical Sciences, 17th Ed., 1985.
C.R. Erskine, "Quality Assurance and Control", Chapter 83, Gennaro (Ed), Remington's Pharmaceutical Sciences, 17th Ed., 1985.
J.G. Nairn, "Solutions, Emulsions, Suspensions and Extractives", Chapter 84, Gennaro (Ed), Remington's Pharmaceutical Sciences, 17th Ed., 1985.
K.E. Avis, "Parenteral Preparations", Chapter 85, Gennaro (Ed), Remington's Pharmaceutical Sciences, 17th Ed., 1985.
S.J. Turco, et al., "Intravenous Admixtures", Chapter 86, Gennaro (Ed), Remington's Pharmaceutical Sciences, 17th Ed., 1985.
J.D. Mullins, "Ophthalmic Preparations", Chapter 87, Gennaro (Ed), Remington's Pharmaceutical Sciences, 17th Ed., 1985.
L.H. Block, "Medicated Applications", Chapter 88, Gennaro (Ed), Remington's Pharmaceutical Sciences, 17th Ed., 1985.
E.G. Ripple, "Powders", Chapter 89, Gennaro (Ed), Remington's Pharmaceutical Sciences, 17th Ed., 1985.
R.E. King, et al., "Oral Solid Dosage Forms", Chapter 90, Gennaro (Ed), Remington's Pharmaceutical Sciences, 17th Ed., 1985.
S. C. Porter, "Coating of Pharmaceutical Dosage Forms", Chapter 91, Gennaro (Ed), Remington's Pharmaceutical Sciences, 17th Ed., 1985.
M.A. Longer, et al., "Sustained-Release Drug Delivery Systems", Chapter 92, Gennaro (Ed), Remington's Pharmaceutical Sciences, 17th Ed., 1985.
J.J.Sclarro, et al., "Aerosols", Chapter 93, Gennaro (Ed), Remington's Pharmaceutical Sciences, 17th Ed., 1985.
W. Liu, et al., "Synthesis and Herbicidal Activity of 2-3)3-(Trifluoromethyl)-5-(alkoxy)-1H-pyrazol-1-yl)-4-arloxypyrimidine Derivatives", Journal of Heterocyclic Chemistry 2007, vol. 44, p. 967.
S. Schroter, et al., "Regioselective cross-coupling reactions of multiple halogenated nitrogen-, oxygen-, and sulfer-containing heterocycles", Tetrahedron, 2005, vol. 61, p. 2245-67.
D.S. Surry, et al., "Biaryl Phosphane Ligands in Palladium-Catalyzed Amination", Angewandte Chemie, International Edition, 2008, vol. 47, p. 6338-6361.
T. Ishiyama, et al., "Palladium (0)-Catalyzed Cross-Coupling Reaction of Alkoxydiboron with Haloarenes: A Direct Procedure for Arylboronic Esters", Journal of Organic Chemistry, 1995, vol. 60, 7508-7510.
N. Saldou, et al. "Comparison of Recombinant Human PD4E Isoforms: Interaction with Substrate and Inhibitors", Cell. Signal., vol. 10, No. 6, 427-440, 1998.
M. Murata, et al., "Palladium-Catalyzed Borylation of Aryl Halides or Triflates with Dialkoxyborane: A Novel and Facile Synthetic Route to Arylboronates", Journal of Organic Chemistry, 2000, vol. 65, p. 164-168.
T.W. Greene, "Protection for the Carboxyl Group", Greene's Protective Groups in Organic Synthesis, Fourth Edition, 2007, p. 533-646.
"Vilsmeier-HAACK Reagent (Halomethyleneiminium Salt", Synlett, Spotlight 55, 2003, No. 1, p. 138-139.

* cited by examiner

2,5-SUBSTITUTED PYRIMIDINES

This application claims foreign priority benefit under 35 U.S.C. §119 of European Patent Application No. 14 002 451.4, filed Jul. 16, 2014, the disclosures of which patent application is incorporated herein by reference.

The present invention relates to novel 2,5-substituted pyrimidines and to their use as pharmaceuticals (medicaments).

It is known that certain pyrimidine compounds are suitable for inhibiting specific phosphodiesterases (abbreviated as PDEs). WO 95/01338 A1 describes, for example, that certain PDE inhibitors can be used for treating inflammatory respiratory diseases, dermatoses, and other proliferative, inflammatory and allergic skin diseases. Phosphodiesterases are a group of enzymes encompassing 11 gene families (PDE1-11), which differ inter alia through their affinity to cAMP and cGMP.

The discovery that the second messenger cAMP plays an important role in many inflammatory processes and that PDE4 is strongly expressed in cells that control inflammation processes (see inter alia Schudt, C. et al. (1995). PDE isoenzymes as targets for anti-asthma drugs. *European Respiratory Journal* 8, 1179-1183), has led to the development of PDE4 inhibitors having an anti-inflammatory effect. One such PDE4 inhibitor having an anti-inflammatory effect is for example roflumilast (known under the trade name Daxas®), which is approved as a medicament for the treatment of COPD (chronic obstructive pulmonary disease). It is however known that roflumilast has quite a number of undesired (adverse) side-effects such as for example nausea, diarrhoea and headaches, which side-effects limit the dose in humans.

Undesired side-effects in humans were not only observed with roflumilast but also with other PDE4 inhibitors, so that the therapeutic range (therapeutic window) of such medicaments is relatively narrow. The provision of PDE4 inhibitors having less severe or no adverse side-effects and a better therapeutic window would therefore be desirable.

Phosphodiesterase 4 (PDE4) is cAMP-specific and encompasses 4 different subtypes (PDE4A, PDE4B, PDE4C and PDE4D). As described below, efforts are being made to find subtype-selective PDE4 inhibitors, above all PDE4B-selective inhibitors, that have less severe or no adverse side-effects, such that the therapeutic range of these compounds is increased significantly.

It is known that the inhibition of PDE4D is associated with the occurrence of the undesired adverse side-effects like diarrhoea, vomiting and nausea (cf. Mori, F. et al. (2010). The human area postrema and other nuclei related to the emetic reflex express cAMP phosphodiesterases 4B and 4D. *Journal of Chemical Neuroanatomy* 40, 36-42; Press, N.J.; Banner K. H (2009). PDE4 inhibitors—A review of the current field. *Progress in Medicinal Chemistry* 47, 37-74; Robichaud, A. et al. (2002). Deletion of phosphodiesterase 4D in mice shortens α2-adrenoceptor-mediated anesthesia, a behavioral correlate of emesis. *The Journal of Clinical Investigation* 110, 1045-52; or Lee et al., (2007). Dynamic regulation of CFTR by competitive interactions of molecular adaptors. *Journal of Biological Chemistry* 282, 10414-10422); or Giembycz, M. A. (2002). 4D or not 4D—the emetogenic basis of PDE4 inhibitors uncovered? *Trends in Pharmacological Sciences* 23, 548).

Based on this knowledge the object of the present invention was to find compounds that are preferably PDE4B-selective (i.e. to find active compounds that with a particular amount of active ingredient inhibit PDE4B subtype but without or only weakly inhibiting the PDE4D subtype). The advantage of such a PDE4B selectivity, as mentioned above, is that various side-effects do not occur or occur only to a small extent and that therefore a greater therapeutic range of the pharmaceutical active ingredient can be obtained. The therapeutic range of a pharmaceutical active ingredient and medicament, respectively, describes the gap between its therapeutic dose and a dose that would lead to a toxic or undesired effect. The greater the therapeutic range, the rarer or more unlikely the occurrence of such toxic or undesired effects and hence the safer and more acceptable the pharmaceutical active ingredient and medicament, respectively. The therapeutic range is often also referred to as the therapeutic window or therapeutic index. These names are used synonymously in the present application.

The inventors now have found 2,5-substituted pyrimidines that display the desired inhibiting and, additionally, a PDE4B-selective property. They are therefore particularly suitable for the treatment of diseases and conditions in which inhibition of the PDE4 enzyme, in particular the PDE4B enzyme, is advantageous.

Therefore, in a first aspect, the invention relates to 2,5-substituted pyrimidines having the following general formula (I)

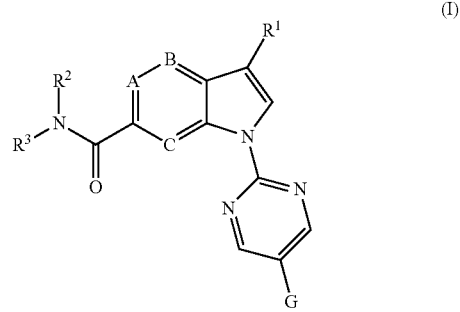

in which
A, B, C each independently of each other stands for N or CH; preferably A, B, C each stands for CH;
$R^1$ stands for $(C_1-C_6)$-alkyl, $(C_1-C_6)$-hydroxyalkyl, $(C_3-C_6)$-cycloalkyl, $SO_x$—$(C_1-C_6)$-alkyl; preferably $R^1$ stands for methyl, ethyl, propyl, i-propyl, n-butyl, hydroxymethyl, hydroxyethyl, hydroxypropyl, cyclopropyl, $SOCH_3$ or $SO_2CH_3$; more preferably $R^1$ stands for methyl, hydroxymethyl, 1-hydroxyethyl, 2-hydroxypropan-2-yl, $SOCH_3$, $SO_2CH_3$; even more preferably $R^1$ stands for 1-hydroxyethyl, 2-hydroxypropan-2-yl, $SOCH_3$, $SO_2CH_3$;
x is 0, 1 or 2; preferably x is 1 or 2;
G is an optionally with at least one substituent Y substituted phenyl or 5- or 6-membered heteroaryl which contains at least one oxygen, sulfur or nitrogen atom, whereas the nitrogen atoms present in the heteroaryl can be substituted with $R^4$; preferably G stands for optionally with at least one substituent Y substituted phenyl, pyridyl, pyrimidyl, furyl, thiophenyl, oxazolyl, thiazolyl; more preferably G stands for one of the groups G1 to G45 as given herein;
$R^4$ is hydrogen, $(C_1-C_6)$-alkyl, $(C_1-C_6)$-haloalkyl, CO—$(C_1-C_6)$-alkyl, SO$(C_1-C_6)$-alkyl, $SO_2(C_1-C_6)$-alkyl; preferably $R^4$ stands for hydrogen or methyl;
Y independently of one another is halogen, OH, CN, SH, $(C_1-C_6)$-alkyl, $(C_2-C_6)$-alkenyl, $(C_2-C_6)$-alkinyl, $(C_3-C_6)$-cycloalkyl, $(C_1-C_6)$-alkoxy, $(C_1-C_6)$-thioalkyl, $(C_1-C_6)$-haloalkyl, $(C_1-C_6)$-thiohaloalkyl, $(C_1-C_6)$-haloalkoxy, $CO_2H$, $CO_2(C_1-C_6)$-alkyl, CHO, $CO(C_1-C_6)$-alkyl, OCO ($C_1$-$C_6$)-alkyl, $CONH_2$, CONH—($C_1$-$C_6$)-alkyl, CON(($C_1$-$C_6$)-alkyl)$_2$, OCO—NH($C_1$-$C_6$)-alkyl, OCO—N(($C_1$-$C_6$)-alkyl)$_2$, $NH_2$, NH($C_1$-$C_6$)-alkyl, N(($C_1$-$C_6$)-alkyl)$_2$, N-pyrrolidinyl, N-piperidinyl, N-morpholinyl, NH—CO—($C_1$-$C_6$)alkyl, NH—CO$_2$($C_1$-$C_6$)-alkyl, NH—CO($C_1$-$C_6$)-alkyl-CO$_2$($C_1$-$C_6$)-alkyl, NH—CO—$NH_2$, NH—CO—NH($C_1$-$C_6$)-alkyl, NH—CO—N($C_1$-$C_6$)-alkyl)$_2$, N($C_1$-$C_6$)-alkyl-CO—$NH_2$, N($C_1$-$C_6$)alkyl-CO—NH($C_1$-$C_6$)-alkyl, N($C_1$-$C_6$)-alkyl-CO—N(($C_1$-$C_6$)-alkyl)$_2$, NH—$SO_2$—($C_1$-$C_6$)-alkyl, N($C_1$-$C_6$)alkyl-$SO_2$—($C_1$-$C_6$)-alkyl, S—($C_1$-$C_6$)-alkyl, SO($C_1$-$C_6$)-alkyl, $SO_2$—($C_1$-$C_6$)-alkyl, $SO_2H$, $SO_2OH$, $SO_2NH_2$, $SO_2NH$($C_1$-$C_6$)-alkyl, $SO_2N$(($C_1$-$C_6$)-alkyl)$_2$, C(=N)—NH, NHC(=N)—$NH_2$, —N=C=O, —S—CN, wherein the aforementioned alkyl chains may be substituted with at least one of the following substituents OH, CN, ($C_3$-$C_6$)-cycloalkyl, ($C_1$-$C_6$)-alkoxy, $CO_2H$, $CO_2$($C_1$-$C_6$)-alkyl or —$NH_2$; preferably Y independently of one another is halogen, CN, OH, $NH_2$, N(($C_1$-$C_4$)-alkyl)$_2$, $CONH_2$, ($C_1$-$C_4$)-alkyl, ($C_1$-$C_4$)-alkoxy, ($C_3$-$C_6$)-cycloalkyl; more preferably Y independently of one another is F, Cl, CN, OH, $NH_2$, N($CH_3$)$_2$, $CONH_2$, $CH_3$, $CH_2CH_3$, $OCH_3$, $OCH_2CH_3$, cyclopropyl;

$R^2$ and $R^3$ independently of one another stand for hydrogen or optionally substituted ($C_1$-$C_6$)-alkyl, ($C_1$-$C_6$)-haloalkyl, ($C_1$-$C_6$)-hydroxyalkyl, ($C_1$-$C_6$)-alkoxy($C_1$-$C_6$)-alkyl en, ($C_1$-$C_6$)-alkylen-$CO_2H$, ($C_1$-$C_6$)-alkylen-$CO_2$($C_1$-$C_6$)-alkyl, ($C_1$-$C_6$)-alkylen-$CONH_2$, ($C_1$-$C_6$)-alkylen-CONH($C_1$-$C_6$)-alkyl, ($C_1$-$C_6$)-alkylen-CON(($C_1$-$C_6$)-alkyl)$_2$, ($C_1$-$C_6$)-alkylen-($C_3$-$C_6$)-cycloalkyl, ($C_1$-$C_6$)-hydroxyalkyl-($C_3$-$C_6$)-cycloalkylen, a group $L^1V$, a group $L^2W$, or $R^2$ and $R^3$ together with the nitrogen atom to which they are attached form an optionally with at least one substituent $X^Q$ substituted 3- to 12-membered mono- or bicyclic heteroaliphatic residue Q which may additionally contain at least one oxygen, sulfur or further nitrogen atom, whereas these one or more additional nitrogen atoms are substituted with $R^5$;

$X^Q$ independently of each other stand for =O (carbonyl), halogen, OH, CN, SH, ($C_1$-$C_6$)-alkyl, ($C_1$-$C_6$)-hydroxyalkyl, ($C_1$-$C_6$)-cyanoalkyl, ($C_2$-$C_6$)-alkenyl, ($C_2$-$C_6$)-alkinyl, ($C_3$-$C_6$)-cycloalkyl, ($C_1$-$C_6$)-alkoxy, ($C_1$-$C_6$)-alkoxy($C_1$-$C_6$)-alkylen, ($C_1$-$C_6$)-thioalkyl, ($C_1$-$C_6$)-haloalkyl, ($C_1$-$C_6$)-thiohaloalkyl, ($C_1$-$C_6$)-haloalkoxy, —$NH_2$, NH($C_1$-$C_6$)-alkyl, N(($C_1$-$C_6$)-alkyl)$_2$, ($C_1$-$C_6$)-alkylen-NH($C_1$-$C_6$)-alkyl, ($C_1$-$C_6$)-alkylen-N(($C_1$-$C_6$)-alkyl)$_2$ NH—CHO, NH—CO($C_1$-$C_6$)-alkyl, N($C_1$-$C_6$)-alkyl-CO($C_1$-$C_6$)-alkyl, NH—CO—O($C_1$-$C_6$)-alkyl, N($C_1$-$C_6$)-alkyl-CO—O($C_1$-$C_6$)-alkyl, NH—CO—$NH_2$, NH—CO—NH($C_1$-$C_6$)-alkyl, NH—CO—N(($C_1$-$C_6$)-alkyl)$_2$, N($C_1$-$C_6$)-alkyl-CO—$NH_2$, N($C_1$-$C_6$)-alkyl-CO—NH($C_1$-$C_6$)-alkyl, N($C_1$-$C_6$)-alkyl-CO—N(($C_1$-$C_6$)-alkyl)$_2$, NH—$SO_2$—($C_1$-$C_6$)-alkyl, N($C_1$-$C_6$)-alkyl-$SO_2$—($C_1$-$C_6$)-alkyl, $CO_2H$, $CO_2$($C_1$-$C_6$)-alkyl, CHO, CO($C_1$-$C_6$)-alkyl, O—CO($C_1$-$C_6$)-alkyl, CO—$NH_2$, CO—NH($C_1$-$C_6$)-alkyl, CO—N(($C_1$-$C_6$)-alkyl)$_2$, O—CO—NH($C_1$-$C_6$)-alkyl, O—CO—N(($C_1$-$C_6$)-alkyl)$_2$, S—($C_1$-$C_6$)-alkyl, SO($C_1$-$C_6$)-alkyl, $SO_2$—($C_1$-$C_6$)-alkyl, SOOH, $SO_2OH$, $SO_2NH_2$, $SO_2NH$($C_1$-$C_6$)-alkyl, $SO_2N$(($C_1$-$C_6$)-alkyl)$_2$, C(=N)—NH, NHC(=N)—$NH_2$, —N=C=O, —S—CN, wherein the aforementioned alkyl chains may be substituted with at least one of the following substituents OH, CN, ($C_3$-$C_6$)-cycloalkyl, ($C_1$-$C_6$)-alkoxy, $CO_2H$, $CO_2$($C_1$-$C_6$)-alkyl or —$NH_2$; preferably $X^Q$ independently of each other stands for carbonyl (=O), F, Cl, CN, $NH_2$, OH, SH, $CH_3$, $CH_2CH_3$, $OCH_3$, $OCH_2CH_3$, $SCH_3$, $SCH_2CH_3$, $CH_2OCH_3$, $CH_2OH$, $CH_2CH_2OH$, $CH_2CN$, $CH_2CH_2CN$, cyclopropyl, N($CH_3$)$_2$, $CH_2NH$($CH_3$), $CF_3$, $CHF_2$, $CH_2F$, $SCF_3$, $SCF_2H$, $SCFH_2$, $OCF_3$, $OCF_2H$, and $OCFH_2$; more preferably for (=O), $NH_2$, OH, $CH_3$, $CH_2CH_3$, $OCH_3$, $OCH_2CH_3$, $CH_2OCH_3$, $CH_2OH$, $CH_2CH_2OH$, $CH_2CN$, $CH_2CH_2CN$, N($CH_3$)$_2$, $CH_2NH$($CH_3$); most preferably $X^Q$ independently of each other stands for (=O), $NH_2$, OH, $CH_3$, $OCH_3$, $CH_2OCH_3$, and $CH_2OH$;

$R^5$ is hydrogen, ($C_1$-$C_6$)-alkyl, ($C_1$-$C_6$)-haloalkyl, CO—($C_1$-$C_6$)-alkyl, SO—($C_1$-$C_6$)-alkyl, $SO_2$—($C_1$-$C_6$)-alkyl; preferably $R^5$ is for hydrogen, methyl or ethyl;

preferably $R^2$ and $R^3$ independently of one another stand for hydrogen, ($C_1$-$C_4$)-alkyl, ($C_1$-$C_4$)-hydroxyalkyl, ($C_1$-$C_4$)-alkoxy($C_1$-$C_4$)-alkylen, ($C_1$-$C_4$)-alkylen-$CO_2H$, ($C_1$-$C_4$)-alkylen-$CO_2$($C_1$-$C_4$)-alkyl, ($C_1$-$C_4$)-alkylen-$CONH_2$, ($C_1$-$C_4$)-alkylen-CONH($C_1$-$C_2$)-alkyl, ($C_1$-$C_4$)-alkylen-CON(($C_1$-$C_2$)-alkyl)$_2$, ($C_1$-$C_4$)-alkylen-($C_3$-$C_6$)-cycloalkyl, ($C_1$-$C_4$)-hydroxyalkyl-($C_3$-$C_6$)-cycloalkylen, a group $L^1V$, a group $L^2W$, or $R^2$ and $R^3$ together with the nitrogen atom to which they are attached form one of the groups Q1 to Q27 as given herein;

more preferably $R^2$ and $R^3$ independently of each other stand for H, $CH_3$, $CH_2$-cyclopropyl, 2-hydroxpropyl, hydroxyethyl, 2-methoxyethyl, 1-hydroxymethylcyclopropyl, 2-hydroxy-2-methylpropyl, $CH_2CO_2H$, $CH_2CONH_2$, $CH_2CO_2CH_3$, $L^1V1$, $L^1V2$, $L^1V7$, $L^1V12$, or $R^2$ and $R^3$ together with the nitrogen atom to which they are attached form one of the groups Q6, Q10, Q17, Q18, Q19, Q20, Q21, Q22, Q24 and Q25 as given herein;

$L^1$ is a bond or a branched or straight-chain optionally substituted ($C_1$-$C_6$)-alkylene group connected to the amide nitrogen; preferably $L^1$ is a bond, or a branched or straight-chain optionally substituted ($C_1$-$C_4$)-alkylene; more preferably $L^1$ is a bond or a methylene or ethylene group;

V is an optionally with at least one substituent $X^V$ substituted 3- to 12-membered (preferably 3- to 8-membered) mono- or bicyclic aliphatic or heteroaliphatic residue, whereas if one or more nitrogen atoms are present in the mono- or bicyclic heteroaliphatic residue, then at least one of these nitrogen atoms is substituted with $R^6$;

$X^V$ independently of each other stand for =O (carbonyl), halogen, OH, CN, SH, ($C_1$-$C_6$)-alkyl, ($C_1$-$C_6$)-hydroxyalkyl, ($C_1$-$C_6$)-cyanoalkyl, ($C_2$-$C_6$)-alkenyl, ($C_2$-$C_6$)-alkinyl, ($C_3$-$C_6$)-cycloalkyl, ($C_1$-$C_6$)-alkoxy, ($C_1$-$C_6$)-alkoxy($C_1$-$C_6$)-alkylen, ($C_1$-$C_6$)-thioalkyl, ($C_1$-$C_6$)-haloalkyl, ($C_1$-$C_6$)-thiohaloalkyl, ($C_1$-$C_6$)-haloalkoxy, —$NH_2$, NH($C_1$-$C_6$)-alkyl, N(($C_1$-$C_6$)-alkyl)$_2$, ($C_1$-$C_6$)-alkylen-NH($C_1$-$C_6$)-alkyl, ($C_1$-$C_6$)-alkylen-N(($C_1$-$C_6$)-alkyl)$_2$ NH—CHO, NH—CO($C_1$-$C_6$)-alkyl, N($C_1$-$C_6$)-alkyl-CO($C_1$-$C_6$)-alkyl, NH—CO—O($C_1$-$C_6$)-alkyl, N($C_1$-$C_6$)-alkyl-CO—O($C_1$-$C_6$)-alkyl, NH—CO—$NH_2$, NH—CO—NH($C_1$-$C_6$)-alkyl, NH—CO—N(($C_1$-$C_6$)-alkyl)$_2$, N($C_1$-$C_6$)-alkyl-CO—$NH_2$, N($C_1$-$C_6$)-alkyl-CO—NH($C_1$-$C_6$)-alkyl, N($C_1$-$C_6$)-alkyl-CO—N(($C_1$-$C_6$)-alkyl)$_2$, NH—$SO_2$—($C_1$-$C_6$)-alkyl, N($C_1$-$C_6$)-alkyl-$SO_2$—($C_1$-$C_6$)-alkyl, $CO_2H$, $CO_2$($C_1$-$C_6$)-alkyl, CHO, CO($C_1$-$C_6$)-alkyl, O—CO($C_1$-$C_6$)-alkyl, CO—$NH_2$, CO—NH($C_1$-$C_6$)-alkyl, CO—N(($C_1$-$C_6$)-alkyl)$_2$, O—CO—NH($C_1$-$C_6$)-alkyl, O—CO—N(($C_1$-$C_6$)-alkyl)$_2$, S—($C_1$-$C_6$)-alkyl, SO($C_1$-$C_6$)-alkyl, $SO_2$—($C_1$-$C_6$)-alkyl, SOOH, $SO_2OH$, $SO_2NH_2$, $SO_2NH$($C_1$-$C_6$)-alkyl, $SO_2N$(($C_1$-$C_6$)-alkyl)$_2$, C(=N)—NH, NHC(=N)—$NH_2$, —N=C=O, —S—CN, wherein the aforementioned alkyl chains may be substituted with at least one of the following substituents OH, CN, ($C_3$-$C_6$)-cycloalkyl, ($C_1$-$C_6$)-alkoxy, $CO_2H$, $CO_2$($C_1$-$C_6$)-alkyl or —$NH_2$; preferably $X^V$ independently of each other stands for carbonyl (=O), F, Cl, CN, NH$_2$, OH, SH, CH$_3$, CH$_2$CH$_3$, OCH$_3$, OCH$_2$CH$_3$, SCH$_3$, SCH$_2$CH$_3$, CH$_2$OCH$_3$, CH$_2$OH, CH$_2$CH$_2$OH, CH$_2$CN, CH$_2$CH$_2$CN, cyclopropyl, N(CH$_3$)$_2$, CH$_2$NH(CH$_3$), CF$_3$, CHF$_2$, CH$_2$F, SCF$_3$, SCF$_2$H, SCFH$_2$, OCF$_3$, OCF$_2$H, and OCFH$_2$; more preferably for (=O), NH$_2$, OH, CH$_3$, CH$_2$CH$_3$, OCH$_3$, OCH$_2$CH$_3$, CH$_2$OCH$_3$, CH$_2$OH, CH$_2$CH$_2$OH, CH$_2$CN, CH$_2$CH$_2$CN, N(CH$_3$)$_2$, CH$_2$NH(CH$_3$); most preferably X$^V$ independently of each other stands for (=O), NH$_2$, OH, CH$_3$, OCH$_3$, CH$_2$OCH$_3$, and CH$_2$OH;

R$^6$ is hydrogen, (C$_1$-C$_6$)-alkyl, (C$_1$-C$_6$)-haloalkyl, CO—(C$_1$-C$_6$)-alkyl, SO(C$_1$-C$_6$)-alkyl, SO$_2$(C$_1$-C$_6$)-alkyl; preferably R$^6$ is hydrogen, methyl or ethyl;

L$^2$ is a bond or a branched or straight-chain optionally substituted (C$_1$-C$_6$)-alkylene group connected to the amide nitrogen; preferably L$^2$ is a bond, or a branched or straight-chain optionally substituted (C$_1$-C$_4$)-alkylene; more preferably L$^2$ is a bond or a methylene or ethylene group;

W is an optionally with at least one substituent Z substituted phenyl or 5- or 6-membered heteroaryl which contains at least one oxygen, sulfur or nitrogen atom; W preferably stands for optionally with at least one substituent Z substituted phenyl, pyridyl, pyrimidyl, furyl; and Z independently of each other stand for halogen, OH, CN, SH, (C$_1$-C$_6$)-alkyl, (C$_2$-C$_6$)-alkenyl, (C$_2$-C$_6$)-alkinyl, (C$_3$-C$_6$)-cycloalkyl, (C$_1$-C$_6$)-alkoxy, (C$_1$-C$_6$)-thioalkyl, (C$_1$-C$_6$)-haloalkyl(C$_1$-C$_6$)-thiohaloalkyl, (C$_1$-C$_6$)-haloalkoxy, —NH$_2$, NH(C$_1$-C$_6$)-alkyl, N((C$_1$-C$_6$)-alkyl)$_2$, N-pyrrolidinyl, N-piperidinyl, N-morpholinyl, NH—CHO, NH—CO(C$_1$-C$_6$)-alkyl, N(C$_1$-C$_6$)-alkyl-CO(C$_1$-C$_6$)-alkyl, NH—CO$_2$(C$_1$-C$_6$)-alkyl, N(C$_1$-C$_6$)-alkyl-CO$_2$(C$_1$-C$_6$)-alkyl, NH—CO—NH$_2$, NH—CO—NH(C$_1$-C$_6$)-alkyl, NH—CO—N((C$_1$-C$_6$)-alkyl)$_2$, N(C$_1$-C$_6$)-alkyl-CO—NH$_2$, N(C$_1$-C$_6$)-alkyl-CO—NH(C$_1$-C$_6$)-alkyl, N(C$_1$-C$_6$)-alkyl-CO—N((C$_1$-C$_6$)-alkyl)$_2$, NH—SO$_2$—(C$_1$-C$_6$)-alkyl, N(C$_1$-C$_6$)-alkyl-SO$_2$—(C$_1$-C$_6$)-alkyl, CO$_2$H, CO$_2$(C$_1$-C$_6$)-alkyl, CHO, CO(C$_1$-C$_6$)-alkyl, O—CO(C$_1$-C$_6$)-alkyl, CO—NH$_2$, CO—NH(C$_1$-C$_6$)-alkyl, CO—N((C$_1$-C$_6$)-alkyl)$_2$, O—CO—NH(C$_1$-C$_6$)-alkyl, O—CO—N((C$_1$-C$_6$)-alkyl)$_2$, S—(C$_1$-C$_6$)-alkyl, SO(C$_1$-C$_6$)-alkyl, SO$_2$—(C$_1$-C$_6$)-alkyl, SO$_2$H, SO$_2$OH, SO$_2$NH$_2$, SO$_2$NH(C$_1$-C$_6$)-alkyl, SO$_2$N((C$_1$-C$_6$)-alkyl)$_2$, C(=N)—NH, NHC(=N)—NH$_2$, —N=C=O, —S—CN, wherein the aforementioned alkyl chains may be substituted with at least one of the following substituents OH, CN, (C$_3$-C$_6$)-cycloalkyl, (C$_1$-C$_6$)-alkoxy, CO$_2$H, CO$_2$(C$_1$-C$_6$)-alkyl or —NH$_2$; preferably Z independently of each other stands halogen, for carbonyl (=O), F, Cl, CN, NH$_2$, OH, SH, CH$_3$, CH$_2$CH$_3$, OCH$_3$, OCH$_2$CH$_3$, SCH$_3$, SCH$_2$CH$_3$, CH$_2$OCH$_3$, CH$_2$OH, CH$_2$CH$_2$OH, CHCN, CH$_2$CH$_2$CN, cyclopropyl, N(CH$_3$)$_2$, CH$_2$NH(CH$_3$), CF$_3$, CHF$_2$, CH$_2$F, SCF$_3$, SCF$_2$H, SCFH$_2$, OCF$_3$, OCF$_2$H, OCFH$_2$, more preferably for (=O), NH$_2$, OH, CH$_3$, CH$_2$CH$_3$, OCH$_3$, OCH$_2$CH$_3$, CH$_2$OCH$_3$, CH$_2$OH, CH$_2$CH$_2$OH, CHCN, CH$_2$CH$_2$CN, N(CH$_3$)$_2$, CH$_2$NH(CH$_3$).

Moreover, in the context of the invention the following groupings (groups or residues) and indices are preferred:

G preferably stands for optionally with at least one substituent Y substituted phenyl, pyridyl, pyrimidyl, furyl, thiophenyl, oxazolyl, thiazolyl, or for one of the following groups G1 to G45

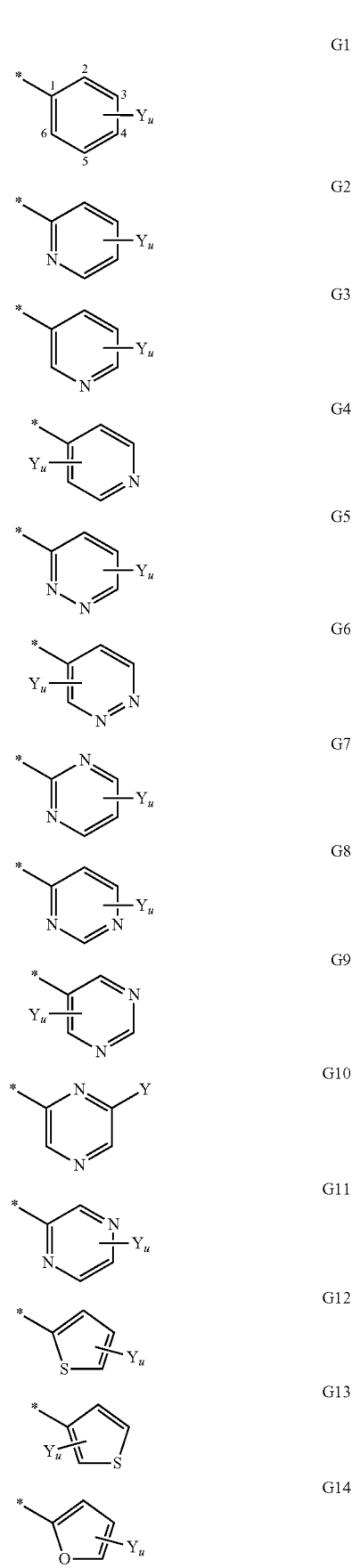

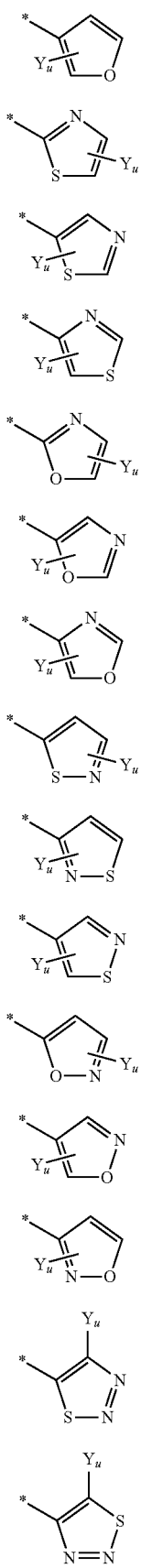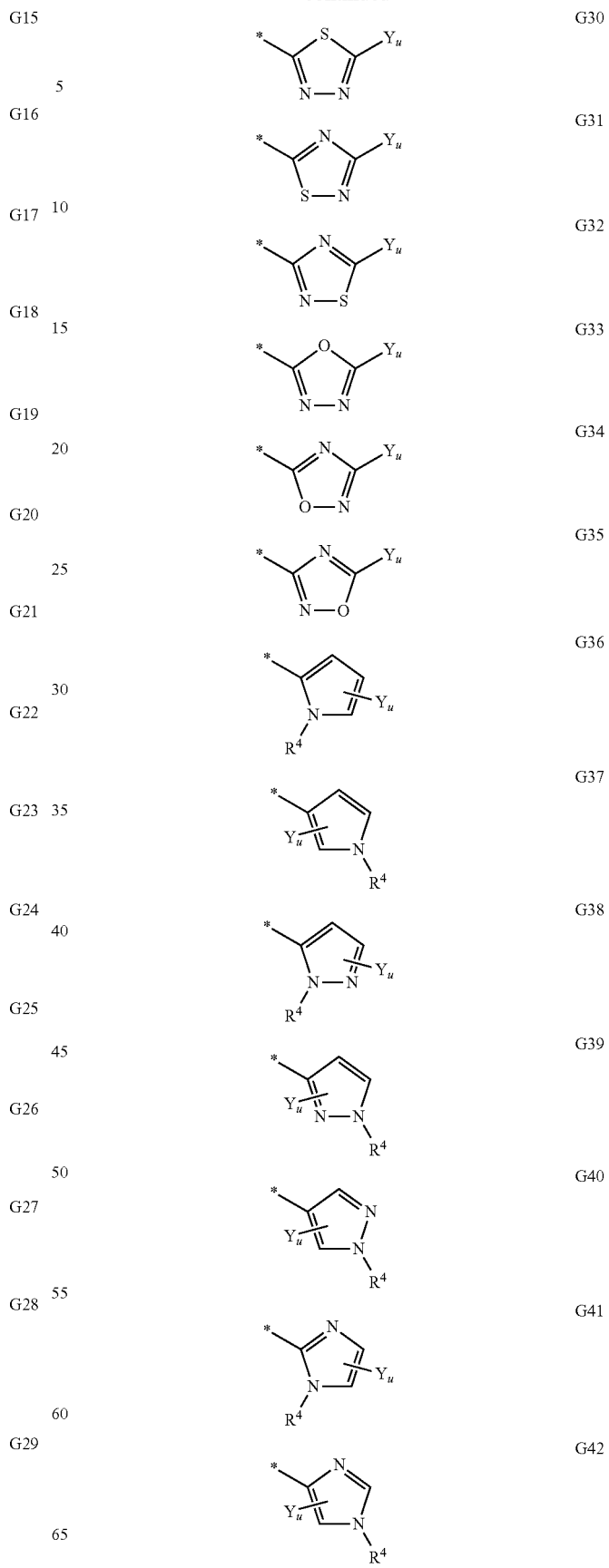

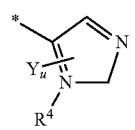 G43

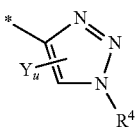 G44

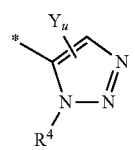 G45 wherein the site marked with an asterisk (*) indicates the binding site to the position 4 of the pyrimidine ring and wherein $R^4$ and Y are as defined above and u is 0, 1, 2, 3 or 4 (preferably u is 0, or 1);

G more preferably stands for one of the following groups G1, G2, G3, G4, G5, G12, G13, G16, or G17; G most preferably stands for G1, G2, G3, G4 or G5.

$R^2$ and $R^3$ preferably and independently of one another stand for hydrogen, $(C_1-C_4)$-alkyl, $(C_1-C_4)$-hydroxyalkyl, $(C_1-C_4)$-alkoxy$(C_1-C_4)$-alkylen, $(C_1-C_4)$-alkylen-$CO_2H$, $(C_1-C_4)$-alkylen-$CO_2(C_1-C_4)$-alkyl, $(C_1-C_4)$-alkylen-$CONH_2$, $(C_1-C_4)$-alkylen-$CONH(C_1-C_2)$-alkyl, $(C_1-C_4)$-alkylen-$CON((C_1-C_2)$-alkyl$)_2$, $(C_1-C_4)$-alkylen-$(C_3-C_6)$-cycloalkyl, $(C_1-C_4)$-hydroxyalkyl-$(C_3-C_6)$-cycloalkylen, a group $L^1V$, a group $L^2W$, or if $R^2$ and $R^3$ together with the nitrogen atom to which they are attached form an optionally with at least one substituent $X^Q$ substituted 3- to 12-membered mono- or bicyclic heteroaliphatic residue Q which may additionally contain at least one oxygen, sulfur or further nitrogen atom, whereas these one or more additional nitrogen atoms are substituted with $R^5$, then the following groups Q1 to Q27 are preferred; more preferably Q stands for one of the following groups Q6, Q10, Q17, Q18, Q19, Q20, Q21, Q22, Q24, and Q25; most preferably for the groups Q6, Q10, Q17, Q20, Q21, Q22, Q24 and Q25; particularly most preferably for Q17;

 Q1

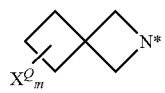 Q2

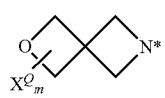 Q3

 Q4

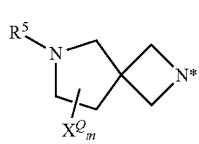 Q5

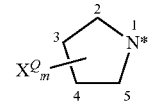 Q6

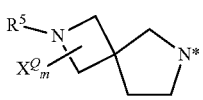 Q7

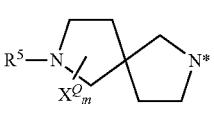 Q8

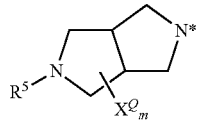 Q9

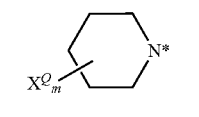 Q10

 Q11

 Q12

 Q12a

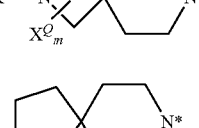 Q13

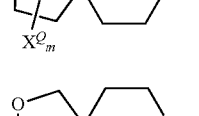 Q14

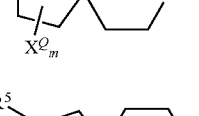 Q15

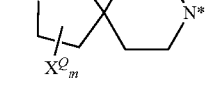 Q16

-continued

Q17 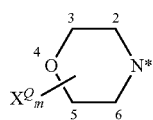

Q18 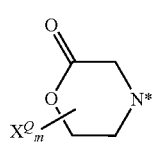

Q19 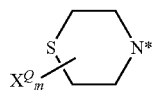

Q20 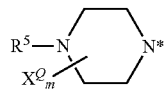

Q21 

Q22 

Q23 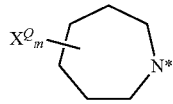

Q24 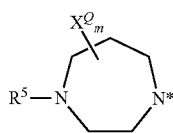

Q25 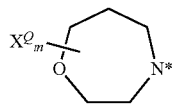

Q26 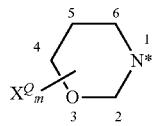

Q27 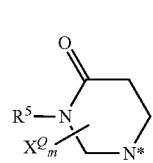

whereas the nitrogen atom marked with the asterisk (*) is bound to the carbonyl carbon atom; and wherein $R^5$ and $X^Q$ are as defined herein and m is 0, 1, 2, 3 or 4 (preferably m is 0, 1, or 2).

If one or both of $R^2$ and $R^3$ stand for a group $L^1V$ with $L^1$ being a branched or straight-chain optionally substituted ($C_1$-$C_6$)- or ($C_1$-$C_4$)-alkylene group, then V preferably stands for one of the following groups V1 to V40; more preferably for one of the groups V1, V2, V3, V4, V6, V7, V8, V11, V12, V14, V18, V19, V20, V21, V22, V24, V27, V28, V29, V30, V31, V34, V37, V40; most preferably for V1, V2, V7 or V12.

V1 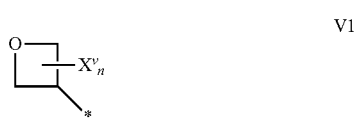

V2 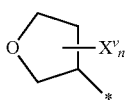

V3 

V4 

V5 

V6 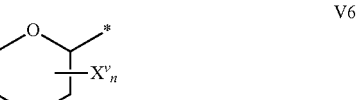

V7 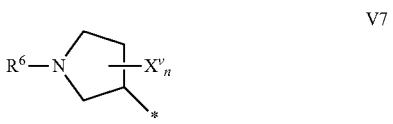

V8 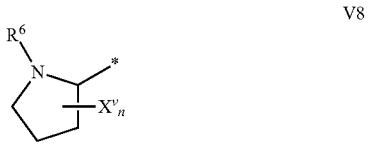

V9 

V10 

V11 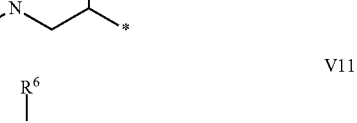

V12 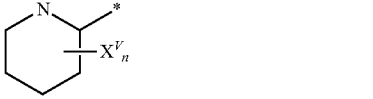

-continued
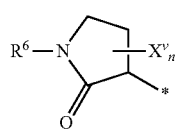 V13
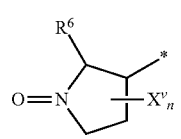 V14
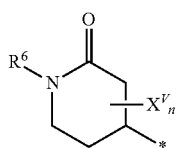 V15
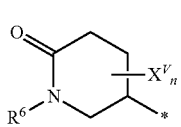 V16
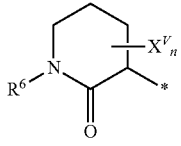 V17
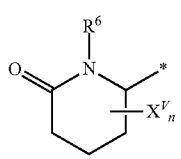 V18
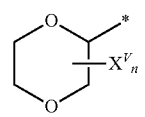 V19
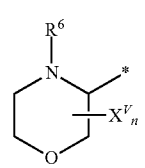 V20
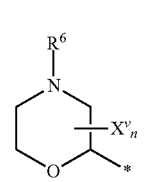 V21
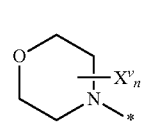 V22
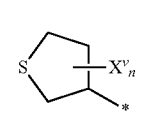 V23
-continued
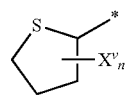 V24
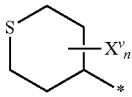 V25
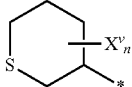 V26
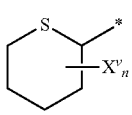 V27
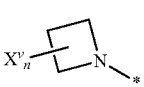 V28
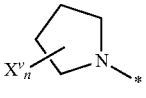 V29
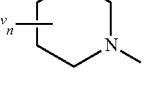 V30
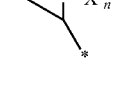 V31
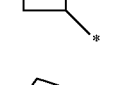 V32
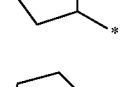 V33
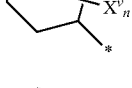 V34
 V35
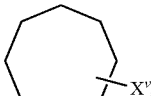 V36
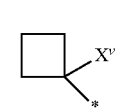 V37

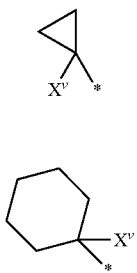

V38

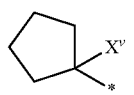

V39

V40 wherein the site marked with an asterisk (*) indicates the binding site to $L^1$; and wherein $R^6$ and $X^V$ are as defined herein and n is 0, 1, 2, 3 or 4 (preferably n is 0, 1 or 2).

If one or both of $R^2$ and $R^3$ stand for a group $L^1V$ with $L^1$ being a bond, then V is preferably selected form one of before mentioned groups V1, V2, V4, V5, V7, V9, V10, V12, V13, V15 to V17, V23, V25, V26, V31 to V36, V38, preferably, for V1, V2, V4, V7, V9, V12, V13, V34, V38; most preferably for V1, V2, V7 or V12.

Compound of formula (I) are preferred which are defined as given herein and wherein A, B and C each stands for CH; or one of A, B or C stands for N while the other groupings stand for CH.

According to the invention, compounds are preferred having the following formula (I-A), (I-A-1), (I-A-2), (I-B), (I-B-1), (I-B-2), (I-C), (I-C-1), (I-C-2), (I-D), (I-D-1), (I-D-2), (I-E), (I-E-1), (I-E-2)

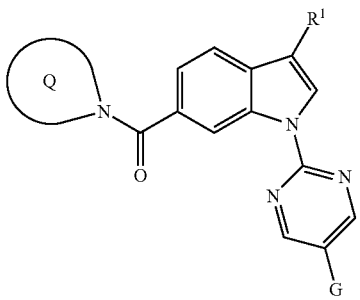

(I-A)

(I-A-1)

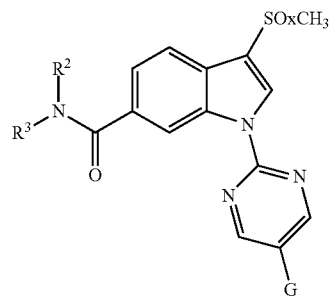

(I-A-2)

(I-B)

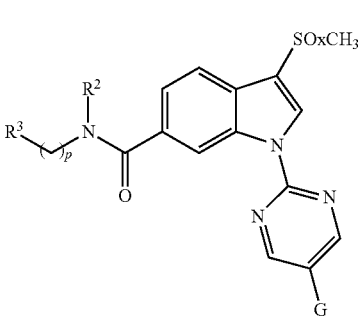

(I-B-1)

(I-B-2)

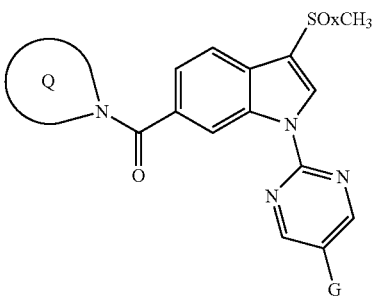

(I-C)

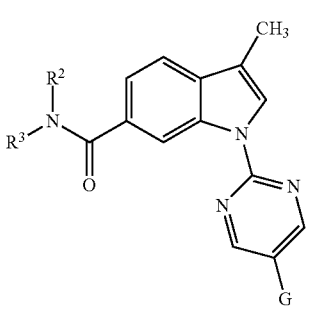

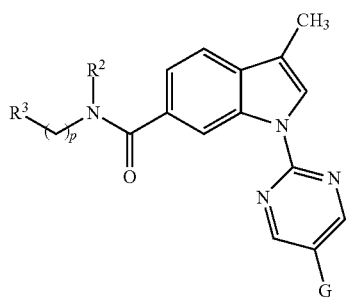
(I-C-1)

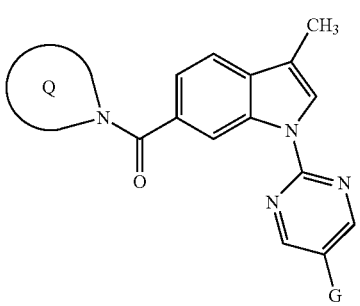
(I-C-2)

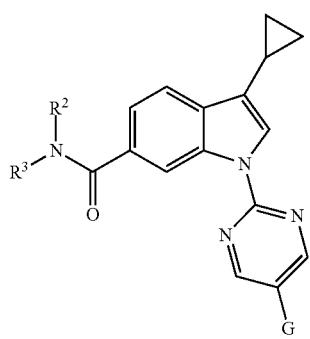
(I-D)

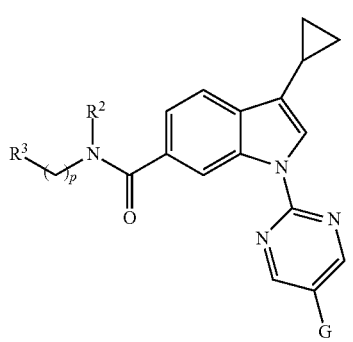
(I-D-1)

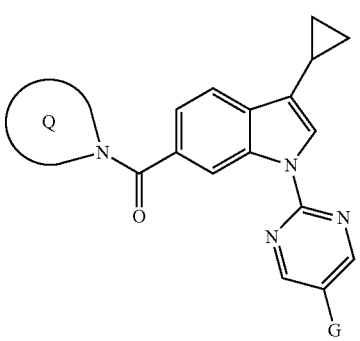
(I-D-2)

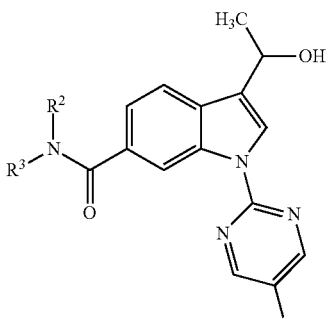
(I-E)

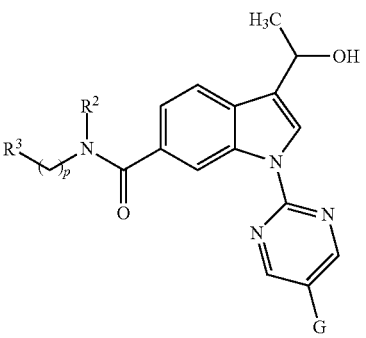
(I-E-1)

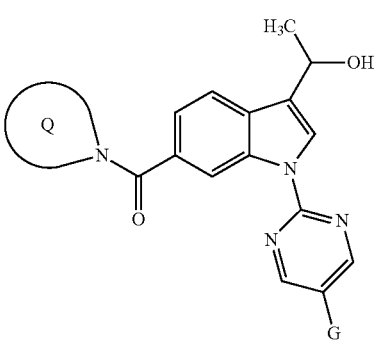
(I-E-2)

p = 0, 1, 2
x = 1, 2

In an [embodiment A] the invention relates to compounds having one of the formulae (I-A), (I-A-1), (I-A-2) wherein $R^1$ stands for methyl, hydroxymethyl, 1-hydroxyethyl, 2-hydroxypropan-2-yl, $SOCH_3$, $SO_2CH_3$ and wherein all other groups and indices are as defined in the context of the compound of general formula (I).

In an [embodiment A-1] the invention relates to compounds having one of the formulae (I-A), (I-A-1), (I-A-2) wherein G stands for G1, G2, G3, G4, G5, G12, G13, G16, and G17, preferably wherein G stands for G1, G2, G3, G4 or G5 which groups G are unsubstituted or substituted with one, two or three substituents Y which are independently of each other selected among F, Cl, CN, OH, $NH_2$, $N(CH_3)_2$, $CONH_2$, $CH_3$, $CH_2CH_3$, $OCH_3$, $OCH_2CH_3$ and cyclopropyl, preferably selected among F, Cl, $CH_3$, $CH_2CH_3$, $OCH_3$, $OCH_2CH_3$ and cyclopropyl, and wherein all other groups and indices are as defined in the context of the compound of general formula (I).

In an [embodiment A-2] the invention relates to compounds according to [embodiment A] or [embodiment A-1] having the formula (I-A-2), wherein Q is selected from Q6, Q10, Q17, Q18, Q19, Q20, Q21, Q22, Q24, and Q25; most preferably for the groups Q6, Q10, Q17, Q20, Q21, Q22, Q24 and Q25 and which groups Q are unsubstituted or substituted with one, two or three substituents $X^Q$ which are independently of each other selected among more preferably from (=O), $NH_2$, OH, $CH_3$, $CH_2CH_3$, $OCH_3$, $OCH_2CH_3$, $CH_2OCH_3$, $CH_2OH$, $CH_2CH_2OH$, $CH_2CN$, $CH_2CH_2CN$, $N(CH_3)_2$, $CH_2NH(CH_3)$, preferably selected among (=O), $NH_2$, OH, $CH_3$, $OCH_3$, $CH_2OCH_3$ and $CH_2OH$; $R^5$ is H, methyl or ethyl, and wherein all other groups and indices are as defined in the context of the compound of general formula (I).

In an [embodiment A-3] the invention relates to compounds according to [embodiment A] or [embodiment A-1] having the formula (I-A) or (I-A-1) with p being 1, wherein $R^2$ and $R^3$ independently of each other stand for H, $CH_3$, $CH_2$-cyclopropyl, 2-hydroxpropyl, hydroxyethyl, 2-methoxyethyl, 1-hydroxymethylcyclopropyl, 2-hydroxy-2-methylpropyl, $CH_2CO_2H$, $CH_2CONH_2$, $CH_2CO_2CH_3$, V1, V2, V12, V7, and wherein all other groups and indices are as defined in the context of the compound of general formula (I).

In an [embodiment B] the invention relates to compounds having one of the formulae (I-B), (I-B-1), (I-B-2) with x being 1 or 2 wherein G stands for G1, G2, G3, G4, G5, G12, G13, G16, or G17, preferably wherein G stands for G1, G2, G3, G4 or G5 which groups G are unsubstituted or substituted with one, two or three substituents Y which are independently of each other selected among F, Cl, CN, OH, $NH_2$, $N(CH_3)_2$, $CONH_2$, $CH_3$, $CH_2CH_3$, $OCH_3$, $OCH_2CH_3$ and cyclopropyl, preferably selected among F, Cl, $CH_3$, $CH_2CH_3$, $OCH_3$, $OCH_2CH_3$ and cyclopropyl and wherein all other groups and indices are as defined in the context of the compound of general formula (I).

In an [embodiment B-1] the invention relates to compounds according to [embodiment B] having the formula (I-B-2), wherein Q is selected from Q6, Q10, Q17, Q18, Q19, Q20, Q21, Q22, Q24, and Q25; most preferably for the groups Q6, Q10, Q17, Q20, Q21, Q22, Q24 and Q25 and which groups Q are unsubstituted or substituted with one, two or three substituents $X^Q$ which are independently of each other selected among more preferably from (=O), $NH_2$, OH, $CH_3$, $CH_2CH_3$, $OCH_3$, $OCH_2CH_3$, $CH_2OCH_3$, $CH_2OH$, $CH_2CH_2OH$, $CH_2CN$, $CH_2CH_2CN$, $N(CH_3)_2$, $CH_2NH(CH_3)$, preferably selected among (=O), $NH_2$, OH, $CH_3$, $OCH_3$, $CH_2OCH_3$ and $CH_2OH$; $R^5$ is H, methyl or ethyl, and wherein all other groups and indices are as defined in the context of the compound of general formula (I).

In an [embodiment B-2] the invention relates to compounds according to [embodiment B] having the formula (I-B) or (I-B-1) with p being 1, wherein $R^2$ and $R^3$ independently of each other stand for H, $CH_3$, $CH_2$-cyclopropyl, 2-hydroxpropyl, hydroxyethyl, 2-methoxyethyl, 1-hydroxymethylcyclopropyl, 2-hydroxy-2-methylpropyl, $CH_2CO_2H$, $CH_2CONH_2$, $CH_2CO_2CH_3$, V1, V2, V12, V7, and wherein all other groups and indices are as defined in the context of the compound of general formula (I).

In an [embodiment C] the invention relates to compounds having one of the formulae (I-C), (I-C-1), (I-C-2) wherein G stands for G1, G2, G3, G4, G5, G12, G13, G16, and G17, preferably wherein G stands for G1, G2, G3, G4 or G5 which groups G are unsubstituted or substituted with one, two or three substituents Y which are independently of each other selected among F, Cl, CN, OH, $NH_2$, $N(CH_3)_2$, $CONH_2$, $CH_3$, $CH_2CH_3$, $OCH_3$, $OCH_2CH_3$ and cyclopropyl, preferably selected among F, Cl, $CH_3$, $CH_2CH_3$, $OCH_3$, $OCH_2CH_3$ and cyclopropyl, and wherein all other groups and indices are as defined in the context of the compound of general formula (I).

In an [embodiment C-1] the invention relates to compounds according to [embodiment C] having the formula (I-C-2), wherein Q is selected from Q6, Q10, Q17, Q18, Q19, Q20, Q21, Q22, Q24, and Q25; most preferably for the groups Q6, Q10, Q17, Q20, Q21, Q22, Q24 and Q25 and which groups Q are unsubstituted or substituted with one, two or three substituents $X^Q$ which are independently of each other selected among more preferably from (=O), $NH_2$, OH, $CH_3$, $CH_2CH_3$, $OCH_3$, $OCH_2CH_3$, $CH_2OCH_3$, $CH_2OH$, $CH_2CH_2OH$, $CH_2CN$, $CH_2CH_2CN$, $N(CH_3)_2$, $CH_2NH(CH_3)$, preferably selected among (=O), $NH_2$, OH, $CH_3$, $OCH_3$, $CH_2OCH_3$ and $CH_2OH$; $R^5$ is H, methyl or ethyl, and wherein all other groups and indices are as defined in the context of the compound of general formula (I).

In an [embodiment C-2] the invention relates to compounds according to [embodiment C] having the formula (I-C) or (I-C-1) with p being 1, wherein $R^2$ and $R^3$ independently of each other stand for H, $CH_3$, $CH_2$-cyclopropyl, 2-hydroxpropyl, hydroxyethyl, 2-methoxyethyl, 1-hydroxymethylcyclopropyl, 2-hydroxy-2-methylpropyl, $CH_2CO_2H$, $CH_2CONH_2$, $CH_2CO_2CH_3$, V1, V2, V12, V7, and wherein all other groups and indices are as defined in the context of the compound of general formula (I).

In an [embodiment D] the invention relates to compounds having one of the formulae (I-D), (I-D-1), (I-D-2) wherein G stands for G1, G2, G3, G4, G5, G12, G13, G16, and G17, preferably wherein G stands for G1, G2, G3, G4 or G5 which groups G are unsubstituted or substituted with one, two or three substituents Y which are independently of each other selected among F, Cl, CN, OH, $NH_2$, $N(CH_3)_2$, $CONH_2$, $CH_3$, $CH_2CH_3$, $OCH_3$, $OCH_2CH_3$ and cyclopropyl, preferably selected among F, Cl, $CH_3$, $CH_2CH_3$, $OCH_3$, $OCH_2CH_3$ and cyclopropyl, and wherein all other groups and indices are as defined in the context of the compound of general formula (I).

In an [embodiment D-1] the invention relates to compounds according to [embodiment D] having the formula (I-D-2), wherein Q is selected from Q6, Q10, Q17, Q18, Q19, Q20, Q21, Q22, Q24, and Q25; most preferably for the groups Q6, Q10, Q17, Q20, Q21, Q22, Q24 and Q25 and which groups Q are unsubstituted or substituted with one, two or three substituents $X^Q$ which are independently of each other selected among more preferably from (=O), $NH_2$, OH, $CH_3$, $CH_2CH_3$, $OCH_3$, $OCH_2CH_3$, $CH_2OCH_3$, $CH_2OH$, $CH_2CH_2OH$, $CH_2CN$, $CH_2CH_2CN$, $N(CH_3)_2$, $CH_2NH(CH_3)$, preferably selected among (=O), $NH_2$, OH, $CH_3$, $OCH_3$, $CH_2OCH_3$ and $CH_2OH$; $R^5$ is H, methyl or ethyl, and wherein all other groups and indices are as defined in the context of the compound of general formula (I).

In an [embodiment D-2] the invention relates to compounds according to [embodiment D] having the formula (I-D) or (I-D-1) with p being 1, wherein $R^2$ and $R^3$ independently of each other stand for H, $CH_3$, $CH_2$-cyclopropyl, 2-hydroxpropyl, hydroxyethyl, 2-methoxyethyl, 1-hydroxymethylcyclopropyl, 2-hydroxy-2-methylpropyl, $CH_2CO_2H$, $CH_2CONH_2$, $CH_2CO_2CH_3$, V1, V2, V12, V7, and wherein all other groups and indices are as defined in the context of the compound of general formula (I).

In an [embodiment E] the invention relates to compounds having one of the formulae (I-E), (I-E-1), (I-E-2) wherein G stands for G1, G2, G3, G4, G5, G12, G13, G16, and G17, preferably wherein G stands for G1, G2, G3, G4 or G5 which groups G are unsubstituted or substituted with one, two or three substituents Y which are independently of each other selected among F, Cl, CN, OH, $NH_2$, $N(CH_3)_2$, $CONH_2$, $CH_3$, $CH_2CH_3$, $OCH_3$, $OCH_2CH_3$ and cyclopropyl, preferably selected among F, Cl, $CH_3$, $CH_2CH_3$, $OCH_3$, $OCH_2CH_3$ and wherein all other groups and indices are as defined in the context of the compound of general formula (I).

In an [embodiment E-1] the invention relates to compounds according to [embodiment E] having the formula (I-E-2), wherein Q is selected from Q6, Q10, Q17, Q18, Q19, Q20, Q21, Q22, Q24, and Q25; most preferably for the groups Q6, Q10, Q17, Q20, Q21, Q22, Q24 and Q25 and which groups Q are unsubstituted or substituted with one, two or three substituents $X^Q$ which are independently of each other selected among more preferably from (=O), $NH_2$, OH, $CH_3$, $CH_2CH_3$, $OCH_3$, $OCH_2CH_3$, $CH_2OCH_3$, $CH_2OH$, $CH_2CH_2OH$, $CH_2CN$, $CH_2CH_2CN$, $N(CH_3)_2$, $CH_2NH(CH_3)$, preferably selected among (=O), $NH_2$, OH, $CH_3$, $OCH_3$, $CH_2OCH_3$ and $CH_2OH$; $R^5$ is H, methyl or ethyl, and wherein all other groups and indices are as defined in the context of the compound of general formula (I).

In an [embodiment E-2] the invention relates to compounds according to [embodiment E] having the formula (I-E) or (I-E-1) with p being 1, wherein $R^2$ and $R^3$ independently of each other stand for H, $CH_3$, $CH_2$-cyclopropyl, 2-hydroxpropyl, hydroxyethyl, 2-methoxyethyl, 1-hydroxymethylcyclopropyl, 2-hydroxy-2-methylpropyl, $CH_2CO_2H$, $CH_2CONH_2$, $CH_2CO_2CH_3$, V1, V2, V12, V7, and wherein all other groups and indices are as defined in the context of the compound of general formula (I).

The term "physiologically acceptable salt" in the sense of this invention preferably comprises a salt of at least one compound according to the present invention and at least one physiologically acceptable acid or base.

A physiologically acceptable salt of at least one compound according to the present invention and at least one physiologically acceptable acid or one physiologically acceptable base preferably refers in the sense of this invention to a salt of at least one compound according to the present invention with at least one inorganic or organic acid or with at least one inorganic or organic base respectively which is physiologically acceptable—in particular when used in human beings and/or other mammals.

The term "physiologically acceptable solvate" in the sense of this invention preferably comprises an adduct of one compound according to the present invention and/or a physiologically acceptable salt of at least one compound according to the present invention with distinct molecular equivalents of one solvent or more solvents.

In the context of the present invention, and unless otherwise specified herein, the term "halogen" preferably represents the radicals F, Cl, Br and I, in particular the radicals F and Cl.

Unless otherwise specified, the term "$(C_1-C_6)$-alkyl" is understood to mean branched and unbranched alkyl groups consisting of 1 to 6 hydrocarbon atoms. Examples of $(C_1-C_6)$-alkyl radicals are methyl, ethyl, n-propyl, 1-methylethyl(iso-propyl), n-butyl, 1-methylpropyl, 2-methylpropyl, 1,1-dimethylethyl(tert-butyl), n-pentyl, 1-methylbutyl, 2-methylbutyl, 3-methylbutyl, 1,1-dimethylpropyl, 1,2-dimethylpropyl, 2,2-dimethylpropyl, n-hexyl, 1-methylpentyl, 2-methylpentyl, 3-methylpentyl, 4-methylpentyl. $(C_1-C_4)$-alkyl radicals are preferred, $(C_1-C_3)$-alkyl radicals being particularly preferred, in particular methyl, ethyl n-propyl or iso-propyl. Unless otherwise stated, the definitions of propyl, butyl, pentyl and hexyl encompass all possible isomeric forms of the individual radicals.

Unless otherwise specified, a haloalkyl radical is understood to be an alkyl radical in which at least one hydrogen is exchanged for a halogen atom, preferably fluorine, chlorine, bromine, particularly preferably fluorine. The haloalkyl radicals can be branched or unbranched and optionally mono- or polysubstituted. Preferred haloalkyl radicals are $CHF_2$, $CH_2F$, $CF_3$, $CH_2$—$CH_2F$, $CH_2$—$CHF_2$, $CH_2CF_3$. $(C_1-C_6)$ haloalkyl radicals are preferred, with $(C_1-C_4)$ haloalkyl radicals being particularly preferred and $(C_1-C_3)$ haloalkyl radicals most particularly preferred, in particular $CHF_2$, $CH_2F$, $CF_3$, $CH_2$—$CH_2F$, $CH_2$—$CHF_2$ and $CH_2CF_3$.

Unless otherwise specified, a haloalkoxy radical is understood to be an alkoxy radical in which at least one hydrogen is exchanged for a halogen atom, preferably fluorine, chlorine, bromine, particularly preferably fluorine. The haloalkoxy radicals can be branched or unbranched and optionally mono- or polysubstituted. Preferred haloalkoxy radicals are $OCHF_2$, $OCH_2F$, $OCF_3$, $OCH_2$—$CFH_2$, $OCH_2$—$CF_2H$, $OCH_2CF_3$. $(C_1-C_6)$ haloalkoxy radicals are preferred, with $(C_1-C_4)$ haloalkoxy radicals being particularly preferred and $(C_1-C_3)$ haloalkoxy radicals most particularly preferred, in particular $OCHF_2$, $OCH_2F$, $OCF_3$, $OCH_2$—$CFH_2$, $OCH_2$—$CF_2H$, $OCH_2CF_3$.

Unless otherwise specified, a hydroxyalkyl radical is understood to be an alkyl radical in which at least one hydrogen is exchanged for a hydroxyl group. The hydroxyalkyl radicals can be branched or unbranched and optionally mono- or polysubstituted. $(C_1-C_6)$-hydroxyalkyl radicals are preferred, with $(C_1-C_4)$-hydroxyalkyl radicals being particularly preferred and $(C_1-C_3)$-hydroxyalkyl radicals most particularly preferred, in particular $CH_2$—OH, $CH_2$—$CH_2$—OH and $CH_2$—$CH_2$—$CH_2$—OH.

Unless otherwise specified, a cyanoalkyl radical is understood to be an alkyl radical in which at least one hydrogen is exchanged for a cyano group. The cyanoalkyl radicals can be branched or unbranched and optionally mono- or polysubstituted. $(C_1-C_6)$-cyanoalkyl radicals are preferred, with $(C_1-C_4)$-cyanoalkyl radicals being particularly preferred and $(C_1-C_3)$-cyanoalkyl radicals most particularly preferred, in particular $CH_2$—CN, $CH_2$—$CH_2$—CN and $CH_2$—$CH_2$—$CH_2$—CN.

In the context of the present invention, the expression "$(C_1-C_6)$-alkylene group" or "$(C_1-C_4)$-alkylene group" includes acyclic saturated hydrocarbon radicals having 1, 2, 3, 4, 5 or 6 carbon atoms or 1, 2, 3 or 4 carbon atoms, respectively, which can be branched or unbranched and unsubstituted or substituted once or several times, for example 2, 3, 4 or 5 times, by identical or different substituents and which link a corresponding moiety to the main structure. Such alkylene groups can preferably be chosen from the group consisting of —$CH_2$—, —$CH_2CH_2$—, —$CH(CH_3)$—, —$CH_2CH_2CH_2$—, —$CH(CH_3)CH_2$—, —$CH(CH_2CH_3)$—, —$CH_2$ $(CH_2)_2$ $CH_2$—, —$CH(CH_3)CH_2CH_2$—, —$CH_2CH(CH_3)CH_2$—, —$CH(CH_3)CH(CH_3)$—, —$CH(CH_2CH_3)CH_2$—, —$C(CH_3)_2$ $CH_2$—, —$CH(CH_2CH_2CH_3)$—, —$C(CH_3)$ $(CH_2CH_3)$—, —$CH_2(CH_2)_3CH_2$—, —$CH(CH_3)$ $CH_2CH_2CH_2$—, —$CH_2CH(CH_3)CH_2CH_2$—, —$CH(CH_3)$ $CH_2CH(CH_3)$—, —$CH(CH_3)CH(CH_3)CH_2$—, —$C(CH_3)_2$ $CH_2CH_2$—, —$CH_2C(CH_3)_2CH_2$—, —$CH(CH_2CH_3)$ $CH_2CH_2$—, —$CH_2CH(CH_2CH_3)CH_2$—, —$C(CH_3)_2CH$ $(CH_3)$—, —$CH(CH_2CH_3)CH(CH_3)$—, —$C(CH_3)$ $(CH_2CH_3)CH_2$—, —$CH(CH_2CH_2CH_3)CH_2$—, —$C(CH_2CH_2CH_3)CH_2$—, —$CH(CH_2CH_2CH_2CH_3)$—, —$C(CH_3)(CH_2CH_2CH_3)$—, —$C(CH_2CH_3)_2$— and —$CH_2(CH_2)_4CH_2$—. The alkylene groups can particularly preferably be chosen from the group consisting of —$CH_2$—, —$CH_2CH_2$— and —$CH_2CH_2CH_2$—.

Unless otherwise specified, the term "$(C_2-C_6)$-alkenyl" is understood to mean branched and unbranched unsaturated alkyl groups consisting of 2 to 6 hydrocarbon atoms and having at least one double bond. Examples of $(C_2-C_6)$-alkenyls are ethenyl (also referred to as vinyl), prop-1-enyl, prop-2-enyl (also referred to as allyl), but-1-enyl, but-2-enyl, but-3-enyl, pent-1-enyl and hex-1-enyl. The designation $(C_2$-

$C_6$)-alkenyl includes all possible isomers, i.e. structural isomers (constitutional isomers) and stereoisomers ((Z) and (E) isomers). Unless otherwise specified, the term "($C_2$-$C_6$)-alkinyl" is understood to mean branched and unbranched unsaturated alkyl groups consisting of 2 to 6 hydrocarbon atoms and having at least one triple bond. Examples of ($C_2$-$C_6$)-alkinyls are ethinyl.

Unless otherwise specified, the term "3- to 12-membered cyclic aliphatic ring" is understood to mean cyclic aliphatic hydrocarbons containing 3, 4, 5, 6, 7, 8, 9, 10, 11 or 12 carbon atoms, wherein the hydrocarbons in each case can be saturated or unsaturated (but not aromatic), unsubstituted or mono- or polysubstituted. The residues may be mono- or bicyclic.

The cycloaliphatic residues can be bound to the respective superordinate general structure via any desired and possible ring member of the cycloaliphatic residue. The ($C_3$-$C_{12}$) cycloaliphatic residue can furthermore be single or multiple bridged such as, for example, in the case of adamantyl, bicyclo[2.2.1]heptyl or bicyclo[2.2.2]octyl. Preferred ($C_3$-$C_{12}$) cycloaliphatic residues are selected from the group consisting of cyclopropyl, cyclobutyl, cyclopentyl, cyclohexyl, cycloheptyl, cyclooctyl, cyclononyl, cyclodecyl, adamantyl, cyclopentenyl, cyclohexenyl, cycloheptenyl, cyclooctenyl,

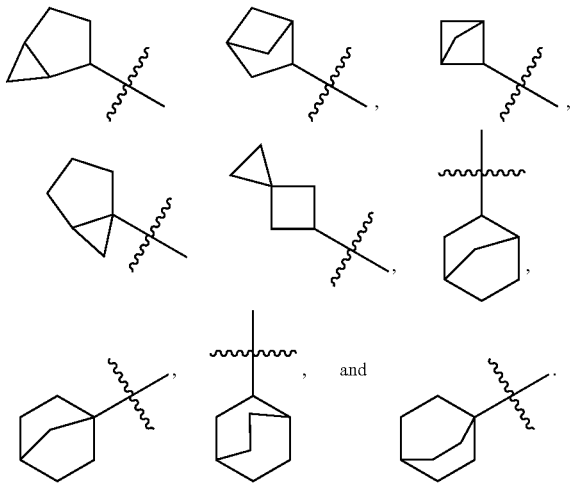

Preferred are ($C_3$-$C_8$)-mono- or bicyclic aliphatic residues which are selected from the group consisting of cyclopropyl, cyclobutyl, cyclopentyl, cyclohexyl, cycloheptyl, and cyclooctyl. Particularly preferred are ($C_3$-$C_6$)-cycloaliphatic residues such as cyclopropyl, cyclobutyl, cyclopentyl, cyclohexyl, cyclopentenyl and cyclohexenyl, in particular cyclopropyl.

Unless otherwise specified, the term "3- to 12-membered heteroaliphatic residue" is understood to mean heterocycloaliphatic saturated or unsaturated (but not aromatic) residues having 3 to 12, i.e. 3, 4, 5, 6, 7, 8, 9, 10, 11 or 12 ring members, in which in each case at least one, if appropriate also two or three carbon atoms are replaced by a heteroatom or a heteroatom group each selected independently of one another from the group consisting of O, S, S(=O), S(=O)$_2$, N, NH and N($C_1$-$C_6$)-alkyl such as N(CH$_3$), wherein the ring members can be unsubstituted or mono- or polysubstituted. The residues may be mono- or bicyclic.

Unless otherwise specified, the term "5- or 6-membered heteroaryl" is understood to represent a 5- or 6-membered cyclic aromatic residue containing at least 1, if appropriate also 2, 3, 4 or 5 heteroatoms, wherein the heteroatoms are each preferably selected independently of one another from the group S, N and O, whereas the sulfur atom may exist in oxidized form as SO or SO$_2$ group, and the heteroaryl residue can be unsubstituted or mono- or polysubstituted; e.g. substituted by 2, 3, 4 or 5 substituents, whereby the substituents can be the same or different and be in any desired and possible position of the heteroaryl. The binding to the superordinate general structure can be carried out via any desired and possible ring member of the heteroaryl residue if not indicated otherwise. The heteroaryl may be condensed with a 4-, 5-, 6- or 7-membered ring, being carbocyclic or heterocyclic, wherein the heteroatoms of the heterocyclic ring are each preferably selected independently of one another from the group S, N and O, and wherein said condensed ring may be saturated, partially unsaturated or aromatic and may be unsubstituted or mono- or polysubstituted; e.g. substituted by 2, 3, 4 or 5 substituents, whereby the substituents can be the same or different and be in any desired and possible position. Examples of such heteroaryl moieties are benzofuranyl, benzoimidazolyl, benzo-thienyl, benzo-thiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl(2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

In connection with non-aromatic moieties such as "alkyl", "alkenyl", "alkinyl", "alkylene", "cycloaliphatic", "heterocycloaliphatic", "carbocyclic ring", "heterocyclic", "cycloalkyl" and "heterocyclyl", in the context of this invention the term "substituted" is understood as meaning replacement of a hydrogen radical by a substituent selected from the group consisting of =O, OH, CN, halogen, SH, nitro, ($C_1$-$C_6$)-alkyl, ($C_2$-$C_6$)-alkenyl, ($C_2$-$C_6$)-alkinyl, ($C_1$-$C_6$)-hydroxyalkyl, ($C_1$-$C_6$)-cyanoalkyl, ($C_1$-$C_6$)-alkoxy, ($C_1$-$C_6$)-thioalkyl, ($C_1$-$C_6$)-haloalkyl, ($C_1$-$C_6$)-thiohaloalkyl, ($C_1$-$C_6$)-haloalkoxy, ($C_1$-$C_6$)-alkylen-S—($C_1$-$C_6$)-alkyl, ($C_3$-$C_8$)-cycloalkyl, ($C_3$-$C_6$)-cycloalkyl-($C_1$-$C_3$)-alkylenyl, ($C_3$-$C_8$)-heterocycloalkyl, NH$_2$, NH($C_1$-$C_6$)-alkyl, N(($C_1$-$C_6$)-alkyl)$_2$, NH—CO—($C_1$-$C_6$)-alkyl, NH—CO—($C_1$-$C_6$)-alkyl, NH—C(O)NH$_2$, NH—CO—NH—($C_1$-$C_6$)-alkyl, NH—CO—N(($C_1$-$C_6$)-alkyl)$_2$, NH(($C_1$-$C_6$)-alkylen)-CO—($C_1$-$C_6$)-alkyl, NH(($C_1$-$C_6$)-alkylen)-CO—O—($C_1$-$C_6$)-alkyl, NH(($C_1$-$C_6$)-alkylen)-CONH$_2$, NH(($C_1$-$C_6$)-alkylen)-CO—NH—($C_1$-$C_6$)-alkyl, NH(($C_1$-$C_6$)-alkylen)-CO—N(($C_1$-$C_6$)-alkyl)$_2$, NH—S(O)$_2$OH, NH—S(O)$_2$($C_1$-$C_6$)-alkyl, NH—S(O)$_2$O($C_1$-$C_6$)-alkyl, NH—S(O)$_2$NH$_2$, NH—S(O)$_2$NH($C_1$-$C_6$)-alkyl, NH—S(O)$_2$N(($C_1$-$C_6$)-alkyl)$_2$, NH(($C_1$-$C_6$)-alkylen)-S(O)$_2$OH, NH(($C_1$-$C_6$)-alkylen)-S(O)$_2$($C_1$-$C_6$)-alkyl, NH(($C_1$-$C_6$)-alkylen)-S(O)$_2$O($C_1$-$C_6$)-alkyl, NH(($C_1$-$C_6$)-alkylen)-S(O)$_2$NH$_2$, NH(($C_1$-$C_6$)-alkylen)-S(O)$_2$NH($C_1$-$C_6$)-alkyl, CO$_2$H, CO($C_1$-$C_6$)-alkyl, CO—O($C_1$-$C_6$)-alkyl, O—CO($C_1$-$C_6$)-alkyl, O—CO—O($C_1$-$C_6$)-alkyl, CONH$_2$, CO—NH($C_1$-$C_6$)-alkyl, CO—N(($C_1$-$C_6$)-alkyl)$_2$, O—CO—NH($C_1$-$C_6$)-alkyl, O—CO—N(($C_1$-$C_6$)-alkyl)$_2$, O—S(O)$_2$—($C_1$-$C_6$)-alkyl, O—S(O)$_2$OH, O—S(O)$_2$—($C_1$-$C_6$)-alkoxy, O—S(O)$_2$NH$_2$, O—S(O)$_2$—NH($C_1$-$C_6$)-alkyl, O—S(O)$_2$—N(($C_1$-$C_6$)-alkyl)$_2$, S(O)($C_1$-$C_6$)-alkyl, S(O)$_2$($C_1$-$C_6$)-alkyl, S(O)$_2$OH, S(O)$_2$O($C_1$-$C_6$)-alkyl, S(O)$_2$NH$_2$, S(O)$_2$NH($C_1$-$C_6$)-alkyl, and S(O)$_2$N(($C_1$-$C_6$)-alkyl)$_2$. If a moiety is substituted with more than 1 substituent, e.g. by 2, 3, 4, or 5 substituents, these substituents may be present either on different or on the same atoms, e.g. as in the case of $CF_3$ or $CH_2CF_3$, or at different places, as in the case of $CH(Cl)$—$CH$=$CH$—$CHCl_2$. Substitution with more than 1 substituent may include identical or different substituents, such as, for example, in the case of $CH(OH)$—$CH$=$CH$—$CHCl_2$. Preferably, the substituents may be selected from the group consisting of F, Cl, Br, $CF_3$, $CHF_2$, $CH_2F$, $OCF_3$, OH, CN, $(C_1$-$C_4)$-alkyl, $(C_1$-$C_4)$-hydroxyalkyl, $(C_1$-$C_4)$-alkoxy, $(C_3$-$C_6)$-cycloalkyl, $NH_2$, $NH(C_1$-$C_4)$-alkyl, $N((C_1$-$C_4)$-alkyl$)_2$, NH—CO—$(C_1$-$C_4)$-alkyl, NH—CO—NH—$(C_1$-$C_6)$-alkyl, NH—CO—N$((C_1$-$C_6)$-alkyl$)_2$, NH—S$(O)_2(C_1$-$C_4)$-alkyl, $CONH_2$, CO—NH$(C_1$-$C_6)$-alkyl, CO—N$((C_1$-$C_6)$-alkyl$)_2$, $S(O)(C_1$-$C_4)$-alkyl and $S(O)_2(C_1$-$C_4)$-alkyl.

In connection with aromatic moieties such as "phenyl" and "heteroaryl", in the context of this invention the term "substituted" is understood as meaning replacement of a hydrogen radical by a substituent selected from the group consisting of OH, halogen, CN, SH, nitro, $(C_1$-$C_6)$-alkyl, $(C_2$-$C_6)$-alkenyl, $(C_2$-$C_6)$-alkinyl, $(C_1$-$C_6)$-hydroxyalkyl, $(C_1$-$C_6)$-cyanoalkyl, $(C_1$-$C_6)$-alkoxy, $(C_1$-$C_6)$-thioalkyl, $(C_1$-$C_6)$-haloalkyl, $(C_1$-$C_6)$-thiohaloalkyl, $(C_1$-$C_6)$-haloalkoxy, $(C_1$-$C_6)$-alkylen-S—$(C_1$-$C_6)$-alkyl, $(C_3$-$C_8)$-cycloalkyl, $(C_3$-$C_6)$-cycloalkyl-$(C_1$-$C_3)$-alkylenyl, $(C_3$-$C_8)$-heterocycloalkyl, $NH_2$, $NH(C_1$-$C_6)$-alkyl, $N((C_1$-$C_6)$-alkyl$)_2$, NH—CO—$(C_1$-$C_6)$-alkyl, NH—CO—O—$(C_1$-$C_6)$-alkyl, NH—C(O)NH$_2$, NH—CO—NH—$(C_1$-$C_6)$-alkyl, NH—CO—N$((C_1$-$C_6)$-alkyl$)_2$, NH$((C_1$-$C_6)$-alkylen)-CO—$(C_1$-$C_6)$-alkyl, NH$((C_1$-$C_6)$-alkylen)-CO—O—$(C_1$-$C_6)$-alkyl, NH$((C_1$-$C_6)$-alkylen)-$CONH_2$, NH$((C_1$-$C_6)$-alkylen)-CO—NH—$(C_1$-$C_6)$-alkyl, NH$((C_1$-$C_6)$-alkylen)-CO—N$((C_1$-$C_6)$-alkyl$)_2$, NH—S$(O)_2$OH, NH—S$(O)_2(C_1$-$C_6)$-alkyl, NH—S$(O)_2$O$(C_1$-$C_6)$-alkyl, NH—S$(O)_2$NH$_2$, NH—S$(O)_2$NH$(C_1$-$C_6)$-alkyl, NH—S$(O)_2$N$((C_1$-$C_6)$-alkyl$)_2$, NH$((C_1$-$C_6)$-alkylen)-S$(O)_2$OH, NH$((C_1$-$C_6)$-alkylen)-S$(O)_2(C_1$-$C_6)$-alkyl, NH$((C_1$-$C_6)$-alkylen)-S$(O)_2$O$(C_1$-$C_6)$-alkyl, NH$((C_1$-$C_6)$-alkylen)-S$(O)_2$NH$_2$, NH$((C_1$-$C_6)$-alkylen)-S$(O)_2$NH$(C_1$-$C_6)$-alkyl, $CO_2H$, $CO(C_1$-$C_6)$-alkyl, CO—O$(C_1$-$C_6)$-alkyl, O—CO$(C_1$-$C_6)$-alkyl, O—CO—O$(C_1$-$C_6)$-alkyl, $CONH_2$, CO—NH$(C_1$-$C_6)$-alkyl, CO—N$((C_1$-$C_6)$-alkyl$)_2$, O—CO—NH$(C_1$-$C_6)$-alkyl, O—CO—N$((C_1$-$C_6)$-alkyl$)_2$, O—S$(O)_2$—$(C_1$-$C_6)$-alkyl, O—S$(O)_2$OH, O—S$(O)_2$—$(C_1$-$C_6)$-alkoxy, O—S$(O)_2$NH$_2$, O—S$(O)_2$—NH$(C_1$-$C_6)$-alkyl, O—S$(O)_2$—N$((C_1$-$C_6)$-alkyl$)_2$, S$(O)(C_1$-$C_6)$-alkyl, S$(O)_2(C_1$-$C_6)$-alkyl, S$(O)_2$OH, S$(O)_2$O$(C_1$-$C_6)$-alkyl, S$(O)_2$NH$_2$, S$(O)_2$NH$(C_1$-$C_6)$-alkyl, and S$(O)_2$N$((C_1$-$C_6)$-alkyl$)_2$. If a moiety is substituted with more than 1 substituent, e.g. by 2, 3, 4, or 5 substituents, these substituents may be identical or different. Preferably, the substituents may be selected from the group consisting of F, Cl, Br, $CF_3$, $CHF_2$, $CH_2F$, $OCF_3$, OH, CN, $(C_1$-$C_4)$-alkyl, $(C_1$-$C_4)$-hydroxyalkyl, $(C_1$-$C_4)$-alkoxy, $(C_3$-$C_6)$-cycloalkyl, $NH_2$, $NH(C_1$-$C_4)$-alkyl, $N((C_1$-$C_4)$-alkyl$)_2$, NH—CO—$(C_1$-$C_4)$-alkyl, NH—CO—NH—$(C_1$-$C_6)$-alkyl, NH—CO—N$((C_1$-$C_6)$-alkyl$)_2$, NH—S$(O)_2(C_1$-$C_4)$-alkyl, $CONH_2$, CO—NH$(C_1$-$C_6)$-alkyl, CO—N$((C_1$-$C_6)$-alkyl$)_2$, $S(O)(C_1$-$C_4)$-alkyl and $S(O)_2(C_1$-$C_4)$-alkyl.

Owing to their excellent pharmacological activity, the compounds according to the first aspect of the invention, in particular according to the general structure of formulae (I), (I-A-1), (I-A-2), (I-B), (I-B-1), (I-B-2), (I-C), (I-C-1), (I-C-2), (I-D), (I-D-1), (I-D-2), (I-E), (I-E-1), (I-E-2) are suitable for the treatment of various diseases or conditions in which inhibition of the PDE4 enzyme is advantageous.

Such conditions and diseases are inter alia inflammatory diseases of the joints, in particular rheumatoid arthritis, psoriatic arthritis, ankylosing spondylitis (Bechterew's disease), gout, osteoarthritis;

inflammatory diseases of the skin, in particular psoriasis, atopic dermatitis, lichen planus;

inflammatory diseases of the eyes, in particular uveitis;

gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps;

inflammatory diseases of the internal organs, in particular SLE (systemic lupus erythematosus) including lupus nephritis, chronic prostatitis, interstitial cystitis;

hyperplastic diseases, in particular benign prostatic hyperplasia;

respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia;

diseases of the fibrotic spectrum, in particular hepatic fibrosis, systemic sclerosis, scleroderma;

cancers, in particular haematopoietic cancers, inter alia B-cell lymphoma, T-cell lymphoma, in particular CLL and CML (chronic lymphatic and chronic myeloid leukaemia), ALL and AML (acute lymphatic and acute myeloid leukaemia), and gliomas;

metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension);

psychological disorders, in particular schizophrenia, depression, in particular bipolar or manic depression, dementia, memory loss, generalised anxiety disorder (GAD); and diseases of the peripheral or central nervous system, in particular Parkinson's disease, multiple sclerosis, Alzheimer's disease, stroke, ALS (amyotrophic lateral sclerosis).

One of the advantages of the compounds according to the first aspect of the invention is that they are selective PDE4B inhibitors. The advantage of this selectivity lies in the fact that the PDE4D enzyme for example is not inhibited or is only partly inhibited, and hence the use of such selective PDE4B inhibitors gives rise to no side-effects or to markedly reduced side-effects. Undesired side-effects are for example emesis and nausea, in particular indisposition, vomiting and sickness. The therapeutic range of the compounds according to the invention is therefore advantageous.

In a second aspect of the invention, the invention therefore also provides a pharmaceutical composition (medicament) containing at least one compound according to the first aspect of the invention, in particular according to formulae (I-A-1), (I-A-2), (I-B), (I-B-1), (I-B-2), (I-C), (I-C-1), (I-C-2), (I-D), (I-D-1), (I-D-2), (I-E), (I-E-1) and (I-E-2) in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio.

In a third aspect of the invention, the invention therefore also provides a compound according to the first aspect of the invention, in particular according to formulae (I), (I-A-1), (I-A-2), (I-B), (I-B-1), (I-B-2), (I-C), (I-C-1), (I-C-2), (I-D), (I-D-1), (I-D-2), (I-E), (I-E-1) and (I-E-2) in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio for use as a medicament, in particular for the treatment of conditions or diseases that can be treated by inhibition of the PDE4 enzyme, in particular the PDE4B enzyme.

In a fourth aspect of the invention, the invention therefore also provides a compound according to the first aspect of the invention, in particular according to formulae (I), (I-A-1), (I-A-2), (I-B), (I-B-1), (I-B-2), (I-C), (I-C-1), (I-C-2), (I-D), (I-D-1), (I-D-2), (I-E), (I-E-1) and (I-E-2) in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio for the treatment of inflammatory diseases of the joints, in particular rheumatoid arthritis, psoriatic arthritis, ankylosing spondylitis (Bechterew's disease), gout, osteoarthritis; and/or inflammatory diseases of the skin, in particular psoriasis, atopic dermatitis, lichen planus; and/or inflammatory diseases of the eyes, in particular uveitis; gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps; inflammatory diseases of the internal organs, in particular SLE (systemic lupus erythematosus) including lupus nephritis, chronic prostatitis, interstitial cystitis; and/or hyperplastic diseases, in particular benign prostatic hyperplasia; respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; diseases of the fibrotic spectrum, in particular hepatic fibrosis, systemic sclerosis, scleroderma; cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas; metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension); psychological disorders, in particular schizophrenia, depression, in particular bipolar or manic depression, dementia, memory loss, generalised anxiety disorder (GAD); and/or diseases of the peripheral or central nervous system, in particular Parkinson's disease, multiple sclerosis, Alzheimer's disease, stroke, ALS (amyotrophic lateral sclerosis).

In a preferred embodiment of the fourth aspect of the invention, the invention therefore provides a compound according to the first aspect of the invention, in particular of formulae (I), (I-A-1), (I-A-2), (I-B), (I-B-1), (I-B-2), (I-C), (I-C-1), (I-C-2), (I-D), (I-D-1), (I-D-2), (I-E), (I-E-1) and (I-E-2) in the presented form or in the form of its acids or bases or in the form of the pharmaceutically safe, in particular physiologically acceptable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio for the treatment of inflammatory diseases of the joints (in particular rheumatoid arthritis, psoriatic arthritis, ankylosing spondylitis (Bechterew's disease), gout, osteoarthritis), the skin (in particular psoriasis, atopic dermatitis, lichen planus) or the eyes (in particular uveitis), of respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; of metabolic diseases, in particular type 2 diabetes, metabolic syndrome, obesity/adiposity, fatty liver disease (not alcohol-induced), and/or cardiovascular diseases, in particular arteriosclerosis, PAH (pulmonary arterial hypertension).

In another aspect of the invention, the invention also provides the use of a compound according to the first aspect of the invention, in particular according to the general structure of formulae (I), (I-A-1), (I-A-2), (I-B), (I-B-1), (I-B-2), (I-C), (I-C-1), (I-C-2), (I-D), (I-D-1), (I-D-2), (I-E), (I-E-1) and (I-E-2) in the presented form or in the form of its acids or bases or in the form of the pharmaceutically safe, in particular physiologically acceptable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of diseases and conditions according to the fourth aspect of the invention.

In yet another aspect of the invention, the invention also provides a method for the treatment of the diseases and conditions according to the fourth aspect of the invention in a human, which is characterised in that a therapeutically effective amount of at least one compound according to the first aspect of the invention, in particular according to the general structure of formulae (I), (I-A-1), (I-A-2), (I-B), (I-B-1), (I-B-2), (I-C), (I-C-1), (I-C-2), (I-D), (I-D-1), (I-D-2), (I-E), (I-E-1) and (I-E-2) in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio, is administered.

The amount of active ingredient to be administered to the person or patient varies and is dependent on the patient's weight, age and medical history and on the type of administration, the indication and the severity of the illness. Generally 0.01 to 500 mg/kg, in particular 0.05 to 50 mg/kg, preferably 0.1 to 25 mg/kg of body weight of at least one compound according to the first aspect of the invention, in particular according to the general structure of formula (I), (I-A-1), (I-A-2), (I-B), (I-B-1), (I-B-2), (I-C), (I-C-1), (I-C-2), (I-D), (I-D-1), (I-D-2), (I-E), (I-E-1) and (I-E-2) in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio, are administered.

All embodiments, in particular the preferred embodiments, of the first aspect of the invention apply mutatis mutandis to all other aspects of the invention.

The medicaments, drugs and pharmaceutical compositions according to the invention can take the form of and be administered as liquid, semi-solid or solid dosage forms and as for example injection solutions, drops, juices, syrups, sprays, suspensions, granules, tablets, pellets, transdermal therapeutic systems, capsules, plasters, suppositories, ointments, creams, lotions, gels, emulsions or aerosols and contain, in addition to at least one compound according to the first aspect of the invention, in particular according to the general structure of formula (I), (I-A-1), (I-A-2), (I-B), (I-B-1), (I-B-2), (I-C), (I-C-1), (I-C-2), (I-D), (I-D-1), (I-D-2), (I-E), (I-E-1) and (I-E-2) in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio, according to the pharmaceutical form and depending on the administration route, pharmaceutical auxiliary substances such as for example carrier materials, fillers, solvents, diluting agents, surface-active substances, dyes, preservatives, disintegrants, slip additives, lubricants, flavourings and/or binders.

The choice of auxiliary substances and the amounts thereof to use depends on whether the medicament/drug is to be administered by oral, subcutaneous, parenteral, intravenous, vaginal, pulmonary, intraperitoneal, transdermal, intramuscular, nasal, buccal or rectal means or locally, for example for infections of the skin, mucous membranes and eyes. Preparations in the form of inter alia tablets, pastilles, capsules, granules, drops, juices and syrups are suitable for oral administration; solutions, suspensions, easily reconstitutable powders for inhalation and sprays are suitable for parenteral, topical and inhalative administration. Compounds according to the first aspect of the invention in a depot formulation, in dissolved form or in a plaster, optionally with addition of agents promoting skin penetration, are suitable preparations for percutaneous administration. Preparation forms that are suitable for rectal, transmucosal, parenteral, oral or percutaneous administration can deliver the compounds according to the first aspect of the invention, on a delayed release basis.

Preparation of the medicaments and pharmaceutical compositions according to the invention takes place using agents, equipment, methods and procedures that are well-known from the prior art of pharmaceutical formulation, such as are described for example in "Remington's Pharmaceutical Sciences", Ed. A. R. Gennaro, 17th edition, Mack Publishing Company, Easton PD (1985), in particular in part 8, chapters 76 to 93. The compounds according to the invention can be produced in the manner described here or in an analogous manner.

Unless indicated otherwise, the compounds according to the first aspect of invention can be synthesized according to general knowledge in the field of organic chemistry or in a manner as described here (cf. reaction schemes below) or analogously. The reaction conditions in the synthesis routes described herein are known to the skilled person and are for some cases exemplified in the synthesis examples herein.

If not stated otherwise, in below reaction scheme all substituents, chemical moieties, variables and indices in the compounds shown in the following reaction schemes are defined herein the context of the first aspect of the invention, and $R^x$ is $(C_1-C_6)$ alkyl, preferably methyl and butyl.

Synthesis Method (01) for the Preparation of a Compound of Formula (I-A):

Reaction scheme 01:

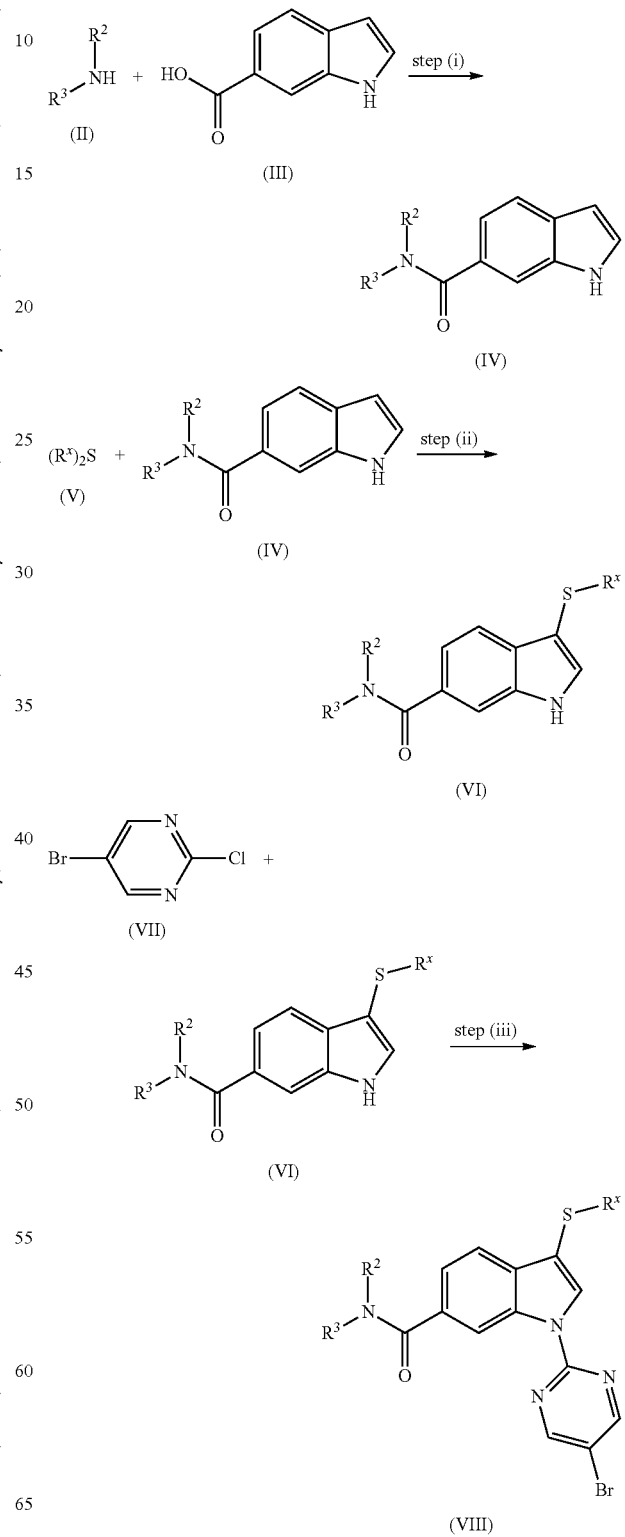

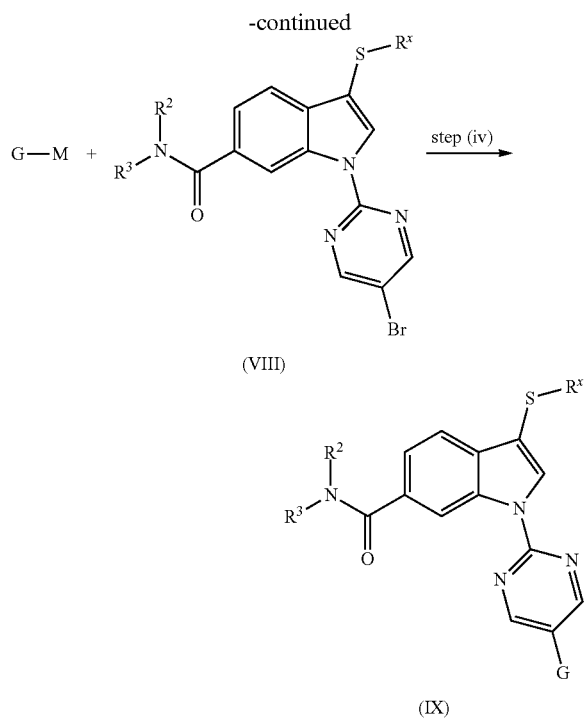

(VIII)

(IX)

Step (i): Reacting the Amine of General Formula (II) with 1H-Indole-6-Carboxylic Acid (III) to Form the Corresponding 1H-Indole-6-Carboxamide Having the General Formula (IV).

In the step (i), the coupling of the amine of general formula (II) and the compound of general formula (III) is performed by known methods from peptide chemistry (e.g. Tetrahedron 2004, 60, 2447-2467). Suitable coupling reagents are known to a person skilled in the art and include e.g. carbodiimides (such as 1-[3-(dimethylamino)propyl]-3-ethylcarbodiimide hydrochloride (EDC)) and are used in a suitable solvent (e.g. N,N-dimethylformamide).

Step (ii): Reaction of a Dialkylthioether of General Formula (V) with the 1H-Indole-6-Carboxamide of General Formula (IV) to Form 3-(Alkylthio)-1H-Indole of General Formula (VI).

In the step (ii), the 1H-indole-6-carboxamide of formula (IV) is converted into the corresponding 3-(alkylthio)-1H-indole of formula (VI) by methods known in the art (e.g. Heterocycles 1976, 4 (4), 729). For example, by treatment of a dialkylthioether of general formula (V) with N-chlorosuccinimide in a solvent like dichloromethane or chloroform leading to a succinimido-sulfonium salt which then reacts with the carboxamide of general formula (IV) at elevated temperatures to the compounds of general formula (VI). The 3-(alkylthio)-1H-indole of formula (VI) can also be obtained via alternative methods, for example, through halogenation at position three of the indol ring of the compounds (VI) followed by a nucleophilic substitution with nucleophiles like NaSMe (cf. Journal of Heterocyclic Chemistry 2007, 44, 967).

Step (iii): Reacting 5-Bromo-2-Chloropyrimidine (VII) with an Alkylthio Compound (3-(Alkylthio)-1H-Indole) of General Formula (VI)

Step (iii) of synthesis method (01) is the reaction of 5-bromo-2-chloropyrimidine (VII) with the alkylthio compound 3-(alkylthio)-1H-indole having general formula (VI) to form compounds of general formula (VIII). This reaction is performed with known methods for nucleophilic aromatic substitution in a solvent and in the presence of a base. Examples of suitable solvents are dioxane, N,N-dimethylformamide, N-methyl-2-pyrrolidone or dimethylsulfoxide. Examples of suitable bases are potassium tert-butylate, 1,8-diazabicyclo[5.4.0]undec-7-ene (DBU), aqueous sodium hydroxide and potassium carbonate. This reaction can take place at a temperature ranging from approximately 50° C. to approximately 200° C. The reaction preferably takes place at a temperature in the range from 100° C. to 150° C. Instead of 5-bromo-2-chloropyrimidine, alternative 2,5-di-substituted pyrimidines could be used wherein the two halogens are replaced by other suitable leaving groups. Alternatively, the compounds of general formula (VIII) can be obtained by reacting compounds of general formula (VI) in the presence of an acid, such as for example hydrochloric acid, in a solvent like N,N-dimethylformamide or under the conditions for palladium-catalyzed cross-coupling reactions, as described in step (i) of synthesis method (02).

Step (iv): Reacting a Compound of Formula (VIII) with a Compound "G-M" to Form a Compound of Formula (IX) Under the Conditions of a Palladium-Catalysed Cross-Coupling Reaction.

G in the compound "G-M" has the meaning described in connection with the compounds according to the invention and M is as defined as follows:

If a Suzuki coupling is performed, then M denotes $B(OH)_2$ (boronic acid), $B(OR^a)_2$ (boronic acid ester) ($R^a$ stands for $(C_1-C_6)$-alkyl, preferably methyl) or an optionally $(C_1-C_6)$ alkyl-substituted 1,3,2-dioxaborolane (e.g. 4,4,5,5-tetramethyl-1,3,2-dioxaborolane; pinacol boronic acid ester) and if a Stille coupling is performed, then M denotes $SnR^b_3$ ($R^b$ stands for $(C_1-C_6)$-alkyl, preferably methyl and butyl; e.g. $M=Sn(CH_3)_3$ (=trimethylstannyl) or $SnBn_3$ (=tributylstannyl)).

This step (iv) of synthesis method (01), namely the reaction under Stille or Suzuki coupling reaction conditions is performed according to methods well known in the art (cf. Tetrahedron 2005, 61, 2245-67). The Suzuki coupling can be performed for example in the presence of a catalyst such as tris(dibenzylideneacetone)dipalladium/tri-tert-butylphosphonium tetrafluoroborate, tetrakis(tri-phenylphosphine)palladium(0) or [1,1'-bis(diphenylphosphino)ferrocene]dichloropalladium(II) complex and a base (e.g. caesium or potassium carbonate) in a solvent or a mixture of solvents (solvent blend) (e.g. THF, dioxane or acetonitrile with or without water).

Optionally, synthesis method (01) further comprises a step (v):

Step (v): Oxidation of an Alkylthio Compound (3-(Alkylthio)-1-(Pyrimidin-2-Yl)-1H-Indole) of General Formula (IX) Towards the Corresponding Sulfoxide or Sulfone of General Formula (X) and (XI), respectively

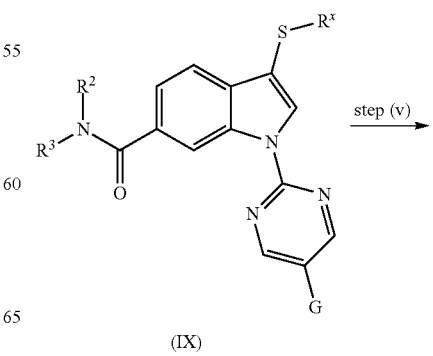

(IX)

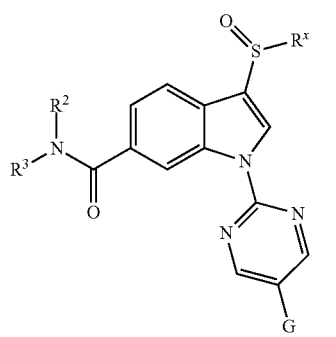

(X) or

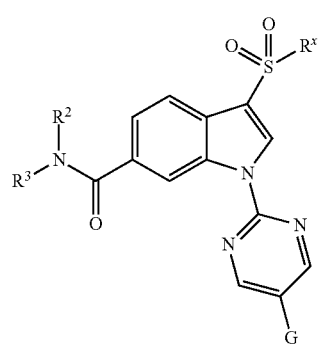

(XI)

This step (v) of synthesis method (01), comprises reacting a compound of formula (IX) with an oxidizing agent under appropriate reaction conditions. A suitable oxidizing agent is for example m-chloroperoxybenzoic acid in a solvent like dichloromethane under cooling or at room temperature for a certain time period. By choosing the appropriate amount or equivalents of the oxidizing agent based on the amount of starting material of formula (IX), the oxidation reaction can be controlled so that either the sulfoxides of formula (X) or the sulfones of formula (XI) are obtained.

Synthesis Method (02) for the Preparation of a Compound of Formula (I-A):

Reaction scheme 02:

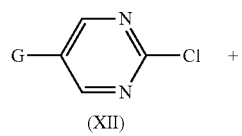

(XII)

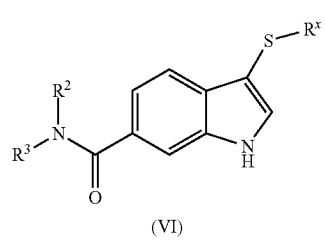

(VI)

step (i)

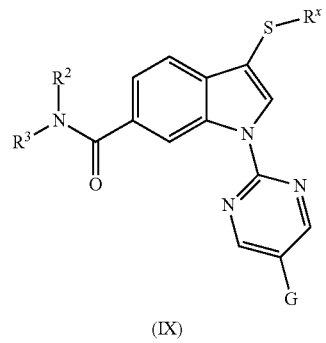

(IX)

Step (i): Reacting 2-Chloropyrimidine Compound of General Formula (XII) with an Alkylthio Compound (3-(Alkylthio)-1H-Indole) of General Formula (VII)

This step (i) of synthesis method (02), namely the reaction of a 2-chloropyrimidine of general formula (XII) with an alkylthio compound (3-(alkylthio)-1H-indole) of general formula (VI) can be performed under the conditions for a nucleophilic aromatic substitution as described in step (iii) of synthesis method (01). Alternatively, the reaction can be performed under the conditions for a palladium-catalyzed cross-coupling reaction also known as Buchwald-Hartwig reaction (cf. Angewandte Chemie, International Edition 2008, 47(34), 6338-6361). A suitable catalyst for this reaction is for example palladium(II) acetate/4,5-bis(diphenylphosphino)-9,9-dimethylxanthene (Xanphos) in a solvent like 1,4-dioxane preferably at temperatures between 50 and 150° C.

Synthesis Method (03) for the Preparation of a Compound of Formula (I-A):

Reaction scheme 03:

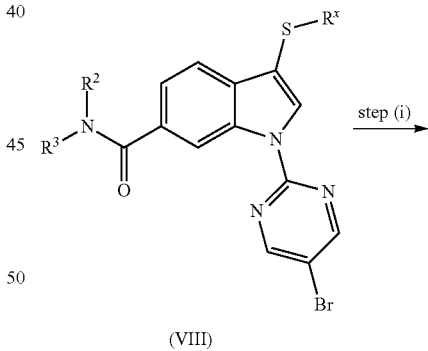

(VIII)

step (i)

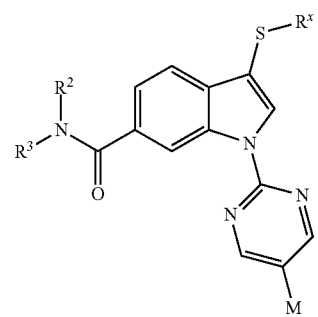

(XIII)

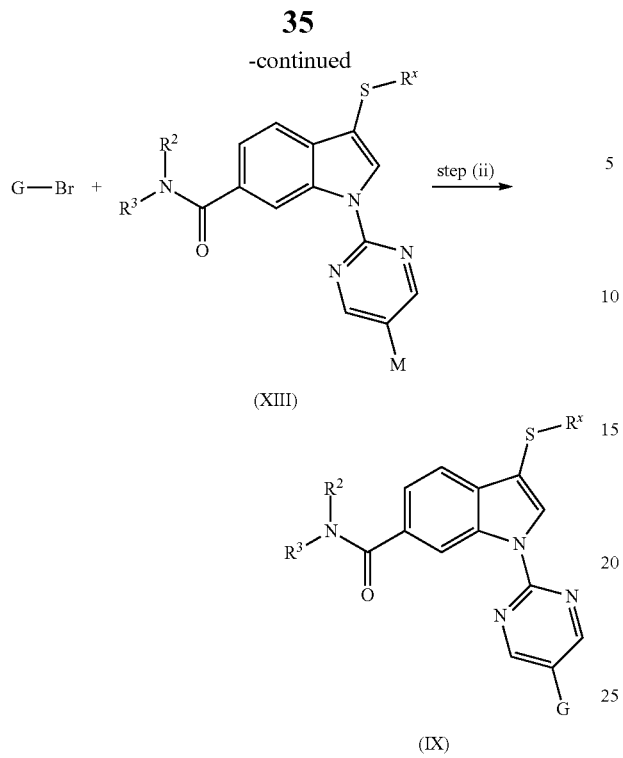

wherein in above reaction scheme 03 M has the meaning described in connection with the compounds "G-M" in synthesis method (01) or wherein M denotes B(OH)$_2$ (boronic acid), B(OR$^a$)$_2$ (boronic acid ester) (R$^a$ stands for (C$_1$-C$_6$)-alkyl, preferably methyl) or an optionally (C$_1$-C$_6$) alkyl-substituted 1,3,2-dioxaborolane such as 4,4,5,5-tetramethyl-1,3,2-dioxaborolane or pinacol boronic acid ester, SnR$^b_3$ with R$^b$ is (C$_1$-C$_6$) alkyl, preferably methyl and butyl such as Sn(CH$_3$)$_3$, SnBn$_3$, trimethylstannyl or tributylstannyl.

Step (i): Transforming a Compound of Formula (VIII) into a Compound of Formula (XIII) Under the Conditions of a Palladium-Catalysed Cross-Coupling Reaction This step (i) of synthesis method (03), namely the transformation of a compound of formula (VIII) to a compound of formula (XIII) wherein) can be performed under the conditions of a palladium-catalysed reaction that are known from the literature (cf. Journal of Organic Chemistry 1995, 60, 7508-7510; Journal of Organic Chemistry 2000, 65, 164-168).

Suitable reaction conditions comprise for example the use of a catalyst like [1,1'-bis(diphenylphosphino)ferrocene] dichloropalladium(II) complex and potassium acetate in a solvent like dioxane or DMSO. Compounds of formula (VIII) wherein the bromo substituent is replaced by a triflate, sulfonate or another halide like iodide could be also used as suitable substrates in this reaction.

Alternatively, the compounds of formula (VIII) can be transformed into compounds of formula (XIII) wherein M denotes SnR$^y_3$ with R$^y$ is (C$_1$-C$_6$) alkyl, preferably methyl and butyl. (e.g. M=Sn(CH$_3$)$_3$, SnBn$_3$, trimethylstannyl or tributylstannyl compounds).

Step (ii): Reacting a Compound of Formula (XIII) with a Compound G-Br Under the Conditions of a Suzuki or Stille Reaction This step (ii) of synthesis method (03), namely the reaction of a compound of formula (XIII) with a compound G-Br are performed under the conditions for a Stille or Suzuki coupling reaction as described in step (iv) of synthesis method (01), The reaction can be also performed with compounds G-Br wherein the bromo substituent "—Br" is replaced by a triflate, sulfonate or another halide like iodide or chloride.

Synthesis Method (04) for the Preparation of a Compound of Formula (I-A):

Reaction scheme 04:

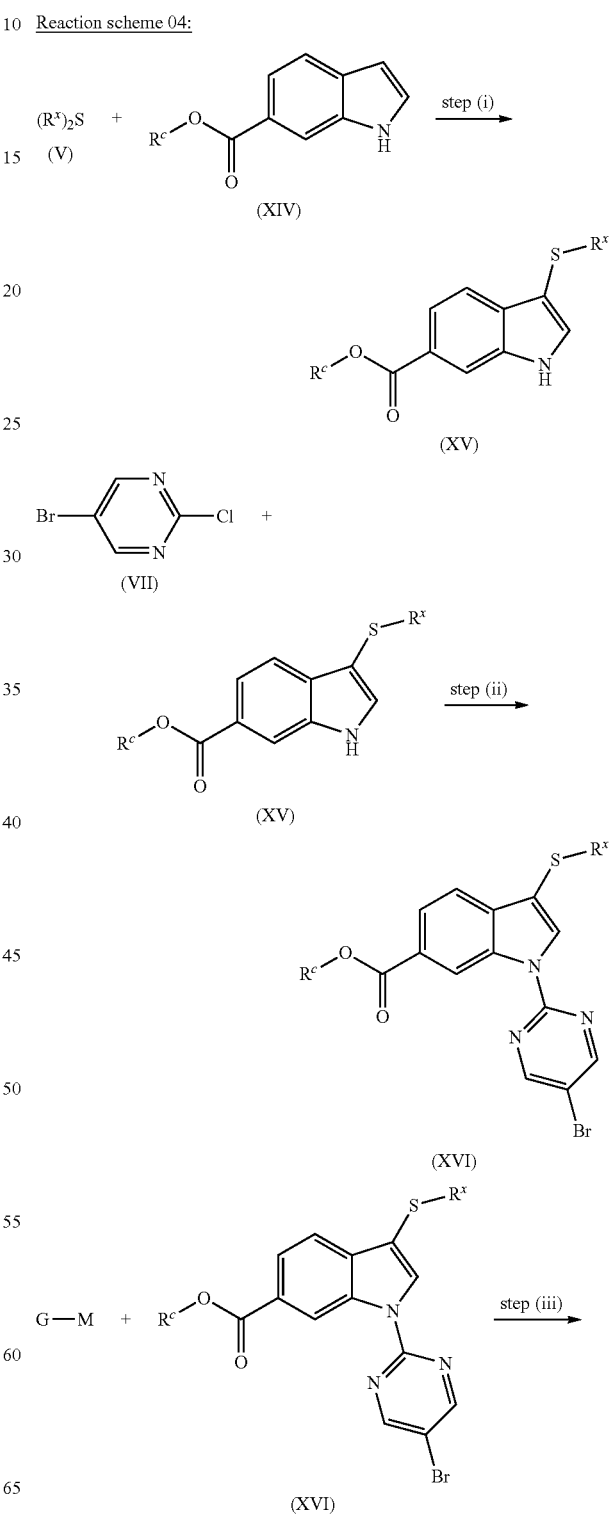

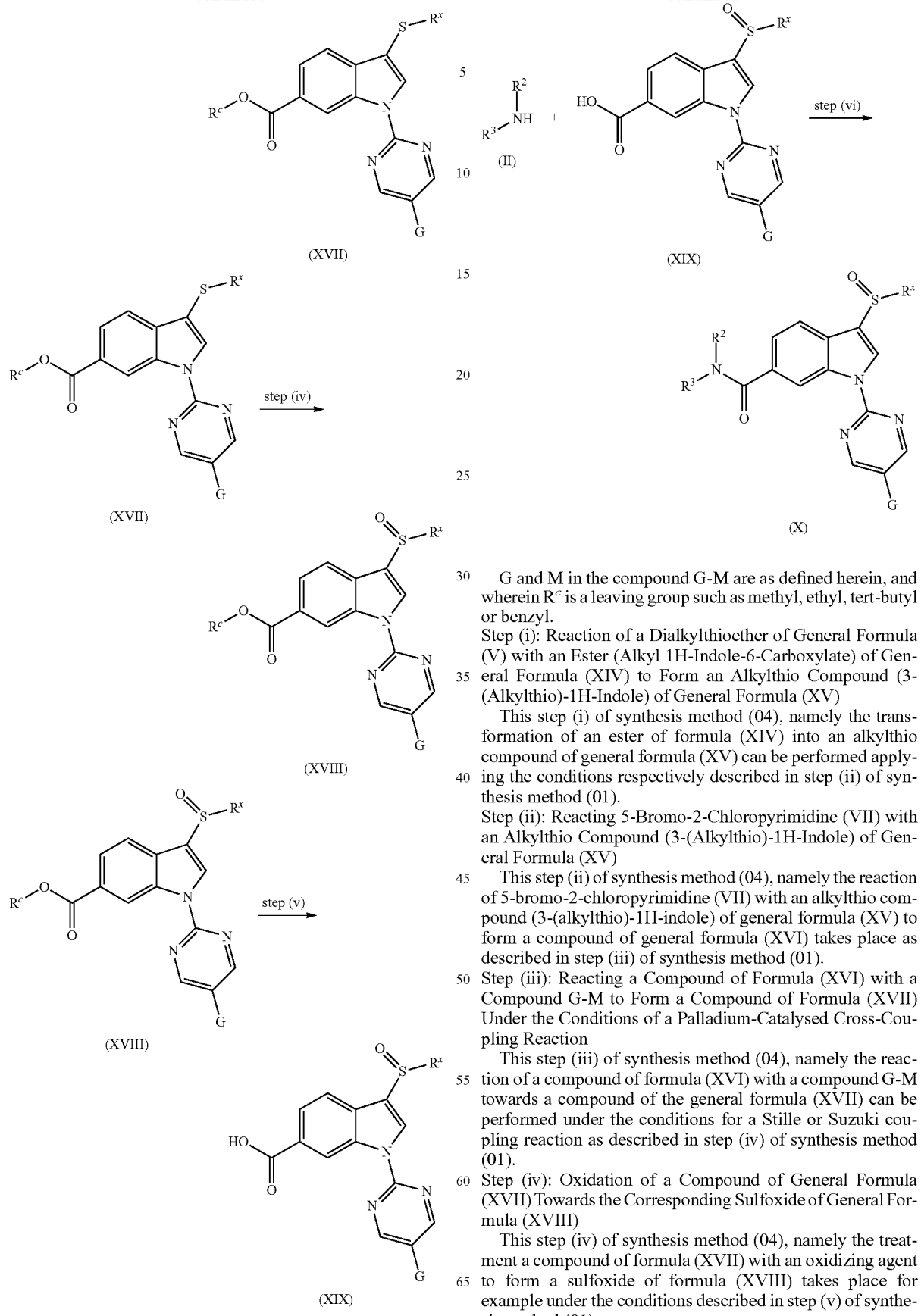

G and M in the compound G-M are as defined herein, and wherein $R^c$ is a leaving group such as methyl, ethyl, tert-butyl or benzyl.

Step (i): Reaction of a Dialkylthioether of General Formula (V) with an Ester (Alkyl 1H-Indole-6-Carboxylate) of General Formula (XIV) to Form an Alkylthio Compound (3-(Alkylthio)-1H-Indole) of General Formula (XV)

This step (i) of synthesis method (04), namely the transformation of an ester of formula (XIV) into an alkylthio compound of general formula (XV) can be performed applying the conditions respectively described in step (ii) of synthesis method (01).

Step (ii): Reacting 5-Bromo-2-Chloropyrimidine (VII) with an Alkylthio Compound (3-(Alkylthio)-1H-Indole) of General Formula (XV)

This step (ii) of synthesis method (04), namely the reaction of 5-bromo-2-chloropyrimidine (VII) with an alkylthio compound (3-(alkylthio)-1H-indole) of general formula (XV) to form a compound of general formula (XVI) takes place as described in step (iii) of synthesis method (01).

Step (iii): Reacting a Compound of Formula (XVI) with a Compound G-M to Form a Compound of Formula (XVII) Under the Conditions of a Palladium-Catalysed Cross-Coupling Reaction This step (iii) of synthesis method (04), namely the reaction of a compound of formula (XVI) with a compound G-M towards a compound of the general formula (XVII) can be performed under the conditions for a Stille or Suzuki coupling reaction as described in step (iv) of synthesis method (01).

Step (iv): Oxidation of a Compound of General Formula (XVII) Towards the Corresponding Sulfoxide of General Formula (XVIII)

This step (iv) of synthesis method (04), namely the treatment a compound of formula (XVII) with an oxidizing agent to form a sulfoxide of formula (XVIII) takes place for example under the conditions described in step (v) of synthesis method (01).

Step (v): Conversion of the Ester of Formula (XVIII) into a Carboxylic Acid of Formula (XIX)

This step (v) of synthesis method (04), namely the ester cleavage (ester hydrolysis) of a compound of formula (XVIII) to form a compound of general formula (XIX) takes place by known methods. Ester cleavages are described for example by P. G. M. Wuts, T. W. Greene in Greene's Protective Groups in Organic Synthesis, 4th Edition, 2007, pages 533-646, Wiley-Interscience. They can be performed hydrolytically, for example, in the presence of acids or bases (e.g. alkali hydroxides such as for example lithium or sodium hydroxide) in an organic solvent to which varying proportions of water can be added. Other frequently used methods of ester cleavage involve the acid-catalyzed cleavage of a tert-butyl ester ($R^c$=tert-butyl) by generally known methods, for example using trifluoroacetic acid in dichloromethane, or the hydrogenolysis of benzyl esters (if $R^c$=benzyl).

Step (vi): Reacting an Amine of Formula (II) with a Carboxylic Acid of Formula (XIX) Towards a Carboxamide (1H-Indole-6-Carboxamide) of General Formula (X)

Step (vi) of synthesis method (04), namely the coupling of an amine of general formula (II) with a carboxylic acid of general formula (XIX) takes place under known conditions as described for example in step (i) of synthesis method (01).

Synthesis Method (05) for the Preparation of a Compound of Formula (I-A):

Reaction scheme 05:

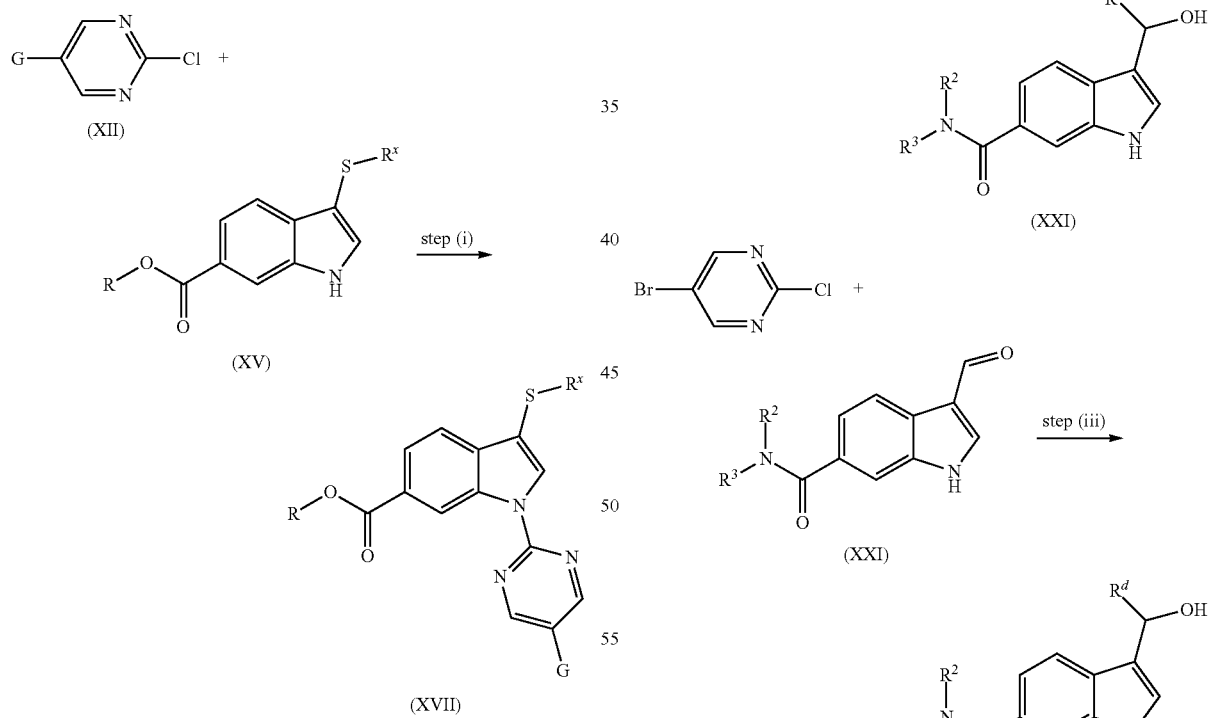

Step (i): Reacting 2-Chloropyrimidine Compound of General Formula (XII) with an Alkylthio Compound (3-(Alkylthio)-1H-Indole) of General Formula (XV)

This step (i) of synthesis method (05), namely the reaction of a 2-chloropyrimidine of general formula (XII) with an alkylthio compound (3-(alkylthio)-1H-indole) of general formula (XV) can be carried out using the methods described in step (i) of synthesis method (02).

Synthesis Method (06) for the Preparation of a Compound of Formula (I-A):

Reaction scheme 06:

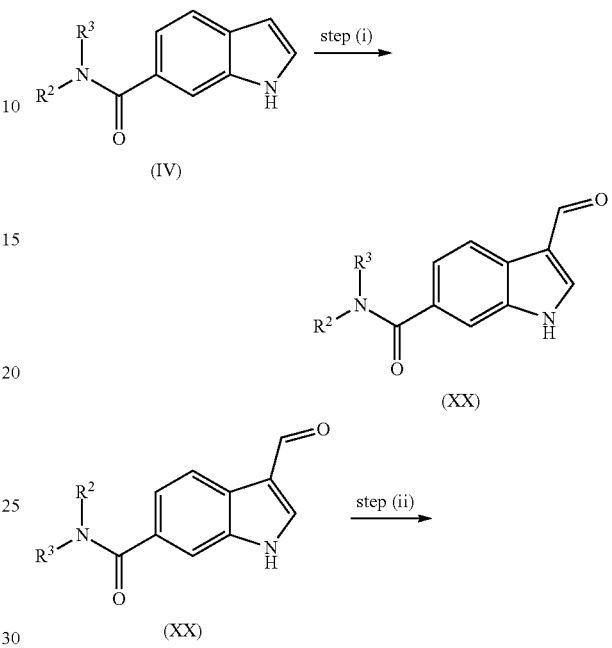

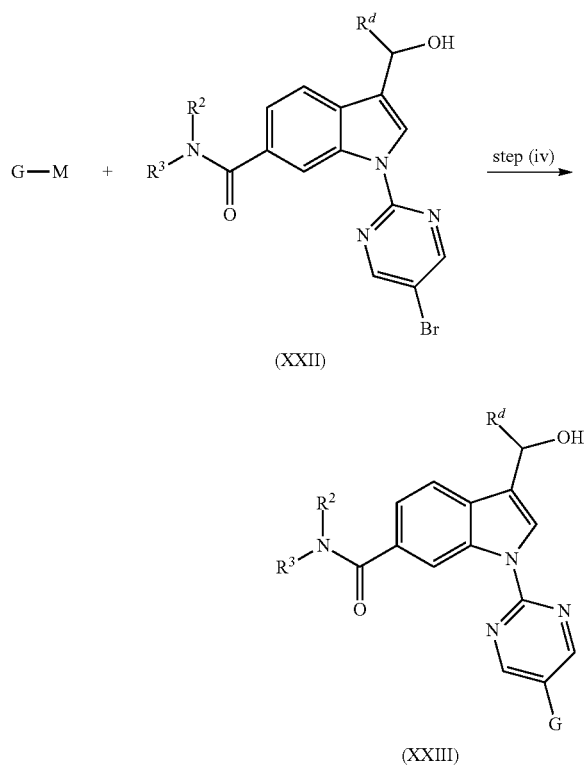

In this reaction scheme 06, $R^d$ stands for hydrogen and $(C_1-C_6)$-alkyl, and G and M in the compound G-M have the aforementioned meaning.

Step (i): Transforming a Compound of Formula (IV) into a Compound of Formula (XX) Under the Conditions of a Vilsmeier-Haack Reaction This step (i) of synthesis method (06), namely the transformation of a compound of (IV) into a compound of general formula (XX) takes place under the conditions of a Vilsmeier-Haack reaction (Synlett 2003, 1, 138-139). Therefore, reaction of N,N-dimethylformamide with phosphorus oxychloride leads to the formation of a chloroiminium salt that reacts with a compound of the general formula (IV) at temperatures between 0° C. and 100° C., preferable at temperatures between 0° C. and 30° C., under formation of a compound of formula (XX).

Step (ii): Transforming a Compound of Formula (XX) into a Compound of General Formula (XXI)

This step (ii) of synthesis method (06), namely the transformation of a compound of formula (XX) into a compound of general formula (XXI) wherein $R^d$ is hydrogen takes place under standard conditions for the reduction of aldehydes towards primary alcohols. Suitable reducing reagents are alkyl borohydrides as for example sodium borohydride or lithium borohydride in a solvent like methanol at temperatures in the range between 0° C. and 30° C. Compounds of the general formula (XXI) wherein $R^d$ is $(C_1-C_6)$-alkyl are obtained from the reaction of compounds of the general formula (XX) with alkyl magnesium halides under the conditions of a Grignard reaction. The reactions are typically performed in solvents like diethyl ether or THF at temperatures preferably in the range from −70° C. to 0° C.

Step (iii): Reacting 5-Bromo-2-Chloropyrimidine (VII) with a Compound of Formula (XXI)

This step (iii) of synthesis method (06), namely the reaction of 5-bromo-2-chloropyrimidine (VII) with a compound of general formula (XXI) to form the compounds of general formula (XXII) takes place respectively by the methods described in step (iii) of synthesis method (01).

Step (iv): Reacting a Compound of Formula (XXII) with a Compound G-M to Form a Compound of Formula (XXIII) Under the Conditions of a Palladium-Catalysed Cross-Coupling Reaction Step (iv) of synthesis method (06), namely the reaction of a compound G-M with a compound of general formula (XXII) takes place under the conditions for a Stille or a Suzuki coupling reaction as described in step (iv) of synthesis method (01).

The compounds according to the first aspect of the invention are specified in the table 1 below, without limiting the invention thereto.

TABLE 1

| Cmpd-No. | Structure | Name |
|---|---|---|
| 1 | 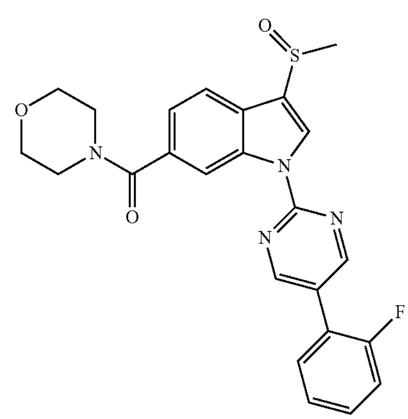 [SMILES: CS(=O)c1cn(-c2ncc(-c3ccccc3F)cn2)c2cc(C(=O)N3CCOCC3)ccc12] | (1-(5-(2-Fluorophenyl)pyrimidin-2-yl)-3-(methylsulfinyl)-1H-indol-6yl)(morpholino)-methanone |

| Cmpd-No. | Structure | Name |
| --- | --- | --- |
| 2 | 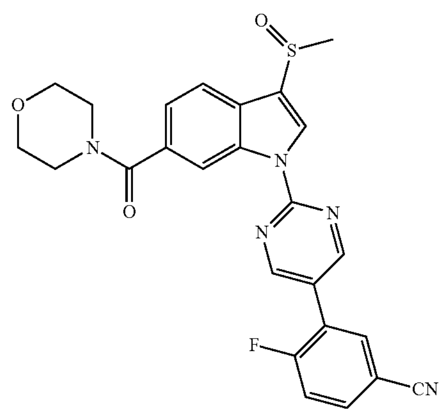 [SMILES: CS(=O)c1cn(-c2ncc(-c3cc(C#N)ccc3F)cn2)c2cc(C(=O)N3CCOCC3)ccc12] | 4-Fluoro-3-(2-(3-(methylsulfinyl)-6-(morpholine-4-carbonyl)-1H-indol-1yl)pyrimidin-5-yl)benzonitrile |
| 3 | 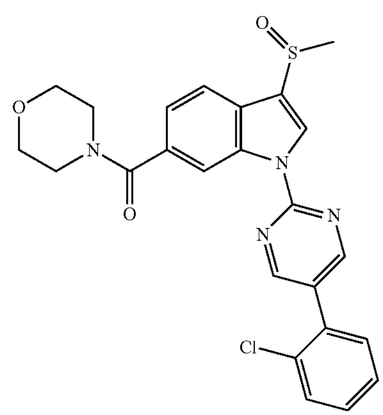 [SMILES: CS(=O)c1cn(-c2ncc(-c3ccccc3Cl)cn2)c2cc(C(=O)N3CCOCC3)ccc12] | (1-(5-(2-Chlorophenyl)pyrimidin-2-yl)-3-(methylsulfinyl)-1H-indol-6-yl)(morpholino)methanone |
| 4 | 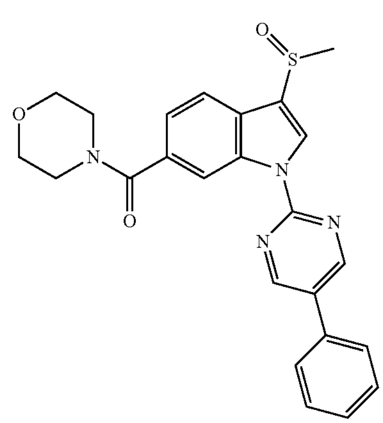 [SMILES: CS(=O)c1cn(-c2ncc(-c3ccccc3)cn2)c2cc(C(=O)N3CCOCC3)ccc12] | (3-(Methylsulfinyl)-1-(5-phenylpyrimidin-2-yl)-1H-indol-6-yl)(morpholino)methanone |

TABLE 1-continued

| Cmpd-No. | Structure | Name |
| --- | --- | --- |
| 5 | 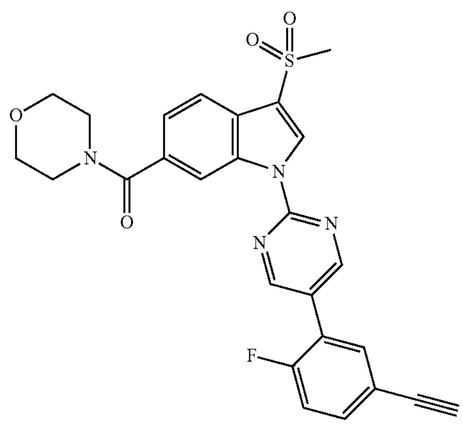 [SMILES: C#Cc1ccc(F)c(-c2cnc(-n3cc(S(C)(=O)=O)c4ccc(C(=O)N5CCOCC5)cc43)nc2)c1] | 4-Fluoro-3-(2-(3-(methylsulfonyl)-6-(morpholine-4-carbonyl)-1H-indol-1-yl) pyrimidin-5-yl)benzonitrile |
| 6 | 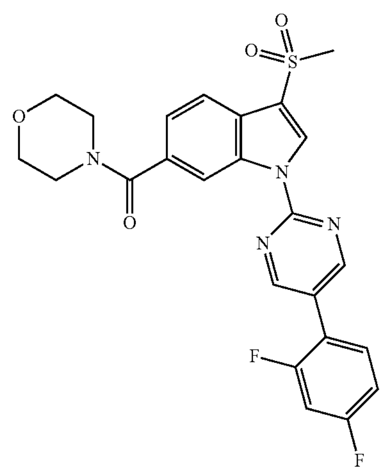 [SMILES: CS(=O)(=O)c1cn(-c2ncc(-c3ccc(F)cc3F)cn2)c2cc(C(=O)N3CCOCC3)ccc12] | (1-(5-(2,4-Difluorophenyl)pyrimidin-2-yl)-3-(methylsulfonyl)-1H-indol-6-yl)(morpholino)methanone |
| 7 | 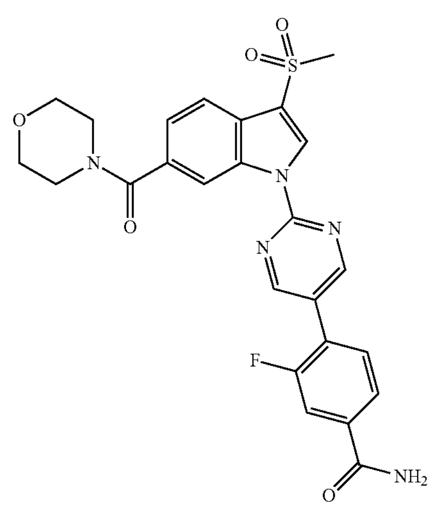 [SMILES: CS(=O)(=O)c1cn(-c2ncc(-c3ccc(C(N)=O)cc3F)cn2)c2cc(C(=O)N3CCOCC3)ccc12] | 3-Fluoro-4-(2-(3-(methylsulfonyl)-6-(morpholine-4-carbonyl)-1H-indol-1-yl)pyrimidin-5-yl)benzamide |

TABLE 1-continued

| Cmpd-No. | Structure | Name |
|---|---|---|
| 8 | 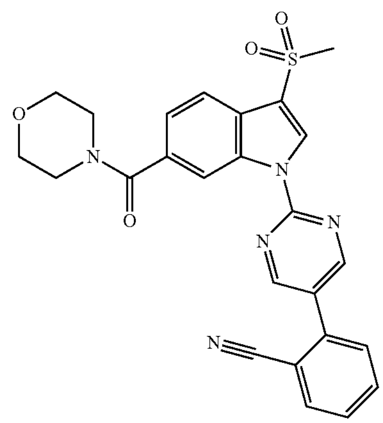 [SMILES: CS(=O)(=O)c1cn(-c2ncc(-c3ccccc3C#N)cn2)c2cc(C(=O)N3CCOCC3)ccc12] | 2-(2-(3-(Methylsulfonyl)-6-(morpholine-4-carbonyl)-1H-indol-1-yl)pyrimidin-5-yl)benzonitrile |
| 9 | 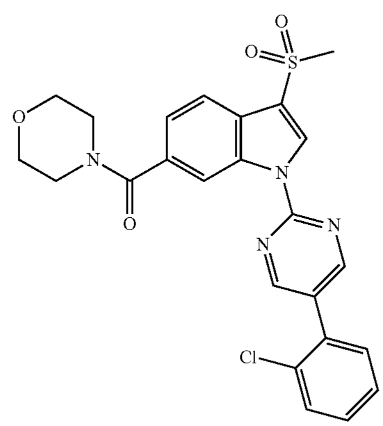 [SMILES: CS(=O)(=O)c1cn(-c2ncc(-c3ccccc3Cl)cn2)c2cc(C(=O)N3CCOCC3)ccc12] | (1-(5-(2-Chlorophenyl)pyrimidin-2-yl)-3-(methylsulfonyl)-1H-indol-6-yl)(morpholino)methanone |
| 10 | 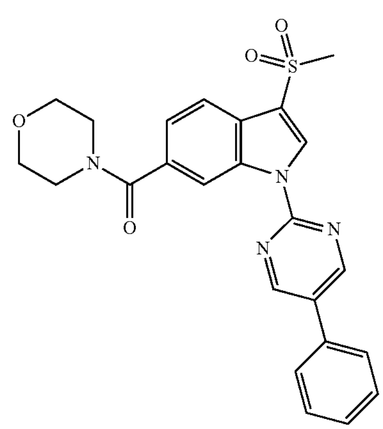 [SMILES: CS(=O)(=O)c1cn(-c2ncc(-c3ccccc3)cn2)c2cc(C(=O)N3CCOCC3)ccc12] | (3-(Methylsulfonyl)-1-(5-phenylpyrimidin-2-yl)-1H-indol-6-yl)(morpholino)methanone |

TABLE 1-continued

| Cmpd-No. | Structure | Name |
|---|---|---|
| 11 | 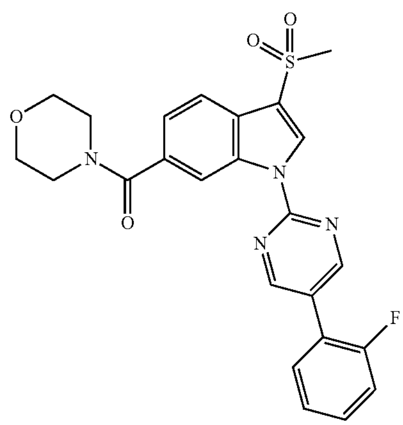 [SMILES: CS(=O)(=O)c1cn(-c2ncc(-c3ccccc3F)cn2)c2cc(C(=O)N3CCOCC3)ccc12] | (1-(5-(2-fluorophenyl)pyrimidin-2-yl)-3-(methylsulfonyl)-1H-indol-6-yl)(morpholino)methanone |
| 12 | 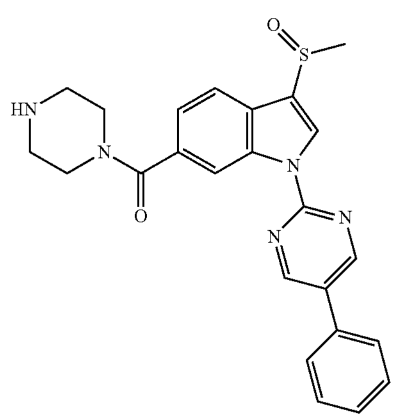 [SMILES: CS(=O)c1cn(-c2ncc(-c3ccccc3)cn2)c2cc(C(=O)N3CCNCC3)ccc12] | (3-(Methylsulfinyl)-1-(5-phenylpyrimidin-2-yl)-1H-indol-6-yl)(piperazin-1-yl)methanone |
| 13 | 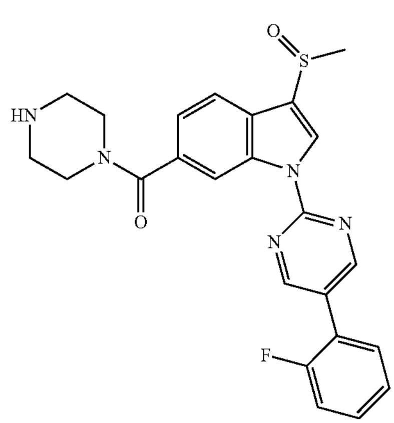 | (1-(5-(2-fluorophenyl)pyrimidin-2-yl)-3-(methylsulfinyl)-1H-indol-6-yl)(piperazin-1-yl)methanone |

TABLE 1-continued

| Cmpd-No. | Structure | Name |
|---|---|---|
| 14 | 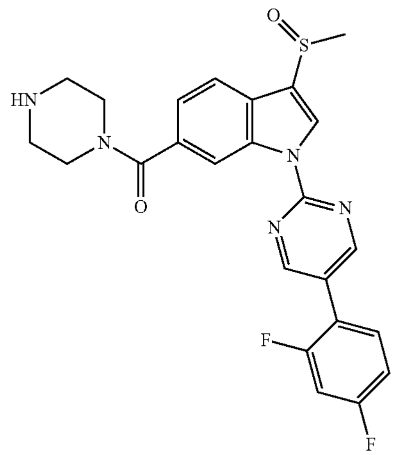 [SMILES: CS(=O)c1cn(-c2ncc(-c3ccc(F)cc3F)cn2)c2cc(C(=O)N3CCNCC3)ccc12] | (1-(5-(2,4-difluorophenyl)pyrimidin-2-yl)-3-(methylsulfinyl)-1H-indol-6-yl)(piperazin-1-yl)methanone |
| 15 | 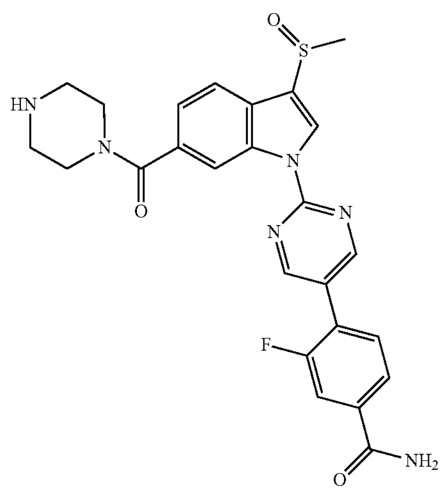 [SMILES: CS(=O)c1cn(-c2ncc(-c3ccc(C(N)=O)cc3F)cn2)c2cc(C(=O)N3CCNCC3)ccc12] | 3-fluoro-4-(2-(3-(methylsulfinyl)-6-(piperazine-1-carbonyl)-1H-indol-1-yl)pyrimidin-5-yl)benzamide |
| 16 | 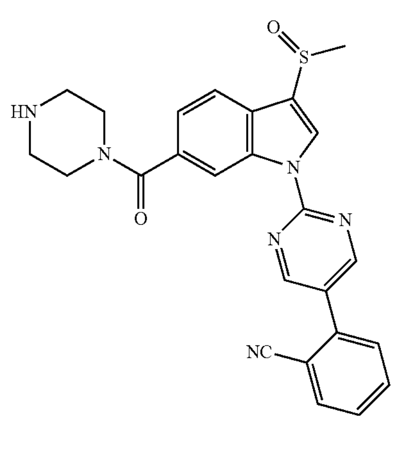 [SMILES: CS(=O)c1cn(-c2ncc(-c3ccccc3C#N)cn2)c2cc(C(=O)N3CCNCC3)ccc12] | 2-(2-(3-(methylsulfinyl)-6-(piperazine-1-carbonyl)-1H-indol-1-yl)pyrimidin-5-yl)benzonitrile |

US 9,315,490 B2
TABLE 1-continued
| Cmpd-No. | Structure | Name |
|---|---|---|
| 17 | 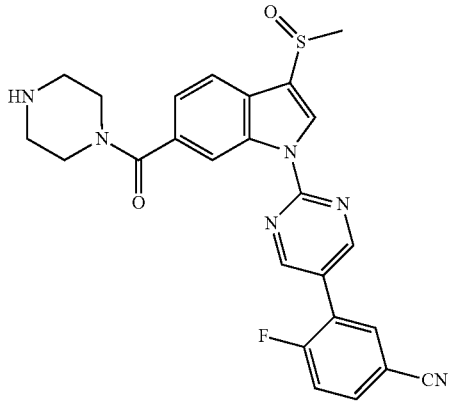 [SMILES: CS(=O)c1cn(-c2ncc(-c3cc(C#N)ccc3F)cn2)c2cc(C(=O)N3CCNCC3)ccc12] | 4-fluoro-3-(2-(3-(methylsulfinyl)-6-(piperazine-1-carbonyl)-1H-indol-1-yl)pyrimidin-5-yl)benzonitrile |
| 18 | 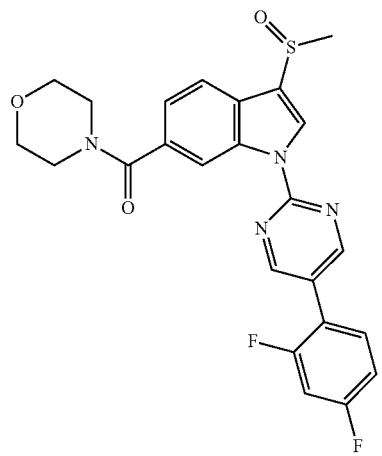 [SMILES: CS(=O)c1cn(-c2ncc(-c3ccc(F)cc3F)cn2)c2cc(C(=O)N3CCOCC3)ccc12] | (1-(5-(2,4-Difluorophenyl)pyrimidin-2-yl)-3-(methylsulfinyl)-1H-indol-6-yl)(morpholino)methanone |
| 19 | 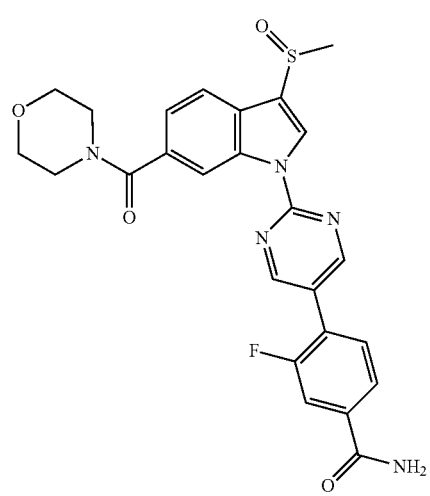 [SMILES: CS(=O)c1cn(-c2ncc(-c3ccc(C(N)=O)cc3F)cn2)c2cc(C(=O)N3CCOCC3)ccc12] | 3-Fluoro-4-(2-(3-(methylsulfinyl)-6-(morpholine-4-carbonyl)-1H-indol-1-yl)pyrimidin-5-yl)benzamide |

TABLE 1-continued

| Cmpd-No. | Structure | Name |
|---|---|---|
| 20 | 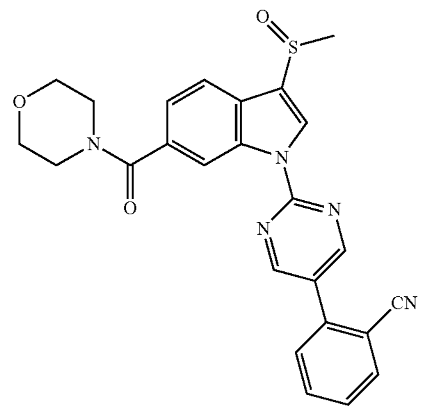 [SMILES: CS(=O)c1cn(-c2ncc(-c3ccccc3C#N)cn2)c2cc(C(=O)N3CCOCC3)ccc12] | 2-(2-(3-(Methylsulfinyl)-6-(morpholine-4-carbonyl)-1H-indol-1-yl)pyrimidin-5-yl)benzonitrile |
| 21 | 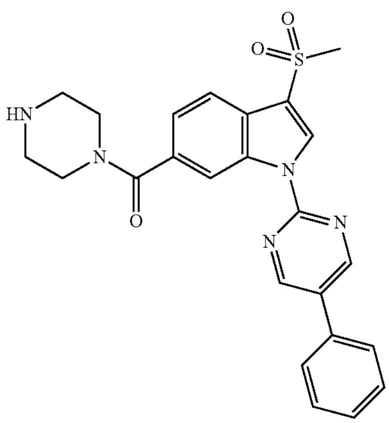 [SMILES: CS(=O)(=O)c1cn(-c2ncc(-c3ccccc3)cn2)c2cc(C(=O)N3CCNCC3)ccc12] | (3-(methylsulfonyl)-1-(5-phenylpyrimidin-2-yl)-1H-indol-6-yl)(piperazin-1-yl)methanone |
| 22 | 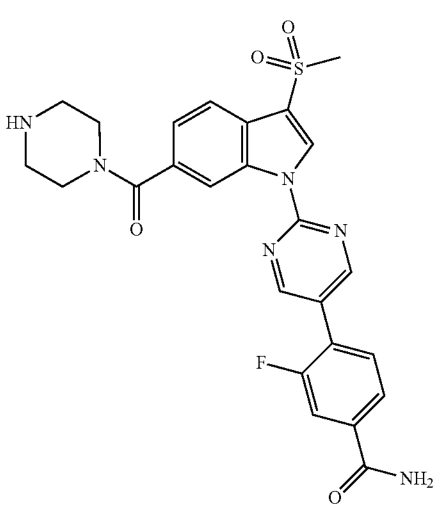 [SMILES: CS(=O)(=O)c1cn(-c2ncc(-c3ccc(C(N)=O)cc3F)cn2)c2cc(C(=O)N3CCNCC3)ccc12] | 3-fluoro-4-(2-(3-(methylsulfonyl)-6-(piperazine-1-carbonyl)-1H-indol-1-yl)pyrimidin-5-yl)benzamide |

| Cmpd-No. | Structure | Name |
|---|---|---|
| 23 | 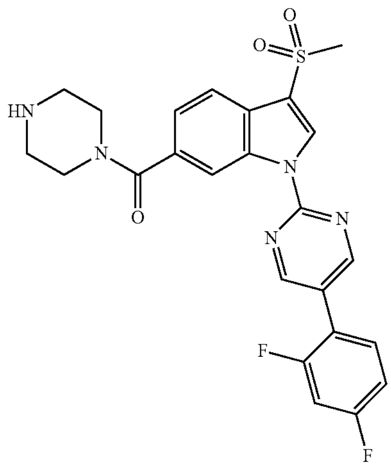 [SMILES: CS(=O)(=O)c1cn(-c2ncc(-c3ccc(F)cc3F)cn2)c2cc(C(=O)N3CCNCC3)ccc12] | (1-(5-(2,4-difluorophenyl)pyrimidin-2-yl)-3-(methylsulfonyl)-1H-indol-6-yl)(piperazin-1-yl)methanone |
| 24 | 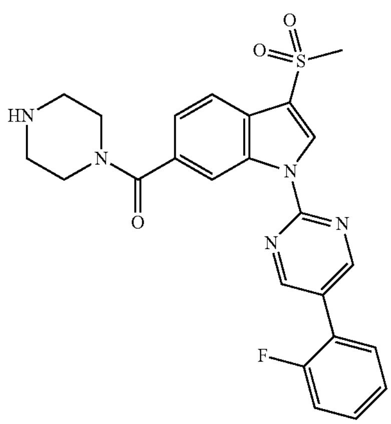 [SMILES: CS(=O)(=O)c1cn(-c2ncc(-c3ccccc3F)cn2)c2cc(C(=O)N3CCNCC3)ccc12] | (1-(5-(2-fluorophenyl)pyrimidin-2-yl)-3-(methylsulfonyl)-1H-indol-6-yl)(piperazin-1-yl)methanone |
| 25 | 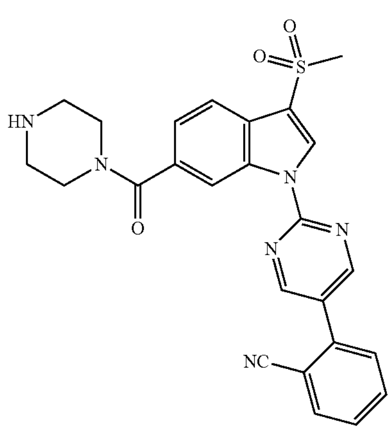 | 2-(2-(3-(methylsulfonyl)-6-(piperazine-1-carbonyl)-1H-indo-1-yl)pyrimidin-5-yl)benzonitrile |

| Cmpd-No. | Structure | Name |
|---|---|---|
| 26 | 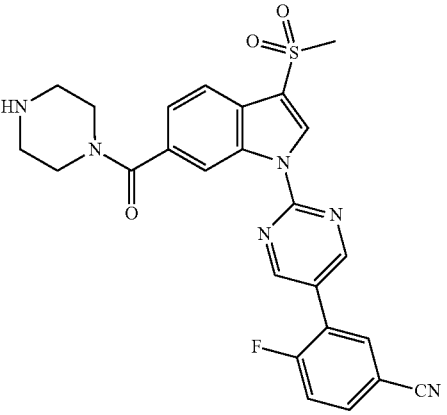 [SMILES: CS(=O)(=O)c1cn(-c2ncc(-c3cc(C#N)ccc3F)cn2)c2cc(C(=O)N3CCNCC3)ccc12] | 4-fluoro-3-(2-(3-(methylsulfonyl)-6-(piperazine-1-carbonyl)-1H-indol-1-yl)pyrimidin-5-yl)benzonitrile |
| 27 | 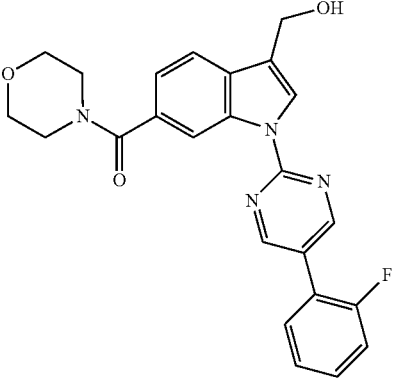 [SMILES: O=C(c1ccc2c(CO)cn(-c3ncc(-c4ccccc4F)cn3)c2c1)N1CCOCC1] | (1-(5-(2-fluorophenyl)pyrimidin-2-yl)-3-(hydroxymethyl)-1H-indol-6-yl)(morpholino)methanone |
| 28 | 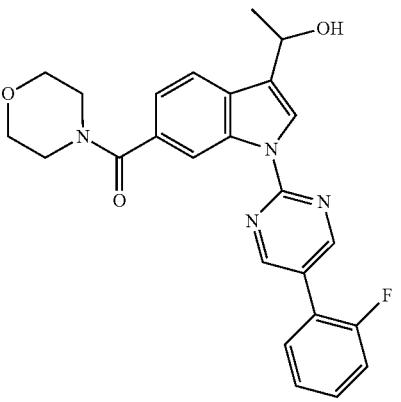 [SMILES: CC(O)c1cn(-c2ncc(-c3ccccc3F)cn2)c2cc(C(=O)N3CCOCC3)ccc12] | (1-(5-(2-Fluorophenyl)pyrimidin-2-yl)-3-(1-hydroxyethyl)-1H-indol-6-yl)(morpholino)methanone |

TABLE 1-continued

| Cmpd-No. | Structure | Name |
|---|---|---|
| 29 | 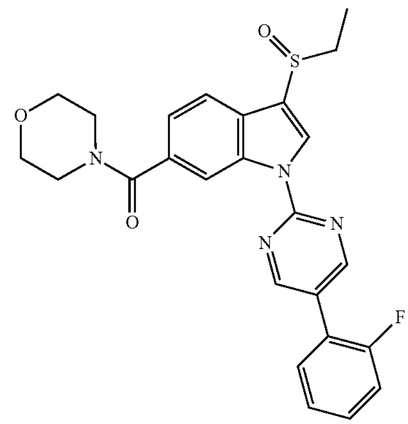 [SMILES: CCS(=O)c1cn(-c2ncc(-c3ccccc3F)cn2)c2cc(C(=O)N3CCOCC3)ccc12] | (3-(ethylsulfinyl)-1-(5-(2-fluorophenyl)pyrimidin-2-yl)-1H-indol-6-yl)(morpholino)methanone |
| 30 | 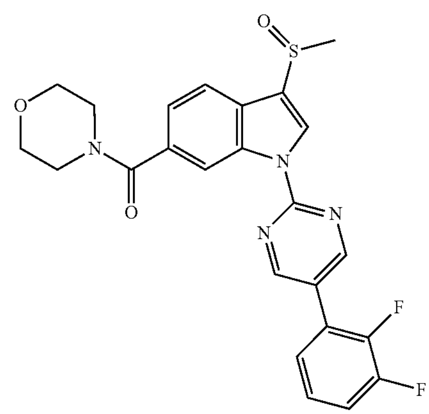 [SMILES: CS(=O)c1cn(-c2ncc(-c3cccc(F)c3F)cn2)c2cc(C(=O)N3CCOCC3)ccc12] | (1-(5-(2,3-Difluorophenyl)pyrimidin-2-yl)-3-(methylsulfinyl)-1H-indol-6-yl)(morpholino)methanone |
| 31 | 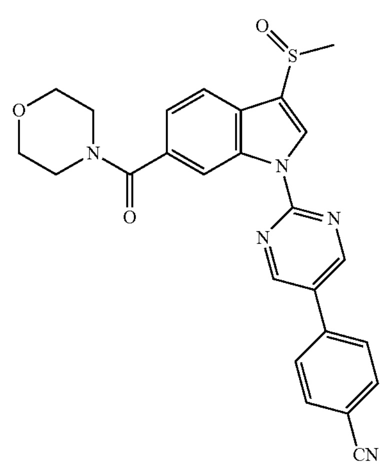 [SMILES: CS(=O)c1cn(-c2ncc(-c3ccc(C#N)cc3)cn2)c2cc(C(=O)N3CCOCC3)ccc12] | 4-(2-(3-(Methylsulfinyl)-6-(morpholine-4-carbonyl)-1H-indol-1-yl)pyrimidin-5-yl)benzonitrile |

TABLE 1-continued

| Cmpd-No. | Structure | Name |
| --- | --- | --- |
| 32 | 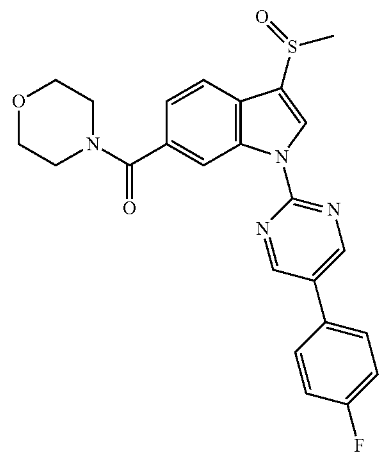 [SMILES: CS(=O)c1cn(-c2ncc(-c3ccc(F)cc3)cn2)c2cc(C(=O)N3CCOCC3)ccc12] | (1-(5-(4-Fluorophenyl)pyrimidin-2-yl)-3-(methylsulfinyl)-1H-indol-6-yl)(morpholino)methanone |
| 33 | 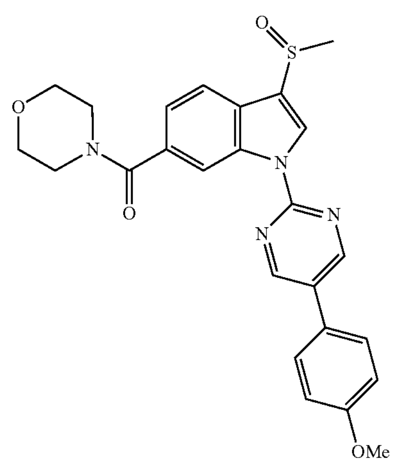 [SMILES: COc1ccc(-c2cnc(-n3cc(S(C)=O)c4ccc(C(=O)N5CCOCC5)cc43)nc2)cc1] | (1-(5-(4-Methoxyphenyl)pyrimidin-2-yl)-3-(methylsulfinyl)-1H-indol-6-yl)(morpholino)methanone |
| 34 | 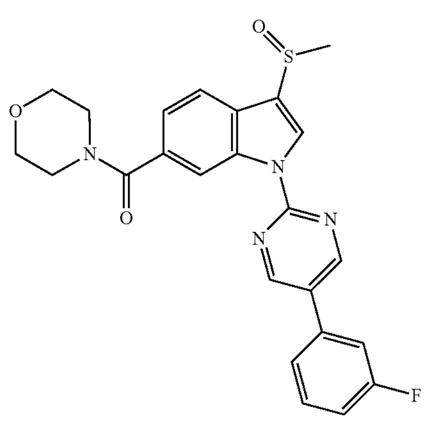 [SMILES: CS(=O)c1cn(-c2ncc(-c3cccc(F)c3)cn2)c2cc(C(=O)N3CCOCC3)ccc12] | (1-(5-(3-Fluorophenyl)pyrimidin-2-yl)-3-(methylsulfinyl)-1H-indol-6-yl)(morpholino)methanone |

| Cmpd-No. | Structure | Name |
|---|---|---|
| 35 | 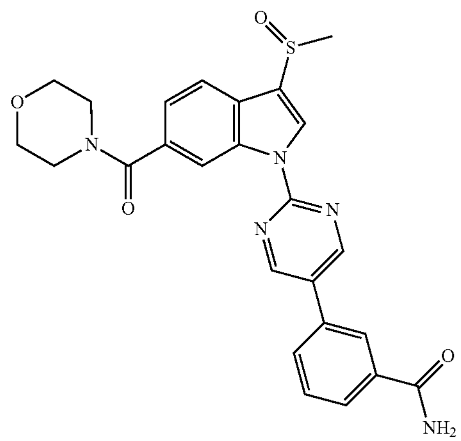 [SMILES: CS(=O)c1cn(-c2ncc(-c3cccc(C(N)=O)c3)cn2)c2cc(C(=O)N3CCOCC3)ccc12] | 3-(2-(3-(methylsulfinyl)-6-(morpholine-4-carbonyl)-1H-indol-1-yl)pyrimidin-5-yl)benzamide |
| 36 | 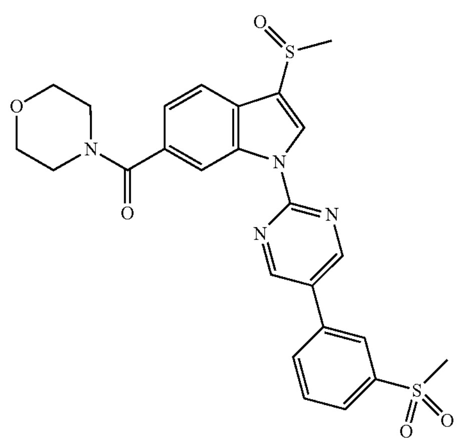 [SMILES: CS(=O)c1cn(-c2ncc(-c3cccc(S(C)(=O)=O)c3)cn2)c2cc(C(=O)N3CCOCC3)ccc12] | (3-(Methylsulfinyl)-1-(5-(3-(methylsulfonyl)phenyl)pyrimidin-2-yl)-1H-indol-6-yl)(morpholino)methanone |
| 37 | 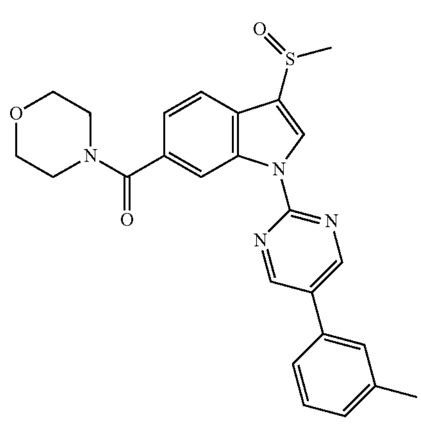 [SMILES: Cc1cccc(-c2cnc(-n3cc(S(C)=O)c4ccc(C(=O)N5CCOCC5)cc43)nc2)c1] | (3-(Methylsulfinyl)-1-(5-(m-tolyl)pyrimidin-2-yl)-1H-indol-6-yl)(morpholino)methanone |

TABLE 1-continued

| Cmpd-No. | Structure | Name |
|---|---|---|
| 38 | 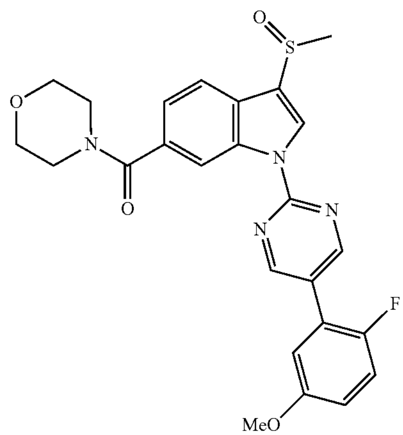 [SMILES: COc1ccc(F)c(-c2cnc(-n3cc(S(C)=O)c4ccc(C(=O)N5CCOCC5)cc43)nc2)c1] | (1-(5-(2-Fluoro-5-methoxyphenyl)pyrimidin-2-yl)-3-(methylsulfinyl)-1H-indol-6-yl)(morpholino)methanone |
| 39 | 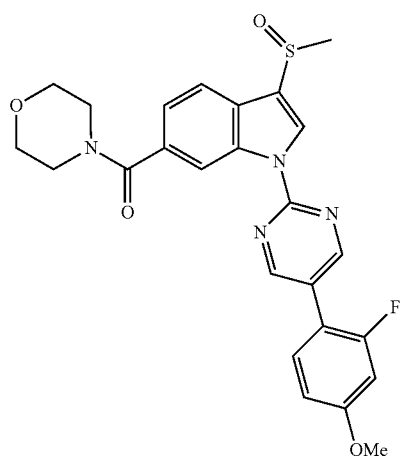 [SMILES: COc1ccc(-c2cnc(-n3cc(S(C)=O)c4ccc(C(=O)N5CCOCC5)cc43)nc2)c(F)c1] | (1-(5-(2-Fluoro-4-methoxyphenyl)pyrimidin-2-yl)-3-(methylsulfinyl)-1H-indol-6-yl)(morpholino)methanone |
| 40 | 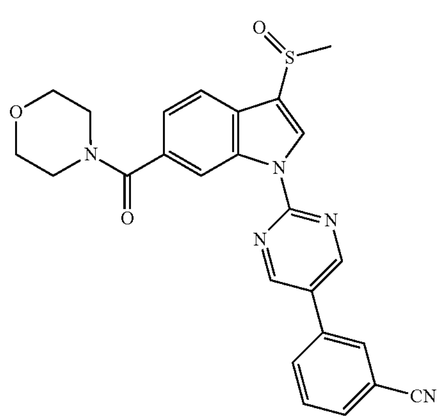 [SMILES: CS(=O)c1cn(-c2ncc(-c3cccc(C#N)c3)cn2)c2cc(C(=O)N3CCOCC3)ccc12] | 3-(2-(3-(Methylsulfinyl)-6-(morpholine-4-carbonyl)-1H-indol-1-yl)pyrimidin-5-yl)benzonitrile |

TABLE 1-continued

| Cmpd-No. | Structure | Name |
|---|---|---|
| 41 | 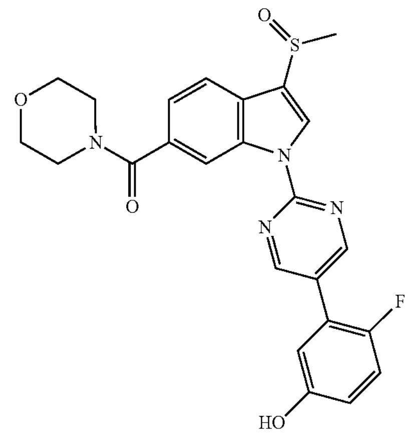 [SMILES: CS(=O)c1cn(-c2ncc(-c3cc(O)ccc3F)cn2)c2cc(C(=O)N3CCOCC3)ccc12] | (1-(5-(2-Fluoro-5-hydroxyphenyl)pyrimidin-2-yl)-3-(methylsulfinyl)-1H-indol-6-yl)(morpholino)methanone |
| 42 | 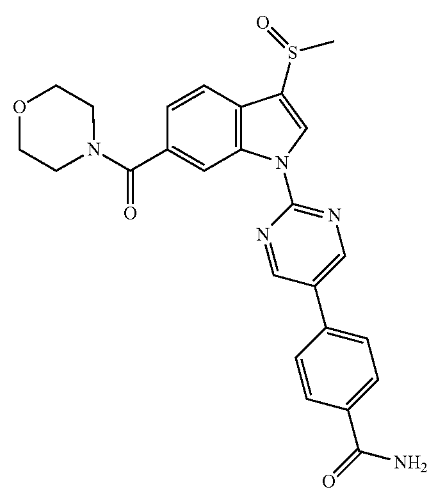 [SMILES: CS(=O)c1cn(-c2ncc(-c3ccc(C(N)=O)cc3)cn2)c2cc(C(=O)N3CCOCC3)ccc12] | 4-(2-(3-(methylsulfinyl)-6-(morpholine-4-carbonyl)-1H-indol-1-yl)pyrimidin-5-yl)benzamide |
| 43 | 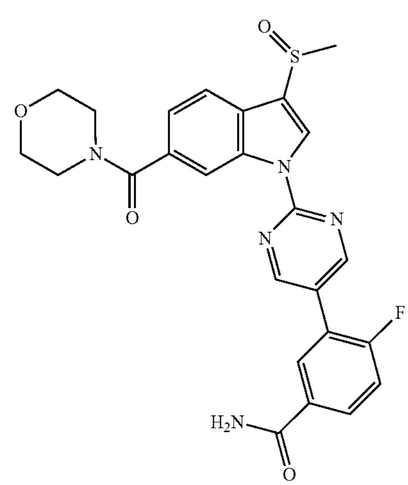 [SMILES: CS(=O)c1cn(-c2ncc(-c3cc(C(N)=O)ccc3F)cn2)c2cc(C(=O)N3CCOCC3)ccc12] | 4-Fluoro-3-(2-(3-(methylsulfinyl)-6-(morpholine-4-carbonyl)-1H-indol-1-yl)pyrimidin-5-yl)benzamide |

TABLE 1-continued

| Cmpd-No. | Structure | Name |
|---|---|---|
| 44 | 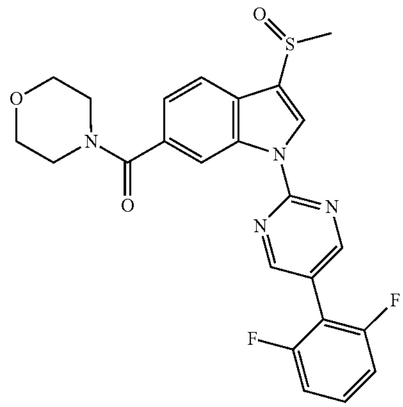 [SMILES: CS(=O)c1cn(-c2ncc(-c3c(F)cccc3F)cn2)c2cc(C(=O)N3CCOCC3)ccc12] | (1-(5-(2,6-difluorophenyl)pyrimidin-2-yl)-3-(methylsulfinyl)-1H-indol-6-yl)(morpholino)methanone |
| 45 | 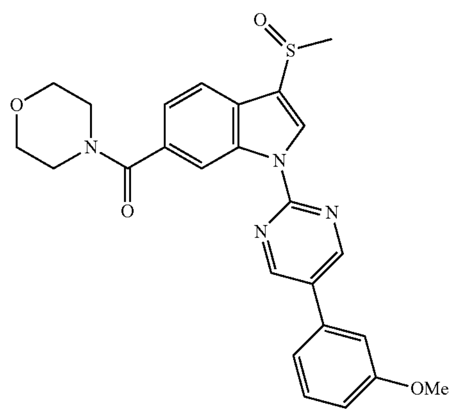 [SMILES: COc1cccc(-c2cnc(-n3cc(S(C)=O)c4ccc(C(=O)N5CCOCC5)cc43)nc2)c1] | (1-(5-(3-methoxyphenyl)pyrimidin-2-yl)-3-(methylsulfinyl)-1H-indol-6-yl)(morpholino)methanone |
| 46 | 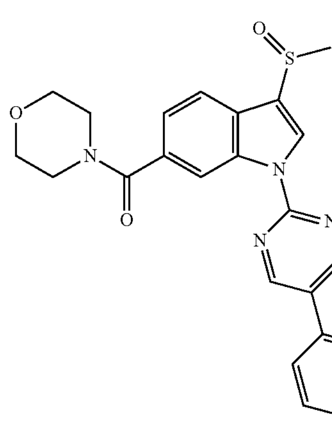 | (3-(Methylsulfinyl)-1-(5-(p-tolyl)pyrimidin-2-yl)-1H-indol-6-yl)(morpholino)methanone |

TABLE 1-continued

| Cmpd-No. | Structure | Name |
|---|---|---|
| 47 | 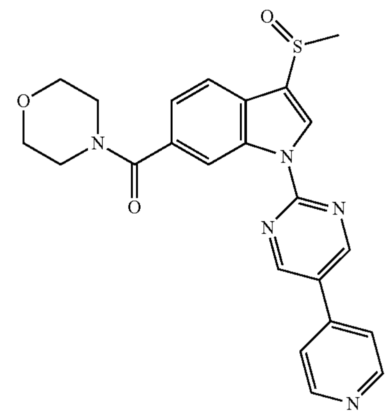 [SMILES: CS(=O)c1cn(-c2ncc(-c3ccncc3)cn2)c2cc(C(=O)N3CCOCC3)ccc12] | (3-(Methylsulfinyl)-1-(5-(pyridin-4-yl)pyrimidin-2-yl)-1H-indol-6-yl)(morpholino)methanone |
| 48 | 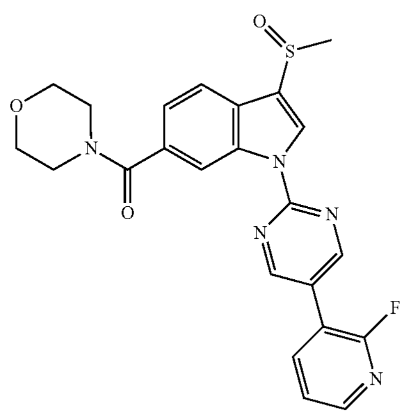 [SMILES: CS(=O)c1cn(-c2ncc(-c3cccnc3F)cn2)c2cc(C(=O)N3CCOCC3)ccc12] | (1-(5-(2-Fluoropyridin-3-yl)pyrimidin-2-yl)-3-(methylsulfinyl)-1H-indol-6-yl)(morpholino)methanone |
| 49 | 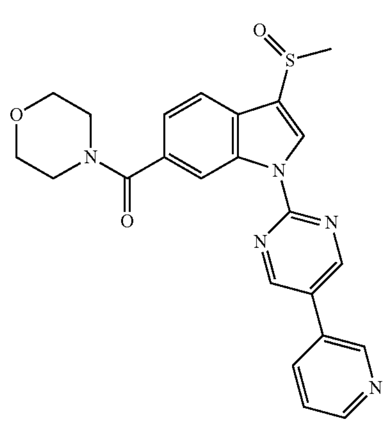 [SMILES: CS(=O)c1cn(-c2ncc(-c3cccnc3)cn2)c2cc(C(=O)N3CCOCC3)ccc12] | (3-(Methylsulfinyl)-1-(5-(pyridin-3-yl)pyrimidin-2-yl)-1H-indol-6-yl)(morpholino)methanone |

TABLE 1-continued

| Cmpd-No. | Structure | Name |
|---|---|---|
| 50 | 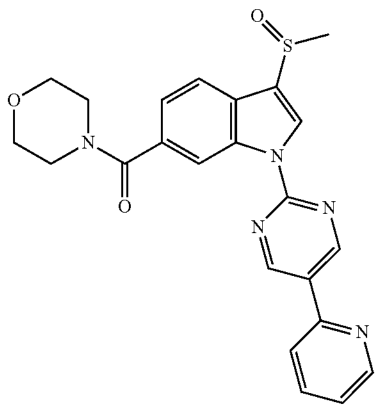 [SMILES: CS(=O)c1cn(-c2ncc(-c3ccccn3)cn2)c2cc(C(=O)N3CCOCC3)ccc12] | (3-(methylsulfinyl)-1-(5-(pyridin-2-yl)pyrimidin-2-yl)-1H-indol-6-yl)(morpholino)methanone |
| 51 | 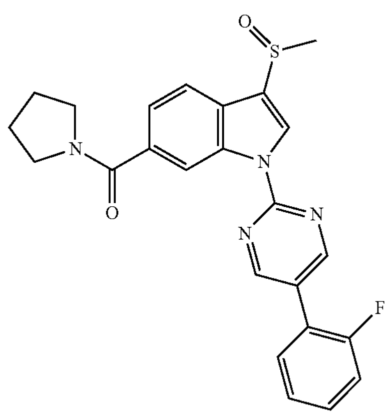 [SMILES: CS(=O)c1cn(-c2ncc(-c3ccccc3F)cn2)c2cc(C(=O)N3CCCC3)ccc12] | (1-(5-(2-Fluorophenyl)pyrimidin-2-yl)-3-(methylsulfinyl)-1H-indol-6-yl)(pyrrolidin-1-yl)methanone |
| 52 | 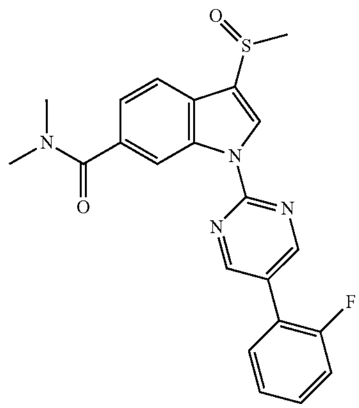 [SMILES: CN(C)C(=O)c1ccc2c(S(C)=O)cn(-c3ncc(-c4ccccc4F)cn3)c2c1] | 1-(5-(2-Fluorophenyl)pyrimidin-2-yl)-N,N-dimethyl-3-(methylsulfinyl)-1H-indole-6-carboxamide |

TABLE 1-continued

| Cmpd-No. | Structure | Name |
|---|---|---|
| 53 | 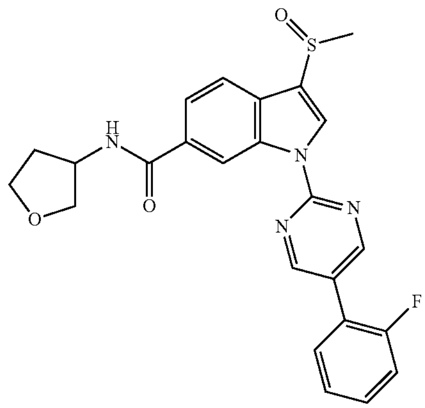 [SMILES: CS(=O)c1cn(-c2ncc(-c3ccccc3F)cn2)c2cc(C(=O)NC3CCOC3)ccc12] | 1-(5-(2-fluorophenyl)pyrimidin-2-yl)-3-(methylsulfinyl)-N-(tetrahydrofuran-3-yl)-1H-indole-6-carboxamide |
| 54 | 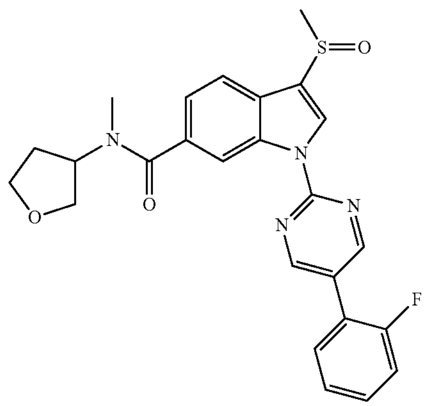 [SMILES: CN(C(=O)c1ccc2c(S(C)=O)cn(-c3ncc(-c4ccccc4F)cn3)c2c1)C1CCOC1] | 1-(5-(2-fluorophenyl)pyrimidin-2-yl)-N-methyl-3-(methylsulfinyl)-N-(tetrahydrofuran-3-yl)-1H-indole-6-carboxamide |
| 55 | 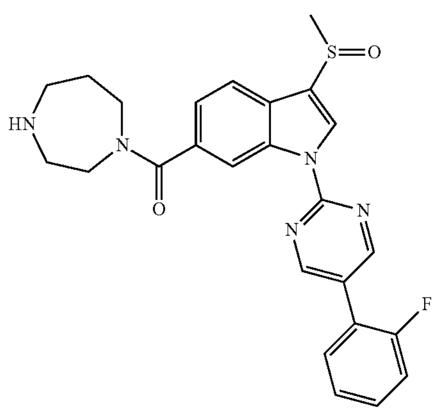 [SMILES: CS(=O)c1cn(-c2ncc(-c3ccccc3F)cn2)c2cc(C(=O)N3CCCNCC3)ccc12] | (1,4-diazepan-1-yl)(1-(5-(2-fluorophenyl)pyrimidin-2-yl)-3-(methylsulfinyl)-1H-indol-6-yl)methanone |
| 56 | 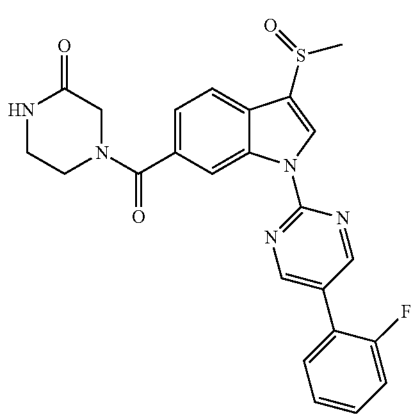 [SMILES: CS(=O)c1cn(-c2ncc(-c3ccccc3F)cn2)c2cc(C(=O)N3CCNC(=O)C3)ccc12] | 4-(1-(5-(2-fluorophenyl)pyrimidin-2-yl)-3-(methylsulfinyl)-1H-indole-6-carbonyl)piperazin-2-one |

| Cmpd-No. | Structure | Name |
| --- | --- | --- |
| 57 | 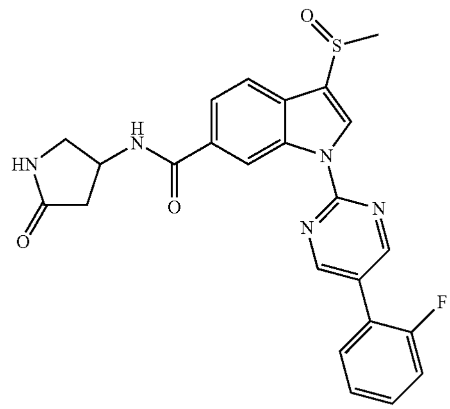 [SMILES: CS(=O)c1cn(-c2ncc(-c3ccccc3F)cn2)c2cc(C(=O)NC3CNC(=O)C3)ccc12] | 1-(5-(2-fluorophenyl)pyrimidin-2-yl)-3-(methylsulfinyl)-N-(5-oxopyrrolidin-3-yl)-1H-indole-6-carboxamide |
| 58 | 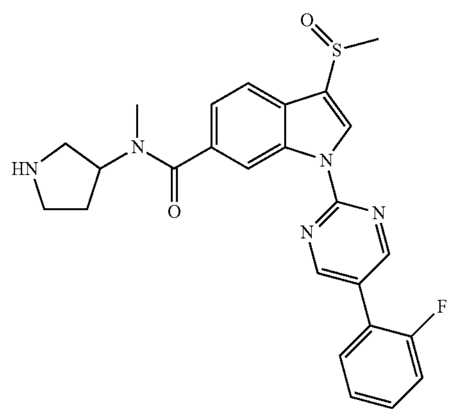 [SMILES: CN(C(=O)c1ccc2c(S(C)=O)cn(-c3ncc(-c4ccccc4F)cn3)c2c1)C1CCNC1] | 1-(5-(2-fluorophenyl)pyrimidin-2-yl)-N-methyl-3-(methylsulfinyl)-N-(pyrrolidin-3-yl)-1H-indole-6-carboxamide |
| 59 | 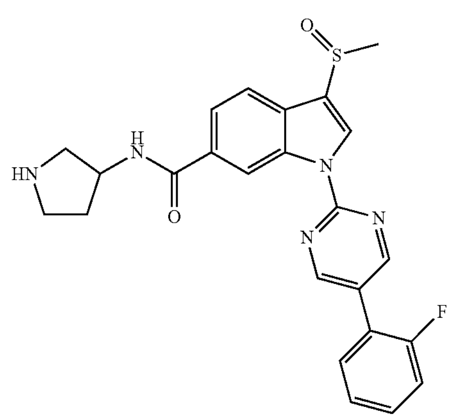 [SMILES: CS(=O)c1cn(-c2ncc(-c3ccccc3F)cn2)c2cc(C(=O)NC3CCNC3)ccc12] | 1-(5-(2-fluorophenyl)pyrimidin-2-yl)-3-(methylsulfinyl)-N-(pyrrolidin-3-yl)-1H-indole-6-carboxamide |

TABLE 1-continued

| Cmpd-No. | Structure | Name |
|---|---|---|
| 60 | 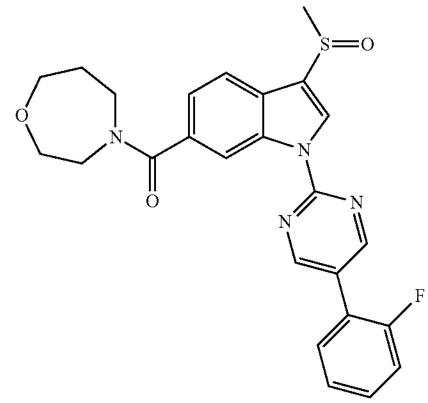 [SMILES: CS(=O)c1cn(-c2ncc(-c3ccccc3F)cn2)c2cc(C(=O)N3CCCOCC3)ccc12] | (1-(5-(2-fluorophenyl)pyrimidin-2-yl)-3-(methylsulfinyl)-1H-indol-6-yl)(1,4-oxazepan-4-yl)methanone |
| 61 | 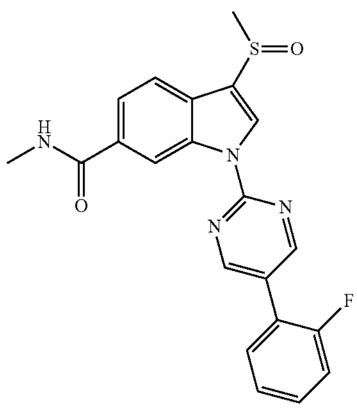 [SMILES: CNC(=O)c1ccc2c(S(C)=O)cn(-c3ncc(-c4ccccc4F)cn3)c2c1] | 1-(5-(2-fluorophenyl)pyrimidin-2-yl)-N-methyl-3-(methylsulfinyl)-1H-indole-6-carboxamide |
| 62 | 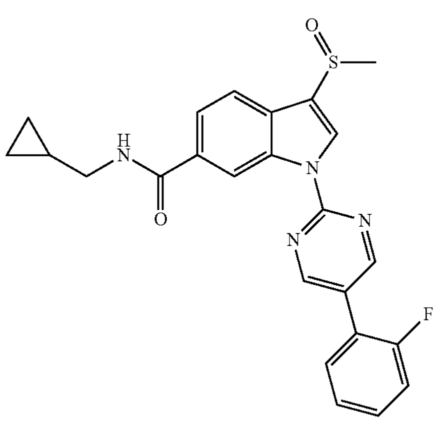 [SMILES: CS(=O)c1cn(-c2ncc(-c3ccccc3F)cn2)c2cc(C(=O)NCC3CC3)ccc12] | N-(cyclopropylmethyl)-1-(5-(2-fluorophenyl)pyrimidin-2-yl)-3-(methylsulfinyl)-1H-indole-6-carboxamide |

TABLE 1-continued

| Cmpd-No. | Structure | Name |
| --- | --- | --- |
| 63 | 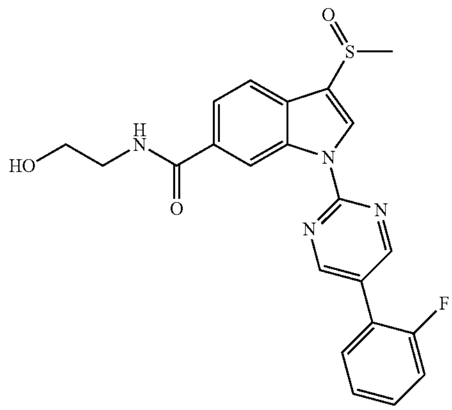 [SMILES: CS(=O)c1cn(-c2ncc(-c3ccccc3F)cn2)c2cc(C(=O)NCCO)ccc12] | 1-(5-(2-fluorophenyl)pyrimidin-2-yl)-N-(2-hydroxyethyl)-3-(methylsulfinyl)-1H-indole-6-carboxamide |
| 64 | 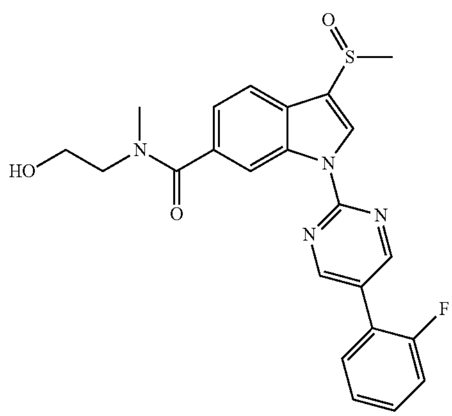 [SMILES: CN(CCO)C(=O)c1ccc2c(S(C)=O)cn(-c3ncc(-c4ccccc4F)cn3)c2c1] | 1-(5-(2-fluorophenyl)pyrimidin-2-yl)-N-(2-hydroxyethyl)-N-methyl-3-(methylsulfinyl)-1H-indole-6-carboxamide |
| 65 | 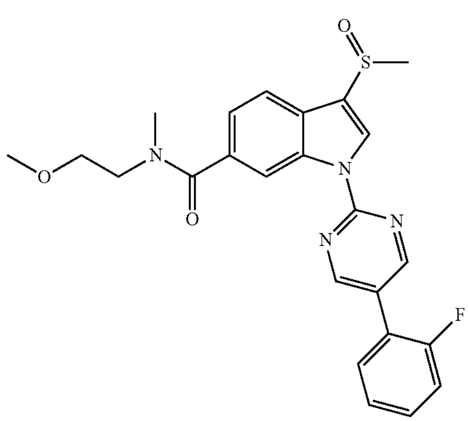 [SMILES: COCCN(C)C(=O)c1ccc2c(S(C)=O)cn(-c3ncc(-c4ccccc4F)cn3)c2c1] | 1-(5-(2-fluorophenyl)pyrimidin-2-yl)-N-(2-methoxyethyl)-N-methyl-3-(methylsulfinyl)-1H-indole-6-carboxamide |

… 85 … 86
TABLE 1-continued
| Cmpd-No. | Structure | Name |
|---|---|---|
| 66 | 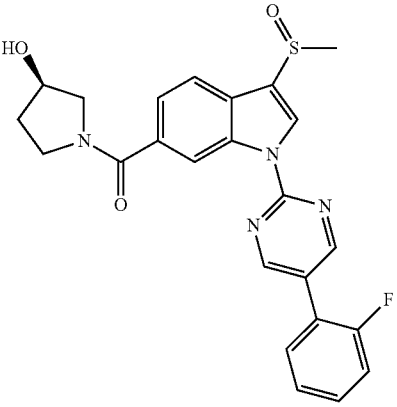 [SMILES: CS(=O)c1cn(-c2ncc(-c3ccccc3F)cn2)c2cc(C(=O)N3CC[C@@H](O)C3)ccc12] | (1-(5-(2-fluorophenyl)pyrimidin-2-yl)-3-(methylsulfinyl)-1H-indol-6-yl)((R)-3-hydroxypyrrolidin-1-yl)methanone |
| 67 | 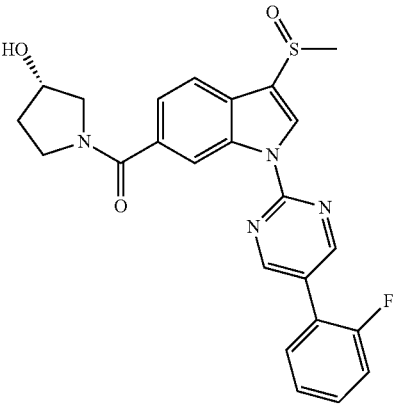 [SMILES: CS(=O)c1cn(-c2ncc(-c3ccccc3F)cn2)c2cc(C(=O)N3CC[C@H](O)C3)ccc12] | (1-(5-(2-fluorophenyl)pyrimidin-2-yl)-3-(methylsulfinyl)-1H-indol-6-yl)((S)-3-hydroxypyrrolidin-1-yl)methanone |
| 68 | 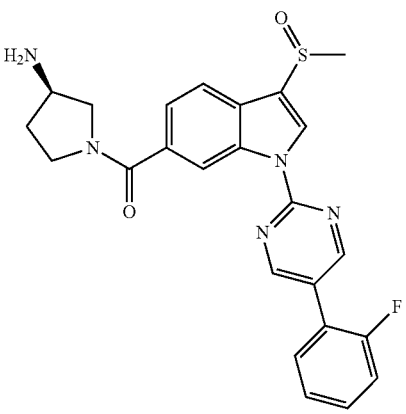 [SMILES: CS(=O)c1cn(-c2ncc(-c3ccccc3F)cn2)c2cc(C(=O)N3CC[C@@H](N)C3)ccc12] | (R)-3-Aminopyrrolidin-1-yl)(1-(5-(2-fluorophenyl)pyrimidin-2-yl)-3-(methylsulfinyl)-1H-indol-6-yl)methanone |

| Cmpd-No. | Structure | Name |
|---|---|---|
| 69 | 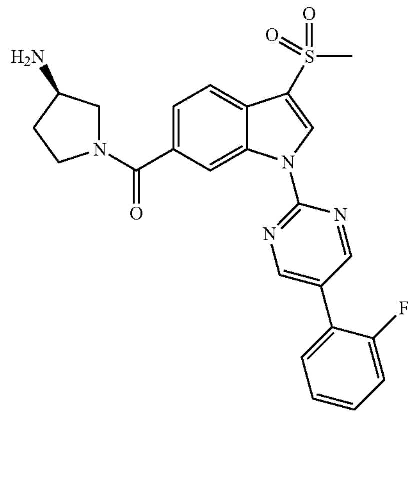 [SMILES: CS(=O)(=O)c1cn(-c2ncc(-c3ccccc3F)cn2)c2cc(C(=O)N3CC[C@@H](N)C3)ccc12] | (R)-(3-Aminopyrrolidin-1-yl)(1-(5-(2-fluorophenyl)pyrimidin-2-yl)-3-(methylsulfonyl)-1H-indol-6-yl)methanone |
| 70 | 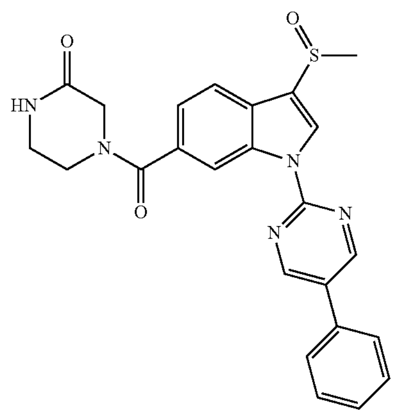 [SMILES: CS(=O)c1cn(-c2ncc(-c3ccccc3)cn2)c2cc(C(=O)N3CCNC(=O)C3)ccc12] | 4-(3-(Methylsulfinyl)-1-(5-phenylpyrimidin-2-yl)-1H-indole-6-carbonyl)piperazin-2-one |
| 71 | 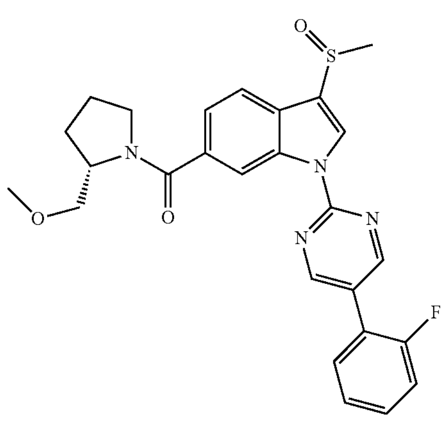 [SMILES: COC[C@@H]1CCCN1C(=O)c1ccc2c(S(C)=O)cn(-c3ncc(-c4ccccc4F)cn3)c2c1] | (1-(5-(2-fluorophenyl)pyrimidin-2-yl)-3-(methylsulfinyl)-1H-indol-6-yl)((S)-2-(methoxymethyl)pyrrolidin-1-yl)methanone |

TABLE 1-continued

| Cmpd-No. | Structure | Name |
|---|---|---|
| 72 | 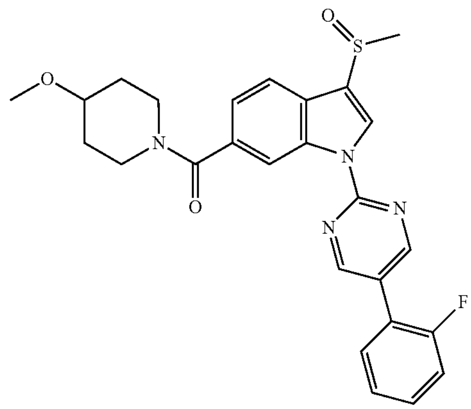 [SMILES: COC1CCN(C(=O)c2ccc3c(S(C)=O)cn(-c4ncc(-c5ccccc5F)cn4)c3c2)CC1] | (1-(5-(2-fluorophenyl)pyrimidin-2-yl)-3-(methylsulfinyl)-1H-indol-6-yl)(4-methoxypiperidin-1-yl)methanone |
| 73 | 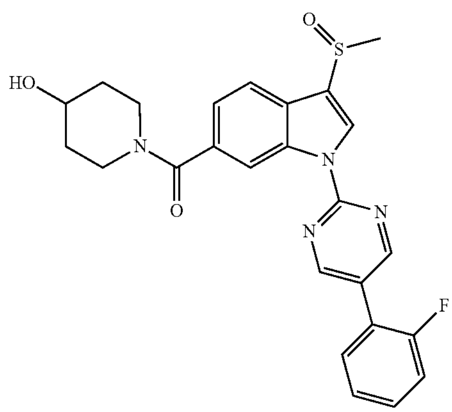 [SMILES: CS(=O)c1cn(-c2ncc(-c3ccccc3F)cn2)c2cc(C(=O)N3CCC(O)CC3)ccc12] | (1-(5-(2-fluorophenyl)pyrimidin-2-yl)-3-(methylsulfinyl)-1H-indol-6-yl)(4-hydroxypiperidin-1-yl)methanone |
| 74 | 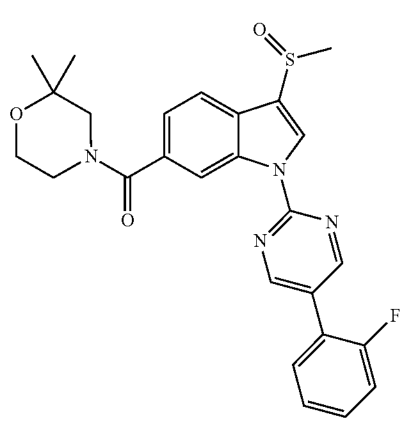 [SMILES: CS(=O)c1cn(-c2ncc(-c3ccccc3F)cn2)c2cc(C(=O)N3CCOC(C)(C)C3)ccc12] | (2,2-dimethylmorpholino)(1-(5-(2-fluorophenyl)pyrimidin-2-yl)-3-(methylsulfinyl)-1H-indol-6-yl)methanone |

TABLE 1-continued

| Cmpd-No. | Structure | Name |
|---|---|---|
| 75 | 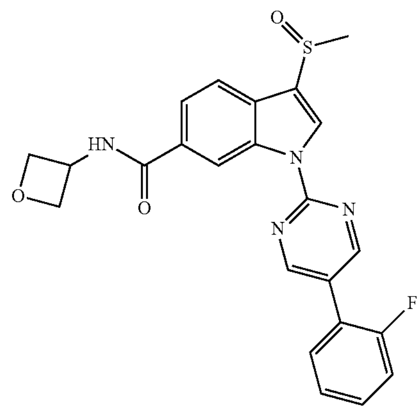 [SMILES: CS(=O)c1cn(-c2ncc(-c3ccccc3F)cn2)c2cc(C(=O)NC3COC3)ccc12] | 1-(5-(2-fluorophenyl)pyrimidin-2-yl)-3-(methylsulfinyl)-N-(oxetan-3-yl)-1H-indole-6-carboxamide |
| 76 | 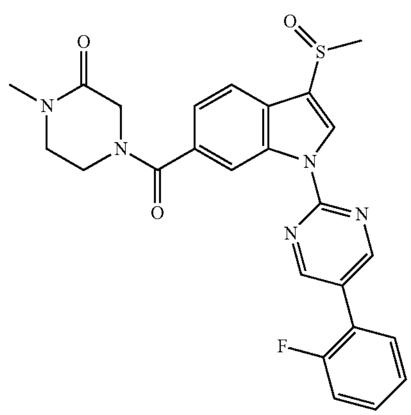 [SMILES: CN1CCN(C(=O)c2ccc3c(S(C)=O)cn(-c4ncc(-c5ccccc5F)cn4)c3c2)CC1=O] | 4-(1-(5-(2-fluorophenyl)pyrimidin-2-yl)-3-(methylsulfinyl)-1H-indole-6-carbonyl)-1-methylpiperazin-2-one |
| 77 | 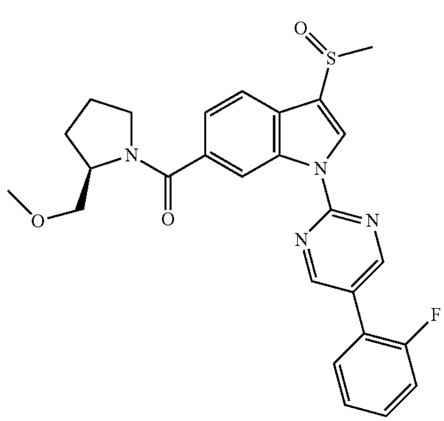 [SMILES: COC[C@H]1CCCN1C(=O)c1ccc2c(S(C)=O)cn(-c3ncc(-c4ccccc4F)cn3)c2c1] | (1-(5-(2-fluorophenyl)pyrimidin-2-yl)-3-(methylsulfinyl)-1H-indol-6-yl)((R)-2-(methoxymethyl)pyrrolidin-1-yl)methanone |

| Cmpd-No. | Structure | Name |
|---|---|---|
| 78 | 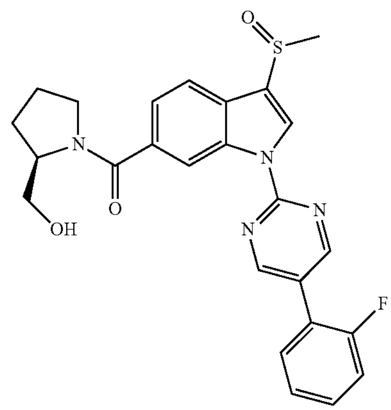 [SMILES: CS(=O)c1cn(-c2ncc(-c3ccccc3F)cn2)c2cc(C(=O)N3CCC[C@@H]3CO)ccc12] | (1-(5-(2-fluorophenyl)pyrimidin-2-yl)-3-(methylsulfinyl)-1H-indol-6-yl)((R)-2-(hydroxymethyl)pyrrolidin-1-yl)methanone |
| 79 | 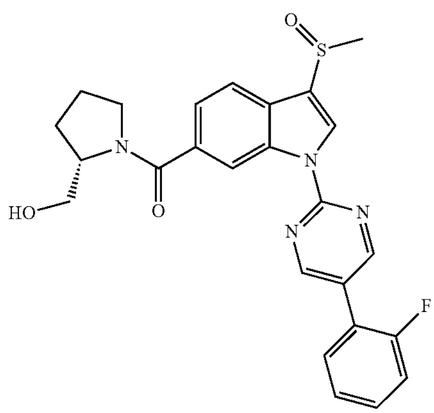 [SMILES: CS(=O)c1cn(-c2ncc(-c3ccccc3F)cn2)c2cc(C(=O)N3CCC[C@H]3CO)ccc12] | (1-(5-(2-fluorophenyl)pyrimidin-2-yl)-3-(methylsulfinyl)-1H-indol-6-yl)((S)-2-(hydroxymethyl)pyrrolidin-1-yl)methanone |
| 80 | 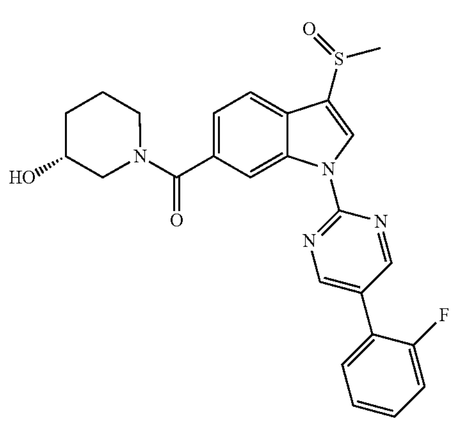 [SMILES: CS(=O)c1cn(-c2ncc(-c3ccccc3F)cn2)c2cc(C(=O)N3CCC[C@@H](O)C3)ccc12] | (1-(5-(2-fluorophenyl)pyrimidin-2-yl)-3-(methylsulfinyl)-1H-indol-6-yl)((R)-3-hydroxypiperidin-1-yl)methanone |

| Cmpd-No. | Structure | Name |
|---|---|---|
| 81 | 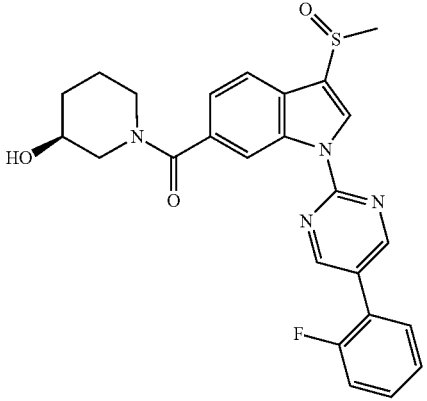 [SMILES: CS(=O)c1cn(-c2ncc(-c3ccccc3F)cn2)c2cc(C(=O)N3CCC[C@H](O)C3)ccc12] | (1-(5-(2-fluorophenyl)pyrimidin-2-yl)-3-(methylsulfinyl)-1H-indol-6-yl)((S)-3-hydroxypiperidin-1-yl)methanone |
| 82 | 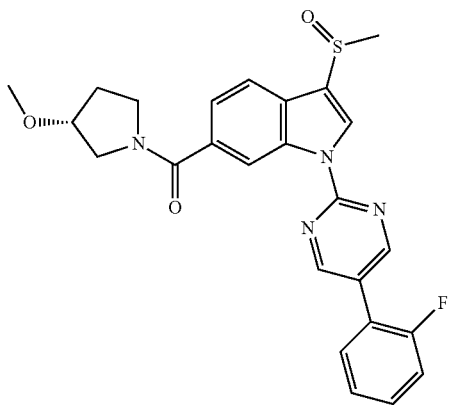 [SMILES: CO[C@@H]1CCN(C(=O)c2ccc3c(S(C)=O)cn(-c4ncc(-c5ccccc5F)cn4)c3c2)C1] | (1-(5-(2-fluorophenyl)pyrimidin-2-yl)-3-(methylsulfinyl)-1H-indol-6-yl)((R)-3-methoxypyrrolidin-1-yl)methanone |
| 83 | 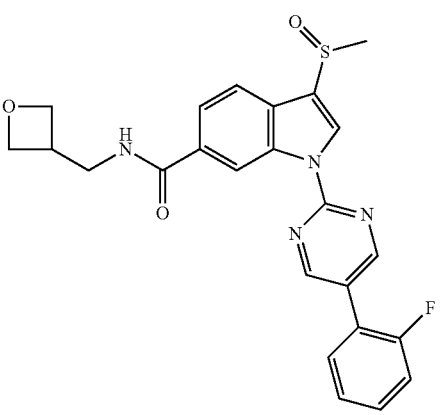 [SMILES: CS(=O)c1cn(-c2ncc(-c3ccccc3F)cn2)c2cc(C(=O)NCC3COC3)ccc12] | 1-(5-(2-fluorophenyl)pyrimidin-2-yl)-3-(methylsulfinyl)-N-(oxetan-3-ylmethyl)-1H-indole-6-carboxamide |

TABLE 1-continued

| Cmpd-No. | Structure | Name |
|---|---|---|
| 84 | 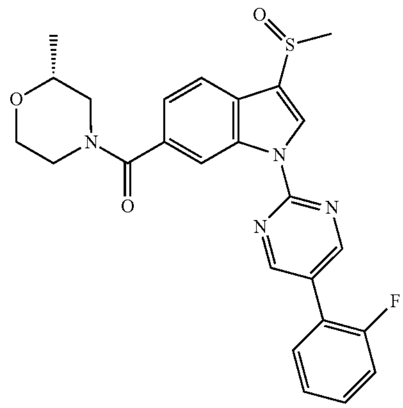 [SMILES: C[C@@H]1CN(C(=O)c2ccc3c(S(C)=O)cn(-c4ncc(-c5ccccc5F)cn4)c3c2)CCO1] | (1-(5-(2-fluorophenyl)pyrimidin-2-yl)-3-(methylsulfinyl)-1H-indol-6-yl)((R)-2-methylmorpholino)methanone |
| 85 | 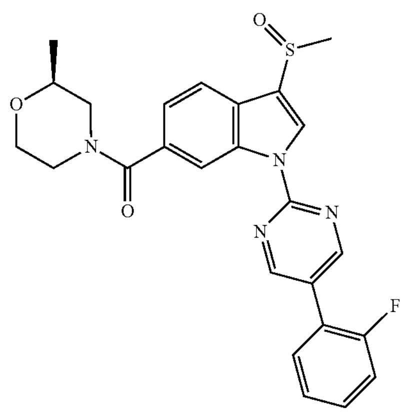 [SMILES: C[C@H]1CN(C(=O)c2ccc3c(S(C)=O)cn(-c4ncc(-c5ccccc5F)cn4)c3c2)CCO1] | (1-(5-(2-fluorophenyl)pyrimidin-2-yl)-3-(methylsulfinyl)-1H-indol-6-yl)((S)-2-methylmorpholino)methanone |
| 86 | 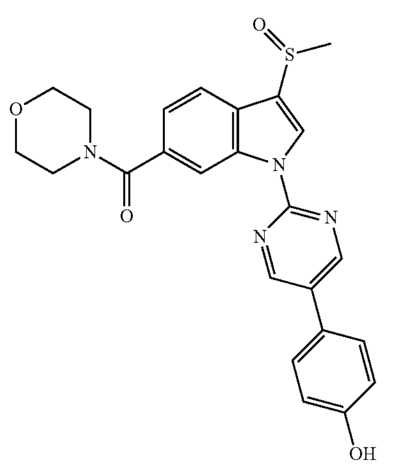 [SMILES: CS(=O)c1cn(-c2ncc(-c3ccc(O)cc3)cn2)c2cc(C(=O)N3CCOCC3)ccc12] | (1-(5-(4-hydroxyphenyl)pyrimidin-2-yl)-3-(methylsulfinyl)-1H-indol-6-yl)(morpholino)methanone |

TABLE 1-continued

| Cmpd-No. | Structure | Name |
|---|---|---|
| 87 | 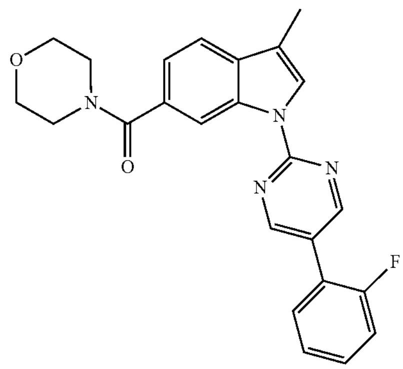 [SMILES: Cc1cn(-c2ncc(-c3ccccc3F)cn2)c2cc(C(=O)N3CCOCC3)ccc12] | (1-(5-(2-fluorophenyl)pyrimidin-2-yl)-3-methyl-1H-indol-6-yl)(morpholino)methanone |
| 88 | 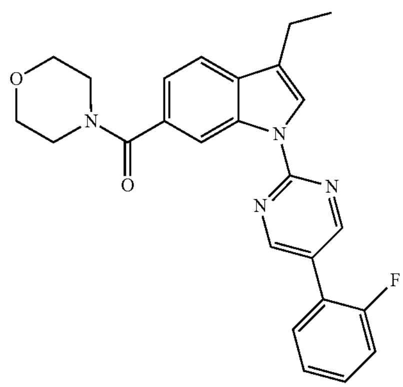 [SMILES: CCc1cn(-c2ncc(-c3ccccc3F)cn2)c2cc(C(=O)N3CCOCC3)ccc12] | (3-Ethyl-1-(5-(2-fluorophenyl)pyrimidin-2-yl)-1H-indol-6-yl)(morpholino)methanone |
| 89 | 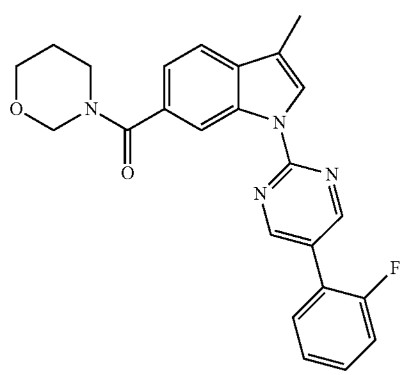 [SMILES: Cc1cn(-c2ncc(-c3ccccc3F)cn2)c2cc(C(=O)N3CCCOC3)ccc12] | (1-(5-(2-fluorophenyl)pyrimidin-2-yl)-3-methyl-1H-indol-6-yl)(1,3-oxazinan-3-yl)methanone |
| 90 | 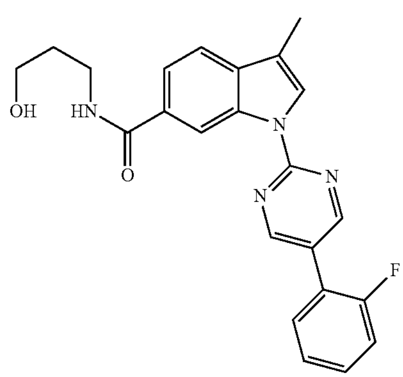 [SMILES: Cc1cn(-c2ncc(-c3ccccc3F)cn2)c2cc(C(=O)NCCCO)ccc12] | 1-(5-(2-fluorophenyl)pyrimidin-2-yl)-N-(3-hydroxypropyl)-3-methyl-1H-indole-6-carboxamide |

TABLE 1-continued

| Cmpd-No. | Structure | Name |
|---|---|---|
| 91 | 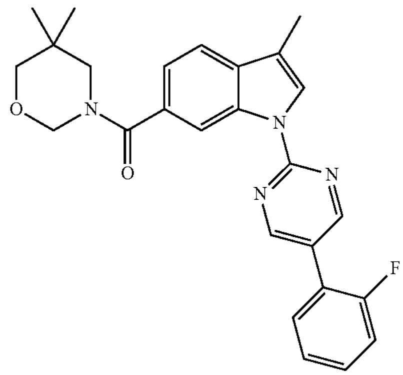 [SMILES: Cc1cn(-c2ncc(-c3ccccc3F)cn2)c2cc(C(=O)N3COCC(C)(C)C3)ccc12] | (5,5-dimethyl-1,3-oxazinan-3-yl)(1-(5-(2-fluorophenyl)pyrimidin-2-yl)-3-methyl-1H-indol-6-yl)methanone |
| 92 | 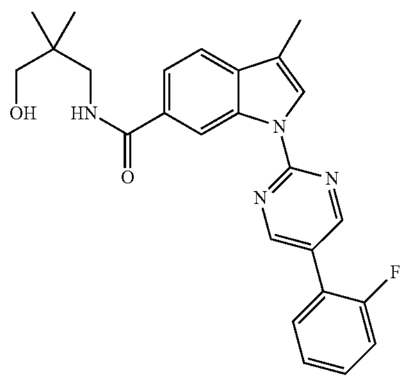 [SMILES: Cc1cn(-c2ncc(-c3ccccc3F)cn2)c2cc(C(=O)NCC(C)(C)CO)ccc12] | 1-(5-(2-fluorophenyl)pyrimidin-2-yl)-N-(3-hydroxy-2,2-dimethylpropyl)-3-methyl-1H-indole-6-carboxamide |
| 93 | 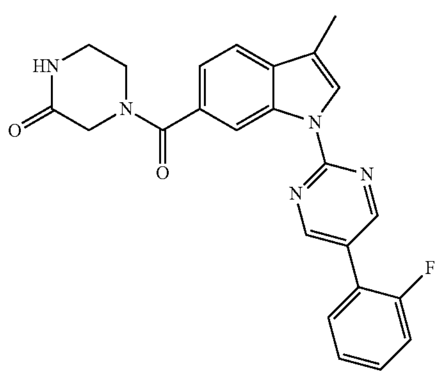 [SMILES: Cc1cn(-c2ncc(-c3ccccc3F)cn2)c2cc(C(=O)N3CCNC(=O)C3)ccc12] | 4-(1-(5-(2-fluorophenyl)pyrimidin-2-yl)-3-methyl-1H-indole-6-carbonyl)piperazin-2-one |
| 94 | 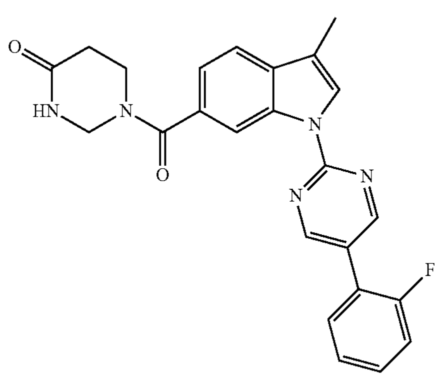 [SMILES: Cc1cn(-c2ncc(-c3ccccc3F)cn2)c2cc(C(=O)N3CCC(=O)NC3)ccc12] | 1-(1-(5-(2-fluorophenyl)pyrimidin-2-yl)-3-methyl-1H-indole-6-carbonyl)tetrahydropyrimidin-4(1H)-one |

| Cmpd-No. | Structure | Name |
|---|---|---|
| 95 | 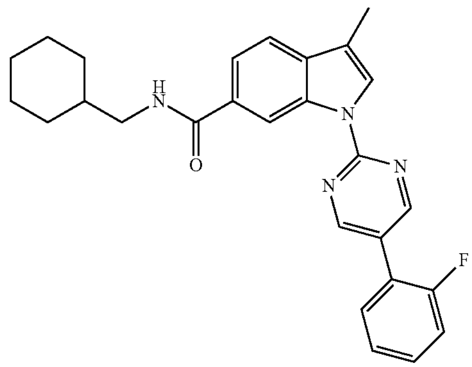 [SMILES: Cc1cn(-c2ncc(-c3ccccc3F)cn2)c2cc(C(=O)NCC3CCCCC3)ccc12] | N-(cyclohexylmethyl)-1-(5-(2-fluorophenyl)pyrimidin-2-yl)-3-methyl-1H-indole-6-carboxamide |
| 96 | 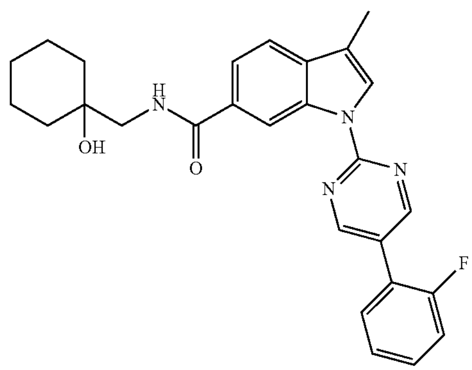 [SMILES: Cc1cn(-c2ncc(-c3ccccc3F)cn2)c2cc(C(=O)NCC3(O)CCCCC3)ccc12] | 1-(5-(2-fluorophenyl)pyrimidin-2-yl)-N-((1-hydroxycyclohexyl)methyl)-3-methyl-1H-indole-6-carboxamide |
| 97 | 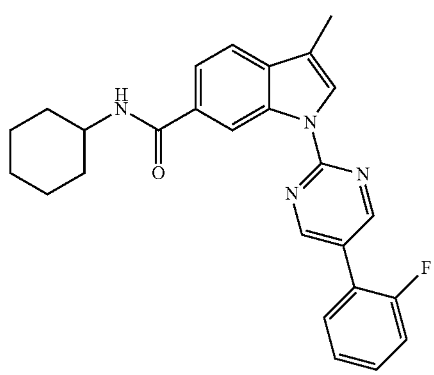 [SMILES: Cc1cn(-c2ncc(-c3ccccc3F)cn2)c2cc(C(=O)NC3CCCCC3)ccc12] | N-cyclohexyl-1-(5-(2-fluorophenyl)pyrimidin-2-yl)-3-methyl-1H-indole-6-carboxamide |
| 98 | 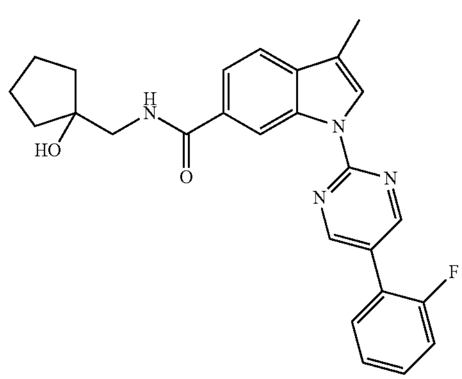 [SMILES: Cc1cn(-c2ncc(-c3ccccc3F)cn2)c2cc(C(=O)NCC3(O)CCCC3)ccc12] | 1-(5-(2-fluorophenyl)pyrimidin-2-yl)-N-((1-hydroxycyclopentyl)methyl)-3-methyl-1H-indole-6-carboxamide |

TABLE 1-continued

| Cmpd-No. | Structure | Name |
| --- | --- | --- |
| 99 | 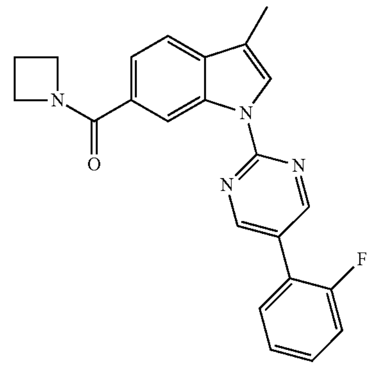 [SMILES: Cc1cn(-c2ncc(-c3ccccc3F)cn2)c2cc(C(=O)N3CCC3)ccc12] | azetidin-1-yl(1-(5-(2-fluorophenyl)pyrimidin-2-yl)-3-methyl-1H-indol-6-yl)methanone |
| 100 | 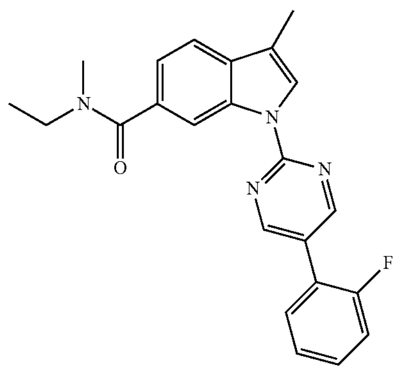 [SMILES: CCN(C)C(=O)c1ccc2c(C)cn(-c3ncc(-c4ccccc4F)cn3)c2c1] | N-ethyl-1-(5-(2-fluorophenyl)pyrimidin-2-yl)-N,3-dimethyl-1H-indole-6-carboxamide |
| 101 | 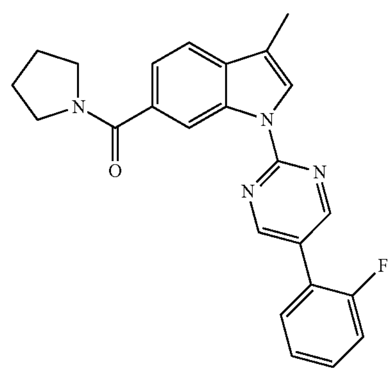 [SMILES: Cc1cn(-c2ncc(-c3ccccc3F)cn2)c2cc(C(=O)N3CCCC3)ccc12] | (1-(5-(2-fluorophenyl)pyrimidin-2-yl)-3-methyl-1H-indol-6-yl)(pyrrolidin-1-yl)methanone |
| 102 | 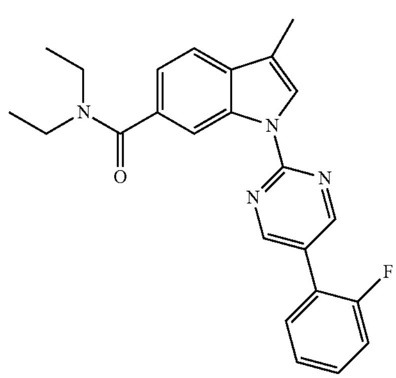 [SMILES: CCN(CC)C(=O)c1ccc2c(C)cn(-c3ncc(-c4ccccc4F)cn3)c2c1] | N,N-diethyl-1-(5-(2-fluorophenyl)pyrimidin-2-yl)-3-methyl-1H-indole-6-carboxamide |

TABLE 1-continued

| Cmpd-No. | Structure | Name |
|---|---|---|
| 103 | 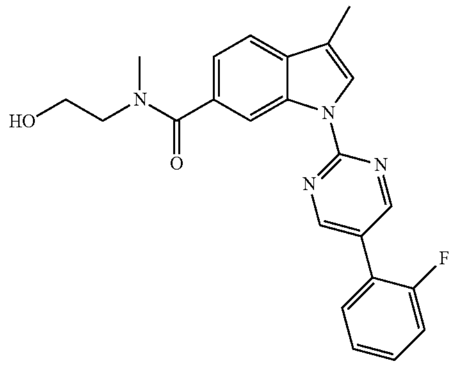 [SMILES: Cc1cn(-c2ncc(-c3ccccc3F)cn2)c2cc(C(=O)N(C)CCO)ccc12] | 1-(5-(2-fluorophenyl)pyrimidin-2-yl)-N-(2-hydroxyethyl)-N,3-dimethyl-1H-indole-6-carboxamide |
| 104 | 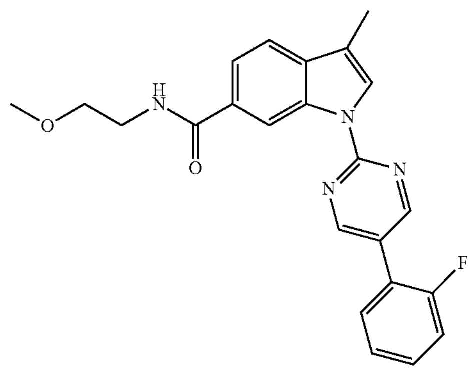 [SMILES: COCCNC(=O)c1ccc2c(C)cn(-c3ncc(-c4ccccc4F)cn3)c2c1] | 1-(5-(2-fluorophenyl)pyrimidin-2-yl)-N-(2-methoxyethyl)-3-methyl-1H-indole-6-carboxamide |
| 105 | 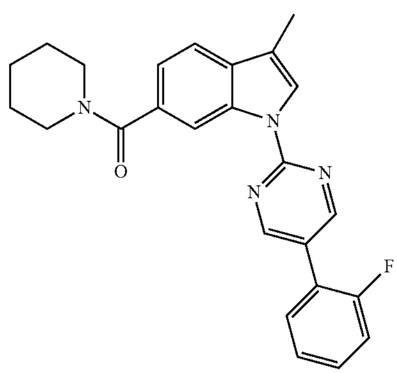 [SMILES: Cc1cn(-c2ncc(-c3ccccc3F)cn2)c2cc(C(=O)N3CCCCC3)ccc12] | (1-(5-(2-fluorophenyl)pyrimidin-2-yl)-3-methyl-1H-indol-6-yl)(piperidin-1-yl)methanone |
| 106 | 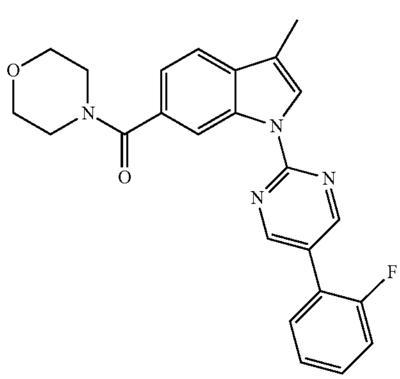 | (1-(5-(2-fluorophenyl)pyrimidin-2-yl)-3-methyl-1H-indol-6-yl)(morpholino)methanone |

TABLE 1-continued

| Cmpd-No. | Structure | Name |
|---|---|---|
| 107 | 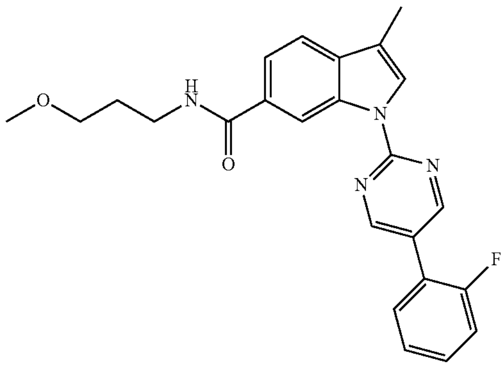 [SMILES: COCCCNC(=O)c1ccc2c(C)cn(-c3ncc(-c4ccccc4F)cn3)c2c1] | 1-(5-(2-fluorophenyl)pyrimidin-2-yl)-N-(3-methoxypropyl)-3-methyl-1H-indole-6-carboxamide |
| 108 | 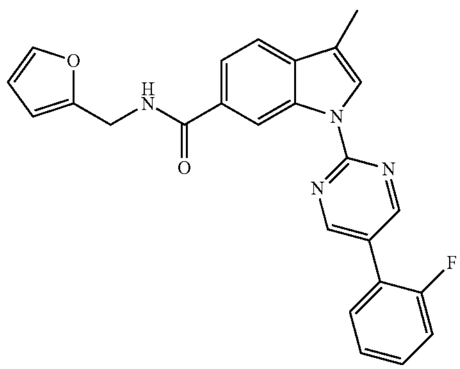 [SMILES: Cc1cn(-c2ncc(-c3ccccc3F)cn2)c2cc(C(=O)NCc3ccco3)ccc12] | 1-(5-(2-fluorophenyl)pyrimidin-2-yl)-N-(furan-2-ylmethyl)-3-methyl-1H-indole-6-carboxamide |
| 109 | 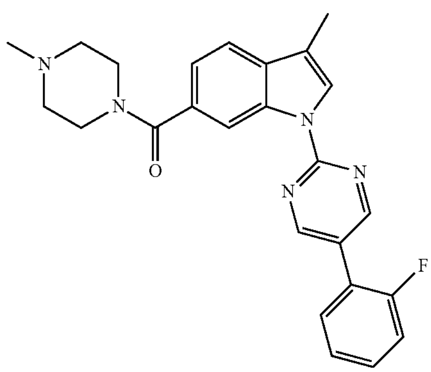 [SMILES: Cc1cn(-c2ncc(-c3ccccc3F)cn2)c2cc(C(=O)N3CCN(C)CC3)ccc12] | (1-(5-(2-fluorophenyl)pyrimidin-2-yl)-3-methyl-1H-indol-6-yl)(4-methylpiperazin-1-yl)methanone |
| 110 | 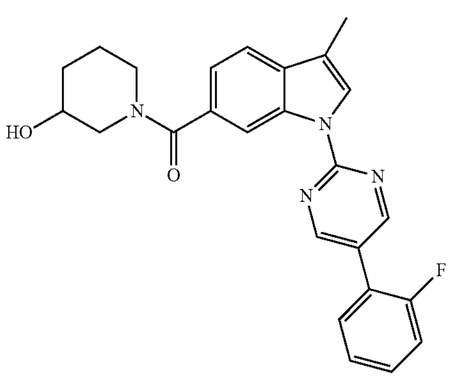 [SMILES: Cc1cn(-c2ncc(-c3ccccc3F)cn2)c2cc(C(=O)N3CCCC(O)C3)ccc12] | (1-(5-(2-fluorophenyl)pyrimidin-2-yl)-3-methyl-1H-indol-6-yl)(3-hydroxypiperidin-1-yl)methanone |

| Cmpd-No. | Structure | Name |
| --- | --- | --- |
| 111 | 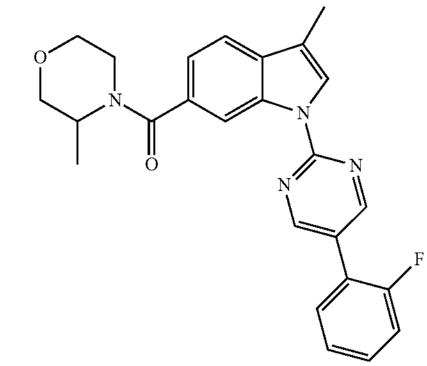 [SMILES: Cc1cn(-c2ncc(-c3ccccc3F)cn2)c2cc(C(=O)N3CCOCC3C)ccc12] | (1-(5-(2-fluorophenyl)pyrimidin-2-yl)-3-methyl-1H-indol-6-yl)(3-methylmorpholino)methanone |
| 112 | 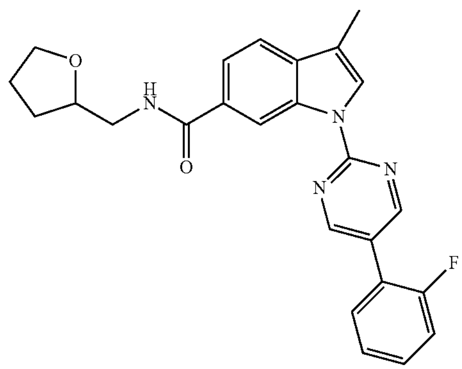 [SMILES: Cc1cn(-c2ncc(-c3ccccc3F)cn2)c2cc(C(=O)NCC3CCCO3)ccc12] | 1-(5-(2-fluorophenyl)pyrimidin-2-yl)-3-methyl-N-((tetrahydrofuran-2-yl)methyl)-1H-indole-6-carboxamide |
| 113 | 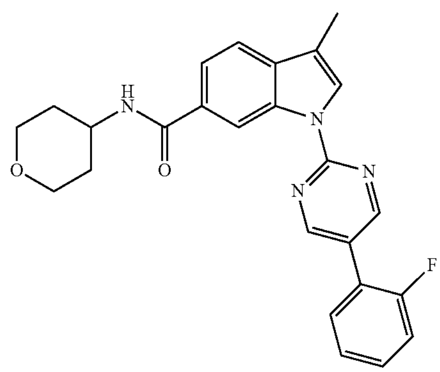 [SMILES: Cc1cn(-c2ncc(-c3ccccc3F)cn2)c2cc(C(=O)NC3CCOCC3)ccc12] | 1-(5-(2-fluorophenyl)pyrimidin-2-yl)-3-methyl-N-(tetrahydro-2H-pyran-4-yl)-1H-indole-6-carboxamide |
| 114 | 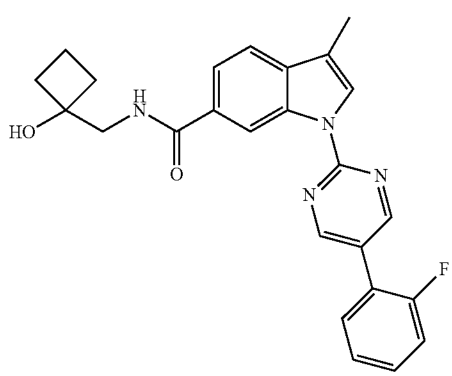 [SMILES: Cc1cn(-c2ncc(-c3ccccc3F)cn2)c2cc(C(=O)NCC3(O)CCC3)ccc12] | 1-(5-(2-fluorophenyl)pyrimidin-2-yl)-N-((1-hydroxycyclobutyl)methyl)-3-methyl-1H-indole-6-carboxamide |

TABLE 1-continued

| Cmpd-No. | Structure | Name |
|---|---|---|
| 115 | 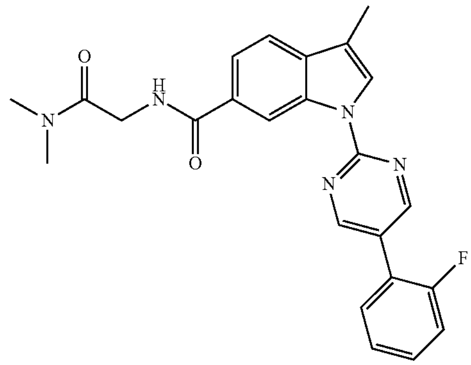 [SMILES: Cc1cn(-c2ncc(-c3ccccc3F)cn2)c2cc(C(=O)NCC(=O)N(C)C)ccc12] | N-(2-(dimethylamino)-2-oxoethyl)-1-(5-(2-fluorophenyl)pyrimidin-2-yl)-3-methyl-1H-indole-6-carboxamide |
| 116 | 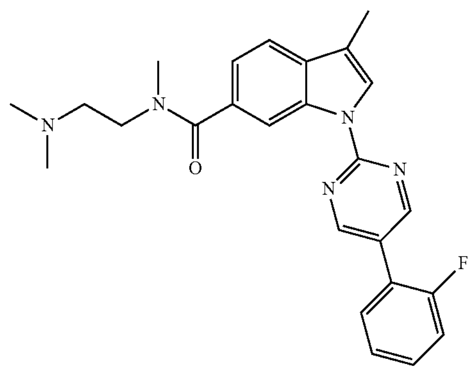 [SMILES: Cc1cn(-c2ncc(-c3ccccc3F)cn2)c2cc(C(=O)N(C)CCN(C)C)ccc12] | N-(2-(dimethylamino)ethyl)-1-(5-(2-fluorophenyl)pyrimidin-2-yl)-N,3-dimethyl-1H-indole-6-carboxamide |
| 117 | 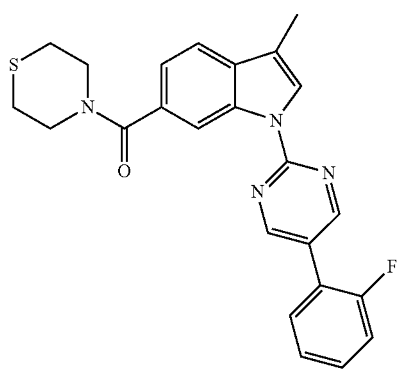 [SMILES: Cc1cn(-c2ncc(-c3ccccc3F)cn2)c2cc(C(=O)N3CCSCC3)ccc12] | (1-(5-(2-fluorophenyl)pyrimidin-2-yl)-3-methyl-1H-indol-6-yl)(thiomorpholino)methanone |
| 118 | 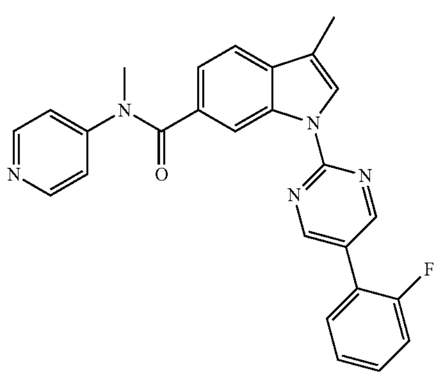 [SMILES: Cc1cn(-c2ncc(-c3ccccc3F)cn2)c2cc(C(=O)N(C)c3ccncc3)ccc12] | 1-(5-(2-fluorophenyl)pyrimidin-2-yl)-N,3-dimethyl-N-(pyridin-4-yl)-1H-indole-6-carboxamide |

| Cmpd-No. | Structure | Name |
| --- | --- | --- |
| 119 | 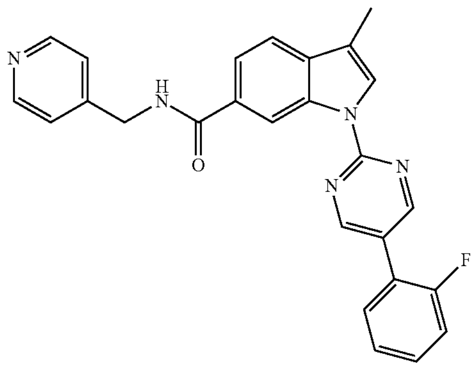 [SMILES: Cc1cn(-c2ncc(-c3ccccc3F)cn2)c2cc(C(=O)NCc3ccncc3)ccc12] | 1-(5-(2-fluorophenyl)pyrimidin-2-yl)-3-methyl-N-(pyridin-4-ylmethyl)-1H-indole-6-carboxamide |
| 120 | 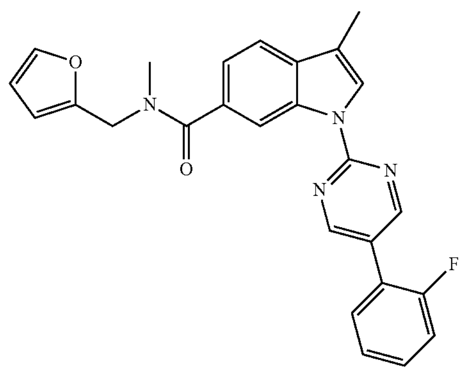 [SMILES: Cc1cn(-c2ncc(-c3ccccc3F)cn2)c2cc(C(=O)N(C)Cc3ccco3)ccc12] | 1-(5-(2-fluorophenyl)pyrimidin-2-yl)-N-(furan-2-ylmethyl)-N,3-dimethyl-1H-indole-6-carboxamide |
| 121 | 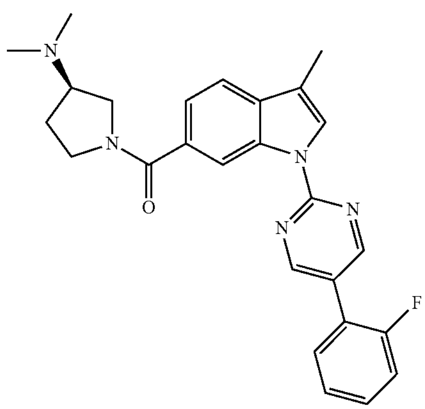 [SMILES: Cc1cn(-c2ncc(-c3ccccc3F)cn2)c2cc(C(=O)N3CC[C@@H](N(C)C)C3)ccc12] | (R)-(3-(dimethylamino)pyrrolidin-1-yl)(1-(5-(2-fluorophenyl)pyrimidin-2-yl)-3-methyl-1H-indol-6-yl)methanone |
| 122 | 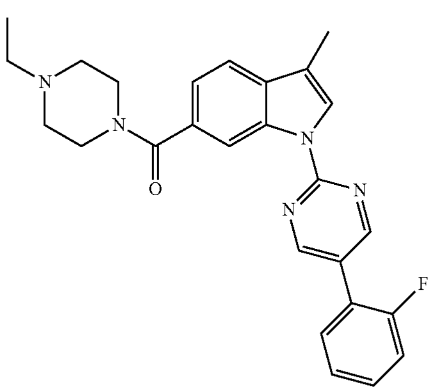 [SMILES: CCN1CCN(C(=O)c2ccc3c(C)cn(-c4ncc(-c5ccccc5F)cn4)c3c2)CC1] | (4-ethylpiperazin-1-yl)(1-(5-(2-fluorophenyl)pyrimidin-2-yl)-3-methyl-1H-indol-6-yl)methanone |

TABLE 1-continued

| Cmpd-No. | Structure | Name |
|---|---|---|
| 123 | 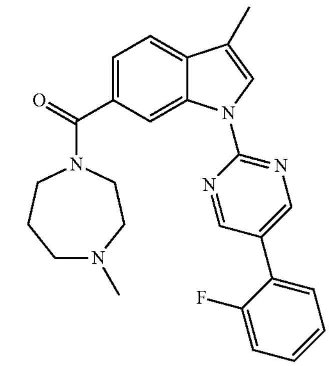 [SMILES: Cc1cn(-c2ncc(-c3ccccc3F)cn2)c2cc(C(=O)N3CCCN(C)CC3)ccc12] | (1-(5-(2-fluorophenyl)pyrimidin-2-yl)-3-methyl-1H-indol-6-yl)(4-methyl-1,4-diazepan-1-yl)methanone |
| 124 | 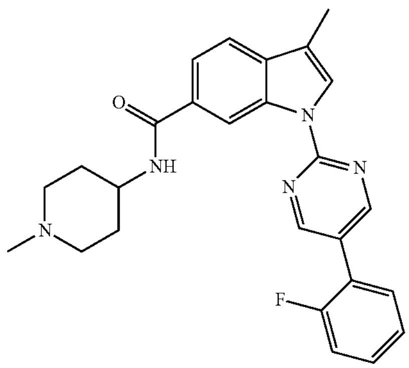 [SMILES: Cc1cn(-c2ncc(-c3ccccc3F)cn2)c2cc(C(=O)NC3CCN(C)CC3)ccc12] | 1-(5-(2-fluorophenyl)pyrimidin-2-yl)-3-methyl-N-(1-methylpiperidin-4-yl)-1H-indole-6-carboxamide |
| 125 | 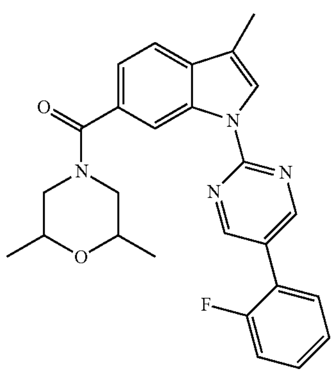 [SMILES: Cc1cn(-c2ncc(-c3ccccc3F)cn2)c2cc(C(=O)N3CC(C)OC(C)C3)ccc12] | (2,6-dimethylmorpholino)(1-(5-(2-fluorophenyl)pyrimidin-2-yl)-3-methyl-1H-indol-6-yl)methanone (isomer 1) |
| 126 | 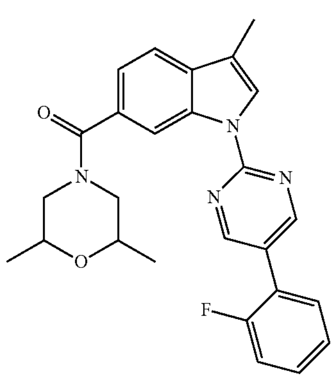 [SMILES: Cc1cn(-c2ncc(-c3ccccc3F)cn2)c2cc(C(=O)N3CC(C)OC(C)C3)ccc12] | (2,6-dimethylmorpholino)(1-(5-(2-fluorophenyl)pyrimidin-2-yl)-3-methyl-1H-indol-6-yl)methanone (isomer 2) |

TABLE 1-continued

| Cmpd-No. | Structure | Name |
| --- | --- | --- |
| 127 | 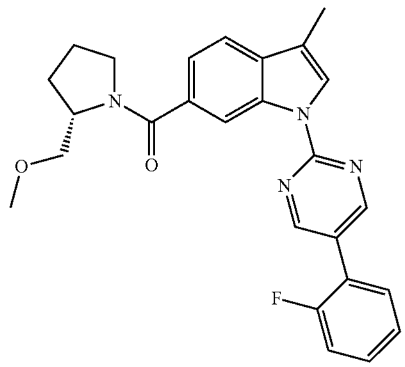 [SMILES: COC[C@@H]1CCCN1C(=O)c1ccc2c(C)cn(-c3ncc(-c4ccccc4F)cn3)c2c1] | (S)-(1-(5-(2-fluorophenyl)pyrimidin-2-yl)-3-methyl-1H-indol-6-yl)(2-(methoxymethyl)pyrrolidin-1-yl)methanone |
| 128 | 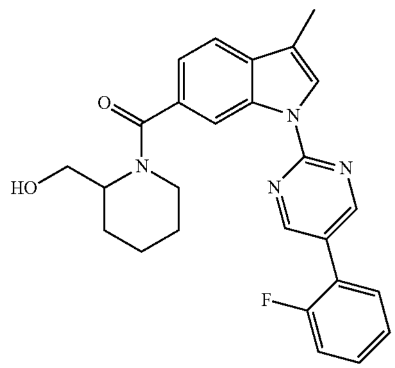 [SMILES: Cc1cn(-c2ncc(-c3ccccc3F)cn2)c2cc(C(=O)N3CCCCC3CO)ccc12] | (1-(5-(2-fluorophenyl)pyrimidin-2-yl)-3-methyl-1H-indol-6-yl)(2-(hydroxymethyl)piperidin-1-yl)methanone |
| 129 | 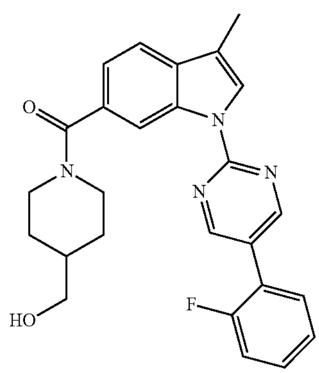 [SMILES: Cc1cn(-c2ncc(-c3ccccc3F)cn2)c2cc(C(=O)N3CCC(CO)CC3)ccc12] | (1-(5-(2-fluorophenyl)pyrimidin-2-yl)-3-methyl-1H-indol-6-yl)(4-(hydroxymethyl)piperidin-1-yl)methanone |
| 130 | 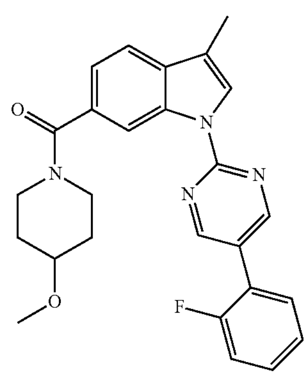 [SMILES: COC1CCN(C(=O)c2ccc3c(C)cn(-c4ncc(-c5ccccc5F)cn4)c3c2)CC1] | (1-(5-(2-fluorophenyl)pyrimidin-2-yl)-3-methyl-1H-indol-6-yl)(4-methoxypiperidin-1-yl)methanone |

| Cmpd-No. | Structure | Name |
|---|---|---|
| 131 | 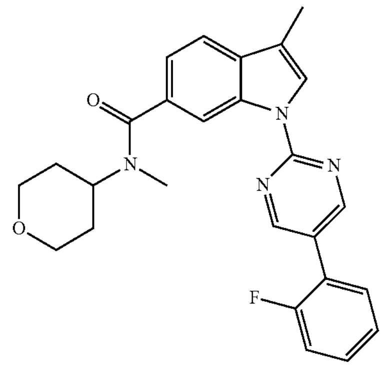 [SMILES: Cc1cn(-c2ncc(-c3ccccc3F)cn2)c2cc(C(=O)N(C)C3CCOCC3)ccc12] | 1-(5-(2-fluorophenyl)pyrimidin-2-yl)-N,3-dimethyl-N-(tetrahydro-2H-pyran-4-yl)-1H-indole-6-carboxamide |
| 132 | 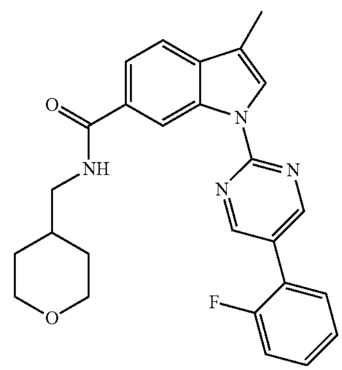 [SMILES: Cc1cn(-c2ncc(-c3ccccc3F)cn2)c2cc(C(=O)NCC3CCOCC3)ccc12] | 1-(5-(2-fluorophenyl)pyrimidin-2-yl)-3-methyl-N-((tetrahydro-2H-pyran-4-yl)methyl)-1H-indole-6-carboxamide |
| 133 | 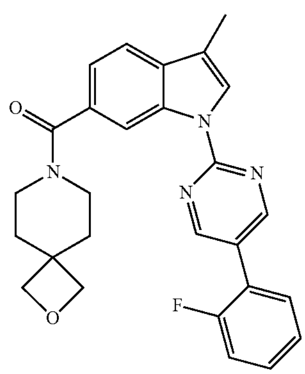 [SMILES: Cc1cn(-c2ncc(-c3ccccc3F)cn2)c2cc(C(=O)N3CCC4(CC3)COC4)ccc12] | (1-(5-(2-fluorophenyl)pyrimidin-2-yl)-3-methyl-1H-indol-6-yl)(2-oxa-7-azaspiro[3.5]nonan-7-yl)methanone |
| 134 | 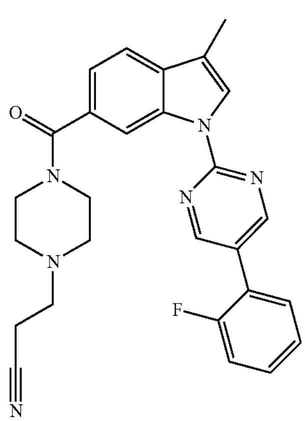 [SMILES: Cc1cn(-c2ncc(-c3ccccc3F)cn2)c2cc(C(=O)N3CCN(CCC#N)CC3)ccc12] | 3-(4-(1-(5-(2-fluorophenyl)pyrimidin-2-yl)-3-methyl-1H-indole-6-carbonyl)piperazin-1-yl)propanenitrile |

TABLE 1-continued

| Cmpd-No. | Structure | Name |
|---|---|---|
| 135 | 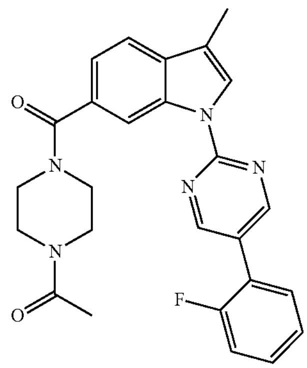 [SMILES: CC(=O)N1CCN(C(=O)c2ccc3c(C)cn(-c4ncc(-c5ccccc5F)cn4)c3c2)CC1] | 1-(4-(1-(5-(2-fluorophenyl)pyrimidin-2-yl)-3-methyl-1H-indole-6-carbonyl)piperazin-1-yl)ethanone |
| 136 | 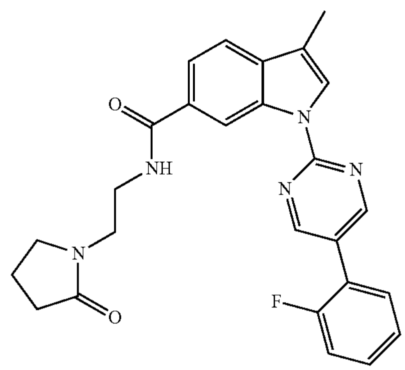 [SMILES: Cc1cn(-c2ncc(-c3ccccc3F)cn2)c2cc(C(=O)NCCN3CCCC3=O)ccc12] | 1-(5-(2-fluorophenyl)pyrimidin-2-yl)-3-methyl-N-(2-(2-oxopyrrolidin-1-yl)ethyl)-1H-indole-6-carboxamide |
| 137 | 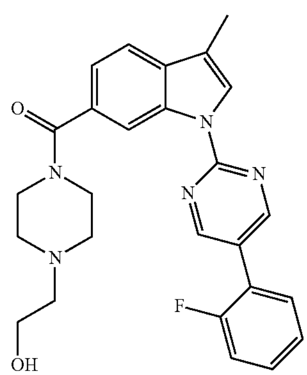 [SMILES: Cc1cn(-c2ncc(-c3ccccc3F)cn2)c2cc(C(=O)N3CCN(CCO)CC3)ccc12] | (1-(5-(2-fluorophenyl)pyrimidin-2-yl)-3-methyl-1H-indol-6-yl)(4-(2-hydroxyethyl)piperazin-1-yl)methanone |
| 138 | 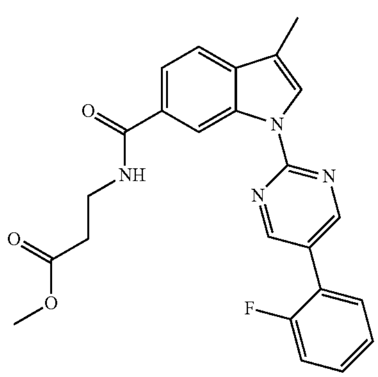 [SMILES: COC(=O)CCNC(=O)c1ccc2c(C)cn(-c3ncc(-c4ccccc4F)cn3)c2c1] | methyl 3-(1-(5-(2-fluorophenyl)pyrimidin-2-yl)-3-methyl-1H-indole-6-carboxamido)propanoate |

TABLE 1-continued

| Cmpd-No. | Structure | Name |
|---|---|---|
| 139 | 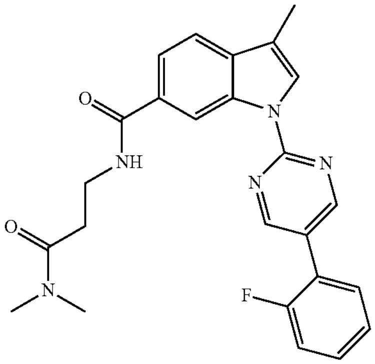 [SMILES: Cc1cn(-c2ncc(-c3ccccc3F)cn2)c2cc(C(=O)NCCC(=O)N(C)C)ccc12] | N-(3-(dimethylamino)-3-oxopropyl)-1-(5-(2-fluorophenyl)pyrimidin-2-yl)-3-methyl-1H-indole-6-carboxamide |
| 140 | 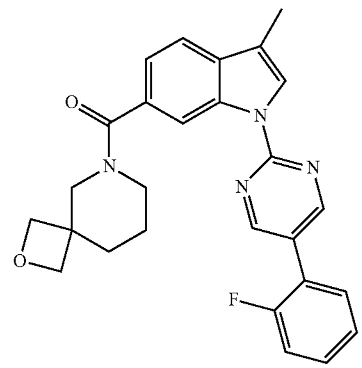 [SMILES: Cc1cn(-c2ncc(-c3ccccc3F)cn2)c2cc(C(=O)N3CCCC4(COC4)C3)ccc12] | (1-(5-(2-fluorophenyl)pyrimidin-2-yl)-3-methyl-1H-indol-6-yl)(2-oxa-6-azaspiro[3.5]nonan-6-yl)methanone |
| 141 | 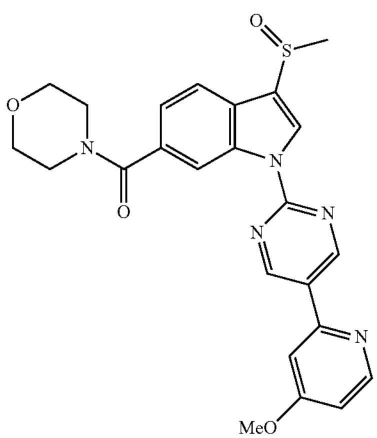 [SMILES: COc1ccnc(-c2cnc(-n3cc(S(C)=O)c4ccc(C(=O)N5CCOCC5)cc43)nc2)c1] | (1-(5-(4-Methoxypyridin-2-yl)pyrimidin-2-yl)-3-(methylsulfinyl)-1H-indol-6-yl)(morpholino)methanone |
| 142 | 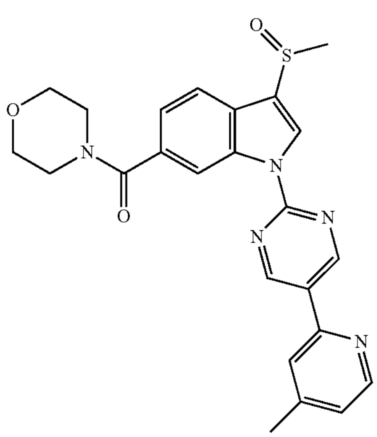 [SMILES: Cc1ccnc(-c2cnc(-n3cc(S(C)=O)c4ccc(C(=O)N5CCOCC5)cc43)nc2)c1] | (1-(5-(4-Methylpyridin-2-yl)pyrimidin-2-yl)-3-(methylsulfinyl)-1H-indol-6-yl)(morpholino)methanone |

| Cmpd-No. | Structure | Name |
|---|---|---|
| 143 | 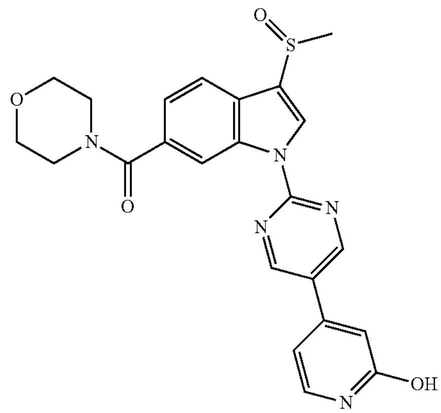 [SMILES: CS(=O)c1cn(-c2ncc(-c3ccnc(O)c3)cn2)c2cc(C(=O)N3CCOCC3)ccc12] | (1-(5-(2-Hydroxypyridin-4-yl)pyrimidin-2-yl)-3-(methylsulfinyl)-1H-indol-6-yl)(morpholino)methanone |
| 144 | 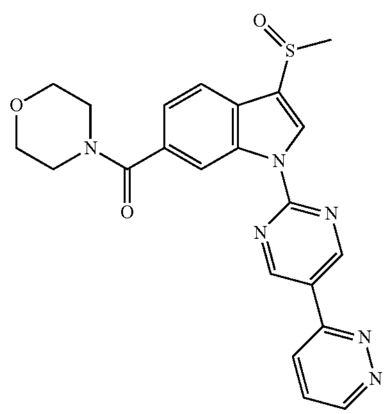 [SMILES: CS(=O)c1cn(-c2ncc(-c3cccnn3)cn2)c2cc(C(=O)N3CCOCC3)ccc12] | (3-(Methylsulfinyl)-1-(5-(pyridazin-3-yl)pyrimidin-2-yl)-1H-indol-6-yl)(morpholino)methanone |
| 145 | 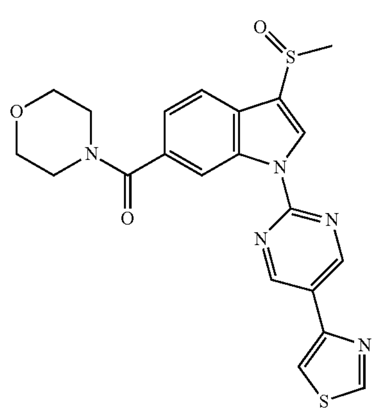 [SMILES: CS(=O)c1cn(-c2ncc(-c3cscn3)cn2)c2cc(C(=O)N3CCOCC3)ccc12] | (3-(Methylsulfinyl)-1-(5-(thiazol-4-yl)pyrimidin-2-yl)-1H-indol-6-yl)(morpholino)methanone |

TABLE 1-continued

| Cmpd-No. | Structure | Name |
|---|---|---|
| 146 | 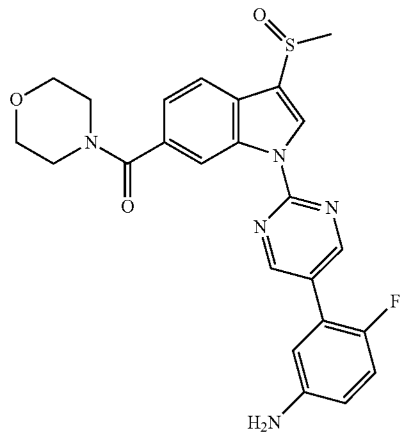 [SMILES: CS(=O)c1cn(-c2ncc(-c3cc(N)ccc3F)cn2)c2cc(C(=O)N3CCOCC3)ccc12] | (1-(5-(5-Amino-2-fluorophenyl)pyrimidin-2-yl)-3-(methylsulfinyl)-1H-indol-6-yl)(morpholino)methanone |
| 147 | 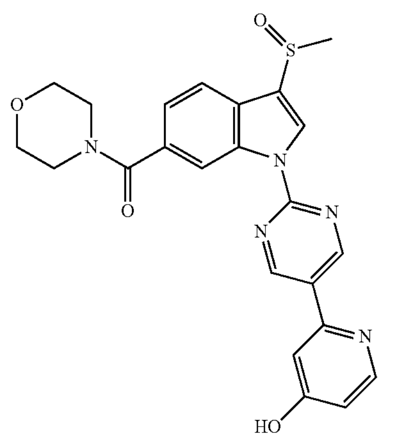 [SMILES: CS(=O)c1cn(-c2ncc(-c3cc(O)ccn3)cn2)c2cc(C(=O)N3CCOCC3)ccc12] | (1-(5-(4-Hydroxypyridin-2-yl)pyrimidin-2-yl)-3-(methylsulfinyl)-1H-indol-6-yl)(morpholino)methanone |
| 148 | 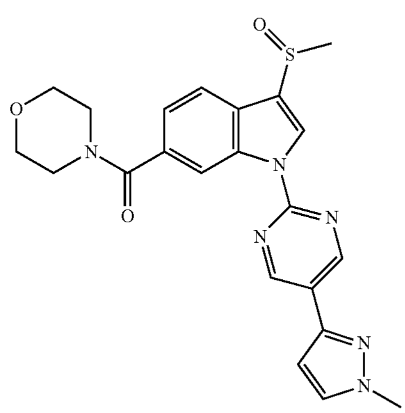 [SMILES: Cn1ccc(-c2cnc(-n3cc(S(C)=O)c4ccc(C(=O)N5CCOCC5)cc43)nc2)n1] | (1-(5-(1-Methyl-1H-pyrazol-4-yl)pyrimidin-2-yl)-3-(methylsulfinyl)-1H-indol-6-yl)(morpholino)methanone |

| Cmpd-No. | Structure | Name |
|---|---|---|
| 149 | 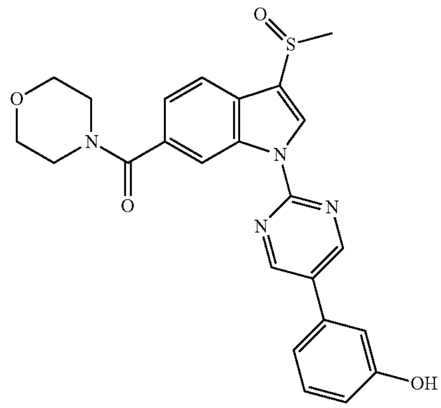 [SMILES: CS(=O)c1cn(-c2ncc(-c3cccc(O)c3)cn2)c2cc(C(=O)N3CCOCC3)ccc12] | (1-(5-(3-Hydroxyphenyl)pyrimidin-2-yl)-3-(methylsulfinyl)-1H-indol-6-yl)(morpholino)methanone |
| 150 | 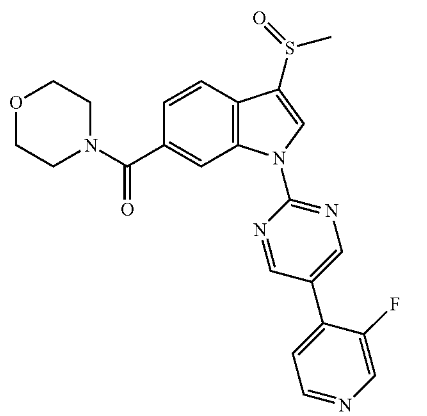 [SMILES: CS(=O)c1cn(-c2ncc(-c3ccncc3F)cn2)c2cc(C(=O)N3CCOCC3)ccc12] | (1-(5-(3-Fluoropyridin-4-yl)pyrimidin-2-yl)-3-(methylsulfinyl)-1H-indol-6-yl)(morpholino)methanone |
| 151 | 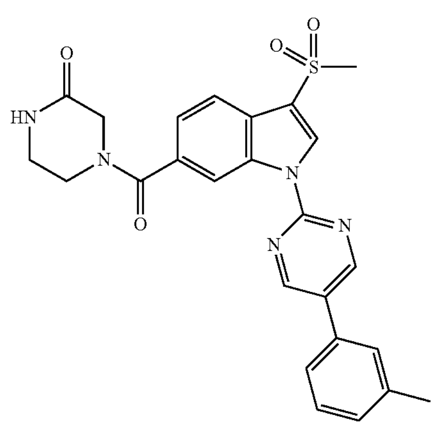 [SMILES: Cc1cccc(-c2cnc(-n3cc(S(C)(=O)=O)c4ccc(C(=O)N5CCNC(=O)C5)cc43)nc2)c1] | 4-(3-(Methylsulfonyl)-1-(5-(m-tolyl)pyrimidin-2-yl)-1H-indole-6-carbonyl)piperazin-2-one |

| Cmpd-No. | Structure | Name |
|---|---|---|
| 152 | 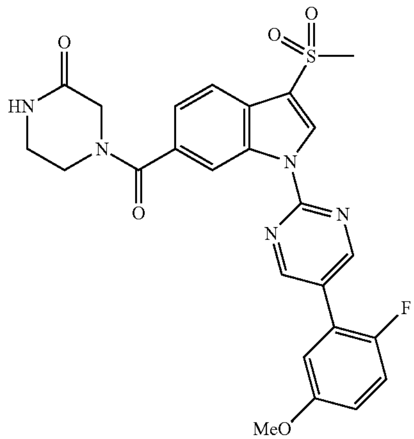 [SMILES: COc1ccc(F)c(-c2cnc(-n3cc(S(C)(=O)=O)c4ccc(C(=O)N5CCNC(=O)C5)cc43)nc2)c1] | 4-(1-(5-(2-Fluoro-5-methoxyphenyl)pyrimidin-2-yl)-3-(methylsulfonyl)-1H-indole-6-carbonyl)piperazin-2-one |
| 153 | 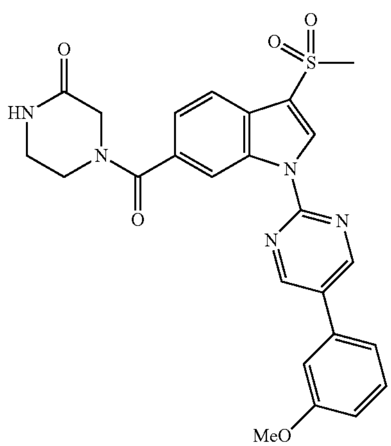 [SMILES: COc1cccc(-c2cnc(-n3cc(S(C)(=O)=O)c4ccc(C(=O)N5CCNC(=O)C5)cc43)nc2)c1] | 4-(1-(5-(3-Methoxyphenyl)pyrimidin-2-yl)-3-(methylsulfonyl)-1H-indole-6-carbonyl)piperazin-2-one |
| 154 | 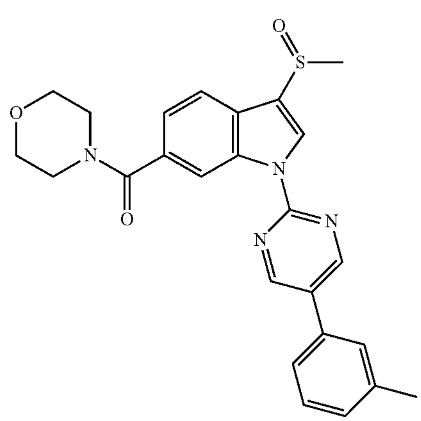 [SMILES: Cc1cccc(-c2cnc(-n3cc(S(C)=O)c4ccc(C(=O)N5CCOCC5)cc43)nc2)c1] | (3-(Methylsulfinyl)-1-(5-(m-tolyl)pyrimidin-2-yl)-1H-indol-6-yl)(morpholino)methanone (Enantiomer 1) |

TABLE 1-continued

| Cmpd-No. | Structure | Name |
|---|---|---|
| 155 | 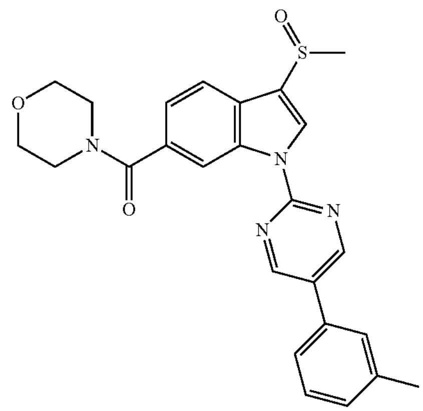 [SMILES: Cc1cccc(-c2cnc(-n3cc(S(C)=O)c4ccc(C(=O)N5CCOCC5)cc43)nc2)c1] | (3-(Methylsulfinyl)-1-(5-(m-tolyl)pyrimidin-2-yl)-1H-indol-6-yl)(morpholino)methanone (Enantiomer 2) |
| 156 | 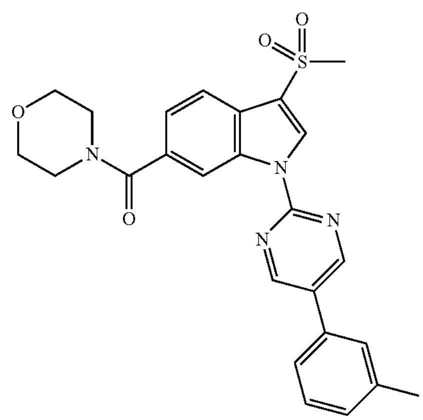 [SMILES: Cc1cccc(-c2cnc(-n3cc(S(C)(=O)=O)c4ccc(C(=O)N5CCOCC5)cc43)nc2)c1] | (3-(Methylsulfonyl)-1-(5-(m-tolyl)pyrimidin-2-yl)-1H-indol-6-yl)(morpholino)methanone |
| 157 | 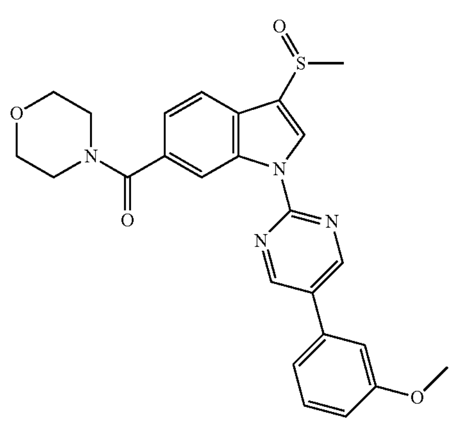 [SMILES: COc1cccc(-c2cnc(-n3cc(S(C)=O)c4ccc(C(=O)N5CCOCC5)cc43)nc2)c1] | (1-(5-(3-Methoxyphenyl)pyrimidin-2-yl)-3-(methylsulfinyl)-1H-indol-6-yl)(morpholino)methanone (Enantiomer 1) |

TABLE 1-continued

| Cmpd-No. | Structure | Name |
|---|---|---|
| 158 | 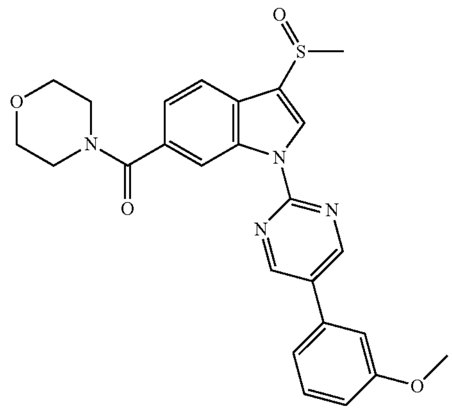 [SMILES: COc1cccc(-c2cnc(-n3cc(S(C)=O)c4ccc(C(=O)N5CCOCC5)cc43)nc2)c1] | (1-(5-(3-Methoxyphenyl)pyrimidin-2-yl)-3-(methylsulfinyl)-1H-indol-6-yl)(morpholino)methanone (Enantiomer 2) |
| 159 | 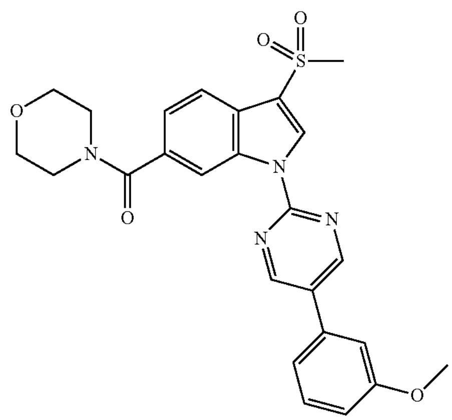 [SMILES: COc1cccc(-c2cnc(-n3cc(S(C)(=O)=O)c4ccc(C(=O)N5CCOCC5)cc43)nc2)c1] | (1-(5-(3-Methoxyphenyl)pyrimidin-2-yl)-3-(methylsulfonyl)-1H-indol-6-yl)(morpholino)methanone |
| 160 | 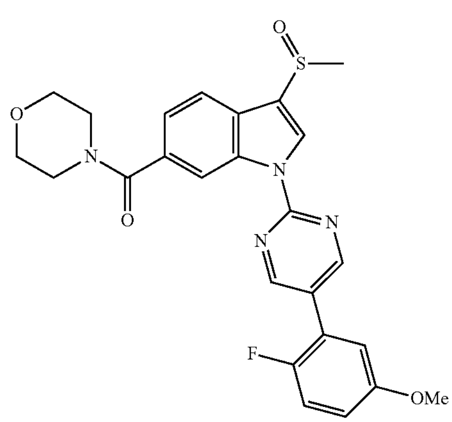 [SMILES: COc1ccc(F)c(-c2cnc(-n3cc(S(C)=O)c4ccc(C(=O)N5CCOCC5)cc43)nc2)c1] | (1-(5-(2-Fluoro-5-methoxyphenyl)pyrimidin-2-yl)-3-(methylsulfinyl)-1H-indol-6-yl)(morpholino)methanone (Enantiomer 1) |

TABLE 1-continued

| Cmpd-No. | Structure | Name |
|---|---|---|
| 161 | 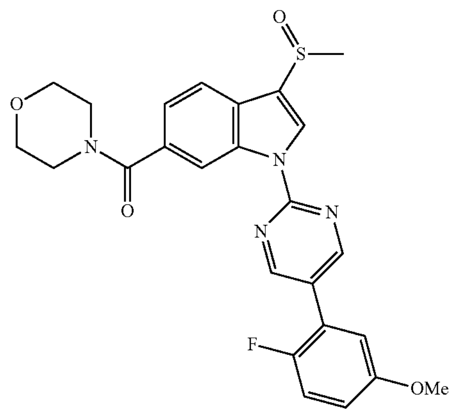 [SMILES: COc1ccc(F)c(-c2cnc(-n3cc(S(C)=O)c4ccc(C(=O)N5CCOCC5)cc43)nc2)c1] | (1-(5-(2-Fluoro-5-methoxyphenyl)pyrimidin-2-yl)-3-(methylsulfinyl)-1H-indol-6-yl)(morpholino)methanone (Enantiomer 2) |
| 162 | 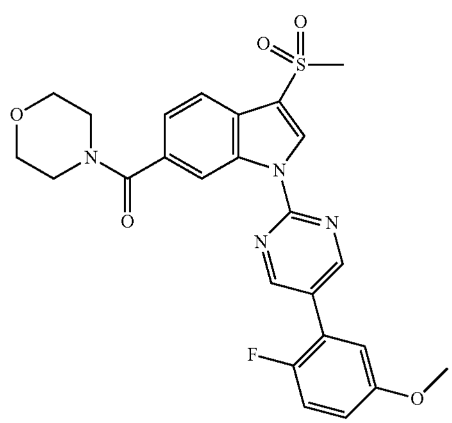 [SMILES: COc1ccc(F)c(-c2cnc(-n3cc(S(C)(=O)=O)c4ccc(C(=O)N5CCOCC5)cc43)nc2)c1] | (1-(5-(2-Fluoro-5-methoxyphenyl)pyrimidin-2-yl)-3-(methylsulfonyl)-1H-indol-6-yl)(morpholino)methanone |
| 163 | 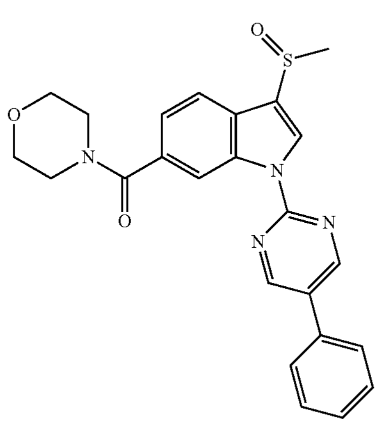 [SMILES: CS(=O)c1cn(-c2ncc(-c3ccccc3)cn2)c2cc(C(=O)N3CCOCC3)ccc12] | (3-(Methylsulfinyl)-1-(5-phenylpyrimidin-2-yl)-1H-indol-6-yl)(morpholino)methanone (Enantiomer 1) |

TABLE 1-continued

| Cmpd-No. | Structure | Name |
|---|---|---|
| 164 | 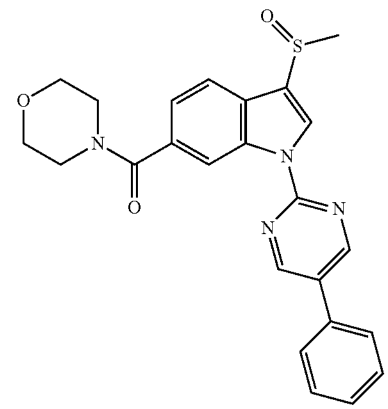 [SMILES: CS(=O)c1cn(-c2ncc(-c3ccccc3)cn2)c2cc(C(=O)N3CCOCC3)ccc12] | (3-(Methylsulfinyl)-1-(5-phenylpyrimidin-2-yl)-1H-indol-6-yl)(morpholino)methanone (Enantiomer 2) |
| 165 | 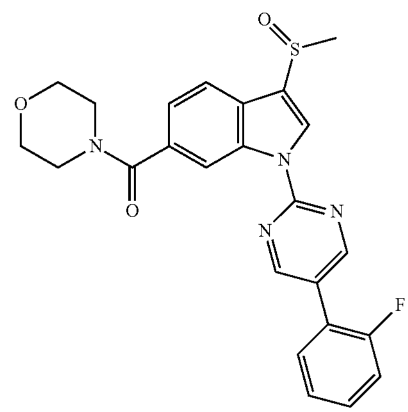 [SMILES: CS(=O)c1cn(-c2ncc(-c3ccccc3F)cn2)c2cc(C(=O)N3CCOCC3)ccc12] | (1-(5-(2-Fluorophenyl)pyrimidin-2-yl)-3-(methylsulfinyl)-1H-indol-6-yl)(morpholino)methanone (Enantiomer 1) |
| 166 | 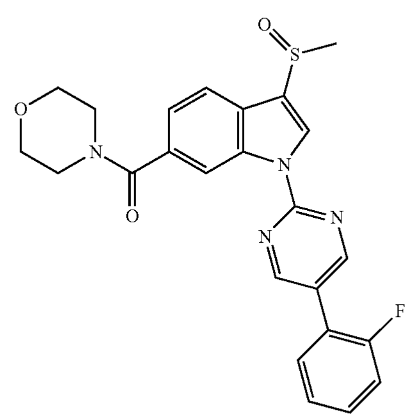 [SMILES: CS(=O)c1cn(-c2ncc(-c3ccccc3F)cn2)c2cc(C(=O)N3CCOCC3)ccc12] | (1-(5-(2-Fluorophenyl)pyrimidin-2-yl)-3-(methylsulfinyl)-1H-indol-6-yl)(morpholino)methanone (Enantiomer 2) |

TABLE 1-continued

| Cmpd-No. | Structure | Name |
|---|---|---|
| 167 | 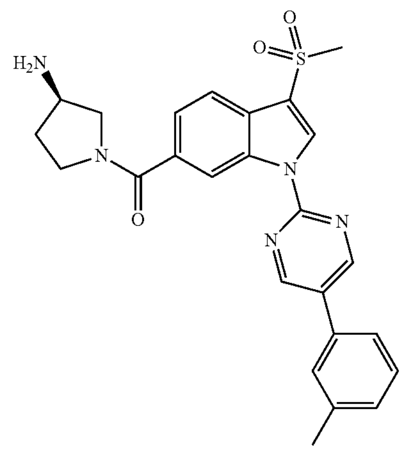 [SMILES: Cc1cccc(-c2cnc(-n3cc(S(C)(=O)=O)c4ccc(C(=O)N5CC[C@@H](N)C5)cc43)nc2)c1] | (R)-(3-Aminopyrrolidin-1-yl)(3-(methylsulfonyl)-1-(5-(m-tolyl)pyrimidin-2-yl)-1H-indol-6-yl)methanone |
| 168 | 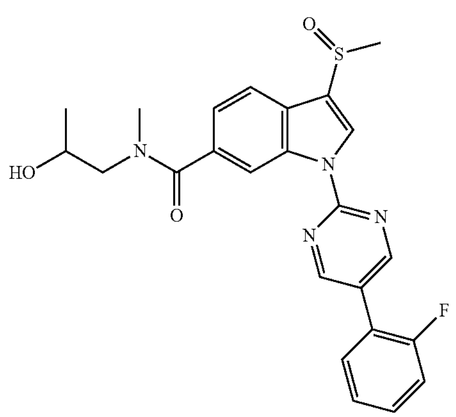 [SMILES: CC(O)CN(C)C(=O)c1ccc2c(S(C)=O)cn(-c3ncc(-c4ccccc4F)cn3)c2c1] | 1-(5-(2-Fluorophenyl)pyrimidin-2-yl)-N-(2-hydroxypropyl)-N-methyl-3-(methylsulfinyl)-1H-indole-6-carboxamide |
| 169 | 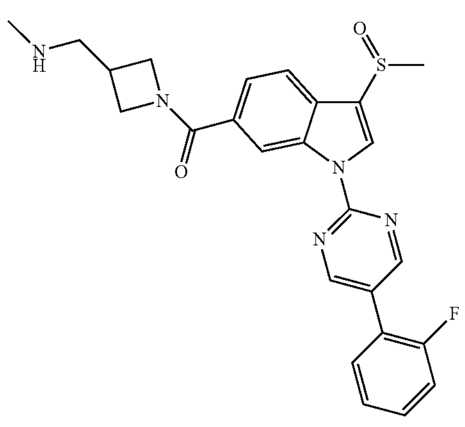 [SMILES: CNCC1CN(C(=O)c2ccc3c(S(C)=O)cn(-c4ncc(-c5ccccc5F)cn4)c3c2)C1] | (1-(5-(2-Fluorophenyl)pyrimidin-2-yl)-3-(methylsulfinyl)-1H-indol-6-yl)(3-((methylamino)methyl)azetidin-1-yl)methanone |

TABLE 1-continued

| Cmpd-No. | Structure | Name |
|---|---|---|
| 170 | 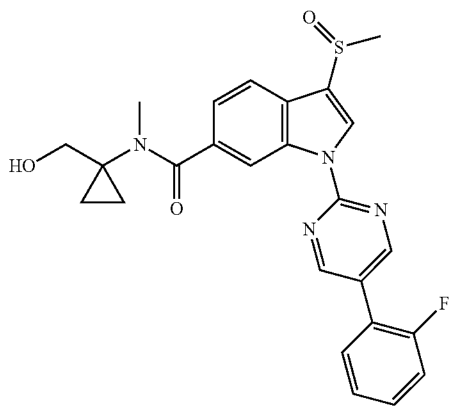 [SMILES: CN(C(=O)c1ccc2c(S(C)=O)cn(-c3ncc(-c4ccccc4F)cn3)c2c1)C1(CO)CC1] | 1-(5-(2-Fluorophenyl)pyrimidin-2-yl)-N-(1-(hydroxymethyl)cyclopropyl)-N-methyl-3-(methylsulfinyl)-1H-indole-6-carboxamide |
| 171 | 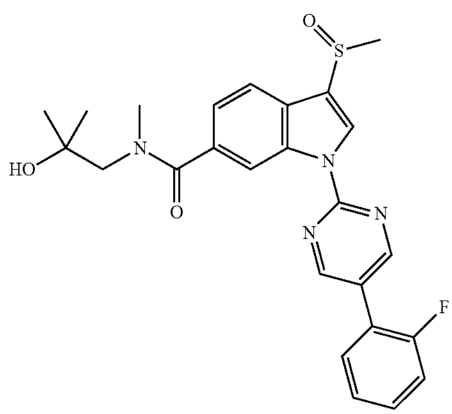 [SMILES: CN(CC(C)(C)O)C(=O)c1ccc2c(S(C)=O)cn(-c3ncc(-c4ccccc4F)cn3)c2c1] | 1-(5-(2-Fluorophenyl)pyrimidin-2-yl)-N-(2-hydroxy-2-methylpropyl)-N-methyl-3-(methylsulfinyl)-1H-indole-6-carboxamide |
| 172 | 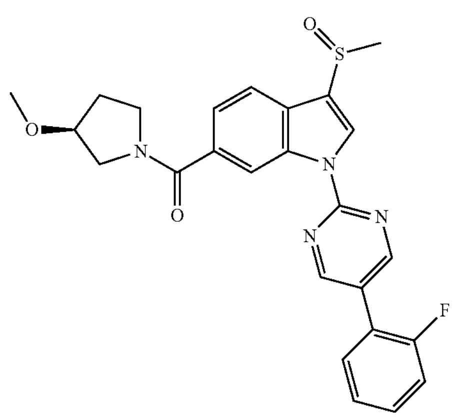 [SMILES: CO[C@H]1CCN(C(=O)c2ccc3c(S(C)=O)cn(-c4ncc(-c5ccccc5F)cn4)c3c2)C1] | (1-(5-(2-Fluorophenyl)pyrimidin-2-yl)-3-(methylsulfinyl)-1H-indol-6-yl)((S)-3-methoxypyrrolidin-1-yl)methanone |

TABLE 1-continued

| Cmpd-No. | Structure | Name |
|---|---|---|
| 173 | 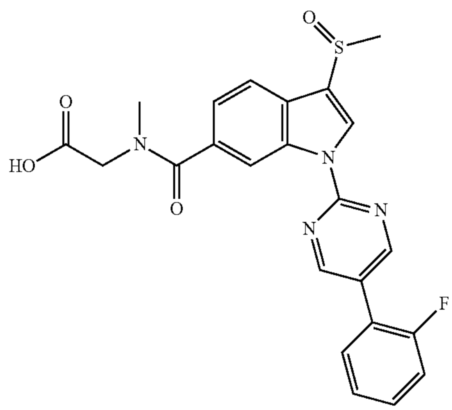 [SMILES: CN(CC(=O)O)C(=O)c1ccc2c(S(C)=O)cn(-c3ncc(-c4ccccc4F)cn3)c2c1] | 2-(1-(5-(2-Fluorophenyl)pyrimidin-2-yl)-N-methyl-3-(methylsulfinyl)-1H-indole-6-carboxamido)acetic acid |
| 174 | 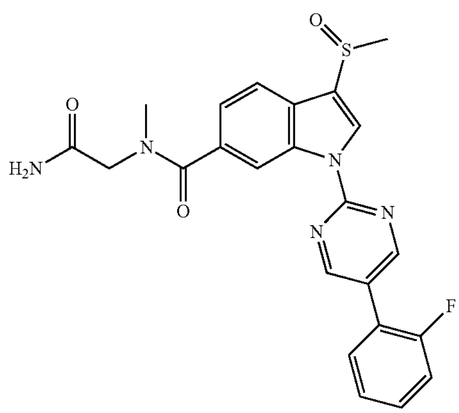 [SMILES: CN(CC(N)=O)C(=O)c1ccc2c(S(C)=O)cn(-c3ncc(-c4ccccc4F)cn3)c2c1] | N-(2-Amino-2-oxoethyl)-1-(5-(2-fluorophenyl)pyrimidin-2-yl)-N-methyl-3-(methylsulfinyl)-1H-indole-6-carboxamide |
| 175 | 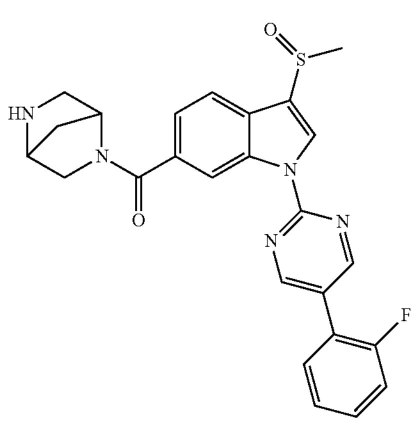 [SMILES: CS(=O)c1cn(-c2ncc(-c3ccccc3F)cn2)c2cc(C(=O)N3CC4CC3CN4)ccc12] | 2,5-Diazabicyclo[2.2.1]heptan-2-yl(1-(5-(2-fluorophenyl)pyrimidin-2-yl)-3-(methylsulfinyl)-1H-indol-6-yl)methanone |

| Cmpd-No. | Structure | Name |
|---|---|---|
| 176 | 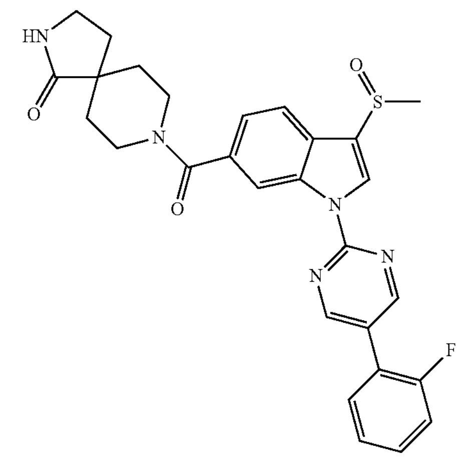 [SMILES: CS(=O)c1cn(-c2ncc(-c3ccccc3F)cn2)c2cc(C(=O)N3CCC4(CCNC4=O)CC3)ccc12] | 8-(1-(5-(2-Fluorophenyl)pyrimidin-2-yl)-3-(methylsulfinyl)-1H-indole-6-carbonyl)-2,8-diazaspiro[4.5]decan-1-one |
| 177 | 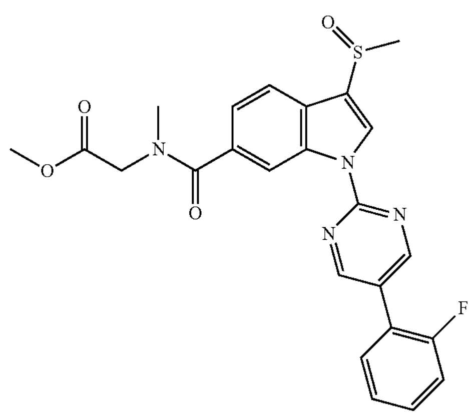 [SMILES: COC(=O)CN(C)C(=O)c1ccc2c(S(C)=O)cn(-c3ncc(-c4ccccc4F)cn3)c2c1] | Methyl 2-(1-(5-(2-fluorophenyl)pyrimidin-2-yl)-N-methyl-3-(methylsulfinyl)-1H-indole-6-carboxamido)acetate |
| 178 | 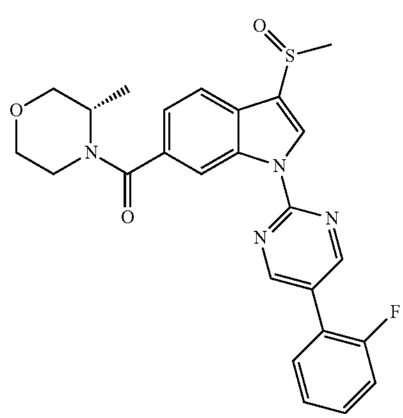 [SMILES: C[C@H]1COCCN1C(=O)c1ccc2c(S(C)=O)cn(-c3ncc(-c4ccccc4F)cn3)c2c1] | (1-(5-(2-Fluorophenyl)pyrimidin-2-yl)-3-(methylsulfinyl)-1H-indol-6-yl)((S)-3-methylmorpholino)methanone |

TABLE 1-continued

| Cmpd-No. | Structure | Name |
| --- | --- | --- |
| 179 | 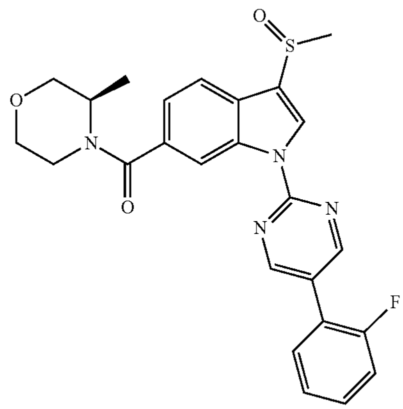 [SMILES: C[C@@H]1COCCN1C(=O)c1ccc2c(S(C)=O)cn(-c3ncc(-c4ccccc4F)cn3)c2c1] | (1-(5-(2-Fluorophenyl)pyrimidin-2-yl)-3-(methylsulfinyl)-1H-indol-6-yl)((R)-3-methylmorpholino)methanone |
| 180 | 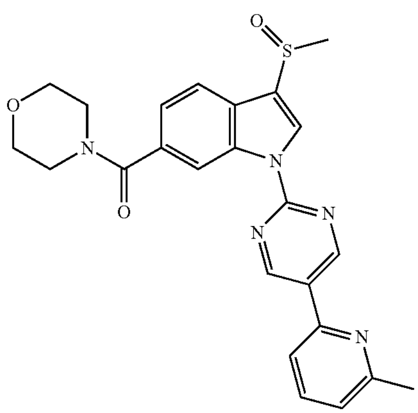 | (1-(5-(6-Methylpyridin-2-yl)pyrimidin-2-yl)-3-(methylsulfinyl)-1H-indol-6-yl)(morpholino)methanone |
| 181 | 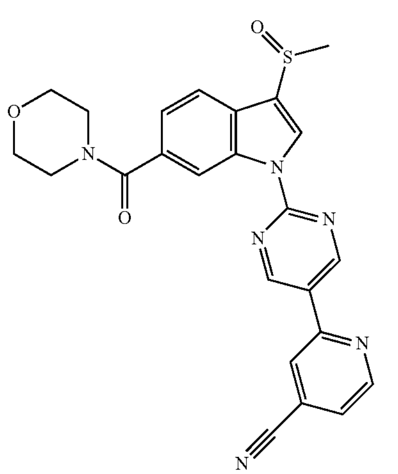 [SMILES: CS(=O)c1cn(-c2ncc(-c3cc(C#N)ccn3)cn2)c2cc(C(=O)N3CCOCC3)ccc12] | 2-(2-(3-(Methylsulfinyl)-6-(morpholine-4-carbonyl)-1H-indol-1-yl)pyrimidin-5-yl)isonicotinonitrile |

| Cmpd-No. | Structure | Name |
|---|---|---|
| 182 | 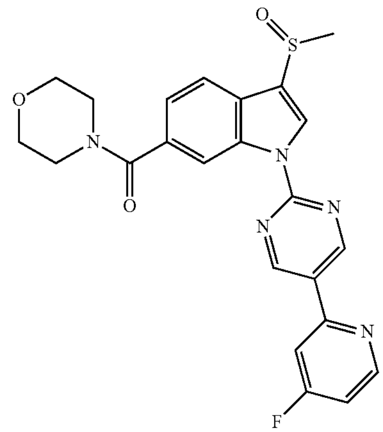 [SMILES: CS(=O)c1cn(-c2ncc(-c3cc(F)ccn3)cn2)c2cc(C(=O)N3CCOCC3)ccc12] | (1-(5-(4-Fluoropyridin-2-yl)pyrimidin-2-yl)-3-(methylsulfinyl)-1H-indol-6-yl)(morpholino)methanone |
| 183 | 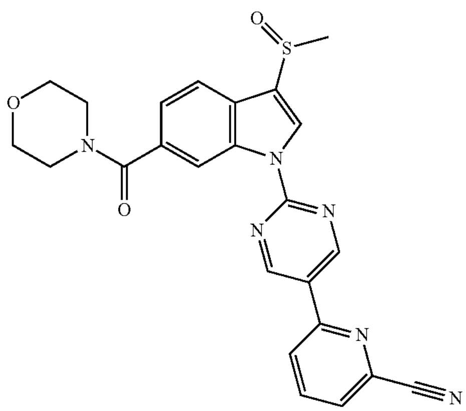 [SMILES: CS(=O)c1cn(-c2ncc(-c3cccc(C#N)n3)cn2)c2cc(C(=O)N3CCOCC3)ccc12] | 6-(2-(3-(Methylsulfinyl)-6-(morpholine-4-carbonyl)-1H-indol-1-yl)pyrimidin-5-yl)picolinonitrile |
| 184 | 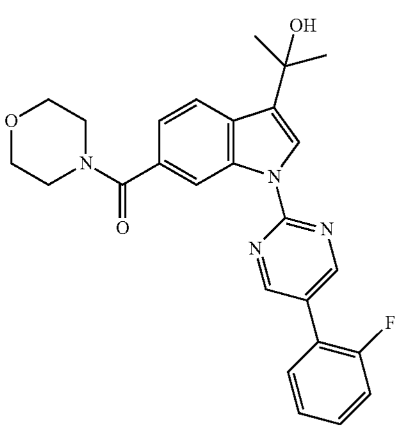 [SMILES: CC(C)(O)c1cn(-c2ncc(-c3ccccc3F)cn2)c2cc(C(=O)N3CCOCC3)ccc12] | (1-(5-(2-Fluorophenyl)pyrimidin-2-yl)-3-(2-hydroxypropan-2-yl)-1H-indol-6-yl)(morpholino)methanone |

TABLE 1-continued

| Cmpd-No. | Structure | Name |
|---|---|---|
| 185 | 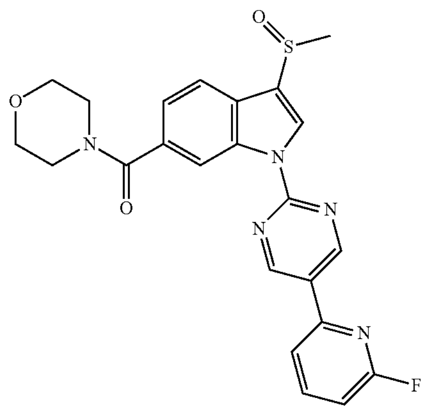 [SMILES: CS(=O)c1cn(-c2ncc(-c3cccc(F)n3)cn2)c2cc(C(=O)N3CCOCC3)ccc12] | (1-(5-(6-Fluoropyridin-2-yl)pyrimidin-2-yl)-3-(methylsulfinyl)-1H-indol-6-yl)(morpholino)methanone |
| 186 | 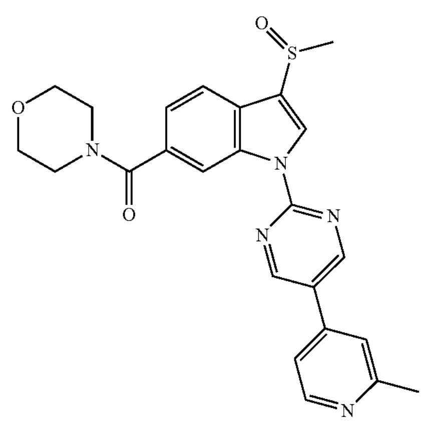 [SMILES: Cc1cc(-c2cnc(-n3cc(S(C)=O)c4ccc(C(=O)N5CCOCC5)cc43)nc2)ccn1] | (1-(5-(2-Methylpyridin-4-yl)pyrimidin-2-yl)-3-(methylsulfinyl)-1H-indol-6-yl)(morpholino)methanone |
| 187 | 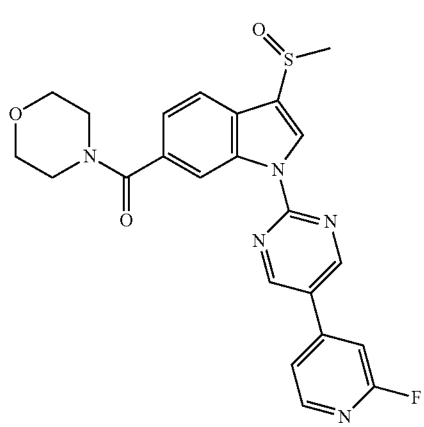 [SMILES: CS(=O)c1cn(-c2ncc(-c3ccnc(F)c3)cn2)c2cc(C(=O)N3CCOCC3)ccc12] | (1-(5-(2-Fluoropyridin-4-yl)pyrimidin-2-yl)-3-(methylsulfinyl)-1H-indol-6-yl)(morpholino)methanone |

TABLE 1-continued

| Cmpd-No. | Structure | Name |
|---|---|---|
| 188 | 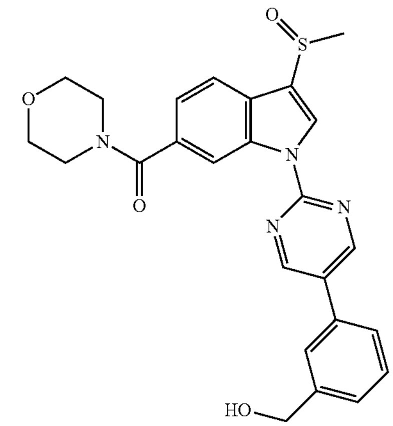 [SMILES: CS(=O)c1cn(-c2ncc(-c3cccc(CO)c3)cn2)c2cc(C(=O)N3CCOCC3)ccc12] | (1-(5-(3-(Hydroxymethyl)phenyl)pyrimidin-2-yl)-3-(methylsulfinyl)-1H-indol-6-yl)(morpholino)methanone |
| 189 | 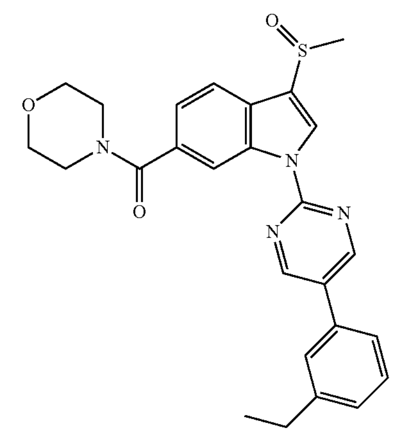 [SMILES: CCc1cccc(-c2cnc(-n3cc(S(C)=O)c4ccc(C(=O)N5CCOCC5)cc43)nc2)c1] | (1-(5-(3-Ethylphenyl)pyrimidin-2-yl)-3-(methylsulfinyl)-1H-indol-6-yl)(morpholino)methanone |
| 190 | 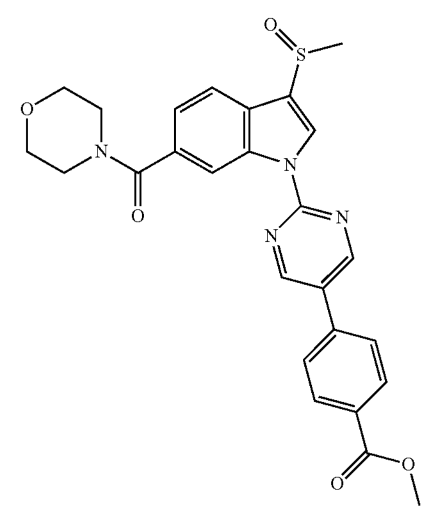 [SMILES: COC(=O)c1ccc(-c2cnc(-n3cc(S(C)=O)c4ccc(C(=O)N5CCOCC5)cc43)nc2)cc1] | Methyl 4-(2-(3-(methylsulfinyl)-6-(morpholine-4-carbonyl)-1H-indol-1-yl)pyrimidin-5-yl)benzoate |

| Cmpd-No. | Structure | Name |
|---|---|---|
| 191 | 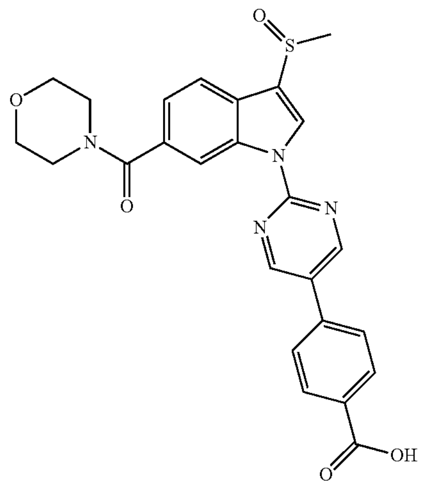 [SMILES: CS(=O)c1cn(-c2ncc(-c3ccc(C(=O)O)cc3)cn2)c2cc(C(=O)N3CCOCC3)ccc12] | 4-(2-(3-(Methylsulfinyl)-6-(morpholine-4-carbonyl)-1H-indol-1-yl)pyrimidin-5-yl)benzoic acid |
| 192 | 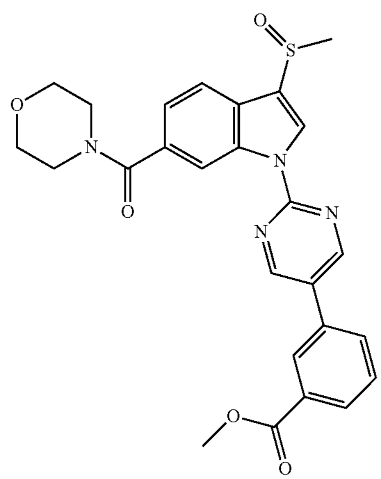 [SMILES: COC(=O)c1cccc(-c2cnc(-n3cc(S(C)=O)c4ccc(C(=O)N5CCOCC5)cc43)nc2)c1] | Methyl 3-(2-(3-(methylsulfinyl)-6-(morpholine-4-carbonyl)-1H-indol-1-yl)pyrimidin-5-yl)benzoate |
| 193 | 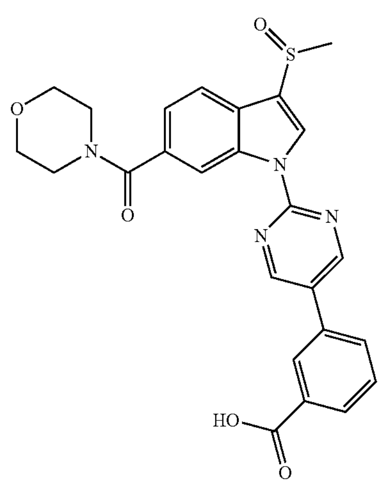 [SMILES: CS(=O)c1cn(-c2ncc(-c3cccc(C(=O)O)c3)cn2)c2cc(C(=O)N3CCOCC3)ccc12] | 3-(2-(3-(Methylsulfinyl)-6-(morpholine-4-carbonyl)-1H-indol-1-yl)pyrimidin-5-yl)benzoic acid |

TABLE 1-continued

| Cmpd-No. | Structure | Name |
|---|---|---|
| 194 | 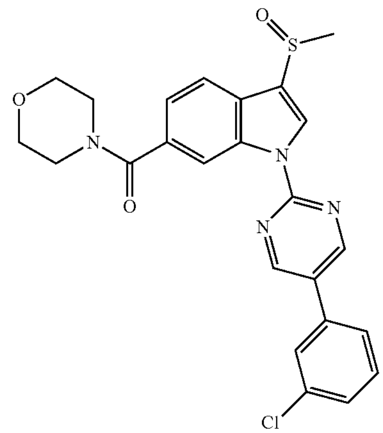 [SMILES: CS(=O)c1cn(-c2ncc(-c3cccc(Cl)c3)cn2)c2cc(C(=O)N3CCOCC3)ccc12] | (1-(5-(3-Chlorophenyl)pyrimidin-2-yl)-3-(methylsulfinyl)-1H-indol-6-yl)(morpholino)methanone |
| 195 | 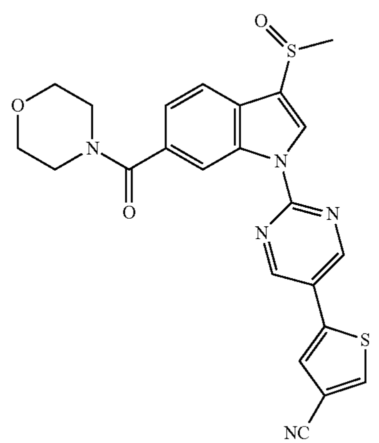 [SMILES: CS(=O)c1cn(-c2ncc(-c3cc(C#N)cs3)cn2)c2cc(C(=O)N3CCOCC3)ccc12] | 5-(2-(3-(Methylsulfinyl)-6-(morpholine-4-carbonyl)-1H-indol-1-yl)pyrimidin-5-yl)thiophene-3-carbonitrile |
| 196 | 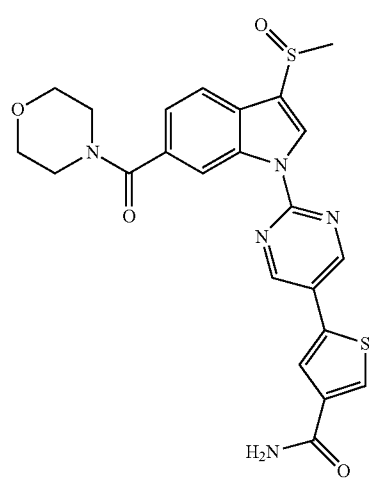 [SMILES: CS(=O)c1cn(-c2ncc(-c3cc(C(N)=O)cs3)cn2)c2cc(C(=O)N3CCOCC3)ccc12] | 5-(2-(3-(Methylsulfinyl)-6-(morpholine-4-carbonyl)-1H-indol-1-yl)pyrimidin-5-yl)thiophene-3-carboxamide |

TABLE 1-continued

| Cmpd-No. | Structure | Name |
|---|---|---|
| 197 | 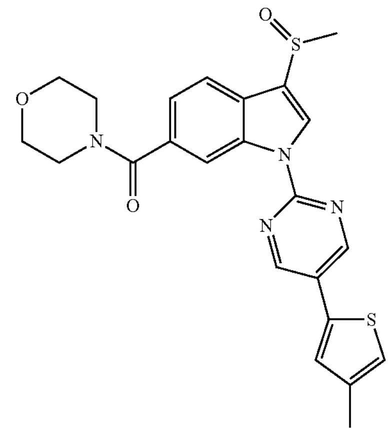 [SMILES: Cc1csc(-c2cnc(-n3cc(S(C)=O)c4ccc(C(=O)N5CCOCC5)cc43)nc2)c1] | 5-(2-(3-(Methylsulfinyl)-1-(5-(4-methylthiophen-2-yl)pyrimidin-2-yl)-1H-indol-6-yl)(morpholino)methanone |
| 198 | 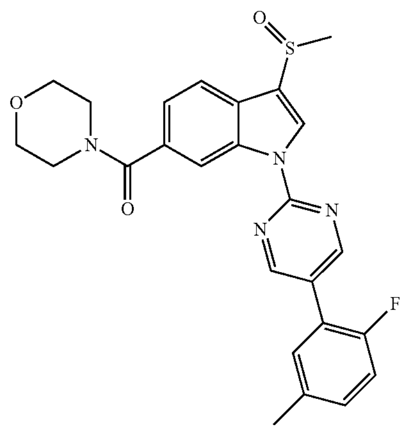 [SMILES: Cc1ccc(F)c(-c2cnc(-n3cc(S(C)=O)c4ccc(C(=O)N5CCOCC5)cc43)nc2)c1] | (1-(5-(2-Fluoro-5-methylphenyl)pyrimidin-2-yl)-3-(methylsulfinyl)-1H-indol-6-yl)(morpholino)methanone |
| 199 | 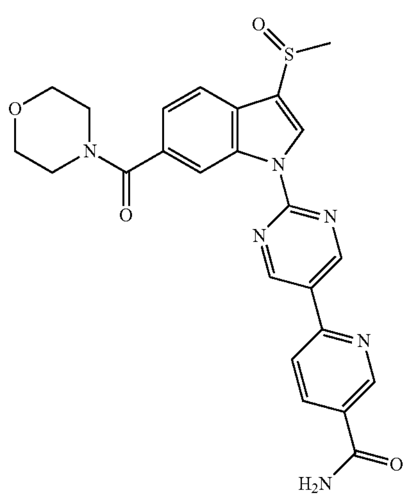 [SMILES: CS(=O)c1cn(-c2ncc(-c3ccc(C(N)=O)cn3)cn2)c2cc(C(=O)N3CCOCC3)ccc12] | 6-(2-(3-(Methylsulfinyl)-6-(morpholine-4-carbonyl)-1H-indol-1-yl)pyrimidin-5-yl)nicotinamide |

TABLE 1-continued

| Cmpd-No. | Structure | Name |
|---|---|---|
| 200 | 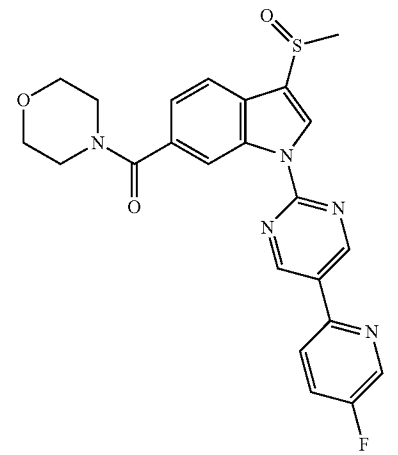 [SMILES: CS(=O)c1cn(-c2ncc(-c3ccc(F)cn3)cn2)c2cc(C(=O)N3CCOCC3)ccc12] | (1-(5-(5-Fluoropyridin-2-yl)pyrimidin-2-yl)-3-(methylsulfinyl)-1H-indol-6-yl)(morpholino)methanone |
| 201 | 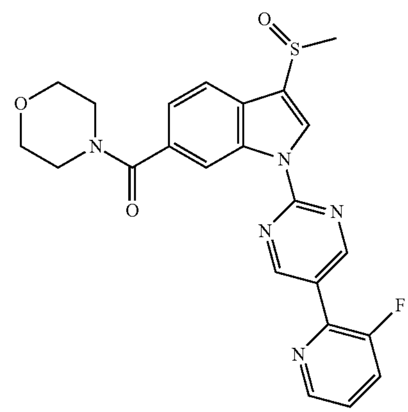 [SMILES: CS(=O)c1cn(-c2ncc(-c3ncccc3F)cn2)c2cc(C(=O)N3CCOCC3)ccc12] | (1-(5-(3-Fluoropyridin-2-yl)pyrimidin-2-yl)-3-(methylsulfinyl)-1H-indol-6-yl)(morpholino)methanone |
| 202 | 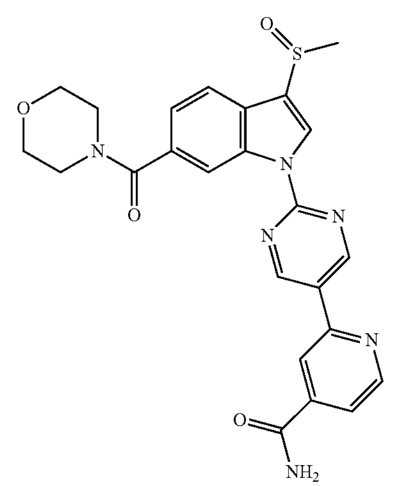 [SMILES: CS(=O)c1cn(-c2ncc(-c3cc(C(N)=O)ccn3)cn2)c2cc(C(=O)N3CCOCC3)ccc12] | 2-(2-(3-(Methylsulfinyl)-6-(morpholine-4-carbonyl)-1H-indol-1-yl)pyrimidin-5-yl)isonicotinamide |

| Cmpd-No. | Structure | Name |
|---|---|---|
| 203 | 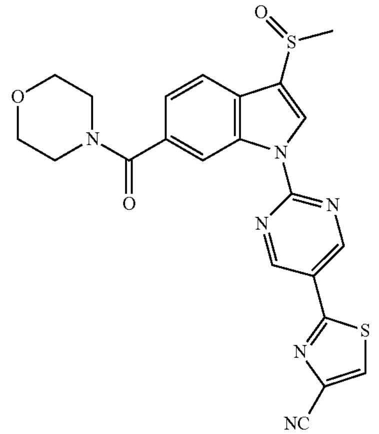 [SMILES: CS(=O)c1cn(-c2ncc(-c3nc(C#N)cs3)cn2)c2cc(C(=O)N3CCOCC3)ccc12] | 2-(2-(3-(Methylsulfinyl)-6-(morpholine-4-carbonyl)-1H-indol-1-yl)pyrimidin-5-yl)thiazole-4-carbonitrile |
| 204 | 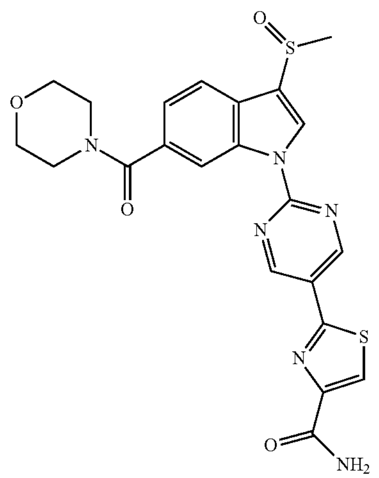 [SMILES: CS(=O)c1cn(-c2ncc(-c3nc(C(N)=O)cs3)cn2)c2cc(C(=O)N3CCOCC3)ccc12] | 2-(2-(3-(Methylsulfinyl)-6-(morpholine-4-carbonyl)-1H-indol-1-yl)pyrimidin-5-yl)thiazole-4-carboxamide |
| 205 | 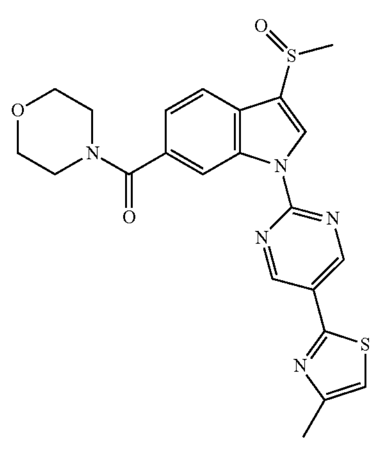 [SMILES: Cc1csc(-c2cnc(-n3cc(S(C)=O)c4ccc(C(=O)N5CCOCC5)cc43)nc2)n1] | (3-(Methylsulfinyl)-1-(5-(4-methylthiazol-2-yl)pyrimidin-2-yl)-1H-indol-6-yl)(morpholino)methanone |

TABLE 1-continued

| Cmpd-No. | Structure | Name |
|---|---|---|
| 206 | 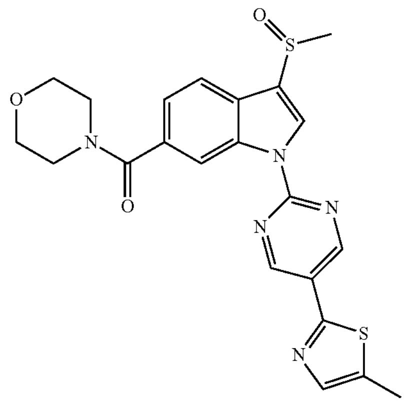 [SMILES: Cc1cnc(-c2cnc(-n3cc(S(C)=O)c4ccc(C(=O)N5CCOCC5)cc43)nc2)s1] | (3-(Methylsulfinyl)-1-(5-(5-methylthiazol-2-yl)pyrimidin-2-yl)-1H-indol-6-yl)(morpholino)methanone |
| 207 | 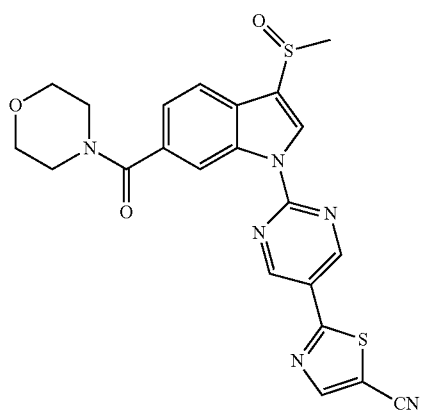 [SMILES: CS(=O)c1cn(-c2ncc(-c3ncc(C#N)s3)cn2)c2cc(C(=O)N3CCOCC3)ccc12] | 2-(2-(3-(Methylsulfinyl)-6-(morpholine-4-carbonyl)-1H-indol-1-yl)pyrimidin-5-yl)thiazole-5-carbonitrile |
| 208 | 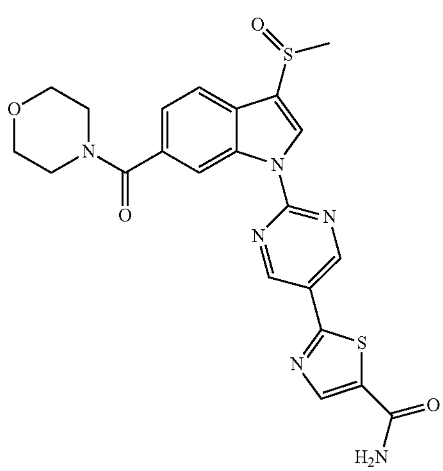 [SMILES: CS(=O)c1cn(-c2ncc(-c3ncc(C(N)=O)s3)cn2)c2cc(C(=O)N3CCOCC3)ccc12] | 2-(2-(3-(Methylsulfinyl)-6-(morpholine-4-carbonyl)-1H-indol-1-yl)pyrimidin-5-yl)thiazole-5-carboxamide |

TABLE 1-continued

| Cmpd-No. | Structure | Name |
|---|---|---|
| 209 | 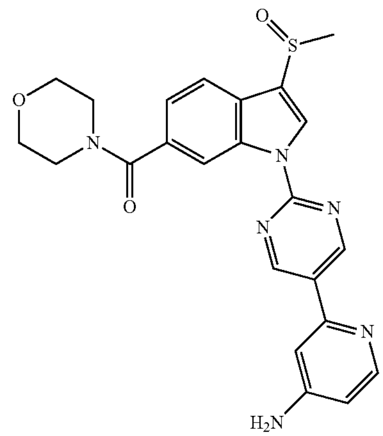 [SMILES: CS(=O)c1cn(-c2ncc(-c3cc(N)ccn3)cn2)c2cc(C(=O)N3CCOCC3)ccc12] | 2-(1-(5-(4-Aminopyridin-2-yl)pyrimidin-2-yl)-3-(methylsulfinyl)-1H-indol-6-yl)(morpholino)methanone |
| 210 | 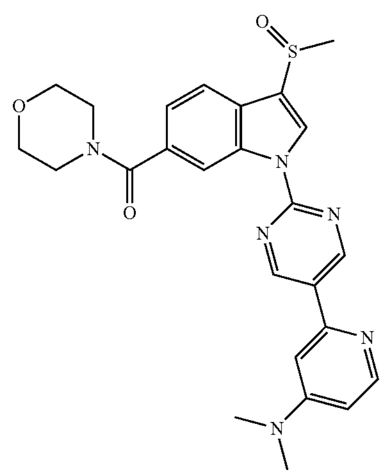 [SMILES: CN(C)c1ccnc(-c2cnc(-n3cc(S(C)=O)c4ccc(C(=O)N5CCOCC5)cc43)nc2)c1] | (1-(5-(4-(Dimethylamino)pyridin-2-yl)pyrimidin-2-yl)-3-(methylsulfinyl)-1H-indol-6-yl)(morpholino)methanone |
| 211 | 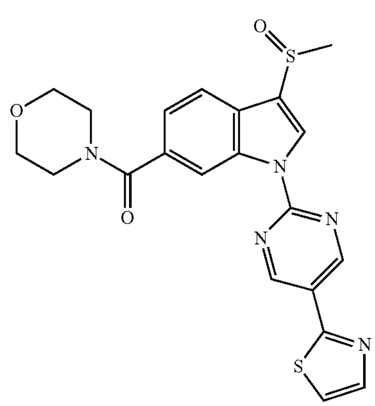 [SMILES: CS(=O)c1cn(-c2ncc(-c3nccs3)cn2)c2cc(C(=O)N3CCOCC3)ccc12] | (3-(Methylsulfinyl)-1-(5-(thiazol-2-yl)pyrimidin-2-yl)-1H-indol-6-yl)(morpholino)methanone |

TABLE 1-continued

| Cmpd-No. | Structure | Name |
|---|---|---|
| 212 | 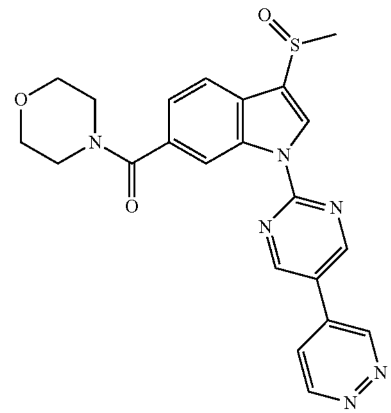 [SMILES: CS(=O)c1cn(-c2ncc(-c3ccnnc3)cn2)c2cc(C(=O)N3CCOCC3)ccc12] | (3-(Methylsulfinyl)-1-(5-(pyridazin-4-yl)pyrimidin-2-yl)-1H-indol-6-yl)(morpholino)methanone |
| 213 and 214 | 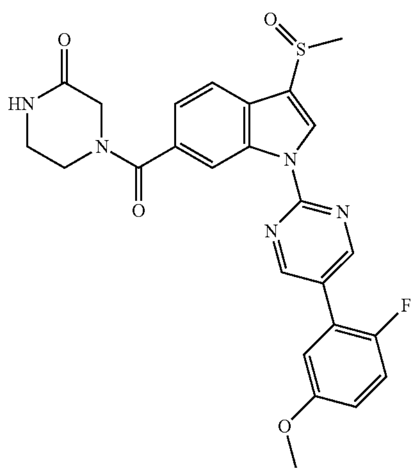 [SMILES: COc1ccc(F)c(-c2cnc(-n3cc(S(C)=O)c4ccc(C(=O)N5CCNC(=O)C5)cc43)nc2)c1] | 4-(1-(5-(2-Fluoro-5-methoxyphenyl)pyrimidin-2-yl)-3-(methylsulfinyl)-1H-indole-6-carbonyl)piperazin-2-one (enantiomer 1 and 2) |
| 215 and 216 | 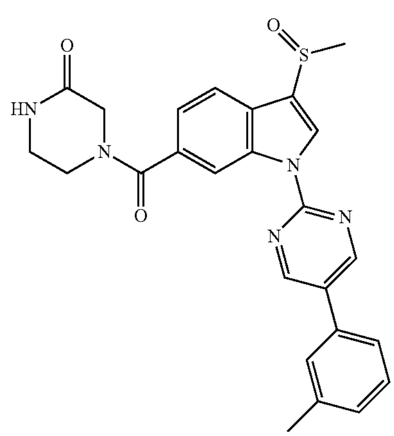 [SMILES: Cc1cccc(-c2cnc(-n3cc(S(C)=O)c4ccc(C(=O)N5CCNC(=O)C5)cc43)nc2)c1] | 4-(3-(Methylsulfinyl)-1-(5-(m-tolyl)pyrimidin-2-yl)-1H-indole-6-carbonyl)piperazin-2-one (enantiomer 1 and 2) |

TABLE 1-continued

| Cmpd-No. | Structure | Name |
|---|---|---|
| 217 and 218 | 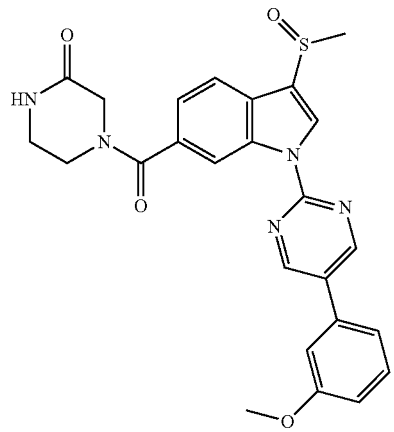 [SMILES: COc1cccc(-c2cnc(-n3cc(S(C)=O)c4ccc(C(=O)N5CCNC(=O)C5)cc43)nc2)c1] | 4-(1-(5-(3-Methoxyphenyl)pyrimidin-2-yl)-3-(methylsulfinyl)-1H-indole-6-carbonyl)piperazin-2-one (enantiomer 1 and 2) |
| 219 | 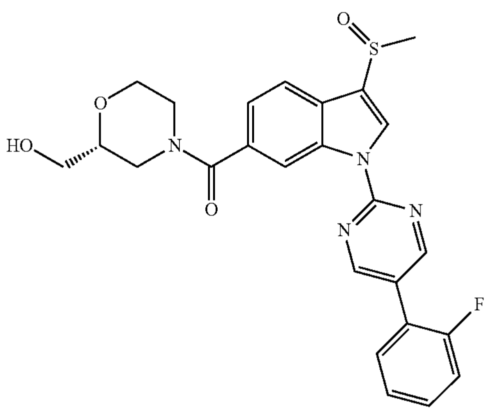 [SMILES: CS(=O)c1cn(-c2ncc(-c3ccccc3F)cn2)c2cc(C(=O)N3CCO[C@@H](CO)C3)ccc12] | (1-(5-(2-Fluorophenyl)pyrimidin-2-yl)-3-(methylsulfinyl)-1H-indol-6-yl)((R)-2-(hydroxymethyl)morpholino)methanone |
| 220 | 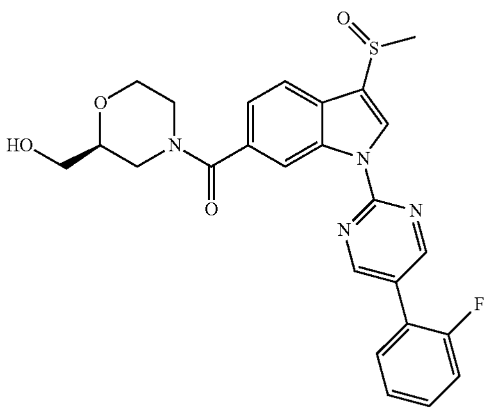 [SMILES: CS(=O)c1cn(-c2ncc(-c3ccccc3F)cn2)c2cc(C(=O)N3CCO[C@H](CO)C3)ccc12] | (1-(5-(2-Fluorophenyl)pyrimidin-2-yl)-3-(methylsulfinyl)-1H-indol-6-yl)((S)-2-(hydroxymethyl)morpholino)methanone |

| Cmpd-No. | Structure | Name |
|---|---|---|
| 221 | 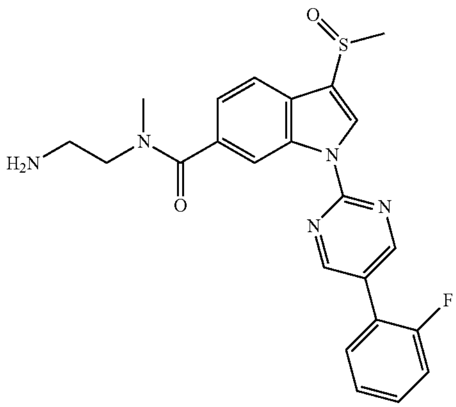 [SMILES: CN(CCN)C(=O)c1ccc2c(S(C)=O)cn(-c3ncc(-c4ccccc4F)cn3)c2c1] | N-(2-Aminoethyl)-1-(5-(2-fluorophenyl)pyrimidin-2-yl)-N-methyl-3-(methylsulfinyl)-1H-indole-6-carboxamide |
| 222 | 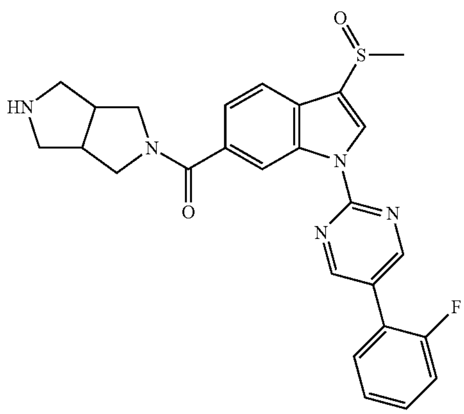 [SMILES: CS(=O)c1cn(-c2ncc(-c3ccccc3F)cn2)c2cc(C(=O)N3CC4CNCC4C3)ccc12] | (1-(5-(2-Fluorophenyl)pyrimidin-2-yl)-3-(methylsulfinyl)-1H-indol-6-yl)(hexahydropyrrolo[3,4-c]pyrrol-2(1H)-yl)methanone |
| 223 | 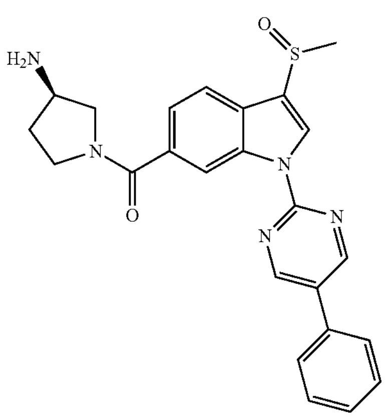 [SMILES: CS(=O)c1cn(-c2ncc(-c3ccccc3)cn2)c2cc(C(=O)N3CC[C@@H](N)C3)ccc12] | ((R)-3-Aminopyrrolidin-1-yl)(3-(methylsulfinyl)-1-(5-phenylpyrimidin-2-yl)-1H-indol-6-yl)methanone |

TABLE 1-continued

| Cmpd-No. | Structure | Name |
|---|---|---|
| 224 | 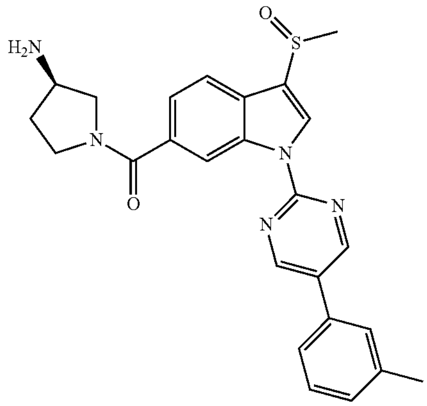 [SMILES: Cc1cccc(-c2cnc(-n3cc(S(C)=O)c4ccc(C(=O)N5CC[C@@H](N)C5)cc43)nc2)c1] | ((R)-3-Aminopyrrolidin-1-yl)(3-(methylsulfinyl)-1-(5-(m-tolyl)pyrimidin-2-yl)-1H-indol-6-yl)methanone |
| 225 | 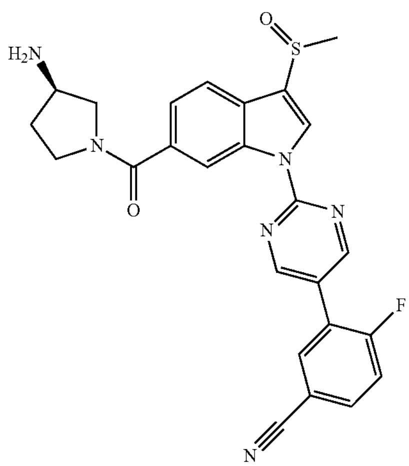 [SMILES: CS(=O)c1cn(-c2ncc(-c3cc(C#N)ccc3F)cn2)c2cc(C(=O)N3CC[C@@H](N)C3)ccc12] | 3-(2-(6-((R)-3-Aminopyrrolidine-1-carbonyl)-3-(methylsulfinyl)-1H-indol-1-yl)pyrimidin-5-yl)-4-fluorobenzonitrile |
| 226 | 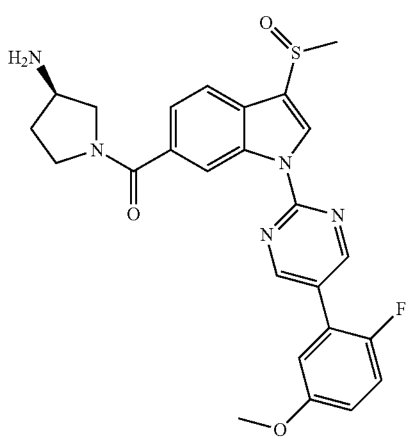 [SMILES: COc1ccc(F)c(-c2cnc(-n3cc(S(C)=O)c4ccc(C(=O)N5CC[C@@H](N)C5)cc43)nc2)c1] | ((R)-3-Aminopyrrolidin-1-yl)(1-(5-(2-fluoro-5-methoxyphenyl)pyrimidin-2-yl)-3-(methylsulfinyl)-1H-indol-6-yl)methanone |

| Cmpd-No. | Structure | Name |
|---|---|---|
| 227 | 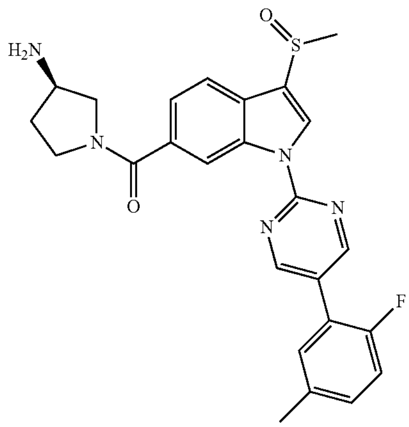 [SMILES: Cc1ccc(F)c(-c2cnc(-n3cc(S(C)=O)c4ccc(C(=O)N5CC[C@@H](N)C5)cc43)nc2)c1] | ((R)-3-Aminopyrrolidin-1-yl)(1-(5-(2-fluoro-5-methylphenyl)pyrimidin-2-yl)-3-(methylsulfinyl)-1H-indol-6-yl)methanone |
| 228 | 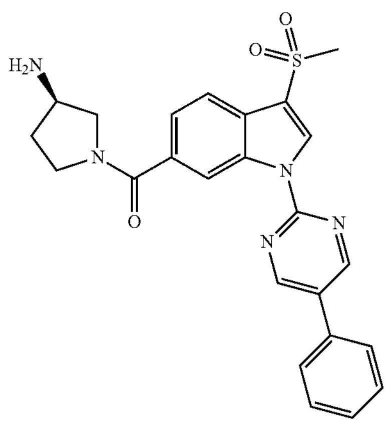 [SMILES: CS(=O)(=O)c1cn(-c2ncc(-c3ccccc3)cn2)c2cc(C(=O)N3CC[C@@H](N)C3)ccc12] | (R)-(3-Aminopyrrolidin-1-yl)(3-(methylsulfonyl)-1-(5-phenylpyrimidin-2-yl)-1H-indol-6-yl)methanone |
| 229 | 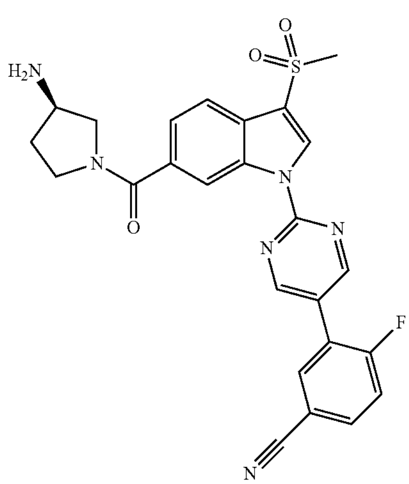 [SMILES: CS(=O)(=O)c1cn(-c2ncc(-c3cc(C#N)ccc3F)cn2)c2cc(C(=O)N3CC[C@@H](N)C3)ccc12] | (R)-3-(2-(6-(3-Aminopyrrolidine-1-carbonyl)-3-(methylsulfonyl)-1H-indol-1-yl)pyrimidin-5-yl)-4-fluorobenzonitrile |

| Cmpd-No. | Structure | Name |
|---|---|---|
| 230 | 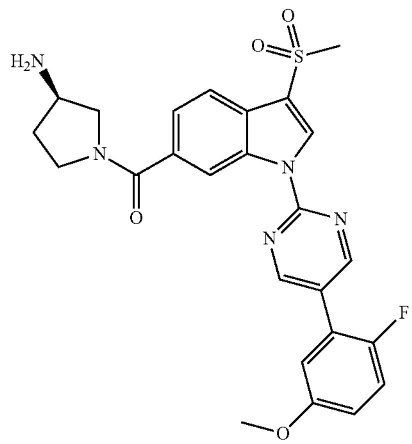 [SMILES: COc1ccc(F)c(-c2cnc(-n3cc(S(C)(=O)=O)c4ccc(C(=O)N5CC[C@@H](N)C5)cc43)nc2)c1] | (R)-(3-Aminopyrrolidin-1-yl)(1-(5-(2-fluoro-5-methoxyphenyl)pyrimidin-2-yl)-3-(methylsulfonyl)-1H-indol-6-yl)methanone |
| 231 | 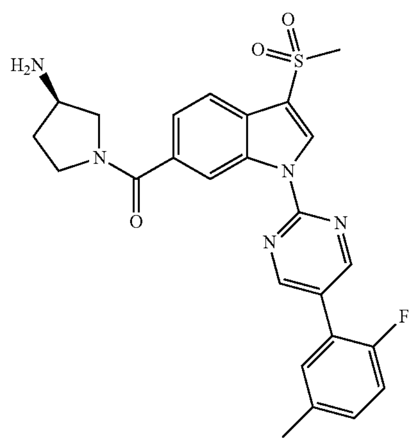 [SMILES: Cc1ccc(F)c(-c2cnc(-n3cc(S(C)(=O)=O)c4ccc(C(=O)N5CC[C@@H](N)C5)cc43)nc2)c1] | (R)-(3-Aminopyrrolidin-1-yl)(1-(5-(2-fluoro-5-methylphenyl)pyimidin-2yl)-3-methylsulfonyl)-1H-indol-6-yl)methanone |
| 232 | 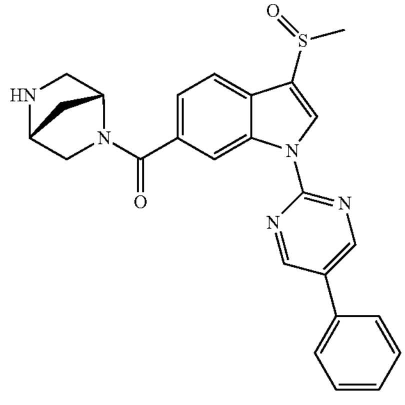 [SMILES: CS(=O)c1cn(-c2ncc(-c3ccccc3)cn2)c2cc(C(=O)N3C[C@H]4C[C@@H]3CN4)ccc12] | (1R,4R)-2,5-Diazabicyclo[2.2.1]heptan-2-yl(3-(methylsulfinyl)-1-(5-phenylpyrimidin-2-yl)-1H-indol-6-yl)methanone |

TABLE 1-continued

| Cmpd-No. | Structure | Name |
|---|---|---|
| 233 | 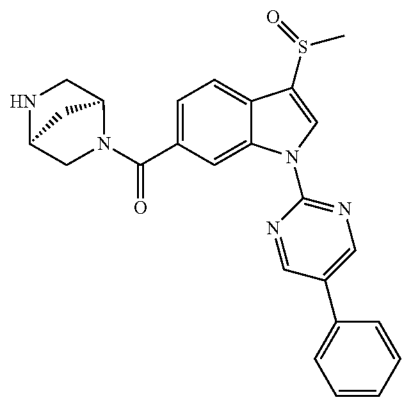 [SMILES: CS(=O)c1cn(-c2ncc(-c3ccccc3)cn2)c2cc(C(=O)N3C[C@@H]4C[C@H]3CN4)ccc12] | (1S,4S)-2,5-Diazabicyclo[2.2.1]heptan-2-yl(3-(methylsulfinyl)-1-(5-phenylpyrimidin-2-yl)-1H-indol-6-yl)methanone |
| 234 | 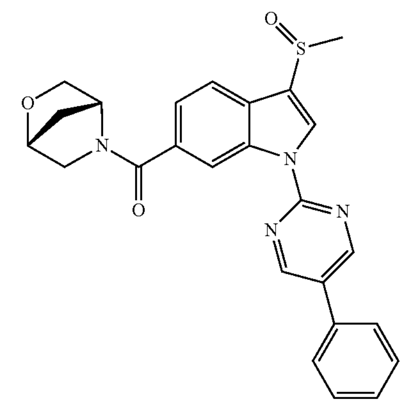 [SMILES: CS(=O)c1cn(-c2ncc(-c3ccccc3)cn2)c2cc(C(=O)N3C[C@H]4C[C@@H]3CO4)ccc12] | (1R,4R)-2-Oxa-5-azabicyclo[2.2.1]heptan-5-yl(3-(methylsulfinyl)-1-(5-phenylpyrimidin-2-yl)-1H-indol-6-yl)methanone |
| 235 | 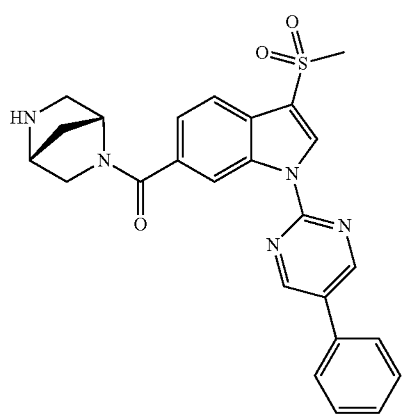 [SMILES: CS(=O)(=O)c1cn(-c2ncc(-c3ccccc3)cn2)c2cc(C(=O)N3C[C@H]4C[C@@H]3CN4)ccc12] | (1R,4R)-2,5-Diazabicyclo[2.2.1]heptan-2-yl(3-(methylsulfonyl)-1-(5-phenylpyrimidin-2-yl)-1H-indol-6-yl)methanone |
| 236 | 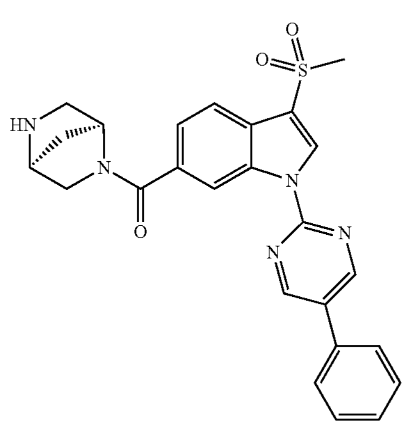 [SMILES: CS(=O)(=O)c1cn(-c2ncc(-c3ccccc3)cn2)c2cc(C(=O)N3C[C@@H]4C[C@H]3CN4)ccc12] | (1S,4S)-2,5-Diazabicyclo[2.2.1]heptan-2-yl(3-(methylsulfonyl)-1-(5-phenylpyrimidin-2-yl)-1H-indol-6-yl)methanone |

TABLE 1-continued

| Cmpd-No. | Structure | Name |
|---|---|---|
| 237 | 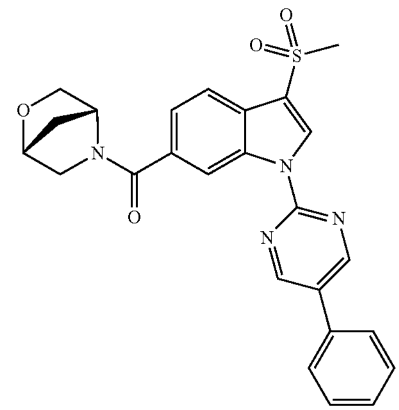 [SMILES: CS(=O)(=O)c1cn(-c2ncc(-c3ccccc3)cn2)c2cc(C(=O)N3C[C@H]4C[C@@H]3CO4)ccc12] | (1R,4R)-2-Oxa-5-azabicyclo[2.2.1]heptan-5-yl(3-(methylsulfonyl)-1-(5-phenylpyrimidin-2-yl)-1H-indol-6-yl)methanone |
| 238 | 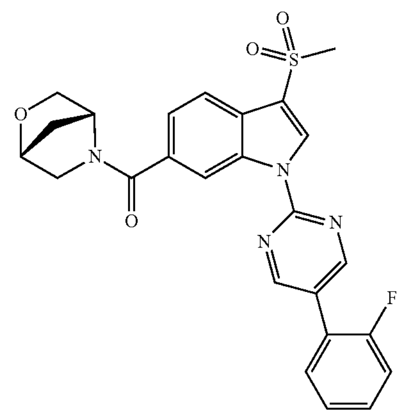 [SMILES: CS(=O)(=O)c1cn(-c2ncc(-c3ccccc3F)cn2)c2cc(C(=O)N3C[C@H]4C[C@@H]3CO4)ccc12] | (1R,4R)-2-Oxa-5-azabicyclo[2.2.1]heptan-5-yl(1-(5-(2-fluorophenyl)pyrimidin-2-yl)-3-(methylsulfonyl)-1H-indol-6-yl)methanone |
| 239 | 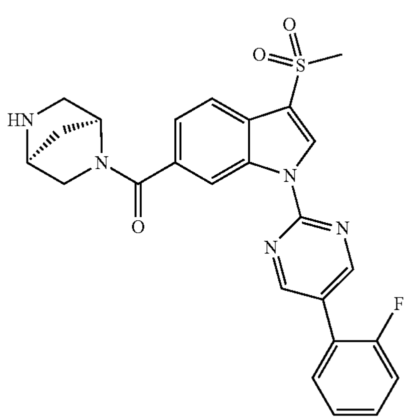 [SMILES: CS(=O)(=O)c1cn(-c2ncc(-c3ccccc3F)cn2)c2cc(C(=O)N3C[C@@H]4C[C@H]3CN4)ccc12] | (1S,4S)-2,5-Diazabicyclo[2.2.1]heptan-2-yl(1-(5-(2-fluorophenyl)pyrimidin-2-yl)-3-(methylsulfonyl)-1H-indol-6-yl)methanone |

TABLE 1-continued

| Cmpd-No. | Structure | Name |
|---|---|---|
| 240 | 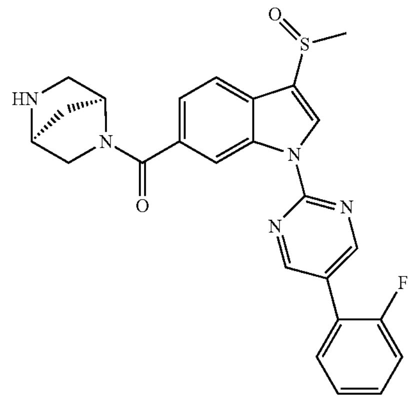 [SMILES: CS(=O)c1cn(-c2ncc(-c3ccccc3F)cn2)c2cc(C(=O)N3C[C@@H]4C[C@H]3CN4)ccc12] | (1S,4S)-2,5-Diazabicyclo[2.2.1]heptan-2-yl(1-(5-(2-fluorophenyl)pyrimidin-2-yl)-3-(methylsulfinyl)-1H-indol-6-yl)methanone |
| 241 | 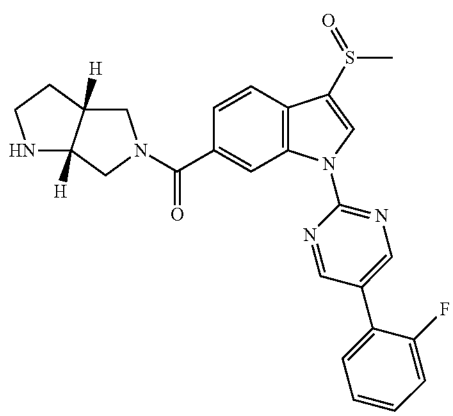 [SMILES: CS(=O)c1cn(-c2ncc(-c3ccccc3F)cn2)c2cc(C(=O)N3C[C@H]4CCN[C@H]4C3)ccc12] | (1-(5-(2-Fluorophenyl)pyrimidin-2-yl)-3-(methylsulfinyl)-1H-indol-6-yl)((3aR,6aR)-hexahydropyrrolo[3,4-b]pyrrol-5(1H)-yl)methanone |
| 242 | 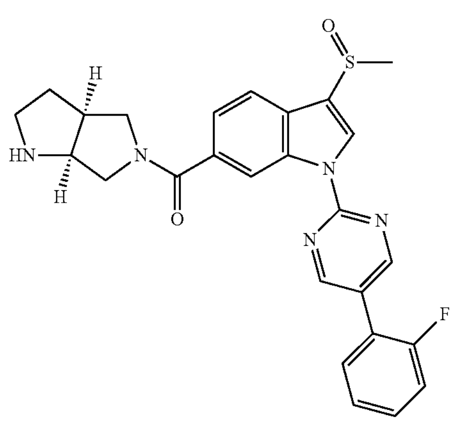 [SMILES: CS(=O)c1cn(-c2ncc(-c3ccccc3F)cn2)c2cc(C(=O)N3C[C@@H]4CCN[C@@H]4C3)ccc12] | (1-(5-(2-Fluorophenyl)pyrimidin-2-yl)-3-(methylsulfinyl)-1H-indol-6-yl)((3aS,6aS)-hexahydropyrrolo[3,4-b]pyrrol-5(1H)-yl)methanone |

TABLE 1-continued

| Cmpd-No. | Structure | Name |
|---|---|---|
| 243 | 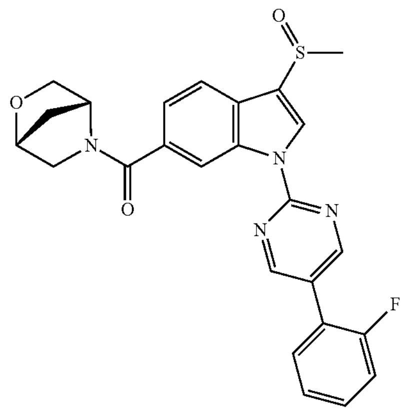 [SMILES: CS(=O)c1cn(-c2ncc(-c3ccccc3F)cn2)c2cc(C(=O)N3C[C@H]4C[C@@H]3CO4)ccc12] | (1R,4R)-2-Oxa-5-azabicyclo[2.2.1]heptan-5-yl(1-(5-(2-fluorophenyl)pyrimidin-2-yl)-3-(methylsulfinyl)-1H-indol-6-yl)methanone |
| 244 | 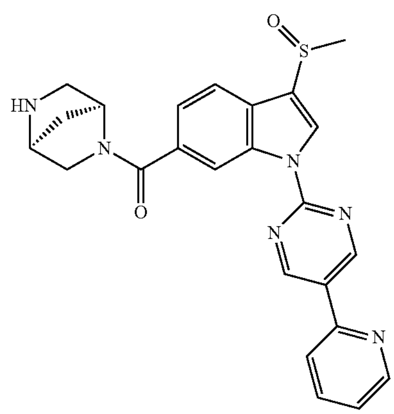 [SMILES: CS(=O)c1cn(-c2ncc(-c3ccccn3)cn2)c2cc(C(=O)N3C[C@@H]4C[C@H]3CN4)ccc12] | (1S,4S)-2,5-Diazabicyclo[2.2.1]heptan-2-yl(3-(methylsulfinyl)-1-(5-(pyridin-2-yl)pyrimidin-2-yl)-1H-indol-6-yl)methanone |
| 245 | 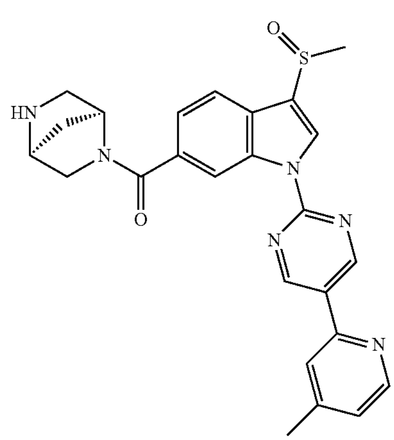 [SMILES: Cc1ccnc(-c2cnc(-n3cc(S(C)=O)c4ccc(C(=O)N5C[C@@H]6C[C@H]5CN6)cc43)nc2)c1] | (1S,4S)-2,5-Diazabicyclo[2.2.1]heptan-2-yl(1-(5-(4-methylpyridin-2-yl)pyrimidin-2-yl)-3-(methylsulfinyl)-1H-indol-6-yl)methanone |

TABLE 1-continued
| Cmpd-No. | Structure | Name |
|---|---|---|
| 246 | 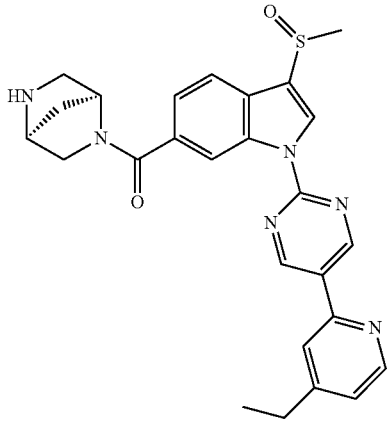 [SMILES: CCc1ccnc(-c2cnc(-n3cc(S(C)=O)c4ccc(C(=O)N5C[C@@H]6C[C@H]5CN6)cc43)nc2)c1] | (1S,4S)-2,5-Diazabicyclo[2.2.1]heptan-2-yl(1-(5-(4-ethylpyridin-2-yl)pyrimidin-2-yl)-3-(methylsulfinyl)-1H-indol-6-yl)methanone |
| 247 | 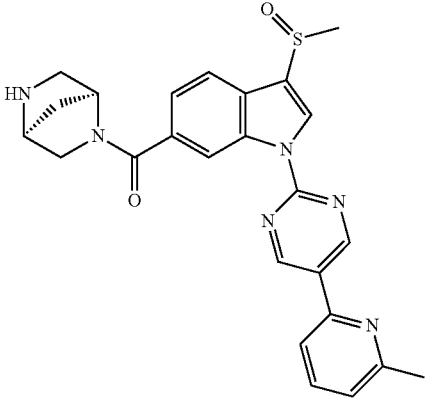 [SMILES: Cc1cccc(-c2cnc(-n3cc(S(C)=O)c4ccc(C(=O)N5C[C@@H]6C[C@H]5CN6)cc43)nc2)n1] | (1S,4S)-2,5-Diazabicyclo[2.2.1]heptan-2-yl(1-(5-(6-methylpyridin-2-yl)pyrimidin-2-yl)-3-(methylsulfinyl)-1H-indol-6-yl)methanone |
| 248 | 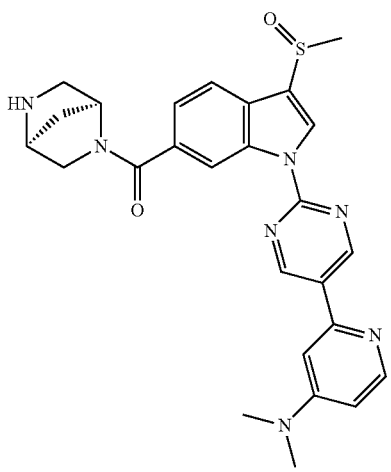 [SMILES: CN(C)c1ccnc(-c2cnc(-n3cc(S(C)=O)c4ccc(C(=O)N5C[C@@H]6C[C@H]5CN6)cc43)nc2)c1] | (1S,4S)-2,5-Diazabicyclo[2.2.1]heptan-2-yl(1-(5-(4-(dimethylamino)pyridin-2-yl)pyrimidin-2-yl)-3-(methylsulfinyl)-1H-indol-6-yl)methanone |

TABLE 1-continued

| Cmpd-No. | Structure | Name |
|---|---|---|
| 249 | 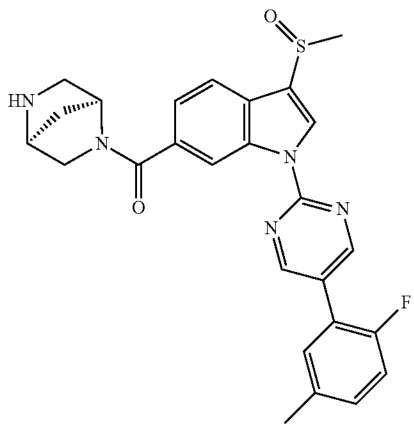 [SMILES: Cc1ccc(F)c(-c2cnc(-n3cc(S(C)=O)c4ccc(C(=O)N5C[C@@H]6C[C@H]5CN6)cc43)nc2)c1] | (1S,4S)-2,5-Diazabicyclo[2.2.1]heptan-2-yl(1-(5-(2-fluoro-5-methylphenyl) pyrimidin-2-yl)-3-(methylsulfinyl)-1H-indol-6-yl)methanone |
| 250 | 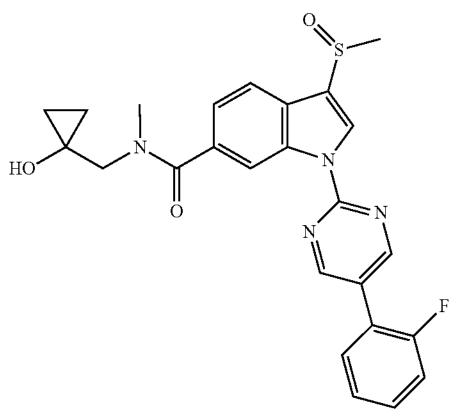 [SMILES: CN(CC1(O)CC1)C(=O)c1ccc2c(S(C)=O)cn(-c3ncc(-c4ccccc4F)cn3)c2c1] | 1-(5-(2-Fluorophenyl)pyrimidin-2-yl)-N-((1-hydroxycyclopropyl)methyl)-N-methyl-3-(methylsulfinyl)-1H-indole-6-carboxamide |
| 251 | 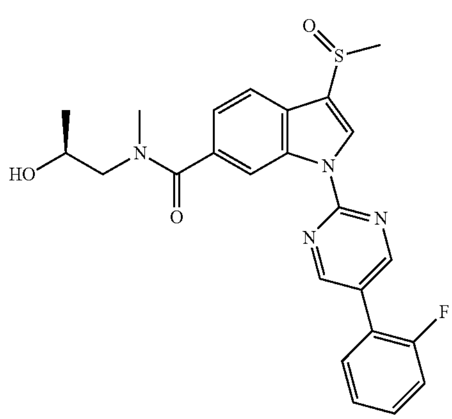 [SMILES: C[C@H](O)CN(C)C(=O)c1ccc2c(S(C)=O)cn(-c3ncc(-c4ccccc4F)cn3)c2c1] | 1-(5-(2-Fluorophenyl)pyrimidin-2-yl)-N-((S)-2-hydroxypropyl)-N-methyl-3-(methylsulfinyl)-1H-indole-6-carboxamide |

TABLE 1-continued

| Cmpd-No. | Structure | Name |
|---|---|---|
| 252 and 253 | 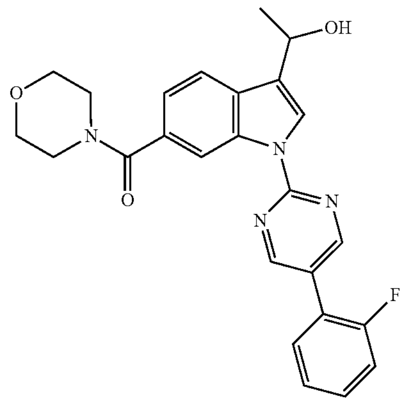 [SMILES: CC(O)c1cn(-c2ncc(-c3ccccc3F)cn2)c2cc(C(=O)N3CCOCC3)ccc12] | (1-(5-(2-Fluorophenyl)pyrimidin-2-yl)-3-(1-hydroxyethyl)-1H-indol-6-yl)(morpholino)methanone (enantiomer 1 and 2) |
| 254 and 255 | 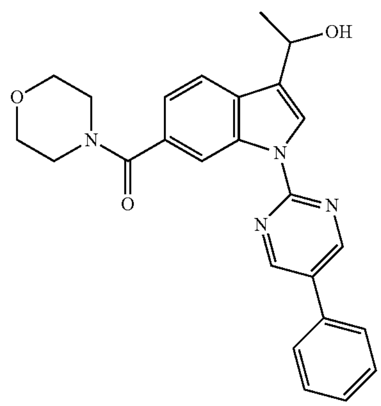 [SMILES: CC(O)c1cn(-c2ncc(-c3ccccc3)cn2)c2cc(C(=O)N3CCOCC3)ccc12] | (3-(1-Hydroxyethyl)-1-(5-phenylpyrimidin-2-yl)-1H-indol-6-yl)(morpholino)methanone (enantiomer 1 and 2) |
| 256 | 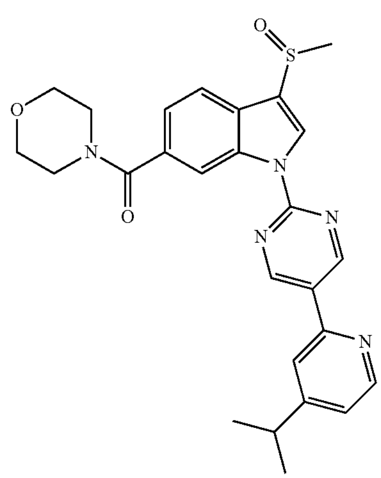 [SMILES: CC(C)c1ccnc(-c2cnc(-n3cc(S(C)=O)c4ccc(C(=O)N5CCOCC5)cc43)nc2)c1] | (1-(5-(4-Isopropylpyridin-2-yl)pyrimidin-2-yl)-3-(methylsulfinyl)-1H-indol-6-yl)(morpholino)methanone |

TABLE 1-continued

| Cmpd-No. | Structure | Name |
|---|---|---|
| 257 | 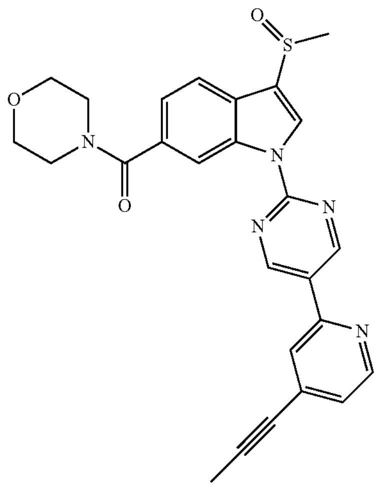 [SMILES: CC#Cc1ccnc(-c2cnc(-n3cc(S(C)=O)c4ccc(C(=O)N5CCOCC5)cc43)nc2)c1] | (3-(Methylsulfinyl)-1-(5-(4-(prop-1-yn-1-yl)pyridin-2-yl)pyrimidin-2-yl)-1H-indol-6-yl)(morpholino)methanone |
| 258 | 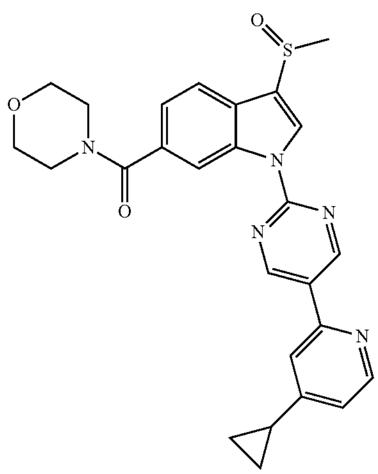 [SMILES: CS(=O)c1cn(-c2ncc(-c3cc(C4CC4)ccn3)cn2)c2cc(C(=O)N3CCOCC3)ccc12] | (1-(5-(4-Cyclopropylpyridin-2-yl)pyrimidin-2-yl)-3-(methylsulfinyl)-1H-indol-6-yl)(morpholino)methanone |
| 259 | 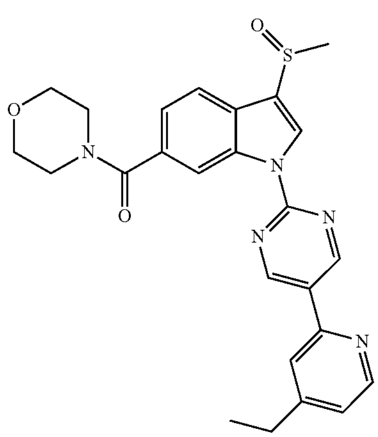 [SMILES: CCc1ccnc(-c2cnc(-n3cc(S(C)=O)c4ccc(C(=O)N5CCOCC5)cc43)nc2)c1] | (1-(5-(4-Ethylpyridin-2-yl)pyrimidin-2-yl)-3-(methylsulfinyl)-1H-indol-6-yl)(morpholino)methanone |

TABLE 1-continued

| Cmpd-No. | Structure | Name |
|---|---|---|
| 260 | 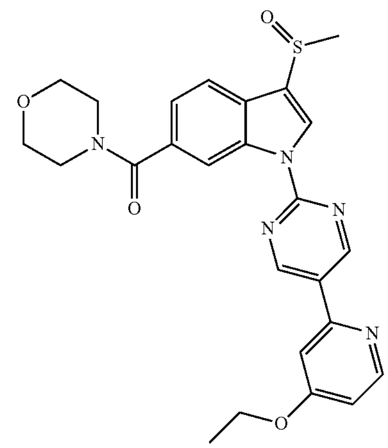 [SMILES: CCOc1ccnc(-c2cnc(-n3cc(S(C)=O)c4ccc(C(=O)N5CCOCC5)cc43)nc2)c1] | (1-(5-(4-Ethoxypyridin-2-yl)pyrimidin-2-yl)-3-(methylsulfinyl)-1H-indol-6-yl)(morpholino)methanone |
| 261 | 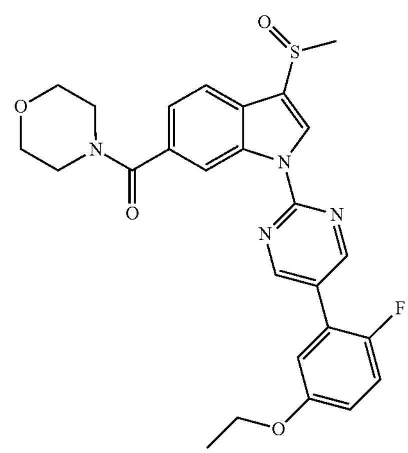 [SMILES: CCOc1ccc(F)c(-c2cnc(-n3cc(S(C)=O)c4ccc(C(=O)N5CCOCC5)cc43)nc2)c1] | (1-(5-(5-Ethoxy-2-fluorophenyl)pyrimidin-2-yl)-3-(methylsulfinyl)-1H-indol-6-yl)(morpholino)methanone |
| 262 | 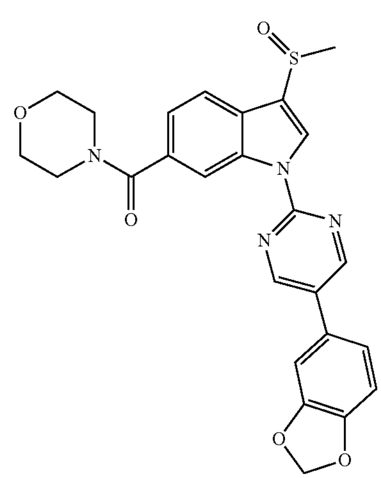 [SMILES: CS(=O)c1cn(-c2ncc(-c3ccc4c(c3)OCO4)cn2)c2cc(C(=O)N3CCOCC3)ccc12] | (1-(5-(Benzo[d][1,3]dioxol-5-yl)pyrimidin-2-yl)-3-(methylsulfinyl)-1H-indol-6-yl)(morpholino)methanone |

TABLE 1-continued

| Cmpd-No. | Structure | Name |
|---|---|---|
| 263 | 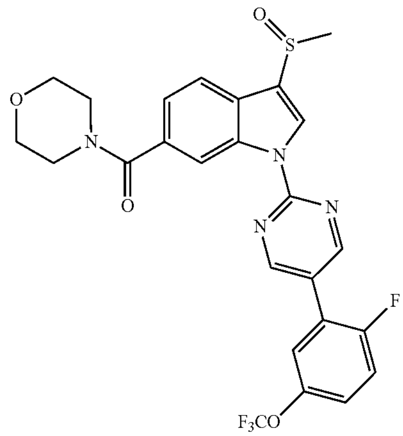 [SMILES: CS(=O)c1cn(-c2ncc(-c3cc(OC(F)(F)F)ccc3F)cn2)c2cc(C(=O)N3CCOCC3)ccc12] | (1-(5-(2-Fluoro-5-(trifluoromethoxy)phenyl)pyrimidin-2-yl)-3-(methylsulfinyl)-1H-indol-6-yl)(morpholino)methanone |
| 264 | 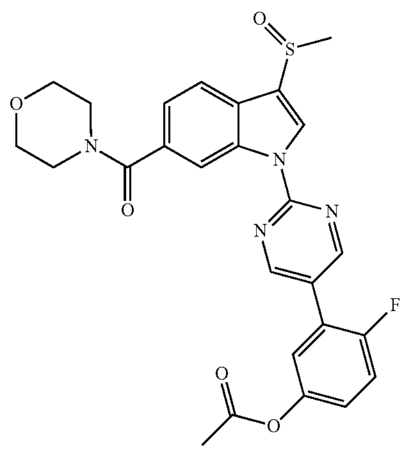 [SMILES: CC(=O)Oc1ccc(F)c(-c2cnc(-n3cc(S(C)=O)c4ccc(C(=O)N5CCOCC5)cc43)nc2)c1] | 4-Fluoro-3-(2-(3-(methylsulfinyl)-6-(morpholine-4-carbonyl)-1H-indol-1-yl)pyrimidin-5-yl)phenyl acetate |
| 265 | 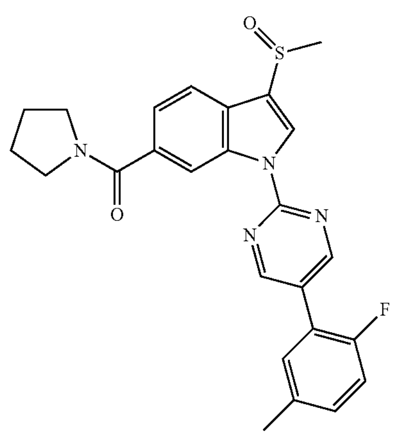 [SMILES: Cc1ccc(F)c(-c2cnc(-n3cc(S(C)=O)c4ccc(C(=O)N5CCCC5)cc43)nc2)c1] | (1-(5-(2-Fluoro-5-methylphenyl)pyrimidin-2-yl)-3-(methylsulfinyl)-1H-indol-6-yl)(pyrrolidin-1-yl)methanone |

TABLE 1-continued

| Cmpd-No. | Structure | Name |
|---|---|---|
| 266 | 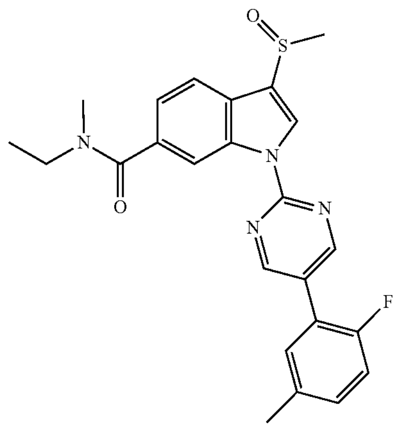 [SMILES: CCN(C)C(=O)c1ccc2c(S(C)=O)cn(-c3ncc(-c4cc(C)ccc4F)cn3)c2c1] | N-Ethyl-1-(5-(2-fluoro-5-methylphenyl)pyrimidin-2-yl)-N-methyl-3-(methylsulfinyl)-1H-indole-6-carboxamide |
| 267 | 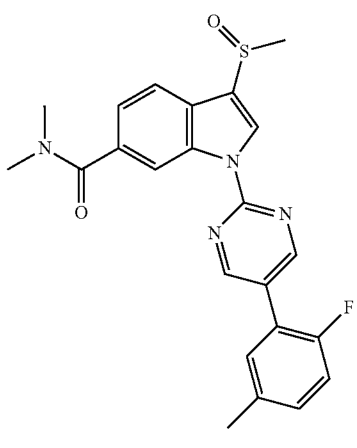 [SMILES: Cc1ccc(F)c(-c2cnc(-n3cc(S(C)=O)c4ccc(C(=O)N(C)C)cc43)nc2)c1] | 1-(5-(2-Fluoro-5-methylphenyl)pyrimidin-2-yl)-N,N-dimethyl-3-(methylsulfinyl)-1H-indole-6-carboxamide |
| 268 | 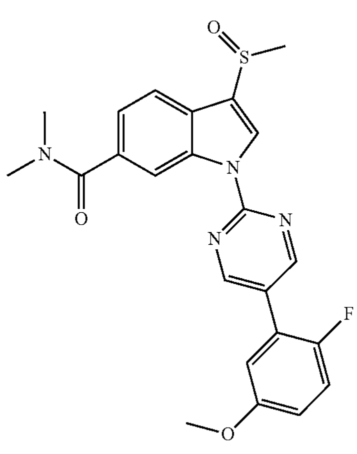 [SMILES: COc1ccc(F)c(-c2cnc(-n3cc(S(C)=O)c4ccc(C(=O)N(C)C)cc43)nc2)c1] | 1-(5-(2-Fluoro-5-methoxyphenyl)pyrimidin-2-yl)-N,N-dimethyl-3-(methylsulfinyl)-1H-indole-6-carboxamide |

| Cmpd-No. | Structure | Name |
|---|---|---|
| 269 | 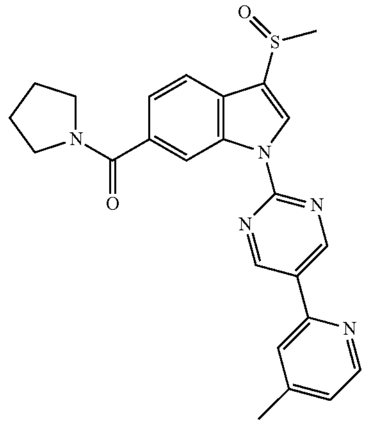 [SMILES: Cc1ccnc(-c2cnc(-n3cc(S(C)=O)c4ccc(C(=O)N5CCCC5)cc43)nc2)c1] | (1-(5-(4-Methylpyridin-2-yl)pyrimidin-2-yl)-3-(methylsulfinyl)-1H-indol-6-yl)(pyrrolidin-1-yl)methanone |
| 270 | 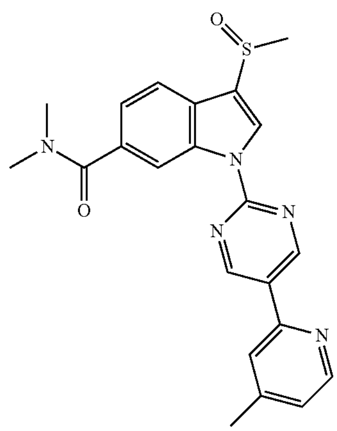 [SMILES: Cc1ccnc(-c2cnc(-n3cc(S(C)=O)c4ccc(C(=O)N(C)C)cc43)nc2)c1] | N,N-Dimethyl-1-(5-(4-methylpyridin-2-yl)pyrimidin-2-yl)-3-(methylsulfinyl)-1H-indole-6-carboxamide |
| 271 | 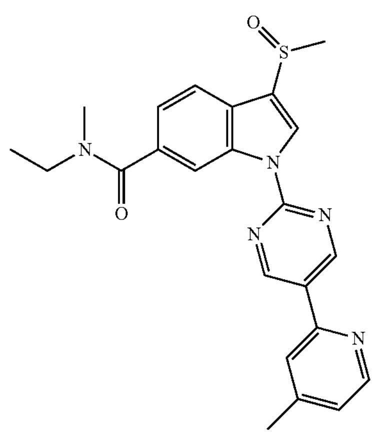 [SMILES: CCN(C)C(=O)c1ccc2c(S(C)=O)cn(-c3ncc(-c4cc(C)ccn4)cn3)c2c1] | N-Ethyl-N-methyl-1-(5-(4-methylpyridin-2-yl)pyrimidin-2-yl)-3-(methylsulfinyl)-1H-indole-6-carboxamide |

TABLE 1-continued

| Cmpd-No. | Structure | Name |
|---|---|---|
| 272 | 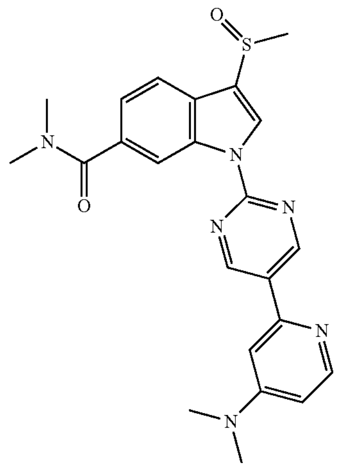 [SMILES: CN(C)C(=O)c1ccc2c(S(C)=O)cn(-c3ncc(-c4cc(N(C)C)ccn4)cn3)c2c1] | 1-(5-(4-(Dimethylamino)pyridin-2-yl)pyrimidin-2-yl)-N,N-dimethyl-3-(methylsulfinyl)-1H-indole-6-carboxamide |
| 273 | 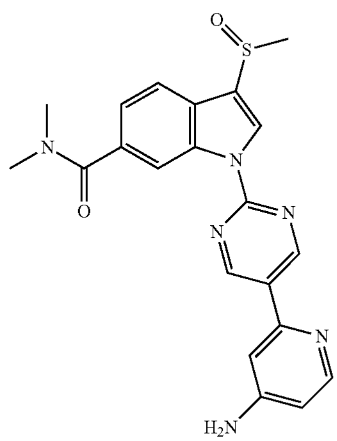 [SMILES: CN(C)C(=O)c1ccc2c(S(C)=O)cn(-c3ncc(-c4cc(N)ccn4)cn3)c2c1] | 1-(5-(4-Aminopyridin-2-yl)pyrimidin-2-yl)-N,N-dimethyl-3-(methylsulfinyl)-1H-indole-6-carboxamide |
| 274 | 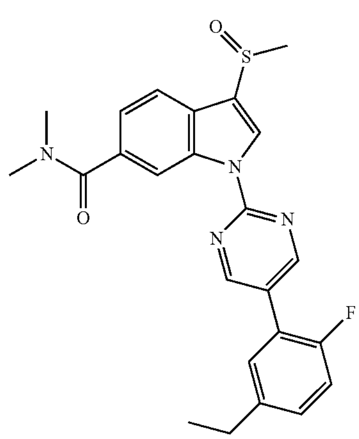 [SMILES: CCc1ccc(F)c(-c2cnc(-n3cc(S(C)=O)c4ccc(C(=O)N(C)C)cc43)nc2)c1] | 1-(5-(5-Ethyl-2-fluorophenyl)pyrimidin-2-yl)-N,N-dimethyl-3-(methylsulfinyl)-1H-indole-6-carboxamide |

TABLE 1-continued

| Cmpd-No. | Structure | Name |
|---|---|---|
| 275 | 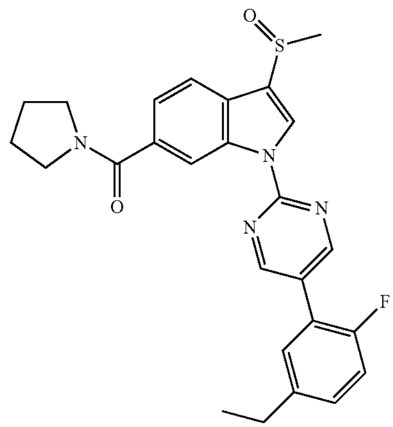 [SMILES: CCc1ccc(F)c(-c2cnc(-n3cc(S(C)=O)c4ccc(C(=O)N5CCCC5)cc43)nc2)c1] | (1-(5-(5-Ethyl-2-fluorophenyl)pyrimidin-2-yl)-3-(methylsulfinyl)-1H-indol-6-yl)(pyrrolidin-1-yl)methanone |
| 276 | 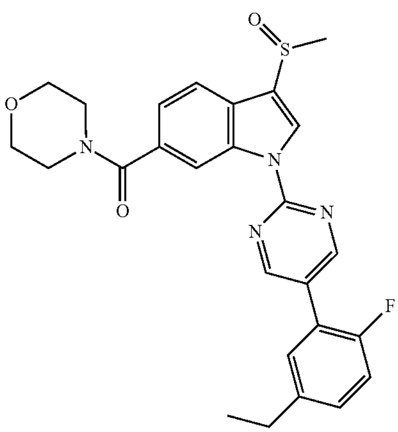 [SMILES: CCc1ccc(F)c(-c2cnc(-n3cc(S(C)=O)c4ccc(C(=O)N5CCOCC5)cc43)nc2)c1] | (1-(5-(5-Ethyl-2-fluorophenyl)pyrimidin-2-yl)-3-(methylsulfinyl)-1H-indol-6-yl)(morpholino)methanone |
| 277 | 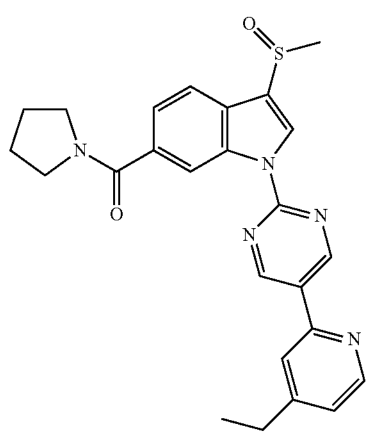 [SMILES: CCc1ccnc(-c2cnc(-n3cc(S(C)=O)c4ccc(C(=O)N5CCCC5)cc43)nc2)c1] | (1-(5-(4-Ethylpyridin-2-yl)pyrimidin-2-yl)-3-(methylsulfinyl)-1H-indol-6-yl)(pyrrolidin-1-yl)methanone |

TABLE 1-continued

| Cmpd-No. | Structure | Name |
|---|---|---|
| 278 | 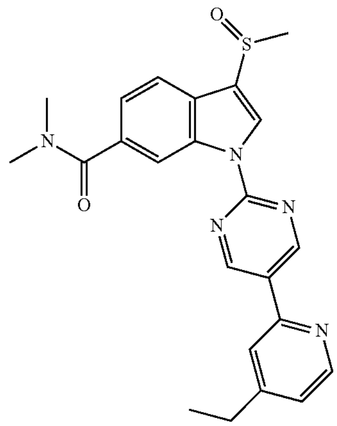 [SMILES: CCc1ccnc(-c2cnc(-n3cc(S(C)=O)c4ccc(C(=O)N(C)C)cc43)nc2)c1] | 1-(5-(4-Ethylpyridin-2-yl)pyrimidin-2-yl)-N,N-dimethyl-3-(methylsulfinyl)-1H-indole-6-carboxamide |
| 279 | 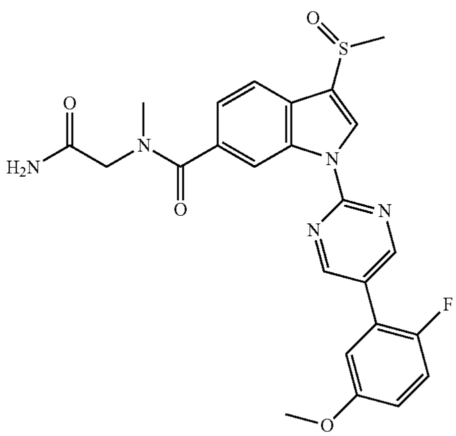 [SMILES: COc1ccc(F)c(-c2cnc(-n3cc(S(C)=O)c4ccc(C(=O)N(C)CC(N)=O)cc43)nc2)c1] | N-(2-Amino-2-oxoethyl)-1-(5-(2-fluoro-5-methoxyphenyl)pyrimidin-2-yl)-N-methyl-3-(methylsulfinyl)-1H-indole-6-carboxamide |
| 280 | 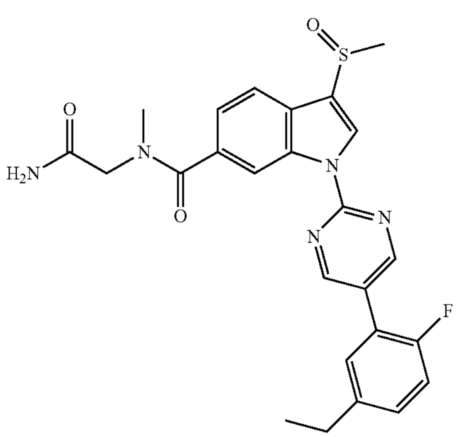 [SMILES: CCc1ccc(F)c(-c2cnc(-n3cc(S(C)=O)c4ccc(C(=O)N(C)CC(N)=O)cc43)nc2)c1] | N-(2-Amino-2-oxoethyl)-1-(5-(5-ethyl-2-fluorophenyl)pyrimidin-2-yl)-N-methyl-3-(methylsulfinyl)-1H-indole-6-carboxamide |

TABLE 1-continued

| Cmpd-No. | Structure | Name |
|---|---|---|
| 281 | 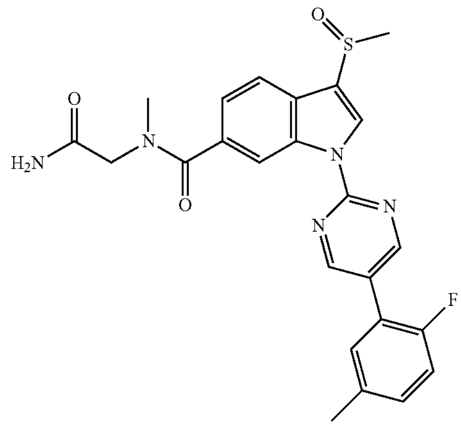 [SMILES: Cc1ccc(F)c(-c2cnc(-n3cc(S(C)=O)c4ccc(C(=O)N(C)CC(N)=O)cc43)nc2)c1] | N-(2-Amino-2-oxoethyl)-1-(5-(2-fluoro-5-methylphenyl)pyrimidin-2-yl)-N-methyl-3-(methylsulfinyl)-1H-indole-6-carboxamide |
| 282 | 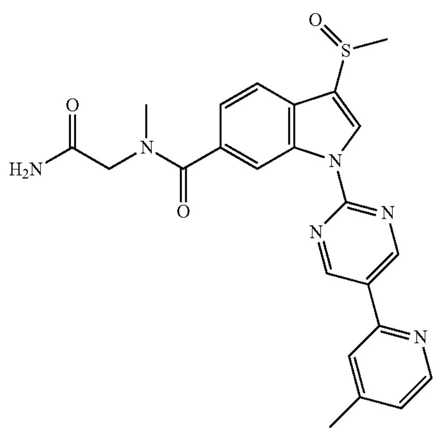 [SMILES: Cc1ccnc(-c2cnc(-n3cc(S(C)=O)c4ccc(C(=O)N(C)CC(N)=O)cc43)nc2)c1] | N-(2-Amino-2-oxoethyl)-N-methyl-1-(5-(4-methylpyridin-2-yl)pyrimidin-2-yl)-3-(methylsulfinyl)-1H-indole-6-carboxamide |
| 283 | 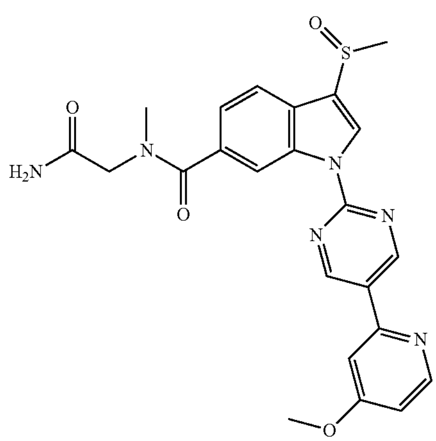 [SMILES: COc1ccnc(-c2cnc(-n3cc(S(C)=O)c4ccc(C(=O)N(C)CC(N)=O)cc43)nc2)c1] | N-(2-Amino-2-oxoethyl)-1-(5-(4-methoxypyridin-2-yl)pyrimidin-2-yl)-N-methyl-3-(methylsulfinyl)-1H-indole-6-carboxamide |

| Cmpd-No. | Structure | Name |
|---|---|---|
| 284 | 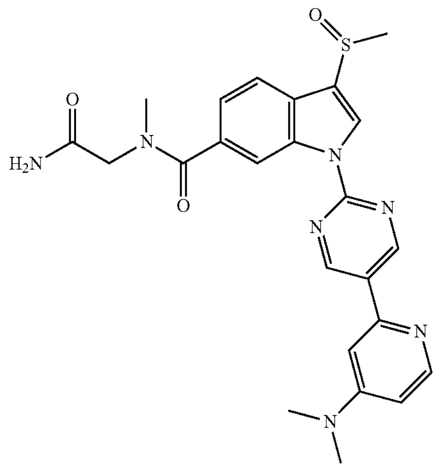 [SMILES: CN(CC(N)=O)C(=O)c1ccc2c(S(C)=O)cn(-c3ncc(-c4cc(N(C)C)ccn4)cn3)c2c1] | N-(2-Amino-2-oxoethyl)-1-(5-(4-(dimethylamino)pyridin-2-yl)pyrimidin-2-yl)-N-methyl-3-(methylsulfinyl)-1H-indole-6-carboxamide |
| 285 | 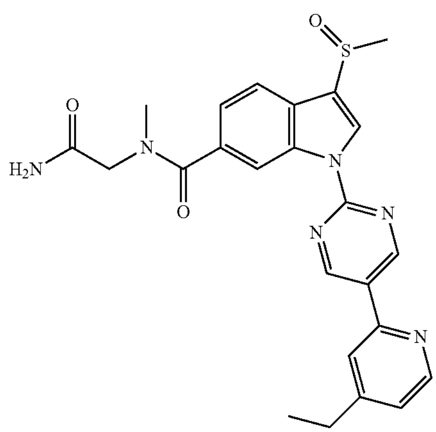 [SMILES: CCc1ccnc(-c2cnc(-n3cc(S(C)=O)c4ccc(C(=O)N(C)CC(N)=O)cc43)nc2)c1] | N-(2-Amino-2-oxoethyl)-1-(5-(4-ethylpyridin-2-yl)pyrimidin-2-yl)-N-methyl-3-(methylsulfinyl)-1H-indole-6-carboxamide |
| 286 | 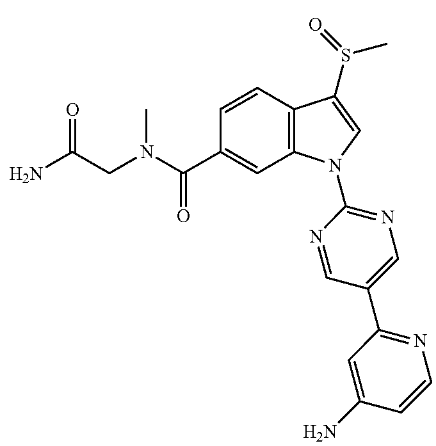 [SMILES: CN(CC(N)=O)C(=O)c1ccc2c(S(C)=O)cn(-c3ncc(-c4cc(N)ccn4)cn3)c2c1] | N-(2-Amino-2-oxoethyl)-1-(5-(4-aminopyridin-2-yl)pyrimidin-2-yl)-N-methyl-3-(methylsulfinyl)-1H-indole-6-carboxamide |

| Cmpd-No. | Structure | Name |
|---|---|---|
| 287 | 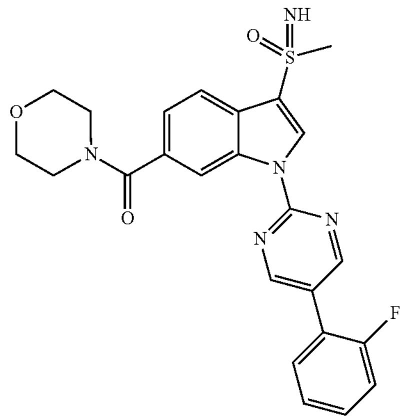 [SMILES: CS(=N)(=O)c1cn(-c2ncc(-c3ccccc3F)cn2)c2cc(C(=O)N3CCOCC3)ccc12] | (1-(5-(2-Fluorophenyl)pyrimidin-2-yl)-3-(S-methylsulfonimidoyl)-1H-indol-6-yl)(morpholino)methanone |
| 288 | 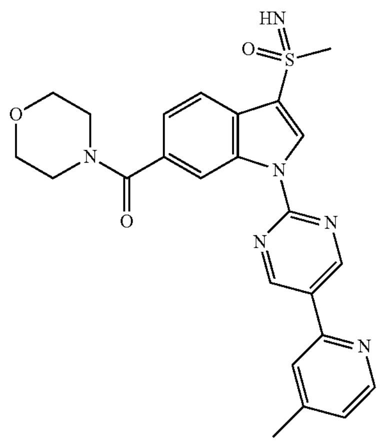 [SMILES: Cc1ccnc(-c2cnc(-n3cc(S(C)(=N)=O)c4ccc(C(=O)N5CCOCC5)cc43)nc2)c1] | (1-(5-(4-Methylpyridin-2-yl)pyrimidin-2-yl)-3-(S-methylsulfonimidoyl)-1H-indol-6-yl)(morpholino)methanone |
| 289 | 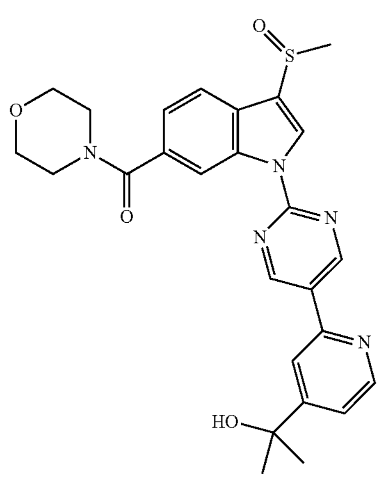 [SMILES: CS(=O)c1cn(-c2ncc(-c3cc(C(C)(C)O)ccn3)cn2)c2cc(C(=O)N3CCOCC3)ccc12] | (1-(5-(4-(2-Hydroxypropan-2-yl)pyridin-2-yl)pyrimidin-2-yl)-3-(methylsulfinyl)-1H-indol-6-yl)(morpholino)methanone |

| Cmpd-No. | Structure | Name |
|---|---|---|
| 290 | 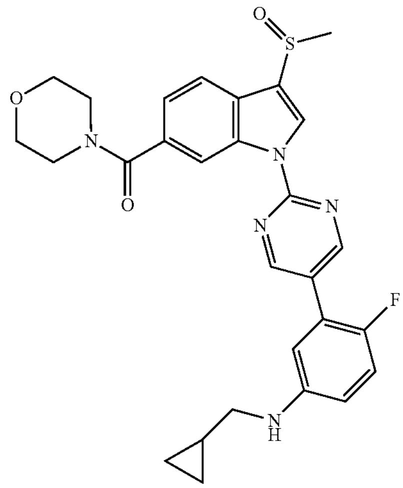 [SMILES: CS(=O)c1cn(-c2ncc(-c3cc(NCC4CC4)ccc3F)cn2)c2cc(C(=O)N3CCOCC3)ccc12] | (1-(5-(5-((Cyclopropylmethyl)amino)-2-fluorophenyl)pyrimidin-2-yl)-3-(methylsulfinyl)-1H-indol-6-yl)(morpholino)methanone |
| 291 | 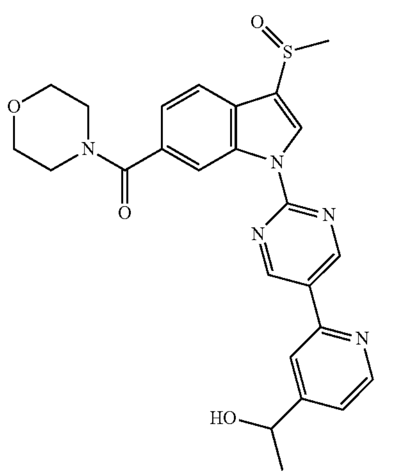 [SMILES: CC(O)c1ccnc(-c2cnc(-n3cc(S(C)=O)c4ccc(C(=O)N5CCOCC5)cc43)nc2)c1] | (1-(5-(4-(1-Hydroxyethyl)pyridin-2-yl)pyrimidin-2-yl)-3-(methylsulfinyl)-1H-indol-6-yl)(morpholino)methanone |
| 292 | 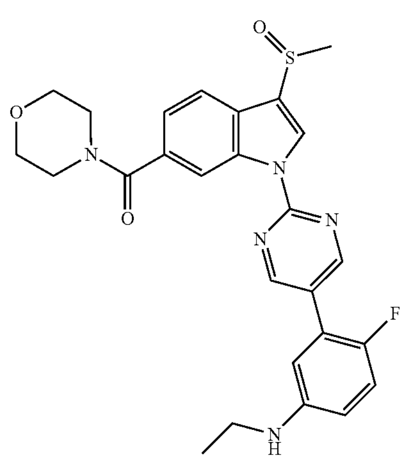 [SMILES: CCNc1ccc(F)c(-c2cnc(-n3cc(S(C)=O)c4ccc(C(=O)N5CCOCC5)cc43)nc2)c1] | (1-(5-(5-(Ethylamino)-2-fluorophenyl)pyrimidin-2-yl)-3-(methylsulfinyl)-1H-indol-6-yl)(morpholino)methanone |

TABLE 1-continued

| Cmpd-No. | Structure | Name |
|---|---|---|
| 293 | 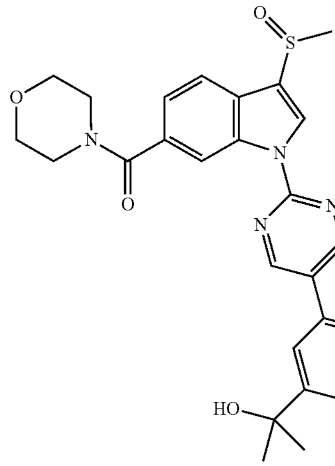 | (1-(5-(2-Fluoro-5-(2-hydroxypropan-2-yl)phenyl)pyrimidin-2-yl)-3-(methylsulfinyl)-1H-indol-6-yl)(morpholino)methanone |
| 294 | 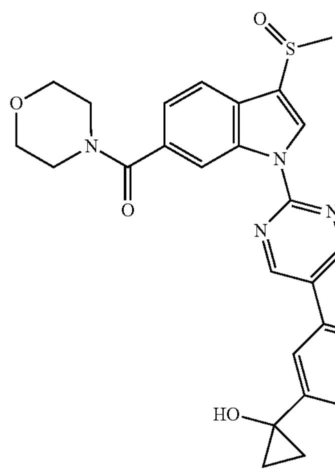 | (1-(5-(2-Fluoro-5-(1-hydroxycyclopropyl)phenyl)pyrimidin-2-yl)-3-(methylsulfinyl)-1H-indol-6-yl)(morpholino)methanone |
| 295 | 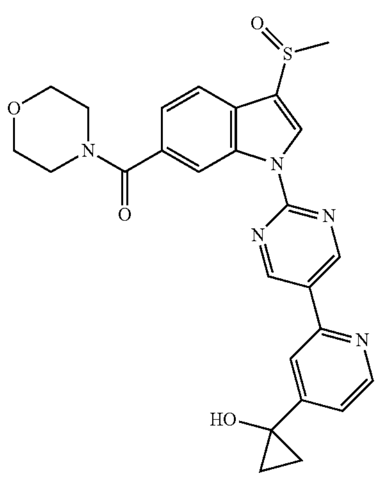 [SMILES: CS(=O)c1cn(-c2ncc(-c3cc(C4(O)CC4)ccn3)cn2)c2cc(C(=O)N3CCOCC3)ccc12] | (1-(5-(4-(1-Hydroxycyclopropyl)pyridin-2-yl)pyrimidin-2-yl)-3-(methylsulfinyl)-1H-indol-6-yl)(morpholino)methanone |

| Cmpd-No. | Structure | Name |
|---|---|---|
| 296 | 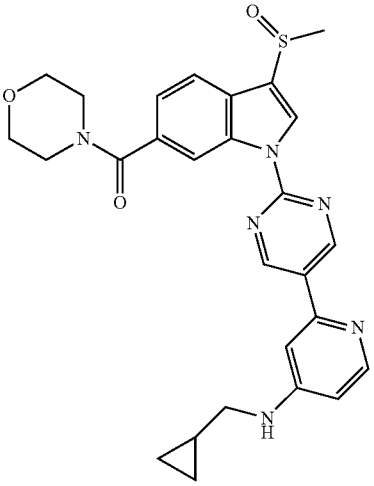 [SMILES: CS(=O)c1cn(-c2ncc(-c3cc(NCC4CC4)ccn3)cn2)c2cc(C(=O)N3CCOCC3)ccc12] | (1-(5-(4-((Cyclopropylmethyl)amino)pyridin-2-yl)pyrimidin-2-yl)-3-(methylsulfinyl)-1H-indol-6-yl)(morpholino)methanone |
| 297 | 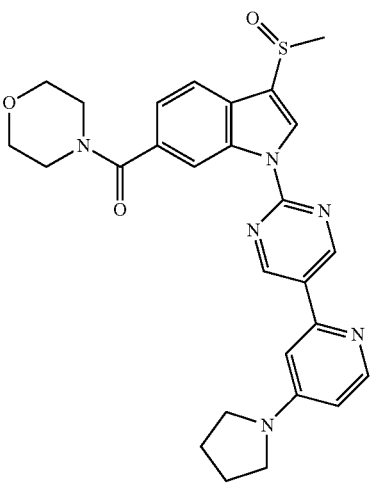 [SMILES: CS(=O)c1cn(-c2ncc(-c3cc(N4CCCC4)ccn3)cn2)c2cc(C(=O)N3CCOCC3)ccc12] | (3-(Methylsulfinyl)-1-(5-(4-(pyrrolidin-1-yl)pyridin-2-yl)pyrimidin-2-yl)-1H-indol-6-yl)(morpholino)methanone |
| 298 | 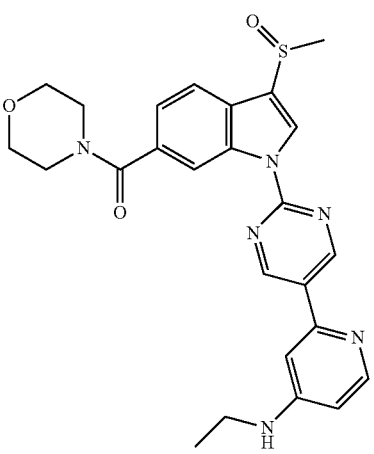 [SMILES: CCNc1ccnc(-c2cnc(-n3cc(S(C)=O)c4ccc(C(=O)N5CCOCC5)cc43)nc2)c1] | (1-(5-(4-(Ethylamino)pyridin-2-yl)pyrimidin-2-yl)-3-(methylsulfinyl)-1H-indol-6-yl)(morpholino)methanone |

TABLE 1-continued

| Cmpd-No. | Structure | Name |
|---|---|---|
| 299 | 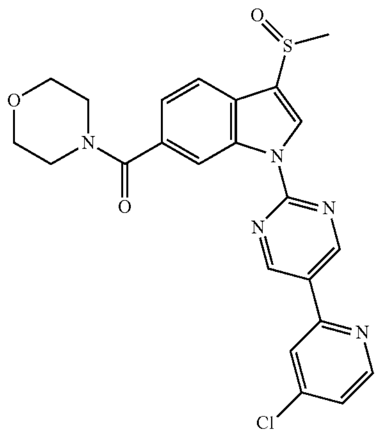 [SMILES: CS(=O)c1cn(-c2ncc(-c3cc(Cl)ccn3)cn2)c2cc(C(=O)N3CCOCC3)ccc12] | (1-(5-(4-Chloropyridin-2-yl)pyrimidin-2-yl)-3-(methylsulfinyl)-1H-indol-6-yl)(morpholino)methanone |
| 300 | 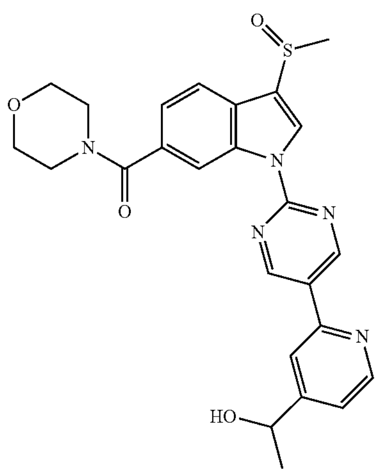 [SMILES: CC(O)c1ccnc(-c2cnc(-n3cc(S(C)=O)c4ccc(C(=O)N5CCOCC5)cc43)nc2)c1] | (1-(5-(4-(1-Hydroxyethyl)pyridin-2-yl)pyrimidin-2-yl)-3-(methylsulfinyl)-1H-indol-6-yl)(morpholino)methanone |
| 301 | 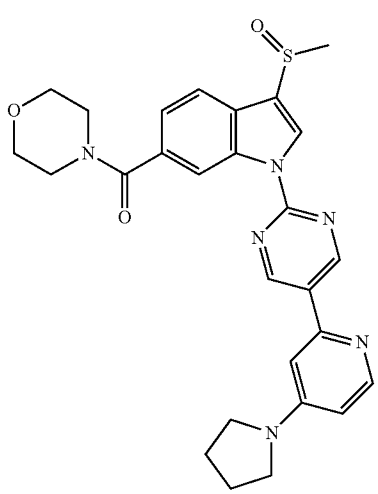 [SMILES: CS(=O)c1cn(-c2ncc(-c3cc(N4CCCC4)ccn3)cn2)c2cc(C(=O)N3CCOCC3)ccc12] | (3-(Methylsulfinyl)-1-(5-(4-(pyrrolidin-1-yl)pyridin-2-yl)pyrimidin-2-yl)-1H-indol-6-yl)(morpholino)methanone |

TABLE 1-continued

| Cmpd-No. | Structure | Name |
|---|---|---|
| 302 | 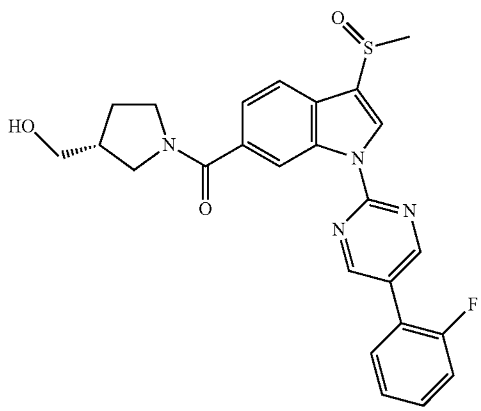 [SMILES: CS(=O)c1cn(-c2ncc(-c3ccccc3F)cn2)c2cc(C(=O)N3CC[C@@H](CO)C3)ccc12] | (1-(5-(2-Fluorophenyl)pyrimidin-2-yl)-3-(methylsulfinyl)-1H-indol-6-yl)((R)-3-(hydroxymethyl)pyrrolidin-1-yl)methanone |
| 303 | 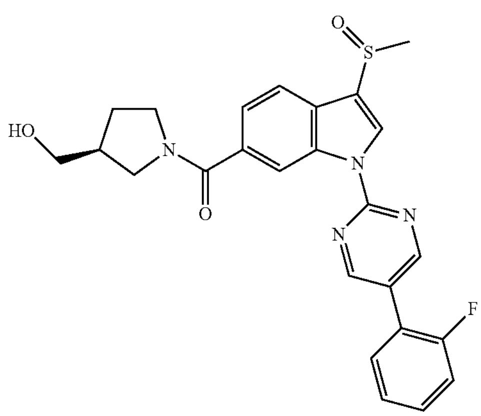 [SMILES: CS(=O)c1cn(-c2ncc(-c3ccccc3F)cn2)c2cc(C(=O)N3CC[C@H](CO)C3)ccc12] | (1-(5-(2-Fluorophenyl)pyrimidin-2-yl)-3-(methylsulfinyl)-1H-indol-6-yl)((S)-3-(hydroxymethyl)pyrrolidin-1-yl)methanone |
| 304 | 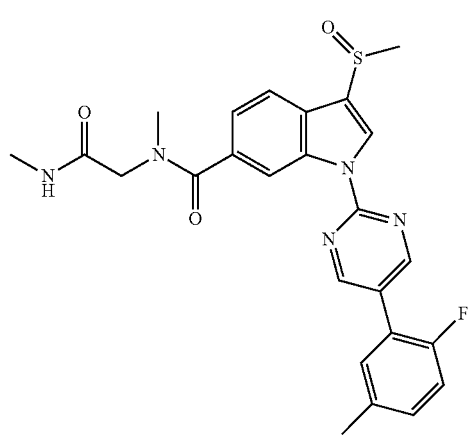 [SMILES: CNC(=O)CN(C)C(=O)c1ccc2c(S(C)=O)cn(-c3ncc(-c4cc(C)ccc4F)cn3)c2c1] | 1-(5-(2-Fluoro-5-methylphenyl)pyrimidin-2-yl)-N-methyl-N-(2-(methylamino)-2-oxoethyl)-3-(methylsulfinyl)-1H-indole-6-carboxamide |

| Cmpd-No. | Structure | Name |
|---|---|---|
| 305 | 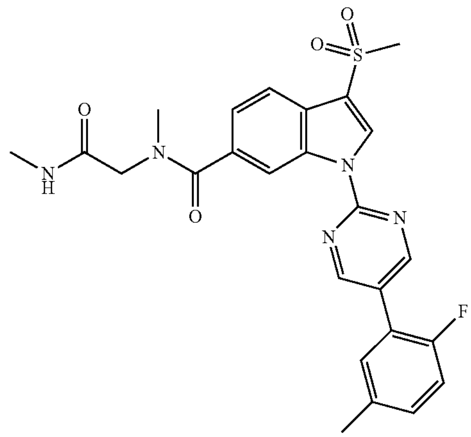 [SMILES: CNC(=O)CN(C)C(=O)c1ccc2c(S(C)(=O)=O)cn(-c3ncc(-c4cc(C)ccc4F)cn3)c2c1] | 1-(5-(2-Fluoro-5-methylphenyl)pyrimidin-2-yl)-N-methyl-N-(2-(methylamino)-2-oxoethyl)-3-(methylsulfonyl)-1H-indole-6-carboxamide |
| 306 | 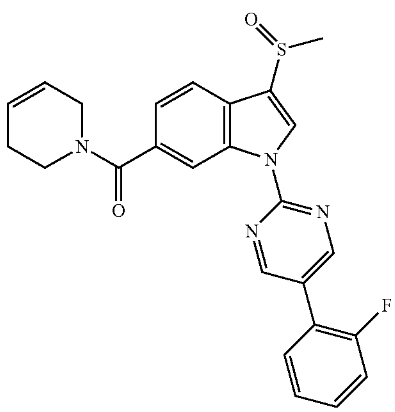 [SMILES: CS(=O)c1cn(-c2ncc(-c3ccccc3F)cn2)c2cc(C(=O)N3CC=CCC3)ccc12] | (5,6-Dihydropyridin-1(2H)-yl)(1-(5-(2-fluorophenyl)pyrimidin-2-yl)-3-(methylsulfinyl)-1H-indol-6-yl)methanone |
| 307 | 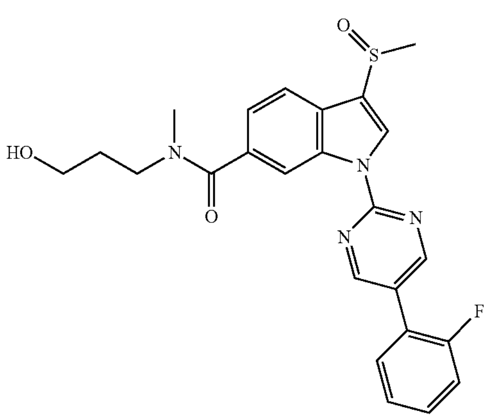 [SMILES: CN(CCCO)C(=O)c1ccc2c(S(C)=O)cn(-c3ncc(-c4ccccc4F)cn3)c2c1] | 1-(5-(2-Fluorophenyl)pyrimidin-2-yl)-N-(3-hydroxypropyl)-N-methyl-3-(methylsulfinyl)-1H-indole-6-carboxamide |

TABLE 1-continued
| Cmpd-No. | Structure | Name |
|---|---|---|
| 308 | 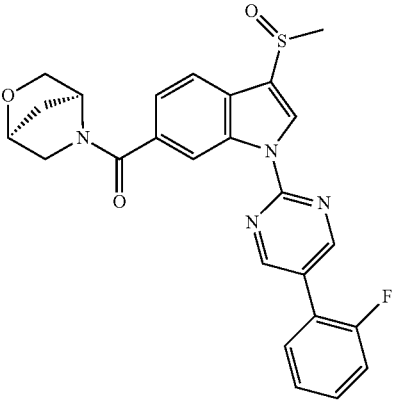 [SMILES: CS(=O)c1cn(-c2ncc(-c3ccccc3F)cn2)c2cc(C(=O)N3C[C@@H]4C[C@H]3CO4)ccc12] | (1S,4S)-2-Oxa-5-azabicyclo[2.2.1]heptan-5-yl(1-(5-(2-fluorophenyl)pyrimidin-2-yl)-3-(methylsulfinyl)-1H-indol-6-yl)methanone |
| 309 | 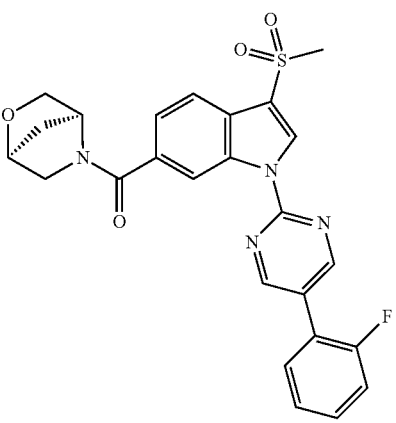 [SMILES: CS(=O)(=O)c1cn(-c2ncc(-c3ccccc3F)cn2)c2cc(C(=O)N3C[C@@H]4C[C@H]3CO4)ccc12] | (1S,4S)-2-Oxa-5-azabicyclo[2.2.1]heptan-5-yl(1-(5-(2-fluorophenyl)pyrimidin-2-yl)-3-(methylsulfonyl)-1H-indol-6-yl)methanone |
| 310 | 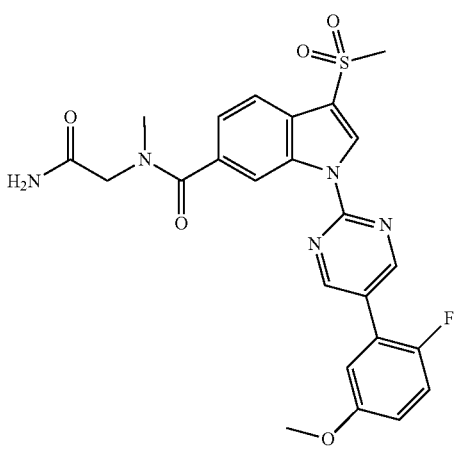 [SMILES: COc1ccc(F)c(-c2cnc(-n3cc(S(C)(=O)=O)c4ccc(C(=O)N(C)CC(N)=O)cc43)nc2)c1] | N-(2-Amino-2-oxoethyl)-1-(5-(2-fluoro-5-methoxyphenyl)pyrimidin-2-yl)-N-methyl-3-(methylsulfonyl)-1H-indole-6-carboxamide |

| Cmpd-No. | Structure | Name |
|---|---|---|
| 311 | 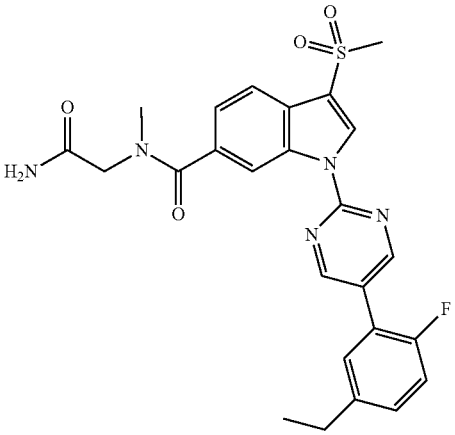 [SMILES: CCc1ccc(F)c(-c2cnc(-n3cc(S(C)(=O)=O)c4ccc(C(=O)N(C)CC(N)=O)cc43)nc2)c1] | N-(2-Amino-2-oxoethyl)-1-(5-(5-ethyl-2-fluorophenyl)pyrimidin-2-yl)-N-methyl-3-(methylsulfonyl)-1H-indole-6-carboxamide |
| 312 | 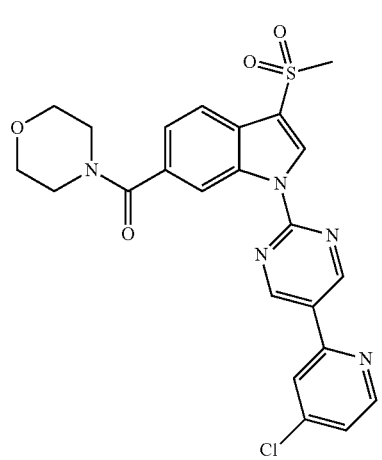 [SMILES: CS(=O)(=O)c1cn(-c2ncc(-c3cc(Cl)ccn3)cn2)c2cc(C(=O)N3CCOCC3)ccc12] | (1-(5-(4-Chloropyridin-2-yl)pyrimidin-2-yl)-3-(methylsulfonyl)-1H-indol-6-yl)(morpholino)methanone |
| 313 | 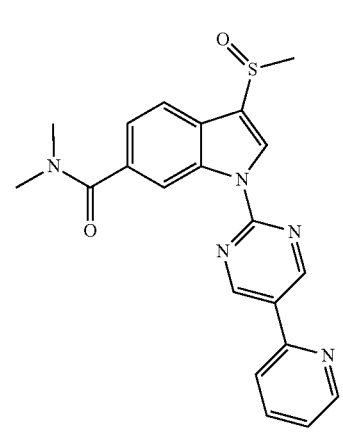 [SMILES: CN(C)C(=O)c1ccc2c(S(C)=O)cn(-c3ncc(-c4ccccn4)cn3)c2c1] | N,N-Dimethyl-3-(methylsulfinyl)-1-(5-(pyridin-2-yl)pyrimidin-2-yl)-1H-indole-6-carboxamide |

TABLE 1-continued

| Cmpd-No. | Structure | Name |
|---|---|---|
| 314 | 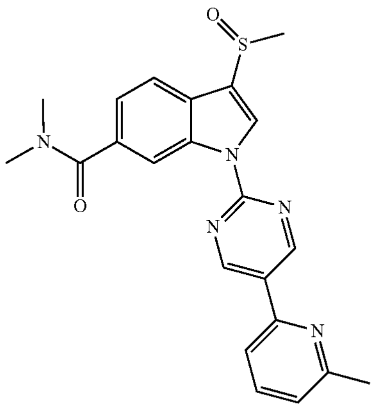 | N,N-Dimethyl-1-(5-(6-methylpyridin-2-yl)pyrimidin-2-yl)-3-(methylsulfinyl)-1H-indole-6-carboxamide |
| 315 | 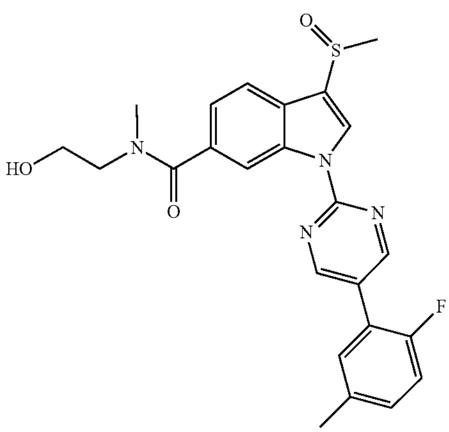 [SMILES: Cc1ccc(F)c(-c2cnc(-n3cc(S(C)=O)c4ccc(C(=O)N(C)CCO)cc43)nc2)c1] | 1-(5-(2-Fluoro-5-methylphenyl)pyrimidin-2-yl)-N-(2-hydroxyethyl)-N-methyl-3-(methylsulfinyl)-1H-indole-6-carboxamide |
| 316 | 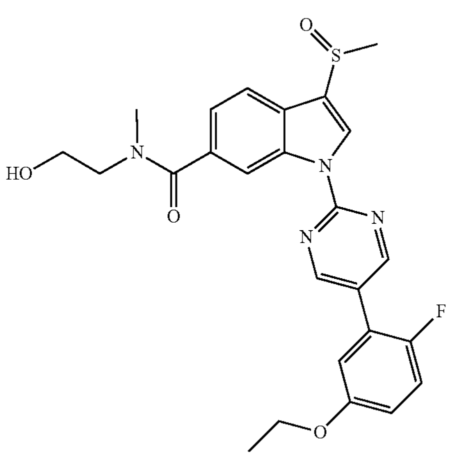 [SMILES: CCOc1ccc(F)c(-c2cnc(-n3cc(S(C)=O)c4ccc(C(=O)N(C)CCO)cc43)nc2)c1] | 1-(5-(5-Ethoxy-2-fluorophenyl)pyrimidin-2-yl)-N-(2-hydroxyethyl)-N-methyl-3-(methylsulfinyl)-1H-indole-6-carboxamide |

TABLE 1-continued

| Cmpd-No. | Structure | Name |
|---|---|---|
| 317 | 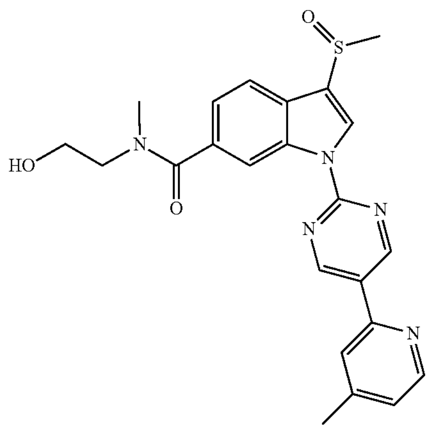 [SMILES: Cc1ccnc(-c2cnc(-n3cc(S(C)=O)c4ccc(C(=O)N(C)CCO)cc43)nc2)c1] | N-(2-Hydroxyethyl)-N-methyl-1-(5-(4-methylpyridin-2-yl)pyrimidin-2-yl)-3-(methylsulfinyl)-1H-indole-6-carboxamide |
| 318 | 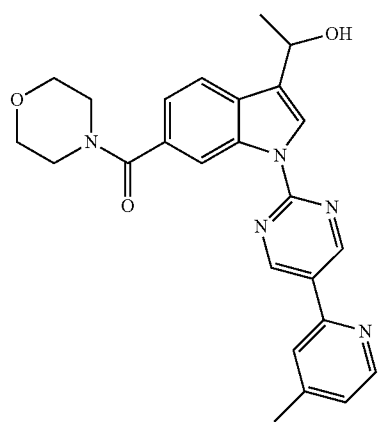 [SMILES: Cc1ccnc(-c2cnc(-n3cc(C(C)O)c4ccc(C(=O)N5CCOCC5)cc43)nc2)c1] | (3-(1-Hydroxyethyl)-1-(5-(4-methylpyridin-2-yl)pyrimidin-2-yl)-1H-indol-6-yl)(morpholino)methanone |
| 319 | 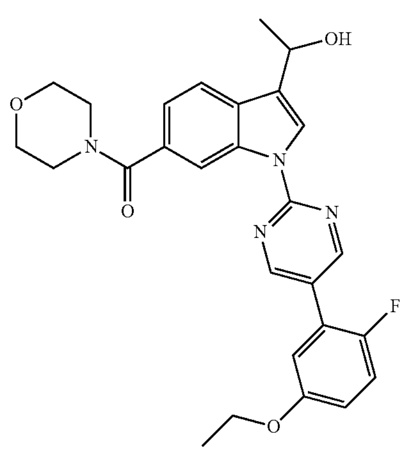 [SMILES: CCOc1ccc(F)c(-c2cnc(-n3cc(C(C)O)c4ccc(C(=O)N5CCOCC5)cc43)nc2)c1] | (1-(5-(5-Ethoxy-2-fluorophenyl)pyrimidin-2-yl)-3-(1-hydroxyethyl)-1H-indol-6-yl)(morpholino)methanone |

TABLE 1-continued

| Cmpd-No. | Structure | Name |
|---|---|---|
| 320 | 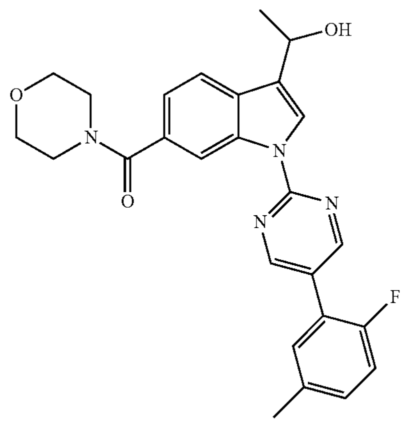 [SMILES: Cc1ccc(F)c(-c2cnc(-n3cc(C(C)O)c4ccc(C(=O)N5CCOCC5)cc43)nc2)c1] | (1-(5-(2-Fluoro-5-methylphenyl)pyrimidin-2-yl)-3-(1-hydroxyethyl)-1H-indol-6-yl)(morpholino)methanone |
| 321 | 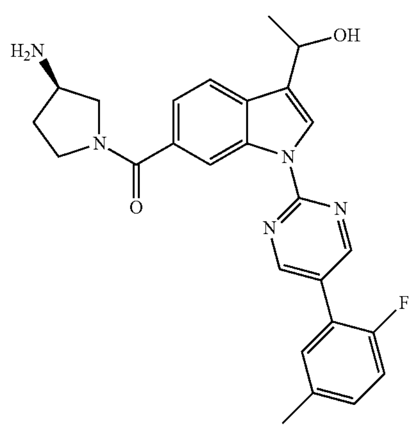 [SMILES: Cc1ccc(F)c(-c2cnc(-n3cc(C(C)O)c4ccc(C(=O)N5CC[C@@H](N)C5)cc43)nc2)c1] | ((R)-3-Aminopyrrolidin-1-yl)(1-(5-(2-fluoro-5-methylphenyl)pyrimidin-2-yl)-3-(1-hydroxyethyl)-1H-indol-6-yl)methanone |
| 322 | 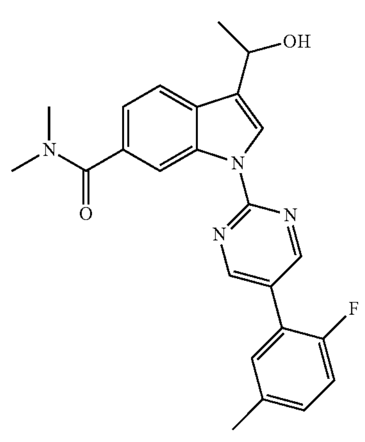 [SMILES: Cc1ccc(F)c(-c2cnc(-n3cc(C(C)O)c4ccc(C(=O)N(C)C)cc43)nc2)c1] | 1-(5-(2-Fluoro-5-methylphenyl)pyrimidin-2-yl)-3-(1-hydroxyethyl)-N,N-dimethyl-1H-indole-6-carboxamide |

TABLE 1-continued

| Cmpd-No. | Structure | Name |
|---|---|---|
| 323 | 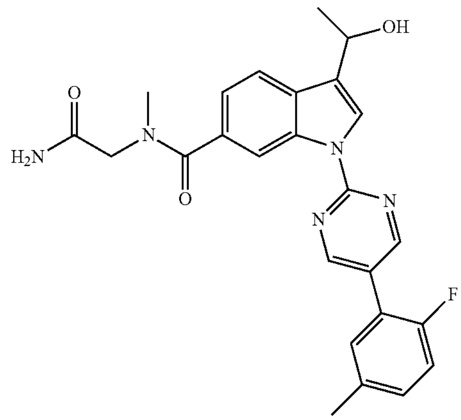 [SMILES: Cc1ccc(F)c(-c2cnc(-n3cc(C(C)O)c4ccc(C(=O)N(C)CC(N)=O)cc43)nc2)c1] | N-(2-Amino-2-oxoethyl)-1-(5-(2-fluoro-5-methylphenyl)pyrimidin-2-yl)-3-(1-hydroxyethyl)-N-methyl-1H-indole-6-carboxamide |
| 324 | 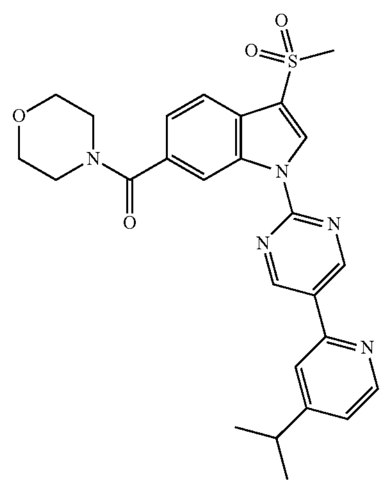 [SMILES: CC(C)c1ccnc(-c2cnc(-n3cc(S(C)(=O)=O)c4ccc(C(=O)N5CCOCC5)cc43)nc2)c1] | (1-(5-(4-Isopropylpyridin-2-yl)pyrimidin-2-yl)-3-(methylsulfonyl)-1H-indol-6-yl)(morpholino)methanone |
| 325 | 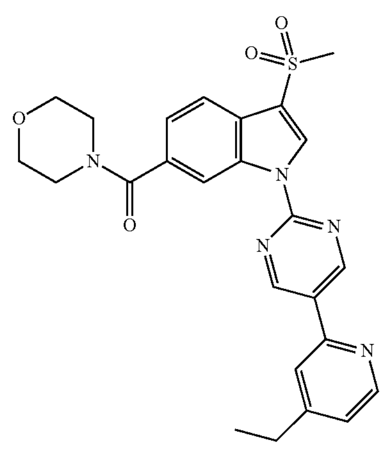 [SMILES: CCc1ccnc(-c2cnc(-n3cc(S(C)(=O)=O)c4ccc(C(=O)N5CCOCC5)cc43)nc2)c1] | (1-(5-(4-Ethylpyridin-2-yl)pyrimidin-2-yl)-3-(methylsulfonyl)-1H-indol-6-yl)(morpholino)methanone |

TABLE 1-continued
| Cmpd-No. | Structure | Name |
|---|---|---|
| 326 | 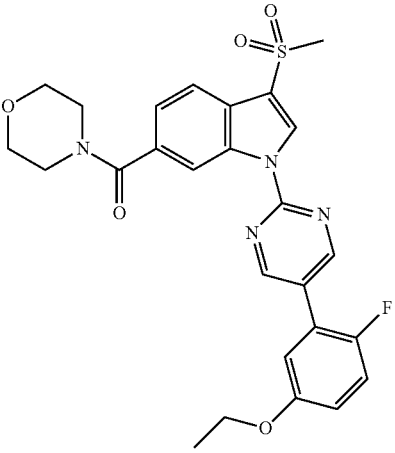 [SMILES: CCOc1ccc(F)c(-c2cnc(-n3cc(S(C)(=O)=O)c4ccc(C(=O)N5CCOCC5)cc43)nc2)c1] | (1-(5-(5-Ethoxy-2-fluorophenyl)pyrimidin-2-yl)-3-(methylsulfonyl)-1H-indol-6-yl)(morpholino)methanone |
| 327 | 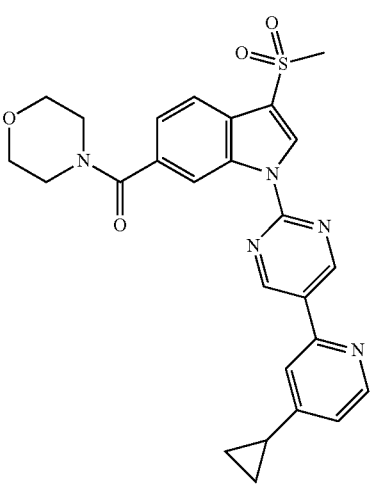 [SMILES: CS(=O)(=O)c1cn(-c2ncc(-c3cc(C4CC4)ccn3)cn2)c2cc(C(=O)N3CCOCC3)ccc12] | (1-(5-(4-Cyclopropylpyridin-2-yl)pyrimidin-2-yl)-3-(methylsulfonyl)-1H-indol-6-yl)(morpholino)methanone |
| 328 | 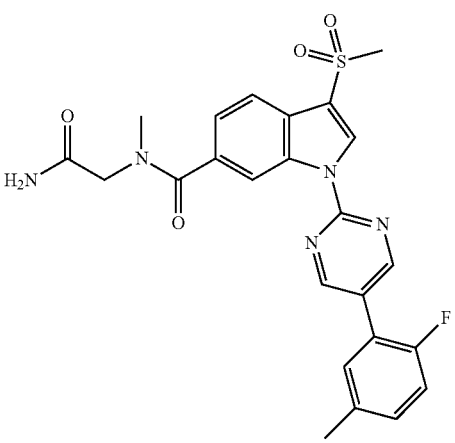 [SMILES: Cc1ccc(F)c(-c2cnc(-n3cc(S(C)(=O)=O)c4ccc(C(=O)N(C)CC(N)=O)cc43)nc2)c1] | N-(2-Amino-2-oxoethyl)-1-(5-(2-fluoro-5-methylphenyl)pyrimidin-2-yl)-N-methyl-3-(methylsulfonyl)-1H-indole-6-carboxamide |

TABLE 1-continued
| Cmpd-No. | Structure | Name |
|---|---|---|
| 329 | 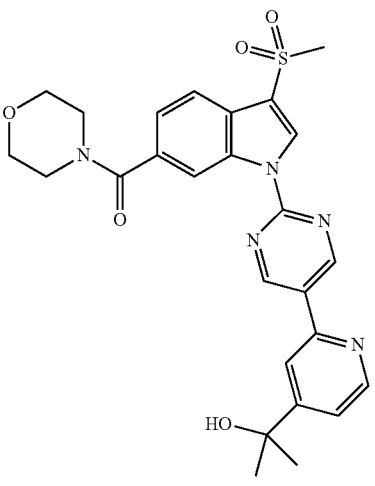 [SMILES: CC(C)(O)c1ccnc(-c2cnc(-n3cc(S(C)(=O)=O)c4ccc(C(=O)N5CCOCC5)cc43)nc2)c1] | (1-(5-(4-(2-Hydroxypropan-2-yl)pyridin-2-yl)pyrimidin-2-yl)-3-(methylsulfonyl)-1H-indol-6-yl)(morpholino)methanone |
| 330 | 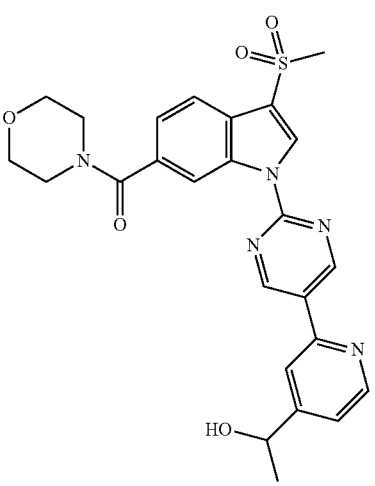 [SMILES: CC(O)c1ccnc(-c2cnc(-n3cc(S(C)(=O)=O)c4ccc(C(=O)N5CCOCC5)cc43)nc2)c1] | (1-(5-(4-(1-Hydroxyethyl)pyridin-2-yl)pyrimidin-2-yl)-3-(methylsulfonyl)-1H-indol-6-yl)(morpholino)methanone |
| 331 | 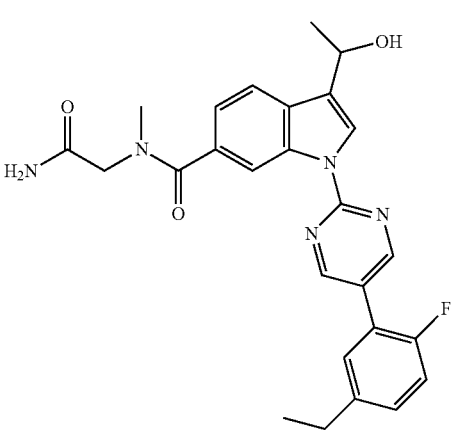 [SMILES: CCc1ccc(F)c(-c2cnc(-n3cc(C(C)O)c4ccc(C(=O)N(C)CC(N)=O)cc43)nc2)c1] | N-(2-Amino-2-oxoethyl)-1-(5-(5-ethyl-2-fluorophenyl)pyrimidin-2-yl)-3-(1-hydroxyethyl)-N-methyl-1H-indole-6-carboxamide |

TABLE 1-continued

| Cmpd-No. | Structure | Name |
|---|---|---|
| 332 | 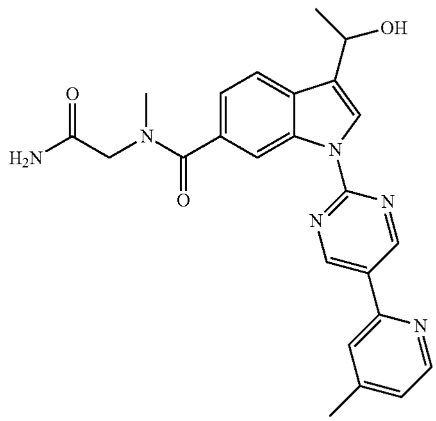 [SMILES: Cc1ccnc(-c2cnc(-n3cc(C(C)O)c4ccc(C(=O)N(C)CC(N)=O)cc43)nc2)c1] | N-(2-Amino-2-oxoethyl)-3-(1-hydroxyethyl)-N-methyl-1-(5-(4-methylpyridin-2-yl)pyrimidin-2-yl)-1H-indole-6-carboxamide |
| 333 | 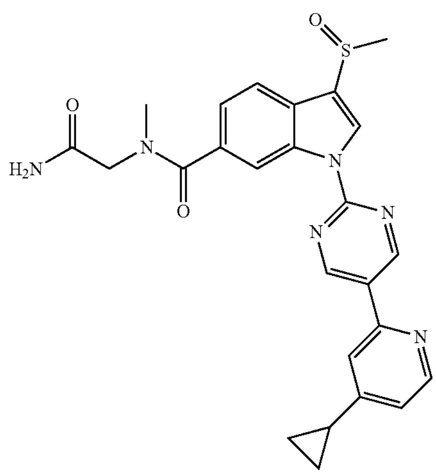 [SMILES: CN(CC(N)=O)C(=O)c1ccc2c(S(C)=O)cn(-c3ncc(-c4cc(C5CC5)ccn4)cn3)c2c1] | N-(2-Amino-2-oxoethyl)-1-(5-(4-cyclopropylpyridin-2-yl)pyrimidin-2-yl)-N-methyl-3-(methylsulfinyl)-1H-indole-6-carboxamide |
| 334 | 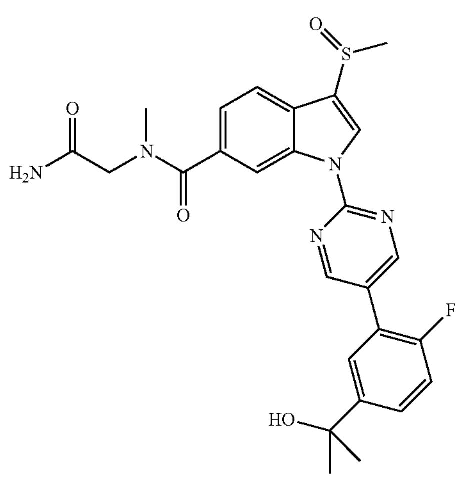 [SMILES: CN(CC(N)=O)C(=O)c1ccc2c(S(C)=O)cn(-c3ncc(-c4cc(C(C)(C)O)ccc4F)cn3)c2c1] | N-(2-Amino-2-oxoethyl)-1-(5-(2-fluoro-5-(2-hydroxypropan-2-yl)phenyl)pyrimidin-2-yl)-N-methyl-3-(methylsulfinyl)-1H-indole-6-carboxamide |

TABLE 1-continued

| Cmpd-No. | Structure | Name |
|---|---|---|
| 335 | 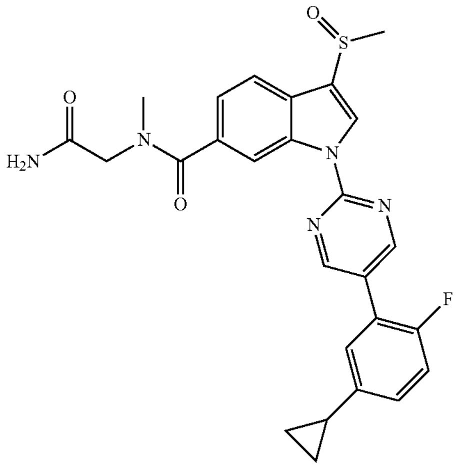 [SMILES: CN(CC(N)=O)C(=O)c1ccc2c(S(C)=O)cn(-c3ncc(-c4cc(C5CC5)ccc4F)cn3)c2c1] | N-(2-Amino-2-oxoethyl)-1-(5-(5-cyclopropyl-2-fluorophenyl)pyrimidin-2-yl)-N-methyl-3-(methylsulfinyl)-1H-indole-6-carboxamide |
| 336 | 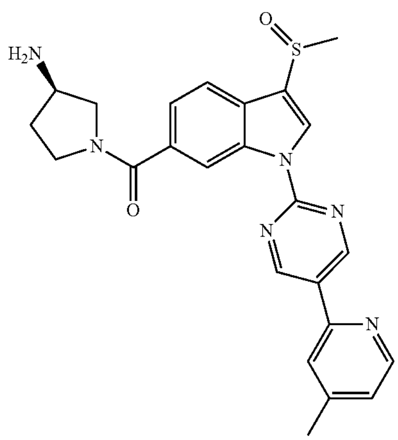 [SMILES: Cc1ccnc(-c2cnc(-n3cc(S(C)=O)c4ccc(C(=O)N5CC[C@@H](N)C5)cc43)nc2)c1] | ((R)-3-Aminopyrrolidin-1-yl)(1-(5-(4-methylpyridin-2-yl)pyrimidin-2-yl)-3-(methylsulfinyl)-1H-indol-6-yl)methanone |
| 337 | 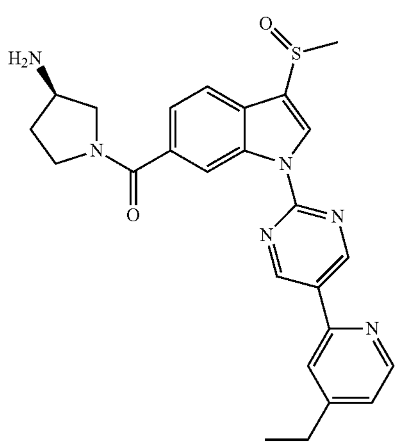 [SMILES: CCc1ccnc(-c2cnc(-n3cc(S(C)=O)c4ccc(C(=O)N5CC[C@@H](N)C5)cc43)nc2)c1] | ((R)-3-Aminopyrrolidin-1-yl)(1-(5-(4-ethylpyridin-2-yl)pyrimidin-2-yl)-3-(methylsulfinyl)-1H-indol-6-yl)methanone |

TABLE 1-continued

| Cmpd-No. | Structure | Name |
|---|---|---|
| 338 | 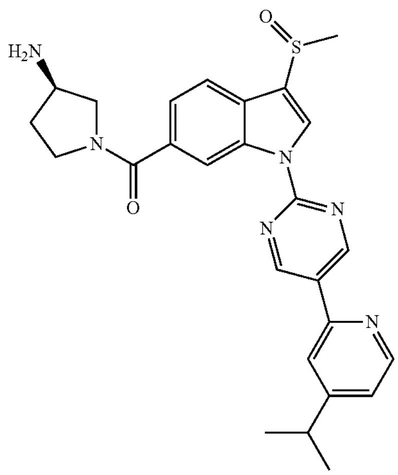 [SMILES: CC(C)c1ccnc(-c2cnc(-n3cc(S(C)=O)c4ccc(C(=O)N5CC[C@@H](N)C5)cc43)nc2)c1] | ((R)-3-Aminopyrrolidin-1-yl)(1-(5-(4-isopropylpyridin-2-yl)pyrimidin-2-yl)-3-(methylsulfinyl)-1H-indol-6-yl)methanone |
| 339 | 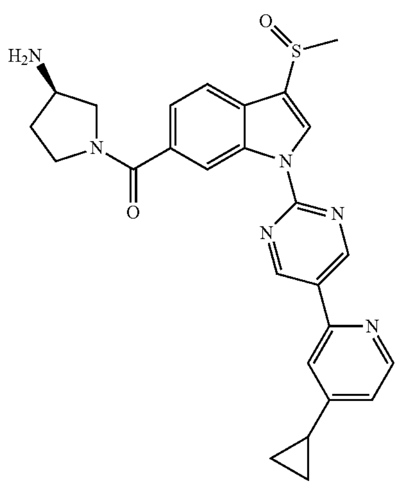 [SMILES: CS(=O)c1cn(-c2ncc(-c3cc(C4CC4)ccn3)cn2)c2cc(C(=O)N3CC[C@@H](N)C3)ccc12] | ((R)-3-Aminopyrrolidin-1-yl)(1-(5-(4-cyclopropylpyridin-2-yl)pyrimidin-2-yl)-3-(methylsulfinyl)-1H-indol-6-yl)methanone |
| 340 | 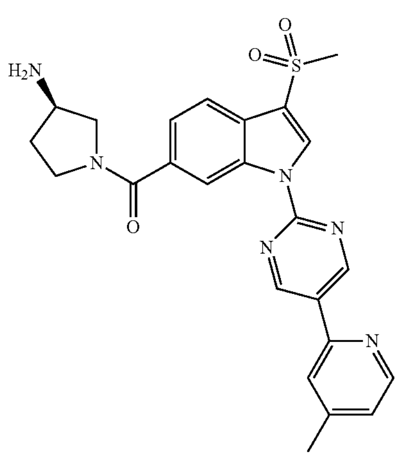 [SMILES: Cc1ccnc(-c2cnc(-n3cc(S(C)(=O)=O)c4ccc(C(=O)N5CC[C@@H](N)C5)cc43)nc2)c1] | (R)-(3-Aminopyrrolidin-1-yl)(1-(5-(4-methylpyridin-2-yl)pyrimidin-2-yl)-3-(methylsulfonyl)-1H-indol-6-yl)methanone |

TABLE 1-continued

| Cmpd-No. | Structure | Name |
|---|---|---|
| 341 | 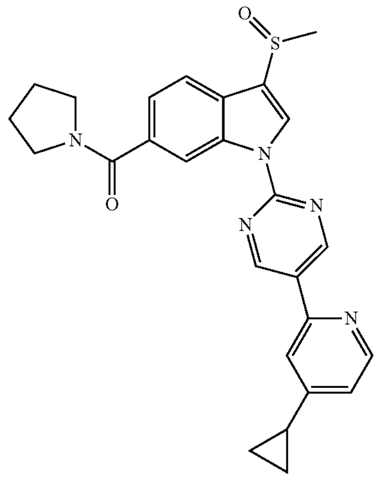 [SMILES: CS(=O)c1cn(-c2ncc(-c3cc(C4CC4)ccn3)cn2)c2cc(C(=O)N3CCCC3)ccc12] | (1-(5-(4-Cyclopropylpyridin-2-yl)pyrimidin-2-yl)-3-(methylsulfinyl)-1H-indol-6-yl)(pyrrolidin-1-yl)methanone |
| 342 | 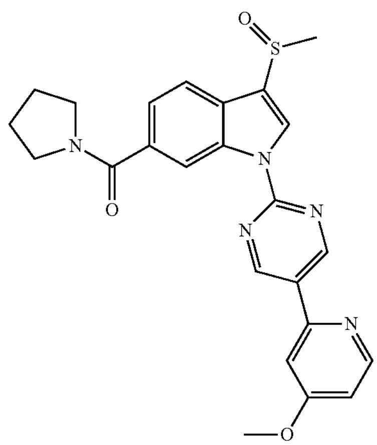 [SMILES: COc1ccnc(-c2cnc(-n3cc(S(C)=O)c4ccc(C(=O)N5CCCC5)cc43)nc2)c1] | (1-(5-(4-Methoxypyridin-2-yl)pyrimidin-2-yl)-3-(methylsulfinyl)-1H-indol-6-yl)(pyrrolidin-1-yl)methanone |
| 343 | 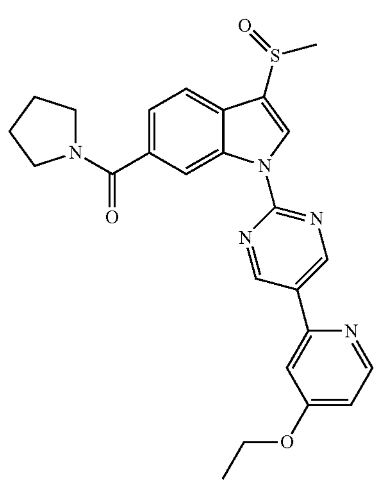 [SMILES: CCOc1ccnc(-c2cnc(-n3cc(S(C)=O)c4ccc(C(=O)N5CCCC5)cc43)nc2)c1] | (1-(5-(4-Ethoxypyridin-2-yl)pyrimidin-2-yl)-3-(methylsulfinyl)-1H-indol-6-yl)(pyrrolidin-1-yl)methanone |

TABLE 1-continued

| Cmpd-No. | Structure | Name |
|---|---|---|
| 344 and 345 | 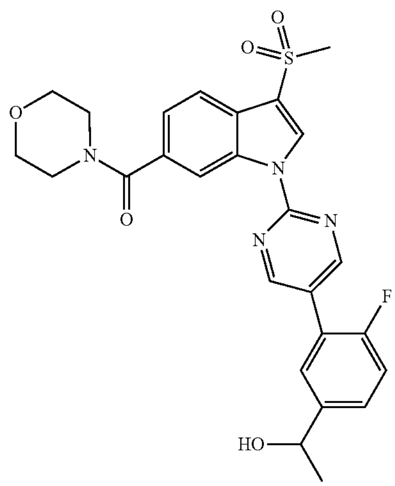 [SMILES: CC(O)c1ccc(F)c(-c2cnc(-n3cc(S(C)(=O)=O)c4ccc(C(=O)N5CCOCC5)cc43)nc2)c1] | (1-(5-(2-Fluoro-5-(1-hydroxyethyl)phenyl)pyrimidin-2-yl)-3-(methylsulfonyl)-1H-indol-6-yl)(morpholino)methanone (enantiomer 1 and 2) |
| 346 | 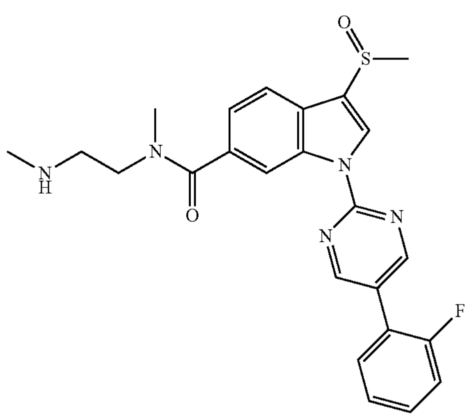 [SMILES: CNCCN(C)C(=O)c1ccc2c(S(C)=O)cn(-c3ncc(-c4ccccc4F)cn3)c2c1] | 1-(5-(2-Fluorophenyl)pyrimidin-2-yl)-N-methyl-N-(2-(methylamino)ethyl)-3-(methylsulfinyl)-1H-indole-6-carboxamide |
| 347 | 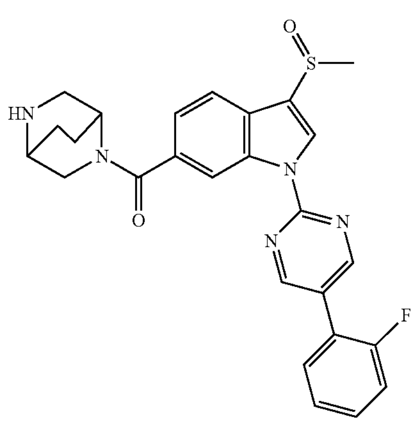 [SMILES: CS(=O)c1cn(-c2ncc(-c3ccccc3F)cn2)c2cc(C(=O)N3CC4CCC3CN4)ccc12] | 2,5-Diazabicyclo[2.2.2]octan-2-yl(1-(5-(2-fluorophenyl)pyrimidin-2-yl)-3-(methylsulfinyl)-1H-indol-6-yl)methanone |

| Cmpd-No. | Structure | Name |
|---|---|---|
| 348 | 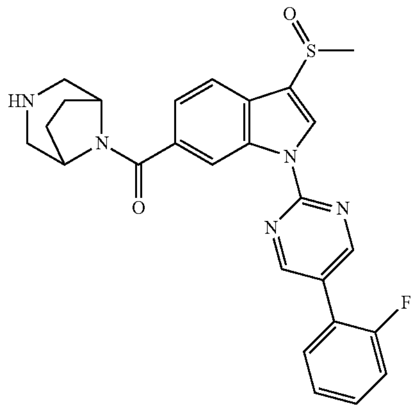 [SMILES: CS(=O)c1cn(-c2ncc(-c3ccccc3F)cn2)c2cc(C(=O)N3C4CCC3CNC4)ccc12] | 3,8-Diazabicyclo[3.2.1]octan-8-yl(1-(5-(2-fluorophenyl)pyrimidin-2-yl)-3-(methylsulfinyl)-1H-indol-6-yl)methanone |
| 349 | 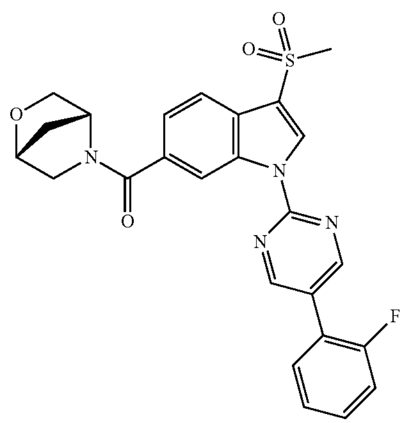 [SMILES: CS(=O)(=O)c1cn(-c2ncc(-c3ccccc3F)cn2)c2cc(C(=O)N3C[C@H]4C[C@@H]3CO4)ccc12] | (1R,4R)-2-Oxa-5-azabicyclo[2.2.1]heptan-5-yl(1-(5-(2-fluorophenyl)pyrimidin-2-yl)-3-(methylsulfonyl)-1H-indol-6-yl)methanone |
| 350 | 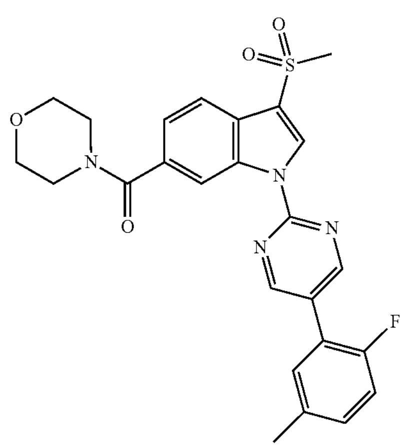 [SMILES: Cc1ccc(F)c(-c2cnc(-n3cc(S(C)(=O)=O)c4ccc(C(=O)N5CCOCC5)cc43)nc2)c1] | (1-(5-(2-Fluoro-5-methylphenyl)pyrimidin-2-yl)-3-(methylsulfonyl)-1H-indol-6-yl)(morpholino)methanone |

TABLE 1-continued

| Cmpd-No. | Structure | Name |
|---|---|---|
| 351 and 352 | 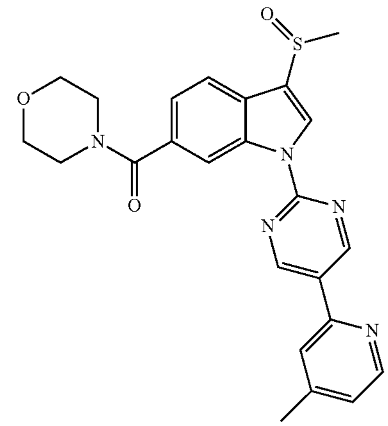 [SMILES: Cc1ccnc(-c2cnc(-n3cc(S(C)=O)c4ccc(C(=O)N5CCOCC5)cc43)nc2)c1] | (1-(5-(4-Methylpyridin-2-yl)pyrimidin-2-yl)-3-(methylsulfinyl)-1H-indol-6-yl)(morpholino)methanone (enantiomer 1 and 2) |
| 353 | 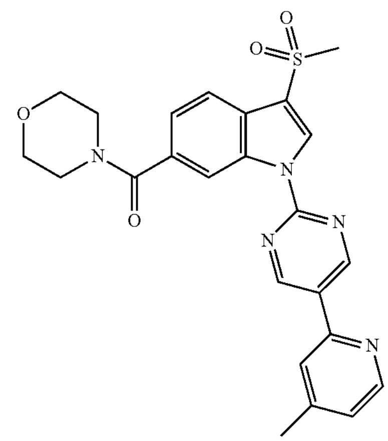 [SMILES: Cc1ccnc(-c2cnc(-n3cc(S(C)(=O)=O)c4ccc(C(=O)N5CCOCC5)cc43)nc2)c1] | (1-(5-(4-Methylpyridin-2-yl)pyrimidin-2-yl)-3-(methylsulfonyl)-1H-indol-6-yl)(morpholino)methanone |
| 354 | 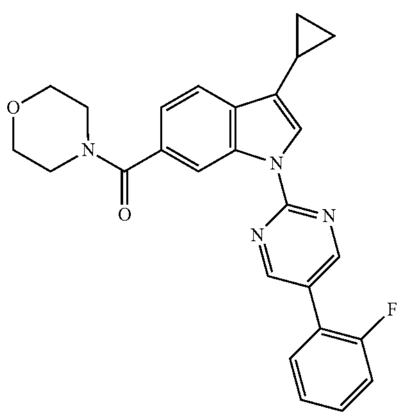 [SMILES: O=C(c1ccc2c(C3CC3)cn(-c3ncc(-c4ccccc4F)cn3)c2c1)N1CCOCC1] | (3-Cyclopropyl-1-(5-(2-fluorophenyl)pyrimidin-2-yl)-1H-indol-6-yl)(morpholino) methanone |
| 355 | 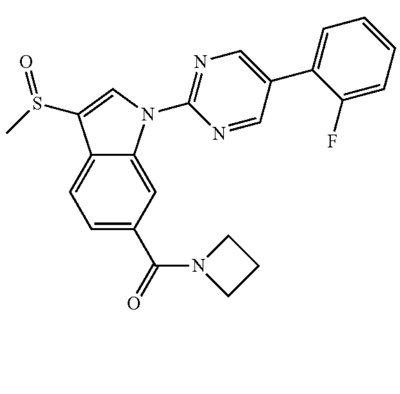 [SMILES: CS(=O)c1cn(-c2ncc(-c3ccccc3F)cn2)c2cc(C(=O)N3CCC3)ccc12] | Azetidin-1-yl(1-(5-(2-fluorophenyl)pyrimidin-2-yl)-3-(methylsulfinyl)-1H-indol-6-yl)methanone |

TABLE 1-continued

| Cmpd-No. | Structure | Name |
|---|---|---|
| 356 | 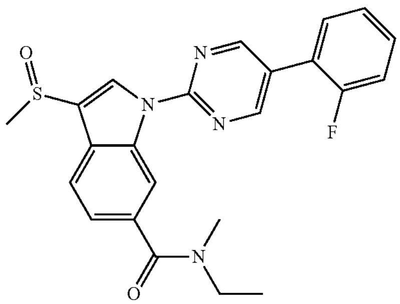 [SMILES: CCN(C)C(=O)c1ccc2c(S(C)=O)cn(-c3ncc(-c4ccccc4F)cn3)c2c1] | N-Ethyl-1-(5-(2-fluorophenyl)pyrimidin-2-yl)-N-methyl-3-(methylsulfinyl)-1H-indole-6-carboxamide |
| 357 | 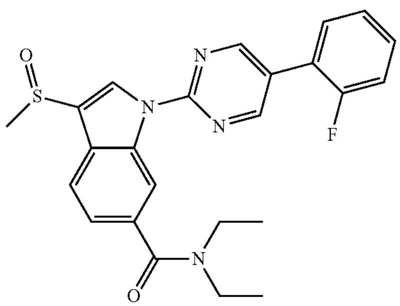 [SMILES: CCN(CC)C(=O)c1ccc2c(S(C)=O)cn(-c3ncc(-c4ccccc4F)cn3)c2c1] | N,N-Diethyl-1-(5-(2-fluorophenyl)pyrimidin-2-yl)-3-(methylsulfinyl)-1H-indole-6-carboxamide |
| 358 | 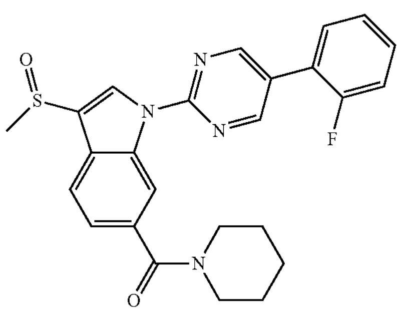 [SMILES: CS(=O)c1cn(-c2ncc(-c3ccccc3F)cn2)c2cc(C(=O)N3CCCCC3)ccc12] | (1-(5-(2-Fluorophenyl)pyrimidin-2-yl)-3-(methylsulfinyl)-1H-indol-6-yl)(piperidin-1-yl)methanone |
| 359 | 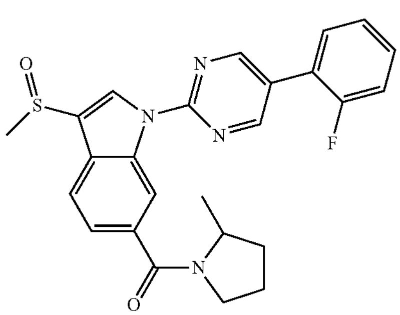 [SMILES: CC1CCCN1C(=O)c1ccc2c(S(C)=O)cn(-c3ncc(-c4ccccc4F)cn3)c2c1] | (1-(5-(2-Fluorophenyl)pyrimidin-2-yl)-3-(methylsulfinyl)-1H-indol-6-yl)(2-methylpyrrolidin-1-yl)methanone |

TABLE 1-continued

| Cmpd-No. | Structure | Name |
|---|---|---|
| 360 | 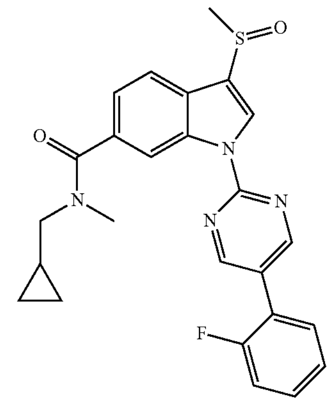 [SMILES: CN(CC1CC1)C(=O)c1ccc2c(S(C)=O)cn(-c3ncc(-c4ccccc4F)cn3)c2c1] | N-(Cyclopropylmethyl)-1-(5-(2-fluorophenyl)pyrimidin-2-yl)-N-methyl-3-(methylsulfinyl)-1H-indole-6-carboxamide |
| 361 | 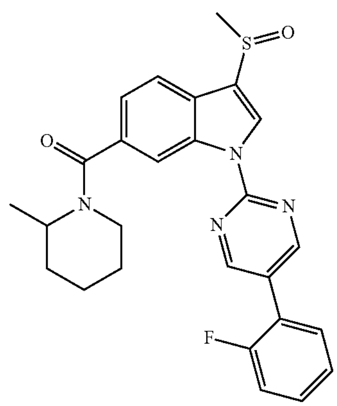 [SMILES: CC1CCCCN1C(=O)c1ccc2c(S(C)=O)cn(-c3ncc(-c4ccccc4F)cn3)c2c1] | (1-(5-(2-Fluorophenyl)pyrimidin-2-yl)-3-(methylsulfinyl)-1H-indol-6-yl)(2-methylpiperidin-1-yl)methanone |
| 362 | 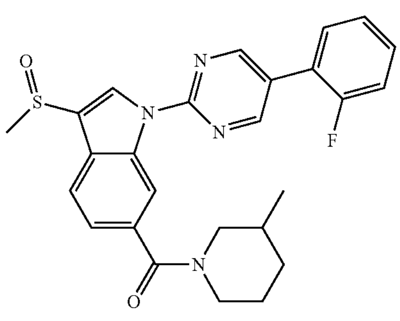 [SMILES: CC1CCCN(C(=O)c2ccc3c(S(C)=O)cn(-c4ncc(-c5ccccc5F)cn4)c3c2)C1] | (1-(5-(2-Fluorophenyl)pyrimidin-2-yl)-3-(methylsulfinyl)-1H-indol-6-yl)(3-methylpiperidin-1-yl)methanone |
| 363 | 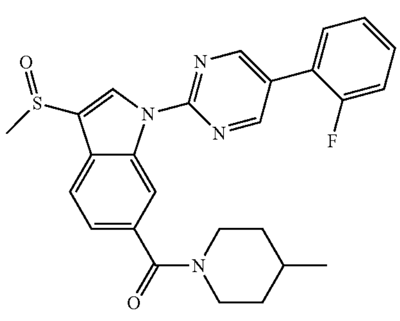 [SMILES: CC1CCN(C(=O)c2ccc3c(S(C)=O)cn(-c4ncc(-c5ccccc5F)cn4)c3c2)CC1] | (1-(5-(2-Fluorophenyl)pyrimidin-2-yl)-3-(methylsulfinyl)-1H-indol-6-yl)(4-methylpiperidin-1-yl)methanone |

TABLE 1-continued

| Cmpd-No. | Structure | Name |
|---|---|---|
| 364 | 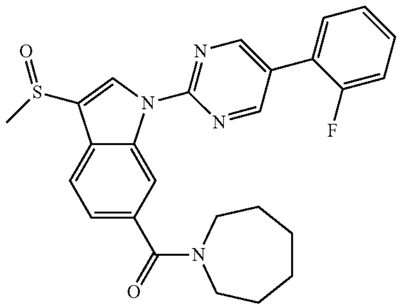 [SMILES: CS(=O)c1cn(-c2ncc(-c3ccccc3F)cn2)c2cc(C(=O)N3CCCCCC3)ccc12] | Azepan-1-yl(1-(5-(2-fluorophenyl)pyrimidin-2-yl)-3-(methylsulfinyl)-1H-indol-6-yl)methanone |
| 365 | 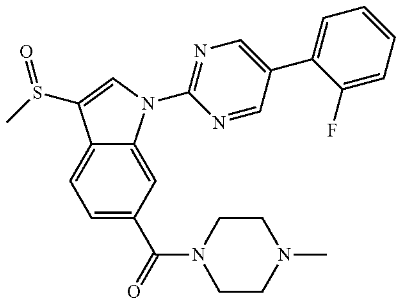 [SMILES: CN1CCN(C(=O)c2ccc3c(S(C)=O)cn(-c4ncc(-c5ccccc5F)cn4)c3c2)CC1] | (1-(5-(2-Fluorophenyl)pyrimidin-2-yl)-3-(methylsulfinyl)-1H-indol-6-yl)(4-methylpiperazin-1-yl)methanone |
| 366 | 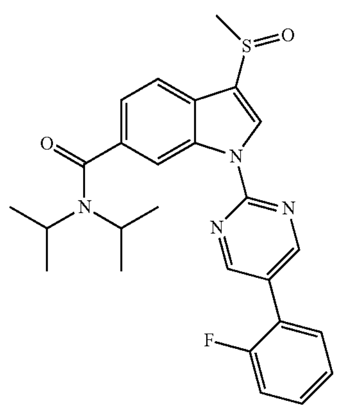 [SMILES: CC(C)N(C(=O)c1ccc2c(S(C)=O)cn(-c3ncc(-c4ccccc4F)cn3)c2c1)C(C)C] | 1-(5-(2-Fluorophenyl)pyrimidin-2-yl)-N,N-diisopropyl-3-(methylsulfinyl)-1H-indole-6-carboxamide |
| 367 | 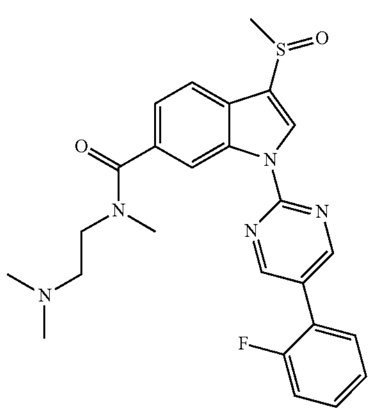 [SMILES: CN(C)CCN(C)C(=O)c1ccc2c(S(C)=O)cn(-c3ncc(-c4ccccc4F)cn3)c2c1] | N-(2-(Dimethylamino)ethyl)-1-(5-(2-fluorophenyl)pyrimidin-2-yl)-N-methyl-3-(methylsulfinyl)-1H-indole-6-carboxamide |

TABLE 1-continued

| Cmpd-No. | Structure | Name |
|---|---|---|
| 368 | 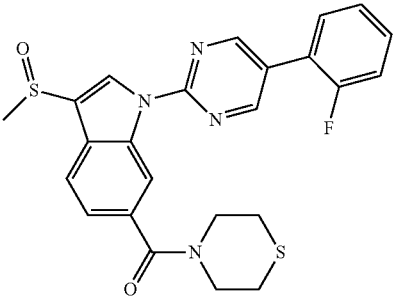 | (1-(5-(2-Fluorophenyl)pyrimidin-2-yl)-3-(methylsulfinyl)-1H-indol-6-yl)(thiomorpholino)methanone |
| 369 | 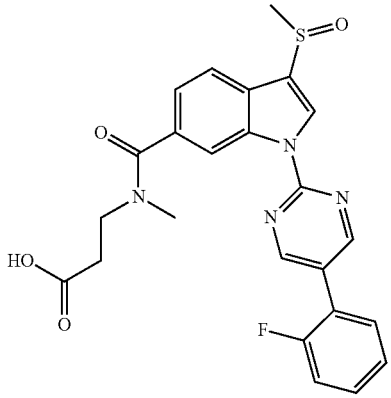 [SMILES: CN(CCC(=O)O)C(=O)c1ccc2c(S(C)=O)cn(-c3ncc(-c4ccccc4F)cn3)c2c1] | 3-(1-(5-(2-Fluorophenyl)pyrimidin-2-yl)-N-methyl-3-(methylsulfinyl)-1H-indole-6-carboxamido)propanoic acid |
| 370 | 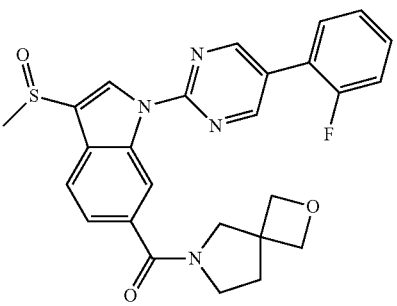 [SMILES: CS(=O)c1cn(-c2ncc(-c3ccccc3F)cn2)c2cc(C(=O)N3CCC4(COC4)C3)ccc12] | (1-(5-(2-Fluorophenyl)pyrimidin-2-yl)-3-(methylsulfinyl)-1H-indol-6-yl)(2-oxa-6-azaspiro[3.4]octan-6-yl)methanone |
| 371 | 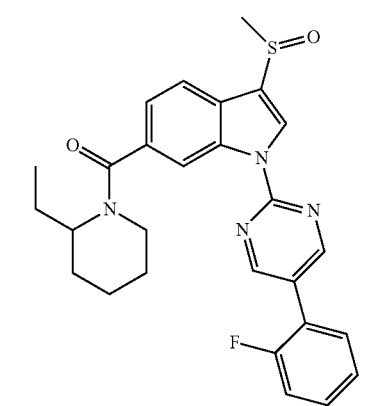 [SMILES: CCC1CCCCN1C(=O)c1ccc2c(S(C)=O)cn(-c3ncc(-c4ccccc4F)cn3)c2c1] | (2-Ehylpiperidin-1-yl)(1-(5-(2-fluorophenyl)pyrimidin-2-yl)-3-(methylsulfinyl)-1H-indol-6-yl)methanone |

TABLE 1-continued

| Cmpd-No. | Structure | Name |
|---|---|---|
| 372 | 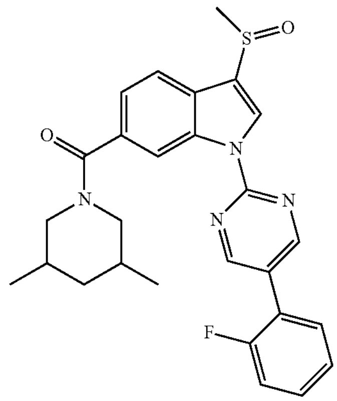 [SMILES: CC1CC(C)CN(C(=O)c2ccc3c(S(C)=O)cn(-c4ncc(-c5ccccc5F)cn4)c3c2)C1] | (3,5-Dimethylpiperidin-1-yl)(1-(5-(2-fluorophenyl)pyrimidin-2-yl)-3-(methylsulfinyl)-1H-indol-6-yl)methanone (diastereomer 1) |
| 373 | 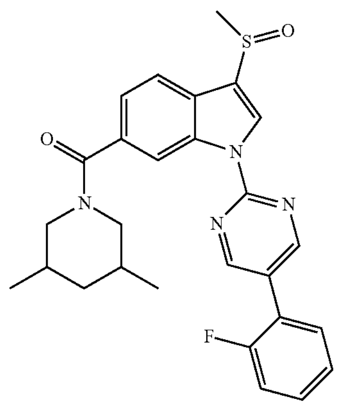 [SMILES: CC1CC(C)CN(C(=O)c2ccc3c(S(C)=O)cn(-c4ncc(-c5ccccc5F)cn4)c3c2)C1] | (3,5-Dimethylpiperidin-1-yl)(1-(5-(2-fluorophenyl)pyrimidin-2-yl)-3-(methylsulfinyl)-1H-indol-6-yl)methanone (diastereomer 2) |
| 374 | 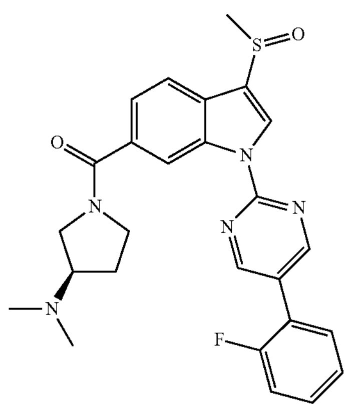 [SMILES: CN(C)[C@@H]1CCN(C(=O)c2ccc3c(S(C)=O)cn(-c4ncc(-c5ccccc5F)cn4)c3c2)C1] | ((R)-3-(Dimethylamino)pyrrolidin-1-yl)(1-(5-(2-fluorophenyl)pyrimidin-2-yl)-3-(methylsulfinyl)-1H-indol-6-yl)methanone |
| 375 | 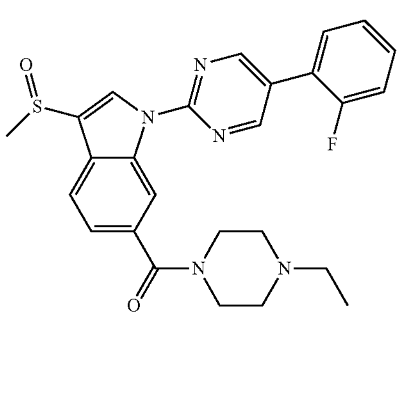 [SMILES: CCN1CCN(C(=O)c2ccc3c(S(C)=O)cn(-c4ncc(-c5ccccc5F)cn4)c3c2)CC1] | (4-Ethylpiperazin-1-yl)(1-(5-(2-fluorophenyl)pyrimidin-2-yl)-3-(methylsulfinyl)-1H-indol-6-yl)methanone |

TABLE 1-continued

| Cmpd-No. | Structure | Name |
|---|---|---|
| 376 | 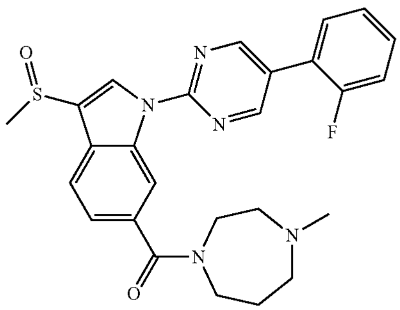 [SMILES: CN1CCCN(C(=O)c2ccc3c(S(C)=O)cn(-c4ncc(-c5ccccc5F)cn4)c3c2)CC1] | (1-(5-(2-Fluorophenyl)pyrimidin-2-yl)-3-(methylsulfinyl)-1H-indol-6-yl)(4-methyl-1,4-diazepan-1-yl)methanone |
| 377 | 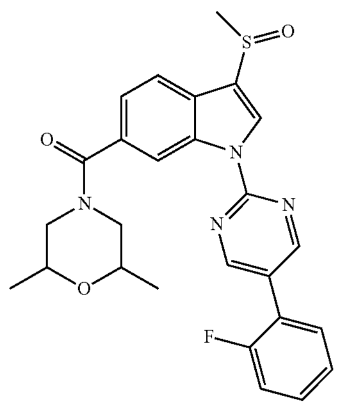 [SMILES: CC1CN(C(=O)c2ccc3c(S(C)=O)cn(-c4ncc(-c5ccccc5F)cn4)c3c2)CC(C)O1] | (2,6-Dimethylmorpholino)(1-(5-(2-fluorophenyl)pyrimidin-2-yl)-3-(methylsulfinyl)-1H-indol-6-yl)methanone (diastereomer 1) |
| 378 | 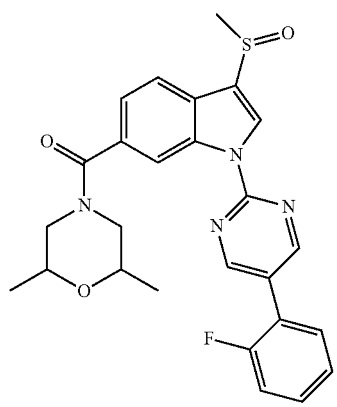 [SMILES: CC1CN(C(=O)c2ccc3c(S(C)=O)cn(-c4ncc(-c5ccccc5F)cn4)c3c2)CC(C)O1] | (2,6-Dimethylmorpholino)(1-(5-(2-fluorophenyl)pyrimidin-2-yl)-3-(methylsulfinyl)-1H-indol-6-yl)methanone (diastereomer 2) |
| 379 | 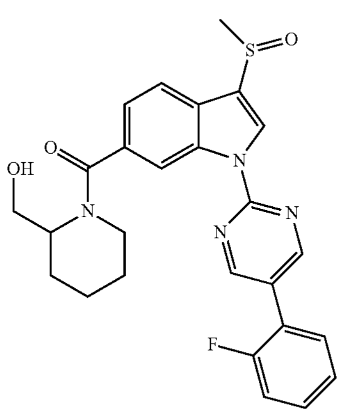 [SMILES: CS(=O)c1cn(-c2ncc(-c3ccccc3F)cn2)c2cc(C(=O)N3CCCCC3CO)ccc12] | (1-(5-(2-Fluorophenyl)pyrimidin-2-yl)-3-(methylsulfinyl)-1H-indol-6-yl)(2-(hydroxymethyl)piperidin-1-yl)methanone |

TABLE 1-continued

| Cmpd-No. | Structure | Name |
|---|---|---|
| 380 | 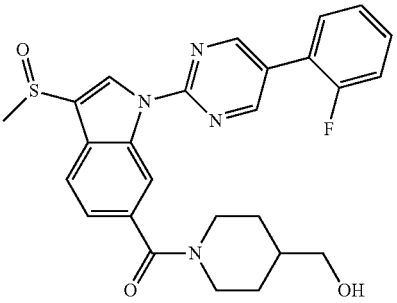 [SMILES: CS(=O)c1cn(-c2ncc(-c3ccccc3F)cn2)c2cc(C(=O)N3CCC(CO)CC3)ccc12] | (1-(5-(2-Fluorophenyl)pyrimidin-2-yl)-3-(methylsulfinyl)-1H-indol-6-yl)(4-(hydroxymethyl)piperidin-1-yl)methanone |
| 381 | 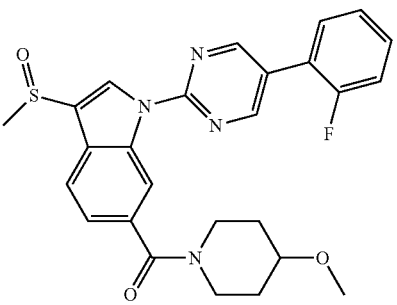 [SMILES: COC1CCN(C(=O)c2ccc3c(S(C)=O)cn(-c4ncc(-c5ccccc5F)cn4)c3c2)CC1] | (1-(5-(2-Fluorophenyl)pyrimidin-2-yl)-3-(methylsulfinyl)-1H-indol-6-yl)(4-methoxypiperidin-1-yl)methanone |
| 382 | 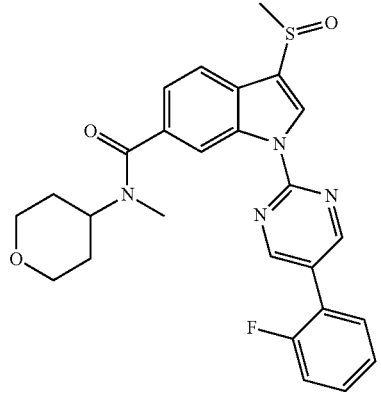 [SMILES: CN(C(=O)c1ccc2c(S(C)=O)cn(-c3ncc(-c4ccccc4F)cn3)c2c1)C1CCOCC1] | 1-(5-(2-Fluorophenyl)pyrimidin-2-yl)-N-methyl-3-(methylsulfinyl)-N-(tetrahydro-2H-pyran-4-yl)-1H-indole-6-carboxamide |
| 383 | 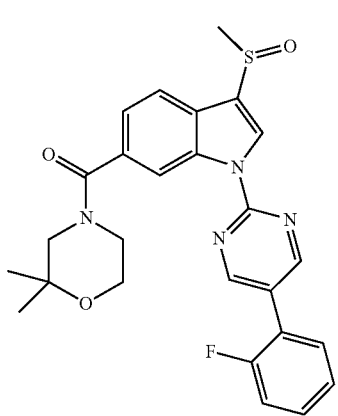 [SMILES: CS(=O)c1cn(-c2ncc(-c3ccccc3F)cn2)c2cc(C(=O)N3CCOC(C)(C)C3)ccc12] | (2,2-Dimethylmorpholino)(1-(5-(2-fluorophenyl)pyrimidin-2-yl)-3-(methylsulfinyl)-1H-indol-6-yl)methanone |

TABLE 1-continued

| Cmpd-No. | Structure | Name |
|---|---|---|
| 384 | 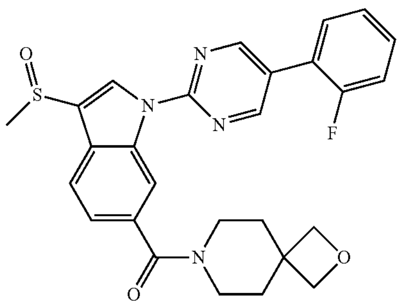 [SMILES: CS(=O)c1cn(-c2ncc(-c3ccccc3F)cn2)c2cc(C(=O)N3CCC4(CC3)COC4)ccc12] | (1-(5-(2-Fluorophenyl)pyrimidin-2-yl)-3-(methylsulfinyl)-1H-indol-6-yl)(2-oxa-7-azaspiro[3.5]nonan-7-yl)methanone |
| 385 | 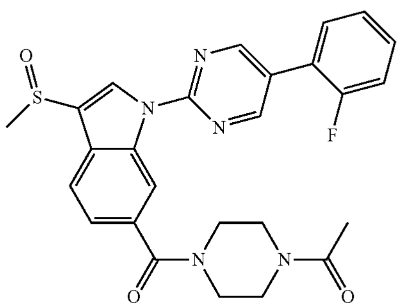 [SMILES: CC(=O)N1CCN(C(=O)c2ccc3c(S(C)=O)cn(-c4ncc(-c5ccccc5F)cn4)c3c2)CC1] | 1-(4-(1-(5-(2-Fluorophenyl)pyrimidin-2-yl)-3-(methylsulfinyl)-1H-indole-6-carbonyl)piperazin-1-yl)ethanone |
| 386 | 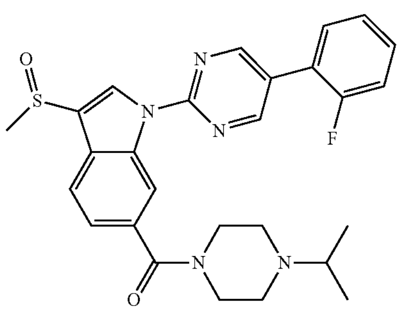 [SMILES: CC(C)N1CCN(C(=O)c2ccc3c(S(C)=O)cn(-c4ncc(-c5ccccc5F)cn4)c3c2)CC1] | (1-(5-(2-Fluorophenyl)pyrimidin-2-yl)-3-(methylsulfinyl)-1H-indol-6-yl)(4-isopropylpiperazin-1-yl)methanone |
| 387 | 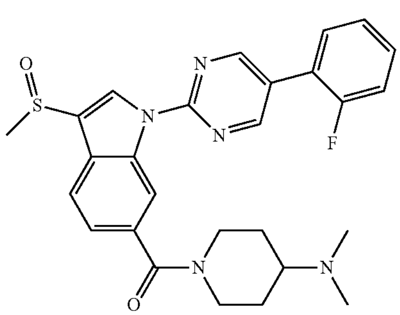 | (4-(Dimethylamino)piperidin-1-yl)(1-(5-(2-fluorophenyl)pyrimidin-2-yl)-3-(methylsulfinyl)-1H-indol-6-yl)methanone |

TABLE 1-continued

| Cmpd-No. | Structure | Name |
|---|---|---|
| 388 | 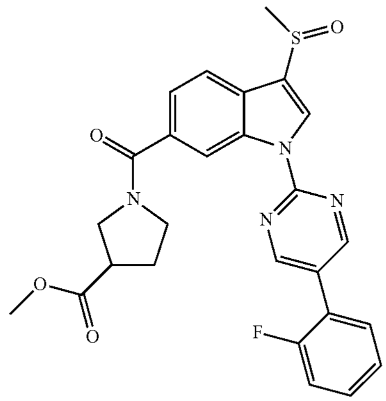 [SMILES: COC(=O)C1CCN(C(=O)c2ccc3c(S(C)=O)cn(-c4ncc(-c5ccccc5F)cn4)c3c2)C1] | Methyl 1-(1-(5-(2-fluorophenyl)pyrimidin-2-yl)-3-(methylsulfinyl)-1H-indole-6-carbonyl)pyrrolidine-3-carboxylate |
| 389 | 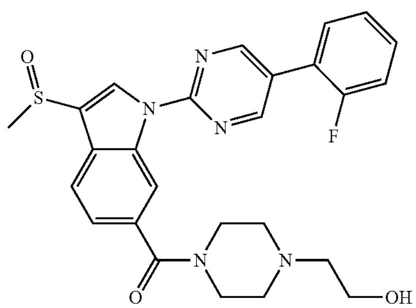 [SMILES: CS(=O)c1cn(-c2ncc(-c3ccccc3F)cn2)c2cc(C(=O)N3CCN(CCO)CC3)ccc12] | (1-(5-(2-Fluorophenyl)pyrimidin-2-yl)-3-(methylsulfinyl)-1H-indol-6-yl)(4-(2-hydroxyethyl)piperazin-1-yl)methanone |
| 390 | 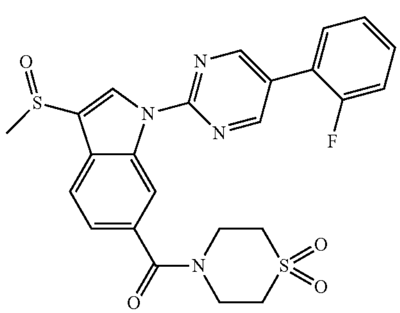 [SMILES: CS(=O)c1cn(-c2ncc(-c3ccccc3F)cn2)c2cc(C(=O)N3CCS(=O)(=O)CC3)ccc12] | (1,1-Dioxidothiomorpholino)(1-(5-(2-fluorophenyl)pyrimidin-2-yl)-3-(methylsulfinyl)-1H-indol-6-yl)methanone |
| 391 | 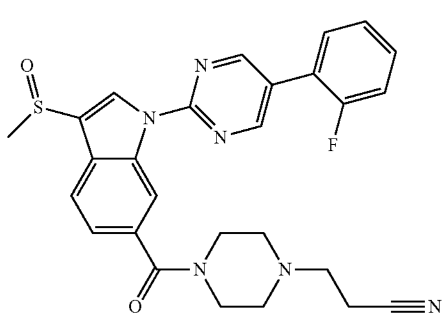 [SMILES: CS(=O)c1cn(-c2ncc(-c3ccccc3F)cn2)c2cc(C(=O)N3CCN(CCC#N)CC3)ccc12] | 3-(4-(1-(5-(2-Fluorophenyl)pyrimidin-2-yl)-3-(methylsulfinyl)-1H-indole-6-carbonyl)piperazin-1-yl)propanenitrile |

TABLE 1-continued

| Cmpd-No. | Structure | Name |
|---|---|---|
| 392 | 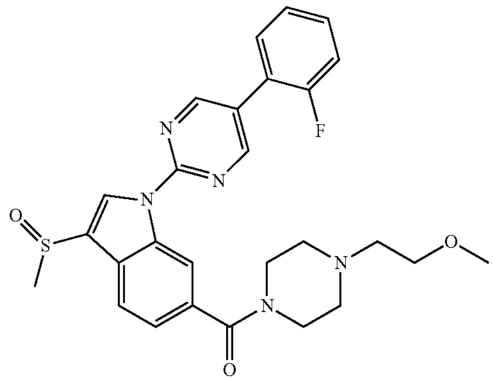 [SMILES: COCCN1CCN(C(=O)c2ccc3c(S(C)=O)cn(-c4ncc(-c5ccccc5F)cn4)c3c2)CC1] | (1-(5-(2-Fluorophenyl)pyrimidin-2-yl)-3-(methylsulfinyl)-1H-indol-6-yl)(4-(2-methoxyethyl)piperazin-1-yl)methanone |
| 393 | 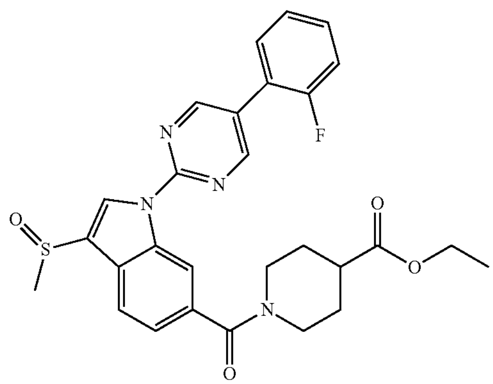 [SMILES: CCOC(=O)C1CCN(C(=O)c2ccc3c(S(C)=O)cn(-c4ncc(-c5ccccc5F)cn4)c3c2)CC1] | Ethyl 1-(1-(5-(2-fluorophenyl)pyrimidin-2-yl)-3-(methylsulfinyl)-1H-indole-6-carbonyl)piperidine-4-carboxylate |
| 394 | 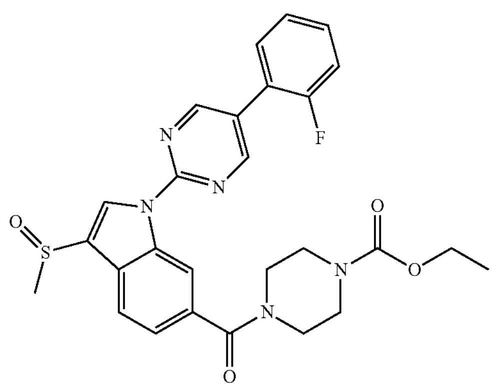 | Ethyl 4-(1-(5-(2-fluorophenyl)pyrimidin-2-yl)-3-(methylsulfinyl)-1H-indole-6-carbonyl)piperazine-1-carboxylat |
| 395 | 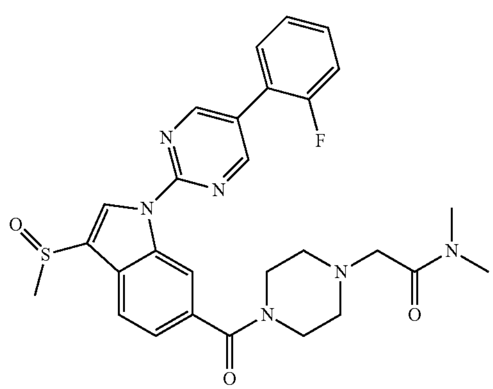 [SMILES: CN(C)C(=O)CN1CCN(C(=O)c2ccc3c(S(C)=O)cn(-c4ncc(-c5ccccc5F)cn4)c3c2)CC1] | 2-(4-(1-(5-(2-Fluorophenyl)pyrimidin-2-yl)-3-(methylsulfinyl)-1H-indole-6-carbonyl)piperazin-1-yl)-N,N-dimethylacetamide |

The following abbreviations are used in the descriptions of the experiments:

APCI=atmospheric pressure chemical ionization; (AtaPhos)2PdCl2=bis(di-tert-butyl(4-dimethylaminophenyl) phosphine)dichloropalladium(II); BINAP=2,2'-bis(diphenylphosphino)-1,1'-binaphthyl; BOP=(benzotriazol-1-yloxy)tris(dimethylamino)phosphonium hexafluorophosphate; calc.=calculated; CDI=carbonyldiimidazole; d=day; dba=dibenzylideneacetone; DavePhos=2-dicyclohexylphosphino-2'-(N,N-dimethylamino)biphenyl; DMAP=N,N-dimethylpyridin-4-amine; DME=dimethoxyethane; DMF=N,N-dimethylformamide; DMSO=dimethylsulfoxide; EDCxHCl=1-[3-(dimethylamino)propyl]-3-ethylcarbodiimide hydrochloride; ES-MS=electrospray mass spectrometry (ES-MS); eq.=equivalent; h=hour; HATU=1-[bis(dimethylamino)methylene]-1H-1,2,3-triazolo[4,5-b]pyridinium 3-oxid hexafluorophosphate; HOBt=1-hydroxybenzotriazole monohydrate; min.=minute; MTBE=methyl-tert-butylether; NMP=N-methyl-2-pyrrolidone; PdCl2(dppf)=[1,1'-bis(diphenylphosphino)ferrocene]dichloropalladium(II) dichloromethane complex; $R_t$=retention time; SFC=supercritical fluid chromatography; T3P=1-propylphoshonic acid cyclic anhydride, tBuXPhos=2-di-tert-butylphosphino-2,4,6-triisopropyl-1,1-biphenyl; tert=tertiary; TFA=2,2,2-trifluoroacetic acid; THF=tetrahydrofuran; TLC=thin layer chromatography; TOFMS=time-of-flight mass spectrometer; Xantphos=4,5-Bis(diphenylphosphino)-9,9-dimethylxanthene.

The following analytical HPLC methods were used:

Method 1:

Column: XBridge C18 (150 mm×4.6 mm, 5.0 μm); Column temperature: 35° C.
Flow rate: 1.0 mL/min
Injection volume: 3 μl
Detection: 215 and 254 nm
Mobile phase A: acetonitrile; mobile phase B: 10 mM ammonium acetate in water
Gradient:

| Time in min | % A | % B | Flow rate in ml/min |
|---|---|---|---|
| 0 | 5 | 95 | 1.0 |
| 1.5 | 5 | 95 | 1.0 |
| 3 | 15 | 85 | 1.0 |
| 7 | 55 | 45 | 1.0 |
| 10 | 95 | 5 | 1.0 |
| 14 | 95 | 5 | 1.0 |
| 17 | 5 | 95 | 1.0 |
| 20 | 5 | 95 | 1.0 |

Method 2:

Column: Sunfire C18 (150 mm×4.6 mm, 3.5 μm); Column temperature: ambient
Flow rate: 1.0 mL/min
Injection volume: 3 μl
Detection: 215 and 254 nm
Mobile phase A: 0.1% formic acid in acetonitrile; mobile phase B: 0.1% formic acid in water
Gradient:

| Time in min | % A | % B | Flow rate in ml/min |
|---|---|---|---|
| 0 | 5 | 95 | 1.0 |
| 1.5 | 5 | 95 | 1.0 |
| 3 | 15 | 85 | 1.0 |
| 7 | 55 | 45 | 1.0 |
| 10 | 95 | 5 | 1.0 |
| 14 | 95 | 5 | 1.0 |
| 17 | 5 | 95 | 1.0 |
| 20 | 5 | 95 | 1.0 |

Method 3:

Column: Acquity UPLC BEH C18 (100 mm×2.1 mm, 1.7 μm); Column temperature: 35° C.
Flow rate: 0.3 mL/min
Injection volume: 0.5 μl
Detection: 215 and 254 nm
Mobile phase A: 5 mM ammonium acetate in water; mobile phase B: acetonitrile
Gradient:

| Time in min | % A | % B | Flow rate in ml/min |
|---|---|---|---|
| 0 | 5 | 95 | 0.3 |
| 0.6 | 5 | 95 | 0.3 |
| 1.5 | 15 | 85 | 0.3 |
| 4 | 55 | 45 | 0.3 |
| 5.5 | 95 | 5 | 0.3 |
| 7.8 | 95 | 5 | 0.3 |
| 9 | 5 | 95 | 0.3 |
| 10 | 5 | 95 | 0.3 |

Method 4:

Column: XBridge C18 (4.6×50 mm, 5.0 μm); Instrument: Shimadzu Prominence
Flow rate: 1.2 mL/min
Detection: 220 and 260 nm
Mobile phase A: 10 mM ammonium acetate in water; mobile phase B: acetonitrile
Gradient:

| Time in min | % A | % B | Flow rate in ml/min |
|---|---|---|---|
| 0 | 90 | 10 | 1.2 |
| 1.5 | 70 | 30 | 1.2 |
| 3.0 | 10 | 90 | 1.2 |
| 4.0 | 10 | 90 | 1.2 |
| 5.0 | 90 | 10 | 1.2 |

Mass Spectroscopy Conditions

Instrument: API 2000 LC/MS/MS from Applied Biosystem; Ionization technique: ESI using API source; Declustering Potential: 10-70 V depending on the ionization of compound;
Mass range: 100-800 amu
Scan type: Q1
Polarity: +Ve
Ion Source: Turbo spray
Ion spray voltage: +5500 for +Ve mode
Mass Source temperature: 200° C.

Method 5:

Column: Zorbax Extend C18 (4.6×50 mm, 5 μm); Instrument: Shimadzu Prominence
Flow rate: 1.2 mL/min
Detection: 220 and 260 nm
Mobile phase A: 10 mM ammonium acetate in water; mobile phase B: acetonitrile
Gradient:

| Time in min | % A | % B | Flow rate in ml/min |
|---|---|---|---|
| 0 | 90 | 10 | 1.2 |
| 1.5 | 70 | 30 | 1.2 |
| 3.0 | 10 | 90 | 1.2 |
| 4.0 | 10 | 90 | 1.2 |
| 5.0 | 90 | 10 | 1.2 |

Mass Spectroscopy Conditions
  Instrument: API 2000 LC/MS/MS from Applied Biosystem
  Ionization technique: ESI using API source
  Declustering Potential: 10-70 V depending on the ionization of compound
  Mass range: 100-800 amu
  Scan type: Q1
  Polarity: +Ve
  Ion Source: Turbo spray
  Ion spray voltage: +5500 for +Ve mode
  Mass Source temperature: 200° C.
Method 6:
  Column: XBridge C18 (150 mm×4.6 mm, 3.5 µm); Column temperature: 25° C.
  Flow rate: 1.0 mL/min
  Injection volume: 2 µl
  Detection: 215 and 254 nm
  Mobile phase A: acetonitrile; mobile phase B: 10 mM ammonium acetate in water
  Gradient:

| Time in min | % A | % B | Flow rate in ml/min |
|---|---|---|---|
| 0 | 5 | 95 | 1.0 |
| 1.5 | 5 | 95 | 1.0 |
| 3 | 15 | 85 | 1.0 |
| 7 | 55 | 45 | 1.0 |
| 10 | 95 | 5 | 1.0 |
| 14 | 95 | 5 | 1.0 |
| 16 | 100 | 0 | 1.0 |
| 18 | 5 | 95 | 1.0 |
| 20 | 5 | 95 | 1.0 |

Method 7:
  Column: Zorbax Extend C18 (4.6×50 mm, 5 µm)
  Instrument: Shimadzu Prominence
  Column temperature: 25° C.
  Injection volume: 2 µl
  Flow rate: 1.0 mL/min
  Detection: 220 and 260 nm
  Mobile phase A: 10 mM ammonium acetate in water
  Mobile phase B: acetonitrile
  Gradient:

| Time in min | % A | % B | Flow rate in ml/min |
|---|---|---|---|
| 0 | 95 | 5 | 1.0 |
| 1 | 95 | 5 | 1.0 |
| 7.0 | 50 | 50 | 1.0 |
| 10.0 | 10 | 90 | 1.0 |
| 11.0 | 10 | 90 | 1.0 |
| 12.0 | 95 | 5 | 1.0 |

Mass Spectroscopy Conditions
  Instrument: API 2000 LC/MS/MS from Applied Biosystem
  Ionization technique: ESI using API source
  Declustering Potential: 10-70 V depending on the ionization of compound
  Mass range: 100-800 amu
  Scan type: Q1
  Polarity: +Ve
  Ion Source: Turbo spray
  Ion spray voltage: +5500 for +Ve mode
  Mass Source temperature: 200° C.
Method 8:
  Column: XBridge C18 (150 mm×4.6 mm, 5.0 µm); Column temperature: 25° C.
  Flow rate: 1.2 mL/min
  Injection volume: 2 µl
  Detection: 215 and 254 nm
  Mobile phase A: 10 mM ammonium acetate in water B: acetonitrile; mobile phase
  Gradient:

| Time in min | % A | % B | Flow rate in ml/min |
|---|---|---|---|
| 0 | 5 | 95 | 1.2 |
| 2 | 55 | 45 | 1.2 |
| 5 | 70 | 30 | 1.2 |
| 7 | 95 | 5 | 1.2 |
| 10 | 95 | 5 | 1.2 |
| 12 | 100 | 0 | 1.2 |
| 14 | 5 | 95 | 1.2 |
| 16 | 5 | 95 | 1.2 |

Method 9:
  Column: Acquity UPLC BEH C18 (100 mm×2.1 mm, 1.7 µm)
  Column temperature: 35° C.
  Flow rate: 0.3 mL/min
  Injection volume: 1 µl
  Detection: 215 and 254 nm
  Mobile phase A: 0.025% TFA in water
  Mobile phase B: 0.025% TFA in acetonitrile
  Gradient:

| Time in min | % A | % B | Flow rate in ml/min |
|---|---|---|---|
| 0 | 5 | 95 | 0.3 |
| 0.6 | 5 | 95 | 0.3 |
| 1.5 | 15 | 85 | 0.3 |
| 4 | 55 | 45 | 0.3 |
| 5.5 | 95 | 5 | 0.3 |
| 7.8 | 95 | 5 | 0.3 |
| 9 | 5 | 95 | 0.3 |
| 10 | 5 | 95 | 0.3 |

Method 10:
  Column: XBridge C18 (150 mm×4.6 mm, 5.0 µm); Column temperature: 25° C.
  Flow rate: 1.0 mL/min
  Injection volume: 2 µl
  Detection: 215 and 254 nm
  Mobile phase A: 10 mM ammonium acetate in water B: acetonitrile; mobile phase
  Gradient:

| Time in min | % A | % B | Flow rate in ml/min |
|---|---|---|---|
| 0 | 5 | 95 | 1.0 |
| 1.5 | 5 | 95 | 1.0 |
| 3 | 15 | 85 | 1.0 |
| 5 | 55 | 45 | 1.0 |
| 8 | 95 | 5 | 1.0 |
| 14 | 95 | 5 | 1.0 |
| 15 | 95 | 5 | 1.0 |

Method 11:
Column: XBridge C18 (150 mm×4.6 mm, 5.0 µm); Column temperature: 25° C.
Flow rate: 1.0 mL/min
Injection volume: 2 µl
Detection: 215 and 254 nm
Mobile phase A: 10 mM ammonium acetate in water B: acetonitrile; mobile phase
Gradient:

| Time in min | % A | % B | Flow rate in ml/min |
|---|---|---|---|
| 0 | 30 | 95 | 1.0 |
| 7 | 55 | 95 | 1.0 |
| 10 | 95 | 85 | 1.0 |
| 15 | 95 | 45 | 1.0 |
| 16 | 100 | 5 | 1.0 |
| 18 | 30 | 5 | 1.0 |
| 20 | 30 | 5 | 1.0 |

Method 12:
Column: XBridge C18 (150 mm×4.6 mm, 5.0 µm); Column temperature: 25° C.
Flow rate: 1.2 mL/min
Injection volume: 2 µl
Detection: 215 and 254 nm
Mobile phase A: 10 mM ammonium acetate in water B: acetonitrile; mobile phase
Gradient:

| Time in min | % A | % B | Flow rate in ml/min |
|---|---|---|---|
| 0 | 5 | 95 | 1.2 |
| 1.2 | 5 | 95 | 1.2 |
| 3 | 55 | 45 | 1.2 |
| 5 | 70 | 30 | 1.2 |
| 7 | 95 | 5 | 1.2 |
| 10 | 95 | 5 | 1.2 |
| 12 | 100 | 0 | 1.2 |
| 14 | 5 | 95 | 1.2 |
| 16 | 5 | 95 | 1.2 |

General Procedure 1 (Suzuki Coupling):
Potassium carbonate (6.9 mmol, 3.0 eq), Pd$_2$(dba)$_3$ (0.21 mmol, 0.1 eq) and tri-tert-butyl phosphonium tetrafluoroborate (0.12 mmol, 0.05 eq) were added at room temperature under an argon atmosphere to a stirred solution of (1-(5-bromopyrimidin-2-yl)-3-(methylthio)-1H-indol-6-yl)(morpholino)-methanone (2.3 mmol, 1.0 eq) and a phenyl boronic acid (2.8 mmol, 1.2 eq) in degassed THF/water (25 mL, 4:1). The reaction mixture was stirred for 2 h at 30° C., then cooled to room temperature and diluted with ethyl acetate (10 mL). For the work up, the mixture was filtered through a plug of celite, washed with water, and dried over sodium sulfate. The solvents were removed under vacuum and the residue was purified by column chromatography [silica gel 100-200 mesh, blend of ethyl acetate and petrolether].

General Procedure 2 (Oxidation Towards Methylsulfoxide):
m-Chloroperoxybenzoic acid (0.22 mmol, 1.0 eq) was added at 0° C. to a stirred solution of a 3-(alkylthio)-1-(pyrimidin-2-yl)-1H-indole-6-carboxamide (0.22 mmol, 1.0 eq) in dichloromethane (10 mL) and stirring was continued for 2 h at room temperature. The mixture was diluted with dichloromethane (10 mL), washed with saturated sodium hydrogen carbonate solution and brine and dried over anhydrous sodium sulphate. The solvent was removed under vacuum and the residue was purified by preparative TLC using for example ethyl acetate as eluent (an alternative solvent system would be a blend methanol and dichloromethane).

General Procedure 3 (Oxidation Towards Methylsulfone):
m-Chloroperoxybenzoic acid (1.2 mmol, 3.0 eq) was added at room temperature to a solution of 3-(alkylthio)-1-(pyrimidin-2-yl)-1H-indole-6-carboxamide (0.4 mmol, 1.0 eq) in dichloromethane (10 mL) and the reaction mixture was stirred for 2 h. Dichloromethane (10 mL) was added and the mixture was washed with saturated sodium hydrogen carbonate solution and brine, and dried over anhydrous sodium sulphate. The solvent was evaporated and the residue was purified by preparative TLC using a blend of methanol and dichloromethane (an alternative solvent system would be a blend ethyl acetate/petrolether) as eluent.

General Procedure 4 (Suzuki Coupling):
A stirred solution of a 1-(5-bromopyrimidin-2-yl)-3-(methylthio)-1H-indole-6-carboxamide (1.88 mmol, 1.0 eq) and a phenyl boronic acid (2.25 mmol, 1.2 eq) in THF/water (25 mL, 4:1) was degassed with argon for 15 min at room temperature. Potassium carbonate (0.78 g, 5.63 mmol, 3.0 eq), Pd$_2$(dba)$_3$ (0.171 g, 0.187 mmol, 0.1 eq), and tri-tert-butyl phosphonium tetrafluoroborate (0.027 g, 0.094 mmol, 0.05 eq) were added and stirring was continued at 30° C. for 3 h. The mixture was diluted with ethyl acetate (10 mL), filtered through a pad of celite, washed with water, dried over sodium sulphate and evaporated under vacuum. The crude was purified by column chromatography [silica gel 100-200 mesh, e.g. ethyl acetate/petrolether 1:2].

SYNTHESIS EXAMPLE 1

(1-(5-(2-Fluorophenyl)pyrimidin-2-yl)-3-(methylsulfinyl)-1H-indol-6yl)(morpholino)-methanone (Compound No. 1)

1a) (1H-Indol-6-yl)(morpholino)methanone

1-Hydroxy-7-azabenzotriazole (0.844 g, 6.21 mmol, 0.05 eq), EDCxHCl (26.09 g, 136.64 mmol, 1.1 eq) and morpholine (12.9 g, 149.06 mmol, 1.2 eq) were added to a stirred solution of 1H-indole-6-carboxylic acid (20.0 g, 124.22 mmol, 1.0 eq) in DMF (150 mL). Stirring was continued for 16 h at room temperature and water (200 mL) was then poured into the reaction mixture. The mixture was extracted with dichloromethane (2×150 mL) and the combined organic layers were washed with brine (100 mL), dried over anhydrous sodium sulphate and evaporated. White solid. Yield: 16.0 g (56% of theory).
1H NMR (400 MHz, DMSO-d6, δ ppm): 11.28 (s, 1H), 7.58 (d, J=8.1 Hz, 1H), 7.49-7.43 (m, 2H), 7.04 (dd, J=8.0, 1.5 Hz, 1H), 6.49 (s, 1H), 3.65-3.48 (m, 8H).

1b) (3-(Methylthio)-1H-indol-6-yl)(morpholino)methanone

Dimethylsulfane (8.17 mL, 109.32 mmol, 1.1 eq) was added dropwise to a stirred suspension of N-chlorosuccinimide (14.53 g, 109.32 mmol, 1.1 eq) in dichloromethane (50 mL) at 0° C. The reaction mixture was cooled to −20° C. and (1H-indol-6-yl)(morpholino)methanone (16.0 g, 99.37 mmol, 1.0 eq) in dichloromethane (120 mL) was added dropwise. After stirring for 1 h at room temperature, the solvent was evaporated and replaced by xylene (100 mL). The mixture was refluxed for 1 h, cooled to ambient temperature and then passed through a silica gel column [100-200 mesh, methanol/dichloromethane=1:19]. The product (16.0 g) obtained was used without further purification.

1H NMR (400 MHz, DMSO-d6, δ ppm): 11.51 (s, 1H), 7.69-7.55 (m, 2H), 7.46 (d, J=3.5 Hz, 1H), 7.13 (dd, J=8.1, 1.4 Hz, 1H), 3.60-3.52 (m, 8H), 2.56 (s, 3H).

1c) (1-(5-Bromopyrimidin-2-yl)-3-(methylthio)-1H-indol-6-yl)(morpholino)methanone Potassium tert-butoxide (9.75 g, 86.95 mmol, 1.5 eq) and 5-bromo-2-chloropyrimidine (11.21 g, 57.97 mmol, 1.0 eq) were added to (3-(methylthio)-1H-indol-6-yl)(morpholino)methanone (16.0 g, 57.97 mmol, 1.0 eq) in DMF (100 mL). The mixture was stirred at 120° C. for 16 h, then cooled to room temperature, diluted with ethyl acetate (100 mL), and filtered through a pad of celite. The filtrate was washed with water (2×100 mL) and brine (50 mL), and dried over sodium sulphate. The solvents were distilled off and the residue was purified by silica gel column chromatography [100-200 mesh; ethyl acetate/petrolether=1:1]. Yield: 8.0 g (32% over two steps).
1H NMR (300 MHz, DMSO-d6, δ ppm): 9.06 (s, 2H), 8.74 (s, 1H), 8.22 (s, 1H), 7.68 (d, J=8.1 Hz, 1H), 7.36 (dd, J=8.0, 1.4 Hz, 1H), 3.78-3.34 (m, 8H), 2.52 (s, 3H).

1d) (1-(5-(2-Fluorophenyl)pyrimidin-2-yl)-3-(methylthio)-1H-indol-6-yl)(morpholino)methanone Potassium carbonate (5.73 g, 41.57 mmol, 3.0 eq), Pd$_2$(dba)$_3$ (1.26 g, 1.39 mmol, 0.1 eq) and tri-tert-butyl phosphonium tetrafluoroborate (0.2 g, 0.69 mmol, 0.05 eq) were added at room temperature under an argon atmosphere to a stirred solution of (1-(5-bromopyrimidin-2-yl)-3-(methylthio)-1H-indol-6-yl)(morpholino)-methanone (6.0 g, 13.85 mmol, 1.0 eq) and (2-fluorophenyl)boronic acid (2.31 g, 16.62 mmol, 1.2 eq) in THF/water (100 mL, 4:1). The mixture was stirred for 2 h at 30° C., diluted with ethyl acetate (50 mL), and filtered through a pad of celite. The filtrate was washed with water, dried over sodium sulphate and evaporated. The residue was purified by column chromatography [100-200 mesh; ethyl acetate/petrolether=2:3]. Yield: 4.0 g (64% of theory).
1H NMR (300 MHz, DMSO-d6, δ ppm): 9.13 (d, J=1.5 Hz, 2H), 8.90 (s, 1H), 8.35 (s, 1H), 7.80-7.68 (m, 2H), 7.56-7.51 (m, 1H), 7.46-7.36 (m, 3H), 3.78-3.34 (s, 8H), 2.54 (s, 3H).

1e) (1-(5-(2-Fluorophenyl)pyrimidin-2-yl)-3-(methylsulfinyl)-1H-indol-6yl)(morpholino)-methanone Prepared from (1-(5-(2-fluorophenyl)pyrimidin-2-yl)-3-(methylthio)-1H-indol-6-yl)(morpholino)-methanone (100 mg, 0.223 mmol) according to general procedure 2. White solid. Yield: 70 mg (67% of theory). Melting range: 214-217° C. HPLC (method 1): R$_t$=9.14 min. Mass spectroscopy: m/z: [M+H]$^+$=464.8
1H NMR (400 MHz, DMSO-d6, δ ppm): 9.20 (s, 2H), 8.94 (s, 1H), 8.79 (s, 1H), 8.05 (d, J=8.2 Hz, 1H), 7.78-7.76 (m, 1H), 7.57-7.55 (m, 1H), 7.47-7.40 (m, 3H), 3.64 (brs, 8H), 3.08 (s, 3H).

SYNTHESIS EXAMPLE 2

4-Fluoro-3-(2-(3-(methylsulfinyl)-6-(morpholine-4-carbonyl)-1H-indol-1yl)pyrimidin-5-yl)benzonitrile (Compound No. 2)

2a) 4-Fluoro-3-(2-(3-(methylthio)-6-(morpholine-4-carbonyl)-1H-indol-1-yl)pyrimidin-5-yl)benzonitrile Synthesized according to general procedure 1 from (1-(5-bromopyrimidin-2-yl)-3-(methylthio)-1H-indol-6-yl)(morpholino)methanone (1.0 g, 2.309 mmol, 1.0 eq) and (5-cyano-2-fluorophenyl)boronic acid (0.451 g, 2.77 mmol, 1.2 eq). Yield: 0.4 g (36% of theory)
1H NMR: (300 MHz, DMSO-d6, δ ppm): 9.18 (d, J=1.4 Hz, 1H), 8.88 (s, 1H), 8.38-8.35 (m, 2H), 8.09-8.05 (m, 1H), 7.75-7.63 (m, 3H), 7.39 (dd, J=8.1, 1.4 Hz, 1H), 3.8-3.36 (m, 8H), 2.55 (s, 3H).

2b) 4-Fluoro-3-(2-(3-(methylsulfinyl)-6-(morpholine-4-carbonyl)-1H-indol-1-yl)pyrimidin-5-yl)-benzonitrile The product obtained under 2a) (200 mg, 0.422 mmol, 1.0 eq) was reacted according to the instructions of the general procedure 2. The crude product was purified by preparative TLC using 5% methanol in dichloromethane as eluent. White solid. Yield: 120 mg (58% of theory). Melting range: 262-266° C. HPLC (method 3): R$_t$=4.54 min. Mass spectroscopy: m/z: [M+H]$^+$=489.8
1H NMR (400 MHz, DMSO-d6, δ ppm): 9.24 (s, 2H), 8.94 (s, 1H), 8.79 (s, 1H), 8.40 (dd, J=7.3, 2.2 Hz, 1H), 8.10-8.04 (m, 2H), 7.72-7.68 (m, 1H), 7.44 (dd, J=8.1, 1.5 Hz, 1H), 3.81-3.39 (m, 8H), 3.08 (s, 3H).

SYNTHESIS EXAMPLE 3

(1-(5-(2-Chlorophenyl)pyrimidin-2-yl)-3-(methylsulfinyl)-1H-indol-6-yl)(morpholino) methanone (Compound No. 3)

3a) (1-(5-(2-Chlorophenyl)pyrimidin-2-yl)-3-(methylthio)-1H-indol-6-yl)(morpholino)methanone Synthesized according to general procedure 1 from (1-(5-bromopyrimidin-2-yl)-3-(methylthio)-1H-indol-6-yl)(morpholino)methanone (1.0 g, 2.30 mmol, 1.0 eq) and (2-chlorophenyl)boronic acid (0.429 g, 2.77 mmol, 1.2 eq). Yield: 0.7 g (65% of theory).
1H NMR (400 MHz, DMSO-d6, δ ppm): 9.04 (s, 2H), 8.86 (s, 1H), 8.35 (s, 1H), 7.70-7.63 (m, 3H), 7.56-7.52 (m, 2H), 7.37 (dd, J=8.1, 1.4 Hz, 1H), 3.71-3.41 (m, 8H), 2.55 (s, 3H).

3b) (1-(5-(2-Chlorophenyl)pyrimidin-2-yl)-3-(methylsulfinyl)-1H-indol-6-yl)(morpholino) methanone The product obtained under 3a) (150 mg, 0.323 mmol) was converted according to the general procedure 2. White solid. Yield: 80 mg (51% of theory). Melting range: 226-230° C. HPLC (method 1): R$_t$=9.55 min. Mass spectroscopy: m/z: [M+H]$^+$=481.1.
1H NMR (400 MHz, DMSO-d6, δ ppm): 9.11 (s, 2H), 8.94 (s, 1H), 8.79 (s, 1H), 8.05 (d, J=8.1 Hz, 1H), 7.70-7.65 (m, 2H), 7.56-7.53 (m, 2H), 7.43 (dd, J=8.0, 1.5 Hz, 1H), 3.71-3.41 (m, 8H), 3.08 (s, 3H).

SYNTHESIS EXAMPLE 4

(3-(Methylsulfinyl)-1-(5-phenylpyrimidin-2-yl)-1H-indol-6-yl)(morpholino) methanone (Compound No. 4)

4a) (3-(Methylthio)-1-(5-phenylpyrimidin-2-yl)-1H-indol-6-yl)(morpholino)methanone Obtained according to general procedure 1 from (1-(5-bromopyrimidin-2-yl)-3-(methylthio)-1H-indol-6-yl)(morpholino)methanone (0.7 g, 1.616 mmol) and phenyl boronic acid (0.232 g, 1.939 mmol). Yield: 0.5 g (72% of theory)

1H NMR (300 MHz, DMSO-d6, δ ppm): 9.25 (s, 2H), 8.90 (s, 1H), 8.35 (s, 1H), 7.87-7.85 (m, 2H), 7.70 (d, J=8.1 Hz, 1H), 7.61-7.52 (m, 2H), 7.52-7.44 (m, 1H), 7.37 (dd, J=8.1, 1.5 Hz, 1H), 3.78-3.34 (m, 8H), 2.54 (s, 3H).

4b) (3-(Methylsulfinyl)-1-(5-phenylpyrimidin-2-yl)-1H-indol-6-yl)(morpholino)methanone The product from the previous step (200 mg, 0.464 mmol) was reacted according to the instructions from general procedure 2. White solid. Yield: 125 mg (60% of theory). Melting range: 239-242° C. HPLC (method 2): $R_t$=9.68 min. Mass spectroscopy: m/z: [M+H]$^+$=447.3

1H NMR (400 MHz, DMSO-d6, δ ppm): 9.31 (s, 2H), 8.96 (s, 1H), 8.78 (s, 1H), 8.05 (d, J=8.4 Hz, 1H), 7.90-7.88 (m, 2H), 7.59-7.55 (m, 2H), 7.51-7.48 (m, 1H), 7.43 (dd, J=8.3, 1.5 Hz, 1H), 3.78-3.34 (m, 8H), 3.08 (s, 3H).

SYNTHESIS EXAMPLE 5

4-Fluoro-3-(2-(3-(methylsulfonyl)-6-(morpholine-4-carbonyl)-1H-indol-1-yl)pyrimidin-5-yl)benzonitrile (Compound No. 5)

Obtained from 4-fluoro-3-(2-(3-(methylthio)-6-(morpholine-4-carbonyl)-1H-indol-1-yl)pyrimidin-5-yl)benzonitrile (200 mg, 0.422 mmol) according to the general procedure 3. White solid. Yield: 110 mg (51% of theory). Melting range: 316-319° C. HPLC (method 3): $R_t$=5.0 min. Mass spectroscopy: m/z: [M+H]$^+$=505.9

1H NMR: (300 MHz, DMSO-d6, δ ppm): 9.29 (s, 2H), 8.93 (d, J=4.7 Hz, 2H), 8.41 (dd, J=7.2, 2.2 Hz, 1H), 8.12-8.07 (m, 1H), 8.01 (d, J=8.3 Hz, 1H), 7.74-7.68 (m, 1H), 7.52 (dd, J=8.2, 1.4 Hz, 1H), 3.81-3.35 (m, 8H), 3.40 (s, 3H).

The following compounds were prepared according to general procedure 3:

Compound No. 6: (1-(5-(2,4-Difluorophenyl)pyrimidin-2-yl)-3-(methylsulfonyl)-1H-indol-6-yl)(morpholino)methanone

SYNTHESIS EXAMPLE 6

White solid. Yield: 140 mg (67% of theory). Melting range: 247-252° C. HPLC (method 3): $R_t$=5.25 min. Mass spectroscopy: m/z: [M+H]$^+$=498.9.

1H NMR (300 MHz, DMSO-d6, δ ppm): 9.21 (s, 2H), 8.93 (s, 1H), 8.90 (s, 1H), 8.01 (d, J=8.2 Hz, 1H), 7.91-7.80 (m, 1H), 7.57-7.49 (m, 2H), 7.37-7.31 (m, 1H), 3.81-3.34 (s, 8H), 3.39 (s, 3H).

Compound No. 7: 3-Fluoro-4-(2-(3-(methylsulfonyl)-6-(morpholine-4-carbonyl)-1H-indol-1-yl)pyrimidin-5-yl)benzamide

SYNTHESIS EXAMPLE 7

White solid. Yield: 80 mg (32% of theory). Melting range: 263-266° C. HPLC (method 3): $R_t$=4.19 min. Mass spectroscopy: m/z: [M+H]$^+$=523.9

1H NMR (300 MHz, DMSO-d6, δ ppm): 9.28 (s, 2H), 8.95 (s, 1H), 8.92 (s, 1H), 8.19 (s, 1H), 8.01 (d, J=8.2 Hz, 1H), 7.94-7.86 (m, 3H), 7.65 (s, 1H), 7.52 (dd, J=8.2, 1.4 Hz, 1H), 3.64 (s, 8H), 3.39 (s, 3H).

Compound No. 8: 2-(2-(3-(Methylsulfonyl)-6-(morpholine-4-carbonyl)-1H-indol-1-yl)pyrimidin-5-yl)benzonitrile

SYNTHESIS EXAMPLE 8

White solid. Yield: 180 mg (84% of theory). Melting range: 265-269° C. HPLC (method 3): $R_t$=4.84 min. Mass spectroscopy: m/z: [M+H]$^+$=487.9

1H NMR (300 MHz, DMSO-d6, δ ppm): 9.29 (s, 2H), 8.95-8.94 (m, 2H), 8.10 (dd, J=7.7, 1.3 Hz, 1H), 8.01 (d, J=8.2 Hz, 1H), 7.97-7.85 (m, 2H), 7.75-7.70 (m, 1H), 7.52 (dd, J=8.1, 1.5 Hz, 1H), 3.71-3.42 (m, 8H), 3.40 (s, 3H).

Compound No. 9: (1-(5-(2-Chlorophenyl)pyrimidin-2-yl)-3-(methylsulfonyl)-1H-indol-6-yl)(morpholino)methanone

SYNTHESIS EXAMPLE 9

White solid. Yield: 165 mg (77% of theory). Melting range: 235-239° C. HPLC (method 2): $R_t$=10.92 min. Mass spectroscopy: m/z: [M+H]$^+$=497.3.

1H NMR (400 MHz, DMSO-d6, δ ppm): 9.16 (s, 2H), 8.95-8.90 (m, 2H), 8.01 (d, J=8.2 Hz, 1H), 7.74-7.64 (m, 2H), 7.59-7.48 (m, 3H), 3.68-3.48 (m, 8H), 3.39 (s, 3H).

Compound No. 10: (3-(Methylsulfonyl)-1-(5-phenylpyrimidin-2-yl)-1H-indol-6-yl)(morpholino)methanone

SYNTHESIS EXAMPLE 10

White solid. Yield: 90 mg (42% of theory). Melting range: 270-274° C. HPLC (method 2): $R_t$=10.61 min. Mass spectroscopy: m/z: [M+H]$^+$=463.3.

1H NMR: (400 MHz, DMSO-d6, δ ppm): 9.36 (s, 2H), 8.95 (s, 1H), 8.91 (s, 1H), 8.01 (d, J=8.2 Hz, 1H), 7.93-7.87 (m, 2H), 7.60-7.56 (m, 2H), 7.52-7.49 (m, 2H), 3.68-3.54 (m, 8H), 3.39 (s, 3H).

Compound No. 11: (1-(5-(2-Fluorophenyl)pyrimidin-2-yl)-3-(methylsulfonyl)-1H-indol-6-yl)(morpholino)methanone

SYNTHESIS EXAMPLE 11

White solid. Yield: 75 mg (70% of theory). Melting range: 267-270° C. HPLC (method 1): $R_t$=9.91 min. Mass spectroscopy: m/z: [M+H]$^+$=480.8

1H NMR (400 MHz, DMSO-d6, δ ppm): 9.24 (d, J=1.3 Hz, 2H), 8.96-8.90 (m, 2H), 8.01 (d, J=8.2 Hz, 1H), 7.81-7.78 (m, 1H), 7.58-7.52 (m, 1H), 7.53-7.40 (m, 3H), 3.64 (brs, 8H), 3.31 (s, 3H)

SYNTHESIS EXAMPLE 12

(3-(Methylsulfinyl)-1-(5-phenylpyrimidin-2-yl)-1H-indol-6-yl)(piperazin-1-yl)methanone (Compound No. 12)

12a) tert-Butyl 4-(1H-indole-6-carbonyl)piperazine-1-carboxylate

Prepared from 1H-indole-6-carboxylic acid (4.0 g, 24.84 mmol, 1.0 eq) and tert-butyl piperazine-1-carboxylate (4.6 g, 24.84 mmol, 1.0 eq) in an analogous manner as described under procedure 1a). White solid. Yield: 5.0 g (61% of theory)

1H NMR (400 MHz, DMSO-d6, δ ppm): 11.29 (s, 1H), 7.58 (d, J=8.1 Hz, 1H), 7.49-7.43 (m, 2H), 7.04 (dd, J=8.1, 1.5 Hz, 1H), 6.48-6.47 (m, 1H), 3.62-3.42 (m, 4H), 3.32-3.42 (m, 4H), 1.41 (s, 9H).

12b) tert-Butyl 4-(3-(methylthio)-1H-indole-6-carbonyl)piperazine-1-carboxylate Synthesized in analogy to the procedure 1b) from tert-butyl 4-(1H-indole-6-carbonyl)piperazine-1-carboxylate (2.0 g, 6.079 mmol). The product (2.0 g) obtained was used without further purification in the next step.

12c) tert-Butyl 4-(3-(methylthio)-1-(5-phenylpyrimidin-2-yl)-1H-indole-6-carbonyl)piperazine-1-carboxylate Prepared from the product of 12b) (1.2 g, 3.2 mmol, 1.0 eq) and 2-chloro-5-phenylpyrimidine (0.604 g, 3.2 mmol, 1.0 eq) following the instructions of 1c). Yield: 700 mg.

1H NMR (300 MHz, DMSO-d6, δ ppm): 9.24 (s, 2H), 8.90 (s, 1H), 8.35 (s, 1H), 7.87-7.85 (d, J=6.9 Hz, 2H), 7.71-7.68 (d, J=8.1 Hz, 1H), 7.58-7.47 (m, 3H), 7.38 (d, J=8.1 Hz, 1H), 3.70-3.38 (m, 8H), 2.54 (s, 3H), 1.41 (s, 9H).

12d) tert-Butyl 4-(3-(methylsulfinyl)-1-(5-phenylpyrimidin-2-yl)-1H-indole-6-carbonyl)piperazine-1-carboxylate Obtained from 12c) (300 mg, 0.56 mmol) according to the general procedure 2. The preparative TLC was performed with 3% methanol in dichloromethane as eluent. White solid. Yield: 170 mg (54% yield).

1H NMR (400 MHz, DMSO-d6, δ ppm): 9.31 (s, 2H), 8.96 (s, 1H), 8.79 (s, 1H), 8.05 (d, J=8.1 Hz, 1H), 7.89 (d, J=7.6 Hz, 2H), 7.61-7.54 (m, 2H), 7.52-7.47 (m, 1H), 7.43 (dd, J=8.1, 1.5 Hz, 1H), 3.70-3.35 (m, 8H), 3.09 (s, 3H), 1.41 (s, 9H).

12e) (3-(Methylsulfinyl)-1-(5-phenylpyrimidin-2-yl)-1H-indol-6-yl)(piperazin-1-yl)methanone TFA (0.5 mL) was added to compound 12d) (170 mg, 0.311 mmol) in dichloromethane (5 mL) at room temperature and the solution was stirred for 2 h. The reaction mixture was then diluted with water, adjusted to pH 8 via addition of saturated sodium hydrogen carbonate solution and extracted with dichloromethane. The combined organic layers were dried over sodium sulfate and evaporated. The remnant was purified by preparative TLC using a blend of 5% methanol in dichloromethane as eluent. White solid. Yield: 75 mg (51% of theory). Melting range: 193-197° C. HPLC (method 3): $R_t$=4.02 min. Mass spectroscopy: m/z: [M+H]$^+$=446.1.

1H NMR (300 MHz, DMSO-d6, δ ppm): 9.31 (s, 2H), 8.92 (s, 1H), 8.77 (s, 1H), 8.03 (d, J=8.2 Hz, 1H), 7.91-7.87 (m, 2H), 7.63-7.45 (m, 3H), 7.38 (dd, J=8.2, 1.4 Hz, 1H), 3.7-3.4 (m, 4H), 3.08 (s, 3H), 2.9-2.6 (s, 4H).

SYNTHESIS EXAMPLE 13

(1-(5-(2-Fluorophenyl)pyrimidin-2-yl)-3-(methylsulfinyl)-1H-indol-6-yl)(piperazin-1-yl)methanone (Compound No. 13)

13a) 2-Chloro-5-(2-fluorophenyl)pyrimidine

Tetrakis(triphenylphosphine)palladium(0) (2.06 g, 1.79 mmol, 0.1 eq) and caesium carbonate (17.4 g, 53.69 mmol, 2.0 eq) were added under an argon atmosphere to a stirred solution of 5-bromo-2-chloropyrimidine (2.5 g, 17.86 mmol, 1 eq) and (2-fluorophenyl)boronic acid (3.45 g, 17.86 mmol, 1.0 eq) in 1,4-dioxane/water (30 mL, 4:1) at room temperature. The mixture was heated to 90° C., stirred for 3 h and then cooled to room temperature. The mixture was diluted with ethyl acetate (10 mL), washed with water, and dried over sodium sulfate. The solvents were removed in vacuo and the residue was purified by column chromatography [silica gel 100-200 mesh, ethyl acetate/petrolether 1:19]. Yield: 2.0 g (53% of theory)

1H NMR (300 MHz, CDCl3, δ ppm): 8.83 (s, 2H), 7.48-7.42 (m, 2H), 7.35-7.25 (m, 2H).

13b) tert-Butyl 4-(1-(5-(2-fluorophenyl)pyrimidin-2-yl)-3-(methylthio)-1H-indole-6-carbonyl)piperazine-1-carboxylate Obtained from the product of 12b) (1.2 g, 3.2 mmol, 1.0 eq) and 2-chloro-5-(2-fluorophenyl)-pyrimidine (0.665 g, 3.2 mmol, 1.0 eq) according to procedure 1c). Yield: 800 mg (46% of theory)

1H NMR (300 MHz, DMSO-d6, δ ppm): 9.13 (s, 2H), 8.89 (s, 1H), 8.35 (s, 1H), 7.81-7.66 (m, 2H), 7.56-7.51 (m, 1H), 7.47-7.31 (m, 3H), 3.81-3.34 (m, 8H), 2.55 (s, 3H), 1.41 (s, 9H).

13c) tert-Butyl 4-(1-(5-(2-fluorophenyl)pyrimidin-2-yl)-3-(methylsulfinyl)-1H-indole-6-carbonyl)piperazine-1-carboxylate The target compound was synthesized from 13b) (250 mg, 0.46 mmol, 1.0 eq) following the instructions of general procedure 2. White solid. Yield: 170 mg (66% of theory)

1H NMR (300 MHz, DMSO-d6, δ ppm): 9.19 (s, 2H), 8.95 (s, 1H), 8.79 (s, 1H), 8.05 (d, J=8.1 Hz, 1H), 7.81-7.76 (m, 1H), 7.63-7.36 (m, 4H), 3.42 (m, 8H), 3.09 (s, 3H), 1.41 (s, 9H).

13d) (1-(5-(2-Fluorophenyl)pyrimidin-2-yl)-3-(methylsulfinyl)-1H-indol-6-yl)(piperazin-1-yl)methanone Prepared from 13c) (170 mg, 0.30 mmol, 1.0 eq) in analogy to the procedure of 12e). White solid. Yield: 130 mg (71% of theory). Melting range: 199-203° C. HPLC (method 3): $R_t$=4.04 min. Mass spectroscopy: m/z: [M+H]$^+$=464.1.

1H NMR (300 MHz, DMSO-d6, δ ppm): 9.19 (d, J=1.4 Hz, 2H), 8.90 (s, 1H), 8.78 (s, 1H), 8.03 (d, J=8.1 Hz, 1H), 7.82-7.76 (m, 1H), 7.58-7.52 (m, 1H), 7.48-7.37 (m, 3H), 3.70-3.37 (m, 4H), 3.08 (s, 3H), 2.73 (bs, 5H).

SYNTHESIS EXAMPLE 14

(1-(5-(2,4-Difluorophenyl)pyrimidin-2-yl)-3-(methylsulfinyl)-1H-indol-6-yl)(piperazin-1-yl)methanone (Compound No. 14)

14a) tert-Butyl 4-(1-(5-(2,4-difluorophenyl)pyrimidin-2-yl)-3-(methylthio)-1H-indole-6-carbonyl)piperazine-1-carboxylate Prepared according to general procedure 1 from tert-butyl 4-(1-(5-bromopyrimidin-2-yl)-3-(methylthio)-1H-indole-6-carbonyl)piperazine-1-carboxylate (1.0 g, 1.876 mmol, 1.0 eq) and (3,4-difluorophenyl)boronic acid (0.353 g, 2.251 mmol, 1.2 eq). Yield: 0.6 g (56% of theory)

1H NMR: (300 MHz, DMSO-d6, δ ppm): 9.10 (s, 2H), 8.88 (s, 1H), 8.35 (s, 1H), 7.88-7.79 (m, 1H), 7.70 (d, J=8.1 Hz, 1H), 7.56-7.46 (m, 1H), 7.41-7.28 (m, 2H), 3.82-3.35 (m, 8H), 2.55 (s, 3H), 1.41 (s, 9H).

14b) tert-Butyl 4-(1-(5-(2,4-difluorophenyl)pyrimidin-2-yl)-3-(methylsulfinyl)-1H-indole-6-carbonyl)piperazine-1-carboxylate Synthesized from 14a) (260 mg, 0.46 mmol) following the instructions of general procedure 2. Yield: 180 mg (67% of theory)

14c) (1-(5-(2,4-Difluorophenyl)pyrimidin-2-yl)-3-(methylsulfinyl)-1H-indol-6-yl)(piperazin-1-yl)methanone Preparation from 14b) (180 mg, 0.31 mmol) in an analogous manner as described under 12e). White solid. Yield: 135 mg (83% of theory). Melting range: 198-201° C. HPLC (method 3): $R_t$=4.20 min. Mass spectroscopy: m/z: [M+H]$^+$=482.2.

1H NMR: (300 MHz, DMSO-d6, δ ppm): 9.17 (s, 2H), 8.90 (s, 1H), 8.77 (s, 1H), 8.03 (d, J=8.2 Hz, 1H), 7.91-7.79 (m, 1H), 7.61-7.42 (m, 1H), 7.44-7.20 (m, 2H), 3.72-3.37 (m, 4H), 3.08 (s, 3H), 2.58-2.78 (m, 4H).

The compounds nos. 15 to 17 were synthesized in three steps from tert-butyl 4-(1-(5-bromopyrimidin-2-yl)-3-(methylthio)-1H-indole-6-carbonyl)piperazine-1-carboxylate in an analogous manner:

Compound No. 15: 3-Fluoro-4-(2-(3-(methylsulfinyl)-6-(piperazine-1-carbonyl)-1H-indol-1-yl)pyrimidin-5-yl)benzamide

SYNTHESIS EXAMPLE 15

White solid. Yield: 170 mg. HPLC (method 1): $R_t$=6.60 min. Mass spectroscopy: m/z: [M+H]$^+$=506.7

1H NMR (300 MHz, DMSO-d6, δ ppm): 9.23 (S, 2H), 8.91 (S, 1H), 8.78 (s, 1H), 8.18 (s, 1H), 8.04 (d, J=8.1 Hz, 1H), 7.90-7.85 (m, 3H), 7.63 (s, 1H), 7.40 (d, J=8.3, 1H), 3.71-3.46 (m, 8H), 3.08 (s, 3H), 2.75 (s, 1H).

Compound No. 16: 2-(2-(3-(Methylsulfinyl)-6-(piperazine-1-carbonyl)-1H-indol-1-yl)pyrimidin-5-yl)benzonitrile

SYNTHESIS EXAMPLE 16

White solid. Yield: 80 mg (75% of theory). Melting range: 230-235° C. HPLC (method 1): $R_t$=7.23 min. Mass spectroscopy: m/z: [M+H]$^+$=471.1

1H NMR (400 MHz, DMSO-d6, δ ppm): 9.24 (s, 2H), 8.92 (s, 1H), 8.82 (s, 1H), 8.10-8.03 (m, 2H), 7.94-7.85 (m, 2H), 7.75-7.70 (m, 1H), 7.40 (dd, J=8.1, 1.6 Hz, 1H), 3.74-3.53 (m, 2H), 3.49-3.3 (m, 2H), 3.09 (s, 3H), 2.91-2.60 (m, 4H).

Compound No. 17: 4-Fluoro-3-(2-(3-(methylsulfinyl)-6-(piperazine-1-carbonyl)-1H-indol-1-yl)pyrimidin-5-yl)benzonitrile

SYNTHESIS EXAMPLE 17

White solid. Yield: 95 mg (76% of theory). Melting range: 159-163° C. HPLC (method 1): $R_t$=7.67 min. Mass spectroscopy: m/z: [M+H]$^+$=489.1

1H NMR (300 MHz, DMSO-d6, δ ppm): 9.24 (s, 2H), 8.90 (s, 1H), 8.80 (s, 1H), 8.40 (dd, J=7.2, 2.2 Hz, 1H), 8.10-8.03 (m, 2H), 7.73-7.67 (m, 1H), 7.40 (dd, J=8.1, 1.5 Hz, 1H), 3.7-3.4 (m, 4H), 3.08 (s, 3H), 2.81-2.60 (m, 4H).

The compound nos. 18 to 20 were prepared in an analogous manner as described in synthesis example 1:

Compound No. 18: (1-(5-(2,4-Difluorophenyl)pyrimidin-2-yl)-3-(methylsulfinyl)-1H-indol-6-yl)(morpholino)methanone

SYNTHESIS EXAMPLE 18

White solid. Yield: 120 mg (58% of theory). Melting range: 230-233° C. HPLC (method 1): $R_t$=9.34 min. Mass spectroscopy: m/z: [M+H]$^+$=482.8

1H NMR (300 MHz, DMSOd6, δ ppm): 9.17 (s, 2H), 8.93 (s, 1H), 8.78 (s, 1H), 8.05-8.03 (m, 1H), 7.89-7.18 (m, 1H), 7.56-7.49 (m, 1H), 7.44-7.37 (m, 1H), 7.36-7.30 (m, 1H), 3.78-3.41 (m, 8H), 3.08 (s, 3H).

Compound No. 19: 3-Fluoro-4-(2-(3-(methylsulfinyl)-6-(morpholine-4-carbonyl)-1H-indol-1-yl)pyrimidin-5-yl)benzamide

SYNTHESIS EXAMPLE 19

White solid. Yield: 72 mg (35% of theory). Melting range: 202-206° C. HPLC (method 3): $R_t$=3.65 min. Mass spectroscopy: m/z: [M+H]$^+$=508.0.

1H NMR (300 MHz, DMSO-d6, δ ppm): 9.23 (s, 2H), 8.94 (s, 1H), 8.79 (s, 1H), 8.19 (s, 1H), 8.05 (d, J=8.1 Hz, 1H), 7.89-7.87 (m, 3H), 7.64 (s, 1H), 7.44 (dd, J=8.1, 1.5 Hz, 1H), 3.64-3.52 (m, 8H), 3.06 (s, 3H).

Compound No. 20: 2-(2-(3-(Methylsulfinyl)-6-(morpholine-4-carbonyl)-1H-indol-1-yl)pyrimidin-5-yl)benzonitrile

SYNTHESIS EXAMPLE 20

White solid. Yield: 185 mg (68% of theory). Melting range: 277-281° C. HPLC (method 3): $R_t$=4.36 min. Mass spectroscopy: m/z: [M+H]$^+$=471.9

1H NMR (300 MHz, DMSO, δ ppm): 9.25 (s, 2H), 8.95 (s, 1H), 8.82 (s, 1H), 8.14-8.02 (m, 2H), 7.96-7.82 (m, 2H), 7.72 (td, J=7.5, 1.7 Hz, 1H), 7.44 (dd, J=8.1, 1.5 Hz, 1H), 3.64-3.41 (m, 8H), 3.09 (s, 3H).

SYNTHESIS EXAMPLE 21

(3-(Methylsulfonyl)-1-(5-phenylpyrimidin-2-yl)-1H-indol-6-yl)(piperazin-1-yl)methanone (Compound No. 21)

21a) tert-Butyl 4-(3-(methylsulfonyl)-1-(5-phenylpyrimidin-2-yl)-1H-indole-6-carbonyl)piperazine-1-carboxylate Preparation according to the general procedure 3 from 12d) (300 mg, 0.567 mmol). Different from the instructions of the general procedure, the crude product was not purified by preparative TLC, instead it was triturated in methanol. White solid. Yield: 180 mg (56% of theory)

1H NMR (400 MHz, DMSO-d6, δ ppm): 9.35 (s, 2H), 8.95 (s, 1H), 8.91 (s, 1H), 8.01 (d, J=8.2 Hz, 1H), 7.91 (d, J=6.8 Hz, 2H), 7.63-7.47 (m, 4H), 3.7-3.3 (m, 11H), 1.41 (s, 9H).

21b) (3-(Methylsulfonyl)-1-(5-phenylpyrimidin-2-yl)-1H-indol-6-yl)(piperazin-1-yl)methanone The target compound was obtained from 21a) (170 mg, 0.303 mmol) in an analogous manner to the procedure of 12e). White solid. Yield: 130 mg (93% of theory)

1H NMR: (300 MHz, DMSO-d6, δ ppm). 9.33 (s, 2H), 8.92 (d, J=7.0 Hz, 2H), 8.01 (d, J=8.1, Hz 1H), 7.91 (d, J=7.2 Hz, 2H), 7.61-7.42 (m, 4H), 3.7-3.4 (m, 4H), 3.39 (s, 3H), 2.7-2.9 (m, 4H).

The compound nos. 22 to 26 were obtained in an analogous manner as described for compound no. 21.

Compound No. 22: 3-Fluoro-4-(2-(3-(methylsulfonyl)-6-(piperazine-1-carbonyl)-1H-indol-1-yl)pyrimidin-5-yl)benzamide

SYNTHESIS EXAMPLE 22

Prepared from tert-butyl 4-(1-(5-(4-carbamoyl-2-fluorophenyl)pyrimidin-2-yl)-3-(methylthio)-1H-indole-6-carbonyl)piperazine-1-carboxylate. Pale brown solid. Yield: 130 mg HPLC (method 3): $R_t$=3.61 min. Mass spectroscopy: m/z: $[M+H]^+$=523.1.

1H NMR (400 MHz, DMSO-d6, δ ppm): 9.27 (s, 2H), 8.91 (s, 2H), 8.20 (s, 1H), 8.00 (d, J=8.2 Hz, 1H), 7.95-7.86 (m, 3H), 7.64 (s, 1H), 7.48 (d, J=8.2 Hz, 1H), 3.7-3.56 (m, 4H), 3.39 (s, 3H), 3.34-3.21 (s, 2H), 2.92-2.61 (m, 3H).

Compound No. 23: (1-(5-(2,4-Difluorophenyl)pyrimidin-2-yl)-3-(methylsulfonyl)-1H-indol-6-yl)(piperazin-1-yl)methanone

SYNTHESIS EXAMPLE 23

Obtained from tert-butyl 4-(1-(5-(2,4-difluorophenyl)pyrimidin-2-yl)-3-(methylthio)-1H-indole-6-carbonyl)piperazine-1-carboxylate. White solid. Yield: 120 mg. Melting range: 229-233° C. HPLC (method 1): $R_t$=8.83 min. Mass spectroscopy: m/z: $[M+H]^+$=498.1

1H NMR (300 MHz, DMSO-d6, δ ppm): 9.20 (s, 2H), 8.93 (d, J=6.9 Hz, 2H), 8.01 (d, J=8.2 Hz, 1H), 7.90-7.82 (m, 1H), 7.58-7.50 (m, 2H), 7.39-7.33 (m, 1H), 3.9-3.42 (m, 4H), 3.40 (s, 3H), 3.17-2.92 (m, 4H).

Compound No. 24: (1-(5-(2-Fluorophenyl)pyrimidin-2-yl)-3-(methylsulfonyl)-1H-indol-6-yl)(piperazin-1-yl)methanone

SYNTHESIS EXAMPLE 24

Synthesized from tert-butyl 4-(1-(5-(2-fluorophenyl)pyrimidin-2-yl)-3-(methylthio)-1H-indole-6-carbonyl)piperazine-1-carboxylate. White solid. Yield: 110 mg. Melting range: 206-210° C. HPLC (method 1): $R_t$=8.10 min. Mass spectroscopy: m/z: $[M+H]^+$=480.1.

1H NMR (300 MHz, DMSO-d6, δ ppm): 9.23 (s, 2H), 8.96 (d, J=12.6 Hz, 2H), 8.79 (s, 2H), 8.03 (d, J=8.2 Hz, 1H), 7.82-7.76 (m, 1H), 7.59-7.413 (m, 4H), 3.74 (s, 4H), 3.40 (s, 3H), 3.16 (s, 4H).

Compound No. 25: 2-(2-(3-(Methylsulfonyl)-6-(piperazine-1-carbonyl)-1H-indol-1-yl)pyrimidin-5-yl)benzonitrile

SYNTHESIS EXAMPLE 25

Preparation from tert-butyl 4-(1-(5-(2-cyanophenyl)pyrimidin-2-yl)-3-(methylthio)-1H-indole-6-carbonyl)piperazine-1-carboxylate. White solid. Yield: 100 mg. Melting range: 193-197° C. HPLC (method 3): $R_t$=4.10 min. Mass spectroscopy: m/z: $[M+H]^+$=487.1

1H NMR (300 MHz, DMSO-d6, δ ppm): 9.23 (s, 2H), 8.96 (d, J=12.6 Hz, 2H), 8.1 (d, J=7.5 Hz, 1H), 8.03 (d, J=8.2 Hz, 1H), 7.96-7.86 (m, 2H), 7.78-7.70 (m, 1H), 7.5-7.46 (m, 1H), 3.74-3.50 (m, 4H), 3.39 (s, 3H), 2.81-2.6 (m, 4H).

Compound No. 26: 4-Fluoro-3-(2-(3-(methylsulfonyl)-6-(piperazine-1-carbonyl)-1H-indol-1-yl)pyrimidin-5-yl)benzonitrile

SYNTHESIS EXAMPLE 26

Synthesized from tert-butyl 4-(1-(5-(5-cyano-2-fluorophenyl)pyrimidin-2-yl)-3-(methylsulfonyl)-1H-indole-6-carbonyl)piperazine-1-carboxylate. White solid. Yield: 110 mg. Melting range: 279-283° C. HPLC (method 3): $R_t$=4.31 min. Mass spectroscopy: m/z: $[M+H]^+$=505.1

1H NMR (400 MHz, DMSO-d6, δ ppm): 9.26 (s, 2H), 8.90 (d, J=8.8 Hz, 2H), 8.37 (dd, J=7.2, 2.2 Hz, 1H), 8.11-8.05 (m, 1H), 8.00 (d, J=8.2 Hz, 1H), 7.73-7.68 (m, 1H), 7.47 (dd, J=8.2, 1.4 Hz, 1H), 3.71-3.59 (m, 2H), 3.39-3.23 (m, 5H), 2.82-2.6 (m, 4H).

SYNTHESIS EXAMPLE 27

(1-(5-(2-Fluorophenyl)pyrimidin-2-yl)-3-(hydroxymethyl)-1H-indol-6-yl)(morpholino)methanone (Compound No. 27)

27a) 6-(Morpholine-4-carbonyl)-1H-indole-3-carbaldehyde

A solution of (1H-indol-6-yl)(morpholino)methanone (200 mg, 0.869 mmol, 1.0 eq) in DMF (3.0 ml) was added dropwise at 0° C. to phosphorus oxychloride (0.34 mL, 2.60 mmol, 3.0 eq) in DMF (5.0 mL) under stirring. The mixture was stirred at room temperature for 3 h, then neutralized with saturated sodium hydrogen carbonate solution, diluted with water (20 mL), and extracted with ethyl acetate (2×10 mL). The organic layers were combined, washed with brine (20 mL), dried over sodium sulfate and evaporated. The residue was purified by silica gel column chromatography [100-200 mesh; methanol/dichloromethane=1:9]. White solid. Yield: 100 mg (45% of theory).

1H NMR (300 MHz, DMSO-d6, δ ppm): 12.23 (s, 1H), 9.95 (s, 1H), 8.39 (s, 1H), 8.12 (d, J=8.7 Hz, 1H), 7.56 (s, 1H), 7.26 (d, J=8.1 Hz, 1H), 3.75-3.41 (m, 8H).

27b) (3-(Hydroxymethyl)-1H-indol-6-yl)(morpholino)methanone

Sodium borohydride (220 mg, 5.81 mmol, 3.0 eq) was added to a stirred solution of product 27a) (500 mg, 1.94 mmol, 1.0 eq) in methanol (10 mL) at room temperature and stirring was continued for 2 h. The methanol was removed under vacuum, water (50 mL) was added, and the mixture was extracted with ethyl acetate (2×30 mL). The combined organic layers were washed with brine (50 mL), dried over sodium sulfate, and evaporated. White solid. Yield: 400 mg (80% of theory).

1H NMR (300 MHz, DMSO-d6, δ ppm): 11.07 (s, 1H), 7.63 (d, J=8.1 Hz, 1H), 7.41 (s, 1H), 7.35 (d, J=2.4 Hz, 1H), 7.04 (dd, J=8.2, 1.4 Hz, 1H), 4.77 (t, J=5.3 Hz, 1H), 4.64 (d, J=5.4 Hz, 2H), 3.65-3.45 (m, 8H).

27c) (1-(5-Bromopyrimidin-2-yl)-3-(hydroxymethyl)-1H-indol-6-yl)(morpholino)methanone Prepared from 27b) (700 mg, 2.69 mmol, 1.0 eq) and 5-bromo-2-chloropyrimidine (520 mg, 2.69 mmol, 1.0 eq) in an analogous manner to the procedure of 1c). The raw product was purified by column chromatography [100-200 mesh; ethyl acetate/petrolether=7:3]. White solid. Yield: 400 mg (35% of theory).
1H NMR (300 MHz, DMSO-d6, δ ppm): 9.04 (s, 2H), 8.71 (s, 1H), 8.21 (s, 1H), 7.75 (d, J=8.1 Hz, 1H), 7.30 (dd, J=8.0, 1.5 Hz, 1H), 5.15 (t, J=5.5 Hz, 1H), 4.72 (d, J=5.7 Hz, 2H), 3.72-3.41 (m, 8H).

27d) (1-(5-(2-Fluorophenyl)pyrimidin-2-yl)-3-(hydroxymethyl)-1H-indol-6-yl)(morpholino)methanone Prepared from 27c) (400 mg, 0.959 mmol, 1.0 eq) and (2-fluorophenyl)boronic acid (133 mg, 0.959 mmol, 1.0 eq) according to general procedure 1. White solid. Yield: 230 mg (55% of theory). Melting range: 190-194° C. HPLC (method 1): $R_t$=9.69 min. Mass spectroscopy: m/z: $[M+H]^+$=433.0
1H NMR (300 MHz, DMSO-d6, δ ppm): 9.11 (d, J=1.4 Hz, 2H), 8.86 (s, 1H), 8.33 (s, 1H), 7.83-7.69 (m, 2H), 7.55-7.50 (m, 1H), 7.47-7.36 (m, 2H), 7.31 (dd, J=8.1, 1.5 Hz, 1H), 5.17 (t, J=5.5 Hz, 1H), 4.75 (d, J=5.1 Hz, 2H), 3.72-3.38 (m, 8H).

SYNTHESIS EXAMPLE 28

(1-(5-(2-Fluorophenyl)pyrimidin-2-yl)-3-(1-hydroxyethyl)-1H-indol-6-yl)(morpholino)methanone (Compound No. 28)

28a) 1-(5-(2-Fluorophenyl)pyrimidin-2-yl)-6-(morpholine-4-carbonyl)-1H-indole-3-carbaldehyde Dess Martin periodinane (235 mg, 0.556 mmol, 1.5 eq) was added to the product of 27d) (160 mg, 0.370 mmol, 1.0 eq) in dichloromethane (10 mL) at 0° C. The mixture was stirred for 2 h at room temperature, and then filtered through a pad of celite. The filter was rinsed with dichloromethane and the filtrate was dried over sodium sulfate, and evaporated. White solid. Yield: 140 mg. Mass spectroscopy: m/z: $[M+H]^+$=430.9

28b) (1-(5-(2-Fluorophenyl)pyrimidin-2-yl)-3-(1-hydroxyethyl)-1H-indol-6-yl)(morpholino)-methanone Methyl magnesium iodide (3M solution in diethyl ether, 0.17 mL, 0.522 mmol, 1.5 eq) was added at −70° C. to a stirred solution of 28a) (150 mg, 0.348 mmol, 1.0 eq) in dry THF (10 mL) and stirring was continued for 2 h at −50° C. The reaction mixture was quenched with ammonium chloride solution, diluted with water (20 mL), and extracted with ethyl acetate (2×20 mL). The organic layers were washed with brine, dried over sodium sulfate, and evaporated. The residue was purified by preparative TLC using 70% ethyl acetate in petrolether as eluent. White solid. Yield: 70 mg (45% of theory). Melting range: 209-213° C. HPLC (method 1): $R_t$=10.09 min. Mass spectroscopy: m/z: $[M+H]^+$=447.0.
1H NMR (300 MHz, DMSO-d6, δ ppm): 9.11 (s, 2H), 8.86 (s, 1H), 8.27 (s, 1H), 7.84-7.74 (m, 2H), 7.56-7.51 (m, 1H), 7.47-7.38 (m, 2H), 7.30 (dd, J=8.1, 1.5 Hz, 1H), 5.26 (d, J=4.9 Hz, 1H), 5.12-5.02 (m, 1H), 3.65-3.41 (m, 8H), 1.55 (d, J=6.4 Hz, 3H).

SYNTHESIS EXAMPLE 29

(3-(Ethylsulfinyl)-1-(5-(2-fluorophenyl)pyrimidin-2-yl)-1H-indol-6-yl)(morpholino)methanone (Compound No. 29)

29a) (3-(Ethylthio)-1H-indol-6-yl)(morpholino)methanone

Synthesized from (1H-indol-6-yl)(morpholino)methanone (1.5 g, 6.52 mmol, 1.0 eq) in an analogous manner as described for 1b). Yield: 1.3 g. Mass spectroscopy: m/z: $[M+H]^+$=291.4.

29b) (1-(5-Bromopyrimidin-2-yl)-3-(ethylthio)-1H-indol-6-yl)(morpholino)methanone The product 29a) (1.5 g, 5.17 mmol, 1.0 eq) and 5-bromo-2-chloropyrimidine (1.0 g, 5.17 mmol, 1.0 eq) were reacted as described in procedure 1c). Yield: 700 mg. Mass spectroscopy: m/z: $[M+H]^+$=446.6/448.7

29c) (3-(Ethylthio)-1-(5-(2-fluorophenyl)pyrimidin-2-yl)-1H-indol-6-yl)(morpholino)methanone Obtained from 29b) (700 mg, 1.56 mmol, 1.0 eq) and (2-fluorophenyl)boronic acid (206 mg, 1.72 mmol, 1.1 eq) according to general procedure 1. Yield: 400 mg. Mass spectroscopy: m/z: $[M+H]^+$=463.4

29d) (3-(Ethylsulfinyl)-1-(5-(2-fluorophenyl)pyrimidin-2-yl)-1H-indol-6-yl)(morpholino)methanone The target compound was prepared from 29c) (400 mg, 0.87 mmol, 1.0 eq) according to general procedure 2. White solid. Yield: 110 mg (7% over the last four steps). Melting range: 122-126° C. HPLC (method 3): $R_t$=4.972 min. Mass spectroscopy: m/z: $[M+H]^+$=479.5
1H NMR (400 MHz, DMSO-d6, δ ppm): 9.19 (s, 2H), 8.94 (s, 1H), 8.75 (s, 1H), 8.01 (d, J=8.4 Hz, 1H), 7.80-7.76 (m, 1H), 7.57-7.53 (m, 1H), 7.47-7.39 (m, 3H), 3.65-3.38 (m, 8H), 3.31-3.18 (m, 2H), 1.16 (t, J=7.4 Hz, 3H).

SYNTHESIS EXAMPLE 30

(1-(5-(2,3-Difluorophenyl)pyrimidin-2-yl)-3-(methylsulfinyl)-1H-indol-6-yl)(morpholino)methanone (Compound No. 30)

30a) (1-(5-Bromopyrimidin-2-yl)-3-(methylsulfinyl)-1H-indol-6-yl)(morpholino)methanone A solution of m-chloroperoxybenzoic acid (77%, 2.10 g, 9.42 mmol) in dichloromethane (20 mL) was added at 0° C. to (1-(5-bromopyrimidin-2-yl)-3-(methylthio)-1H-indol-6-yl)(morpholino)methanone (0.18 g, 0.25 mmol) in dry dichloromethane (300 mL). The mixture was stirred at room temperature for 4 h and then poured onto saturated sodium sulfite solution (20 mL). The organic layer was separated after stirring for 15 min and washed with saturated sodium hydrogen carbonate solution and brine. The organic phase was then dried over sodium sulphate and concentrated. The residue was purified by flash column chromatography [methanol/dichloromethane=1:40]. White solid. Yield: 3.2 g.

30b) (1-(5-(2,3-Difluorophenyl)pyrimidin-2-yl)-3-(methylsulfinyl)-1H-indol-6-yl)(morpholino)-methanone Potassium fluoride (0.048 g, 0.83 mmol), 2,3-difluoro phenyl boronic acid (0.10 g, 0.67 mmol), and bis(tri-tert-butylphosphine)palladium(0) (0.026 g, 0.05 mmol) were added at room temperature under an argon atmosphere to a solution of [1-(5-bromo-pyrimidin-2-yl)-3-methanesulfinyl-1H-indol-6-yl]-morpholin-4-yl-methanone (0.15 g, 0.33 mmol) in dry THF (12 mL). The reaction mixture was heated at 70° C. for 16 h, then filtered through a plug of celite and concentrated. The residue was purified by flash column chromatography [methanol/dichloromethane=1:40]. White solid. Yield: 100 mg (63% of theory).

1H NMR (400 MHz, DMSO-d6, 100° C., δ ppm): 9.17 (s, 2H), 8.94 (s, 1H), 8.75 (s, 1H), 8.04 (d, 1H, J=8.0 Hz), 7.59-7.49 (m, 2H), 7.43-7.39 (m, 2H), 3.67-3.58 (m, 8H), 3.07 (s, 3H).

The compound nos. 31 to 46 were synthesized in an analogous manner:

Compound No. 31: 4-(2-(3-(Methylsulfinyl)-6-(morpholine-4-carbonyl)-1H-indol-1-yl)pyrimidin-5-yl)benzonitrile

SYNTHESIS EXAMPLE 31

The raw product was purified by flash column chromatography [methanol/dichloromethane=1:50] followed by trituration with dichloromethane/hexane (1:2). White solid. Yield: 0.35 g (83% of theory)

1H NMR (400 MHz, DMSO-d6, 80° C., δ ppm): 9.35 (s, 2H), 8.94 (s, 1H), 8.75 (s, 1H), 8.09 (d, 2H, J=8.0 Hz), 8.04-7.99 (m, 3H), 7.43 (d, 1H, J=8.0 Hz), 3.66-3.58 (m, 8H), 3.07 (s, 3H).

Compound No. 32: (1-(5-(4-Fluorophenyl)pyrimidin-2-yl)-3-(methylsulfinyl)-1H-indol-6-yl)(morpholino)methanone

SYNTHESIS EXAMPLE 32

Notwithstanding from procedure 30b), the target product was purified by HPLC and not by flash chromatography. White solid. Yield: 0.07 g (34% of theory)

1H NMR (400 MHz, DMSO-d6, 80° C., δ ppm): 9.25 (s, 2H), 8.94 (s, 1H), 8.74 (s, 1H), 8.03 (d, 1H, J=8.0 Hz), 7.92 (t, 2H, J=8.4 Hz), 7.43-7.36 (m, 3H), 3.66-3.58 (m, 8H), 3.07 (s, 3H).

Compound No. 33: (1-(5-(4-Methoxyphenyl)pyrimidin-2-yl)-3-(methylsulfinyl)-1H-indol-6-yl)(morpholino)methanone

SYNTHESIS EXAMPLE 33

Purification by preparative HPLC. Light yellow solid. Yield: 0.09 g (42% of theory)

1H NMR (400 MHz, DMSO-d6, 80° C., δ ppm): 9.21 (s, 2H), 8.93 (s, 1H), 8.73 (s, 1H), 8.03 (d, 1H, J=8.0 Hz), 7.82-7.8 (m, 2H, J=8.0 Hz), 7.42 (d, 1H, J=8 Hz), 7.13 (d, 2H, J=8 Hz), 3.86 (s, 3H), 3.66-3.58 (m, 8H), 3.07 (s, 3H).

Compound No. 34: (1-(5-(3-Fluorophenyl)pyrimidin-2-yl)-3-(methylsulfinyl)-1H-indol-6-yl)(morpholino)methanone

SYNTHESIS EXAMPLE 34

The raw product was purified by preparative HPLC. White solid. Yield: 75 mg (49% of theory)

1H NMR (400 MHz, DMSO-d6, 80° C., δ ppm): 9.28 (s, 2H), 8.94 (s, 1H), 8.74 (s, 1H), 8.03 (d, 1H, J=8 Hz), 7.74-7.7 (m, 2H), 7.62-7.58 (m, 1H), 7.42 (d, 1H, J=8 Hz), 7.29 (t, 1H, J=8 Hz), 3.67 (bs, 4H), 3.59 (bs, 4H), 3.07 (3H).

Compound No. 35: 3-(2-(3-(Methylsulfinyl)-6-(morpholine-4-carbonyl)-1H-indol-1-yl)pyrimidin-5-yl)benzamide

SYNTHESIS EXAMPLE 35

Purification by HPLC. White solid. Yield: 0.10 g (62% of theory)

1H NMR (400 MHz, DMSO-d6, δ ppm): 9.37 (s, 2H), 8.96 (s, 1H), 8.79 (s, 1H), 8.35 (s, 1H), 8.13 (s, 1H), 8.05 (d, 2H, J=8 Hz), 7.97 (d, 1H, J=8 Hz), 7.67 (t, 1H, J=8.0 Hz), 7.55 (s, 1H), 7.43 (d, 1H, J=8 Hz), 3.67 (bs, 4H), 3.64 (bs, 8H), 3.08 (s, 3H).

Compound No. 36: (3-(Methylsulfinyl)-1-(5-(3-(methylsulfonyl)phenyl)pyrimidin-2-yl)-1H-indol-6-yl)(morpholino)methanone

SYNTHESIS EXAMPLE 36

Purification of the raw product by preparative HPLC. White solid. Yield: 0.08 g (46% of theory)

1H NMR (400 MHz, DMSO-d6, 100° C., δ ppm): 9.34 (s, 2H), 8.95 (s, 1H), 8.75 (s, 1H), 8.37 (s, 1H), 8.2 (d, 1H, J=8 Hz), 8.03 (d, 2H, J=4 Hz), 7.84 (t, 1H, J=8 Hz), 7.42 (d, 1H, J=4 Hz), 3.67 (bs, 4H), 3.59 (bs, 4H), 3.29 (s, 3H), 3.08 (s, 3H).

Compound No. 37: (3-(Methylsulfinyl)-1-(5-(m-tolyl)pyrimidin-2-yl)-1H-indol-6-yl)(morpholino)methanone

SYNTHESIS EXAMPLE 37

Purification by preparative HPLC. White solid. Yield: 0.05 g (40% of theory)

1H NMR (400 MHz, DMSO-d6, 100° C., δ ppm): 9.23 (bs, 2H), 8.93 (bs, 1H), 8.74 (bs, 1H), 8.03 (bs, 1H), 7.67-7.63 (m, 2H), 7.45-7.41 (m, 2H), 7.32 (bs, 1H), 3.67 (bs, 4H), 3.59 (bs, 4H), 3.07 (s, 3H), 2.44 (s, 3H).

Compound No. 38: (1-(5-(2-Fluoro-5-methoxyphenyl)pyrimidin-2-yl)-3-(methylsulfinyl)-1H-indol-6-yl)(morpholino)methanone

SYNTHESIS EXAMPLE 38

The raw product was purified by flash chromatography followed by preparative HPLC. White solid. Yield: 0.04 g (37% of theory)

1H NMR (400 MHz, DMSO-d6, 100° C., δ ppm): 9.15 (s, 2H), 8.93 (s, 1H), 8.74 (s, 1H), 8.03 (d, 1H, J=8 Hz), 7.42 (d, 1H, J=Hz), 7.34-7.29 (m, 2H), 7.09 (bs, 1H), 3.87 (s, 3H), 3.66 (bs, 4H), 3.58 (bs, 4H), 3.07 (s, 3H).

Compound No. 39: (1-(5-(2-Fluoro-4-methoxyphenyl)pyrimidin-2-yl)-3-(methylsulfinyl)-1H-indol-6-yl)(morpholino)methanone

SYNTHESIS EXAMPLE 39

White solid. Yield: 0.09 g (41% of theory)
1H NMR (400 MHz, DMSO-d6, 80° C., δ ppm): 9.1 (s, 2H), 8.92 (s, 1H), 8.74 (s, 1H), 8.03 (d, 1H, J=8 Hz), 7.69 (t, 1H, J=8 Hz), 7.41 (d, 1H, J=8 Hz), 7.04-6.98 (m, 2H), 3.88 (s, 3H), 3.66-3.57 (m, 8H), 3.07 (s, 3H).

Compound No. 40: 3-(2-(3-(Methylsulfinyl)-6-(morpholine-4-carbonyl)-1H-indol-1-yl)pyrimidin-5-yl)benzonitrile

SYNTHESIS EXAMPLE 40

White solid. Yield: 0.35 g (83% of theory)
1H NMR (400 MHz, DMSO-d6, 80° C., δ ppm): 9.34 (s, 2H), 8.94 (s, 1H), 8.75 (s, 1H), 8.36 (s, 1H), 8.2 (d, 1H, J=8 Hz), 8.03 (d, 1H, J=8 Hz), 7.92 (d, 1H, J=8 Hz), 7.79-7.75 (m, 1H), 7.2 (d, 1H, J=8 Hz), 3.67 (bs, 4H), 3.59 (bs, 4H), 3.07 (s, 3H).

Compound No. 41: (1-(5-(2-Fluoro-5-hydroxyphenyl)pyrimidin-2-yl)-3-(methylsulfinyl)-1H-indol-6-yl)(morpholino)methanone

SYNTHESIS EXAMPLE 41

White solid. Yield: 0.14 g (67% of theory)
1H NMR (400 MHz, DMSO-d6, 80° C., δ ppm): 9.44 (s, 1H), 9.1 (s, 2H), 8.92 (s, 1H), 8.75 (s, 1H), 8.03 (d, 1H, J=8 Hz), 7.41 (d, 1H, J=8 Hz), 7.2 (t, 1H, J=10 Hz), 7.05 (bs, 1H), 6.91 (bs, 1H), 3.66 (bs, 4H), 3.58 (bs, 4H), 3.07 (s, 3H).

Compound No. 42: 4-(2-(3-(Methylsulfinyl)-6-(morpholine-4-carbonyl)-1H-indol-1-yl)pyrimidin-5-yl)benzamide

SYNTHESIS EXAMPLE 42

Purification of the raw product by preparative HPLC. White solid. Yield: 0.11 g (68% of theory)
1H NMR (400 MHz, DMSO-d6, δ ppm): 9.37 (s, 2H), 8.95 (s, 1H), 8.78 (s, 1H), 8.01-7.98 (m, 6H) 7.48 (s, 1H), 7.43 (d, 1H, J=8.28 Hz), 3.64 (bs, 8H), 3.08 (s, 3H).

Compound No. 43: 4-Fluoro-3-(2-(3-(methylsulfinyl)-6-(morpholine-4-carbonyl)-1H-indol-1-yl)pyrimidin-5-yl)benzamide

SYNTHESIS EXAMPLE 43

Purified by preparative HPLC. White solid. Yield: 0.11 g (66% of theory)
1H NMR (400 MHz, DMSO-d6, δ ppm): 9.25 (s, 2H), 8.94 (s, 1H), 8.79 (s, 1H), 8.28 (d, 1H, J=5.96 Hz), 8.11 (s, 1H), 8.05-8.03 (m, 2H), 7.54 (m, 2H), 7.43 (d, 1H, J=8.2 Hz), 3.63 (bs, 8H), 3.08 (s, 3H).

Compound No. 44: (1-(5-(2,6-Difluorophenyl)pyrimidin-2-yl)-3-(methylsulfinyl)-1H-indol-6-yl)(morpholino)methanone

SYNTHESIS EXAMPLE 44

Purified by flash column chromatography and preparative TLC [ethyl acetate/hexane=4:5]. White solid. Yield: 0.10 g (47% of theory)
1H NMR (400 MHz, DMSO-d6, δ ppm): 9.14 (s, 2H), 8.93 (s, 1H), 8.79 (s, 1H), 8.04 (d, 1H, J=8.0 Hz), 7.64-7.6 (m, 1H), 7.43 (d, 1H, J=8 Hz), 7.36 (t, 2H, J=8.0 Hz), 3.66 (bs, 8H), 3.08 (s, 3H).

Compound No. 45: (1-(5-(3-Methoxyphenyl)pyrimidin-2-yl)-3-(methylsulfinyl)-1H-indol-6-yl)(morpholino)methanone

SYNTHESIS EXAMPLE 45

The raw product was purified first by flash column chromatography and then by preparative HPLC. White solid. Yield: 0.08 mg (49% of theory)
1H NMR (400 MHz, DMSO-d6, 80° C., δ ppm): 9.25 (s, 2H), 8.94 (s, 1H), 8.74 (s, 1H), 8.02 (d, 1H, J=8.0 Hz), 7.46 (t, 1H, J=8 Hz), 7.42-7.41 (m, 3H), 7.06 (d, 1H, J=8 Hz), 3.9 (s, 3H), 3.67-3.59 (m, 8H), 3.07 (s, 3H).

Compound No. 46: (3-(Methylsulfinyl)-1-(5-(p-tolyl)pyrimidin-2-yl)-1H-indol-6-yl)(morpholino)methanone

SYNTHESIS EXAMPLE 46

For purification, the raw product was first subjected to flash chromatography and then to preparative HPLC. White solid. Yield: 0.06 g (29% of theory)
1H NMR (400 MHz, DMSO-d6, 80° C., δ ppm): 9.23 (s, 2H), 8.93 (s, 1H), 8.74 (s, 1H), 8.02 (d, 1H, J=8.0 Hz), 7.76 (d, 2H, J=8 Hz), 7.42-7.37 (m, 3H), 3.66-3.58 (m, 8H), 3.07 (s, 3H), 2.33 (s, 3H).

Compound No. 47: (3-(Methylsulfinyl)-1-(5-(pyridin-4-yl)pyrimidin-2-yl)-1H-indol-6-yl)(morpholino)methanone

SYNTHESIS EXAMPLE 47

Tetrakis(triphenylphosphine)palladium(0) (11 mg, 0.0092 mmol) and 2 M sodium carbonate solution (0.51 mL) were added under an argon atmosphere and at room temperature to a solution of 30a) (0.18 g, 0.40 mmol) in DME (6 mL). 4-Pyridylboronic acid (0.06 g, 0.52 mmol) in ethanol (6 mL) were added and the resulting mixture was stirred for 5 h at 90° C., then cooled to room temperature and filtered. The filtrate was concentrated and the residue purified by flash column chromatography [methanol/dichloromethane=1:50] followed by trituration with acetone/hexane (1:3). White solid. Yield: 0.10 g (56% of theory)
1H NMR (400 MHz, DMSO-d6, 100° C., δ ppm): 9.37 (s, 2H), 8.94 (s, 1H), 8.75-8.74 (m, 3H), 8.03 (d, 1H, J=8.0 Hz), 7.88 (d, 2H, J=8.12 Hz), 7.43 (d, 1H, J=8 Hz), 3.67 (t, 4H, J=4 Hz), 3.59 (t, 4H, J=4 Hz), 3.08 (s, 3H).

Compound No. 48: (1-(5-(2-Fluoropyridin-3-yl)pyrimidin-2-yl)-3-(methylsulfinyl)-1H-indol-6-yl)(morpholino)methanone

SYNTHESIS EXAMPLE 48

[1-(5-Bromo-pyrimidin-2-yl)-3-methanesulfinyl-1H-indol-6-yl]-morpholin-4-yl-methanone (0.20 g, 0.44 mmol) and 2-fluoro-3-pyridylboronic acid (0.078 g, 0.56 mmol) were reacted in an analogous manner as described for example 47. The residue that was obtained from the filtrate after removal of the solvents was purified by flash column chromatography. White solid. Yield: 0.12 g (58% of theory)

1H NMR (400 MHz, DMSO-d6, 80° C., δ ppm): 9.21 (s, 2H), 8.93 (s, 1H), 8.75 (s, 1H), 8.36-8.32 (m, 2H), 8.03 (d, 1H, J=8 Hz), 7.56 (dd, 1H, J=4 and 8 Hz), 7.43 (d, 1H, J=8 Hz), 3.67 (t, 4H, J=4 Hz), 3.58 (t, 4H, J=4 Hz), 3.07 (s, 3H).

SYNTHESIS EXAMPLE 49

(3-(Methylsulfinyl)-1-(5-(pyridin-3-yl)pyrimidin-2-yl)-1H-indol-6-yl)(morpholino)methanone (Compound No. 49)

49a) (3-(Methylthio)-1-(5-(pyridin-3-yl)pyrimidin-2-yl)-1H-indol-6-yl)(morpholino)methanone The target compound was synthesized from 1-(5-bromopyrimidin-2-yl)-3-(methylthio)-1H-indol-6-yl)(morpholino)methanone (0.22 g, 0.51 mmol) and 3-pyridylboronic acid (0.078 mg, 0.63 mmol) following the procedure for example 47. White solid. Yield: 0.17 g (77% of theory)

49b) (3-(Methylsulfinyl)-1-(5-(pyridin-3-yl)pyrimidin-2-yl)-1H-indol-6-yl)(morpholino)methanone m-Chloroperoxybenzoic acid (48 mg, 0.21 mmol) was added at 0° C. to a solution of 49a) (0.18 g, 0.25 mmol) in dichloromethane (20 mL) and the resulting mixture was stirred at room temperature for 4 h. The reaction was quenched with saturated sodium sulfite solution (20 mL) and stirred for further 5 min. The organic layer was separated, washed with saturated sodium hydrogen carbonate solution (2×20 mL) and brine (1×20 mL), dried over sodium sulphate and concentrated. The residue was purified by flash column chromatography [methanol/dichloromethane=1:25]. White solid. Yield: 0.06 g (53% of theory)

1H NMR (400 MHz, DMSO-d6, 80° C., δ ppm): 9.31 (s, 2H), 9.07 (s, 1H), 8.94 (s, 1H), 8.75 (s, 1H), 8.68 (d, 1H, J=4 Hz), 8.26 (d, 1H, J=8 Hz), 8.03 (d, 1H, J=8 Hz), 7.57 (t, 1H, J=4 Hz), 7.41 (d, 1H, J=8 Hz), 3.67-3.59 (m, 8H), 3.07 (s, 3H).

SYNTHESIS EXAMPLE 50

(3-(Methylsulfinyl)-1-(5-(pyridin-2-yl)pyrimidin-2-yl)-1H-indol-6-yl)(morpholino)methanone (Compound No. 50)

[1,1'-bis(diphenylphosphino)ferrocene]dichloropalladium(II) dichloromethane complex (0.014 g, 0.016 mmol) was added under an argon atmosphere at room temperature to a solution of [(1-(5-bromopyrimidin-2-yl)-3-(methylsulfinyl)-1H-indol-6-yl)(morpholino)methanone (0.15 g, 0.33 mmol), bis(pinacolato)diboron (0.093 g, 0.37 mmol) and potassium acetate (0.099 g, 0.99 mmol) in dioxane (6 mL). The reaction mixture was heated at 115° C. for 40 min and then cooled to ambient temperature. For the Suzuki coupling, which was also carried out under an inert atmosphere, 2-bromopyridine (0.078 g, 0.49 mmol), tetrakis(triphenylphosphine)palladium(0) (0.019 g, 0.016 mmol) and 2M potassium carbonate solution (0.5 mL) were added. The mixture was stirred at 100° C. for 2.5 h and then filtered through a plug of celite. The filtrate was concentrated and the resulting residue purified by flash column chromatography [methanol/dichloromethane=1:50] and a subsequent trituration with dichloromethane/hexane (1:2). White solid. Yield: 45 mg (30% of theory)

1H NMR (400 MHz, DMSO-d6, 100° C., δ ppm): 9.55 (s, 2H), 8.95 (s, 1H), 8.76 (s, 2H), 8.14 (d, 1H, J=8.0 Hz), 8.04-7.96 (m, 2H), 7.48-7.42 (m, 2H), 3.66 (bs, 4H), 3.59 (bs, 4H), 3.07 (s, 3H).

SYNTHESIS EXAMPLE 51

(1-(5-(2-Fluorophenyl)pyrimidin-2-yl)-3-(methylsulfinyl)-1H-indol-6-yl)(pyrrolidin-1-yl)methanone (Compound No. 51)

51a) Methyl 3-(methylthio)-1H-indole-6-carboxylate

Dimethyl sulfide (0.54 mL, 7.42 mmol) was added dropwise at 0° C. to a suspension of N-chlorosuccinimide (0.99 g, 7.42 mmol) in dichloromethane (10 mL). The reaction mixture was cooled to −20° C. and a solution of 1H-indole-6-carboxylic acid methyl ester (1.0 g, 5.71 mmol) in dichloromethane (10 mL) was added. The reaction mixture was warmed to room temperature and stirred for 1 h. The solvent was evaporated and the residue and xylene (50 mL) were refluxed at 140-150° C. for 1 h. The xylene was removed under vacuum and the remnant purified by column chromatography [100-200 mesh silica; dichloromethane/hexane=1:1]. Light brown solid. Yield: 0.9 g (71% of theory). HPLC-MS (method 5): $R_t$=3.26 min; m/z [M+H]$^+$=222

51b) Methyl 1-(5-bromopyrimidin-2-yl)-3-(methylthio)-1H-indole-6-carboxylate

Potassium tert-butylate (4.41 g, 39.36 mmol) and 5-bromo-2-chloro-pyrimidine (5.0 g, 26.2 mmol) were added to a solution of methyl 3-(methylthio)-1H-indole-6-carboxylate (5.8 g, 26.2 mmol) in DMF (60 mL). The resulting mixture was heated at 120° C. for 16 h, then cooled and poured onto ice-cold water (100 mL). The mixture was extracted with MTBE (3×50 mL) and the combined organic layers were dried over sodium sulfate and evaporated. The crude material was purified by column chromatography [100-200 mesh silica; ethyl acetate/hexane=1:9]. White solid. Yield: 6.0 g (61% of theory). HPLC-MS (method 5): $R_t$=4.15 min; m/z [M+H]$^+$=379

51c) Methyl 1-(5-(2-fluorophenyl)pyrimidin-2-yl)-3-(methylthio)-1H-indole-6-carboxylate Tetrakis(triphenylphosphine)palladium(0) (0.15 g, 0.13 mmol), 2-fluorophenylboronic acid (0.93 g, 6.64 mmol) and ethanol (40 mL) were added under an argon atmosphere to a mixture of 51b) (2.0 g, 5.3 mmol) in DME (40 mL) and 2M sodium carbonate solution (5.3 mL). The resulting mixture was heated at 90° C. for 3 h and then filtered through a pad of celite that was subsequently rinsed with dichloromethane (2×50 mL). The filtrate was concentrated and the remnant purified by column chromatography [100-200 mesh silica; dichloromethane/hexane=1:1]. White solid. Yield: 2.0 g (96% of theory). HPLC-MS (method 5): $R_t$=4.41 min; m/z $[M+H]^+$=394

51d) Methyl 1-(5-(2-fluorophenyl)pyrimidin-2-yl)-3-(methylsulfinyl)-1H-indole-6-carboxylate m-Chloroperoxybenzoic acid (77%, 0.98 g, 4.38 mmol) in dichloromethane (5 mL) was added dropwise to an ice-cooled solution of 51c) (2.3 g, 5.85 mmol) in dichloromethane (25 mL). The resulting mixture was stirred at room temperature for 2 h, then diluted with dichloromethane (50 mL), and successively washed with saturated sodium hydrogen carbonate solution (2×50 mL) and brine (1×50 mL). The organic phase was dried over sodium sulfate and evaporated to obtain the crude product that was purified by column chromatography [100-200 mesh silica; 2% methanol in dichloromethane]. White solid. Yield: 2.2 g (92% of theory). HPLC-MS (method 5): $R_t$=3.38 min; m/z $[M+H]^+$=410

51e) 1-(5-(2-Fluorophenyl)pyrimidin-2-yl)-3-(methylsulfinyl)-1H-indole-6-carboxylic acid Lithium hydroxide monohydrate (0.34 g, 8.05 mmol) in water (2 mL) was added to an ice-cooled suspension of methyl ester 51d) (2.2 g, 5.37 mmol) in THF/water (1:1; 40 mL) and the resulting mixture was stirred at room temperature for 16 h. The solvent was removed under vacuum and the remnant was dissolved in water (20 mL) and washed with ethyl acetate (2×20 mL). The aqueous phase was acidified with sodium hydrogen sulfate and extracted with dichloromethane (2×50 mL). The organic layers were dried over sodium sulfate and evaporated. White solid. Yield: 1.8 g (85% of theory). HPLC-MS (method 5): $R_t$=2.6 min; m/z $[M+H]^+$=396

51f) (1-(5-(2-Fluorophenyl)pyrimidin-2-yl)-3-(methylsulfinyl)-1H-indol-6-yl)(pyrrolidin-1-yl)methanone EDCxHCl (115 mg, 0.60 mmol), hydroxybenzothiazol (82 mg, 0.60 mmol), diisopropylethylamine (0.35 ml, 2.02 mmol) and pyrrolidine (0.05 mL, 0.60 mmol) were added to an ice-cooled suspension of 51e) (200 mg, 0.50 mmol) in dichloromethane (10 mL). The reaction mixture was stirred at room temperature for 16 h and then diluted with dichloromethane (40 mL). The organic phase was successively washed with saturated ammonium chloride solution (2×50 mL), saturated sodium hydrogen carbonate solution (2×30 mL), water (30 mL), and brine (30 mL), dried over anhydrous sodium sulfate and evaporated. The residue was purified by column chromatography [100-200 mesh silica; 2% methanol in dichloromethane]. White solid. Yield: 65 mg (28% of theory). HPLC-MS (method 5): $R_t$=3.13 min; m/z $[M+H]^+$=449.1

1H NMR (400 MHz, DMSO-d6, δ ppm): 9.19 (s, 2H), 9.03 (s, 1H), 8.78 (s, 1H), 8.02 (d, 1H, J=8.2 Hz), 7.8-7.76 (m, 1H), 7.57-7.52 (m, 2H), 7.46-7.4 (m, 2H), 3.55-3.45 (m, 4H), 3.08 (s, 3H), 1.92-1.81 (m, 4H).

SYNTHESIS EXAMPLE 52

1-(5-(2-Fluorophenyl)pyrimidin-2-yl)-N,N-dimethyl-3-(methylsulfinyl)-1H-indole-6-carboxamide (Compound No. 52)

HATU (158 mg, 0.41 mmol), diisopropylethylamine (0.32 ml, 0.41 mmol) and dimethylamine (2M in THF) (0.95 mL, 1.89 mmol) were added to an ice-cooled suspension of 51e) (150 mg, 0.38 mmol) in dichloromethane (10 mL) and the resulting mixture was stirred at room temperature for 4 h. The reaction mixture was diluted with dichloromethane (40 mL) and washed with saturated ammonium chloride solution (2×30 mL), saturated sodium hydrogen carbonate solution (2×30 mL), water (30 mL), and brine (30 mL). The organic phase was dried over sodium sulfate and evaporated. The remnant was purified by column chromatography [100-200 mesh silica; 2% methanol in dichloromethane]. White solid. Yield: 62 mg (38% of theory). LC-MS (method 5): $R_t$=2.99 min; m/z $[M+H]^+$=423.2

1H NMR (400 MHz, DMSO-d6, 100° C., δ ppm): 9.14 (s, 2H), 8.9 (s, 1H), 8.74 (s, 1H), 8.01 (d, 1H, J=8.0 Hz), 7.76 (t, 1H, J=8.0 Hz), 7.57-7.54 (m, 1H), 7.42-7.37 (m, 3H), 3.07 (s, 3H), 3.04 (s, 6H).

The compounds nos. 53 to 67 were synthesized in an analogous manner according to the synthesis examples 53 to 67.

Compound No. 53: 1-(5-(2-Fluorophenyl)pyrimidin-2-yl)-3-(methylsulfinyl)-N-(tetrahydrofuran-3-yl)-1H-indole-6-carboxamide

SYNTHESIS EXAMPLE 53

White solid. Yield: 110 mg (47% of theory for the last step). LC-MS (method 5): $R_t$=2.93 min; m/z $[M+H]^+$=465.4

1H NMR (400 MHz, DMSO-d6, δ ppm): 9.32 (s, 1H), 9.2 (s, 2H), 8.8 (s, 1H), 8.68 (d, 1H, J=6 Hz), 8.04-8.03 (d, 1H, J=8.2 Hz), 7.88 (d, 1H, J=8.1 Hz), 7.8 (t, 1H, J=7.2 Hz), 7.57-7.54 (m, 1H), 7.47-7.4 (m, 2H), 4.5 (bs, 1H), 3.92-3.85 (m, 2H), 3.76-3.71 (m, 1H), 3.65-3.62 (m, 1H), 3.08 (s, 3H), 2.23-2.14 (m, 1H), 2.01-1.96 (m, 1H).

Compound No. 54: 1-(5-(2-Fluorophenyl)pyrimidin-2-yl)-N-methyl-3-(methylsulfinyl)-N-(tetrahydrofuran-3-yl)-1H-indole-6-carboxamide

SYNTHESIS EXAMPLE 54

White solid. Yield: 55 mg (23% of theory for the last step). HPLC-MS (method 5): $R_t$=3.0 min; m/z $[M+H]^+$=479

1H NMR (400 MHz, DMSO-d6, 100° C., δ ppm): 9.14 (s, 2H), 8.89 (s, 1H), 8.74 (s, 1H), 8.02 (d, 1H, J=12.0 Hz), 7.76 (t, 1H, J=8.0 Hz), 7.57-7.54 (m, 1H), 7.42-7.38 (m, 3H), 4.81 (bs, 1H), 3.97-3.94 (m, 1H), 3.84-3.82 (m, 1H), 3.75-3.71 (m, 1H), 3.63-3.57 (m, 1H), 3.08 (s, 3H), 2.21-2.19 (m, 1H), 2.95 (s, 3H, obscured under H₂O peak), 2.08-2.04 (m, 1H).

Compound No. 55: (1,4-Diazepan-1-yl)(1-(5-(2-fluorophenyl)pyrimidin-2-yl)-3-(methylsulfinyl)-1H-indol-6-yl)methanone

SYNTHESIS EXAMPLE 55

White solid. Yield: 70 mg (29% of theory for the last step). HPLC-MS (method 4): $R_t$=2.5 min; m/z $[M+H]^+$=478.2

1H NMR (400 MHz, DMSO-d6, 100° C., δ ppm): 9.14 (s, 2H), 8.89 (s, 1H), 8.73 (bs, 1H), 8.0 (bs, 1H), 7.76 (bs, 1H), 7.54 (s, 1H), 7.4 (bs, 3H), 3.59 (bs, 4H), 3.07 (s, 3H), 2.89 (bs, 4H), 1.76 (bs, 2H).

Compound No. 56: 4-(1-(5-(2-Fluorophenyl)pyrimidin-2-yl)-3-(methylsulfinyl)-1H-indole-6-carbonyl)piperazin-2-one

SYNTHESIS EXAMPLE 56

White solid. Yield: 131 mg (72% of theory for the last step). HPLC-MS (method 4): $R_t$=2.6 min; m/z $[M+H]^+$=478

1H NMR (400 MHz, DMSO-d6, 100° C., δ ppm): 9.14 (s, 2H), 8.96 (s, 1H), 8.76 (s, 1H), 8.05 (d, 1H, J=8.0 Hz), 7.76-7.74 (m, 2H), 7.55 (bs, 1H), 7.46-7.4 (m, 3H), 4.11 (s, 2H), 3.72 (bs, 2H), 3.32 (bs, 2H), 3.12 (s, 3H).

Compound No. 57: 1-(5-(2-Fluorophenyl)pyrimidin-2-yl)-3-(methylsulfinyl)-N-(5-oxopyrrolidin-3-yl)-1H-indole-6-carboxamide

SYNTHESIS EXAMPLE 57

White solid. Yield: 280 mg (77% of theory for the last step). HPLC-MS (method 4): $R_t$=2.58 min; m/z [M+H]$^+$=478.2

1H NMR (400 MHz, DMSO-d6, δ ppm): 9.34 (s, 1H), 9.2 (s, 2H), 8.89 (d, 1H, J=6.2 Hz), 8.8 (s, 1H), 8.04 (d, 1H, J=8.1 Hz), 7.89 (d, 1H, J=8.1 Hz), 7.8 (t, 1H, J=7.7 Hz), 7.67 (s, 1H), 7.59-7.54 (m, 1H), 7.47-7.4 (m, 2H), 4.67-4.64 (m, 1H), 3.62 (t, 1H, J=8.0 Hz), 3.23-3.2 (m, 1H), 3.08 (s, 3H), 2.58-2.54 (m, 1H), 2.35-2.3 (m, 1H).

Compound No. 58: 1-(5-(2-Fluorophenyl)pyrimidin-2-yl)-N-methyl-3-(methylsulfinyl)-N-(pyrrolidin-3-yl)-1H-indole-6-carboxamide

SYNTHESIS EXAMPLE 58

Synthesized via amide coupling of 51e) with tert-butyl 3-(methylamino)pyrrolidine-1-carboxylate in analogy to the instructions for 52) followed by deprotection with trifluoroacetic acid in dichloromethane. White solid. Yield: 100 mg (44% of theory for the last step). LC-MS (method 4): $R_t$=2.58 min; m/z [M+H]$^+$=477.9

1H NMR (400 MHz, DMSO-d6, 100° C., δ ppm): 9.14 (s, 2H), 8.88 (s, 1H), 8.74 (s, 1H), 8.02 (d, 1H, J=8.0 Hz), 7.76 (t, 1H, J=8.0 Hz), 7.57-7.53 (m, 1H), 7.42-7.37 (m, 3H), 4.59-4.54 (m, 1H), 3.13 (s, 3H), 3.07-2.87 (m, 3H, obscured under water peak), 2.95 (3H, obscured under water peak), 2.8-2.74 (m, 1H), 2.04-1.83 (m, 2H).

Compound No. 59: 1-(5-(2-Fluorophenyl)pyrimidin-2-yl)-3-(methylsulfinyl)-N-(pyrrolidin-3-yl)-1H-indole-6-carboxamide

SYNTHESIS EXAMPLE 59

Obtained from 51e) and tert-butyl 3-aminopyrrolidine-1-carboxylate via amide coupling and a subsequent deprotection step with trifluoroacetic acid in dichloromethane. White solid. Yield: 65 mg (26% of theory for the last step). HPLC-MS (method 4): $R_t$=2.58 min; m/z [M+H]$^+$=464.3

1H NMR (400 MHz, DMSO-d6, δ ppm): 9.31 (s, 1H), 9.2 (s, 2H), 8.8 (s, 1H), 8.46 (d, 1H, J=6.8 Hz), 8.03-8.01 (m, 1H), 7.86-7.78 (m, 2H), 7.58-7.54 (m, 1H), 7.47-7.4 (m, 2H), 4.37-4.33 (m, 1H), 3.08 (s, 3H), 3.01-2.9 (m, 2H), 2.79-2.66 (m, 2H), 2.03-1.98 (m, 1H), 1.74-1.68 (m, 1H).

Compound No. 60: (1-(5-(2-Fluorophenyl)pyrimidin-2-yl)-3-(methylsulfinyl)-1H-indol-6-yl)(1,4-oxoazepan-4-yl)methanone

SYNTHESIS EXAMPLE 60

White solid. Yield: 50 mg (27% of theory for the last step). HPLC-MS (method 5): $R_t$=3.06 min; m/z [M+H]$^+$=479

1H NMR (400 MHz, DMSO-d6, 80° C., δ ppm): 9.15 (s, 2H), 8.9 (s, 1H), 8.75 (s, 1H), 8.03 (d, 1H, J=8.0 Hz), 7.79-7.75 (m, 1H), 7.58-7.53 (m, 1H), 7.43-7.39 (m, 3H), 3.78-3.66 (m, 8H), 3.08 (s, 3H), 1.87 (bs, 2H).

Compound No. 61: 1-(5-(2-Fluorophenyl)pyrimidin-2-yl)-N-methyl-3-(methylsulfinyl)-1H-indole-6-carboxamide

SYNTHESIS EXAMPLE 61

White solid. Yield: 68 mg (33% of theory for the last step). HPLC-MS (method 5): $R_t$=2.93 min; m/z [M+H]$^+$=409.2

1H NMR (400 MHz, DMSO-d6, δ ppm): 9.33 (s, 1H), 9.2 (s, 2H), 8.8 (s, 1H), 8.58-8.53 (m, 1H), 8.03 (d, 1H, J=8.3 Hz), 7.84-7.72 (m, 2H), 7.59-7.54 (m, 1H), 7.47-7.4 (m, 2H), 3.08 (s, 3H), 2.83 (d, 3H, J=4.4 Hz).

Compound No. 62: N-(Cyclopropylmethyl)-1-(5-(2-fluorophenyl)pyrimidin-2-yl)-3-(methylsulfinyl)-1H-indole-6-carboxamide

SYNTHESIS EXAMPLE 62

White solid. Yield: 80 mg (36% of theory for the last step). HPLC-MS (method 5): $R_t$=3.16 min; m/z [M+H]$^+$=449.4

1H NMR (400 MHz, DMSO-d6, δ ppm): 9.34 (s, 1H), 9.2 (s, 2H), 8.8 (s, 1H), 8.69 (t, 1H, J=5.4 Hz), 8.03 (d, 1H, J=8.3 Hz), 7.86 (d, 1H, J=8.4 Hz), 7.8 (t, 1H, J=7.8 Hz), 7.59-7.53 (m, 1H), 7.47-7.4 (m, 2H), 3.2 (t, 2H, J=6.1 Hz), 3.08 (s, 3H), 1.1-1.07 (m, 1H), 0.47-0.43 (m, 2H), 0.28-0.24 (m, 2H).

Compound No. 63: 1-(5-(2-Fluorophenyl)pyrimidin-2-yl)-N-(2-hydroxyethyl)-3-(methylsulfinyl)-1H-indole-6-carboxamide

SYNTHESIS EXAMPLE 63

White solid. Yield: 95 mg (43% of theory for the last step). HPLC-MS (method 4): $R_t$=2.66 min; m/z [M+H]$^+$=439.2

1H NMR (400 MHz, DMSO-d6, δ ppm): 9.34 (s, 1H), 9.19 (s, 2H), 8.8 (s, 1H), 8.56 (t, 1H, J=5.5 Hz), 8.03 (d, 1H, J=8.3 Hz), 7.86 (d, 1H, J=8.4 Hz), 7.8 (t, 1H, J=7.7 Hz), 7.58-7.54 (m, 1H), 7.47-7.4 (m, 2H), 4.75 (t, 1H, J=5.6 Hz), 3.58-3.54 (m, 2H), 3.41-3.37 (m, 2H), 3.08 (s, 3H).

Compound No. 64: 1-(5-(2-Fluorophenyl)pyrimidin-2-yl)-N-(2-hydroxyethyl)-N-methyl-3-(methylsulfinyl)-1H-indole-6-carboxamide

SYNTHESIS EXAMPLE 64

White solid. Yield: 160 mg (70% of theory for the last step). HPLC-MS (method 4): $R_t$=2.69 min; m/z [M+H]$^+$=453.2

1H NMR (400 MHz, DMSO-d6, 100° C., δ ppm): 9.14 (s, 2H), 8.91 (s, 1H), 8.73 (s, 1H), 7.99 (d, 1H, J=8.0 Hz), 7.76 (t, 1H, J=8.0 Hz), 7.56-7.54 (m, 1H), 7.42-7.37 (m, 3H), 4.43 (bs, 1H), 3.64 (bs, 2H), 3.49 (bs, 2H), 3.06 (s, 3H), 3.07 (s, 3H).

Compound No. 65: 1-(5-(2-Fluorophenyl)pyrimidin-2-yl)-N-(2-methoxyethyl)-N-methyl-3-(methylsulfinyl)-1H-indole-6-carboxamide

SYNTHESIS EXAMPLE 65

White solid. Yield: 110 mg (47% of theory for the last step). HPLC-MS (method 5): $R_t$=3.12 min; m/z [M+H]$^+$=466.9

1H NMR (400 MHz, DMSO-d6, 100° C., δ ppm): 9.14 (s, 2H), 8.89 (s, 1H), 8.74 (s, 1H), 8.0 (d, 1H, J=8.0 Hz), 7.76 (t, 1H, J=8.0 Hz), 7.56-7.53 (m, 1H), 7.42-7.37 (m, 3H), 3.58 (s, 3H), 3.29 (s, 3H), 3.07 (s, 3H), 3.05 (s, 3H), 2.92 (obscured under water peak, 1H).

Compound No. 66: (1-(5-(2-Fluorophenyl)pyrimidin-2-yl)-3-(methylsulfinyl)-1H-indol-6-yl)((R)-3-hydroxypyrrolidin-1-yl)methanone

SYNTHESIS EXAMPLE 66

White solid. Yield: 0.17 g (73% of theory for the last step). HPLC-MS (method 4): $R_t$=2.69 min; m/z [M+H]$^+$=465.4
1H NMR (400 MHz, DMSO-d6, 100° C., δ ppm): 9.14 (s, 2H), 9.01 (s, 1H), 8.74 (s, 1H), 8.01 (d, 1H, J=8.0 Hz), 7.76 (t, 1H, J=8.0 Hz), 7.55-7.52 (m, 2H), 7.42-7.37 (m, 2H), 4.66 (bs, 1H), 4.34 (bs, 1H), 3.67-3.56 (m, 3H), 3.41-3.38 (m, 1H), 3.07 (s, 3H), 2.01-2.0 (m, 1H), 1.88-1.86 (m, 1H).

Compound No. 67: (1-(5-(2-Fluorophenyl)pyrimidin-2-yl)-3-(methylsulfinyl)-1H-indol-6-yl)((S)-3-hydroxypyrrolidin-1-yl)methanone

SYNTHESIS EXAMPLE 68

White solid. Yield: 0.1 g (43% of theory for the last step). HPLC-MS (method 4): $R_t$=2.67 min; m/z [M+H]$^+$=465
1H NMR (400 MHz DMSO-d6, 100° C., δ ppm): 9.14 (s, 2H), 9.01 (s, 1H), 8.74 (s, 1H), 8 (d, 1H, J=8.0 Hz), 7.76 (t, 1H, J=8.0 Hz), 7.56-7.5 (m, 2H), 7.42-7.4 (m, 2H), 4.67 (bs, 1H), 4.33 (bs, 1H), 3.71-3.64 (m, 2H), 3.55 (bs, 1H), 3.42-3.38 (m, 1H), 3.07 (s, 3H), 2.01-1.83 (m, 2H).

SYNTHESIS EXAMPLE NO. 68

(R)-3-Aminopyrrolidin-1-yl)(1-(5-(2-fluorophenyl)pyrimidin-2-yl)-3-(methylsulfinyl)-1H-indol-6-yl)methanone (Compound No. 68)

68a) (3S)-1-(1-(5-(2-Fluorophenyl)pyrimidin-2-yl)-3-(methylsulfinyl)-1H-indole-6-carbonyl)pyrrolidin-3-yl 4-methylbenzenesulfonate Methanesulfonylchloride (0.32 mL, 4.12 mmol) and triethylamine (1.56 mL, 10.29 mmol) were added dropwise at 5° C. to a solution of example 67 (1.6 g, 3.43 mmol) in dichloromethane (15 mL). The resulting mixture was stirred at room temperature for 2 h, then poured onto water and extracted with dichloromethane (2×40 mL). The organic layer was dried over sodium sulfate and evaporated. The residue was purified by flash column chromatography [silica; 3% methanol in dichloromethane]. White solid. Yield: 1.5 g (80% of theory). HPLC-MS (method 4): $R_t$=2.93 min; m/z [M+H]$^+$=542.9

68b) ((R)-3-Azidopyrrolidin-1-yl)(1-(5-(2-fluorophenyl)pyrimidin-2-yl)-3-(methylsulfinyl)-1H-indol-6-yl)methanone Sodium azide (0.31 g, 4.79 mmol) was added to a solution of 68a) (0.75 g, 1.37 mmol) in DMF (8.65 mL) and the resulting mixture was stirred at 60° C. for 2 h. After cooling to ambient temperature, the reaction mixture was poured onto water and extracted with dichloromethane (3×30 mL). The organic phase was dried over sodium sulfate and concentrated. The remnant was purified by flash column chromatography [silica; 2.5% methanol in dichloromethane]. White solid. Yield: 0.4 g (59% of theory). HPLC-MS (method 4): $R_t$=3.04 min; m/z [M+H]$^+$=490.2

68c) (R)-3-Aminopyrrolidin-1-yl)(1-(5-(2-fluorophenyl)pyrimidin-2-yl)-3-(methylsulfinyl)-1H-indol-6-yl)methanone Palladium hydroxide (0.16 g; 20% wt.) was added under an argon atmosphere to 68b) (0.42 g, 0.85 mmol) in methanol (10 ml). The resulting mixture was hydrogenated for 2 h using a balloon as hydrogen source and then filtered through a celite pad. The filtrate was concentrated under vacuum and the residue purified by preparative HPLC. White solid. Yield: 45 mg (11% of theory). HPLC-MS (method 4): $R_t$=2.47 min; m/z [M+H]$^+$=464.3
1H NMR (400 MHz, DMSO-d6, 100° C., δ ppm): 9.14 (s, 2H), 9.01 (s, 1H), 8.74 (s, 1H), 7.99 (d, 1H, J=8.0 Hz), 7.76-7.73 (m, 1H), 7.54-7.49 (m, 2H), 7.42-7.38 (m, 2H), 4.11 (bs, 2H), 3.67 (bs, 2H), 3.21 (bs, 1H), 3.07 (s, 3H), 2.09-1.28 (m, 4H).

SYNTHESIS EXAMPLE 69

(R)-(3-Aminopyrrolidin-1-yl)(1-(5-(2-fluorophenyl)pyrimidin-2-yl)-3-(methylsulfonyl)-1H-indol-6-yl)methanone (Compound No. 69)

The target compound was obtained in three chemical steps from 68a). In the first step, compound 68a) was oxidized to the corresponding methylsulfone with use of m-chloroperoxybenzoic acid. The methylsulfone was then reacted with sodium azide and afterwards hydrogenated in analogy to the procedures 68b) and 68c), respectively. White solid. Yield: 75 mg. HPLC-MS (method 4): $R_t$=2.72 min; m/z [M+H]$^+$=479.9
1H NMR (400 MHz, DMSO-d6, 100° C., δ ppm): 9.19 (s, 2H), 9.01 (s, 1H), 8.91 (s, 1H), 7.99 (d, 1H, J=8.0 Hz), 7.79-7.76 (m, 1H), 7.6-7.54 (m, 2H), 7.43-7.38 (m, 2H), 3.67-3.63 (m, 2H), 3.53 (bs, 2H), 3.35 (s, 3H), 3.21-3.18 (m, 1H), 2.04-2.01 (m, 1H), 1.7-1.64 (m, 1H), 1.28 (bs, 2H).

SYNTHESIS EXAMPLE 70

4-(3-(Methylsulfinyl)-1-(5-phenylpyrimidin-2-yl)-1H-indole-6-carbonyl)piperazin-2-one (Compound No. 70)

Synthesized from 3-(methylsulfinyl)-1-(5-phenylpyrimidin-2-yl)-1H-indole-6-carboxylic acid (200 mg, 0.53 mmol) and piperazin-2-one (64 mg, 0.63 mmol) in an analogous manner as described for example 52. White solid. Yield: 148 mg (61% of theory). HPLC-MS (method 4): $R_t$=2.6 min; m/z [M+H]$^+$=460.3
1H NMR (400 MHz, DMSO-d6, 100° C., δ ppm): 9.24 (s, 2H), 8.97 (s, 1H), 8.75 (s, 1H), 8.04 (d, 1H, J=8.0 Hz), 7.86-7.84 (m, 2H), 7.74 (bs, 1H), 7.59-7.55 (m, 2H), 7.51-7.44 (m, 2H), 4.12 (s, 2H), 3.73-3.71 (m, 2H), 3.32 (bs. 2H), 3.08 (s, 3H).

SYNTHESIS EXAMPLE 71

(1-(5-(2-Fluorophenyl)pyrimidin-2-yl)-3-(methylsulfinyl)-1H-indol-6-yl)((S)-2-(methoxyethyl)pyrrolidin-1-yl)methanone (Compound No. 71)

HATU (144 mg, 0.379 mmol, 1.5 eq) and diisopropylethylamine (0.13 mL, 0.759 mmol, 3.0 eq) were added at room temperature to a stirred solution of compound 51e) (100 mg, 0.253 mmol, 1.0 eq) and (S)-2-(methoxymethyl)pyrrolidine (0.02 mL, 0.303 mmol, 1.2 eq) in dry DMF (10 mL). The reaction mixture was stirred for 30 min and then diluted with ice water (20 mL). The precipitating solid was filtered off and dried. White solid. Yield: 110 mg (88% of theory). Melting range: 143-146° C. HPLC (method 1): $R_t$=10.03 min 1H NMR (400 MHz, DMSO-d6, δ ppm): 9.36 (s, 2H), 9.24 (s, 1H), 9.21 (s, 1H), 8.07 (d, J=8.3 Hz, 1H), 7.80-7.70 (m, 1H), 7.58-7.39 (m, 4H), 4.35-4.30 (m, 1H), 3.65-3.29 (m, 7H) 3.09 (s, 4H), 2.05-2.00 (m, 1H), 1.88-1.84 (m, 1H), 1.72-1.1.66 (m, 1H).

The compounds nos. 72 to 85 were synthesized in an analogous manner according to the synthesis examples 72 to 85.

Compound No. 72: (1-(5-(2-Fluorophenyl)pyrimidin-2-yl)-3-(methylsulfinyl)-1H-indol-6-yl)(4-methoxypiperidin-1-yl)methanone

SYNTHESIS EXAMPLE 72

White solid. Yield: 76 mg (40% of theory). Melting range: 153-156° C. HPLC (method 1): $R_t$=9.60 min.

1H NMR (400 MHz, DMSO-d6, δ ppm): 9.18 (s, 2H), 8.91 (s, 1H), 8.78 (s, 1H), 8.03 (d, J=8.4 Hz, 1H), 7.80-7.76 (m, 1H), 7.56-7.55 (m, 1H), 7.46-7.39 (m, 3H), 4.15-3.90 (m, 2H), 3.64-2.52 (m, 1H), 3.50-3.42 (m, 1H), 3.26 (s, 3H), 3.08 (s, 4H), 1.90-1.80 (m, 2H), 1.51-1.42 (m, 2H).

Compound No. 73: (1-(5-(2-Fluorophenyl)pyrimidin-2-yl)-3-(methylsulfinyl)-1H-indol-6-yl)(4-hydroxypiperidin-1-yl)methanone

SYNTHESIS EXAMPLE 73

White solid. Yield: 100 mg (82% of theory). Melting range: 196-200° C. HPLC (method 1): $R_t$=8.51 min.

1H NMR (400 MHz, DMSO-d6, δ ppm): δ 9.18 (s, 2H), 8.91 (s, 1H), 8.78 (s, 1H), 8.03 (d, J=8.1 Hz, 1H), 7.80-7.76 (m, 1H), 7.62-7.51 (m, 1H), 7.49-7.37 (m, 3H), 4.77 (d, J=4.1 Hz, 1H), 4.30-3.90 (m, 1H), 3.80-3.70 (m, 1H), 3.71-3.50 (m, 1H), 3.30-3.20 (m, 2H), 3.08 (s, 3H), 1.90-1.60 (m, 2H), 1.50-1.30 (m, 2H).

Compound No. 74: (2,2-Dimethylmorpholino)(1-(5-(2-fluorophenyl)pyrimidin-2-yl)-3-(methylsulfinyl)-1H-indol-6-yl)methanone

SYNTHESIS EXAMPLE 74

White solid. Yield: 90 mg (81% of theory). Melting range: 206-209° C. HPLC (method 1): $R_t$=9.77 min 1H NMR (400 MHz, CDCl3, δ ppm): 9.07 (s, 1H), 8.95 (s, 2H), 8.82 (s, 1H), 8.02 (d, J=8.0 Hz, 1H), 7.54-7.43 (m, 2H), 7.42-7.32 (m, 3H), 3.81-3.60 (m, 6H), 3.08 (s, 3H), 1.26 (s, 6H).

Compound No. 75: 1-(5-(2-Fluorophenyl)pyrimidin-2-yl)-3-(methylsulfinyl)-N-(oxetan-3-yl)-1H-indole-6-carboxamide

SYNTHESIS EXAMPLE 75

White solid. Yield: 100 mg (88% of theory). Melting range: 236-240° C. HPLC (method 1): $R_t$=8.90 min.

1H NMR (400 MHz, DMSO-d6, δ ppm): 9.36 (s, 1H), 9.24-9.20 (m, 3H), 8.82 (s, 1H), 8.07 (d, J=8.3 Hz, 1H), 7.91 (dd, J=8.4, 1.6 Hz, 1H), 7.82-7.78 (m, 1H), 7.62-7.51 (m, 1H), 7.48-7.34 (m, 2H), 5.08-5.033 (m, 1H), 4.81 (t, J=6.9 Hz, 2H), 4.66 (t, J=6.4 Hz, 2H), 3.09 (s, 3H).

Compound No. 76: 4-(1-(5-(2-Fluorophenyl)pyrimidin-2-yl)-3-(methylsulfinyl)-1H-indole-6-carbonyl)-1-methylpiperazin-2-one

SYNTHESIS EXAMPLE 76

White solid. Yield: 155 mg (83% of theory). Melting range: 244-248° C. HPLC (method 1): $R_t$=8.67 min 1H NMR (400 MHz, DMSO-d6, δ ppm): 9.19 (s, 2H), 8.98 (s, 1H), 8.81 (s, 1H), 8.07 (d, J=7.6 Hz, 1H), 7.80-7.76 (m, 1H), 7.55-7.48 (m, 1H), 7.48-7.37 (m, 3H), 4.20-4.15 (m, 2H), 3.71-3.68 (m, 2H), 3.41-3.44 (m, 2H), 3.09 (s, 3H), 2.89 (s, 3H).

Compound No. 77: (1-(5-(2-Fluorophenyl)pyrimidin-2-yl)-3-(methylsulfinyl)-1H-indol-6-yl)((R)-2-(methoxymethyl)pyrrolidin-1-yl)methanone

SYNTHESIS EXAMPLE 77

White solid. Yield: 85 mg (56% of theory). Melting range: 93-96° C. HPLC (method 1): $R_t$=9.98 min 1H NMR (300 MHz, DMSO-d6, δ ppm): 9.19 (s, 2H), 8.99 (s, 1H), 8.79 (s, 1H), 8.03 (d, J=8.2 Hz, 1H), 7.82-7.76 (m, 1H), 7.62-7.33 (m, 4H), 4.41-4.31 (m, 1H), 3.75-3.59 (m, 1H), 3.48-3.34 (m, 5H), 3.21-2.91 (m, 4H), 2.12-1.61 (m, 4H).

Compound No. 78: (1-(5-(2-Fluorophenyl)pyrimidin-2-yl)-3-(methylsulfinyl)-1H-indol-6-yl)((R)-2-(hydroxymethyl)pyrrolidin-1-yl)methanone

SYNTHESIS EXAMPLE 78

White solid. Yield: 150 mg (41% of theory). Melting range: 163-166° C. HPLC (method 1): $R_t$=9.10 min 1H NMR (400 MHz, DMSO-d6, δ ppm): 9.19 (s, 2H), 8.99 (s, 1H), 8.81 (s, 1H), 8.02 (d, J=8.0, 1H), 7.81-7.75 (m, 1H), 7.59-7.52 (m, 2H), 7.46-7.39 (m, 2H), 4.91-4.78 (m, 1H), 4.39-4.15 (m, 1H), 3.71-3.62 (m, 1H), 3.56-3.48 (m, 2H), 3.43-3.31 (m, 1H), 3.09 (s, 3H), 2.10-1.65 (m, 4H).

Compound No. 79: (1-(5-(2-Fluorophenyl)pyrimidin-2-yl)-3-(methylsulfinyl)-1H-indol-6-yl)((S)-2-(hydroxymethyl)pyrrolidin-1-yl)methanone

SYNTHESIS EXAMPLE 79

White solid. Yield: 120 mg (66% of theory). Melting range: 133-137° C. HPLC (method 1): $R_t$=9.03 min 1H NMR (400 MHz, DMSO-d6, δ ppm): 9.19 (s, 2H), 8.99 (s, 1H), 8.78 (s, 1H), 8.02 (d, J=7.7 Hz, 1H), 7.79 (t, J=7.5 Hz, 1H), 7.58-7.40 (m, 4H), 4.84 (s, 1H), 4.23-4.20 (m, 1H), 3.65-3.36 (m, 4H), 3.09 (s, 3H), 1.98-1.90 (m, 3H), 1.72-1.67 (m, 1H).

Compound No. 80: (1-(5-(2-Fluorophenyl)pyrimidin-2-yl)-3-(methylsulfinyl)-1H-indol-6-yl)((R)-3-hydroxypiperidin-1-yl)methanone

SYNTHESIS EXAMPLE 80

White solid. Yield: 130 mg (71% of theory). Melting range: 213-216° C. HPLC (method 1): $R_t$=8.86 min 1H NMR (400 MHz, DMSO-d6, δ ppm): 9.19 (s, 2H), 8.92 (s, 1H), 8.78 (s, 1H), 8.03 (d, J=8.1 Hz, 1H), 7.81-7.76 (m, 1H), 7.59-7.53 (m, 1H), 7.48-7.33 (m, 3H), 5.12-4.75 (m, 1H), 4.33-3.75 (m, 1H), 3.62-3.41 (m, 2H), 3.08-3.06 (m, 5H), 1.95-1.72 (m, 2H), 1.51-1.39 (m, 2H).

Compound No. 81: (1-(5-(2-Fluorophenyl)pyrimidin-2-yl)-3-(methylsulfinyl)-1H-indol-6-yl)((S)-3-hydroxypiperidin-1-yl)methanone

SYNTHESIS EXAMPLE 81

White solid. Yield: 95 mg (52% of theory). Melting range: 220-224° C. HPLC (method 1): $R_t$=8.93 min.
1H NMR (400 MHz, DMSO-d6, δ ppm): 9.16 (s, 2H), 8.92 (s, 1H), 8.78 (s, 1H), 8.03 (d, J=8.1 Hz, 1H), 7.80-7.76 (m, 1H), 7.58-7.53 (m, 1H), 7.48-7.32 (m, 3H), 4.98-4.79 (m, 1H), 4.22-3.87 (m, 1H), 3.55 (s, 2H), 3.08 (s, 3H), 2.98-2.49 (m, 2H), 1.88-169 (m, 2H), 1.44-133 (m, 2H).

Compound No. 82: (1-(5-(2-Fluorophenyl)pyrimidin-2-yl)-3-(methylsulfinyl)-1H-indol-6-yl)((R)-3-methoxypyrrolidin-1-yl)methanone

SYNTHESIS EXAMPLE 82

White solid. Yield: 91 mg (38% of theory). Melting range: 101-104° C. HPLC (method 1): $R_t$=9.34 min.
1H NMR (400 MHz, DMSO-d6, δ ppm): 9.19 (s, 2H), 9.02 (s, 1H), 8.79 (s, 1H), 8.03 (d, J=8.1 Hz, 1H), 7.80-7.70 (m, 1H), 7.58-7.52 (m, 2H), 7.49-7.37 (m, 2H), 4.04-3.93 (m, 1H), 3.68-3.35 (m, 4H), 3.26 (s, 1H), 3.16 (s, 2H), 3.09 (s, 3H), 2.02-1.97 (m, 2H).

Compound No. 83: 1-(5-(2-Fluorophenyl)pyrimidin-2-yl)-3-(methylsulfinyl)-N-(oxetan-3-ylmethyl)-1H-indole-6-carboxamide

SYNTHESIS EXAMPLE 83

White solid. Yield: 100 mg (85% of theory). Melting range: 209-212° C. HPLC (method 1): $R_t$=8.82 min.
1H NMR (400 MHz, DMSO-d6, δ ppm): 9.33 (s, 1H), 9.20 (s, 2H), 8.80 (s, 1H), 8.75-8.73 (m, 1H), 8.04 (d, J=8.3 Hz, 1H), 7.90-7.74 (m, 2H), 7.61-7.54 (m, 1H), 7.49-7.35 (m, 2H), 4.67-4.64 (m, 2H), 4.39 (t, J=6.0 Hz, 2H), 3.66-3.53 (m, 2H), 3.31-3.14 (m, 1H), 3.08 (s, 3H).

Compound No. 84: (1-(5-(2-Fluorophenyl)pyrimidin-2-yl)-3-(methylsulfinyl)-1H-indol-6-yl)((R)-2-methylmorpholino)methanone

SYNTHESIS EXAMPLE 84

White solid. Yield: 80 mg (67% of theory). Melting range: 208-211° C. HPLC (method 1): $R_t$=9.57 min
1H NMR (400 MHz, DMSO-d6, δ ppm): 9.19 (s, 2H), 8.94 (s, 1H), 8.79 (s, 1H), 8.05 (d, J=8.1 Hz, 1H), 7.82-7.65 (m, 1H), 7.57-7.3 (m, 1H), 7.49-7.38 (m, 3H), 4.49-4.21 (m, 1H), 3.98-3.41 (m, 4H), 3.27-3.12 (m, 1H), 3.08 (s, 3H), 3.05-2.71 (m, 1H), 1.19-0.9 (m, 3H).

Compound No. 85: (1-(5-(2-Fluorophenyl)pyrimidin-2-yl)-3-(methylsulfinyl)-1H-indol-6-yl)((S)-2-methylmorpholino)methanone

SYNTHESIS EXAMPLE 85

White solid. Yield: 80 mg (67% of theory). Melting range: 205-208° C. HPLC (method 1): $R_t$=9.64 min 1H NMR (400 MHz, DMSO-d6, δ ppm): 9.16 (s, 2H), 8.90 (s, 1H), 8.76 (s, 1H), 8.01 (d, J=8.1 Hz, 1H), 7.77-7.73 (m, 1H), 7.51-7.43 (m, 1H), 7.461-7.36 (m, 3H), 4.45-4.19 (m, 1H), 3.95-3.61 (m, 2H), 3.58-3.41 (m, 2H), 3.05 (s, 5H), 1.2-0.9 (m, 3H).

SYNTHESIS EXAMPLE 86

(1-(5-(4-Hydroxyphenyl)pyrimidin-2-yl)-3-(methylsulfinyl)-1H-indol-6-yl)(morpholino)methanone
(Compound No. 86)

86a) (1-(5-(4-Hydroxyphenyl)pyrimidin-2-yl)-3-(methylthio)-1H-indol-6-yl)(morpholino)-methanone Synthesized from (1-(5-bromopyrimidin-2-yl)-3-(methylthio)-1H-indol-6-yl)(morpholino)methanone (400 mg, 0.923 mmol) and 4-hydroxyphenyl boronic acid (153 mg, 1.108 mmol) in analogy to procedure 1d). Pale brown solid. Yield: 280 mg (68% of theory)
1H NMR (400 MHz, DMSO-d6, δ ppm): 9.76 (s, 1H), 9.15 (s, 2H), 8.88 (s, 1H), 8.34 (s, 1H), 7.71-7.67 (m, 3H), 7.36 (dd, J=8.0, 1.4 Hz, 1H), 6.93 (d, J=8.5 Hz, 2H), 3.70-3.60 (m, 8H), 2.52 (s, 3H).

86b) (1-(5-(4-Hydroxyphenyl)pyrimidin-2-yl)-3-(methylsulfinyl)-1H-indol-6-yl)(morpholino)-methanone m-Chloroperoxybenzoic acid (134 mg, 0.5022 mmol, 0.8 eq) was added at 0° C. to a stirred solution of 86a) (280 mg, 0.6278 mmol, 1.0 eq) in dichloromethane/DMF (10:1; 22 mL) and the solution was stirred for 1 h at this temperature. The reaction mixture was then diluted with dichloromethane (20 mL), washed with saturated sodium hydrogen carbonate solution and brine, and dried over anhydrous sodium sulfate. The solvents were removed under vacuum and the residue was purified by preparative TLC using ethyl acetate as eluent. White solid. Yield: 65 mg (21% of theory)
1H NMR (400 MHz, DMSO-d6, δ ppm): 9.80 (s, 1H), 9.21 (s, 2H), 8.93 (s, 1H), 8.76 (s, 1H), 8.04 (d, J=8.1 Hz, 1H), 7.71 (d, J=8.4 Hz, 2H), 7.41 (dd, J=8.2, 1.5 Hz, 1H), 6.93 (d, J=8.8 Hz, 2H), 3.80-3.49 (m, 8H), 3.07 (s, 3H).

SYNTHESIS EXAMPLE 87

(1-(5-(2-Fluorophenyl)pyrimidin-2-yl)-3-methyl-1H-indol-6-yl)(morpholino)methanone
(Compound No. 87)

Palladium(II) acetate (8 mg, 0.036 mmol) and Xantphos (42 mg, 0.072 mmol) were added under an argon atmosphere to a solution of 2-chloro-5-(2-fluorophenyl)pyrimidine (150 mg, 0.72 mmol), (3-methyl-1H-indol-6-yl)(morpholino)methanone (176 mg, 0.72 mmol; synthesized from morpholine and 3-methyl-1H-indole-6-carboxylic acid) and cesium carbonate (422 mg, 1.29 mmol) in dry THF (5 mL). The reaction mixture was heated in a microwave at 120° C. for 1 h. After cooling to room temperature, water was added and the mixture was extracted with ethyl acetate (2×15 mL). Purification by flash chromatography [silica, heptane with 25% to 75% ethyl acetate] afforded the target compound as white solid. Yield: 185 mg (62% of theory). HPLC-MS: m/z [M+H]$^+$=417.1

SYNTHESIS EXAMPLE 88

(3-Ethyl-1-(5-(2-fluorophenyl)pyrimidin-2-yl)-1H-indol-6-yl)(morpholino)-methanone (Compound No. 88)

88a) 1-(6-(Morpholine-4-carbonyl)-1H-indol-3-yl)ethanone 1-(6-(Morpholine-4-carbonyl)-1H-indol-3-yl)ethanone (717 mg, 3.11 mmol) was added to a solution of aluminium trichloride (913 mg, 6.85 mmol) and acetyl chloride (0.24 ml, 3.43 mmol) in dichloromethane (15 ml). After stirring at room temperature for 18 h, water (50 ml) was added and the mixture was extracted with ethyl acetate (2×50 mL). The organic layer was dried over sodium sulfate and concentrated. Light yellow solid. Yield: 730 mg (86% of theory). HPLC-MS: m/z [M+H]$^+$=273

88b) (3-Ethyl-1H-indol-6-yl)(morpholino)methanone 1-(6-(Morpholine-4-carbonyl)-1H-indol-3-yl)ethanone (730 mg, 2.68 mmol) in acetic acid (1.53 ml, 26.8 mmol) and ethanol (50 ml) was hydrogenated in the presence of 10% Pd/C (285 mg, 0.27 mmol) for 72 h at room temperature, and then for 3 h at 50° C. After cooling to room temperature, the suspension was filtered over Celite and washed with ethanol. The solvent was evaporated and the residue repeatedly co-distilled with toluene and dichloromethane. White solid. Yield: 228 mg (33% of theory). HPLC-MS: m/z [M+H]$^+$=259

88c) (3-Ethyl-1-(5-(2-fluorophenyl)pyrimidin-2-yl)-1H-indol-6-yl)(morpholino)methanone Obtained from 88b) (100 mg, 0.39 mmol) and 2-chloro-5-(2-fluorophenyl)pyrimidine (81 mg, 0.39 mmol) analogously to the procedure for example 87. White solid. Yield: 115 mg (69% of theory). HPLC-MS: m/z [M+H]$^+$=431.2

SYNTHESIS EXAMPLE 89

(1-(5-(2-Fluorophenyl)pyrimidin-2-yl)-3-methyl-1H-indol-6-yl)(1,3-oxazinan-3-yl)methanone (Compound No. 89)

89a) Methyl 1-(5-(2-fluorophenyl)pyrimidin-2-yl)-3-methyl-1H-indole-6-carboxylate Potassium carbonate (1.61 g, 11.6 mmol) and DMAP (0.18 g, 1.45 mmol) were added to a solution of methyl 3-methyl-1H-indole-6-carboxylate (1.1 g, 5.81 mmol) and 2-chloro-5-(2-fluorophenyl)-pyrimidine (1.21 g, 5.81 mmol) in dry DMSO (10 mL). The solution was stirred at 100° C. for 1 h, then cooled to room temperature and slowly poured into vigorously stirred water (100 mL). The precipitating solid was filtered off, washed with water and dried in vacuum. Light-brown solid. Yield: 1.89 g (80% chemical purity). HPLC-MS: m/z [M+H]$^+$=362.

89b) 1-(5-(2-Fluorophenyl)pyrimidin-2-yl)-3-methyl-1H-indole-6-carboxylic acid Lithium hydroxide monohydrate (293 mg, 6.97 mmol) was added to a solution of ester xxa) (504 mg, 1.40 mmol) in methanol (10 mL), THF (10 mL) and water (5 mL) and the mixture was stirred at room temperature for 72 h. The organic solvents were removed under vacuum, water was added and the suspension was washed with diethyl ether and ethyl acetate. The aqueous phase was then acidified to pH~3 by addition of 2N hydrochloride solution and the turbid solution was extracted with ethyl acetate. The combined organic layers were evaporated and the remnant co-distilled with toluene and dichloromethane. The remaining solid was triturated with diisopropyl ether, filtered, and washed with diisopropyl ether. Light-yellow solid. Yield: 388 mg (86% chemical purity). HPLC-MS: m/z [M+H]$^+$=348.

89c) (1-(5-(2-Fluorophenyl)pyrimidin-2-yl)-3-methyl-1H-indol-6-yl)(1,3-oxazinan-3-yl)methanone EDCxHCl (109 mg, 0.57 mmol) and 1-hydroxy-7-azabenzotriazole (17 mg, 0.12 mmol) were added to a solution of acid 89b) (200 mg, 0.50 mmol), 1,3-oxazinane (43.1 mg, 0.50 mmol) and diisopropylethylamine (0.13 mL, 0.74 mmol) in dichloromethane (2 mL) and the reaction mixture was stirred at room temperature for 18 h. The solvent was evaporated and the residue purified by column chromatography [silica, heptane with 5 to 100% ethyl acetate]. White solid. Yield: 51 mg. HPLC-MS: m/z [M+H]$^+$=417.2

SYNTHESIS EXAMPLE 90

1-(5-(2-Fluorophenyl)pyrimidin-2-yl)-N-(3-hydroxypropyl)-3-methyl-1H-indole-6-carboxamide (Compound No. 90)

Obtained as a side product in the reaction 89c). White solid. Yield: 67 mg (33% of theory). HPLC-MS: m/z [M+H]$^+$=405.2

SYNTHESIS EXAMPLE 91

(5,5-Dimethyl-1,3-oxazinan-3-yl)(1-(5-(2-fluorophenyl)pyrimidin-2-yl)-3-methyl-1H-indol-6-yl)methanone (Compound No. 91)

Synthesized from the carboxylic acid 89b) (350 mg, 1.01 mmol) and 2,2-dimethyl-1,3-oxazinane (230 mg, 2.00 mmol) in an analogous manner as described under 89c). White solid. Yield: 250 mg (56% of theory). HPLC-MS: m/z [M+H]$^+$=445.2

SYNTHESIS EXAMPLE 92

1-(5-(2-Fluorophenyl)pyrimidin-2-yl)-N-(3-hydroxy-2,2-dimethylpropyl)-3-methyl-1H-indole-6-carboxamide (Compound No. 92)

The target compound was obtained as side product in the final step towards compound no. 91. White solid. Yield: 100 mg (23% of theory). HPLC-MS: m/z [M+H]$^+$=433.2

SYNTHESIS EXAMPLE 93

4-(1-(5-(2-Fluorophenyl)pyrimidin-2-yl)-3-methyl-1H-indole-6-carbonyl)piperazin-2-one (Compound No. 93)

Synthesized analogously to the instructions of procedure 89c). White solid. Yield: 55 mg
HPLC-MS: m/z [M+H]$^+$=430.2
The compounds nos. 94 to 98 as given in below table 2 were synthesized in an analogous manner:

TABLE 2

| Cpd. No. | Name | Mass peak [M + H]+ |
|---|---|---|
| 94 | 1-(1-(5-(2-Fluorophenyl)pyrimidin-2-yl)-3-methyl-1H-indole-6-carbonyl)tetrahydropyrimidin-4(1H)-one | 430.2 |
| 95 | N-(Cyclohexylmethyl)-1-(5-(2-fluorophenyl)pyrimidin-2-yl)-3-methyl-1H-indole-6-carboxamide | 443.2 |
| 96 | 1-(5-(2-Fluorophenyl)pyrimidin-2-yl)-N-((1-hydroxycyclohexyl)methyl)-3-methyl-1H-indole-6-carboxamide | 459.2 |
| 97 | N-Cyclohexyl-1-(5-(2-fluorophenyl)pyrimidin-2-yl)-3-methyl-1H-indole-6-carboxamide | 429.2 |
| 98 | 1-(5-(2-Fluorophenyl)pyrimidin-2-yl)-N-((1-hydroxycyclopentyl)methyl)-3-methyl-1H-indole-6-carboxamide | 445.2 |

The compounds nos. 99 to 140 as given in below table 3 were synthesized according to the following general procedure:

EDCxHCl (150 µmol) and N,N-diisopropylethylamine (380 µmol) were added to a solution of 1-(5-(2-fluorophenyl)pyrimidin-2-yl)-3-methyl-1H-indole-6-carboxylic acid (100 µmol) and hydroxybenzothiazol (30 µmol) in dichloromethane (4 mL) and the mixture was stirred for 15 min at room temperature. The appropriate amine (125 µmol) was added and the reaction mixture was stirred for 16 h at room temperature. The reaction was stopped by addition of saturated sodium hydrogen carbonate solution (2.5 mL) and the mixture was extracted with dichloromethane (3×3 mL). The solvent was removed under reduced pressure and the residue purified by preparative HPLC to furnish the desired compound.

TABLE 3

| Cpd No. | Name | Mass peak [M + H]+ |
|---|---|---|
| 99 | azetidin-1-yl(1-(5-(2-fluorophenyl)pyrimidin-2-yl)-3-methyl-1H-indol-6-yl)methanone | 387.2 |
| 100 | N-ethyl-1-(5-(2-fluorophenyl)pyrimidin-2-yl)-N,3-dimethyl-1H-indole-6-carboxamide | 389.2 |
| 101 | (1-(5-(2-fluorophenyl)pyrimidin-2-yl)-3-methyl-1H-indol-6-yl)(pyrrolidin-1-yl)methanone | 401.2 |
| 102 | N,N-diethyl-1-(5-(2-fluorophenyl)pyrimidin-2-yl)-3-methyl-1H-indole-6-carboxamide | 403.2 |
| 103 | 1-(5-(2-fluorophenyl)pyrimidin-2-yl)-N-(2-hydroxyethyl)-N,3-dimethyl-1H-indole-6-carboxamide | 405.2 |
| 104 | 1-(5-(2-fluorophenyl)pyrimidin-2-yl)-N-(2-methoxyethyl)-3-methyl-1H-indole-6-carboxamide | 405.2 |
| 105 | (1-(5-(2-fluorophenyl)pyrimidin-2-yl)-3-methyl-1H-indol-6-yl)(piperidin-1-yl)methanone | 415.2 |
| 106 | (1-(5-(2-fluorophenyl)pyrimidin-2-yl)-3-methyl-1H-indol-6-yl)(morpholino)methanone | 417.2 |
| 107 | 1-(5-(2-fluorophenyl)pyrimidin-2-yl)-N-(3-methoxypropyl)-3-methyl-1H-indole-6-carboxamide | 419.2 |
| 108 | 1-(5-(2-fluorophenyl)pyrimidin-2-yl)-N-(furan-2-ylmethyl)-3-methyl-1H-indole-6-carboxamide | 427.2 |
| 109 | (1-(5-(2-fluorophenyl)pyrimidin-2-yl)-3-methyl-1H-indol-6-yl)(4-methylpiperazin-1-yl)methanone | 430.2 |
| 110 | (1-(5-(2-fluorophenyl)pyrimidin-2-yl)-3-methyl-1H-indol-6-yl)(3-hydroxypiperidin-1-yl)methanone | 431.2 |
| 111 | (1-(5-(2-fluorophenyl)pyrimidin-2-yl)-3-methyl-1H-indol-6-yl)(3-methylmorpholino)methanone | 431.2 |
| 112 | 1-(5-(2-fluorophenyl)pyrimidin-2-yl)-3-methyl-N-((tetrahydrofuran-2-yl)methyl)-1H-indole-6-carboxamide | 431.2 |
| 113 | 1-(5-(2-fluorophenyl)pyrimidin-2-yl)-3-methyl-N-(tetrahydro-2H-pyran-4-yl)-1H-indole-6-carboxamide | 431.2 |
| 114 | 1-(5-(2-fluorophenyl)pyrimidin-2-yl)-N-((1-hydroxycyclobutyl)methyl)-3-methyl-1H-indole-6-carboxamide | 431.2 |
| 115 | N-(2-(dimethylamino)-2-oxoethyl)-1-(5-(2-fluorophenyl)pyrimidin-2-yl)-3-methyl-1H-indole-6-carboxamide | 432.2 |
| 116 | N-(2-(dimethylamino)ethyl)-1-(5-(2-fluorophenyl)pyrimidin-2-yl)-N,3-dimethyl-1H-indole-6-carboxamide | 432.2 |
| 117 | (1-(5-(2-fluorophenyl)pyrimidin-2-yl)-3-methyl-1H-indol-6-yl)(thiomorpholino)methanone | 433.1 |
| 118 | 1-(5-(2-fluorophenyl)pyrimidin-2-yl)-N,3-dimethyl-N-(pyridin-4-yl)-1H-indole-6-carboxamide | 438.2 |
| 119 | 1-(5-(2-fluorophenyl)pyrimidin-2-yl)-3-methyl-N-(pyridin-4-ylmethyl)-1H-indole-6-carboxamide | 438.2 |
| 120 | 1-(5-(2-fluorophenyl)pyrimidin-2-yl)-N-(furan-2-ylmethyl)-N,3-dimethyl-1H-indole-6-carboxamide | 441.2 |
| 121 | (R)-(3-(dimethylamino)pyrrolidin-1-yl)(1-(5-(2-fluorophenyl)pyrimidin-2-yl)-3-methyl-1H-indol-6-yl)methanone | 444.2 |
| 122 | (4-ethylpiperazin-1-yl)(1-(5-(2-fluorophenyl)pyrimidin-2-yl)-3-methyl-1H-indol-6-yl)methanone | 444.2 |

TABLE 3-continued

| Cpd No. | Name | Mass peak [M + H]+ |
|---|---|---|
| 123 | (1-(5-(2-fluorophenyl)pyrimidin-2-yl)-3-methyl-1H-indol-6-yl)(4-methyl-1,4-diazepan-1-yl)methanone | 444.2 |
| 124 | 1-(5-(2-fluorophenyl)pyrimidin-2-yl)-3-methyl-N-(1-methylpiperidin-4-yl)-1H-indole-6-carboxamide | 444.2 |
| 125 | (2,6-dimethylmorpholino)(1-(5-(2-fluorophenyl)pyrimidin-2-yl)-3-methyl-1H-indol-6-yl)methanone (Isomer 1) | 445.2 |
| 126 | (2,6-dimethylmorpholino)(1-(5-(2-fluorophenyl)pyrimidin-2-yl)-3-methyl-1H-indol-6-yl)methanone (Isomer 2) | 445.2 |
| 127 | (S)-(1-(5-(2-fluorophenyl)pyrimidin-2-yl)-3-methyl-1H-indol-6-yl)(2-(methoxymethyl)pyrrolidin-1-yl)methanone | 445.2 |
| 128 | (1-(5-(2-fluorophenyl)pyrimidin-2-yl)-3-methyl-1H-indol-6-yl)(2-(hydroxymethyl)piperidin-1-yl)methanone | 445.2 |
| 129 | (1-(5-(2-fluorophenyl)pyrimidin-2-yl)-3-methyl-1H-indol-6-yl)(4-(hydroxymethyl)piperidin-1-yl)methanone | 445.2 |
| 130 | (1-(5-(2-fluorophenyl)pyrimidin-2-yl)-3-methyl-1H-indol-6-yl)(4-methoxypiperidin-l-yl)methanone | 445.2 |
| 131 | 1-(5-(2-fluorophenyl)pyrimidin-2-yl)-N,3-dimethyl-N-(tetrahydro-2H-pyran-4-yl)-1H-indole-6-carboxamide | 445.2 |
| 132 | 1-(5-(2-fluorophenyl)pyrimidin-2-yl)-3-methyl-N-((tetrahydro-2H-pyran-4-yl)methyl)-1H-indole-6-carboxamide | 445.2 |
| 133 | (1-(5-(2-fluorophenyl)pyrimidin-2-yl)-3-methyl-1H-indol-6-yl)(2-oxa-7-azaspiro[3.5]nonan-7-yl)methanone | 457.2 |
| 134 | 3-(4-(1-(5-(2-fluorophenyl)pyrimidin-2-yl)-3-methyl-1H-indole-6-carbonyl)piperazin-1-yl)propanenitrile | 469.2 |
| 135 | 1-(4-(1-(5-(2-fluorophenyl)pyrimidin-2-yl)-3-methyl-1H-indole-6-carbonyl)piperazin-1-yl)ethanone | 458.2 |
| 136 | 1-(5-(2-fluorophenyl)pyrimidin-2-yl)-3-methyl-N-(2-(2-oxopyn-olidin-1-yl)ethyl)-1H-indole-6-carboxamide | 458.2 |
| 137 | (1-(5-(2-fluorophenyl)pyrimidin-2-yl)-3-methyl-1H-indol-6-yl)(4-(2-hydroxyethyl)piperazin-1-yl)methanone | 460.2 |
| 138 | methyl 3-(1-(5-(2-fluorophenyl)pyrimidin-2-yl)-3-methyl-1H-indole-6-carboxamido)propanoate | 433.2 |
| 139 | N-(3-(dimethylamino)-3-oxopropyl)-1-(5-(2-fluorophenyl)pyrimidin-2-yl)-3-methyl-1H-indole-6-carboxamide | 446.2 |
| 140 | (1-(5-(2-fluorophenyl)pyrimidin-2-yl)-3-methyl-1H-indol-6-yl)(2-oxa-6-azaspiro[3.5]nonan-6-yl)methanone | 457.2 |

SYNTHESIS EXAMPLE 141

(1-(5-(4-Methoxypyridin-2-yl)pyrimidin-2-yl)-3-(methylsulfinyl)-1H-indol-6-yl)(morpholino)methanone (Compound No. 141)

141a) (3-(Methylthio)-1-(5-(4,4,5,5-tetramethyl-1,3,2-dioxaborolan-2-yl)pyrimidin-2-yl)-1H-indol-6-yl)(morpholino)methanone Bis(pinacolato)diboron (322 mg, 1.27 mmol, 1.1 eq), potassium acetate (339 mg, 3.464 mmol, 3.0 eq), and PdCl2 (dppf) (94.2 mg, 0.115 mmol, 0.1 eq) were added at room temperature to a solution of (1-(5-bromopyrimidin-2-yl)-3-(methylthio)-1H-indol-6-yl)(morpholino)methanone (500 mg, 1.154 mmol, 1.0 eq) in 1,4-dioxane (10 mL) stirred under an argon atmosphere. The reaction mixture was stirred for 16 h at 100° C., then cooled to room temperature and filtered through a pad of celite. The celite was rinsed with dichloromethane (20 mL) and the filtrate was evaporated. The crude product (500 mg) was so obtained as dark brown oil and used for the next step without further purification.

141b) (1-(5-(4-Methoxypyridin-2-yl)pyrimidin-2-yl)-3-(methylthio)-1H-indol-6-yl)(morpholino)methanone 2-Bromo-4-methoxypyridine (215 mg, 1.145 mmol, 1.1 eq), potassium carbonate (431 mg, 3.124 mmol, 3.0 eq) and PdCl2(dppf) (85 mg, 0.104 mmol, 0.1 eq) were added at room temperature and under an inert atmosphere to a solution of the raw product from 141a) (500 mg, 1.041 mmol, 1.0 eq) in DMF (10 mL). The reaction mixture was stirred at 100° C. for 3 h and then cooled to room temperature. For the work up, the mixture was diluted with ethyl acetate (20 mL), washed with water (2×20 mL) and brine, and dried over anhydrous sodium sulfate. The solvents were removed under reduced pressure and the remnant was purified by column chromatography [100-200 mesh silica gel; 5% methanol in dichloromethane]. White solid. Yield: 200 mg (41% of theory over two steps)

1H NMR (400 MHz, DMSO-d6, δ ppm): 9.53 (s, 2H), 8.90 (s, 1H), 8.55 (d, J=5.5 Hz, 1H), 8.35 (s, 1H), 7.78-7.63 (m, 2H), 7.38 (d, J=8.2 Hz, 1H), 7.06-7.04 (m, 1H), 3.95 (s, 3H), 3.72-3.4 (m, 8H), 2.55 (s, 3H).

141c) (1-(5-(4-Methoxypyridin-2-yl)pyrimidin-2-yl)-3-(methylsulfinyl)-1H-indol-6-yl)(morpholino)methanone m-Chloroperoxybenzoic acid (65%; 91.6 mg, 0.345 mmol, 0.8 eq,) was added at 0° C. to a stirred solution of the product 141b) (200 mg, 0.432 mmol, 1.0 eq) in dichloromethane (10 mL). Stirring was continued at this temperature for 30 min and the reaction mixture was then diluted with dichloromethane (10 mL), washed with saturated natrium hydrogen carbonate solution and brine, and dried over sodium sulfate. The solvent was removed under reduced pressure and the residue was purified by column chromatography [100-200 mesh silica gel; methanol/ethyl acetate=1:9]. White solid. Yield 70 mg (34% of theory). Melting range: 216-220° C. HPLC (method 6): $R_t$=7.24 min. Mass spectroscopy: m/z: [M+H]+=478.2.

1H NMR (400 MHz, DMSO-d6, δ ppm): 9.57 (s, 2H), 8.93 (s, 1H), 8.77 (s, 1H), 8.55 (d, J=5.7 Hz, 1H), 8.02 (d, J=8.1 Hz, 1H), 7.75 (s, 1H), 7.42-7.39 (m, 1H), 7.06-7.03 (m, 1H), 3.93 (s, 3H), 3.71-3.43 (m, 8H), 3.05 (s, 3H).

The compounds nos. 142 to 147 were synthesized analogously to synthesis example 141a)

Compound No. 142: (1-(5-(4-Methylpyridin-2-yl)pyrimidin-2-yl)-3-(methylsulfinyl)-1H-indol-6-yl)(morpholino)methanone

SYNTHESIS EXAMPLE 142

White solid. Yield: 90 mg (57% of theory for the last step). Melting range: 167-171° C. HPLC (method 6): $R_t$=8.61 min. Mass spectroscopy: m/z: [M+H]$^+$=462.2

1H NMR (400 MHz, DMSO-d6, δ ppm): 9.34 (s, 2H), 9.09 (s, 1H), 8.84 (s, 1H), 8.61 (d, J=5.2 Hz, 1H), 8.01 (d, J=8.1, 1H), 7.59 (s, 1H), 7.43-7.40 (m, 1H), 7.19-7.17 (m, 1H), 3.91-3.62 (m, 8H), 3.07 (s, 3H), 2.48 (s, 3H).

Compound No. 143: (1-(5-(2-Hydroxypyridin-4-yl)pyrimidin-2-yl)-3-(methylsulfinyl)-1H-indol-6-yl)(morpholino)methanone

SYNTHESIS EXAMPLE 143

Pale brown solid. Yield: 50 mg (9% over the last three steps). Melting range: 262-265° C. HPLC (method 6): $R_t$=6.75 min. Mass spectroscopy: m/z: [M+H]$^+$=464.1.

1H NMR (400 MHz, DMSO-d6, δ ppm): 11.75 (s, 1H), 9.33 (s, 2H), 8.93 (s, 1H), 8.76 (s, 1H), 8.04 (d, J=8.4 Hz, 1H), 7.56 (d, J=6.8 Hz, 1H), 7.43 (d, J=7.6 Hz, 1H), 6.86 (s, 1H), 6.74-6.72 (d, J=6.4 Hz, 1H), 3.72-3.48 (m, 8H), 3.0 (s, 3H).

Compound No. 144: (3-(Methylsulfinyl)-1-(5-(pyridazin-3-yl)pyrimidin-2-yl)-1H-indol-6-yl)(morpholino)methanone

SYNTHESIS EXAMPLE 144

White solid. Yield: 70 mg (33% of theory for the last step). Melting range: 261-265° C. HPLC (method 6): $R_t$=7.24 min. Mass spectroscopy: m/z: [M+H]$^+$=449.2.

1H NMR (400 MHz, DMSO-d6, δ ppm): 9.65 (s, 2H), 9.31 (d, J=5.2, 1H), 8.95 (s, 1H), 8.80 (s, 1H), 8.43 (d, J=8.7, 1H), 8.03 (d, J=8.1 Hz, 1H), 7.92-7.88 (m, 1H), 7.42 (d, J=8.1, 1H), 3.71-3.43 (m, 8H), 3.06 (s, 3H).

Compound No. 145: (3-(Methylsulfinyl)-1-(5-(thiazol-4-yl)pyrimidin-2-yl)-1H-indol-6-yl)(morpholino)methanone

SYNTHESIS EXAMPLE 145

White solid. Yield: 100 mg (48% of theory for the last step). Melting range: 254-257° C. HPLC (method 6): $R_t$=7.96 min. Mass spectroscopy: m/z: [M+H]$^+$=454.1

1H NMR (400 MHz, DMSO-d6, δ ppm): 9.50 (s, 2H), 9.35 (d, J=1.6 Hz, 1H), 8.93 (s, 1H), 8.77 (s, 1H), 8.50 (d, J=1.6 Hz, 1H), 8.04 (d, J=8.0 Hz, 1H), 7.43-7.41 (m, 1H), 3.73-3.48 (m, 8H), 3.07 (s, 3H).

Compound No. 146: (1-(5-(5-Amino-2-fluorophenyl)pyrimidin-2-yl)-3-(methylsulfinyl)-1H-indol-6-yl)(morpholino)methanone

SYNTHESIS EXAMPLE 146

White solid. Yield: 100 mg (48% of theory for the last step). Melting range: 188-192° C. HPLC (method 6): $R_t$=8.27 min. Mass spectroscopy: m/z: [M+H]$^+$=480.3

1H NMR (400 MHz, DMSO-d6, δ ppm): 9.08 (s, 2H), 8.92 (s, 1H), 8.77 (s, 1H), 8.04 (d, J=8.4 Hz, 1H), 7.42 (dd, J=8.4, 1.4 Hz, 1H), 7.10-7.05 (m, 1H), 6.82-6.79 (m, 1H), 6.69-6.67 (m, 1H), 5.18 (s, 2H), 3.81-3.48 (m, 8H), 3.07 (s, 3H).

Compound No. 147: (1-(5-(4-Hydroxypyridin-2-yl)pyrimidin-2-yl)-3-(methylsulfinyl)-1H-indol-6-yl)(morpholino)methanone

SYNTHESIS EXAMPLE 147

White solid. Yield: 67 mg. Melting range: 272-276° C. HPLC (method 6): $R_t$=6.645 min. Mass spectroscopy: m/z: [M−H]$^+$=462.1

1H NMR (400 MHz, DMSO-d6, δ ppm): 10.99 (bs, 1H), 9.49 (s, 2H), 8.95 (s, 1H), 8.79 (s, 1H), 8.41 (s, 1H), 8.04 (d, J=8.4 Hz, 1H), 7.59-7.34 (m, 2H), 6.84 (s, 1H), 3.72-3.41 (m, 8H), 3.08 (s, 3H).

SYNTHESIS EXAMPLE 148

(1-(5-(1-Methyl-1H-pyrazol-4-yl)pyrimidin-2-yl)-3-(methylsulfinyl)-1H-indol-6-yl)(morpholino)methanone (Compound No. 148)

148a) (1-(5-(1-Methyl-1H-pyrazol-4-yl)pyrimidin-2-yl)-3-(methylthio)-1H-indol-6-yl)(morpholino)methanone Potassium carbonate (254 mg, 1.846 mmol, 2.0 eq), Pd$_2$(dba)$_3$ (84 mg, 0.0923 mmol, 0.1 eq) and tri-tert-butylphosphonium tetrafluoroborate (13 mg, 0.046 mmol, 0.05 eq) were added to a solution of (1-(5-bromopyrimidin-2-yl)-3-(methylthio)-1H-indol-6-yl)(morpholino)methanone (400 mg, 0.923 mmol, 1.0 eq) and (1-methyl-1H-pyrazol-4-yl)boronic acid (140 mg, 1.108 mmol, 1.2 eq) in THF/water (20 mL, 4:1) stirred under an argon atmosphere at 30° C. The reaction mixture was stirred at the same temperature for 2 h and the cooled to ambient temperature and diluted with ethyl acetate (10 mL). The mixture was filtered through a pad of celite, washed with water, dried over sodium sulfate and evaporated. The residue was purified by column chromatography [100-200 mesh, 2% methanol in dichloromethane]. White solid. Yield: 380 mg (95% of theory)

1H NMR (400 MHz, DMSO-d6, δ ppm): 9.13 (s, 2H), 8.84 (s, 1H), 8.33 (d, J=7.8 Hz, 2H), 8.07 (s, 1H), 7.69 (d, J=8.1 Hz, 1H), 7.36-7.34 (m, 1H), 3.92 (s, 3H), 3.80-3.60 (m, 8H), 2.53 (s, 3H).

148b) (1-(5-(1-Methyl-1H-pyrazol-4-yl)pyrimidin-2-yl)-3-(methylsulfinyl)-1H-indol-6-yl)(morpholino)methanone The compound obtained in 148a) (380 mg, 0.921 mmol, 1.0 eq) was oxidized with m-chloroperoxybenzoic acid in analogy to the instructions from 141c). White solid. Yield:

150 mg (36% of theory). Melting range: 208-212° C. HPLC (method 6): $R_t$=7.51 min. Mass spectroscopy: m/z: [M+H]$^+$=451.2.

1H NMR (400 MHz, DMSO-d6, δ ppm): 9.19 (s, 2H), 8.89 (s, 1H), 8.74 (s, 1H), 8.38 (s, 1H), 8.11 (s, 1H), 8.02 (d, J=8.1 Hz, 1H), 7.41 (dd, J=8.1, 1.5 Hz, 1H), 3.92 (s, 3H), 3.80-3.60 (m, 8H), 3.07 (s, 3H).

The compound nos. 149 and 150 were obtained analogously to synthesis example 148:

Compound No. 149: (1-(5-(3-Hydroxyphenyl)pyrimidin-2-yl)-3-(methylsulfinyl)-1H-indol-6-yl)(morpholino)methanone

SYNTHESIS EXAMPLE 149

Pale brown solid. Yield: 100 mg (48% of theory for the last step). Melting range: 249-253° C. HPLC (method 6): $R_t$=8.16 min. Mass spectroscopy: m/z: [M−H]$^+$=461.1

1H NMR (400 MHz, DMSO-d6, δ ppm): 9.72 (s, 1H), 9.22 (s, 2H), 8.94 (s, 1H), 8.77 (s, 1H), 8.03 (d, J=8.4, 1H), 7.45-7.32 (m, 2H), 7.29-7.26 (m, 1H), 7.22-7.20 (m, 1H), 6.91-6.88 (m, 1H), 3.71-3.40 (m, 8H), 3.08 (s, 3H).

EXAMPLE 150

(1-(5-(3-Fluoropyridin-4-yl)pyrimidin-2-yl)-3-(methylsulfinyl)-1H-indol-6-yl)(morpholino)methanone

SYNTHESIS EXAMPLE 150

Different to the instructions from procedure 141c), the oxidation step with m-chloroperoxybenzoic acid as oxidizing reagent was carried out at −30° C. (30 min). White solid. Yield: 140 mg (31% of theory for the last step). Melting range: 241-244° C. HPLC (method 6): $R_t$=7.77 min. Mass spectroscopy: m/z: [M+H]$^+$=465.9

1H NMR (400 MHz, DMSO-d6, δ ppm): 9.31 (s, 2H), 8.94 (s, 1H), 8.79 (s, 2H), 8.63 (d, J=4.8 Hz, 1H), 8.05 (d, J=8.1 Hz, 1H), 7.93-7.82 (m, 1H), 7.45-7.42 (m, 1H), 3.81-3.41 (m, 8H), 3.08 (s, 3H).

The compounds nos. 151 to 153 were synthesized from 4-(1-(5-bromopyrimidin-2-yl)-3-(methylthio)-1H-indole-6-carbonyl)piperazin-2-one in two steps comprising a Suzuki reaction and an oxidation according to the instructions of procedure 148a) and general procedure 3, respectively.

Compound No. 151: 4-(3-(Methylsulfonyl)-1-(5-(m-tolyl)pyrimidin-2-yl)-1H-indole-6-carbonyl)piperazin-2-one

SYNTHESIS EXAMPLE 151

White solid. Yield: 65 mg (24% of theory over 2 steps). Melting range: 283-287° C. HPLC (method 6): $R_t$=9.55 min. Mass spectroscopy: m/z: [M+H]$^+$=490.1

1H NMR (400 MHz, DMSO-d6, δ ppm): 9.32 (s, 2H), 8.97 (s, 1H), 8.91 (s, 1H), 8.12 (s, 1H), 8.02 (d, J=8.4 Hz, 1H), 7.74-7.72 (m, 1H), 7.68 (d, J=7.6 Hz, 1H), 7.55 (d, J=8.0, 1H), 7.86-7.44 (m, 1H), 7.32 (d, J=7.6 Hz, 1H), 4.31-3.95 (m, 2H), 3.65-3.45 (m, 2H), 3.39 (s, 3H), 3.25 (s, 2H), 2.42 (s, 3H).

Compound No. 152: 4-(1-(5-(2-Fluoro-5-methoxyphenyl)pyrimidin-2-yl)-3-(methylsulfonyl)-1H-indole-6-carbonyl)piperazin-2-one

SYNTHESIS EXAMPLE 152

White solid. Yield: 65 mg. Melting range: 293-295° C. HPLC (method 6): $R_t$=9.28 min. Mass spectroscopy: m/z: [M+H]$^+$=524.3

1H NMR (400 MHz, DMSO-d6, δ ppm): 9.24 (s, 2H), 8.97 (s, 1H), 8.92 (s, 1H), 8.14 (s, 1H), 8.02 (d, J=8.2 Hz, 1H), 7.55 (d, J=8.3 Hz, 1H), 7.42-7.25 (m, 2H), 7.10-7.08 (m, 1H), 4.16-4.02 (m, 2H), 3.84 (s, 3H), 3.60-3.54 (m, 2H), 3.40 (s, 3H), 3.31-3.27 (m, 2H).

Compound No. 153: 4-(1-(5-(3-Methoxyphenyl)pyrimidin-2-yl)-3-(methylsulfonyl)-1H-indole-6-carbonyl)piperazin-2-one

SYNTHESIS EXAMPLE 153

White solid. Yield: 90 mg (28% of theory over 2 steps). Melting range: 270-273° C. HPLC (method 6): $R_t$=9.21 min. Mass spectroscopy: m/z: [M+H]$^+$=506.1

1H NMR (400 MHz, DMSO-d6, δ ppm): 9.35 (s, 2H), 8.98 (s, 1H), 8.91 (s, 1H), 8.09-8.14 (m, 1H), 8.02 (d, J=8.4 Hz, 1H), 7.54 (d, J=8.0 Hz, 1H), 7.51-7.40 (m, 3H), 7.06-7.09 (m, 1H), 4.20-4.02 (m, 2H), 3.87 (s, 3H), 3.90-3.52 (m, 2H), 3.39 (s, 3H), 3.29 (s, 2H).

EXAMPLE 154 and 155

(3-(Methylsulfinyl)-1-(5-(m-tolyl)pyrimidin-2-yl)-1H-indol-6-yl)(morpholino)methanone (faster and slower eluting enantiomer)

Racemic (3-(methylsulfinyl)-1-(5-(m-tolyl)pyrimidin-2-yl)-1H-indol-6-yl)(morpholino)methanone was prepared from methyl 1-(5-bromopyrimidin-2-yl)-3-(methylthio)-1H-indole-6-carboxylate (2.0 g, 5.30 mmol) in analogy to the experimental procedures detailed for synthesis examples 157/158. Yield: 1.2 g (racemate)

HPLC-MS (method 5): $R_t$=2.99 min; m/z [M+H]$^+$=461

The racemate (0.7 g) was separated into its single enantiomers via chiral preparative HPLC (column: YMC-Actus-Chiral Amylose-C IC 250×20 mm, 5 μm; mobile phase: ethanol/diethylamine=100/0.1).

Faster eluting enantiomer (example 154):
Yield: 0.30 g
1H NMR (400 MHz, DMSO-d6, δ ppm): 9.21 (s, 2H), 8.95 (s, 1H), 8.78 (s, 1H), 8.05 (d, 1H, J=8.2 Hz), 7.71 (s, 1H), 7.68 (d, 1H, J=7.6 Hz), 7.47-7.41 (m, 2H), 7.32 (d, 1H, J=7.1 Hz), 3.64 (s, 8H), 3.08 (s, 3H), 2.42 (s, 3H).

Slower eluting enantiomer (example 155):
Yield: 0.18 g
1H NMR (400 MHz, DMSO-d6, δ ppm): 9.29 (s, 2H), 8.95 (s, 1H), 8.78 (s, 1H), 8.05 (d, 1H, J=8.1 Hz), 7.71-7.66 (m, 2H), 7.47-7.41 (m, 2H), 7.32-7.30 (d, 1H, J=7.6 Hz), 3.64 (s, 8H), 3.08 (s, 3H), 2.42 (s, 3H).

EXAMPLE 156

(3-(Methylsulfonyl)-1-(5-(m-tolyl)pyrimidin-2-yl)-1H-indol-6-yl)(morpholino) methanone Prepared from 3-methanesulfinyl-1-(5-m-tolyl-pyrimidin-2-yl)-1H-indol-6-yl]-morpholin-4-yl-methanone (0.25 g, 0.54 mmol) through oxidation with m-chloroperoxybenzoic acid. White solid. Yield: 0.16 g (62% of theory)

HPLC-MS (method 5): $R_t$=3.28 min; m/z [M+H]$^+$=477.1
1H NMR (400 MHz, DMSO-d6, 100° C., δ ppm): 9.26 (s, 2H), 8.94 (s, 1H), 8.9 (s, 1H), 8.03 (d, 1H, J=8.0 Hz), 7.69-7.64 (m, 2H), 7.51-7.44 (m, 2H), 7.33 (d, 1H, J=8.0 Hz), 3.67-3.6 (m, 8H), 3.35 (s, 3H), 2.42 (s, 3H).

EXAMPLE 157 and 158

(1-(5-(3-Methoxyphenyl)pyrimidin-2-yl)-3-(methylsulfinyl)-1H-indol-6-yl)(morpholino)methanone (faster and slower eluting enantiomer)

a) Methyl 1-(5-(3-methoxyphenyl)pyrimidin-2-yl)-3-(methylthio)-1H-indole-6-carboxylate Tetrakis(triphenylphosphine)palladium(0) (0.23 g, 0.20 mmol) and a 2M solution of sodium carbonate (8 mL) were added at room temperature and under an argon atmosphere to methyl 1-(5-bromopyrimidin-2-yl)-3-(methylthio)-1H-indole-6-carboxylate (3.0 g, 7.96 mmol) in DME (50 mL). The addition of 3-methoxy phenyl boronic acid (1.53 g, 9.94 mmol) and ethanol (50 mL) followed 10 min later, and the resulting mixture was heated at 90° C. for 5 h. The reaction mixture was then cooled to room temperature and filtered through a pad of celite. The filtrate was concentrated and the residue was purified by flash column chromatography [silica; ethyl acetate/hexane=3:7]. Yellow solid. Yield: 2.6 g (80% of theory)

HPLC-MS (method 5): $R_t$=2.57 min; m/z [M+H]$^+$=406 b) Methyl 1-(5-(3-methoxyphenyl)pyrimidin-2-yl)-3-(methylsulfinyl)-1H-indole-6-carboxylate m-Chloroperoxybenzoic acid (77%, 1.29 g, 5.77 mmol) in dichloromethane (10 mL) was added at 0° C. to a solution of the product from the aforementioned reaction (2.6 g, 6.41 mmol) in dichloromethane (170 mL) and the reaction mixture was stirred at room temperature for 2 h. Saturated sodium hydrogen carbonate solution was added at 0° C., and the aqueous phase was separated and extracted with dichloromethane (2×50 mL). The combined organic layers were washed with brine, dried over sodium sulfate and concentrated. The remnant was purified by flash column chromatography [silica; dichloromethane with 2.5% methanol]. Yellow solid. Yield: 2.0 g (74% of theory)

HPLC-MS (method 5): $R_t$=3.25 min; m/z [M+H]$^+$=422 c) 1-(5-(3-Methoxyphenyl)pyrimidin-2-yl)-3-(methylsulfinyl)-1H-indole-6-carboxylic acid Lithium hydroxide monohydrate (0.59 g, 14.25 mmol) was added at room temperature to a solution of the sulfoxide b) (2.0 g, 4.75 mmol) in THF/water (1:1, 40 mL) and the reaction mixture was stirred at this temperature for 18 h. The mixture was concentrated, then diluted with water (20 mL) and washed with ethyl acetate (2×30 mL). The aqueous phase was acidified with sodium hydrogen sulfate to a pH value of 2 and extracted with THF (3×30 mL). The combined organic layers were dried over sodium sulfate and the solvent was removed under vacuum. Yellow solid. Yield: 1.7 g (88% of theory)

HPLC-MS (method 5): $R_t$=2.46 min; m/z [M+H]$^+$=408 d) (1-(5-(3-Methoxyphenyl)pyrimidin-2-yl)-3-(methylsulfinyl)-1H-indol-6-yl)(morpholino)methanone HATU (2.23 g, 5.89 mmol), diisopropylethylamine (3.25 mL, 19.64 mmol) and morpholine (0.5 mL, 5.89 mmol) were added at 0° C. to a solution the carboxylic acid obtained in the above mentioned reaction (2.0, 4.91 mmol) in dry dichloromethane (30 mL). The reaction mixture was stirred at room temperature for 16 h and then diluted with dichloromethane (50 mL). The mixture was successively washed with saturated ammonium chloride solution, saturated sodium hydrogen carbonate solution and brine. The combined organic layers were dried over sodium sulfate, the solvent was distilled off, and the residue was purified by flash column chromatography [silica, dichloromethane with 2% methanol], followed by trituration with ether/hexane (1:2). Yield: 1.4 g (60% of theory, racemate)

HPLC-MS (method 5): $R_t$=2.88 min; m/z [M+H]$^+$=477

The single enantiomers were derived from the racemate (0.7 g) through chiral preparative HPLC (column: Chiralpak IC, 250×20 mm, 5 μm; mobile phase: dichloromethane/isopropyl alcohol/diethylamine=90/10/0.1)

Slower eluting enantiomer (example 157):
Yield: 0.24 g
1H NMR (400 MHz, DMSO-d6, δ ppm): 9.31 (s, 2H), 8.95 (s, 1H), 8.77 (s, 1H), 8.05 (d, 1H, J=8.0 Hz), 7.48-7.41 (m, 4H), 7.07 (d, 1H, J=7.2 Hz), 3.87 (s, 3H), 3.64 (s, 8H), 3.08 (s, 3H).

Faster eluting enantiomer (example 158):
Yield: 0.25 g
1H NMR (400 MHz, DMSO-d6, δ ppm): 9.31 (s, 2H), 8.94 (s, 1H), 8.77 (s, 1H), 8.05 (d, 1H, J=8.0 Hz), 7.48-7.41 (m, 4H), 7.07 (d, 1H, J=7.6 Hz), 3.87 (s, 3H), 3.64 (s, 8H), 3.08 (s, 3H).

EXAMPLE 159

(1-(5-(3-Methoxyphenyl)pyrimidin-2-yl)-3-(methylsulfonyl)-1H-indol-6-yl)(morpholino)methanone Prepared from methyl 1-(5-(3-methoxyphenyl)pyrimidin-2-yl)-3-(methylthio)-1H-indole-6-carboxylate in three chemical steps comprising an oxidation with m-chloroperoxybenzoic acid, a saponification of the methyl ester with lithium hydroxide and an amide coupling with HATU as reagent. White solid. Yield: 0.10 g (58% of theory)

HPLC-MS (method 4): $R_t$=3.12 min; m/z [M+H]$^+$=493.0
1H NMR (400 MHz, DMSO-d6, 100° C., δ ppm): 9.29 (s, 2H), 8.94 (s, 1H), 8.9 (s, 1H), 8.03 (d, 1H, J=8.0 Hz), 7.51-7.43 (m, 4H), 7.09 (d, 1H, J=8.0 Hz), 3.90 (s, 3H), 3.67-3.58 (m, 8H), 3.35 (s, 3H).

EXAMPLE 160 and 161

(1-(5-(2-Fluoro-5-methoxyphenyl)pyrimidin-2-yl)-3-(methylsulfinyl)-1H-indol-6-yl)(morpholino)methanone (faster and slower eluting enantiomer)

Racemic (1-(5-(2-fluoro-5-methoxyphenyl)pyrimidin-2-yl)-3-(methyl sulfinyl)-1H-indol-6-yl)(morpholino)methanone was prepared in four chemical steps from methyl 1-(5-bromopyrimidin-2-yl)-3-(methylthio)-1H-indole-6-carboxylate (3.0 g, 7.98 mmol) in analogy to the procedures of synthesis examples 157/158. White solid. Yield: 1.0 g (racemate)

HPLC-MS (method 5): $R_t$=2.99 min; m/z [M+H]$^+$=495.2

The single enantiomers were obtained from the racemate (0.6 g) via chiral preparative HPLC (column: Chiralpak IC, 250×20 mm, μm; mobile phase: dichloromethane/isopropyl alcohol/diethylamine=90/10/0.1).

Slower eluting enantiomer (example 160):
Yield: 0.22 g
1H NMR (400 MHz, DMSO-d6, δ ppm): 9.20 (s, 2H), 8.94 (s, 1H), 8.78 (s, 1H), 8.06 (d, 1H, J=8.0 Hz), 7.44-7.41 (d, 1H, J=8.0 Hz), 7.36 (s, 1H), 7.34-7.32 (m, 1H), 7.09 (m, 1H), 3.84 (s, 3H), 3.63 (s, 8H), 3.08 (s, 3H)

Faster eluting enantiomer (example 161):
Yield: 0.18 g
1H NMR (400 MHz, DMSO-d6, δ ppm): 9.20 (s, 2H), 8.94 (s, 1H), 8.78 (s, 1H), 8.06 (d, 1H, J=8.0 Hz), 7.44-7.32 (m, 3H), 7.09-7.07 (m, 1H), 3.84 (s, 3H), 3.63 (s, 8H), 3.08 (s, 3H).

EXAMPLE 162

(1-(5-(2-Fluoro-5-methoxyphenyl)pyrimidin-2-yl)-3-(methylsulfonyl)-1H-indol-6-yl)(morpholino)methanone Prepared from methyl 1-(5-(2-fluoro-5-methoxyphenyl)pyrimidin-2-yl)-3-(methylthio)-1H-indole-6-carboxylate in an analogous manner as synthesis example 159. Yield: 0.11 g
HPLC-MS (method 5): $R_t$=3.18 min; m/z [M+H]$^+$=511.2
1H NMR (400 MHz, DMSO-d6, 100° C., δ ppm): 9.19 (s, 2H), 8.93 (d, 2H, J=8.0 Hz), 8.78 (s, 1H), 8.03 (d, 1H, J=8.0 Hz), 7.51 (d, 1H, J=8.0 Hz), 7.32 (d, 2H, J=12.0 Hz), 7.10 (d, 1H, J=8.0 Hz), 3.87 (s, 3H), 3.67-3.58 (m, 8H), 3.35 (s, 3H).

EXAMPLE 163 and 164

(3-(Methylsulfinyl)-1-(5-phenylpyrimidin-2-yl)-1H-indol-6-yl)(morpholino)methanone (slower and faster eluting enantiomer)

a) (1-(5-Bromopyrimidin-2-yl)-3-(methylsulfinyl)-1H-indol-6-yl)(morpholino)methanone m-Chloroperoxybenzoic acid (77%, 2.10 g, 9.42 mmol) in dichloromethane (20 mL) was added at 0° C. to a solution of (1-(5-bromopyrimidin-2-yl)-3-(methylthio)-1H-indol-6-yl)(morpholino) methanone (4.8 g, 11.08 mmol) in dry dichloromethane (300 mL). The mixture was stirred at room temperature for 3 h and then poured onto saturated sodium sulfite solution. The organic layer was separated after stirring for 15 min and washed with saturated sodium hydrogen carbonate solution and brine. The organic phase was dried over sodium sulfate and concentrated and the remnant was purified by flash column chromatography [dichloromethane with 2.5% methanol]. White solid. Yield: 3.2 g
HPLC-MS (method 4): $R_t$=2.71 min; m/z [M+H]$^+$=448.8/450.8 b) (3-(Methylsulfinyl)-1-(5-phenylpyrimidin-2-yl)-1H-indol-6-yl)(morpholino)methanone Tetrakis(triphenylphosphine)palladium(0) (66 mg, 0.057 mmol) was added under an argon atmosphere to a solution of the pyrimidyl bromide obtained in the preceding conversion a) (1.0 g, 2.29 mmol) in DME (20 mL) and 2M sodium carbonate solution (2.3 mL). Phenyl boronic acid (0.35 g, 2.88 mmol) and ethanol (20 mL) were added and the resulting mixture was heated at 90° C. for 3 h. The reaction mixture was then filtered through a pad of celite bed and the filter was washed with dichloromethane (2×50 mL). The filtrate was concentrated and the residue was purified by flash column chromatography [silica; dichloromethane with 2% methanol]. White solid. Yield: 0.8 g (78% of theory, racemate)

HPLC-MS (method 5): $R_t$=2.98 min; m/z [M+H]$^+$=447.2
The racemic compound (0.8 g) was submitted to chiral preparative HPLC (column: Chiralpak IA, 250×20 mm, 5 µm; mobile phase: hexane/ethyl acetate/ethanol/diethylamine=50/25/25/0.1) in order to obtain its single enantiomers.

Slower eluting enantiomer (example 163):
Yield: 0.22 g
1H NMR (400 MHz, DMSO-d6, δ ppm): 9.31 (s, 2H), 8.95 (s, 1H), 8.78 (s, 1H), 8.05 (d, 1H, J=8.0 Hz), 7.9-7.88 (m, 2H), 7.59-7.41 (m, 4H), 3.64 (bs, 8H), 3.08 (s, 3H).

Faster eluting enantiomer (example 164):
Yield: 0.28 g
1H NMR (400 MHz, DMSO-d6, δ ppm): 9.31 (s, 2H), 8.95 (s, 1H), 8.78 (s, 1H), 8.05 (bs, 1H), 7.88 (bs, 2H), 7.57-7.41 (m, 4H), 3.64 (bs, 8H), 3.08 (s, 3H).

EXAMPLE 165 and 166

(1-(5-(2-Fluorophenyl)pyrimidin-2-yl)-3-(methylsulfinyl)-1H-indol-6-yl)(morpholino)methanone (faster and slower eluting enantiomer)

800 mg of the racemate were separated into the single enantiomers via SFC using a chiral HPLC column. For the determination of the enantiomeric purity the following analytical method was used: column: Chiracel OJ-H 4.6×250 mm, 5 µm; injection volume=6 µL; column temperature: 25° C.; co-solvent: methanol with 0.5% diethylamine; amount of co-solvent: 20%; flow rate: 3 g/min; pressure: 100 bar.

Faster eluting enantiomer (example 165):
White solid. Yield: 304 mg. Melting range: 219-222° C.
Mass spectroscopy: m/z: [M+H]$^+$=464.9
Enantiomeric excess determined by analytical SFC: 99.9% ($R_t$=6.68 min; detection at 314 nm)
1H NMR (400 MHz, DMSO-d6, δ ppm): 9.20 (s, 2H), 8.95 (s, 1H), 8.79 (s, 1H), 8.05 (d, J=8.0 Hz, 1H), 7.83-7.70 (m, 1H), 7.59-7.54 (m, 1H), 7.50-7.35 (m, 2H), 3.85-3.43 (m, 8H), 3.08 (s, 3H).

Slower eluting enantiomer (example 166):
White solid. Yield: 337 mg. Melting range: 217-220° C.
Mass spectroscopy: m/z: [M+H]$^+$=465.0
Enantiomeric excess determined by analytical SFC: 99.7% ($R_t$=7.67 min; detection at 314 nm)
1H NMR (400 MHz, DMSO-d6, δ ppm): 9.20 (s, 2H), 8.95 (s, 1H), 8.79 (s, 1H), 8.05 (d, J=8.0 Hz, 1H), 7.83-7.70 (m, 1H), 7.57-7.54 (m, 1H), 7.49-7.36 (m, 3H), 3.81-3.41 (m, 8H), 3.08 (s, 3H).

EXAMPLE 167

(R)-(3-Aminopyrrolidin-1-yl)(3-(methylsulfonyl)-1-(5-(m-tolyl)pyrimidin-2-yl)-1H-indol-6-yl)methanone The compound was obtained in analogy to examples 222 and 227. White solid. Yield: 72 mg
HPLC-MS (method 5): $R_t$=2.90 min; m/z [M+H]$^+$=476.3
1H NMR (400 MHz, DMSO-d6, 100° C., δ ppm): 9.28 (s, 2H), 9.02 (s, 1H), 8.90 (s, 1H), 8.00 (d, J=8.0 Hz, 1H), 7.77-7.65 (m, 2H), 7.59 (d, J=8.0 Hz, 1H), 7.47-7.44 (m, 1H), 7.33 (d, J=4.0 Hz, 1H), 3.67 (bs, 2H), 3.53 (bs, 2H), 3.36 (s, 3H), 3.20 (bs, 1H), 2.44 (s, 3H), 2.02 (bs, 1H), 1.71-1.66 (m, 3H).

EXAMPLE 168

1-(5-(2-Fluorophenyl)pyrimidin-2-yl)-N-(2-hydroxypropyl)-N-methyl-3-(methylsulfinyl)-1H-indole-6-carboxamide HATU coupling of 1-(5-(2-fluorophenyl)pyrimidin-2-yl)-3-(methylsulfinyl)-1H-indole-6-carboxylic acid with 1-(methylamino)propan-2-ol. White solid. Yield: 0.16 g HPLC-MS (method 5): $R_t$=2.77 min; m/z [M+H]$^+$=467.2

1H NMR (400 MHz, DMSO-d6, 100° C., δ ppm): 9.13 (s, 2H), 8.9 (s, 1H), 8.73 (s, 1H), 7.99 (d, 1H, J=8.0 Hz), 7.76 (t, 1H, J=8.0 Hz), 7.58-7.54 (m, 1H), 7.42-7.37 (m, 3H), 4.44 (bs, 1H), 4.0 (bs, 1H), 3.39-3.38 (m, 2H), 3.07 (s, 6H), 1.07 (d, 3H, J=4.0 Hz).

EXAMPLE 169

(1-(5-(2-Fluorophenyl)pyrimidin-2-yl)-3-(methylsulfinyl)-1H-indol-6-yl)(3-((methylamino)methyl)azetidin-1-yl)methanone Coupling of 1-(5-(2-fluorophenyl)pyrimidin-2-yl)-3-(methylsulfinyl)-1H-indole-6-carboxylic acid with tert-butyl 3-((methylamino)methyl)azetidine-1-carboxylate under use of T3P as reagent followed by a TFA-catalyzed removal of the protection group.

HPLC-MS: m/z [M+H]$^+$=478.1

EXAMPLE 170

1-(5-(2-Fluorophenyl)pyrimidin-2-yl)-N-(1-(hydroxymethyl)cyclopropyl)-N-methyl-3-(methylsulfinyl)-1H-indole-6-carboxamide Prepared from 1-(5-(2-fluorophenyl)pyrimidin-2-yl)-3-(methylsulfinyl)-1H-indole-6-carboxylic acid and (1-(methylamino)cyclopropyl)methanol hydrochloride under use of HATU as reagent. White solid. Yield: 42 mg HPLC-MS (method 5): $R_t$=2.83 min; m/z [M+H]$^+$=479.2

1H NMR (400 MHz, DMSO-d6, 100° C., δ ppm): 9.14 (s, 2H), 8.95 (s, 1H), 8.73 (s, 1H), 7.97 (d, 1H, J=8.0 Hz), 7.76 (t, 1H, J=7.6 Hz), 7.57-7.52 (m, 1H), 7.46-7.38 (m, 3H), 4.6 (t, 1H, J=4.0 Hz), 3.67 (d, 2H, J=5.6 Hz), 3.07 (s, 6H), 0.76 (bs, 4H).

EXAMPLE 171

1-(5-(2-Fluorophenyl)pyrimidin-2-yl)-N-(2-hydroxy-2-methylpropyl)-N-methyl-3-(methylsulfinyl)-1H-indole-6-carboxamide HATU coupling of 1-(5-(2-fluorophenyl)pyrimidin-2-yl)-3-(methylsulfinyl)-1H-indole-6-carboxylic acid with 2-methyl-1-(methylamino)propan-2-ol. White solid. Yield: 110 mg HPLC-MS (method 5): $R_t$=2.81 min; m/z [M+H]$^+$=481.3

1H NMR (400 MHz, DMSO-d6, 100° C., δ ppm): 9.14 (s, 2H), 8.89 (s, 1H), 8.73 (s, 1H), 8 (d, 1H, J=8.0 Hz), 7.76 (t, 1H, J=8.0 Hz), 7.58-7.52 (m, 1H), 7.42-7.38 (m, 3H), 4.27 (s, 1H), 3.51 (s, 2H), 3.12 (s, 3H), 3.07 (s, 3H), 1.18 (s, 6H).

EXAMPLE 172

(1-(5-(2-Fluorophenyl)pyrimidin-2-yl)-3-(methylsulfinyl)-1H-indol-6-yl)((S)-3-methoxypyrrolidin-1-yl)methanone Amide coupling of 1-(5-(2-fluorophenyl)pyrimidin-2-yl)-3-(methylsulfinyl)-1H-indole-6-carboxylic acid with (S)-3-methoxypyrrolidine utilizing HATU as coupling reagent. White solid. Yield: 100 mg (85% of theory)

Melting range: 164-166° C.

HPLC-MS (method 6): $R_t$=9.34 min; m/z [M+H]$^+$=479.2

1H NMR (400 MHz, DMSO-d6, δ ppm): 9.19 (s, 2H), 9.02 (s, 1H), 8.79 (s, 1H), 8.03 (d, J=8.1 Hz, 1H), 7.84-7.74 (m, 1H), 7.58-7.50 (m, 2H), 7.49-7.37 (m, 2H), 4.05-3.94 (m, 1H), 3.71-3.35 (m, 4H), 3.29 (s, 1H), 3.16 (s, 2H), 3.09 (s, 3H), 2.08-1.95 (m, 2H).

EXAMPLE 173

2-(1-(5-(2-Fluorophenyl)pyrimidin-2-yl)-N-methyl-3-(methylsulfinyl)-1H-indole-6-carboxamido)acetic acid Lithium hydroxide monohydrate (0.076 g, 1.82 mmol) was added to an ice-cooled suspension of synthesis example 177 (0.35 g, 0.73 mmol) in THF/water (1:1, 20 mL) and the resulting mixture was stirred at room temperature for 4 h. The solvent was evaporated and the residue was dissolved in water (20 mL) and washed with ethyl acetate (2×20 mL). The aqueous phase was then acidified with sodium hydrogen sulfate and extracted with dichloromethane (3×50 mL). The combined organic layers were dried over sodium sulfate and evaporated. The raw product was finally washed with dichloromethane/hexane (3×30 mL). White solid. Yield: 0.30 g (88% of theory)

HPLC-MS (method 5): $R_t$=2.3 min; m/z [M+H]$^+$=467.2

1H NMR (400 MHz, DMSO-d6, 100° C., δ ppm): 12.3 (bs, 1H), 9.14 (s, 2H), 8.93 (s, 1H), 8.74 (s, 1H), 8.01 (d, 1H, J=8.0 Hz), 7.76 (t, 1H, J=8.0 Hz), 7.56-7.53 (m, 1H), 7.42-7.37 (m, 3H), 4.14 (s, 2H), 3.06 (s, 6H).

EXAMPLE 174

N-(2-Amino-2-oxoethyl)-1-(5-(2-fluorophenyl)pyrimidin-2-yl)-N-methyl-3-(methylsulfinyl)-1H-indole-6-carboxamide EDCxHCl (0.123 g, 0.64 mmol), diisopropylethylamine (0.22 ml, 1.28 mmol) and HOBt ammonium salt (0.098 g, 0.64 mmol) were added to an ice cooled suspension of synthesis example 173 (0.2 g, 0.43 mmol) in DMF (2.5 mL). The resulting mixture was stirred at room temperature for 16 h, then poured onto cold water and filtered. The precipitate was dissolved in dichloromethane/methanol (95:5), dried over sodium sulfate and evaporated to dryness. The remnant was purified by column chromatography [100-200 mesh silica; dichloromethane with 4% methanol]. White solid. Yield: 0.10 g (51% of theory)

HPLC-MS (method 5): $R_t$=2.61 min; m/z [M+H]$^+$=466.4

1H NMR (400 MHz, DMSO-d6, 100° C., δ ppm): 9.14 (s, 2H), 8.95 (s, 1H), 8.74 (s, 1H), 7.99 (d, 1H, J=8.0 Hz), 7.79-7.74 (m, 1H), 7.58-7.53 (m, 1H), 7.45-7.37 (m, 3H), 7.6 (bs, 2H), 4.01 (s, 2H), 3.07 (s, 3H), 3.04 (s, 3H).

EXAMPLE 175

2,5-Diazabicyclo[2.2.1]heptan-2-yl(1-(5-(2-fluorophenyl)pyrimidin-2-yl)-3-(methylsulfinyl)-1H-indol-6-yl)methanone Prepared from 1-(5-(2-fluorophenyl)pyrimidin-2-yl)-3-(methylsulfinyl)-1H-indole-6-carboxylic acid and tert-butyl 2,5-diazabicyclo[2.2.1]heptane-2-carboxylate in two steps comprising a T3P coupling and a TFA-catalyzed removal of the Boc protecting group. Light yellow solid.
HPLC-MS: m/z [M+H]$^+$=476.1

EXAMPLE 176

8-(1-(5-(2-Fluorophenyl)pyrimidin-2-yl)-3-(methylsulfinyl)-1H-indole-6-carbonyl)-2,8-diazaspiro[4.5]decan-1-one The target compound was prepared in an analogous manner as example 178. Light yellow solid.
HPLC-MS: m/z [M+H]$^+$=532.1

EXAMPLE 177

Methyl 2-(1-(5-(2-fluorophenyl)pyrimidin-2-yl)-N-methyl-3-(methylsulfinyl)-1H-indole-6-carboxamido)acetate Prepared from 1-(5-(2-fluorophenyl)pyrimidin-2-yl)-3-(methylsulfinyl)-1H-indole-6-carboxylic acid in analogy to the procedure for example 52). White solid. Yield: 0.475 g
HPLC-MS (method 5): R$_t$=3.03 min; m/z [M+H]$^+$=481.0
1H NMR (400 MHz, DMSO-d6, 100° C., δ ppm): 9.14 (s, 2H), 8.91 (s, 1H), 8.75 (s, 1H), 8.02 (d, 1H, J=8.0 Hz), 7.76 (t, 1H, J=8.0 Hz), 7.56-7.53 (m, 1H), 7.4-7.39 (m, 3H), 4.24 (s, 2H), 3.72 (s, 3H), 3.07 (s, 6H).

EXAMPLE 178

(1-(5-(2-Fluorophenyl)pyrimidin-2-yl)-3-(methylsulfinyl)-1H-indol-6-yl)((S)-3-methylmorpholino)methanone T3P (50 wt % solution in ethyl acetate, 179 μl, 0.304 mmol) was added to a solution of (S)-3-methylmorpholine (46 mg, 0.456 mmol) and 1-(5-(2-fluorophenyl)pyrimidin-2-yl)-3-(methylsulfinyl)-1H-indole-6-carboxylic acid (60 mg, 0.152 mmol) in dichloromethane (3 mL) at room temperature and the mixture was stirred overnight. 1 M sodium carbonate solution (20 mL) was poured into the reaction mixture and stirring was continued for 1 h. The mixture was extracted with dichloromethane (3×) and the combined organic layers were dried over magnesium sulfate and concentrated. The residue was purified by flash chromatography [dichloromethane with 0-5% ethanol]. White foam. Yield: 68 mg (93% of theory).
HPLC-MS: m/z [M+H]$^+$=479.1

EXAMPLE 179

(1-(5-(2-Fluorophenyl)pyrimidin-2-yl)-3-(methylsulfinyl)-1H-indol-6-yl)((R)-3-methylmorpholino)methanone Synthesized in an analogous manner as example 178. White foam. Yield: 61 mg (84% of theory).
HPLC-MS: m/z [M+H]$^+$=479.1

EXAMPLE 180

(1-(5-(6-Methylpyridin-2-yl)pyrimidin-2-yl)-3-(methylsulfinyl)-1H-indol-6-yl)(morpholino)methanone Synthesis in analogy to example 50. White solid. Yield: 48 mg
HPLC-MS (method 5): R$_t$=2.78 min; m/z [M+H]$^+$=462.2
1H NMR (400 MHz, DMSO-d6, 100° C., δ ppm): 9.52 (bs, 2H), 8.95 (s, 1H), 8.75 (s, 1H), 8.02 (d, 1H, J=8.0 Hz), 7.93 (d, 1H, J=8.0 Hz), 7.87 (t, 1H, J=8.0 Hz), 7.43 (d, 1H, J=8.0 Hz), 7.34 (d, 1H, J=8.0 Hz) 3.67 (bs, 4H), 3.59 (bs, 4H), 3.07 (s, 3H), 2.67 (s, 3H).

EXAMPLE 181

2-(2-(3-(Methylsulfinyl)-6-(morpholine-4-carbonyl)-1H-indol-1-yl)pyrimidin-5-yl)isonicotinonitrile Synthesis in analogy to example 50. Grey solid. Yield: 50 mg
HPLC-MS (method 5): R$_t$=2.7 min; m/z [M+H]$^+$=473.2
1H NMR (400 MHz, DMSO-d6, 100° C., δ ppm): 9.60 (bs, 2H), 8.99 (d, 1H, J=4.0 Hz), 8.95 (s, 1H), 8.76 (s, 1H), 8.60 (s, 1H), 8.04 (d, 1H, J=8.0 Hz), 7.87 (s, 1H), 7.44 (d, 1H, J=8.0 Hz), 3.67 (bs, 4H), 3.59 (bs, 4H), 3.08 (s, 3H).

EXAMPLE 182

(1-(5-(4-Fluoropyridin-2-yl)pyrimidin-2-yl)-3-(methylsulfinyl)-1H-indol-6-yl)(morpholino)methanone Synthesis in analogy to example 50. Light yellow solid. Yield: 40 mg
HPLC-MS (method 7): R$_t$=6.29 min; m/z [M+H]$^+$=466
1H NMR (400 MHz, DMSO-d6, 100° C., δ ppm): 9.57 (bs, 2H), 8.95 (s, 1H), 8.81 (t, 2H, J=8.0 Hz), 8.08 (d, 1H, J=8.0 Hz), 8.02 (d, 1H, J=8.0 Hz), 7.44 (d, 1H, J=8.0 Hz), 7.38-7.35 (m, 1H), 3.68 (s, 4H), 3.60 (s, 4H), 3.07 (s, 3H).

EXAMPLE 183

6-(2-(3-(Methylsulfinyl)-6-(morpholine-4-carbonyl)-1H-indol-1-yl)pyrimidin-5-yl)picolinonitrile White solid. Yield: 60 mg
HPLC-MS (method 5): R$_t$=2.69 min; m/z [M+H]$^+$=473.1
1H NMR (400 MHz, DMSO-d6, 100° C., δ ppm): 9.56 (bs, 2H), 8.95 (s, 1H), 8.76 (s, 1H), 8.46 (d, 1H, J=8.0 Hz), 8.23 (t, 1H, J=8.0 Hz), 8.05-8.03 (m, 2H), 7.44 (d, 1H, J=8.0 Hz), 3.68 (bs, 4H), 3.60 (bs, 4H), 3.08 (s, 3H).

EXAMPLE 184

(1-(5-(2-Fluorophenyl)pyrimidin-2-yl)-3-(2-hydroxypropan-2-yl)-1H-indol-6-yl)(morpholino)methanone 184a) 1-(1-(5-(2-Fluorophenyl)pyrimidin-2-yl)-6-(morpholine-4-carbonyl)-1H-indol-3-yl) ethanone Dess-Martin periodinane reagent (437 mg, 1.008 mmol, 1.5 eq) was added at 0° C. to a stirred solution of (1-(5-(2-fluorophenyl)pyrimidin-2-yl)-3-(1-hydroxyethyl)-1H-indol-6-yl)(morpholino)methanone (synthesis example 28, 300 mg, 0.672 mmol, 1.0 eq) in dichloromethane (10 mL). Stirring was continued for 2 h at room temperature and the reaction mixture was then filtered through a bed of celite. The celite was washed with dichloromethane (10 mL) and the filtrate was dried over anhydrous sodium sulfate and evaporated in vacuo. White solid. Yield: 250 mg (72% of theory).

1H NMR (400 MHz, DMSO-d6, δ ppm): 9.28-9.16 (m, 3H), 8.89 (s, 1H), 8.36 (d, J=8.4 Hz, 1H), 7.86-7.71 (m, 1H), 7.64-7.50 (m, 1H), 7.49-7.31 (m, 3H), 3.81-3.41 (m, 8H), 2.64 (s, 3H).

184b) (1-(5-(2-Fluorophenyl)pyrimidin-2-yl)-3-(2-hydroxypropan-2-yl)-1H-indol-6-yl)(morpholino)methanone Methyl magnesium iodide (3M solution in diethyl ether, 0.14 mL, 0.439 mmol, 1.5 eq) was added at −50° C. to a stirred solution of 184a) (130 mg, 0.292 mmol, 1.0 eq) in dry THF (10 mL). The reaction mixture was stirred for 2 h at −30° C., then quenched with ammonium chloride solution, diluted with water (20 mL) and extracted with ethyl acetate (2×20 mL). The combined organic layers were washed with brine, dried over sodium sulfate, and concentrated. The remnant was purified by preparative TLC using ethyl acetate/pet ether (7:3) as eluent. White solid. Yield: 50 mg (37% of theory).

Melting range: 116-119° C.
HPLC (method 6): $R_t$=10.44 min
Mass spectroscopy: m/z: [M+H]$^+$=461.2
1H NMR (400 MHz, DMSO-d6, δ ppm): 9.11 (s, 2H), 8.88 (s, 1H), 8.22 (s, 1H), 7.97 (d, J=8.1 Hz, 1H), 7.76-7.74 (m, 1H), 7.60-7.46 (m, 1H), 7.47-7.35 (m, 2H), 7.29 (dd, J=8.1, 1.5 Hz, 1H), 5.19 (s, 1H), 3.75-3.41 (m, 8H), 1.63 (s, 6H).

EXAMPLE 185

(1-(5-(6-Fluoropyridin-2-yl)pyrimidin-2-yl)-3-(methylsulfinyl)-1H-indol-6-yl)(morpholino)methanone Synthesis in analogy to example 50. White solid. Yield: 45 mg
HPLC-MS (method 5): $R_t$=2.76 min; m/z [M+H]$^+$=466.1
1H NMR (400 MHz, DMSO-d6, 100° C., δ ppm): 9.51 (bs, 2H), 8.94 (s, 1H), 8.75 (s, 1H), 8.18 (t, 1H, J=8.0 Hz), 8.10 (d, 1H, J=8.0 Hz), 8.04 (d, 1H, J=8.0 Hz), 7.44 (d, 1H, J=8.0 Hz), 7.23 (d, 1H, J=4.0 Hz) 3.68 (bs, 4H), 3.60 (bs, 4H), 3.07 (s, 3H).

EXAMPLE 186

(1-(5-(2-Methylpyridin-4-yl)pyrimidin-2-yl)-3-(methylsulfinyl)-1H-indol-6-yl)(morpholino)methanone Hydrogen peroxide (30%, 0.4 mL, 3.595 mmol, 4.0 eq) was added to a stirred solution of (1-(5-(2-methylpyridin-4-yl)pyrimidin-2-yl)-3-(methylthio)-1H-indol-6-yl)(morpholino)methanone (400 mg, 0.898 mmol, 1.0 eq, synthesized analogously to procedure 1d) in acetic acid (10 mL). The reaction mixture was stirred for 1 h at room temperature and then diluted with dichloromethane (20 mL). The mixture was washed with saturated sodium hydrogen carbonate solution and brine, dried over anhydrous sodium sulfate, and evaporated under vacuum. The remnant was purified by preparative silica gel TLC [dichloromethane with 3% methanol]. White solid. Yield: 250 mg
Melting range: 230-232° C.
HPLC (method 6): $R_t$=7.92 min
Mass spectroscopy: m/z: [M+H]$^+$=462.2
1H NMR (400 MHz, DMSO-d6, δ ppm): 9.37 (s, 2H), 8.91 (s, 1H), 8.74 (s, 1H), 8.56 (d, J=5.2 Hz, 1H), 8.05 (d, J=8.4 Hz, 1H), 7.82 (s, 1H), 7.73 (d, J=5.1 Hz, 1H), 7.40 (d, J=8.0 Hz, 1H), 3.60-3.50 (m, 8H), 3.08 (s, 3H), 2.58 (s, 3H).

The following examples 187, 188, 189, 190, 192, 194, 195, 197 and 198 were synthesized analogously:

EXAMPLE 187

(1-(5-(2-Fluoropyridin-4-yl)pyrimidin-2-yl)-3-(methylsulfinyl)-1H-indol-6-yl)(morpholino)methanone White solid. Yield: 290 mg. Melting range: 285-288° C.
HPLC (method 6): $R_t$=8.39 min
Mass spectroscopy: m/z: [M+H]$^+$=466.1
1H NMR (400 MHz, DMSO-d6, δ ppm): δ 9.49 (s, 2H), 8.95 (s, 1H), 8.79 (s, 1H), 8.43 (d, J=5.3 Hz, 1H), 8.05 (d, J=8.2 Hz, 1H), 7.94 (d, J=5.3 Hz, 1H), 7.82 (s, 1H), 7.43 (d, J=8.0 Hz, 1H), 3.60-3.50 (m, 8H), 3.08 (s, 3H).

EXAMPLE 188

(1-(5-(3-(Hydroxymethyl)phenyl)pyrimidin-2-yl)-3-(methylsulfinyl)-1H-indol-6-yl)(morpholino)methanone White solid. Yield: 159 mg. Melting range: 193-196° C.
HPLC (method 6): $R_t$=8.12 min
Mass spectroscopy: m/z: [M+H]$^+$=477.1
1H NMR (400 MHz, DMSO-d6, δ ppm): 9.28 (s, 2H), 8.95 (s, 1H), 8.78 (s, 1H), 8.04 (d, J=8.4 Hz, 1H), 7.80-7.78 (m, 1H), 7.75 (d, J=7.6 Hz, 1H), 7.53-7.51 (m, 1H), 7.47-7.41 (m, 2H), 5.29 (t, J=5.7 Hz, 1H), 4.62 (d, J=5.6 Hz, 2H), 3.82-3.54 (m, 8H), 3.07 (s, 3H).

EXAMPLE 189

(1-(5-(3-Ethylphenyl)pyrimidin-2-yl)-3-(methylsulfinyl)-1H-indol-6-yl)(morpholino)methanone White solid. Yield: 130 mg. Melting range: 162-165° C.
HPLC (method 6): $R_t$=10.38 min
Mass spectroscopy: m/z: [M+H]$^+$=475.2
1H NMR (400 MHz, DMSO-d6, δ ppm): 9.30 (s, 2H), 8.95 (s, 1H), 8.77 (s, 1H), 8.04 (d, J=8.0 Hz, 1H), 7.80-7.64 (m, 2H), 7.52-7.41 (m, 2H), 7.34 (d, J=7.6 Hz, 1H), 3.84-3.45 (m, 8H), 3.08 (s, 3H), 2.72 (q, J=7.5 Hz, 2H), 1.27 (t, J=7.6 Hz, 3H).

EXAMPLE 190

Methyl 4-(2-(3-(methylsulfinyl)-6-(morpholine-4-carbonyl)-1H-indol-1-yl)pyrimidin-5-yl)benzoate White solid. Yield: 400 mg. Melting range: 256-258° C.
HPLC (method 6): $R_t$=9.23 min
Mass spectroscopy: m/z: [M+H]$^+$=505.2
1H NMR (400 MHz, DMSO-d6, δ ppm): 9.39 (s, 2H), 8.95 (s, 1H), 8.78 (s, 1H), 8.13-8.11 (m, 2H), 8.05-8.03 (m, 3H), 7.42 (d, J=8.0, 1H), 3.90 (s, 3H), 3.71-3.56 (m, 8H), 3.08 (s, 3H).

EXAMPLE 191

4-(2-(3-(Methylsulfinyl)-6-(morpholine-4-carbonyl)-1H-indol-1-yl)pyrimidin-5-yl)benzoic acid The target compound was prepared from methyl 4-(2-(3-(methylthio)-6-(morpholine-4-carbonyl)-1H-indol-1-yl)pyrimidin-5-yl)benzoate (precursor of synthesis example 190) via hydrolysis of the ester (trimethylsilanolate in THF/water) and subsequent oxidation of the thioether (hydrogen peroxide in acetic acid). White solid. Yield: 70 mg. Melting range: 219-223° C.

HPLC (method 6): $R_t$=6.78 min
Mass spectroscopy: m/z: [M−H]⁻=489.2
1H NMR (400 MHz, DMSO-d6, δ ppm): 9.35 (s, 2H), 8.95 (s, 1H), 8.78 (s, 1H), 8.08-8.03 (m, 3H), 7.96 (d, J=8.0, 2H), 7.43 (dd, J=8.0, 1.2 Hz, 1H), 3.80-3.44 (m, 8H), 3.08 (s, 3H).

EXAMPLE 192

Methyl 3-(2-(3-(methylsulfinyl)-6-(morpholine-4-carbonyl)-1H-indol-1-yl)pyrimidin-5-yl)benzoate White solid. Yield: 50 mg. Melting range: 217-220° C.
HPLC (method 6): $R_t$=9.27 min
Mass spectroscopy: m/z: [M+H]⁺=505.2
1H NMR (400 MHz, DMSO-d6, δ ppm): 9.35 (s, 2H), 8.99-8.95 (m, 1H), 8.78 (s, 1H), 8.40 (d, J=1.9 Hz, 1H), 8.16 (d, J=7.9, 1.4 Hz, 1H), 8.08-8.03 (m, 2H), 7.75-7.71 (m, 1H), 7.43 (dd, J=8.3, 1.5 Hz, 1H), 3.92 (s, 3H), 3.82-3.41 (m, 8H), 3.08 (s, 3H).

EXAMPLE 193

3-(2-(3-(Methylsulfinyl)-6-(morpholine-4-carbonyl)-1H-indol-1-yl)pyrimidin-5-yl)benzoic acid Prepared from methyl 3-(2-(3-(methylthio)-6-(morpholine-4-carbonyl)-1H-indol-1-yl)pyrimidin-5-yl)benzoate (precursor of example 192) in two reaction steps comprising an ester hydrolysis with potassium trimethylsilanolate in THF and water and an oxidation of the thioether with hydrogen peroxide in acetic acid. White solid. Yield: 90 mg. Melting range: 230-235° C.

HPLC (method 6): $R_t$=6.94 min
Mass spectroscopy: m/z: [M−H]⁻=489.2
1H NMR (400 MHz, DMSO-d6, δ ppm): 9.29 (s, 2H), 8.94 (s, 1H), 8.77 (s, 1H), 8.33 (s, 1H), 8.05-7.99 (m, 2H), 7.91 (d, J=7.6 Hz, 1H), 7.58-7.53 (m, 1H), 7.42 (dd, J=8.2, 1.5 Hz, 1H), 3.70-3.60 (m, 8H), 3.07 (s, 3H).

EXAMPLE 194

(1-(5-(3-Chlorophenyl)pyrimidin-2-yl)-3-(methylsulfinyl)-1H-indol-6-yl)(morpholino)methanone White solid. Yield: 148 mg. Melting range: 211-213° C.
HPLC (method 6): $R_t$=9.961 min
Mass spectroscopy: m/z: [M+H]⁺=481.1
1H NMR (400 MHz, DMSO-d6, δ ppm): 9.34 (s, 2H), 8.94 (s, 1H), 8.77 (s, 1H), 8.04 (d, J=8.0 Hz, 1H), 8.02-8.01 (m, 1H), 7.88-7.85 (m, 1H), 7.61-7.54 (m, 2H), 7.43 (dd, J=8.3, 1.5 Hz, 1H), 3.89-3.38 (m, 8H), 3.08 (s, 3H).

EXAMPLE 195

5-(2-(3-(Methylsulfinyl)-6-(morpholine-4-carbonyl)-1H-indol-1-yl)pyrimidin-5-yl)thiophene-3-carbonitrile White solid. Yield: 80 mg. Melting range: 253-256° C.
HPLC (method 6): $R_t$=8.83 min
Mass spectroscopy: m/z: [M+H]⁺=478.0
1H NMR (400 MHz, DMSO-d6, δ ppm): 9.32 (s, 2H), 8.91 (s, 1H), 8.75-8.72 (m, 2H), 8.18 (s, 1H), 8.05 (d, J=8.4 Hz, 1H), 7.43 (dd, J=8.0, 1.2 Hz, 1H), 3.85-3.45 (m, 8H), 3.07 (s, 3H).

EXAMPLE 196

5-(2-(3-(Methylsulfinyl)-6-(morpholine-4-carbonyl)-1H-indol-1-yl)pyrimidin-5-yl)thiophene-3-carboxamide Potassium carbonate (90 mg, 0.650 mmol, 1.5 eq) and hydrogen peroxide (30%, 2.0 mL) were added at room temperature to a stirred solution of 5-(2-(3-(methylthio)-6-(morpholine-4-carbonyl)-1H-indol-1-yl)pyrimidin-5-yl) thiophene-3-carbonitrile (precursor of synthesis example 195, 200 mg, 0.433 mmol, 1.0 eq) in DMSO (2 mL). The reaction mixture was stirred at this temperature for 48 h and then diluted with water (10 mL). The precipitating solid was filtered off, washed with water, and dried under vacuum. The remnant was purified by column chromatography [silica gel 100-200 mesh, dichloromethane with 2% methanol].

White solid. Yield: 40 mg. Melting range: 302-305° C.
HPLC (method 6): $R_t$=7.56 min
Mass spectroscopy: m/z: [M+H]⁺=496.1
1H NMR (400 MHz, DMSO-d6, δ ppm): 9.26 (s, 2H), 8.90 (s, 1H), 8.74 (s, 1H), 8.27 (s, 1H), 8.09 (s, 1H), 8.04 (d, J=8.0 Hz, 1H), 7.85 (s, 1H), 7.43 (d, J=8.4 Hz, 1H), 7.34 (s, 1H), 3.71-3.59 (m, 8H), 3.08 (s, 3H).

EXAMPLE 197

5-(2 3-(Methylsulfinyl)-1-(5-(4-methylthiophen-2-yl)pyrimidin-2-yl)-1H-indol-6-yl)(morpholino)methanone White solid. Yield: 195 mg. Melting range: 232-235° C.
HPLC (method 6): $R_t$=9.78 min
Mass spectroscopy: m/z: [M+H]⁺=467.1
1H NMR (400 MHz, DMSO-d6, δ ppm): 9.20 (s, 2H), 8.90 (s, 1H), 8.73 (s, 1H), 8.03 (d, J=8.4 Hz, 1H), 7.61 (s, 1H), 7.42 (d, J=8.4 Hz, 1H), 7.32 (s, 1H), 3.71-3.51 (m, 8H), 3.07 (s, 3H), 2.29 (s, 3H).

EXAMPLE 198

(1-(5-(2-Fluoro-5-methylphenyl)pyrimidin-2-yl)-3-(methylsulfinyl)-1H-indol-6-ethanone White solid. Yield: 45 mg. Melting range: 120-123° C.
HPLC (method 6): $R_t$=9.96 min
Mass spectroscopy: m/z: [M+H]⁺=479.2
1H NMR (400 MHz, DMSO-d6, δ ppm): 9.17 (s, 2H), 8.94 (s, 1H), 8.78 (s, 1H), 8.04 (d, J=8.0 Hz, 1H), 7.58 (d, J=6.8 Hz, 1H), 7.43 (d, J=8.0 Hz, 1H), 7.38-7.25 (m, 2H), 3.81-3.51 (m, 8H), 3.08 (s, 3H), 2.39 (s, 3H).

EXAMPLE 199

6-(2-(3-(Methylsulfinyl)-6-(morpholine-4-carbonyl)-1H-indol-1-yl)pyrimidin-5-yl)nicotinamide (1-(5-Bromopyrimidin-2-yl)-3-(methylthio)-1H-indol-6-yl)(morpholino)methanone was reacted first with bis(pinacolato)diboron and then with 6-bromonicotinamide as described in the protocols 141a) and 141b). A subsequent oxidation with hydrogen peroxide in acetic acid provided the target compound. White solid. Yield: 67 mg. Melting range: 288-290° C.

HPLC (method 6): $R_t$=7.24 min

Mass spectroscopy: m/z: [M+H]$^+$=491.2

1H NMR (400 MHz, DMSO-d6, δ ppm): 9.64 (s, 2H), 9.19 (s, 1H), 8.97 (s, 1H), 8.80 (s, 1H), 8.40 (dd, J=8.3, 2.3 Hz, 1H), 8.30 (d, J=8.4 Hz, 1H), 8.24 (s, 1H), 8.05 (d, J=8.0 Hz, 1H), 7.67 (s, 1H), 7.44 (dd, J=8.1, 1.5 Hz, 1H), 3.71-3.51 (m, 8H), 3.08 (s, 3H).

The following synthesis examples 200 to 212 were prepared in an analogous manner:

EXAMPLE 200

(1-(5-(5-Fluoropyridin-2-yl)pyrimidin-2-yl)-3-(methylsulfinyl)-1H-indol-6-yl)(morpholino)methanone White solid. Yield: 145 mg. Melting range: 244-248° C.

HPLC (method 6): $R_t$=8.78 min

Mass spectroscopy: m/z: [M+H]$^+$=466.1

1H NMR (400 MHz, DMSO-d6, δ ppm): 9.56 (s, 2H), 8.95 (s, 1H), 8.79-8.77 (m, 2H), 8.30-8.27 (m, 1H), 8.05 (d, J=8.4 Hz, 1H), 8.00-7.95 (m, 1H), 7.43 (d, J=8.4 Hz, 1H), 3.82-3.41 (m, 8H), 3.07 (s, 3H).

EXAMPLE 201

(1-(5-(3-Fluoropyridin-2-yl)pyrimidin-2-yl)-3-(methylsulfinyl)-1H-indol-6-yl)(morpholino)methanone White solid. Yield: 110 mg. Melting range: 222-225° C.

HPLC (method 6): $R_t$=8.52 min

Mass spectroscopy: m/z: [M+H]$^+$=466.1

1H NMR (400 MHz, DMSO-d6, δ ppm): 9.44 (s, 2H), 8.95 (s, 1H), 8.80 (s, 1H), 8.66-8.65 (m, 1H), 8.05 (d, J=8.0 Hz, 1H), 8.00-7.95 (m, 1H), 7.64-7.60 (m, 1H), 7.43 (dd, J=8.0, 1.5 Hz, 1H), 3.82-3.41 (m, 8H), 3.08 (s, 3H).

EXAMPLE 202

2-(2-(3-(Methylsulfinyl)-6-(morpholine-4-carbonyl)-1H-indol-1-yl)pyrimidin-5-yl)isonicotinamide White solid. Yield: 260 mg. Melting range: 303-306° C.

HPLC (method 6): $R_t$=7.34 min

Mass spectroscopy: m/z: [M+H]$^+$=491.2

1H NMR (400 MHz, DMSO-d6, δ ppm): 9.62 (s, 2H), 8.96 (s, 1H), 8.90 (d, J=4.8 Hz, 1H), 8.81 (s, 1H), 8.53 (s, 1H), 8.32 (s, 1H), 8.05 (d, J=8.0 Hz, 1H), 7.85-7.83 (m, 2H), 7.44 (dd, J=8.4, 1H), 3.80-3.42 (m, 8H), 3.08 (s, 3H).

EXAMPLE 203

2-(2-(3-(Methylsulfinyl)-6-(morpholine-4-carbonyl)-1H-indol-1-yl)pyrimidin-5-yl)thiazole-4-carbonitrile Pale yellow solid. Yield: 120 mg. Melting range: 273-276° C.

HPLC (method 9): $R_t$=4.13 min

Mass spectroscopy: m/z: [M+H]$^+$=479.0

1H NMR (400 MHz, DMSO-d6, δ ppm): 9.52 (s, 2H), 9.05 (s, 1H), 8.93 (s, 1H), 8.77 (s, 1H), 8.05 (d, J=8.0 Hz, 1H), 7.45 (d, J=8.0 Hz, 1H), 3.75-3.51 (m, 8H), 3.08 (s, 3H).

EXAMPLE 204

2-(2-(3-(Methylsulfinyl)-6-(morpholine-4-carbonyl)-1H-indol-1-yl)pyrimidin-5-yl)thiazole-4-carboxamide The target compound was prepared from 2-(2-(3-(methylthio)-6-(morpholine-4-carbonyl)-1H-indol-1-yl)pyrimidin-5-yl)thiazole-4-carbonitrile (precursor of example 203) analogously to the synthesis protocol for example 196. White solid. Pale yellow solid. Yield: 75 mg. Melting range: 286-288° C.

HPLC (method 6): $R_t$=7.44 min

Mass spectroscopy: m/z: [M+H]$^+$=497.4

1H NMR (400 MHz, DMSO-d6, δ ppm): 9.57 (s, 2H), 8.94 (s, 1H), 8.78 (s, 1H), 8.42 (s, 1H), 8.08-7.97 (m, 2H), 7.73 (s, 1H), 7.44 (dd, J=8.1, 1.5 Hz, 1H), 3.75-3.48 (m, 8H), 3.08 (s, 3H).

EXAMPLE 205

(3-(Methylsulfinyl)-1-(5-(4-methylthiazol-2-yl)pyrimidin-2-yl)-1H-indol-6-yl)(morpholino)methanone White solid. Yield: 170 mg. Melting range: 247-249° C.

HPLC (method 8): $R_t$=4.58 min

Mass spectroscopy: m/z: [M+H]$^+$=468.4

1H NMR (400 MHz, DMSO-d6, δ ppm): δ 9.41 (s, 2H), 8.2 (s, 1H), 8.76 (s, 1H), 8.04 (d, J=8.4 Hz, 1H), 7.51 (s, 1H), 7.43 (dd, J=8.5, 1.4 Hz, 1H), 3.75-3.48 (m, 8H), 3.07 (s, 3H), 2.49 (s, 3H).

EXAMPLE 206

(3-(Methylsulfinyl)-1-(5-(5-methylthiazol-2-yl)pyrimidin-2-yl)-1H-indol-6-yl)(morpholino)methanone White solid. Yield: 120 mg. Melting range: 257-260° C.

HPLC (method 8): $R_t$=4.61 min

Mass spectroscopy: m/z: [M+H]$^+$=468.4

1H NMR (400 MHz, DMSO-d6, δ ppm): 9.38 (s, 2H), 8.92 (s, 1H), 8.75 (s, 1H), 8.04 (d, J=8.4 Hz, 1H), 7.76 (s, 1H), 7.43 (d, J=8.0 Hz, 1H), 3.86-3.55 (m, 8H), 3.07 (s, 3H), 2.56 (s, 3H).

EXAMPLE 207

2-(2-(3-(Methylsulfinyl)-6-(morpholine-4-carbonyl)-1H-indol-1-yl)pyrimidin-5-yl)thiazole-5-carbonitrile Pale yellow solid. Yield: 50 mg. Melting range: 280-283° C.

HPLC (method 8): $R_t$=4.02 min

Mass spectroscopy: m/z: [M+H]$^+$=479.5

1H NMR (400 MHz, DMSO-d6, δ ppm): 9.53 (s, 2H), 8.93 (s, 1H), 8.89 (s, 1H), 8.66 (s, 1H), 8.05 (d, J=8.0 Hz, 1H), 7.45 (d, J=9.2 Hz, 1H), 3.75-3.54 (m, 8H), 3.08 (s, 3H).

EXAMPLE 208

2-(2-(3-(Methylsulfinyl)-6-(morpholine-4-carbonyl)-1H-indol-1-yl)pyrimidin-5-yl)thiazole-5-carboxamide Yield: 110 mg. Melting range: 286-289° C.

HPLC (method 9): $R_t$=3.42 min

Mass spectroscopy: m/z: [M+H]$^+$=497.5

1H NMR (400 MHz, DMSO-d6, δ ppm): 9.48 (s, 2H), 8.93 (s, 1H), 8.76 (s, 1H), 8.56 (s, 1H), 8.28 (s, 1H), 8.05 (d, J=8.0 Hz, 1H), 7.74 (s, 1H), 7.44 (d, J=7.6 Hz, 1H), 3.72-3.57 (m, 8H), 3.08 (s, 3H).

EXAMPLE 209

2-(1-(5-(4-Aminopyridin-2-yl)pyrimidin-2-yl)-3-(methylsulfinyl)-1H-indol-6-yl)(morpholino)methanone White solid. Yield: 75 mg. Melting range: 293-297° C.

HPLC (method 6): $R_t$=7.47 min

Mass spectroscopy: m/z: $[M+H]^+$=463.2

1H NMR (400 MHz, DMSO-d6, δ ppm): 9.39 (s, 2H), 8.94 (s, 1H), 8.78 (s, 1H), 8.16 (d, J=5.6 Hz, 1H), 8.04 (d, J=8.4 Hz, 1H), 7.43 (dd, J=8.0, 1.2 Hz, 1H), 7.14 (d, J=1.6 Hz, 1H), 6.57 (dd, J=5.6, 2.0 Hz, 1H), 6.24 (s, 2H), 3.71-3.51 (m, 8H), 3.07 (s, 3H).

EXAMPLE 210

(1-(5-(4-(Dimethylamino)pyridin-2-yl)pyrimidin-2-yl)-3-(methylsulfinyl)-1H-indol-6-yl)(morpholino)methanone White solid. Yield: 82 mg. Melting range: 213-217° C.

HPLC (method 10): $R_t$=8.43 min

Mass spectroscopy: m/z: $[M+H]^+$=491.3

1H NMR (400 MHz, DMSO-d6, δ ppm): 9.57 (s, 2H), 8.96 (s, 1H), 8.79 (s, 1H), 8.28 (d, J=5.9 Hz, 1H), 8.05 (d, J=8.1 Hz, 1H), 7.43 (dd, J=8.1, 1.5 Hz, 1H), 7.32 (d, J=2.5 Hz, 1H), 6.68 (dd, J=6.0, 2.5 Hz, 1H), 3.81-3.42 (m, 8H), 3.07 (s, 9H).

EXAMPLE 211

(3-(Methylsulfinyl)-1-(5-(thiazol-2-yl)pyrimidin-2-yl)-1H-indol-6-yl)(morpholino)methanone The final oxidation was performed with use of m-chloroperoxybenzoic acid analogously to synthesis protocol 141c). White solid. Yield: 122 mg. Melting range: 235-237° C.

HPLC (method 6): $R_t$=8.24 min

Mass spectroscopy: m/z: $[M+H]^+$=454.1

1H NMR (400 MHz, DMSO-d6, δ ppm): 9.46 (s, 2H), 8.93 (s, 1H), 8.76 (s, 1H), 8.08-8.03 (m, 2H), 7.98 (d, J=3.6 Hz, 1H), 7.44 (dd, J=8.1, 1.5 Hz, 1H), 3.84-3.34 (m, 8H), 3.07 (s, 3H).

EXAMPLE 212

(3-(Methylsulfinyl)-1-(5-(pyridazin-4-yl)pyrimidin-2-yl)-1H-indol-6-yl)(morpholino)methanone White solid. Yield: 85 mg. Melting range: 278-282° C.

HPLC (method 11): $R_t$=7.12 min

Mass spectroscopy: m/z: $[M+H]^+$=449.3

1H NMR (400 MHz, DMSO-d6, δ ppm): 9.85 (s, 1H), 9.54 (s, 2H), 9.40 (d, J=5.2 Hz, 1H), 8.95 (s, 1H), 8.79 (s, 1H), 8.25 (dd, J=5.6, 2.4 Hz, 1H), 8.05 (d, J=8.0 Hz, 1H), 7.45 (dd, J=8.0, 1.2 Hz, 1H), 3.64-3.39 (m, 8H), 3.08 (s, 3H).

EXAMPLES 213 AND 214

4-(1-(5-(2-Fluoro-5-methoxyphenyl)pyrimidin-2-yl)-3-(methylsulfinyl)-1H-indole-6-carbonyl)piperazin-2-one (faster and slower eluting enantiomer)

4-(1-(5-(2-Fluoro-5-methoxyphenyl)pyrimidin-2-yl)-3-(methylsulfinyl)-1H-indole-6-carbonyl)piperazin-2-one Hydrogen peroxide (30%, 5 ml) was added at room temperature to a stirred solution of 4-(1-(5-(2-fluoro-5-methoxyphenyl)pyrimidin-2-yl)-3-(methylthio)-1H-indole-6-carbonyl)piperazin-2-one (1.8 gm, 3.665 mmol, 1.0 eq, precursor of example 152) in acetic acid (20 ml). Stirring was continued for 1 h at this temperature and the solution was then diluted with water (30 mL) and extracted with dichloromethane. The combined organic layers were washed with saturated sodium hydrogen carbonate solution and brine, dried over anhydrous sodium sulfate, and evaporated under vacuum. The residue was purified by column chromatography [silica gel 100-200 mesh, dichloromethane with 4% methanol]. Pale yellow solid. Yield: 1.6 g.

The single enantiomers were obtained from the racemate via SFC utilizing a chiral HPLC column and the enantiomeric excess of the isolated enantiomers was measured with the following analytical method: column: Chiracel OJ-H 4.6× 250 mm, 5 μm; injection volume=10 μL; column temperature: 25° C.; co-solvent: methanol; amount of co-solvent: 45%; flow rate: 3 g/min; pressure: 100 bar.

Faster eluting enantiomer (example 213):

White solid. Yield: 404 mg

HPLC (method 6): $R_t$=8.68 min

Mass spectroscopy: m/z: $[M+H]^+$=508.1

Enantiomeric excess determined by analytical SFC: 99.6% ($R_t$=2.86 min)

1H NMR (400 MHz, DMSO-d6, δ ppm): 9.19 (s, 2H), 8.97 (s, 1H), 8.79 (s, 1H), 8.11 (s, 1H), 8.06 (d, J=8.4 Hz, 1H), 7.46 (dd, J=8.1, 1.5 Hz, 1H), 7.39-7.29 (m, 2H), 7.10-7.07 (m, 1H), 4.22-4.08 (m, 2H), 3.84 (s, 3H), 3.70-3.48 (m, 2H), 3.27 (s, 2H), 3.09 (s, 3H).

Slower eluting enantiomer (example 214):

Pale yellow solid. Yield: 326 mg

HPLC (method 6): $R_t$=8.67 min

Mass spectroscopy: m/z: $[M+H]^+$=508.2

Enantiomeric excess determined by analytical SFC: 99.8% ($R_t$=4.99 min)

1H NMR (400 MHz, DMSO-d6, δ ppm): 9.19 (d, J=1.2 Hz, 2H), 8.97 (s, 1H), 8.79 (s, 1H), 8.11 (s, 1H), 8.06 (d, J=8.4 Hz, 1H), 7.46 (dd, J=8.1, 1.5 Hz, 1H), 7.39-7.29 (m, 2H), 7.15-7.03 (m, 1H), 4.22-4.08 (m, 2H), 3.84 (s, 3H), 3.70-3.48 (m, 2H), 3.27 (s, 2H), 3.09 (s, 3H).

EXAMPLES 215 AND 216

4-(3-(Methylsulfinyl)-1-(5-(m-tolyl)pyrimidin-2-yl)-1H-indole-6-carbonyl)piperazin-2-one (faster and slower eluting enantiomer)

4-(3-(Methylsulfinyl)-1-(5-(m-tolyl)pyrimidin-2-yl)-1H-indole-6-carbonyl)piperazin-2-one 4-(3-(Methylthio)-1-(5-(m-tolyl)pyrimidin-2-yl)-1H-indole-6-carbonyl)piperazin-2-one (precursor of example 151)

was oxidized to the corresponding sulfoxide through treatment with hydrogen peroxide in acetic acid. Pale yellow solid. Yield: 1.2 g The single enantiomers were obtained from the racemate via SFC utilizing a chiral HPLC column and the enantiomeric purity was measured with the following analytical method: column: Chiracel OJ-H 4.6×250 mm, 5 μm; injection volume=10 μL; column temperature: 25° C.; co-solvent: methanol; amount of co-solvent: 45%; flow rate: 3 g/min; pressure: 100 bar.

Faster eluting enantiomer (example 215):
White solid. Yield: 405 mg. Melting range: 168-171° C.
HPLC (method 6): $R_t$=8.91 min
Mass spectroscopy: m/z: [M+H]$^+$=474.2
Enantiomeric excess determined by analytical SFC: 99.2% ($R_t$=3.45 min)
1H NMR (400 MHz, DMSO-d6, δ ppm): 9.28 (s, 2H), 8.97 (s, 1H), 8.79 (s, 1H), 8.12 (s, 1H), 8.06 (d, J=8.0 Hz, 1H), 7.70 (s, 1H), 7.66 (d, J=8.0 Hz, 1H), 7.49-7.38 (m, 2H), 7.31 (d, J=7.6 Hz, 1H), 4.41-4.01 (m, 2H), 3.81-3.51 (m, 2H), 3.29 (s, 2H), 3.08 (s, 3H), 2.42 (s, 3H).

Slower eluting enantiomer (example 216):
White solid. Yield: 281 mg. Melting range: 168-172° C.
HPLC (method 6): $R_t$=8.91 min
Mass spectroscopy: m/z: [M+H]$^+$=474.3
Enantiomeric excess determined by analytical SFC: 99.0% ($R_t$=4.03 min)
1H NMR (400 MHz, DMSO-d6, δ ppm): 9.28 (s, 2H), 8.97 (s, 1H), 8.79 (s, 1H), 8.12 (s, 1H), 8.06 (d, J=8.0 Hz, 1H), 7.70 (s, 1H), 7.66 (d, J=8.0 Hz, 1H), 7.49-7.38 (m, 2H), 7.31 (d, J=7.6 Hz, 1H), 4.41-4.01 (m, 2H), 3.81-3.51 (m, 2H), 3.29 (s, 2H), 3.08 (s, 3H), 2.42 (s, 3H).

EXAMPLES 217 AND 218

4-(1-(5-(3-Methoxyphenyl)pyrimidin-2-yl)-3-(methylsulfinyl)-1H-indole-6-carbonyl)piperazin-2-one (faster and slower eluting enantiomer)

4-(1-(5-(3-Methoxyphenyl)pyrimidin-2-yl)-3-(methylsulfinyl)-1H-indole-6-carbonyl)piperazin-2-one Prepared from 4-(1-(5-(3-methoxyphenyl)pyrimidin-2-yl)-3-(methylthio)-1H-indole-6-carbonyl)piperazin-2-one (precursor of example 153) using hydrogen peroxide in acetic acid as oxidation method. Pale yellow solid. Yield: 1.7 g.

The single enantiomers were obtained from the racemate via SFC utilizing a chiral HPLC column and the enantiomeric purity was measured with the following analytical method: column: Chiracel OJ-H 4.6×250 mm, 5 μm; injection volume=10 μL; column temperature: 25° C.; co-solvent: methanol; amount of co-solvent: 45%; flow rate: 3 g/min; pressure: 100 bar.

Faster eluting enantiomer (example 217):
White solid. Yield: 500 mg. Melting range: 164-168° C.
HPLC (method 11): $R_t$=8.59 min
Mass spectroscopy: m/z: [M+H]$^+$=490.3
Enantiomeric excess determined by analytical SFC: 99.9% ($R_t$=4.78 min)
1H NMR (400 MHz, DMSO-d6, δ ppm): 9.31 (s, 2H), 8.98 (s, 1H), 8.78 (s, 1H), 8.12 (s, 1H), 8.06 (d, J=8.0 Hz, 1H), 7.54-7.38 (m, 4H), 7.10-7.02 (m, 1H), 4.19-4.03 (m, 2H), 3.87 (s, 3H), 3.75-3.55 (m, 2H), 3.29 (s, 2H), 3.09 (s, 3H).

Slower eluting enantiomer (example 218):
White solid. Yield: 312 mg. Melting range: 162-166° C.
HPLC (method 11): $R_t$=8.58 min
Mass spectroscopy: m/z: [M+H]$^+$=490.2
Enantiomeric excess determined by analytical SFC: 99.3% ($R_t$=6.22 min)
1H NMR (400 MHz, DMSO-d6, δ ppm): 9.31 (s, 2H), 8.98 (s, 1H), 8.78 (s, 1H), 8.12 (s, 1H), 8.06 (d, J=8.0 Hz, 1H), 7.54-7.38 (m, 4H), 7.10-7.02 (m, 1H), 4.19-4.03 (m, 2H), 3.87 (s, 3H), 3.75-3.55 (m, 2H), 3.29 (s, 2H), 3.09 (s, 3H).

The following synthesis examples 219 to 222 were prepared from 1-(5-(2-fluorophenyl)pyrimidin-2-yl)-3-(methylsulfinyl)-1H-indole-6-carboxylic acid in one or two steps comprising a HATU coupling and if necessary a BOC deprotection with trifluoroacetic acid.

EXAMPLE 219

(1-(5-(2-Fluorophenyl)pyrimidin-2-yl)-3-(methylsulfinyl)-1H-indol-6-yl)((R)-2-(hydroxymethyl)morpholino)methanone White solid. Yield: 125 mg. Melting range: 206-210° C.
HPLC (method 12): $R_t$=5.10 min
Mass spectroscopy: m/z: [M+H]$^+$=495.2
1H NMR (400 MHz, DMSO-d6, δ ppm): 9.19 (s, 2H), 8.95 (s, 1H), 8.79 (s, 1H), 8.05 (d, J=8.0 Hz, 1H), 7.81-7.76 (m, 1H), 7.59-7.53 (m, 1H), 7.48-7.37 (m, 3H), 4.88-3.38 (m, 8H), 3.23-2.78 (m, 5H).

EXAMPLE 220

(1-(5-(2-Fluorophenyl)pyrimidin-2-yl)-3-(methylsulfinyl)-1H-indol-6-yl)((S)-2-(hydroxymethyl)morpholino)methanone White solid. Yield: 75 mg. Melting range: 194-198° C.
HPLC (method 12): $R_t$=5.10 min
Mass spectroscopy: m/z: [M+H]$^+$=495.2
H NMR (400 MHz, DMSO-d6, δ ppm): 9.19 (s, 2H), 8.95 (s, 1H), 8.79 (s, 1H), 8.05 (d, J=8.0 Hz, 1H), 7.81-7.76 (m, 1H), 7.57-7.55 (m, 1H), 7.47-7.40 (m, 3H), 4.88-4.12 (m, 3H), 4.11-3.65 (m, 2H), 3.60-3.39 (m, 3H) 3.08-2.78 (m, 5H).

EXAMPLE 221

N-(2-Aminoethyl)-1-(5-(2-fluorophenyl)pyrimidin-2-yl)-N-methyl-3-(methylsulfinyl)-1H-indole-6-carboxamide Pale yellow solid. Yield: 70 mg. Melting range: 88-92° C.
HPLC (method 12): $R_t$=4.85 min
Mass spectroscopy: m/z: [M+H]$^+$=490.2
1H NMR (400 MHz, DMSO-d6, δ ppm): 9.19 (s, 2H), 8.91 (s, 1H), 8.77 (s, 1H), 8.03 (d, J=8.0 Hz, 1H), 7.80-7.76 (m, 1H), 7.57-7.53 (m, 1H), 7.46-7.39 (m, 3H), 3.65-3.41 (m, 2H), 3.08 (s, 3H), 3.05-2.95 (s, 3H), 2.85-2.69 (m, 2H).

EXAMPLE 222

(1-(5-(2-Fluorophenyl)pyrimidin-2-yl)-3-(methylsulfinyl)-1H-indol-6-yl)(hexahydropyrrolo[3,4-c]pyrrol-2(1H)-yl)methanone White solid. Yield: 85 mg. Melting range: 219-222° C.
HPLC (method 12): $R_t$=4.85 min
Mass spectroscopy: m/z: [M+H]$^+$=452.2
1H NMR (400 MHz, DMSO-d6, δ ppm): 9.18 (s, 2H), 9.00 (d, J=1.5 Hz, 1H), 8.79 (s, 1H), 8.03 (d, J=8.2 Hz, 1H), 7.81-7.76 (m, 1H), 7.59-7.33 (m, 4H), 3.88-3.40 (m, 5H), 3.08 (s, 3H), 3.05-2.60 (d, J=70.2 Hz, 6H).

EXAMPLE 223

((R)-3-Aminopyrrolidin-1-yl)(3-(methylsulfinyl)-1-(5-phenylpyrimidin-2-yl)-1H-indol-6-yl)methanone

223a) 1-(5-Bromopyrimidin-2-yl)-3-(methylthio)-1H-indole-6-carboxylic acid

Lithium hydroxide monohydrate (1.63 g, 39.78 mmol) was added to an ice-cooled suspension of 51b) (5 g, 13.26 mmol) in THF/water (1:1, 50 mL) and the resulting mixture was stirred at room temperature for 16 h. The solvents were removed under reduced pressure and the residue was dissolved in water (20 mL). The aqueous solution was washed with ethyl acetate (2×20 mL), acidified with sodium hydrogen sulfate and extracted with dichloromethane (3×50 mL). The combined organic layers were dried over sodium sulfate and evaporated. White solid. Yield: 4 g (83% of theory)
HPLC-MS (method 5): $R_t$=2.88 min; m/z [M+H]$^+$=365.8

223b) (R)-tert-Butyl (1-(1-(5-bromopyrimidin-2-yl)-3-(methylthio)-1H-indole-6-carbonyl)pyrrolidin-3-yl)carbamate HATU (2.41 g, 6.363 mmol), diisopropylethylamine (3.02 ml, 17.355 mmol) and (R)-pyrrolidin-3-yl-carbamic acid tert-butyl ester (1.18 g, 6.363 mmol) were added to an ice cooled suspension of 223a) (2.1 g, 5.787 mmol) in DMF (20 mL). The resulting mixture was stirred at room temperature for 16 h and then diluted with ice cold water (40 mL). The precipitate was filtered off, washed with water and hexane (3 times) and dissolved in dichloromethane. The solution was successively washed with saturated ammonium chloride solution (2×30 mL), saturated sodium hydrogen solution (2×30 mL), and brine (30 mL). The organic layer was dried over sodium sulfate and concentrated. The residue was triturated with ether. White solid. Yield: 3 g (97% of theory)
HPLC-MS (method 5): $R_t$=3.79 min; m/z [M+H]$^+$=534.1

223c) (R)-tert-Butyl (1-(3-(methylthio)-1-(5-phenylpyrimidin-2-yl)-1H-indole-6-carbonyl)pyrrolidin-3-yl)carbamate Potassium carbonate (1.16 g, 8.45 mmol) and bis(di-tert-butyl(4-dimethylaminophenyl)phosphine)dichloropalladium(II) (0.2 g, 0.28 mmol) were added under an argon atmosphere and at room temperature to a solution of 223b) (1.5 g, 2.8 mmol) and phenyl boronic acid (0.69 g, 5.63 mmol) in tert-butanol/water (10:1, 66 mL). The resulting mixture was heated at 90° C. for 2 h, then cooled to room temperature and filtered through a pad of celite. The filtrate was concentrated and the remnant purified by flash column chromatography [silica gel, dichloromethane with 2% methanol] and then triturated with ether. White solid. Yield: 1 g (67% of theory)
HPLC-MS (method 5): $R_t$=3.92 min; m/z [M+H]$^+$=530.3

223d) tert-Butyl ((3R)-1-(3-(methylsulfinyl)-1-(5-phenylpyrimidin-2-yl)-1H-indole-6-carbonyl)pyrrolidin-3-yl)carbamate m-Chloroperoxybenzoic acid (77%, 0.20 g, 0.92 mmol) in THF (5 mL) was added to an ice-cooled solution of 223c) (0.54 g, 1.02 mmol) in THF (100 mL) and the resulting mixture was stirred at room temperature for 4 h. The reaction mixture was then diluted with ethyl acetate (50 mL) and successively washed with saturated sodium hydrogen carbonate solution (2×50 mL) and brine (1×50 mL). The organic phase was dried over sodium sulfate and evaporated. The residue was purified by flash column chromatography [silica gel; dichloromethane with 2% methanol]. White solid. Yield: 0.28 g (51% of theory)
HPLC-MS (method 5): $R_t$=3.14 min; m/z [M+H]$^+$=546.3

223e) ((R)-3-Aminopyrrolidin-1-yl)(3-(methylsulfinyl)-1-(5-phenylpyrimidin-2-yl)-1H-indol-6-yl)methanone A 4M solution of TFA in dichloromethane (5.22 mL, 20.91 mmol) was added to 223d) (0.28 g, 0.52 mmol) in dichloromethane (16 mL) and the resulting mixture was stirred at room temperature for 3 h. The solution was concentrated, diluted with dichloromethane (40 mL), then washed with saturated potassium carbonate solution (2×20 mL) and dried over sodium sulfate. After evaporation of the solvent, the remnant was triturated with ether, pentane and acetone. Light yellow solid. Yield: 0.11 g (46% of theory)
HPLC-MS (method 5): $R_t$=2.44 min; m/z [M+H]$^+$=446.3
1H NMR (400 MHz, DMSO-d6, 100° C., δ ppm): 9.24 (s, 2H), 9.01 (s, 1H), 8.73 (s, 1H), 8.00 (d, J=8.0 Hz, 1H), 7.85 (d, J=8.0 Hz, 2H), 7.58-7.55 (m, 2H), 7.51-7.47 (m, 2H), 3.63-3.67 (m, 2H), 3.53 (bs, 2H), 3.22-3.19 (m, 1H), 3.07 (s, 3H), 2.04-2.00 (m, 1H), 1.67-1.64 (m, 2H).

EXAMPLE 224

((R)-3-Aminopyrrolidin-1-yl)(3-(methylsulfinyl)-1-(5-(m-tolyl)pyrimidin-2-yl)-1H-indol-6-yl)methanone Prepared in analogy to synthesis example 223. Light yellow solid. Yield: 90 mg.
HPLC-MS (method 5): $R_t$=2.54 min; m/z [M+H]$^+$=460.3
1H NMR (400 MHz, DMSO-d6, 100° C., δ ppm): 9.22 (s, 2H), 9.01 (s, 1H), 8.73 (s, 1H), 7.99 (d, J=8.0 Hz, 1H), 7.66-7.62 (m, 2H), 7.50 (d, J=8.0 Hz, 1H), 7.46-7.32 (m, 1H), 7.30 (d, J=8.0 Hz, 1H), 3.67-3.63 (m, 2H), 3.52 (bs, 2H), 3.19 (d, J=8.0 Hz, 1H), 3.06 (s, 3H), 2.43 (s, 3H), 2.03-2.00 (m, 1H), 1.68-1.62 (m, 1H), 1.53 (bs, 2H).

EXAMPLE 225

3-(2-(6-((R)-3-Aminopyrrolidine-1-carbonyl)-3-(methylsulfinyl)-1H-indol-1-yl)pyrimidin-5-yl)-4-fluorobenzonitrile Prepared in analogy to example 223. White solid. Yield: 75 mg
HPLC-MS (method 5): $R_t$=2.47 min; m/z [M+H]$^+$=489.0
1H NMR (400 MHz, DMSO-d6, 100° C., δ ppm): 9.19 (s, 2H), 9.00 (s, 1H), 8.74 (s, 1H), 8.31-8.29 (m, 1H), 8.01-7.99 (m, 2H), 7.65-7.60 (m, 1H), 7.51 (d, J=8.0 Hz, 1H), 3.71-3.63 (m, 2H), 3.53 (bs, 2H), 3.21-3.18 (m, 1H), 3.07 (s, 3H), 2.05-2.00 (m, 1H), 1.70-1.62 (m, 3H).

EXAMPLE 226

((R)-3-Aminopyrrolidin-1-yl)(1-(5-(2-fluoro-5-methoxyphenyl)pyrimidin-2-yl)-3-(methylsulfinyl)-1H-indol-6-yl)methanone Prepared in analogy to example 223. White solid. Yield: 135 mg
HPLC-MS (method 5): $R_t$=2.49 min; m/z [M+H]$^+$=493.9
1H NMR (400 MHz, DMSO-d6, 100° C., δ ppm): 9.15 (s, 2H), 9.00 (s, 1H), 8.73 (s, 1H), 8.00 (d, J=8.0 Hz, 1H), 7.50 (d, J=8.0 Hz, 1H), 7.33-7.28 (m, 2H), 7.08-7.06 (m, 1H), 3.86 (s, 3H), 3.66-3.62 (m, 2H), 3.52 (bs, 2H), 3.19 (d, J=8.0 Hz, 1H), 3.07 (s, 3H), 2.03-2.00 (m, 1H), 1.68-1.58 (m, 3H).

EXAMPLE 227

((R)-3-Aminopyrrolidin-1-yl)(1-(5-(2-fluoro-5-methylphenyl)pyrimidin-2-yl)-3-(methylsulfinyl)-1H-indol-6-yl)methanone Synthesized in analogy to example 223. White solid. Yield: 80 mg HPLC-MS (method 5): $R_t$=2.60 min; m/z [M+H]$^+$=478.2

1H NMR (400 MHz, DMSO-d6, 100° C., δ ppm): 9.12 (s, 2H), 9.00 (s, 2H), 8.73 (s, 1H), 8.00 (d, J=8.0 Hz, 1H), 7.56-7.49 (m, 2H), 7.34-7.23 (m, 2H), 3.67-3.63 (m, 2H), 3.53 (bs, 2H), 3.21-3.18 (m, 1H), 3.06 (s, 3H), 2.40 (s, 3H), 2.05-1.99 (m, 1H), 1.68-1.62 (m, 3H).

EXAMPLE 228

(R)-(3-Aminopyrrolidin-1-yl)(3-(methylsulfonyl)-1-(5-phenylpyrimidin-2-yl)-1H-indol-6-yl)methanone Synthesized in analogy to example 223 with the difference that the oxidation towards the sulfone was performed with 2.2 equivalents of m-chloroperoxybenzoic acid. White solid. Yield: 65 mg HPLC-MS (method 5): $R_t$=2.65 min; m/z [M+H]$^+$=462.0

1H NMR (400 MHz, DMSO-d6, 100° C., δ ppm): 9.28 (s, 2H), 9.02 (s, 1H), 8.90 (s, 1H), 8.00 (d, J=8.0 Hz, 1H), 7.87 (d, J=8.0 Hz, 2H), 7.59-7.49 (m, 4H), 3.67-3.63 (m, 2H), 3.54 (bs, 2H), 3.35 (s, 3H), 3.21-3.19 (m, 1H), 2.07-1.99 (m, 1H), 1.69-1.65 (m, 3H).

EXAMPLE 229

(R)-3-(2-(6-(3-Aminopyrrolidine-1-carbonyl)-3-(methylsulfonyl)-1H-indol-1-yl)pyrimidin-5-yl)-4-fluorobenzonitrile White solid. Yield: 0.22 g HPLC-MS (method 4): $R_t$=2.70 min; m/z [M+H]$^+$=505.0

1H NMR (400 MHz, DMSO-d6, 100° C., δ ppm): 9.24 (s, 2H), 9.00 (s, 1H), 8.91 (s, 1H), 8.32 (d, J=8.0 Hz, 1H), 8.04-8.00 (m, 2H), 7.66-7.59 (m, 2H), 3.67-3.63 (m, 2H), 3.54 (bs, 2H), 3.36 (s, 3H), 3.21-3.19 (m, 1H), 2.07-2.01 (m, 1H), 1.76-1.63 (m, 3H).

EXAMPLE 230

(R)-(3-Aminopyrrolidin-1-yl)(1-(5-(2-fluoro-5-methoxyphenyl)pyrimidin-2-yl)-3-(methylsulfonyl)-1H-indol-6-yl)methanone White solid. Yield: 180 mg HPLC-MS (method 5): $R_t$=2.83 min; m/z [M+H]$^+$=510.0

1H NMR (400 MHz, DMSO-d6, 100° C., δ ppm): 9.19 (s, 2H), 9.01 (s, 1H), 8.90 (s, 1H), 8.00 (d, J=8.0 Hz, 1H), 7.59 (d, J=8.0 Hz, 1H), 7.35-7.30 (m, 2H), 7.11-7.07 (m, 1H), 3.87 (s, 3H), 3.67-3.62 (m, 2H), 3.53 (bs, 2H), 3.35 (s, 3H), 3.19 (d, J=8.0 Hz, 1H), 2.05-2.01 (m, 1H), 1.70-1.63 (m, 3H).

EXAMPLE 231

(R)-(3-Aminopyrrolidin-1-yl)(1-(5-(2-fluoro-5-methylphenyl)pyrimidin-2-yl)-3-(methylsulfonyl)-1H-indol-6-yl)methanone White solid. Yield: 0.11 g HPLC-MS (method 5): $R_t$=2.79 min; m/z [M+H]$^+$=494.2

1H NMR (400 MHz, DMSO-d6, 100° C., δ ppm): 9.17 (s, 2H), 9.00 (s, 1H), 8.90 (s, 1H), 8.00 (d, J=8.0 Hz, 1H), 7.60-7.56 (m, 2H), 7.34-7.25 (m, 2H), 3.67-3.65 (m, 2H), 3.53 (bs, 2H), 3.35 (s, 3H), 3.20 (d, J=4.0 Hz, 2H), 2.41 (s, 3H), 2.05-2.01 (m, 1H), 1.69-1.62 (m, 1H), 1.57 (bs, 2H).

The examples 232 to 234 were prepared from 3-(methylsulfinyl)-1-(5-phenylpyrimidin-2-yl)-1H-indole-6-carboxylic acid in 1-2 chemical steps comprising a HATU coupling and if necessary a removal of a BOC protecting group with TFA.

EXAMPLE 232

(1R,4R)-2,5-Diazabicyclo[2.2.1]heptan-2-yl(3-(methylsulfinyl)-1-(5-phenylpyrimidin-2-yl)-1H-indol-6-yl)methanone White solid. Yield: 55 mg HPLC-MS (method 5): $R_t$=2.54 min; m/z [M+H]$^+$=458.2

1H NMR (400 MHz, DMSO-d6, 100° C., δ ppm): 9.22 (s, 2H), 9.04 (s, 1H), 8.74 (s, 1H), 8.00 (d, J=8.0 Hz, 1H), 7.84-7.82 (m, 2H), 7.55-7.48 (m, 4H), 4.6 (bs, 1H), 3.98 (bs, 1H), 3.6 (bs, 1H), 3.51-3.49 (m, 2H), 3.24 (bs, 1H), 3.07 (s, 3H), 1.91-1.77 (m, 2H).

EXAMPLE 233

(1S,4S)-2,5-Diazabicyclo[2.2.1]heptan-2-yl(3-(methylsulfinyl)-1-(5-phenylpyrimidin-2-yl)-1H-indol-6-yl)methanone White solid. Yield: 55 mg HPLC-MS (method 5): $R_t$=2.53 min; m/z [M+H]$^+$=458.3

1H NMR (400 MHz, DMSO-d6, 100° C., δ ppm): 9.23 (s, 2H), 9.04 (s, 1H), 8.74 (s, 1H), 8.00 (d, J=8.0 Hz, 1H), 7.84-7.83 (m, 2H), 7.56-7.48 (m, 4H), 4.61 (bs, 1H), 3.98 (bs, 1H), 3.62 (bs, 1H), 3.5-3.47 (m, 2H), 3.24 (bs, 1H), 3.07 (s, 3H), 1.91-1.76 (m, 2H).

EXAMPLE 234

(1R,4R)-2-Oxa-5-azabicyclo[2.2.1]heptan-5-yl(3-(methylsulfinyl)-1-(5-phenylpyrimidin-2-yl)-1H-indol-6-yl)methanone White solid. Yield: 0.135 g HPLC-MS (method 5): $R_t$=2.78 min; m/z [M+H]$^+$=459.2

1H NMR (400 MHz, DMSO-d6, 100° C., δ ppm): 9.24 (s, 2H), 9.04 (s, 1H), 8.75 (s, 1H), 8.03 (d, 1H, J=8.1 Hz), 7.86 (d, J=7.8 Hz, 2H), 7.58-7.47 (m, 4H), 4.82-4.64 (m, 2H), 3.97 (d, 1H, J=7.3 Hz), 3.81 (d, 1H, J=7.3 Hz), 3.62 (d, 1H, J=10.9 Hz), 3.41 (d, 1H, J=10.9 Hz), 3.07 (s, 3H), 1.95-1.82 (m, 2H).

The examples 235 to 237 were prepared from 3-(methylsulfonyl)-1-(5-phenylpyrimidin-2-yl)-1H-indole-6-carboxylic acid.

EXAMPLE 235

(1R,4R)-2,5-Diazabicyclo[2.2.1]heptan-2-yl(3-(methylsulfonyl)-1-(5-phenylpyrimidin-2-yl)-1H-indol-6-yl)methanone White solid. Yield: 0.11 g
HPLC-MS (method 5): $R_t$=2.68 min; m/z [M+H]$^+$=474.3
1H NMR (400 MHz, DMSO-d6, 100° C., δ ppm): 9.27 (s, 2H), 9.03 (s, 1H), 8.90 (s, 1H), 8.00 (d, J=8.3 Hz, 1H), 7.87-7.86 (m, 2H), 7.59-7.56 (m, 3H), 7.52-7.5 (m, 1H), 3.98 (bs, 1H), 3.67 (bs, 1H), 3.59-3.56 (m, 1H), 3.34 (s, 3H), 3.31-3.29 (m, 1H), 3.09-3.07 (m, 1H), 2.94 (1H, obscured from water peak), 1.79-1.77 (m, 1H), 1.64-1.62 (m, 1H).

EXAMPLE 236

(1S,4S)-2,5-Diazabicyclo[2.2.1]heptan-2-yl(3-(methylsulfonyl)-1-(5-phenylpyrimidin-2-yl)-1H-indol-6-yl)methanone White solid. Yield: 0.15 g
HPLC-MS (method 5): $R_t$=2.63 min; m/z [M+H]$^+$=444.1
1H NMR (400 MHz, DMSO-d6, 100° C., δ ppm): 9.27 (s, 2H), 9.03 (s, 1H), 8.90 (s, 1H), 8.01-7.99 (m, 1H), 7.87-7.85 (m, 2H), 7.59-7.48 (m, 4H), 4.67 (bs, 1H), 3.68 (bs, 1H), 3.59-3.56 (m, 1H), 3.34-3.29 (m, 4H), 3.1-3.07 (m, 1H), 2.94 (1H, obscured from water peak), 1.79-1.77 (m, 1H), 1.65-1.53 (m, 1H).

EXAMPLE 237

(1R,4R)-2-Oxa-5-azabicyclo[2.2.1]heptan-5-yl(3-(methylsulfonyl)-1-(5-phenylpyrimidin-2-yl)-1H-indol-6-yl)methanone White solid. Yield: 0.115 g
HPLC-MS (method 5): $R_t$=3.03 min; m/z [M+H]$^+$=475.3
1H NMR (400 MHz, DMSO-d6, 100° C., δ ppm): 9.28 (s, 2H), 9.04 (s, 1H), 8.91 (s, 1H), 8.01 (d, 1H, J=8.0 Hz), 7.86 (d, 2H, J=7.6 Hz), 7.62-7.48 (m, 4H), 4.85-4.65 (m, 2H), 3.95 (d, 1H, J=7.6 Hz), 3.79 (d, 1H, J=7.2 Hz), 3.59 (d, 1H, J=11.2 Hz), 3.38 (d, 1H, J=10.8 Hz), 3.35 (s, 3H), 1.95-1.82 (m, 2H).

EXAMPLE 238

(1R,4R)-2-Oxa-5-azabicyclo[2.2.1]heptan-5-yl(1-(5-(2-fluorophenyl)pyrimidin-2-yl)-3-(methylsulfonyl)-1H-indol-6-yl)methanone Prepared from 1-(5-bromopyrimidin-2-yl)-3-(methylthio)-1H-indole-6-carboxylic acid in three steps comprising an amide coupling with (1R,4R)-2-oxa-5-azabicyclo[2.2.1]heptane hydrochloride, a Suzuki reaction and an oxidation with m-chloroperoxybenzoic acid. White solid. Yield: 0.16 g
HPLC-MS (method 5): $R_t$=3.06 min; m/z [M+H]$^+$=493.2
1H NMR (400 MHz, DMSO-d6, 100° C., δ ppm): 9.18 (s, 2H), 9.03 (s, 1H), 8.92 (s, 1H), 8.03-8.01 (m, 1H), 7.77 (t, 1H, J=6.9 Hz), 7.62-7.53 (m, 2H), 7.43-7.38 (m, 2H), 4.83-4.64 (m, 2H), 3.95 (d, 1H, J=7.1 Hz), 3.78 (d, 1H, J=7.1 Hz), 3.58 (d, 1H, J=10.8 Hz), 3.41-3.35 (m, 4H), 1.95-1.93 (m, 1H), 1.84-1.82 (m, 1H).

EXAMPLE 239

(1S,4S)-2,5-Diazabicyclo[2.2.1]heptan-2-yl(1-(5-(2-fluorophenyl)pyrimidin-2-yl)-3-(methylsulfonyl)-1H-indol-6-yl)methanone Synthesized from 1-(5-bromopyrimidin-2-yl)-3-(methylthio)-1H-indole-6-carboxylic acid and (1S,4S)-tert-butyl 2,5-diazabicyclo[2.2.1]heptane-2-carboxylate in four steps (amide coupling, Suzuki reaction, oxidation, deprotection). White solid. Yield: 0.21 g
HPLC-MS (method 5): $R_t$=2.77 min; m/z [M+H]$^+$=492.4
1H NMR (400 MHz, DMSO-d6, 100° C., δ ppm): 9.18 (s, 2H), 9.02 (s, 1H), 8.91 (s, 1H), 8.0 (d, 1H, J=8.0 Hz), 7.77 (t, 1H, J=7.8 Hz), 7.59-7.53 (m, 2H), 7.43-7.38 (m, 2H), 4.5 (bs, 1H), 3.66 (bs, 1H), 3.58 (d, 1H, J=10.1 Hz), 3.34-2.88 (m, 4H), 3.09-3.07 (m, 1H), 2.94 (1H, obscured from water peak), 2.2 (bs, 1H), 1.79-1.76 (m, 1H), 1.64-1.62 (m, 1H).

Synthesis examples 240 to 243 were prepared from 1-(5-(2-fluorophenyl)pyrimidin-2-yl)-3-(methylsulfinyl)-1H-indole-6-carboxylic acid via an amide coupling (HATU) followed by a BOC deprotection (TFA) in cases where a secondary amine was present.

EXAMPLE 240

(1S,4S)-2,5-Diazabicyclo[2.2.1]heptan-2-yl(1-(5-(2-fluorophenyl)pyrimidin-2-yl)-3-(methylsulfinyl)-1H-indol-6-yl)methanone White solid. Yield: 85 mg
HPLC-MS (method 5): $R_t$=2.55 min; m/z [M+H]$^+$=476.2
1H NMR (400 MHz, DMSO-d6, 100° C., δ ppm): 9.14 (s, 2H), 9.02 (s, 1H), 8.74 (s, 1H), 8.0 (d, 1H, J=8.0 Hz), 7.77-7.74 (m, 1H), 7.54-7.5 (m, 2H), 7.42-7.39 (m, 2H), 4.52 (bs, 1H), 3.82 (bs, 1H), 3.73-3.71 (m, 1H), 3.58-3.48 (m, 1H), 3.13-3.07 (m, 4H), 2.98 (1H, obscured from water peak), 1.87-1.8 (m, 1H), 1.67-1.64 (m, 1H).

EXAMPLE 241

(1-(5-(2-Fluorophenyl)pyrimidin-2-yl)-3-(methylsulfinyl)-1H-indol-6-yl)((3aR,6aR)-hexahydropyrrolo[3,4-b]pyrrol-5(1H)-yl)methanone White solid. Yield: 0.07 g
HPLC-MS (method 5): $R_t$=2.48 min; m/z [M+H]$^+$=490.1
1H NMR (400 MHz, DMSO-d6, 100° C., δ ppm): 9.13 (s, 2H), 8.98 (s, 1H), 8.74 (s, 1H), 8.00 (d, J=8.0 Hz, 1H), 7.77-7.73 (m, 1H), 7.55 (d, J=4.0 Hz, 1H), 7.48 (d, J=8.0 Hz, 1H), 7.42-7.37 (m, 2H), 3.80-3.65 (m, 3H), 3.58-3.42 (m, 2H), 3.07 (s, 3H), 2.89 (s, 2H), 2.66 (bs, 1H), 1.91-1.86 (m, 1H), 1.60 (bs, 1H).

EXAMPLE 242

(1-(5-(2-Fluorophenyl)pyrimidin-2-yl)-3-(methylsulfinyl)-1H-indol-6-yl)((3aS,6aS)-hexahydropyrrolo[3,4-b]pyrrol-5(1H)-yl)methanone White solid. Yield: 0.098 g
HPLC-MS (method 5): $R_t$=2.49 min; m/z [M+H]$^+$=490.1
1H NMR (400 MHz, DMSO-d6, 100° C., δ ppm): 9.13 (s, 2H), 8.98 (s, 1H), 7.99 (d, J=8.0 Hz, 1H), 7.77-7.73 (m, 1H), 7.55 (d, J=4.0 Hz, 1H), 7.47 (d, J=8.0 Hz, 1H), 7.42-7.37 (m, 2H), 3.78-3.65 (m, 3H), 3.49-3.42 (m, 2H), 3.07 (s, 3H), 2.75 (bs, 2H), 2.66 (s, 1H), 1.91-1.85 (m, 1H), 1.59 (bs, 1H).

EXAMPLE 243

(1R,4R)-2-Oxa-5-azabicyclo[2.2.1]heptan-5-yl(1-(5-(2-fluorophenyl)pyrimidin-2-yl)-3-(methylsulfinyl)-1H-indol-6-yl)methanone White solid. Yield: 70 mg
HPLC-MS (method 5): $R_t$=2.87 min; m/z [M+H]$^+$=477.2
1H NMR (400 MHz, DMSO-d6, 100° C., δ ppm): 9.14 (s, 2H), 9.03 (s, 1H), 8.75 (s, 1H), 8.01 (d, 1H, J=8.2 Hz), 7.76 (t, 1H, J=7.5 Hz), 7.54-7.52 (m, 2H), 7.42-7.37 (m, 2H), 4.78-4.64 (m, 2H), 3.95 (d, 1H, J=7.1 Hz), 3.79 (d, 1H, J=7.3 Hz), 3.58 (d, 1H, J=10.8 Hz), 3.38 (d, 1H, J=10.5 Hz), 3.07 (s, 3H), 1.95-1.92 (m, 1H), 1.84-1.82 (m, 1H).

EXAMPLE 244

(1S,4S)-2,5-Diazabicyclo[2.2.1]heptan-2-yl(3-(methylsulfinyl)-1-(5-(pyridin-2-yl)pyrimidin-2-yl)-1H-indol-6-yl)methanone 244a) Methyl 3-(methylthio)-1-(5-(pyridin-2-yl)pyrimidin-2-yl)-1H-indole-6-carboxylate PdCl2(dppf) (0.323 g, 0.39 mmol, 0.05 eq) was added at room temperature and under an argon atmosphere to a suspension of 1-(5-bromo-pyrimidin-2-yl)-3-methyl sulfanyl-1H-indole-6-carboxylic acid-methyl ester (3.0 g, 7.93 mmol, 1 eq), bis(pinacolato)diboron (4.01 g, 15.87 mmol, 2 eq) and potassium acetate (1.16 g, 11.90 mmol, 1.5 eq) in 1,4-dioxane (125 mL). The reaction mixture was stirred for 16 h at 100° C., then cooled to room temperature and filtered through a pad of celite. The filtrate was concentrated and 2-bromopyridine (1.38 g, 8.76 mmol, 1.5 eq) and a 2 M solution of potassium carbonate (5.8 mL, 11.66 mmol, 2 eq) in 1,4-dioxane (125 mL) were added. Tetrakis(triphenylphosphine)palladium(0) (0.336 g, 0.29 mmol, 0.05 eq) was introduced under an inert atmosphere and the mixture was stirred for 16 h at 100° C. After cooling to room temperature, the mixture was filtered. The filtrate was evaporated and the remnant was dissolved in ethyl acetate (150 mL) and successively washed by water (2×50 mL) and brine (50 mL). The organic layer was dried over sodium sulfate, the solvent was removed under reduced pressure, and the residue was purified by column chromatography [230-400 mesh silica gel; ethyl acetate/hexane=2:3]. White solid. Yield: 2.5 g (84% of theory)
HPLC-MS (method 5): $R_t$=4.22 min; m/z [M+H]$^+$=377.3

244b) 3-(Methylthio)-1-(5-(pyridin-2-yl)pyrimidin-2-yl)-1H-indole-6-carboxylic acid Lithium hydroxide monohydrate (0.837 g, 19.94 mmol, 3 eq) was added to a solution of 244a) (2.5 g, 6.64 mmol, 1 eq) in water/THF (1:1, 40 mL) and the reaction mixture was stirred for 16 h at room temperature. The solvents were removed under reduced pressure and the residue was dissolved in water (100 mL), washed with ether (50 mL) and acidified with 2N hydrogen chloride solution. The aqueous phase was then extracted with ethyl acetate (2×100 mL) and the combined organic layers were washed with water and brine (50 mL), dried over sodium sulfate, and evaporated. White solid. Yield: 1.5 g (63% of theory)
HPLC-MS (method 5): $R_t$=2.76 min; m/z [M+H]$^+$=363

244c) (1S,4S)-tert-Butyl 5-(3-(methylthio)-1-(5-(pyridin-2-yl)pyrimidin-2-yl)-1H-indole-6-carbonyl)-2,5-diazabicyclo[2.2.1]heptane-2-carboxylate TBTU (0.532 g, 1.65 mmol, 1.2 eq), 4-methyl-morpholine (0.30 mL, 2.75 mmol, 1.2 eq) and finally (1S,4S)-tert-butyl 2,5-diazabicyclo[2.2.1]heptane-2-carboxylate (0.328 g, 1.65 mmol, 1.2 eq) were added to a stirred solution 244b) (0.5 g, 1.3 mmol, 1 eq) in DMF (10 mL). The reaction mixture stirred for 16 h at room temperature and then quenched with ice cold water (20 mL). The precipitating solid was filtered off, dried and purified by washing with pentane and ether. Yield: 0.400 g (54% of theory)
HPLC-MS (method 5): $R_t$=3.91 min; m/z [M+H+NH$_3$]$^+$=543.4

244d) (1S,4S)-tert-Butyl 5-(3-(methylsulfinyl)-1-(5-(pyridin-2-yl)pyrimidin-2-yl)-1H-indole-6-carbonyl)-2,5-diazabicyclo[2.2.1]heptane-2-carboxylate m-Chloroperoxybenzoic acid (0.114 g, 0.66 mmol, 0.9 eq) was added at 0° C. to a stirred solution of 244c) (0.400 g, 0.61 mmol, 1 eq) in dichloromethane (30 mL). The reaction mixture was stirred for 3 h at room temperature, then diluted with dichloromethane (50 mL) and successively washed with saturated sodium hydrogen carbonate solution (2×30 mL) and brine (30 mL). The organic layer was dried over sodium sulfate and concentrated under reduced pressure. The residue was purified by column chromatography [230-400 mesh silica gel, dichloromethane/methanol=95:5]. White solid. Yield: 0.290 g (71% of theory)
HPLC-MS (method 5): $R_t$=3.02 min; m/z [M+H]$^+$=559.4

244e) (1S,4S)-2,5-Diazabicyclo[2.2.1]heptan-2-yl(3-(methylsulfinyl)-1-(5-(pyridin-2-yl)pyrimidin-2-yl)-1H-indol-6-yl)methanone 4 M solution of trifluoroacetic acid in dichloromethane (5.1 mL, 20.78 mmol, 40 eq) was added at 0° C. to 244d) (0.29 g, 0.51 mmol, 1 eq) in dichloromethane (10 mL). The reaction mixture was then stirred for 3 h at room temperature. The solvent was removed under vacuum and the residue was co-distilled twice with dichloromethane, diluted with dichloromethane (50 mL) and washed with saturated potassium carbonate solution (2×20 mL) and brine (20 mL). The organic layer was dried over sodium sulfate, concentrated and finally chromatographed by preparative HPLC. White solid. Yield: 0.200 g (84% by theory)
HPLC-MS (method 5): $R_t$=2.00 min; m/z [M+H]$^+$=459.3
1H-NMR (400 MHz, DMSO-d6, 100° C., δ ppm): 9.53 (s, 2H), 9.04 (s, 1H), 8.75 (s, 2H), 8.14 (d, 1H, J=8 Hz), 7.95-8.02 (m, 2H), 7.44-7.52 (m, 2H), 4.50 (bs, 1H), 3.67 (s, 1H), 3.58 (d, 1H, J=12 Hz), 3.31 (d, 1H, J=12 Hz), 3.21 (s, 1H), 3.07 (s, 3H), 1.78 (d, 1H, J=8 Hz), 1.63 (d, 1H, J=8 Hz).
Synthesis examples 245 to 248 were prepared analogously to example 244.

EXAMPLE 245

(1S,4S)-2,5-Diazabicyclo[2.2.1]heptan-2-yl(1-(5-(4-methylpyridin-2-yl)pyrimidin-2-yl)-3-(methylsulfinyl)-1H-indol-6-yl)methanone White solid. Yield: 0.065 g
HPLC-MS (method 5): $R_t$=2.23 min; m/z [M+H]$^+$=473.1

1H-NMR (400 MHz, DMSO-d6, 100° C., δ ppm): 9.52 (s, 2H), 9.05 (s, 1H), 8.76 (s, 1H), 8.61 (d, 1H, J=4.8 Hz), 8.02-7.99 (m, 2H), 7.52 (d, 1H, J=8 Hz), 7.30 (d, 1H, J=4.8 Hz), 4.48 (bs, 1H), 3.68 (s, 1H), 3.59 (d, 1H, J=10.4 Hz), 3.31 (d, 1H, J=10 Hz), 3.11 (s, 1H), 3.09 (s, 3H), 2.96 (s, 1H), 2.46 (s, 3H), 1.78 (d, 1H, J=8.8 Hz), 1.64 (d, 1H, J=9.2 Hz).

EXAMPLE 246

(1S,4S)-2,5-Diazabicyclo[2.2.1]heptan-2-yl(1-(5-(4-ethylpyridin-2-yl)pyrimidin-2-yl)-3-(methylsulfinyl)-1H-indol-6-yl)methanone White solid. Yield: 0.115 g
HPLC-MS (method 5): $R_t$=2.58 min; m/z [M+H]$^+$=487.1
1H-NMR (400 MHz, DMSO-d6, 100° C., δ ppm): 9.54 (s, 2H), 9.05 (s, 1H), 8.76 (s, 1H), 8.63 (d, 1H, J=4.8 Hz), 8.01 (d, 2H, J=8.4 Hz), 7.51 (d, 1H, J=8.1 Hz), 7.32 (d, 1H, J=4.6 Hz), 4.5 (bs, 1H), 3.68 (s, 1H), 3.59 (d, 1H, J=10.2 Hz), 3.31 (d, 1H, J=10.1 Hz), 3.12 (s, 1H), 3.07 (s, 3H), 2.80-2.74 (q, 2H), 1.79 (d, 1H, J=9.6 Hz), 1.64 (d, 1H, J=9.1 Hz), 1.31 (t, 3H, J=7.5 Hz)

EXAMPLE 247

(1S,4S)-2,5-Diazabicyclo[2.2.1]heptan-2-yl(1-(5-(6-methylpyridin-2-yl)pyrimidin-2-yl)-3-(methylsulfinyl)-1H-indol-6-yl)methanone White solid. Yield: 0.22 g
HPLC-MS (method 5): $R_t$=2.44 min; m/z [M+H]$^+$=473
1H-NMR (400 MHz, DMSO-d6, 100° C., δ ppm): 9.51 (s, 2H), 9.04 (s, 1H), 8.75 (s, 1H), 8.01 (d, 1H, J=8.2 Hz), 7.92 (d, 1H, J=7.7 Hz), 7.85 (t, 1H, J=7.6 Hz), 7.51 (d, 1H, J=8.2 Hz), 7.33 (d, 1H, J=7.52 Hz), 4.5 (bs, 1H), 3.67 (s, 1H), 3.59 (d, 1H, J=10.2 Hz), 3.31 (d, 1H, J=10.0 Hz), 3.11 (s, 1H), 3.07 (s, 3H), 2.61 (s, 3H), 1.79 (d, 1H, J=9.1 Hz), 1.64 (d, 1H, J=9.2 Hz).

EXAMPLE 248

(1S,4S)-2,5-Diazabicyclo[2.2.1]heptan-2-yl(1-(5-(4-(dimethylamino)pyridin-2-yl)pyrimidin-2-yl)-3-(methylsulfinyl)-1H-indol-6-yl)methanone White solid. Yield: 0.066 g
HPLC-MS (method 5): $R_t$=2.42 min; m/z [M+H]$^+$=502.2
1H-NMR (400 MHz, DMSO-d6, 100° C., δ ppm): 9.52 (s, 2H), 9.05 (s, 1H), 8.75 (s, 1H), 8.29 (d, 1H, J=5.9 Hz), 8.01 (d, 1H, J=8.0 Hz), 7.50 (d, 1H, J=8.1 Hz), 7.29 (d, 1H, J=2.1 Hz), 6.68-6.66 (m, 1H), 4.45 (bs, 1H), 3.67 (s, 1H), 3.58 (d, 1H, J=10.2 Hz), 3.30 (d, 1H, J=10.5 Hz), 3.07 (s, 9H), 1.78 (d, 1H, J=9.3 Hz), 1.64 (d, 1H, J=9.1 Hz).

EXAMPLE 249

(1S,4S)-2,5-Diazabicyclo[2.2.1]heptan-2-yl(1-(5-(2-fluoro-5-methylphenyl)pyrimidin-2-yl)-3-(methylsulfinyl)-1H-indol-6-yl)methanone Synthesized in analogy to example 244 with the difference that 1-(5-bromo-pyrimidin-2-yl)-3-methyl sulfanyl-1H-indole-6-carboxylic acid-methyl ester was not transferred into a pincol boronic acid ester but instead directly reacted with 2-(2-fluoro-5-methylphenyl)-4,4,5,5-tetramethyl-1,3,2-dioxaborolane. White solid. Yield: 0.11 g
HPLC-MS (method 5): $R_t$=2.65 min; m/z [M+H]$^+$=490.2

1H-NMR (400 MHz, DMSO-d6, 100° C., δ ppm): 9.12 (s, 2H), 9.02 (s, 1H), 8.75 (s, 1H), 8.02 (d, 1H, J=8.4 Hz), 7.56-7.51 (m, 2H), 7.33 (bs, 1H), 7.26 (t, 1H, J=10 Hz), 4.54 (bs, 1H), 3.78 (s, 1H), 3.60 (d, 1H, J=10.4 Hz), 3.36 (d, 1H, J=10.8 Hz), 3.15 (d, 1H, J=9.6 Hz), 3.07 (s, 3H), 3.02 (s, 1H), 2.41 (s, 3H), 1.83 (d, 1H, J=8.4 Hz), 1.68 (d, 1H, J=8.4 Hz).

Examples 250 and 251 were prepared from 1-(5-(2-fluorophenyl)pyrimidin-2-yl)-3-(methylsulfinyl)-1H-indole-6-carboxylic acid and the respective amines via an amide coupling utilizing HATU as reagent.

EXAMPLE 250

1-(5-(2-Fluorophenyl)pyrimidin-2-yl)-N-((1-hydroxycyclopropyl)methyl)-N-methyl-3-(methylsulfinyl)-1H-indole-6-carboxamide White solid. Yield: 0.079 g
HPLC-MS (method 4): $R_t$=2.96 min; m/z [M+H]$^+$=479.0
1H NMR (400 MHz, DMSO-d6, 100° C., δ ppm): 9.13 (s, 2H), 8.91 (s, 1H), 8.72 (s, 1H), 7.98 (d, 1H, J=8.4 Hz), 7.75 (t, 1H, J=7.2 Hz), 7.57-7.52 (m, 1H), 7.44-7.37 (m, 3H), 5.06 (s, 1H), 3.56 (bs, 2H), 3.13 (s, 3H), 3.07 (s, 3H), 0.66 (bs, 2H), 0.52 (bs, 2H).

EXAMPLE 251

1-(5-(2-Fluorophenyl)pyrimidin-2-yl)-N—((S)-2-hydroxypropyl)-N-methyl-3-(methylsulfinyl)-1H-indole-6-carboxamide White solid. Yield: 75 mg
HPLC-MS (method 5): $R_t$=2.82 min; m/z [M+H]$^+$=467.3
1H NMR (400 MHz, DMSO-d6, 100° C., δ ppm): 9.13 (s, 2H), 8.9 (s, 1H), 8.73 (s, 1H), 7.99 (d, 1H, J=8.0 Hz), 7.76 (t, 1H, J=8.0 Hz), 7.58-7.52 (m, 1H), 7.42-7.37 (m, 3H), 4.45 (bs, 1H), 4.02-3.97 (m, 1H), 3.39 (d, 2H, J=8.0 Hz), 3.07 (s, 6H), 1.07 (d, 3H, J=4.0 Hz).

EXAMPLES 252 AND 253

(1-(5-(2-Fluorophenyl)pyrimidin-2-yl)-3-(1-hydroxyethyl)-1H-indol-6-yl)(morpholino)methanone (faster and slower elution enantiomer)

a) 6-(Morpholine-4-carbonyl)-1H-indole-3-carbaldehyde (1H-Indol-6-yl)(morpholino)methanone (36.0 g, 156.5 mmol) in DMF (540 mL) was added drop wise at 0° C. to a solution of phosphoryl chloride (43.9 mL, 469 mmol) in DMF (884 mL) and the mixture was stirred at room temperature for 4 h. The reaction mixture was then neutralized with saturated sodium hydrogen carbonate solution and extracted with ethyl acetate (3×). The combined organic layers were dried over sodium sulfate and evaporated. The residue was finally purified by column chromatography [100-200 mesh silica; dichloromethane with 10% methanol]. White solid. Yield: 36 g (89% of theory)
HPLC-MS (method 5): $R_t$=1.86 min; m/z [M+H]$^+$=259.1 b) (3-(Hydroxymethyl)-1H-indol-6-yl)(morpholino)methanone

Sodium borohydride (2.2 g, 58.34 mmol) was added at 0° C. portion wise to a suspension of 6-(morpholine-4-carbonyl)-1H-indole-3-carbaldehyde (5 g, 19.44 mmol) in methanol (106 mL) and the mixture was stirred at room temperature for 3 h. The methanol was removed under vacuum whereby the temperature was kept below <35° C. The residue was diluted with water (100 mL) and extracted with ethyl acetate (3×100 mL). The combined organic layers were washed with brine, dried over sodium sulfate and evaporated. Washing of the remnant with ether provided the product as white solid. Yield: 4 g (79% of theory)

HPLC-MS (method 5): $R_t$=1.72 min; m/z [M+H]$^+$=261.2 c) (1-(5-Bromopyrimidin-2-yl)-3-(hydroxymethyl)-1H-indol-6-yl)(morpholino)methanone Potassium tert-butylate (1.72 g, 15.38 mmol) and 5-bromo-2-chloro-pyrimidine (2.97 g, 15.38 mmol) were added to a solution of the indol obtained under b) (4 g, 15.38 mmol) in DMF (57 mL). The resulting mixture was heated at 120° C. for 16 h, then filtered through a pad of celite and washed with ethyl acetate (3×50 mL). The filtrate was washed with water (2×50 mL) and brine (1×50 mL), and evaporated. The residue was purified through flash column chromatography [silica; dichloromethane with 0-4% methanol]. The raw product was triturated with ether/dichloromethane=95/5. White solid. Yield: 3.1 g (48% of theory)

HPLC-MS (method 5): $R_t$=2.84 min; m/z [M+H]$^+$=419.1 d) (1-(5-(2-Fluorophenyl)pyrimidin-2-yl)-3-(hydroxymethyl)-1H-indol-6-yl)(morpholino)methanone Potassium carbonate (4.35 g, 31.58 mmol) was added to the product of c) (4.39 g, 10.52 mmol) in THF/water (4.5:1, 165 mL). The reaction apparatus was flushed with argon and Pd2(dba)3 (0.96 g, 1.052 mmol), tert-butylphosphonium tetrafluoroborate (0.15 g, 0.52 mmol) and 2-fluorophenylboronic acid (1.49 g, 10.52 mmol) were added. The resulting mixture was stirred at 30° C. for 2 h and then filtered through a pad of celite. The celite was washed with dichloromethane (2×75 mL) and the filtrate was concentrated. The remnant was purified by flash column chromatography [silica; dichloromethane with 1.5% methanol]. Yellow solid. Yield: 4 g (88% of theory)

HPLC-MS (method 4): $R_t$=3.0 min; m/z [M+H]$^+$=433.0 e) 1-(5-(2-Fluorophenyl)pyrimidin-2-yl)-6-(morpholine-4-carbonyl)-1H-indole-3-carbaldehyde Dess-Martin periodinane (5.89 g, 13.8 mmol) was added at 0° C. to a solution of the product from the preceding procedure d) (4.0 g, 9.25 mmol) in dichloromethane (250 mL) and the resulting mixture was stirred at room temperature for 30 min. The reaction mixture was then filtered through a pad of celite and the filter was washed with dichloromethane (2×60 mL). The filtrate was concentrated and the residue purified by flash column chromatography [silica; dichloromethane with 0-1.5% methanol]. White solid. Yield: 3 g (75% of theory)

HPLC-MS (method 5): $R_t$=3.27 min; m/z [M+H]$^+$=431.1.

f) (1-(5-(2-Fluorophenyl)pyrimidin-2-yl)-3-(hydroxymethyl)-1H-indol-6-yl)(morpholino)methanone Methyl magnesium iodide (3 M in ether, 5.57 mL, 16.72 mmol) was added at −70° C. to a solution of d) (2.4 g, 5.57 mmol) in THF (163 mL) and the resulting mixture was stirred at −50° C. for 4 h. The reaction mixture was quenched with ammonium chloride solution (50 mL) and extracted with ethyl acetate (2×100 mL). The combined organic layers were washed with brine, dried over sodium sulfate and concentrated. The residue was purified by flash column chromatography [silica; dichloromethane with 0-2% methanol]. Light yellow solid. Yield: 1.9 g (76% of theory; racemate).

HPLC-MS (method 5): $R_t$=3.13 min; m/z [M+H]$^+$=447.3.

The single enantiomers were obtained from the racemate (0.5 g) via chiral SFC (column: Chiracel OJ-H 250×21 mm, 5 μm; column temperature: 35° C.; co-solvent: isopropylamine in acetonitrile=60/40; amount of co-solvent: 0.5%; flow rate: 30 g/min; pressure: 80 bar).

Faster eluting enantiomer (example 252):
Yield: 0.180 g
1H NMR (400 MHz, DMSO-d6, δ ppm): 9.1 (s, 2H), 8.86 (s, 1H), 8.27 (s, 1H), 7.81 (d, 1H, J=8.0 Hz), 7.78-7.74 (m, 1H), 7.5-7.51 (m, 1H), 7.45-7.38 (m, 2H), 7.3 (dd, 1H, J=8.1, 1.1 Hz), 5.27 (d, 1H, J=5.1 Hz), 5.12-5.07 (m, 1H), 3.63 (bs, 8H), 1.54 (d, 3H, J=6.4 Hz).

Slower eluting enantiomer (example 253):
Yield: 0.125 g
1H NMR (400 MHz, DMSO-d6, δ ppm): 9.1 (s, 2H), 8.86 (s, 1H), 8.27 (s, 1H), 7.81 (d, 1H, J=8.0 Hz), 7.78-7.74 (m, 1H), 7.5-7.51 (m, 1H), 7.45-7.38 (m, 2H), 7.3 (dd, 1H, J=8.1, 1.1 Hz), 5.27 (d, 1H, J=5.1 Hz), 5.12-5.07 (m, 1H), 3.63 (bs, 8H), 1.54 (d, 3H, J=6.4 Hz).

EXAMPLES 254 AND 255

(3-(1-Hydroxyethyl)-1-(5-phenylpyrimidin-2-yl)-1H-indol-6-yl)(morpholino)methanone faster and slower elution enantiomer)

Racemic (3-(1-hydroxyethyl)-1-(5-phenylpyrimidin-2-yl)-1H-indol-6-yl)(morpholino)methanone was prepared in three chemical steps from (1-(5-bromopyrimidin-2-yl)-3-(hydroxymethyl)-1H-indol-6-yl)(morpholino)methanone analogously to the procedures for examples 252/253. White solid. Yield: 1.6 g HPLC-MS (method 5): $R_t$=3.04 min; m/z [M+H]$^+$=429.2

The racemate (0.4 g) was submitted to chiral SFC to obtain the single enantiomers (column: Chiracel OJ-H 250×21 mm, 5 μm; column temperature: 35° C.; co-solvent: isopropylamine in acetonitrile=65/35; amount of co-solvent: 0.5%; flow rate: 25 g/min; pressure: 80 bar).

Faster eluting enantiomer (example 254):
Yield: 0.13 g
1H NMR (400 MHz, DMSO-d6, δ ppm): 9.2 (s, 2H), 8.76 (s, 1H), 8.27 (s, 1H), 7.87-7.81 (m, 3H), 7.57-7.45 (m, 3H), 7.3 (d, 1H, J=8.0 Hz), 5.25 (d, 1H, J=4.8 Hz), 5.12-5.06 (m, 1H), 3.63 (bs, 8H), 1.54 (d, 3H, J=6.4 Hz).

Slower eluting enantiomer (example 255):
Yield: 0.10 g
1H NMR (400 MHz, DMSO-d6, δ ppm): 9.2 (s, 2H), 8.76 (s, 1H), 8.27 (s, 1H), 7.87-7.81 (m, 3H), 7.57-7.45 (m, 3H), 7.3 (d, 1H, J=8.0 Hz), 5.25 (d, 1H, J=4.8 Hz), 5.12-5.06 (m, 1H), 3.63 (bs, 8H), 1.54 (d, 3H, J=6.4 Hz).

Synthesis examples 256 to 260 were prepared from (1-(5-bromopyrimidin-2-yl)-3-(methylsulfinyl)-1H-indol-6-yl)(morpholino)methanone and the respective 2-bromo-pyridines in an analogous manner as described for example 50.

EXAMPLE 256

(1-(5-(4-Isopropylpyridin-2-yl)pyrimidin-2-yl)-3-(methylsulfinyl)-1H-indol-6-yl)(morpholino)methanone White solid. Yield: 0.15 g
HPLC-MS (method 5): $R_t$=3.04 min; m/z [M+H]$^+$=490.2

1H NMR (400 MHz, DMSO-d6, 100° C., δ ppm): 9.56 (s, 2H), 8.95 (s, 1H), 8.75 (s, 1H), 8.63 (d, 1H, J=8.0 Hz), 8.03-8.01 (m, 2H), 7.41 (d, 1H, J=8.0 Hz), 7.34 (d, 1H, J=4.8 Hz), 3.67-3.66 (m, 4H), 3.6-3.59 (m, 4H), 3.07-3.01 (m, 4H), 1.32 (d, 6H, J=6.9 Hz).

EXAMPLE 257

(3-(Methylsulfinyl)-1-(5-(4-(prop-1-yn-1-yl)pyridin-2-yl)pyrimidin-2-yl)-1H-indol-6-yl)(morpholino)methanone White solid. Yield: 0.13 g
HPLC-MS (method 5): $R_t$=2.89 min; m/z [M+H]$^+$=486.1
1H NMR (400 MHz, DMSO-d6, 100° C., δ ppm): 9.54 (s, 2H), 8.94 (s, 1H), 8.75 (s, 1H), 8.7 (d, 1H, J=4.8 Hz), 8.11 (s, 1H), 8.03 (d, 1H, J=8.0 Hz), 7.43-7.39 (m, 2H), 3.68-3.66 (m, 4H), 3.6-3.59 (m, 4H), 3.07 (s, 3H), 2.15 (s, 3H).

EXAMPLE 258

(1-(5-(4-Cyclopropylpyridin-2-yl)pyrimidin-2-yl)-3-(methylsulfinyl)-1H-indol-6-yl)(morpholino)methanone White solid. Yield: 0.125 g
HPLC-MS (method 5): $R_t$=2.83 min; m/z [M+H]$^+$=488.3
1H NMR (400 MHz, DMSO-d6, 100° C., δ ppm): 9.54 (s, 2H), 8.94 (s, 1H), 8.75 (s, 1H), 8.54 (d, 1H, J=5.0 Hz), 8.03 (d, 1H, J=8.0 Hz), 7.81 (s, 1H), 7.4 (d, 1H, J=8.1 Hz), 7.16 (d, 1H, J=4.9 Hz), 3.67-3.66 (m, 4H), 3.59-3.58 (m, 4H), 3.06 (s, 3H), 2.08-2.04 (m, 1H), 1.16-1.13 (m, 2H), 0.98-0.96 (m, 2H).

EXAMPLE 259

(1-(5-(4-Ethylpyridin-2-yl)pyrimidin-2-yl)-3-(methylsulfinyl)-1H-indol-6-ethanone White solid. Yield: 0.1 g
HPLC-MS (method 5): $R_t$=2.86 min; m/z [M+H]$^+$=476.3
1H NMR (400 MHz, DMSO-d6, 100° C., δ ppm): 9.54 (s, 2H), 8.96 (s, 1H), 8.75 (s, 1H), 8.63 (bs, 1H), 8.03-7.99 (m, 2H), 7.43-7.41 (m, 1H), 7.32 (bs, 1H), 3.67 (bs, 4H), 3.59 (bs, 4H), 3.07 (s, 3H), 2.81-2.74 (m, 2H), 1.31 (t, 3H, J=7.5 Hz).

EXAMPLE 260

(1-(5-(4-Ethoxypyridin-2-yl)pyrimidin-2-yl)-3-(methylsulfinyl)-1H-indol-6-yl)(morpholino)methanone White solid. Yield: 0.085 g
HPLC-MS (method 5): $R_t$=2.77 min; m/z [M+H]$^+$=492.2
1H NMR (400 MHz, DMSO-d6, 100° C., δ ppm): 9.54 (s, 2H), 8.94 (s, 1H), 8.75 (s, 1H), 8.54 (d, 1H, J=5.7 Hz), 8.03 (d, 1H, J=8.2 Hz), 7.67 (s, 1H), 7.43-7.41 (m, 1H), 7.02-7.0 (m, 1H), 4.3 (q, 2H, J=7 Hz), 3.68-3.66 (m, 4H), 3.6-3.58 (m, 4H), 3.07 (s, 3H), 1.42 (t, 3H, J=6.9 Hz).

EXAMPLE 261

(1-(5-(5-Ethoxy-2-fluorophenyl)pyrimidin-2-yl)-3-(methylsulfinyl)-1H-indol-6-yl)(morpholino)methanone Potassium carbonate (0.185 g, 1.34 mmol) and (Ataphos)2PdCl2 (0.032 g, 0.044 mmol) were added under an argon atmosphere to a solution of (1-(5-bromopyrimidin-2-yl)-3-(methylsulfinyl)-1H-indol-6-yl)(morpholino)methanone (0.2 g, 0.445 mmol) and 2-fluoro-5-ethoxyphenylboronic acid (0.165 g, 0.89 mmol) in tert-amylalcohol (8.0 mL) and water (0.8 mL). The reaction mixture was stirred at 90° C. for 4 h, then cooled to ambient temperatures and filtered over celite. The filtrate was concentrated and the residue purified by flash column chromatography [silica; dichloromethane with 2% methanol]. White solid. Yield: 0.14 g (62% of theory)
HPLC-MS (method 5): $R_t$=3.15 min; m/z [M+H]$^+$=509.3
1H NMR (400 MHz, DMSO-d6, 100° C., δ ppm): 9.15 (s, 2H), 8.92 (s, 1H), 8.74 (s, 1H), 8.03 (d, 1H, J=8.0 Hz), 7.4 (dd, 1H, J=8.0, 1.2 Hz), 7.32-7.27 (m, 2H), 7.07-7.04 (m, 1H), 4.14 (q, 2H, J=6.9 Hz), 3.67-3.65 (m, 4H), 3.59-3.57 (m, 4H), 3.07 (s, 3H), 1.37 (t, 3H, J=7.0 Hz).

EXAMPLE 262

(1-(5-(Benzo[d][1,3]dioxol-5-yl)pyrimidin-2-yl)-3-(methylsulfinyl)-1H-indol-6-yl)(morpholino)methanone Prepared from (1-(5-bromopyrimidin-2-yl)-3-(methylsulfinyl)-1H-indol-6-yl)(morpholino)-methanone (0.3 g, 0.67 mmol) and benzo[1,3]dioxole-5-boronic acid (0.22 g, 1.33 mmol) analogously to synthesis example 261. White solid. Yield: 0.145 g (44% of theory)
HPLC-MS (method 5): $R_t$=2.94 min; m/z [M+H]$^+$=491.3
1H NMR (400 MHz, DMSO-d6, 100° C., δ ppm): 9.18 (s, 2H), 8.9 (s, 1H), 8.72 (s, 1H), 8.01 (d, 1H, J=8.0 Hz), 7.44-7.33 (m, 3H), 7.05 (d, 1H, J=8.0 Hz), 6.09 (s, 2H), 3.67-3.66 (m, 4H), 3.59-3.58 (m, 4H), 3.06 (s, 3H).

EXAMPLE 263

(1-(5-(2-Fluoro-5-(trifluoromethoxy)phenyl)pyrimidin-2-yl)-3-(methylsulfinyl)-1H-indol-6-yl)(morpholino)methanone The product was obtained through a Suzuki-Miyaura reaction of [1-(5-bromo-pyrimidin-2-yl)-3-methanesulfinyl-1H-indol-6-yl]-morpholin-4-yl-methanone (0.2 g, 0.445 mmol) and 2-fluoro-5-trifluoromethoxyphenylboronic acid (0.2 g, 0.89 mmol) analogously to the procedure for synthesis example 261. White solid. Yield: 0.14 g (57% of theory)
HPLC-MS (method 5): $R_t$=3.21 min; m/z [M+H]$^+$=549.1
1H NMR (400 MHz, DMSO-d6, 80° C., δ ppm): 9.19 (s, 2H), 8.92 (s, 1H), 8.75 (s, 1H), 8.02 (d, 1H, J=8.0 Hz), 7.82 (d, 1H, J=4.0 Hz), 7.58-7.54 (m, 2H), 7.41 (d, 1H, J=8.0 Hz), 3.67-3.65 (m, 4H), 3.58-3.57 (m, 4H), 3.07 (s, 3H).

EXAMPLE 264

4-Fluoro-3-(2-(3-(methylsulfinyl)-6-(morpholine-4-carbonyl)-1H-indol-1-yl)pyrimidin-5-yl)phenyl acetate 264a) (1-(5-(2-Fluoro-5-hydroxyphenyl)pyrimidin-2-yl)-3-(methylsulfinyl)-1H-indol-6-yl)(morpholino)methanone Bis(tri-tert-butylphosphine) palladium(0)(0.51 g, 1.0 mmol) was added under an argon atmosphere to a suspension of [1-(5-bromo-pyrimidin-2-yl)-3-methanesulfinyl-1H-indol-6-yl]-morpholin-4-yl-methanone (1.0 g, 2.0 mmol), 2-fluoro-5-hydroxyphenylboronic acid (0.625 g, 4.0 mmol) and potassium fluoride (0.29 g, 5.0 mmol) in dioxane (50 ml).

The reaction mixture was stirred at 90° C. for 4 h and then filtered through a pad of celite. The filter was washed with dichloromethane (2×20 mL) and concentrated. The residue was purified by flash column chromatography [silica; dichloromethane with 2% methanol]. Light yellow solid. Yield: 0.44 g (46% of theory)

HPLC-MS (method 5): $R_t$=2.72 min; m/z [M+H]$^+$=481.4

264b) 4-Fluoro-3-(2-(3-methylsulfinyl)-6-(morpholine-4-carbonyl)-1H-indol-1-yl)pyrimidin-5-yl)phenyl acetate Acetic anhydride (0.18 mL, 1.9 mmol) was added at 0° C. to 264a) (0.45 g, 0.94 mmol) in pyridine (2.0 mL) and the resulting solution was stirred at room temperature for 3 h. The reaction mixture was diluted with cold water and extracted with dichloromethane/methanol (9:1; 3×30 mL). The organic layers were washed with saturated sodium hydrogen carbonate solution (2×20 mL) and brine (20 mL), dried over sodium sulfate and evaporated. The remnant was purified by flash column chromatography [silica; dichloromethane with 1.5% methanol]. Yield: 0.09 g (38% of theory)

HPLC-MS (method 5): $R_t$=2.91 min; m/z [M+H]$^+$=523.2

1H NMR (400 MHz, DMSO-d6, 100° C., δ ppm): 9.15 (s, 2H), 8.92 (s, 1H), 8.74 (s, 1H), 8.03 (d, 1H, J=8.0 Hz), 7.57 (dd, 1H, J=6.8, 2.8 Hz), 7.46-7.41 (m, 2H), 7.32-7.29 (m, 1H), 3.68-3.65 (m, 4H), 3.59-3.57 (m, 4H), 3.07 (s, 3H), 2.31 (s, 3H).

EXAMPLE 265

(1-(5-(2-Fluoro-5-methylphenyl)pyrimidin-2-yl)-3-(methylsulfinyl)-1H-indol-6-yl)(pyrrolidin-1-yl)methanone The synthesis example was prepared from methyl 1-(5-bromopyrimidin-2-yl)-3-(methylthio)-1H-indole-6-carboxylate in four chemical steps comprising a Suzuki reaction with (2-fluoro-5-methylphenyl)boronic acid, an oxidation with m-chloroperoxybenzoic acid, a hydrolysis of the methyl ester under use of lithium hydroxide and finally an amidation with HATU as coupling reagent and pyrrolidine as amine. White solid. Yield: 0.08 g HPLC-MS (method 5): $R_t$=3.2 min; m/z [M+H]$^+$=463.3

1H NMR (400 MHz, DMSO-d6, δ ppm): 9.16 (s, 2H), 9.02 (s, 1H), 8.78 (s, 1H), 8.01 (d, 1H, J=8.16 Hz), 7.6-7.52 (m, 2H), 7.33-7.31 (m, 2H), 3.53-3.46 (m, 4H), 3.08 (s, 3H), 2.38 (s, 3H), 1.91-1.83 (m, 4H).

EXAMPLE 266

N-Ethyl-1-(5-(2-fluoro-5-methylphenyl)pyrimidin-2-yl)-N-methyl-3-(methylsulfinyl)-1H-indole-6-carboxamide Prepared in an analogous manner as synthesis example 265. White solid. Yield: 0.13 g HPLC-MS (method 5): $R_t$=3.27 min; m/z [M+H]$^+$=451.0

1H NMR (400 MHz, DMSO-d6, 100° C., δ ppm): 9.12 (s, 2H), 8.88 (s, 1H), 8.73 (s, 1H), 8.02 (d, 1H, J=8.0 Hz), 7.54 (d, 1H, J=7.7 Hz), 7.39-7.23 (m, 3H), 3.46-3.41 (m, 2H), 3.07 (s, 3H), 3.0 (s, 3H), 2.4 (s, 3H), 1.18 (t, 3H, J=7.0 Hz).

EXAMPLE 267

1-(5-(2-Fluoro-5-methylphenyl)pyrimidin-2-yl)-N,N-dimethyl-3-(methylsulfinyl)-1H-indole-6-carboxamide The synthesis example was obtained from 1-(5-bromopyrimidin-2-yl)-3-(methylthio)-1H-indole-6-carboxylic acid in three chemical steps comprising an amide coupling with HATU as reagent, an oxidation with m-chloroperoxybenzoic acid and a Suzuki reaction with (2-fluoro-5-methylphenyl) boronic acid. White solid. Yield: 0.11 g HPLC-MS (method 7): $R_t$=7.81 min; m/z [M+H]$^+$=437.2

1H NMR (400 MHz, DMSO-d6, δ ppm): 9.16 (s, 2H), 8.91 (s, 1H), 8.77 (s, 1H), 8.01 (d, 1H, J=8.1 Hz), 7.57 (d, 1H, J=7.6 Hz), 7.42-7.29 (m, 3H), 3.08-2.98 (m, 9H), 2.38 (s, 3H).

EXAMPLE 268

1-(5-(2-Fluoro-5-methoxyphenyl)pyrimidin-2-yl)-N,N-dimethyl-3-(methylsulfinyl)-1H-indole-6-carboxamide Suzuki reaction of 1-(5-bromopyrimidin-2-yl)-N,N-dimethyl-3-(methylsulfinyl)-1H-indole-6-carboxamide (0.15 g, 0.37 mmol; intermediate in the preparation of synthesis example 267) with 2-fluoro-5-methoxyphenylboronic acid (0.13 g, 0.74 mmol) in analogy to the procedure detailed for example 261). White solid. Yield: 0.06 g (36% of theory)

HPLC-MS (method 7): $R_t$=7.26 min; m/z [M+H]$^+$=453.1

1H NMR (400 MHz, DMSO-d6, δ ppm): 9.19 (s, 2H), 8.91 (s, 1H), 8.77 (s, 1H), 8.02 (d, 1H, J=8.1 Hz), 7.42-7.31 (m, 3H), 7.1-7.06 (m, 1H), 3.84 (s, 3H), 3.08 (s, 3H), 3.04-2.98 (m, 6H).

EXAMPLE 269

(1-(5-(4-Methylpyridin-2-yl)pyrimidin-2-yl)-3-(methylsulfinyl)-1H-indol-6-yl)(pyrrolidin-1-yl)methanone 269a) Methyl 1-(5-(4-methylpyridin-2-yl)pyrimidin-2-yl)-3-(methylthio)-1H-indole-6-carboxylate PdCl2(dppf) (0.325 g, 0.397 mmol) was added to a suspension of methyl 1-(5-bromopyrimidin-2-yl)-3-(methylthio)-1H-indole-6-carboxylate (3.0 g, 7.96 mmol), bis(pinacolato) diboron (2.26 g, 8.91 mmol) and potassium acetate (2.34 g, 23.87 mmol) in dioxane (80 mL) that was stirred under an argon atmosphere. The reaction mixture was stirred for 1 h at 110° C. and then cooled to room temperature. 2-Bromo-4-methyl-pyridine (2.05 g, 11.93 mmol), 2M potassium carbonate solution (8.0 mL) and tetrakis(triphenylphosphine)palladium(0) (0.46 g, 0.398 mmol) were added at this temperature and the resulting mixture was stirred for 16 h at 100° C. The reaction mixture was filtered through a pad of celite, the filter was washed with dichloromethane/methanol (9:1) and the filtrate was concentrated under reduced pressure. The remnant was purified by column chromatography [100-200 mesh silica; dichloromethane ethyl acetate/hexane=5/20/75]. Yellow solid. Yield: 2.0 g (64% of theory)

HPLC-MS (method 5): $R_t$=4.50 min; m/z [M+H]$^+$=391.3

269b) 1-(5-(4-Methylpyridin-2-yl)pyrimidin-2-yl)-3-(methylthio)-1H-indole-6-carboxylic acid Lithium hydroxide monohydrate (0.27 g, 6.4 mmol) was added to an ice-cooled suspension of the methyl ester 269a)

(1.0 g, 2.56 mmol) in THF/water (1:1, 50 mL) and the resulting mixture was stirred at room temperature for 16 h. The solvent was removed under vacuum, and the residue was dissolved in water (20 mL) and washed with dichloromethane (2×20 mL). The aqueous phase was acidified with sodium hydrogen sulfate and extracted with dichloromethane (3×50 mL). The combined organic layers were dried over sodium sulfate and evaporated to dryness. White solid. Yield: 0.9 g (93% of theory)

HPLC-MS (method 5): $R_t$=3.05 min; m/z [M+H]$^+$=377.2

269c) (1-(5-(4-Methylpyridin-2-yl)pyrimidin-2-yl)-3-(methylthio)-1H-indol-6-yl)(pyrrolidin-1-yl)methanone HATU (0.36 g, 0.95 mmol), diisopropylethylamine (0.41 mL, 2.39 mmol) and pyrrolidine (0.079 mL, 0.96 mmol) were added at 0° C. to a solution of the carboxylic acid 269b) (0.3 g, 0.79 mmol) in DMF (2 mL) and the resulting mixture was stirred at room temperature for 16 h. The reaction mixture was then poured onto water and extracted with dichloromethane (3×20 mL). The combined organic layers were washed with saturated sodium hydrogen carbonate solution and brine, dried over sodium sulfate and evaporated. The remnant was purified by flash column chromatography [silica; dichloromethane with 1% methanol]. White solid. Yield: 0.33 g (97% of theory)

HPLC-MS (method 5): $R_t$=3.93 min; m/z [M+H]$^+$=430.0

269d) (1-(5-(4-Methylpyridin-2-yl)pyrimidin-2-yl)-3-(methylsulfinyl)-1H-indol-6-yl)(pyrrolidin-1-yl)methanone m-Chloroperoxybenzoic acid (77%, 0.14 g, 0.62 mmol) in dichloromethane (10 mL) was added at 0° C. to a solution of 269c) (0.33 g, 0.77 mmol) in dichloromethane (40 mL) and the reaction mixture was stirred at room temperature for 3 h. The mixture was then washed successively with saturated sodium hydrogen carbonate solution (2×20 mL) and brine (1×30 mL), dried over sodium sulfate and evaporated. The residue was purified by flash column chromatography [silica gel; dichloromethane with 2% methanol]. White solid. Yield: 0.215 g (63% of theory)

HPLC-MS (method 5): $R_t$=2.84 min; m/z [M+H]$^+$=446.2

1H NMR (400 MHz, DMSO-d6, 100° C., δ ppm): 9.56 (s, 2H), 9.05 (s, 1H), 8.79 (s, 1H), 8.6 (d, 1H, J=4.8 Hz), 8.05-8 (m, 2H), 7.53 (d, 1H, J=8.1 Hz), 7.31 (d, 1H, J=4.6 Hz), 3.55-3.49 (m, 4H), 3.08 (s, 3H), 2.43 (s, 3H), 1.93-1.84 (m, 4H).

EXAMPLE 270

N,N-Dimethyl-1-(5-(4-methylpyridin-2-yl)pyrimidin-2-yl)-3-(methylsulfinyl)-1H-indole-6-carboxamide Synthesized from 1-(5-(4-methylpyridin-2-yl)pyrimidin-2-yl)-3-(methylthio)-1H-indole-6-carboxylic acid as described for example 269. White solid. Yield: 0.158 g HPLC-MS (method 5): $R_t$=2.70 min; m/z [M+H]$^+$=420.2

1H NMR (400 MHz, DMSO-d6, δ ppm): 9.55 (s, 2H), 8.92 (s, 1H), 8.78 (s, 1H), 8.6 (d, 1H, J=4.9 Hz), 8.04-8.01 (m, 2H), 7.4 (d, 1H, J=8.2 Hz), 7.31 (s, 1H, J=4.7 Hz), 3.05-2.99 (m, 9H), 2.43 (s, 3H).

EXAMPLE 271

N-Ethyl-N-methyl-1-(5-(4-methylpyridin-2-yl)pyrimidin-2-yl)-3-(methylsulfinyl)-1H-indole-6-carboxamide The target compound was obtained from 1-(5-(4-methylpyridin-2-yl)pyrimidin-2-yl)-3-(methylthio)-1H-indole-6-carboxylic acid analogously to synthesis example 269. White solid. Yield: 0.175 g HPLC-MS (method 5): $R_t$=2.79 min; m/z [M+H]$^+$=434.2

1H NMR (400 MHz, DMSO-d6, δ ppm): 9.55 (s, 2H), 8.91 (s, 1H), 8.78 (s, 1H), 8.59 (d, 1H, J=4.8 Hz), 8.04-8.01 (m, 2H), 7.4 (d, 1H, J=7.9 Hz), 7.31 (d, 1H, J=4.5 Hz), 3.51 (bs, 1H), 3.25 (bs, 1H), 3.08 (s, 3H), 3.0 (bs, 3H), 2.43 (s, 3H), 1.08 (bs, 3H).

EXAMPLE 272

1-(5-(4-(Dimethylamino)pyridin-2-yl)pyrimidin-2-yl)-N,N-dimethyl-3-(methylsulfinyl)-1H-indole-6-carboxamide Prepared using the same synthetic route as detailed for synthesis example 269. White solid. Yield: 0.14 g HPLC-MS (method 5): $R_t$=2.70 min; m/z [M+H]$^+$=449.0

1H NMR (400 MHz, DMSO-d6, δ ppm): 9.56 (s, 2H), 8.94 (s, 1H), 8.78 (s, 1H), 8.26 (d, 1H, J=5.9 Hz), 8.01 (d, 1H, J=8.1 Hz), 7.39 (d, 1H, J=8.0 Hz), 7.32 (d, 1H, J=2 Hz), 6.68-6.66 (m, 1H), 3.08-2.99 (m, 15H).

EXAMPLE 273

1-(5-(4-Aminopyridin-2-yl)pyrimidin-2-yl)-N,N-dimethyl-3-(methylsulfinyl)-1H-indole-6-carboxamide 1-(5-Bromopyrimidin-2-yl)-N,N-dimethyl-3-(methylthio)-1H-indole-6-carboxamide was converted into a boronic ester that was reacted in a Suzuki reaction with 2-bromopyridin-4-amine and the resulting product was then oxidized towards the sulfoxide (analogously to the protocols 269a) and 269d), respectively). White solid. Yield: 0.095 g HPLC-MS (method 5): $R_t$=2.28 min; m/z [M+H]$^+$=421.3

1H NMR (400 MHz, DMSO-d6, δ ppm): 9.38 (s, 2H), 8.91 (s, 1H), 8.78 (s, 1H), 8.15 (d, 1H, J=5.2 Hz), 8.01 (d, 1H, J=7.9 Hz), 7.41 (d, 1H, J=7.9 Hz), 6.55 (bs, 1H), 6.26 (bs, 2H), 3.07-2.99 (m, 9H).

Examples 274 to 276 were prepared analogously to synthesis example 265.

EXAMPLE 274

1-(5-(5-Ethyl-2-fluorophenyl)pyrimidin-2-yl)-N,N-dimethyl-3-(methylsulfinyl)-1H-indole-6-carboxamide Light yellow solid. Yield: 95 mg HPLC-MS (method 7): $R_t$=8.40 min; m/z [M+H]$^+$=451

1H NMR (400 MHz, DMSO-d6, δ ppm): 9.18 (s, 2H,), 8.91 (s, 1H), 8.77 (s, 1H), 8.04 (d, 1H, J=8.12 Hz), 7.61-7.59

(m, 1H), 7.42-7.31 (m, 3H), 3.08 (s, 3H), 3.04-2.98 (m, 6H), 2.72-2.66 (m, 2H), 1.26-1.22 (m, 3H).

EXAMPLE 275

(1-(5-(5-Ethyl-2-fluorophenyl)pyrimidin-2-yl)-3-(methylsulfinyl)-1H-indol-6-yl)(pyrrolidin-1-yl)methanone White solid. Yield: 75 mg HPLC-MS (method 7): $R_t$=8.64 min; m/z [M+H]$^+$=477

1H NMR (400 MHz, DMSO-d6, 100° C., δ ppm): 9.13 (s, 2H), 9.01 (s, 1H), 8.73 (s, 1H), 7.99 (d, 1H, J=8.0 Hz), 7.56 (d, 1H, J=7.6 Hz), 7.5 (d, 1H, J=8.0 Hz), 7.36-7.26 (m, 2H), 3.53 (bs, 4H), 3.07 (s, 3H), 2.71 (q, 2H, J=7.6 Hz), 1.9 (bs, 4H), 1.27 (t, 3H, J=7.6 Hz).

EXAMPLE 276

(1-(5-(5-Ethyl-2-fluorophenyl)pyrimidin-2-yl)-3-(methylsulfinyl)-1H-indol-6-yl)(morpholino)methanone Light yellow solid. Yield: 65 mg HPLC-MS (method 5): $R_t$=3.27 min; m/z [M+H]$^+$=493.2

1H NMR (400 MHz, DMSO-d6, δ ppm): 9.18 (s, 2H), 8.94 (s, 1H), 8.78 (s, 1H), 8.03 (d, 1H, J=8.1 Hz), 7.6 (d, 1H, J=7.6 Hz), 7.42 (d, 1H, J=8 Hz), 7.37-7.31 (m, 2H), 3.63-3.5 (m, 8H), 3.08 (s, 3H), 2.68 (q, 2H, J=7.6 Hz), 1.24 (t, 3H, J=7.5 Hz).

EXAMPLE 277

(1-(5-(4-Ethylpyridin-2-yl)pyrimidin-2-yl)-3-(methylsulfinyl)-1H-indol-6-yl)(pyrrolidin-1-yl)methanone Prepared from methyl 1-(5-bromopyrimidin-2-yl)-3-(methylthio)-1H-indole-6-carboxylate analogously to the procedures of synthesis example 269. White solid. Yield: 0.13 g HPLC-MS (method 5): $R_t$=3.08 min; m/z [M+H]$^+$=460.2

1H NMR (400 MHz, DMSO-d6, 100° C., δ ppm): 9.54 (s, 2H), 9.04 (s, 1H), 8.75 (s, 1H), 8.63 (d, 1H, J=4.6 Hz), 8.01 (d, 2H, J=7.7 Hz), 7.53 (d, 1H, J=8.0 Hz), 7.32 (d, 1H, J=4.4 Hz), 3.54 (s, 4H), 3.07 (s, 3H), 2.79-2.74 (m, 2H), 1.91 (s, 4H), 1.33 (m, 3H).

EXAMPLE 278

1-(5-(4-Ethylpyridin-2-yl)pyrimidin-2-yl)-N,N-dimethyl-3-(methylsulfinyl)-1H-indole-6-carboxamide Prepared from 1-(5-(4-ethylpyridin-2-yl)pyrimidin-2-yl)-3-(methylthio)-1H-indole-6-carboxylic acid (intermediate of synthesis example 277) in two steps analogously to example 269. White solid. Yield: 0.18 g HPLC-MS (method 5): $R_t$=2.87 min; m/z [M+H]$^+$=434

1H NMR (400 MHz, DMSO-d6, δ ppm): 9.58 (s, 2H), 8.94 (s, 1H), 8.79 (s, 1H), 8.64 (d, 1H, J=4.8 Hz), 8.07 (m, 2H), 7.43 (d, 1H, J=8.1 Hz), 7.36 (d, 1H, J=4.5 Hz), 3.08 (s, 3H), 3.05-2.99 (m, 6H), 2.76-2.71 (m, 2H), 1.30-1.26 (m, 3H).

EXAMPLE 279

N-(2-Amino-2-oxoethyl)-1-(5-(2-fluoro-5-methoxyphenyl)pyrimidin-2-yl)-N-methyl-3-(methylsulfinyl)-1H-indole-6-carboxamide

279a) N-(2-Amino-2-oxoethyl)-1-(5-bromopyrimidin-2-yl)-N-methyl-3-(methylsulfinyl)-1H-indole-6-carboxamide Diisopropylethylamine (0.34 mL, 1.99 mmol), EDCxHCl (0.19 g, 0.992 mmol) and HOBt ammonium salt (0.15 g, 0.997 mmol) were added to 2-(1-(5-bromopyrimidin-2-yl)-N-methyl-3-(methylsulfinyl)-1H-indole-6-carboxamido) acetic acid (0.3 g, 0.66 mmol, synthesized from 1-(5-bromopyrimidin-2-yl)-3-(methylthio)-1H-indole-6-carboxylic acid in three steps comprising a TBTU mediated amide coupling of methyl 2-(methylamino)acetate hydrochloride, the oxidation of the thioether and the hydrolysis of the methyl ester) in DMF (3.0 mL). The reaction mixture was stirred at room temperature for 16 h, diluted with ice water and extracted with methanol/dichloromethane (5:95; 3×40 mL). The combined organic layers were successively washed with saturated sodium hydrogen carbonate, saturated ammonium chloride solution, and brine, dried over sodium sulfate and concentrated to yield the raw product which was purified by column chromatography [silica; methanol/dichloromethane=5:95]. White solid. Yield: 0.13 g (43% of theory)

HPLC-MS (method 7): $R_t$=4.84 min; m/z [M+H]$^+$=450.0

279b) N-(2-Amino-2-oxoethyl)-1-(5-(2-fluoro-5-methoxyphenyl)pyrimidin-2-yl)-N-methyl-3-(methylsulfinyl)-1H-indole-6-carboxamide Potassium carbonate (110 mg, 0.79 mmol) and (Ataphos)2PdCl2 (19 mg, 0.026 mmol) were added under an inert atmosphere to a solution of 279a) (120 mg, 0.26 mmol) and 2-fluoro-5-methoxyphenylboronic acid (91 mg, 0.53 mmol) in tert-amylalcohol (4.0 mL) and water (0.4 mL). The reaction mixture was stirred for 4 h at 95° C., then cooled to ambient temperature and filtered over celite. The filtrate was evaporated to dryness and the residue was purified by flash column chromatography [silica; methanol/dichloromethane=4:96]. White solid. Yield: 35 mg (27% of theory)

HPLC-MS (method 5): $R_t$=2.64 min; m/z [M+H]$^+$=496.2

1H NMR (400 MHz, DMSO-d6, 100° C., δ ppm): 9.14 (s, 2H), 8.94 (s, 1H), 8.73 (s, 1H), 7.99 (d, 1H, J=8.1 Hz), 7.42 (d, 1H, J=8.1 Hz), 7.33-7.28 (m, 2H), 7.09-7.06 (m, 1H), 6.92 (bs, 2H), 4.0 (s, 2H), 3.86 (s, 3H), 3.07 (s, 3H), 3.03 (s, 3H).

EXAMPLE 280

N-(2-Amino-2-oxoethyl)-1-(5-(5-ethyl-2-fluorophenyl)pyrimidin-2-yl)-N-methyl-3-(methylsulfinyl)-1H-indole-6-carboxamide Prepared from N-(2-amino-2-oxoethyl)-1-(5-bromopyrimidin-2-yl)-N-methyl-3-(methylsulfinyl)-1H-indole-6-carboxamide analogously to synthesis example 279). White solid. Yield: 85 mg, HPLC-MS (method 5): $R_t$=2.93 min; m/z [M+H]$^+$=494.1

1H NMR (400 MHz, DMSO-d6, 100° C., δ ppm): 9.13 (s, 2H), 8.94 (s, 1H), 8.73 (s, 1H), 7.99 (d, 1H, J=8.1 Hz), 7.58-7.56 (m, 1H), 7.44-7.26 (m, 3H), 6.92 (bs, 2H), 4.0 (s, 2H), 3.07 (s, 3H), 3.03 (s, 3H), 2.72 (q, 2H, J=7.4 Hz), 1.28 (t, 3H, J=7.5 Hz).

EXAMPLE 281

N-(2-Amino-2-oxoethyl)-1-(5-(2-fluoro-5-methylphenyl)pyrimidin-2-yl)-N-methyl-3-(methylsulfinyl)-1H-indole-6-carboxamide Methyl 1-(5-bromopyrimidin-2-yl)-3-(methylthio)-1H-indole-6-carboxylate and 2-fluoro-5-methylphenylboronic acid were submitted to a Suzuki reaction as described under 279b). The resulting coupling product was oxidized (m-CPBA) to the corresponding sulfoxide, transformed into its carboxylic acid (LiOH/THF/water) and then reacted with methyl 2-(methylamino)acetate hydrochloride (TBTU). Ester hydrolysis of the product methyl 2-(1-(5-(2-fluoro-5-methylphenyl)pyrimidin-2-yl)-N-methyl-3-(methylsulfinyl)-1H-indole-6-carboxamido)acetate, and subsequent reaction with HOBt ammonium salt provided the target compound as white solid. Yield: 0.13 g HPLC-MS (method 5): $R_t$=2.76 min; m/z [M+H]$^+$=480.3
1H NMR (400 MHz, DMSO-d6, 100° C., δ ppm): 9.11 (s, 2H), 8.94 (s, 1H), 8.73 (s, 1H), 7.98 (d, 1H, J=8.2 Hz), 7.55 (d, 1H, J=7.2 Hz), 7.42 (d, 1H, J=8.1 Hz), 7.33-7.24 (m, 2H), 6.93 (bs, 2H), 4.0 (s, 2H), 3.07 (s, 3H), 3.03 (s, 3H), 2.4 (s, 3H).

EXAMPLE 282

N-(2-Amino-2-oxoethyl)-N-methyl-1-(5-(4-methylpyridin-2-yl)pyrimidin-2-yl)-3-(methylsulfinyl)-1H-indole-6-carboxamide The synthesis example was obtained from 1-(5-(4-methylpyridin-2-yl)pyrimidin-2-yl)-3-(methylthio)-1H-indole-6-carboxylic acid in two steps comprising a TBTU mediated coupling of methyl 2-(methylamino)acetate hydrochloride and a subsequent oxidation under use of m-chloroperoxybenzoic acid. White solid. Yield: 0.08 g HPLC-MS (method 5): $R_t$=2.39 min; m/z [M+H]$^+$=462.3
1H NMR (400 MHz, DMSO-d6, 100° C., δ ppm): 9.52 (s, 2H), 8.96 (s, 1H), 8.74 (s, 1H), 8.6 (d, 1H, J=4.5 Hz), 8.0-7.98 (m, 2H), 7.42 (d, 1H, J=8.1 Hz), 7.29 (d, 1H, J=3.6 Hz), 6.93 (bs, 2H), 4.09 (s, 2H), 3.07 (s, 3H), 3.04 (s, 3H), 2.32 (s, 3H).

EXAMPLE 283

N-(2-Amino-2-oxoethyl)-1-(5-(4-methoxypyridin-2-yl)pyrimidin-2-yl)-N-methyl-3-(methylsulfinyl)-1H-indole-6-carboxamide 283a) N-(2-Amino-2-oxoethyl)-1-(5-(4-methoxypyridin-2-yl)pyrimidin-2-yl)-N-methyl-3-(methylthio)-1H-indole-6-carboxamide PdCl2(dppf) (0.094 g, 0.115 mmol) was added under an argon atmosphere to a suspension of N-(2-amino-2-oxoethyl)-1-(5-bromopyrimidin-2-yl)-N-methyl-3-(methylthio)-1H-indole-6-carboxamide (1.0 g, 2.3 mmol), bis(pinacolato)diboron (0.655 g, 2.58 mmol) and potassium acetate (0.68 g, 6.91 mmol) in dioxane (40 mL) and the mixture was stirred at 110° C. for 1 h. After cooling to room temperature, 2-bromo-4-ethoxy-pyridine (0.65 g, 3.45 mmol), a 2M potassium carbonate solution (8.0 mL) and tetrakis(triphenylphosphine)palladium(0) (0.133 g, 0.115 mmol) were added. The reaction mixture was stirred at 100° C. for 16 h, and then filtered through celite. The filter was washed with methanol/dichloromethane (1:9), the filtrate was concentrated and the residue purified by flash column chromatography [silica; methanol/dichloromethane=3.5:96.5]. White solid. Yield: 0.185 g HPLC-MS (method 7): $R_t$=7.48 min; m/z [M+H]$^+$=463.2

283b) N-(2-Amino-2-oxoethyl)-1-(5-(4-methoxypyridin-2-yl)pyrimidin-2-yl)-N-methyl-3-(methylsulfinyl)-1H-indole-6-carboxamide Oxidation of 283a) with m-chloroperoxybenzoic acid (0.18 g, 0.39 mmol). White solid. Yield: 0.065 g (35% of theory)

HPLC-MS (method 7): $R_t$=5.15 min; m/z [M+H]$^+$=479.0
1H NMR (400 MHz, DMSO-d6, 100° C., δ ppm): 9.54 (s, 2H), 8.96 (s, 1H), 8.74 (s, 1H), 8.55 (d, 1H, J=5.6 Hz), 7.98 (d, 1H, J=8.1 Hz), 7.69 (d, 1H, J=1.6 Hz), 7.42 (d, 1H, J=8 Hz), 7.03 (d, 1H, J=1.8 Hz), 6.93 (bs, 2H), 4.0 (s, 2H), 3.97 (s, 3H), 3.07 (s, 3H), 3.04 (s, 3H).

Examples 284 and 285 were prepared analogously to example 283:

EXAMPLE 284

N-(2-Amino-2-oxoethyl)-1-(5-(4-(dimethylamino)pyridin-2-yl)pyrimidin-2-yl)-N-methyl-3-(methylsulfinyl)-1H-indole-6-carboxamide White solid. Yield: 86 mg
HPLC-MS (method 7): $R_t$=5.17 min; m/z [M+H]$^+$=492.4
1H NMR (400 MHz, DMSO-d6, δ ppm): 9.57 (s, 2H), 8.96 (s, 1H), 8.77 (s, 1H), 8.27 (d, 1H, J=5.7 Hz), 8.05-7.99 (m, 1H), 7.47-7.32 (m, 3H), 7.13 (bs, 1H), 6.67 (d, 1H, J=4.3 Hz), 4.08 (s, 1H), 3.87 (s, 1H), 3.07-3.0 (m, 12H).

EXAMPLE 285

N-(2-Amino-2-oxoethyl)-1-(5-(4-ethylpyridin-2-yl)pyrimidin-2-yl)-N-methyl-3-(methylsulfinyl)-1H-indole-6-carboxamide White solid. Yield: 0.066 g
HPLC-MS (method 7): $R_t$=6.03 min; m/z [M+H]$^+$=477.1
1H NMR (400 MHz, THF-d8+1drop D$_2$O, δ ppm): 9.54 (s, 2H), 9.15 (s, 1H), 8.88 (s, 1H), 8.59 (d, 1H, J=4.9 Hz), 8.02 (bs, 2H), 7.53 (bs, 1H), 7.28 (d, 1H, J=4.7 Hz), 4.24-4.0 (m, 2H), 3.11 (s, 3H), 3.08 (s, 3H), 2.78 (q, 2H, J=7.3 Hz), 1.3 (t, 3H, J=7.5 Hz).

EXAMPLE 286

N-(2-Amino-2-oxoethyl)-1-(5-(4-aminopyridin-2-yl)pyrimidin-2-yl)-N-methyl-3-(methylsulfinyl)-1H-indole-6-carboxamide Methyl 1-(5-(4-aminopyridin-2-yl)pyrimidin-2-yl)-3-(methylthio)-1H-indole-6-carboxylate was treated with m-chloroperoxybenzoic acid, the methyl ester of the resulting sulfoxide was saponified next, and the liberated carboxylic acid was coupled with methyl 2-(methylamino)acetate hydrochloride providing thereby the target compound. White solid. Yield: 60 mg HPLC-MS (method 5): $R_t$=1.82 min; m/z [M+H]$^+$=464.4
1H NMR (400 MHz, DMSO-d6, δ ppm): 9.39-9.37 (m, 2H), 8.95 (s, 1H), 8.77 (s, 1H), 8.17 (d, 1H, J=5.5 Hz), 8.04-7.99 (m, 1H), 7.5-7.37 (m, 2H), 7.18-7.12 (m, 2H), 6.54 (d, 1H, J=4.3 Hz), 6.26 (bs, 2H), 4.08 (s, 1H), 3.87 (s, 1H), 3.07 (s, 3H), 3.01 (s, 3H).

EXAMPLE 287

(1-(5-(2-Fluorophenyl)pyrimidin-2-yl)-3-(S-methyl-sulfonimidoyl)-1H-indol-6-yl)(morpholino)methanone

287a) 2,2,2-Trifluoro-N-{methyl[1-[5-(2-fluorophenyl)pyrimidin-2-yl]-6-(morpholin-4-ylcarbonyl)-1H-indol-3-yl]oxido-λ⁴-sulfanylidene}acetamide Iodobenzene diacetate (0.96 g, 1.72 mmol) was added to a stirred suspension of (1-(5-(2-fluorophenyl)pyrimidin-2-yl)-3-(methylsulfinyl)-1H-indol-6-yl)(morpholino)methanone (0.7 g, 1.5 mmol; example 1), magnesium(II) oxide (0.27 g, 6.6 mmol), rhodium(II) acetate dimer (0.066 g, 0.15 mmol) and 2,2,2-trifluoro acetamide (0.37 g, 3.3 mmol) in dioxane (7 mL) at 40° C. and the resulting mixture was stirred at this temperature for 30 min. The reaction mixture was cooled to room temperature, the solvent was evaporated and the remnant was purified by flash chromatography [silica; dichloromethane with 1% methanol]. White solid. Yield: 0.3 g (35% of theory)

HPLC-MS (method 5): $R_t$=3.43 min; m/z [M+H]⁺=576.1

287b) (1-(5-(2-Fluorophenyl)pyrimidin-2-yl)-3-(S-methylsulfonimidoyl)-1H-indol-6-yl)(morpholino)methanone Potassium carbonate (0.143 g, 1.04 mmol) was added at room temperature to a stirred suspension of 287a) (0.3 g, 0.52 mmol) in acetonitrile/methanol (1:1, 9.6 mL) and the mixture was stirred for 1 h. The solvents were evaporated and the residue was purified by column chromatography [alumina; dichloromethane with 1% methanol] and washed with ether. Pink solid. Yield: 0.12 g (48% of theory)

HPLC-MS (method 5): $R_t$=2.81 min; m/z [M+H]⁺=480.1
1H NMR (400 MHz, DMSO-d6, δ ppm): 9.22 (s, 2H), 8.92 (s, 1H), 8.8 (s, 1H), 8.04 (d, 1H, J=8.1 Hz), 7.79 (t, 1H, J=7.2 Hz), 7.6-7.54 (m, 1H), 7.49-7.4 (m, 3H), 4.64 (s, 1H), 3.63-3.47 (m, 8H), 3.24 (s, 3H).

EXAMPLE 288

(1-(5-(4-Methylpyridin-2-yl)pyrimidin-2-yl)-3-(S-methylsulfonimidoyl)-1H-indol-6-yl)(morpholino)methanone Prepared from (1-(5-(4-methylpyridin-2-yl)pyrimidin-2-yl)-3-(methylsulfinyl)-1H-indol-6-yl)(morpholino)methanone (0.4 g, 0.87 mmol, example 142) in two steps analogously to synthesis example 287.

White solid. Yield: 0.09 g

HPLC-MS (method 5): $R_t$=2.66 min; m/z [M+H]⁺=476.9
1H NMR (400 MHz, DMSO-d6, δ ppm): 9.59 (s, 2H), 8.94 (s, 1H), 8.81 (s, 1H), 8.61 (d, 1H, J=4.9 Hz), 8.06-8.04 (m, 2H), 7.49-7.47 (m, 1H), 7.32 (d, 1H, J=4.7 Hz), 4.65 (s, 1H), 3.65 (bs, 8H), 3.24 (s, 3H), 2.32 (s, 3H).

EXAMPLE 289

(1-(5-(4-(2-Hydroxypropan-2-yl)pyridin-2-yl)pyrimidin-2-yl)-3-(methylsulfinyl)-1H-indol-6-yl)(morpholino)methanone

289a) (1-(5-(4-(2-Hydroxypropan-2-yl)pyridin-2-yl)pyrimidin-2-yl)-3-(methylthio)-1H-indol-6-yl)(morpholino)methanone Bis(pinacolato)diboron (0.52 g, 2.08 mmol) and potassium acetate (0.34 g, 3.46 mmol) were added at room temperature to a solution of (1-(5-bromopyrimidin-2-yl)-3-(methylthio)-1H-indol-6-yl)(morpholino)methanone (0.5 g, 1.15 mmol) in dry dioxane (20 mL). The reaction apparatus was set under an inert atmosphere, PdCl2(dppf) (47 mg, 0.057 mmol) was added and the reaction mixture was stirred at 110° C. for 40 min. After cooling to ambient temperature, 2-(2-bromo-pyridin-4-yl)-propan-2-ol (0.37 g, 1.73 mmol), 2M aqueous potassium carbonate solution (2 mL) and tetrakis(triphenylphosphine)palladium(0) (67 mg, 0.057 mmol) were added. The reaction mixture was stirred at 100° C. for 2 h, then cooled to room temperature and filtered through a sintered funnel. The filtrate was concentrated and the remnant was purified by flash column chromatography [silica; dichloromethane with 3% methanol]. Light yellow solid. Yield: 0.18 g (33% of theory)

Mass spectroscopy: m/z [M+H]⁺=490.3

Treatment of 289a) (0.18 g, 0.38 mmol) with m-chloroperoxybenzoic acid in dichloromethane provided the target compound. Light yellow solid. Yield: 65 mg (34% of theory)

HPLC-MS (method 5): $R_t$=2.44 min; m/z [M+H]⁺=506.1
1H NMR (400 MHz, DMSO-d6, δ ppm): 9.59 (s, 2H), 8.96 (s, 1H), 8.80 (s, 1H), 8.69 (d, 1H, J=5 Hz), 8.18 (s, 1H), 8.05 (d, 1H, J=8.1 Hz), 7.58 (d, 1H, J=4.9 Hz), 7.44 (d, 1H, J=8.1 Hz), 5.37 (s, 1H), 3.64 (bs, 8H), 3.08 (s, 3H), 1.51 (s, 6H).

EXAMPLE 290

(1-(5-(5-(((Cyclopropylmethyl)amino)-2-fluorophenyl)pyrimidin-2-yl)-3-(methylsulfinyl)-1H-indol-6-yl)(morpholino)methanone Prepared from (1-(5-bromopyrimidin-2-yl)-3-(methylthio)-1H-indol-6-yl)(morpholino)methanone and 3-bromo-N-(cyclopropylmethyl)-4-fluoroaniline analogously to synthesis example 289. White solid. Yield: 45 mg HPLC-MS (method 5): $R_t$=3.17 min; m/z [M+H]⁺=534.1
1H NMR (400 MHz, DMSO-d6, δ ppm): 9.12 (s, 2H), 8.93 (s, 1H), 8.77 (s, 1H), 8.05 (d, 1H, J=8.1 Hz), 7.43 (d, 1H, J=8.1 Hz), 7.15 (t, 1H, J=9.6 Hz), 6.8-6.79 (m, 1H), 6.73-6.7 (m, 1H), 5.8-5.77 (m, 1H), 3.63 (bs, 8H), 3.07 (s, 3H), 2.96 (t, 2H, J=6.0 Hz), 1.07 (bs, 1H), 0.49-0.46 (m, 2H), 0.24-0.2 (m, 2H).

EXAMPLE 291

(1-(5-(4-(1-Hydroxyethyl)pyridin-2-yl)pyrimidin-2-yl)-3-(methylsulfinyl)-1H-indol-6-yl)(morpholino)methanone Synthesized from (1-(5-bromopyrimidin-2-yl)-3-(methylthio)-1H-indol-6-yl)(morpholino) methanone and 1-(2-bromopyridin-4-yl)ethanol analogously to example 289. White solid. Yield: 0.15 g HPLC-MS (method 5): $R_t$=2.36 min; m/z [M+H]⁺=492.2
1H NMR (400 MHz, DMSO-d6, δ ppm): 9.57 (s, 2H), 8.95 (s, 1H), 8.79 (s, 1H), 8.69 (d, 1H, J=4.9 Hz), 8.11 (s, 1H), 8.05 (d, 1H, J=8.1 Hz), 7.47-7.41 (m, 2H), 5.53 (d, 1H, J=4.3 Hz), 4.86 (t, 1H, J=5.6 Hz), 3.65 (bs, 8H), 3.07 (s, 3H), 1.43 (d, 3H, J=6.5 Hz).

EXAMPLE 292

(1-(5-(5-(Ethylamino)-2-fluorophenyl)pyrimidin-2-yl)-3-(methylsulfinyl)-1H-indol-6-yl)(morpholino)methanone Prepared from (1-(5-bromopyrimidin-2-yl)-3-(methylthio)-1H-indol-6-yl)(morpholino)methanone and 3-bromo-N-ethyl-4-fluoroaniline analogously to synthesis example 289. White solid. Yield: 130 mg HPLC-MS (method 5): $R_t$=3.09 min; m/z [M+H]$^+$=508.8
1H NMR (400 MHz, DMSO-d6, δ ppm): 9.12 (s, 2H), 8.93 (s, 1H), 8.77 (s, 1H), 8.05 (d, 1H, J=8.1 Hz), 7.43 (d, 1H, J=8.1 Hz), 7.16 (t, 1H, J=9.6 Hz), 6.77-6.75 (m, 1H), 6.68-6.66 (m, 1H), 5.68 (t, 1H, J=5.2 Hz), 3.63 (bs, 8H), 3.12-3.05 (m, 5H), 1.20 (t, 3H, J=7.0 Hz).

EXAMPLE 293

(1-(5-(2-Fluoro-5-(2-hydroxypropan-2-yl)phenyl) pyrimidin-2-yl)-3-(methylsulfinyl)-1H-indol-6-yl) (morpholino)methanone Prepared from (1-(5-bromopyrimidin-2-yl)-3-(methylthio)-1H-indol-6-yl)(morpholino)methanone and 2-(3-bromo-4-fluorophenyl)propan-2-ol analogously to synthesis example 289. Light yellow solid. Yield: 65 mg HPLC-MS (method 5): $R_t$=2.80 min; m/z [M+H]$^+$=523.6
1H NMR (400 MHz, DMSO-d6, δ ppm): 9.18 (s, 2H), 8.94 (s, 1H), 8.78 (s, 1H), 8.05 (d, 1H, J=8 Hz), 7.78 (d, 1H, J=5.6 Hz), 7.63 (bs, 1H), 7.43 (d, 1H, J=7.9 Hz), 7.37 (t, 1H, J=10.1 Hz), 5.19 (s, 1H), 3.64 (bs, 8H), 3.08 (s, 3H), 1.49 (s, 6H).

EXAMPLE 294

(1-(5-(2-Fluoro-5-(1-hydroxycyclopropyl)phenyl) pyrimidin-2-yl)-3-(methylsulfinyl)-1H-indol-6-yl) (morpholino)methanone Prepared from (1-(5-bromopyrimidin-2-yl)-3-(methylthio)-1H-indol-6-yl)(morpholino)methanone and 1-(3-bromo-4-fluorophenyl)cyclopropanol analogously to synthesis example 289. White solid. Yield: 50 mg HPLC-MS (method 7): $R_t$=6.67 min; m/z [M+H]$^+$=521
1H NMR (400 MHz, DMSO-d6, δ ppm): 9.17 (s, 2H), 8.94 (s 1H), 8.78 (s, 1H), 8.05 (d, 1H, J=8.0 Hz), 7.47-7.41 (m, 3H), 7.37-7.33 (m, 1H), 6.07 (s, 1H), 3.63 (bs, 8H), 3.08 (s, 3H), 1.15-1.12 (m, 2H), 1.09-1.06 (m, 2H).

EXAMPLE 295

(1-(5-(4-(1-Hydroxycyclopropyl)pyridin-2-yl)pyrimidin-2-yl)-3-(methylsulfinyl)-1H-indol-6-yl)(morpholino)methanone Prepared from (1-(5-bromopyrimidin-2-yl)-3-(methylthio)-1H-indol-6-yl)(morpholino)methanone and 1-(2-chloropyridin-4-yl)cyclopropanol analogously to synthesis example 289. White solid. Yield: 78 mg HPLC-MS (method 5): $R_t$=2.64 min; m/z [M+H]$^+$=504
1H NMR (400 MHz, DMSO-d6, δ ppm): 9.57 (s, 2H), 8.96 (s, 1H), 8.79 (s, 1H), 8.63 (d, 1H, J=5 Hz), 8.05 (d, 1H, J=8.1 Hz), 7.77 (s, 1H), 7.43-7.41 (m, 2H), 6.27 (bs, 1H), 3.64 (bs, 8H), 3.07 (s, 3H), 1.28-1.26 (m, 4H).

EXAMPLE 296

(1-(5-(4-((Cyclopropylmethyl)amino)pyridin-2-yl) pyrimidin-2-yl)-3-(methylsulfinyl)-1H-indol-6-yl) (morpholino)methanone 296a) (1-(5-(4-Chloropyridin-2-yl)pyrimidin-2-yl)-3-(methylthio)-1H-indol-6-yl)(morpholino)methanone Coupling of (1-(5-bromopyrimidin-2-yl)-3-(methylthio)-1H-indol-6-yl)(morpholino) methanone and 2-bromo-4-chloropyridine analogously in an analogous manner as described for 289a). White solid. Yield: 1.7 g (79% of theory)

HPLC-MS (method 5): $R_t$=3.77 min; m/z [M+H]$^+$=466.3

296b) (1-(5-(4-((Cyclopropylmethyl)amino)pyridin-2-yl)pyrimidin-2-yl)-3-(methylthio)-1H-indol-6-yl) (morpholino)methanone Cesium carbonate (0.62 g, 1.89 mmol), BINAP (64 mg, 0.10 mmol) and palladium(II) acetate (19.3 mg, 0.086 mmol) were added at room temperature and under an argon atmosphere to a solution of cyclopropyl methyl amine (0.07 mL, 0.86 mmol) and of 296a) (0.40 g, 0.86 mmol) in dry dioxane (16 mL). The reaction mixture was stirred at 90° C. for 16 h, then cooled to room temperature and filtered through a sintered funnel. The filtrate was evaporated and the remnant was purified by flash column chromatography [silica; dichloromethane with 3% methanol]. White solid. Yield: 0.25 g (58% of theory)

HPLC-MS (method 5): $R_t$=3.61 min; m/z [M+H]$^+$=501.2

296c) (1-(5-(4-((Cyclopropylmethyl)amino)pyridin-2-yl)pyrimidin-2-yl)-3-(methylsulfinyl)-1H-indol-6-yl)(morpholino)methanone Oxidation of 296b) (0.25 g, 0.49 mmol) with m-chloroperoxybenzoic acid in dichloromethane. White solid. Yield: 80 mg (31% of theory)

HPLC-MS (method 5): $R_t$=2.81 min; m/z [M+H]$^+$=517.4
1H NMR (400 MHz, DMSO-d6, 100° C., δ ppm): 9.43 (s, 2H), 8.94 (s, 1H), 8.74 (s, 1H), 8.2 (d, 1H, J=5.7 Hz), 8.03 (d, 1H, J=8.1 Hz), 7.42 (d, 1H, J=8.0 Hz), 7.20 (s, 1H), 6.63-6.61 (m, 1H), 6.50 (s, 1H), 3.67 (bs, 4H), 3.59 (bs, 4H), 3.14 (t, 2H, J=5.8 Hz), 3.06 (s, 3H), 1.13-1.06 (m, 1H), 0.55 (d, 2H, J=7.9 Hz), 0.30 (d, 2H, J=4.5 Hz).

The examples 297 and 298 were synthesized from (1-(5-(4-chloropyridin-2-yl)pyrimidin-2-yl)-3-(methylthio)-1H-indol-6-yl)(morpholino)methanone analogously.

EXAMPLE 297

(3-(Methylsulfinyl)-1-(5-(4-(pyrrolidin-1-yl)pyridin-2-yl)pyrimidin-2-yl)-1H-indol-6-yl)(morpholino) methanone White solid. Yield: 70 mg
HPLC-MS (method 5): $R_t$=2.84 min; m/z [M+H]$^+$=517.4
1H NMR (400 MHz, DMSO-d6, 100° C., δ ppm): 9.50 (s, 2H), 8.94 (s, 1H), 8.74 (s, 1H), 8.27 (d, 1H, J=5.8 Hz), 8.03 (d, 1H, J=8.1 Hz), 7.42 (d, 1H, J=8.1 Hz), 7.14 (s, 1H), 6.54-6.52 (m, 1H), 3.68-3.66 (m, 4H), 3.60-3.57 (m, 4H), 3.43-3.40 (m, 4H), 3.06 (s, 3H), 2.05-2.02 (m, 4H).

EXAMPLE 298

(1-(5-(4-(Ethylamino)pyridin-2-yl)pyrimidin-2-yl)-3-(methylsulfinyl)-1H-indol-6-yl)(morpholino) methanone White solid. Yield: 97 mg
HPLC-MS (method 5): $R_t$=2.61 min; m/z [M+H]$^+$=491
1H NMR (400 MHz, DMSO-d6, 100° C., δ ppm): 9.43 (s, 2H), 8.94 (s, 1H), 8.74 (s, 1H), 8.20 (d, 1H, J=4.9 Hz), 8.03 (d, 1H, J=8.1 Hz), 7.42 (d, 1H, J=7.6 Hz), 7.15 (s, 1H), 6.57 (bs, 1H), 6.39 (bs, 1H), 3.67 (bs, 4H), 3.58 (bs, 4H), 3.27-3.24 (m, 2H), 3.07 (s, 3H), 1.25-1.21 (m, 3H).

EXAMPLE 299

(1-(5-(4-Chloropyridin-2-yl)pyrimidin-2-yl)-3-(methylsulfinyl)-1H-indol-6-yl)(morpholino)methanone Prepared from (1-(5-bromopyrimidin-2-yl)-3-(methylsulfinyl)-1H-indol-6-yl)(morpholino)-methanone (0.5 g, 1.11 mmol) and 2-bromo-4-chloropyridine (0.23 g, 1.22 mmol) analogously to the experimental procedure for 289a). White solid. Yield: 61 mg (11% of theory)

HPLC-MS (method 5): $R_t$=2.89 min; m/z [M+H]$^+$=482

1H NMR (400 MHz, DMSO-d6, δ ppm): 9.61 (s, 2H), 8.95 (s, 1H), 8.79 (s, 1H), 8.75 (d, 1H, J=5.3 Hz), 8.40 (d, 1H, J=1.4 Hz), 8.06 (d, 1H, J=8.16 Hz), 7.65-7.63 (m, 1H), 7.45 (d, 1H, J=8.5 Hz), 3.65 (bs, 8H), 3.08 (s, 3H).

EXAMPLE 300

(1-(5-(4-(1-Hydroxyethyl)pyridin-2-yl)pyrimidin-2-yl)-3-(methylsulfinyl)-1H-indol-6-yl)(morpholino)methanone

300a) Methyl 1-(5-(2-fluoro-5-(1-hydroxyethyl)phenyl)pyrimidin-2-yl)-3-(methylthio)-1H-indole-6-carboxylate Synthesized from methyl 1-(5-bromopyrimidin-2-yl)-3-(methylthio)-1H-indole-6-carboxylate (1.0 g, 2.65 mmol) and 1-(3-bromo-4-fluorophenyl)ethanol (0.87 g, 3.98 mmol) analogously to the experimental procedure 289a). Yellow solid. Yield: 1.0 g (89% of theory)

HPLC-MS (method 5): $R_t$=3.98 min; m/z [M+H]$^+$=438.1

300b) 1-(5-(2-Fluoro-5-(1-hydroxyethyl)phenyl)pyrimidin-2-yl)-3-(methylthio)-1H-indole-6-carboxylic acid Lithium hydroxide monohydrate (0.30 g, 7.07 mmol) was added at room temperature to a solution of 300a) (1.0 g, 2.36 mmol) in THF/water (1:1, 40 mL). The reaction mixture was stirred at this temperature for 16 h and then concentrated. The residue was diluted with water (20 mL) and washed with ethyl acetate (2×30 mL). The aqueous phase was adjusted with sodium hydrogen sulfate to a pH value of 2. The precipitating solid was filtered off through a sintered funnel and residual water was removed by azeotropic distillation with toluene. Light brown solid. Yield: 0.75 g (75% of theory)

HPLC-MS (method 5): $R_t$=2.95 min; m/z [M+H]$^+$=424.3

300c) (1-(5-(2-Fluoro-5-(1-hydroxyethyl)phenyl)pyrimidin-2-yl)-3-(methylthio)-1H-indol-6-yl)(morpholino)methanone HATU (0.38 g, 0.99 mmol), diisopropylethylamine (0.41 mL, 2.48 mmol) and morpholine (0.08 mL, 0.99 mmol) were added at 0° C. to a solution of 300b) (0.35, 0.83 mmol) in dry DMF (2 mL). The reaction mixture was stirred at room temperature for 6 h and then quenched with ice-cold water. The mixture was extracted with dichloromethane (2×50 mL), the combined organic layers were dried over sodium sulfate and the solvent was removed in vacuo. The remnant was purified by flash column chromatography [silica, dichloromethane with 1.5% methanol]. White solid. Yield: 0.32 g (80% of theory)

LC-MS (Method A): m/z [M+H]+=493.3 (MW calc. 492.57); Rt=3.48 min.

HPLC-MS (method 5): $R_t$=3.48 min; m/z [M+H]$^+$=493.3

300d) (1-(5-(4-(1-Hydroxyethyl)pyridin-2-yl)pyrimidin-2-yl)-3-(methylsulfinyl)-1H-indol-6-yl)(morpholino)methanone m-Chloroperoxybenzoic acid (77%, 0.12 g, 0.53 mmol) was added at 0° C. to a solution of 300c) (0.32 g, 0.66 mmol) in dichloromethane (20 mL) and the reaction mixture was stirred at room temperature for 2 h. The mixture was diluted with saturated sodium hydrogen carbonate solution and the aqueous phase was separated and extracted with dichloromethane (2×20 mL). The combined organic layers were dried, the solvent was removed in vacuo and the residue was purified by flash column chromatography [silica; dichloromethane with 2% methanol]. White solid. Yield: 0.20 g (60% of theory)

HPLC-MS (method 5): $R_t$=2.66 min; m/z [M+H]$^+$=509.2

1H NMR (400 MHz, DMSO-d6, δ ppm): 9.19 (s, 2H), 8.94 (s, 1H), 8.78 (s, 1H), 8.05 (d, 1H, J=8.1 Hz), 7.70 (d, 1H, J=7.5 Hz), 7.53-7.50 (m, 1H), 7.44-7.35 (m, 2H), 5.32 (d, 1H, J=4.3 Hz), 4.84-4.81 (m, 1H), 3.64 (m, 8H), 3.08 (s, 3H), 1.40 (d, 3H, J=6.4 Hz).

EXAMPLE 301

(3-(Methylsulfinyl)-1-(5-(4-(pyrrolidin-1-yl)pyridin-2-yl)pyrimidin-2-yl)-1H-indol-6-yl)(morpholino)methanone

301a) (1-(5-(5-Chloro-2-fluorophenyl)pyrimidin-2-yl)-3-(methylthio)-1H-indol-6-yl)(morpholino)methanone Prepared from (1-(5-bromopyrimidin-2-yl)-3-(methylthio)-1H-indol-6-yl)(morpholino)methanone (2.5 g, 5.77 mmol) and 1-bromo-4-chloro-2-fluorobenzene (1.82 g, 8.66 mmol) applying the reaction conditions described under 289a). White solid. Yield: 1.0 g (37% of theory)

HPLC-MS (method 5): $R_t$=4.01 min; m/z [M+H]$^+$=483

301b) 1-(5-(2-Fluoro-5-(pyrrolidin-1-yl)phenyl)pyrimidin-2-yl)-3-(methylthio)-1H-indol-6-yl)(morpholino)methanone Sodium tert-butylate (0.08 g, 0.81 mmol), DavePhos (0.01 mg, 0.031 mmol) and Pd2(dba)3 (0.03 mg, 0.031 mmol) were added at room temperature to a solution of 301a) (0.3 g, 0.62 mmol) and pyrrolidine (0.26 mL, 3.1 mmol) in dry dioxane (15 mL) that was kept under an inert atmosphere. The reaction mixture was stirred at 90° C. for 16 h, then cooled to ambient temperature and filtered through a sintered funnel. The filtrate was evaporated and the residue was purified by flash column chromatography [dichloromethane with 3% methanol]. White solid. Yield: 0.20 g (62% of theory)

HPLC-MS (method 5): $R_t$=4.90 min; m/z [M+H]$^+$=518.2

301c) (3-(Methylsulfinyl)-1-(5-(4-(pyrrolidin-1-yl)pyridin-2-yl)pyrimidin-2-yl)-1H-indol-6-yl)(morpholino)methanone Oxidation of 301b) (0.20 g, 0.39 mmol) with m-chloroperoxybenzoic acid in dichloromethane under conditions described in the preceding experimental section. Light yellow solid. Yield: 31 mg (14% of theory)

Mass spectroscopy: m/z [M+H]$^+$=534.2

1H NMR (400 MHz, DMSO-d6, δ ppm): 9.17 (s, 2H), 8.94 (s, 1H), 8.78 (s, 1H), 8.05 (d, 1H, J=8.1 Hz), 7.43 (d, 1H, J=8.2 Hz), 7.2 (t, J=9.9 Hz, 1H), 6.78-6.76 (m, 1H), 6.64-6.62 (m, 1H), 3.63 (bs, 8H), 3.29-3.28 (m, 4H), 3.08 (s, 3H), 1.97 (bs, 4H).

EXAMPLE 302

(1-(5-(2-Fluorophenyl)pyrimidin-2-yl)-3-(methylsulfinyl)-1H-indol-6-yl)((R)-3-(hydroxymethyl)pyrrolidin-1-yl)methanone Prepared from 1-(5-(2-fluorophenyl)pyrimidin-2-yl)-3-(methylthio)-1H-indole-6-carboxylic acid in two reaction steps comprising a TBTU mediated amide coupling with (R)-pyrrolidin-3-ylmethanol (see also procedure 244c) and an oxidation utilizing m-chloroperoxybenzoic acid as oxidizing agent. Yellow solid. Yield: 0.12 g HPLC-MS (method 5): $R_t$=2.64 min; m/z [M+H]$^+$=478.8

1H NMR (400 MHz, DMSO-d6, δ ppm): 9.19 (s, 2H), 9.02 (s, 1H), 8.79 (s, 1H), 8.03 (d, 1H, J=7.3 Hz), 7.78 (t, 1H, J=7.7 Hz), 7.56-7.52 (m, 2H), 7.47-7.39 (m, 2H), 4.74-4.62 (m, 1H), 3.66-3.61 (m, 1H), 3.53-3.29 (m, 5H, obscured by water signal), 3.08 (s, 3H), 2.38-2.29 (m, 1H), 1.97-1.89 (m, 1H), 1.96-1.89 (m, 1H), 1.71-1.66 (m, 1H).

EXAMPLE 303

(1-(5-(2-Fluorophenyl)pyrimidin-2-yl)-3-(methylsulfinyl)-1H-indol-6-yl)((S)-3-(hydroxymethyl)pyrrolidin-1-yl)methanone White solid. Yield: 70 mg HPLC-MS (method 5): $R_t$=2.79 min; m/z [M+H]$^+$=478.9

1H NMR (400 MHz, DMSO-d6, δ ppm): 9.19 (s, 2H), 9.02 (s, 1H), 8.78 (s, 1H), 8.03-8.01 (m, 1H), 7.80-7.77 (m, 1H), 7.58-7.52 (m, 2H), 7.47-7.39 (m, 2H), 4.74-4.62 (m, 1H), 3.66-3.61 (m, 1H), 3.55-3.46 (m, 3H), 3.39-3.26 (m, 2H), 3.08 (s, 3H), 2.39-2.28 (m, 1H), 1.98-1.87 (m, 1H), 1.7-1.64 (m, 1H).

EXAMPLE 304

1-(5-(2-Fluoro-5-methylphenyl)pyrimidin-2-yl)-N-methyl-N-(2-(methylamino)-2-oxoethyl)-3-(methylsulfinyl)-1H-indole-6-carboxamide 304a) Methyl 2-(1-(5-bromopyrimidin-2-yl)-N-methyl-3-(methylthio)-1H-indole-6-carboxamido)acetate Amide coupling of 1-(5-bromopyrimidin-2-yl)-3-(methylthio)-1H-indole-6-carboxylic acid (2.0 g, 5.49 mmol) with methyl 2-(methylamino)acetate hydrochloride (1.53 g, 10.9 mmol) analogously to the protocol 244c). White solid. Yield: 0.6 g (24% of theory)

HPLC-MS (method 5): $R_t$=3.61 min; m/z [M+H]$^+$=451.0

304b) Methyl 2-(1-(5-(2-fluoro-5-methylphenyl)pyrimidin-2-yl)-N-methyl-3-(methylthio)-1H-indole-6-carboxamido)acetate Suzuki coupling of 304a) (0.5 g, 1.11 mmol) and (2-fluoro-5-methylphenyl)boronic acid (0.34 g, 2.22 mmol) under use of (Ataphos)2PdCl2 (79 mg, 0.11 mmol) as catalyst analogously to the protocol for example 261. White solid. Yield: 0.51 g (96% of theory)

HPLC-MS (method 5): $R_t$=4.02 min; m/z [M+H]$^+$=479.2

304c) 2-(1-(5-(2-Fluoro-5-methylphenyl)pyrimidin-2-yl)-N-methyl-3-(methylthio)-1H-indole-6-carboxamido)acetic acid Ester hydrolysis of 304b) (0.5 g, 1.05 mmol) with lithium hydroxide monohydrate in THF/water. White solid. Yield: 0.48 g (98% of theory)

HPLC-MS (method 5): $R_t$=2.82 min; m/z [M+H]$^+$=365.3

304d) 1-(5-(2-Fluoro-5-methylphenyl)pyrimidin-2-yl)-N-methyl-N-(2-(methylamino)-2-oxoethyl)-3-(methylthio)-1H-indole-6-carboxamide Methylamine (2M in THF, 1.54 ml, 3.09 mmol) was coupled with TBTU to 304c) (0.48 g, 1.03 mmol). Light yellow solid. Yield: 0.22 g (45% of theory)

HPLC-MS (method 5): $R_t$=3.65 min; m/z [M+H]$^+$=478.2

304e) 1-(5-(2-Fluoro-5-methylphenyl)pyrimidin-2-yl)-N-methyl-N-(2-(methylamino)-2-oxoethyl)-3-(methylsulfinyl)-1H-indole-6-carboxamide Oxidation of 304d) (0.1 g, 0.209 mmol) with m-chloroperoxybenzoic acid (77%, 0.038 g, 0.167 mmol) in dichloromethane (10 mL). White solid. Yield: 0.065 g (63% of theory)

HPLC-MS (method 5): $R_t$=2.81 min; m/z [M+H]$^+$=494.2

1H NMR (400 MHz, DMSO-d6, 100° C., δ ppm): 9.11 (s, 2H), 8.92 (s, 1H), 8.72 (s, 1H), 8.01 (d, J=7.9 Hz, 1H), 7.56-7.54 (m, 2H), 7.43 (d, 1H, J=7.96 Hz), 7.33-7.23 (m, 2H), 4.00 (bs, 2H), 3.06-3.03 (m, 6H), 2.65 (d, 3H, J=3.92 Hz), 2.32 (s, 3H).

EXAMPLE 305

1-(5-(2-Fluoro-5-methylphenyl)pyrimidin-2-yl)-N-methyl-N-(2-(methylamino)-2-oxoethyl)-3-(methylsulfonyl)-1H-indole-6-carboxamide Prepared from 304d) (0.1 g, 0.209 mmol) via oxidation with m-chloroperoxybenzoic acid (77%, 0.091 g, 0.524 mmol) in dichloromethane (10 mL). White solid. Yield: 0.06 g (56% of theory)

HPLC-MS (method 5): $R_t$=3.12 min; m/z [M+H]$^+$=510.3

1H NMR (400 MHz, DMSO-d6, 100° C., δ ppm): 9.16 (s, 2H), 8.89-8.93 (m, 2H), 8.01 (d, 1H, J=8.0 Hz), 7.57-7.50 (m, 3H), 7.34-7.25 (m, 2H), 4.00 (bs, 2H), 3.35 (s, 3H), 3.03 (s, 3H), 2.64 (d, 3H, J=4.0 Hz), 2.32 (bs, 3H).

Synthesis examples 306 to 312 were prepared analogously to aforementioned methods.

EXAMPLE 306

(5,6-Dihydropyridin-1(2H)-yl)(1-(5-(2-fluorophenyl)pyrimidin-2-yl)-3-(methylsulfinyl)-1H-indol-6-yl)methanone White solid. Yield: 0.2 g HPLC-MS (method 5): $R_t$=3.13 min; m/z [M+H]$^+$=460.9

1H NMR (400 MHz, DMSO-d6, 100° C., δ ppm): 9.14 (s, 2H), 8.91 (s, 1H), 8.74 (s, 1H), 8.02 (d, J=8 Hz, 1H), 7.77-7.73 (m, 1H), 7.55-7.54 (m, 1H), 7.41-7.39 (m, 3H), 5.89 (bs, 1H), 5.75 (bs, 1H), 4.07 (bs, 2H), 3.62 (bs, 2H), 3.07 (s, 3H), 2.22 (bs, 2H).

EXAMPLE 307

1-(5-(2-Fluorophenyl)pyrimidin-2-yl)-N-(3-hydroxypropyl)-N-methyl-3-(methylsulfinyl)-1H-indole-6-carboxamide White solid. Yield: 0.07 g
HPLC-MS (method 5): $R_t$=2.73 min; m/z [M+H]$^+$=467.0
1H NMR (400 MHz, DMSO-d6, 100° C., δ ppm): 9.14 (s, 2H), 8.88 (s, 1H), 8.73 (s, 1H), 8.0 (d, J=8.0 Hz, 1H), 7.77-7.73 (m, 1H), 7.57-7.52 (m, 1H), 7.41-7.37 (m, 3H), 4.09 (bs, 1H), 3.49-3.46 (m, 4H), 3.07 (s, 3H), 3.00 (s, 3H), 1.83-1.78 (m, 2H).

EXAMPLE 308

(1S,4S)-2-Oxa-5-azabicyclo[2.2.1]heptan-5-yl(1-(5-(2-fluorophenyl)pyrimidin-2-yl)-3-(methylsulfinyl)-1H-indol-6-yl)methanone White solid. Yield: 0.1 g
HPLC-MS: m/z [M+H]$^+$=477.0
$[\alpha]_{589}^{25}$=+35.57° (c. 0.5, chloroform)
1H NMR (400 MHz, DMSO-d6, 100° C., δ ppm): 9.15 (s, 2H), 9.03 (s, 1H), 8.75 (s, 1H), 8.04-8.01 (m, 1H), 7.78-7.74 (m, 1H), 7.57-7.52 (m, 2H), 7.42-7.37 (m, 2H), 4.64 (bs, 2H), 3.96 (d, J=8.0 Hz, 1H), 3.80 (d, J=4.0 Hz, 1H), 3.60 (d, J=8.0 Hz, 1H), 3.41-3.38 (m, 1H), 3.07 (s, 3H), 1.93-1.82 (m, 2H).

EXAMPLE 309

(1S,4S)-2-Oxa-5-azabicyclo[2.2.1]heptan-5-yl(1-(5-(2-fluorophenyl)pyrimidin-2-yl)-3-(methylsulfonyl)-1H-indol-6-yl)methanone White solid. Yield: 60 mg
HPLC-MS (method 5): $R_t$=3.16 min; m/z [M+H]$^+$=493.2
$[\alpha]_{589}^{25}$=+40.5° (c. 0.49, chloroform)
1H NMR (400 MHz, DMSO-d6, 100° C., δ ppm): 9.19 (s, 2H), 9.03 (s, 1H), 8.92 (s, 1H), 8.02 (d, J=8.0 Hz, 1H), 7.79-7.75 (m, 1H), 7.62-7.54 (m, 2H), 7.43-7.38 (m, 2H), 4.64 (bs, 2H), 3.96 (d, J=8.0 Hz, 1H), 3.79 (d, J=8.0 Hz, 1H), 3.60 (d, J=8.0 Hz, 1H), 3.41-3.35 (m, 4H), 1.95-1.82 (m, 2H).

EXAMPLE 310

N-(2-Amino-2-oxoethyl)-1-(5-(2-fluoro-5-methoxyphenyl)pyrimidin-2-yl)-N-methyl-3-(methylsulfonyl)-1H-indole-6-carboxamide White solid. Yield: 0.15 g
HPLC-MS (method 5): $R_t$=2.91 min; m/z [M+H]$^+$=512.1
1H NMR (400 MHz, DMSO-d6, 100° C., δ ppm): 9.18 (s, 2H), 8.94 (s, 1H), 8.89 (s, 1H), 7.98 (d, 1H, J=8.2 Hz), 7.5 (d, 1H, J=8.1 Hz), 7.34-7.29 (m, 2H), 7.1-7.07 (m, 2H), 6.92 (bs, 2H), 4.0 (s, 2H), 3.87 (s, 3H), 3.35 (s, 3H), 3.03 (s, 3H).

EXAMPLE 311

N-(2-Amino-2-oxoethyl)-1-(5-(5-ethyl-2-fluorophenyl)pyrimidin-2-yl)-N-methyl-3-(methylsulfonyl)-1H-indole-6-carboxamide White solid. Yield: 0.155 g
HPLC-MS (method 5): $R_t$=3.11 min; m/z [M+H]$^+$=510.0
1H NMR (400 MHz, DMSO-d6, 100° C., δ ppm): 9.17 (s, 2H), 8.95 (s, 1H), 8.89 (s, 1H), 7.99 (d, 1H, J=8.2 Hz), 7.6-7.57 (m, 2H), 7.39-7.27 (m, 2H), 6.92 (bs, 2H), 4.0 (s, 2H), 3.35 (s, 3H), 3.04 (s, 3H), 2.72 (q, 2H, J=7.5 Hz), 1.28 (t, 3H, J=7.6 Hz).

EXAMPLE 312

(1-(5-(4-Chloropyridin-2-yl)pyrimidin-2-yl)-3-(methylsulfonyl)-1H-indol-6-yl)(morpholino)methanone White solid. Yield: 0.145 g
HPLC-MS (method 5): $R_t$=3.18 min; m/z [M+H]$^+$=497.9
1H NMR (400 MHz, DMSO-d6, 100° C., δ ppm): 9.65 (s, 2H), 8.94 (s, 1H), 8.92 (s, 1H), 8.74 (d, 1H, J=5.2 Hz), 8.42 (s, 1H), 7.99 (d, 1H, J=8.1 Hz), 7.65 (d, 1H, J=5.2 Hz), 7.51 (d, 1H, J=8.1 Hz), 3.65 (bs, 8H), 3.39 (s, 3H).

Example 313 and 314 were prepared analogously to synthesis example 269.

EXAMPLE 313

N,N-Dimethyl-3-(methylsulfinyl)-1-(5-(pyridin-2-yl)pyrimidin-2-yl)-1H-indole-6-carboxamide White solid. Yield: 160 mg
HPLC-MS: m/z [M+H]$^+$=406.2
1H NMR (400 MHz, DMSO-d6, 20° C., δ ppm): 9.58 (s, 2H), 8.93 (s, 1H), 8.79 (s, 1H), 8.77 (d, J=4.4 Hz, 1H), 8.18 (d, J=7.84 Hz, 1H), 8.04-7.99 (m, 2H), 7.50-7.47 (m, 1H), 7.41 (d, J=8.12 Hz, 1H), 3.08 (s, 3H), 3.05 (s, 3H), 2.99 (s, 3H).

EXAMPLE 314

N,N-Dimethyl-1-(5-(6-methylpyridin-2-yl)pyrimidin-2-yl)-3-(methylsulfinyl)-1H-indole-6-carboxamide White solid. Yield: 0.17 g
HPLC-MS: m/z [M+H]$^+$=419.9
1H NMR (400 MHz, DMSO-d6, 20° C., δ ppm): δ 9.56 (s, 2H), 8.95 (s, 1H), 8.78 (s, 1H), 8.03 (d, J=8.1 Hz, 1H), 7.98 (d, J=7.7 Hz, 1H), 7.88 (t, 7.4 Hz, 1H), 7.41 (d, J=8 Hz, 1H), 7.35 (d, J=7.6 Hz, 1H), 3.08 (s, 3H), 3.05 (s, 3H), 3.00 (s, 3H), 2.59 (s, 3H).

EXAMPLE 315

1-(5-(2-Fluoro-5-methylphenyl)pyrimidin-2-yl)-N-(2-hydroxyethyl)-N-methyl-3-(methylsulfinyl)-1H-indole-6-carboxamide White solid. Yield: 109 mg
HPLC-MS (method 7): $R_t$=6.99 min; m/z [M+H]$^+$=467.0
1H NMR (400 MHz, DMSO-d6, 100° C., δ ppm): 9.12 (s, 2H), 8.9 (s, 1H), 8.72 (s, 1H), 7.98 (d, 1H, J=8.0 Hz), 7.54 (d, 1H, J=6.6 Hz), 7.41-7.39 (m, 1H), 7.33-7.23 (m, 2H), 4.41 (t, 1H, J=5.1 Hz), 3.66-3.62 (m, 2H), 3.5-3.47 (m, 2H), 3.07 (s, 3H), 3.06 (s, 3H), 2.4 (s, 3H).

EXAMPLE 316

1-(5-(5-Ethoxy-2-fluorophenyl)pyrimidin-2-yl)-N-(2-hydroxyethyl)-N-methyl-3-(methylsulfinyl)-1H-indole-6-carboxamide White solid. Yield: 0.09 g
HPLC-MS (method 7): $R_t$=7.18 min; m/z [M+H]$^+$=497.4

1H NMR (400 MHz, DMSO-d6, 100° C., δ ppm): 9.18 (s, 2H), 8.91 (s, 1H), 8.76 (s, 1H), 8.02 (d, 1H, J=6.1 Hz), 7.4 (d, 1H, J=8.1 Hz), 7.37-7.3 (m, 2H), 7.08-7.04 (m, 1H), 4.82-4.76 (m, 1H), 4.1 (q, 2H, J=6.9 Hz), 3.67 (bs, 1H), 3.56-3.51 (m, 2H), 3.32 (1H, obscured under water peak), 3.08 (s, 3H), 3.03 (bs, 3H), 1.35 (t, 3H, J=6.9 Hz).

EXAMPLE 317

N-(2-Hydroxyethyl)-N-methyl-1-(5-(4-methylpyridin-2-yl)pyrimidin-2-yl)-3-(methylsulfinyl)-1H-indole-6-carboxamide White solid. Yield: 60 mg,
HPLC-MS (method 5): $R_t$=2.59 min; m/z [M+H]$^+$=450.0
1H NMR (400 MHz, DMSO-d6, δ ppm): 9.56 (s, 2H), 8.93 (s, 1H), 8.78 (s, 1H), 8.61 (d, 1H, J=4.7 Hz), 8.05-8.0 (m, 2H), 7.41 (d, 1H, J=8.0 Hz), 7.32 (d, 1H, J=4.5 Hz), 4.84-4.78 (m, 1H), 3.68-3.54 (m, 3H), 3.32 (1H, obscured under water peak), 3.08-3.04 (m, 6H), 2.43 (s, 3H).

EXAMPLE 318

(3-(1-Hydroxyethyl)-1-(5-(4-methylpyridin-2-yl)pyrimidin-2-yl)-1H-indol-6-yl)(morpholino)methanone (1-(5-Bromopyrimidin-2-yl)-3-(hydroxymethyl)-1H-indol-6-yl)(morpholino)methanone (intermediate 27c) was converted into a boronic ester that was subsequently reacted with 2-bromo-4-methylpyridine under Suzuki conditions. The resulting product was oxidized to the corresponding aldehyde and then submitted to a Grignard reaction analogously to the protocols 28a) and 28b), respectively. Light yellow solid. Yield: 70 mg
HPLC-MS (method 5): $R_t$=2.92 min; m/z [M+H]$^+$=444.2
1H NMR (400 MHz, DMSO-d6, δ ppm): 9.49 (s, 2H), 8.87 (s, 1H), 8.58 (d, 1H, J=4.9 Hz), 8.28 (s, 1H), 8.01 (s, 1H), 7.81 (d, 1H, J=8.0 Hz), 7.31-7.29 (m, 2H), 5.26 (d, 1H, J=4.9 Hz), 5.1-5.07 (m, 1H), 3.64-3.56 (m, 8H), 2.43 (s, 3H), 1.54 (d, 3H, J=6.4 Hz).

EXAMPLE 319

(1-(5-(5-Ethoxy-2-fluorophenyl)pyrimidin-2-yl)-3-(1-hydroxyethyl)-1H-indol-6-yl)(morpholino)methanone The target compound was prepared from intermediate 27c in three reaction steps comprising a Suzuki reaction with (5-ethoxy-2-fluorophenyl)boronic acid, an oxidation with Dess-Martin periodinane and a Grignard reaction with methylmagnesium bromide. White solid. Yield: 110 mg
HPLC-MS: m/z [M+H]$^+$=491.4
1H NMR (400 MHz, DMSO-d6, δ ppm): 9.1 (s, 2H), 8.86 (s, 1H), 8.26 (s, 1H), 7.81 (d, 1H, J=8.0 Hz), 7.35-7.28 (m, 3H), 7.05-7.03 (m, 1H), 5.25 (d, 1H, J=4.7 Hz), 5.1-5.07 (m, 1H), 4.1 (q, 2H, J=6.9 Hz), 3.63 (bs, 8H), 1.53 (d, 3H, J=6.3 Hz), 1.35 (t, 3H, J=6.9 Hz).

EXAMPLE 320

1-(5-(2-Fluoro-5-methylphenyl)pyrimidin-2-yl)-3-(1-hydroxyethyl)-1H-indol-6-ethanone Prepared in an analogous manner as synthesis example 28. White solid. Yield: 0.1 g
HPLC-MS (method 5): $R_t$=3.47 min; m/z [M+H]$^+$=461.1
1H NMR (400 MHz, DMSO-d6, δ ppm): 9.08 (s, 2H), 8.85 (s, 1H), 8.26 (s, 1H), 7.81 (d, 1H, J=8.0 Hz), 7.55 (d, 1H, J=7.2 Hz), 7.31-7.28 (m, 3H), 5.26 (d, 1H, J=4.9 Hz), 5.1-5.07 (m, 1H), 3.63 (bs, 8H), 2.38 (s, 3H), 1.55 (d, 3H, J=6.4 Hz).

EXAMPLE 321

((R)-3-Aminopyrrolidin-1-yl)(1-(5-(2-fluoro-5-methylphenyl)pyrimidin-2-yl)-3-(1-hydroxyethyl)-1H-indol-6-yl)methanone Prepared from (R)-tert-butyl (1-(1H-indole-6-carbonyl)pyrrolidin-3-yl)carbamate following the synthetic route applied for the preparation of example 28. White solid. Yield: 70 mg
HPLC-MS (method 7): $R_t$=6.71 min; m/z [M+H]$^+$=460.4
1H NMR (400 MHz, DMSO-d6, 100° C., δ ppm): 9.04 (s, 2H), 8.92 (s, 1H), 8.26 (s, 1H), 7.79 (d, 1H, J=8.1 Hz), 7.52 (d, 1H, J=7.1 Hz), 7.39-7.18 (m, 3H), 5.12 (bs, 1H), 4.88 (bs, 1H), 3.65 (bs, 2H), 3.51 (bs, 2H), 3.21-3.18 (m, 1H), 3.01 (1H, obscured under water peak), 2.39 (s, 3H), 2.02 (bs, 1H), 1.67-1.58 (m, 4H).

EXAMPLE 322

1-(5-(2-Fluoro-5-methylphenyl)pyrimidin-2-yl)-3-(1-hydroxyethyl)-N,N-dimethyl-1H-indole-6-carboxamide Prepared from N,N-dimethyl-1H-indole-6-carboxamide analogously to the synthesis route of example 28. Light yellow solid. Yield: 0.08 g
HPLC-MS: m/z [M+H]$^+$=419.0
1H NMR (400 MHz, DMSO-d6, δ ppm): 9.08 (s, 2H), 8.82 (s, 1H), 8.25 (s, 1H), 7.81 (d, 1H, J=8 Hz), 7.55 (d, 1H, J=7.2 Hz), 7.31-7.27 (m, 3H), 5.26 (bs, 1H), 5.09 (d, 1H, J=6.1 Hz), 3.0 (bs, 6H), 2.37 (s, 3H), 1.54 (d, 3H, J=6.2 Hz).

EXAMPLE 323

N-(2-Amino-2-oxoethyl)-1-(5-(2-fluoro-5-methylphenyl)pyrimidin-2-yl)-3-(1-hydroxyethyl)-N-methyl-1H-indole-6-carboxamide Obtained from methyl 1-(5-(2-fluoro-5-methylphenyl)pyrimidin-2-yl)-3-(1-hydroxyethyl)-1H-indole-6-carboxylate in two steps namely an ester hydrolysis and an amidation with TBTU as coupling reagent. White solid. Yield: 43 mg
HPLC-MS (method 5): $R_t$=2.97 min; m/z [M+H]$^+$=461.9
1H NMR (400 MHz, DMSO-d6, δ ppm): 9.03 (s, 2H), 8.86 (s, 1H), 8.26 (s, 1H), 7.79 (d, 1H, J=8 Hz), 7.52 (d, 1H, J=6.6 Hz), 7.32-7.22 (m, 3H), 6.91 (bs, 2H), 5.14-5.11 (m, 1H), 4.87 (bs, 1H), 4.0 (s, 2H), 3.03 (s, 3H), 2.4 (s, 3H), 1.58 (d, 3H, J=6.1 Hz).

EXAMPLE 324

(1-(5-(4-Isopropylpyridin-2-yl)pyrimidin-2-yl)-3-(methylsulfonyl)-1H-indol-6-yl)(morpholino)methanone Magnesium monoperoxyphthalate (1.04 g, 2.11 mmol) was added to an ice-cooled solution of (1-(5-(4-isopropylpyridin-2-yl)pyrimidin-2-yl)-3-(methylthio)-1H-indol-6-yl)(morpholino)methanone (0.250 g, 0.52 mmol) in THF (36 mL). The resulting mixture was stirred at room temperature for 3.5 h and then diluted with ethyl acetate (25 mL). The organic phase was washed successively with saturated sodium hydrogen carbonate solution (2×20 mL) and brine (1×10 mL), dried over sodium sulfate and evaporated. The remnant was purified by flash column chromatography [silica gel; dichloromethane with 2.5% methanol] followed by preparative TLC [dichloromethane with 2% methanol]. Light yellow solid. Yield: 80 mg (30% of theory)

HPLC-MS (method 5): $R_t$=3.26 min; m/z [M+H]$^+$=506.2
1H NMR (400 MHz, DMSO-d6, δ ppm): 9.64 (s, 2H), 8.96 (s, 1H), 8.92 (s, 1H), 8.65 (d, J=5 Hz, 1H), 8.11 (s, 1H), 8.01 (d, J=8.2 Hz, 1H), 7.5 (d, J=8.2 Hz, 1H), 7.38 (d, J=4.8 Hz, 1H), 3.65 (bs, 8H), 3.39 (s, 3H), 3.05-2.98 (m, 1H), 1.29 (d, J=6.9 Hz, 6H).

EXAMPLE 325

(1-(5-(4-Ethylpyridin-2-yl)pyrimidin-2-yl)-3-(methylsulfonyl)-1H-indol-6-yl)(morpholino)methanone Prepared from (1-(5-(4-ethylpyridin-2-yl)pyrimidin-2-yl)-3-(methylthio)-1H-indol-6-yl)(morpholino)methanone (0.19 g, 0.41 mmol) analogously to synthesis example 324. White solid. Yield: 80 mg (40% of theory)

HPLC-MS (method 5): $R_t$=3.12 min; m/z [M+H]$^+$=492.2
1H NMR (400 MHz, DMSO-d6, δ ppm): 9.62 (s, 2H), 8.95 (s, 1H), 8.92 (s, 1H), 8.63 (d, J=4.9 Hz, 1H), 8.09 (s, 1H), 7.99 (d, J=8.1 Hz, 1H), 7.52 (d, J=8.9 Hz, 1H), 7.35 (d, J=4.5 Hz, 1H), 3.64 (bs, 8H), 3.44 (s, 3H), 2.73 (q, J=7.5 Hz, 2H), 1.28 (t, J=7.5 Hz, 3H).

EXAMPLE 326

(1-(5-(5-Ethoxy-2-fluorophenyl)pyrimidin-2-yl)-3-(methylsulfonyl)-1H-indol-6-yl)(morpholino)methanone (1-(5-(5-Ethoxy-2-fluorophenyl)pyrimidin-2-yl)-3-(methylthio)-1H-indol-6-yl)(morpholino)methanone (0.2 g, 0.406 mmol) was oxidized with m-chloroperoxybenzoic acid. White solid. Yield: 0.12 g (56% of theory)

HPLC-MS (method 5): $R_t$=3.35 min; m/z [M+H]$^+$=525.0
1H NMR (400 MHz, DMSO-d6, δ ppm): 9.23 (s, 2H), 8.93 (s, 1H), 8.9 (s, 1H), 7.99 (d, 1H, J=8.1 Hz), 7.5 (d, 1H, J=8.2 Hz), 7.38-7.31 (m, 2H), 7.09-7.06 (m, 1H), 4.12 (q, 2H, J=6.9 Hz), 3.64 (bs, 8H), 3.39 (s, 3H), 1.36 (t, 3H, J=6.9 Hz).

EXAMPLE 327

(1-(5-(4-Cyclopropylpyridin-2-yl)pyrimidin-2-yl)-3-(methylsulfonyl)-1H-indol-6-yl)(morpholino)methanone Obtained from (1-(5-(4-cyclopropylpyridin-2-yl)pyrimidin-2-yl)-3-(methylthio)-1H-indol-6-yl)(morpholino)methanone (0.250 g, 0.53 mmol) via oxidation with magnesium monoperoxyphthalate analogously to synthesis example 324. White solid. Yield: 0.17 g (64% of theory)

HPLC-MS (method 5): $R_t$=3.10 min; m/z [M+H]$^+$=504.0
1H NMR (400 MHz, DMSO-d6, δ ppm): 9.61 (s, 2H), 8.95 (s, 1H), 8.91 (s, 1H), 8.54 (d, J=4.8 Hz, 1H), 7.99 (d, J=8.1 Hz, 1H), 7.86 (s, 1H), 7.5 (d, J=8.1 Hz, 1H), 7.2 (d, J=4.6 Hz, 1H), 3.65 (bs, 8H), 3.47 (s, 3H), 2.0 (bs, 1H), 1.14 (bs, 2H), 0.98 (bs, 2H).

EXAMPLE 328

N-(2-Amino-2-oxoethyl)-1-(5-(2-fluoro-5-methylphenyl)pyrimidin-2-yl)-N-methyl-3-(methylsulfonyl)-1H-indole-6-carboxamide N-(2-amino-2-oxoethyl)-1-(5-(2-fluoro-5-methylphenyl)pyrimidin-2-yl)-N-methyl-3-(methylthio)-1H-indole-6-carboxamide was oxidized (0.17 g, 0.367 mmol) with m-chloroperoxybenzoic acid. White solid. Yield: 0.08 g (44% of theory)

HPLC-MS (method 7): $R_t$=7.52 min; m/z [M+H]$^+$=496.2
1H NMR (400 MHz, DMSO-d6, 100° C., δ ppm): 9.16 (s, 2H), 8.94 (s, 1H), 8.89 (s, 1H), 8 (d, J=8.1 Hz, 1H), 7.58-7.5 (m, 2H), 7.34-7.24 (m, 2H), 6.92 (bs, 2H), 4.0 (s, 2H), 3.34 (s, 3H), 3.0 (s, 3H), 2.41 (s, 3H).

EXAMPLE 329

(1-(5-(4-(2-Hydroxypropan-2-yl)pyridin-2-yl)pyrimidin-2-yl)-3-(methylsulfonyl)-1H-indol-6-yl)(morpholino)methanone Prepared from (1-(5-(4-(2-hydroxypropan-2-yl)pyridin-2-yl)pyrimidin-2-yl)-3-(methylthio)-1H-indol-6-yl)(morpholino)methanone via oxidation with m-chloroperoxybenzoic acid. Light yellow solid. Yield: 0.13 g (53% of theory)

HPLC-MS (method 7): $R_t$=7.86 min; m/z [M+H]$^+$=522.2
1H NMR (400 MHz, DMSO-d6, 100° C., δ ppm): 9.58 (s, 2H), 8.95 (s, 1H), 8.92 (s, 1H), 8.68 (d, J=4.9 Hz, 1H), 8.16 (s, 1H), 8.01 (d, 1H, J=8.1 Hz), 7.57-7.49 (m, 2H), 5.03 (bs, 1H), 3.67 (bs, 4H), 3.59 (bs, 4H), 3.35 (s, 3H), 1.55 (s, 6H).

EXAMPLE 330

(1-(5-(4-(1-Hydroxyethyl)pyridin-2-yl)pyrimidin-2-yl)-3-(methylsulfonyl)-1H-indol-6-yl)(morpholino)methanone Obtained from (1-(5-(4-(1-hydroxyethyl)pyridin-2-yl)pyrimidin-2-yl)-3-(methylthio)-1H-indol-6-yl)(morpholino)methanone (0.2 g, 0.42 mmol) via oxidation with magnesium monoperoxyphthalate. White solid. Yield: 80 mg (38% of theory)

HPLC-MS (method 5): $R_t$=2.65 min; m/z [M+H]$^+$=508.3
1H NMR (400 MHz, DMSO-d6, δ ppm): 9.62 (s, 2H), 8.95 (s, 1H), 8.92 (s, 1H), 8.69 (d, J=4.9 Hz, 1H), 8.13 (s, 1H), 7.99 (d, 1H, J=8.1 Hz), 7.52-7.47 (m, 2H), 5.54 (bs, 1H), 4.85-4.84 (m, 1H), 3.65 (bs, 8H), 3.39 (s, 3H), 1.43 (d, 3H, J=6.5 Hz).

EXAMPLE 331

N-(2-Amino-2-oxoethyl)-1-(5-(5-ethyl-2-fluorophenyl)pyrimidin-2-yl)-3-(1-hydroxyethyl)-N-methyl-1H-indole-6-carboxamide 331a) Methyl 1-(5-bromopyrimidin-2-yl)-3-(hydroxymethyl)-1H-indole-6-carboxylate Prepared in three chemical steps from methyl 1H-indole-6-carboxylate in analogy to the protocols 27a) to c). White solid. Yield: 4.5 g HPLC-MS (method 5): $R_t$=3.30 min; m/z [M+H]+=362.0

331b) Methyl 1-(5-(5-ethyl-2-fluorophenyl)pyrimidin-2-yl)-3-(hydroxymethyl)-1H-indole-6-carboxylate Potassium carbonate (0.915 g, 6.62 mmol) and 2-fluoro-5-ethylphenylboronic acid (0.742 g, 4.14 mmol) were added at room temperature to a solution 331a) (0.8 g, 2.2 mmol) in 2-methyl-2-butanol 1/water (44 mL, 10:1). The reaction apparatus was set under an argon atmosphere and (Ataphos)2PdCl2 (0.156 g, 0.22 mmol) was introduced. The reaction mixture was stirred at 100° C. for 4 h, cooled to room temperature and filtered through a pad of celite. The filtrate was concentrated and the remnant purified by flash column chromatography [silica; dichloromethane with 1-2% methanol]. White solid. Yield: 0.5 g (56% of theory)

HPLC-MS (method 5): $R_t$=3.83 min; m/z [M+H]$^+$=406.3

331c) Methyl 1-(5-(5-ethyl-2-fluorophenyl)pyrimidin-2-yl)-3-formyl-1H-indole-6-carboxylate Dess-Martin periodinane (0.541 g, 1.27 mmol) was added at 0° C. to a solution of 331b) (0.345 g, 0.85 mmol) in dichloromethane (25 mL). The resulting mixture was stirred at this temperature for 3 h and then filtered through celite. The filter was rinsed with dichloromethane (2×30 mL) and the filtrate was washed with saturated sodium hydrogen carbonate solution (3×20 mL) and brine (20 mL), dried over sodium sulfate and concentrated. Light yellow solid. Yield: 0.32 g (93% of theory)

HPLC-MS (method 5): $R_t$=4.23 min; m/z [M+H]$^+$=404.2

331d) Methyl 1-(5-(5-ethyl-2-fluorophenyl)pyrimidin-2-yl)-3-(1-hydroxyethyl)-1H-indole-6-carboxylate Methylmagnesium bromide (3 M in ether, 0.45 mL, 1.33 mmol) was added at 0° C. to a solution of 331c) (0.36 g, 0.89 mmol) in THF (70 mL) and the resulting mixture was stirred at this temperature for 6 h. The mixture was quenched with ammonium chloride solution (20 mL) and extracted with ethyl acetate (2×50 mL). The organic phase was washed with brine, dried over sodium sulfate and evaporated. The residue was purified by flash column chromatography [silica; dichloromethane with 0-1.5% methanol]. Light yellow solid. Yield: 0.22 g (59% of theory)

HPLC-MS (method 5): $R_t$=3.93 min; m/z [M+H]$^+$=420.2

331e) 1-(5-(5-Ethyl-2-fluorophenyl)pyrimidin-2-yl)-3-(1-hydroxyethyl)-1H-indole-6-carboxylic acid Lithium hydroxide monohydrate (33 mg, 0.786 mmol) was added to an ice-cooled suspension of 331d) (0.22 g, 0.524 mmol) in THF/water (1:1, 10 mL) and the resulting mixture was stirred at room temperature for 48 h. The THF was distilled off and the residue was diluted with water (5 mL) and acidified with saturated sodium hydrogen sulfate solution. A precipitating solid was filtered off and washed with water. Remaining humidity was removed by repeated azeotropic distillation of toluene. White solid. Yield: 0.17 g (80% of theory)

HPLC-MS (method 5): $R_t$=2.93 min; m/z [M+H]$^+$=406.3

331f) N-(2-Amino-2-oxoethyl)-1-(5-(5-ethyl-2-fluorophenyl)pyrimidin-2-yl)-3-(1-hydroxyethyl)-N-methyl-1H-indole-6-carboxamide N-methylmorpholine (0.107 mL, 0.986 mmol), TBTU (0.191 g, 0.592 mmol) and 2-(methylamino)acetamide hydrochloride (0.123 g, 0.986 mmol) were added to an ice-cooled suspension of 331e) (0.2 g, 0.493 mmol) in DMF (4 mL). The reaction mixture was stirred at room temperature for 16 h and then diluted with ice-cold water. A precipitate was filtered off and dissolved in dichloromethane. The organic phase was washed with sodium hydrogen carbonate solution (20 mL) and brine (20 mL), dried over sodium sulfate and evaporated. The remnant was purified by flash column chromatography [silica gel; dichloromethane with 4% methanol] followed by preparative HPLC. White solid. Yield: 65 mg (28% of theory)

HPLC-MS (method 5): $R_t$=3.13 min; m/z [M+H]$^+$=476.2

1H NMR (400 MHz, DMSO-d6, 100° C., δ ppm): 9.05 (s, 2H), 8.86 (s, 1H), 8.26 (s, 1H), 7.81 (d, 1H, J=8.0 Hz), 7.56 (d, 1H, J=7.6 Hz), 7.32-7.24 (m, 3H), 6.92 (bs, 2H), 5.13-5.1 (m, 1H), 4.88 (bs, 1H), 4.0 (s, 2H), 3.03 (s, 3H), 2.74-2.69 (m, 2H), 1.58 (d, 3H, J=6.0 Hz), 1.27 (t, 3H, J=7.2 Hz).

EXAMPLE 332

N-(2-Amino-2-oxoethyl)-3-(1-hydroxyethyl)-N-methyl-1-(5-(4-methylpyridin-2-yl)pyrimidin-2-yl)-1H-indole-6-carboxamide The target compound was synthesized from methyl 3-(hydroxymethyl)-1-(5-(4-methylpyridin-2-yl)pyrimidin-2-yl)-1H-indole-6-carboxylate in analogy to example 331. The substrate, methyl 3-(hydroxymethyl)-1-(5-(4-methylpyridin-2-yl)pyrimidin-2-yl)-1H-indole-6-carboxylate, was obtained from methyl 1-(5-bromopyrimidin-2-yl)-3-(hydroxymethyl)-1H-indole-6-carboxylate applying the chemistry described under 141a) and b). White solid. Yield: 0.12 g HPLC-MS (method 7): $R_t$=2.64 min; m/z [M+H]$^+$=443.4

1H NMR (400 MHz, DMSO-d6, 100° C., δ ppm): 9.44 (s, 2H), 8.86 (s, 1H), 8.59 (d, 1H, J=5.2 Hz), 8.27 (s, 1H), 7.93 (s, 1H), 7.79 (d, 1H, J=8 Hz), 7.3 (d, 1H, J=8.0 Hz), 7.26 (d, 1H, J=4.8 Hz), 6.9 (bs, 2H), 5.15-5.09 (m, 1H), 4.86 (d, 1H, J=4.8 Hz), 4.01 (s, 2H), 3.04 (s, 3H), 2.44 (s, 3H), 1.58 (d, 3H, J=6.4 Hz).

EXAMPLE 333

N-(2-Amino-2-oxoethyl)-1-(5-(4-cyclopropylpyridin-2-yl)pyrimidin-2-yl)-N-methyl-3-(methylsulfinyl)-1H-indole-6-carboxamide (single enantiomer)

333a) Methyl 1-(5-(4-cyclopropylpyridin-2-yl)pyrimidin-2-yl)-3-(methylthio)-1H-indole-6-carboxylate Synthesized from methyl 1-(5-bromopyrimidin-2-yl)-3-(methylthio)-1H-indole-6-carboxylate (1.7 g, 4.49 mmol) and 2-chloro-4-cyclopropylpyridine (1.03 g, 6.73 mmol) in analogy to the procedures 141a) and b). White solid. Yield: 1.2 g (64% of theory)

HPLC-MS (method 7): $R_t$=11.53 min; m/z [M+H]$^+$=417.3

333b) Methyl 1-(5-(4-cyclopropylpyridin-2-yl)pyrimidin-2-yl)-3-(methylsulfinyl)-1H-indole-6-carboxylate (single enantiomer)

N1,N2-bis(2-((R)-4-isopropyl-4,5-dihydrooxazol-2-yl)phenyl)benzene-1,2-diamine (6.95 mg, 0.014 mmol) and Mn(OTf)2 (5.09 mg, 0.014 mmol; for synthesis and application of this ligand see: Dai. W. et al. Org. Lett. 2013, 15, 5658; Dai. W. et al. Org. Lett. 2013, 15, 4138) in dichloromethane (10 mL) were stirred at room temperature for 3 h. 333a) (0.3 g, 0.721 mmol), acetic acid (0.263 mL, 4.61 mmol) and 30% aqueous hydrogen peroxide solution (0.147 mL, 1.47 mmol) were added at room temperature and the resulting mixture was immediately cooled with an ice bath to 5-8° C. The reaction mixture was stirred at this temperature for 30 min, quenched with saturated sodium sulfite solution (10 mL) and further stirred for 15 min. The mixture was then diluted with dichloromethane (30 mL) and washed with brine (20 mL). The combined organic layers were dried over sodium sulfate and evaporated. The residue was purified by flash column chromatography [silica; dichloromethane with 1.5% methanol]. White solid. Yield: 0.14 g (45% of theory). Enantiomeric excess: >99% (chiral HPLC)

HPLC-MS (method 7): $R_t$=8.48 min; m/z [M+H]$^+$=433.4

333c) N-(2-Amino-2-oxoethyl)-1-(5-(4-cyclopropylpyridin-2-yl)pyrimidin-2-yl)-N-methyl-3-(methylsulfinyl)-1H-indole-6-carboxamide (single enantiomer)

The target compound was derived from 333b) in two steps comprising an ester hydrolysis and an amidation reaction in analogy to the procedures 331e) and f). White solid. Yield: 0.08 g HPLC-MS (method 7): $R_t$=6.11 min; m/z [M+H]$^+$=489.3
Specific optical rotation: $[\alpha]_{589}^{25}$=−25.22° (c. 0.23, DMSO)
1H NMR (400 MHz, DMSO-d6, 100° C., δ ppm): 9.53 (s, 2H), 8.96 (s, 1H), 8.72 (s, 1H), 8.55 (d, 1H, J=4.8 Hz), 7.98 (d, 1H, J=7.6 Hz), 7.81 (s, 1H), 7.42 (d, 1H, J=7.7 Hz), 7.17 (s, 1H), 6.92 (bs, 2H), 4.01 (s, 2H), 3.07 (s, 3H), 3.04 (s, 3H), 2.05-2.01 (m, 1H), 1.14-1.12 (m, 2H), 0.97 (bs, 2H).

EXAMPLE 334

N-(2-Amino-2-oxoethyl)-1-(5-(2-fluoro-5-(2-hydroxypropan-2-yl)phenyl)pyrimidin-2-yl)-N-methyl-3-(methylsulfinyl)-1H-indole-6-carboxamide (single enantiomer)

Prepared analogously to synthesis example 333. White solid. Yield: 70 mg
UPLC-MS: m/z [M+H]$^+$=524.1
Specific optical rotation: $[\alpha]_{589}^{25}$=−48.19° (c. 0.38, chloroform).
1H NMR (400 MHz, DMSO-d6, δ ppm): 9.18-9.15 (m, 2H), 8.95 (s, 1H), 8.78-8.76 (m, 1H), 8.05-7.99 (m, 1H), 7.78-7.77 (m, 1H), 7.64-7.61 (m, 1H), 7.48-7.32 (m, 3H), 7.15-7.12 (m, 1H), 5.18 (s, 1H), 4.08 (s, 1H), 3.87 (s, 1H), 3.08 (s, 3H), 3 (s, 3H), 1.49 (s, 6H).

EXAMPLE 335

N-(2-Amino-2-oxoethyl)-1-(5-(5-cyclopropyl-2-fluorophenyl)pyrimidin-2-yl)-N-methyl-3-(methylsulfinyl)-1H-indole-6-carboxamide (single enantiomer)

Methyl 1-(5-bromopyrimidin-2-yl)-3-(methylthio)-1H-indole-6-carboxylate (1 g, 2.64 mmol) and (5-cyclopropyl-2-fluorophenyl)boronic acid (1.09 g, 7.92 mmol) were coupled according to procedure 331b). The remaining steps were performed in analogy to synthesis example 333. White solid. White solid. Yield: 0.2 g HPLC-MS (method 5): $R_t$=2.89 min; m/z [M+H]$^+$=506.3
Specific optical rotation: $[\alpha]_{589}^{25}$=−51.6° (c. 0.5, chloroform).
1H NMR (400 MHz, DMSO-d6, 100° C., δ ppm): 9.12 (s, 2H), 8.94 (s, 1H), 8.72 (s, 1H), 7.98 (d, 1H, J=8.1 Hz), 7.44 (d, 2H, J=6.7 Hz), 7.24 (d, 2H, J=8.1 Hz), 6.92 (bs, 2H), 4.0 (s, 2H), 3.06 (s, 3H), 3.03 (s, 3H), 2.05-2.03 (m, 1H), 1.0-0.98 (m, 2H), 0.78-0.77 (m, 2H).

EXAMPLE 336

((R)-3-Aminopyrrolidin-1-yl)(1-(5-(4-methylpyridin-2-yl)pyrimidin-2-yl)-3-(methylsulfinyl)-1H-indol-6-yl)methanone

336a) (R)-tert-Butyl (1-(1H-indole-6-carbonyl)pyrrolidin-3-yl)carbamate

EDCxHCl (17.7 g, 93.00 mmol, 1.5 eq), 1-hydroxy-7-azabenzotriazole (4.2 g, 31.01 mmol, 0.5 eq) followed by triethylamine (28.7 mL, 204 mmol, 3.3 eq) were added at room temperature to a stirred solution of 1H-indole-6-carboxylic acid (10 g, 62.03 mmol, 1.0 eq) in dry DMF (50 mL). (R)-tert-butyl pyrrolidin-3-ylcarbamate (13.86 g, 74.44 mmol, 1.2 eq) was added after 10 min and stirring was continued for 16 h at room temperature. The reaction mixture was diluted with icy water (100 mL), and the precipitating solid was filtered off, washed with water (50 mL) and pet ether (50 mL), and dried under vacuum. White solid. Yield: 11.0 g (55% of theory)

Mass spectroscopy: m/z: [M+H]$^+$=330.2
1H NMR (400 MHz, CDCl3, δ ppm): 8.44 (s, 1H), 7.64 (d, J=7.6 Hz, 2H), 7.31 (t, J=2.8 Hz, 1H), 6.57 (t, J=2.2 Hz, 1H), 4.66-4.59 (m, 1H), 4.30-4.11 (m, 1H), 3.92-3.38 (m, 3H), 2.23-2.04 (m, 1H), 1.92-1.85 (m, 1H), 1.61-1.46 (m, 2H), 1.39-1.27 (m, 9H).

336b) (R)-tert-Butyl (1-(3-(methylthio)-1H-indole-6-carbonyl)pyrrolidin-3-yl)carbamate Dimethylsulfane (2.0 mL, 26.74 mmol, 1.1 eq) was added drop wise at 0° C. to a stirred suspension of N-chlorosuccinimide (3.55 g, 26.74 mmol, 1.1 eq) in dichloromethane (20 mL). The mixture was cooled to −20° C., compound 336a) (8.0 g, 24.31 mmol, 1.0 eq) in dichloromethane (50 mL) was added drop wise at this temperature and the mixture was then stirred for 1 h at room temperature. The volatiles were evaporated and the residue was dissolved in xylene (30 mL) and stirred at 120° C. for 16 h. The solvent was removed in vacuo, ethyl acetate was added (50 mL), and the organic phase was washed with water (100 mL), dried over sodium sulfate and evaporated. The residue was purified by column chromatography [100-200 mesh silica, ethyl acetate/pet ether=1:4]. Yield: 5.5 g (60% of theory)

Mass spectroscopy: m/z: [M+H]$^+$=376.2
1H NMR (400 MHz, CDCl3, δ ppm): 7.74 (d, J=8.4 Hz, 1H), 7.57 (s, 1H), 7.37 (d, J=2.8 Hz, 1H), 7.32-7.30 (m, 1H), 4.84-4.67 (m, 1H), 4.31-4.16 (m, 1H), 4.01-3.35 (m, 5H), 2.36 (s, 3H), 2.23-2.10 (m, 1H), 1.92-1.85 (m, 1H), 1.39-1.27 (m, 9H).

336c) (R)-tert-Butyl (1-(1-(5-(4-methylpyridin-2-yl)pyrimidin-2-yl)-3-(methylthio)-1H-indole-6-carbonyl)pyrrolidin-3-yl)carbamate Compound 336b) (500 mg, 1.33 mmol, 1.0 eq), 2-chloro-5-(4-methylpyridin-2-yl)pyrimidine (300 mg, 1.46 mmol, 1.1 eq) and potassium tert-butylate (225 mg, 1.99 mmol, 1.5 eq) in DMF (10 mL) were stirred at 120° C. for 4 h. The reaction mixture was diluted with ethyl acetate (50 mL), washed with cold water (2×20 mL) and brine (20 mL), dried over anhydrous sodium sulfate, and evaporated. The remnant was puri fied by silica gel column chromatography [100-200 mesh, ethyl acetate/pet ether=1:1]. Yield: 320 mg (44% of theory).
Mass spectroscopy: m/z: [M+H]$^+$=545.3
1H NMR (400 MHz, CDCl3, δ ppm): 9.29 (s, 2H), 9.10 (s, 1H), 8.60 (d, J=5.2 Hz, 1H), 8.39 (s, 1H), 7.73 (d, J=8.0 Hz, 1H), 7.57 (s, 1H), 7.52-7.47 (m, 1H), 7.17 (d, J=4.8 Hz, 1H), 5.30 (s, 1H), 4.85-4.73 (m, 1H), 4.41-4.25 (m, 1H), 3.91-3.75 (m, 2H), 3.71-3.48 (m, 2H), 2.51 (s, 3H), 2.47 (s, 3H), 2.36-2.21 (m, 1H), 2.19-2.12 (m, 1H), 1.49-1.37 (m, 9H).

The target compound was obtained from 336c) in two steps comprising an oxidation with m-chloroperoxybenzoic acid (1.0 eq., in dichloromethane) followed by a removal of the protecting group (TFA in dichloromethane). White solid. Yield: 75 mg
Melting range: 154-158° C.
HPLC-MS (method 12): R$_t$=4.66 min; m/z [M+H]$^+$=475.2
1H NMR (400 MHz, DMSO-d6, 90° C., δ ppm): 9.51 (s, 2H), 9.02 (s, 1H), 8.74 (s, 1H), 8.59 (d, J=4.8 Hz, 1H), 8.00-7.96 (m, 2H), 7.51 (dd, J=8.4 Hz, J=1.0 Hz, 1H), 7.28 (d, J=4.8 Hz, 1H), 3.73-3.50 (m, 6H), 3.30-3.28 (m, 1H), 3.03 (s, 3H), 2.43 (s, 3H), 2.09-2.04 (m, 1H), 1.76-1.71 (m, 1H).

Examples 337 to 340 were prepared analogously to synthesis example 336.

EXAMPLE 337

((R)-3-Aminopyrrolidin-1-yl)(1-(5-(4-ethylpyridin-2-yl)pyrimidin-2-yl)-3-(methylsulfinyl)-1H-indol-6-yl)methanone White solid. Yield: 75 mg
Melting range: 160-163° C.
HPLC-MS (method 12): R$_t$=4.82 min; m/z [M+H]$^+$=475.2
1H NMR (400 MHz, DMSO-d6, 90° C., δ ppm): 9.52 (s, 2H), 9.01 (s, 1H), 8.73 (s, 1H), 8.61 (d, J=4.8 Hz, 1H), 7.99-7.97 (m, 2H), 7.50 (d, J=8.0 Hz, 1H), 7.30 (d, J=5.2 Hz, 1H), 3.66-3.61 (m, 2H), 3.57-3.46 (m, 2H), 3.20-3.10 (m, 1H), 3.05 (s, 3H), 2.80-2.71 (m, 2H), 2.02-1.62 (m, 4H), 1.31-1.24 (m, 3H).

EXAMPLE 338

((R)-3-Aminopyrrolidin-1-yl)(1-(5-(4-isopropylpyridin-2-yl)pyrimidin-2-yl)-3-(methylsulfinyl)-1H-indol-6-yl)methanone White solid. Yield: 65 mg
Melting range: 264-268° C.
HPLC-MS (method 12): R$_t$=4.97 min; m/z [M+H]$^+$=489.3
1H NMR (300 MHz, DMSO-d6, 90° C., δ ppm): 9.54 (s, 2H), 9.02 (s, 1H), 8.74 (s, 1H), 8.63 (d, J=5.1 Hz, 1H), 8.00-7.97 (m, 2H), 7.51 (dd, J=8.1 Hz, J=1.5 Hz, 1H), 7.34 (dd, J=5.1 Hz, J=1.5 Hz, 1H), 3.65-3.61 (m, 3H), 3.55-3.53 (m, 2H), 3.22-3.18 (m, 1H), 3.05 (s, 3H), 2.02-1.96 (m, 3H), 1.67-1.65 (m, 1H), 1.32 (d, J=7.2 Hz, 6H).

EXAMPLE 339

((R)-3-Aminopyrrolidin-1-yl)(1-(5-(4-cyclopropylpyridin-2-yl)pyrimidin-2-yl)-3-(methylsulfinyl)-1H-indol-6-yl)methanone Pale yellow solid. Yield: 65 mg
Melting range: 278-281° C.
HPLC-MS (method 12): R$_t$=4.84 min; m/z [M+H]$^+$=487.2
1H NMR (400 MHz, DMSO-d6, 1H NMR (400 MHz, DMSO-d6, δ ppm): δ ppm): 9.58 (s, 2H), 9.05 (s, 1H), 8.79 (s, 1H), 8.55 (d, J=4.8 Hz, 1H), 8.03 (d, J=8.4 Hz, 1H), 7.85 (s, 1H), 7.55-7.51 (m, 1H), 7.21-7.19 (m, 1H), 3.67-3.58 (m, 6H), 3.25-3.18 (m, 1H), 3.08 (s, 3H), 2.06-1.91 (m, 2H), 1.71-1.64 (m, 1H), 1.16-1.12 (m, 2H), 1.11-0.97 (m, 2H).

EXAMPLE 340

(R)-(3-Aminopyrrolidin-1-yl)(1-(5-(4-methylpyridin-2-yl)pyrimidin-2-yl)-3-(methylsulfonyl)-1H-indol-6-yl)methanone Prepared in analogy to synthesis example 336 with the difference that the oxidation was performed at 0° C. with 1.5 equivalents of m-chloroperoxybenzoic acid. White solid: Yield: 65 mg
Melting range: 157-160° C.
HPLC-MS (method 12): R$_t$=4.90 min; m/z [M+H]$^+$=477.2
1H NMR (400 MHz, DMSO-d6, 90° C., δ ppm): 9.55 (s, 2H), 9.01 (s, 1H), 8.90 (s, 1H), 8.60 (d, J=4.8 Hz, 1H), 7.99-7.97 (m, 2H), 7.58 (d, J=8.0 Hz, 1H), 7.30 (d, J=4.8 Hz, 1H), 3.71-3.62 (m, 2H), 3.56-3.43 (m, 2H), 3.33 (s, 3H), 3.15-3.27 (m, 1H), 2.44 (s, 3H), 1.94-2.13 (m, 1H), 1.76-1.86 (m, 2H), 1.61-1.74 (m, 1H).

EXAMPLE 341

(1-(5-(4-Cyclopropylpyridin-2-yl)pyrimidin-2-yl)-3-(methylsulfinyl)-1H-indol-6-yl)(pyrrolidin-1-yl)methanone 341a) (1-(5-Bromopyrimidin-2-yl)-3-(methylthio)-1H-indol-6-yl)(pyrrolidin-1-yl)methanone HATU (3.1 g, 8.24 mmol), diisopropylethylamine (3.6 ml, 20.6 mmol) and pyrrolidine (0.6 g, 8.24 mmol) were added to an ice cooled suspension of 1-(5-bromopyrimidin-2-yl)-3-(methylthio)-1H-indole-6-carboxylic acid (2.5 g, 6.86 mmol) in DMF (20 mL). The resulting mixture was stirred at room temperature for 16 h and then quenched with crushed ice. The precipitating solid was filtered off, washed with water and dissolved in dichloromethane. The organic phase was dried over sodium sulfate and evaporated. White solid. Yield: 2.1 g (73% of theory)
HPLC-MS (method 5): R$_t$=3.80 min; m/z [M+H]$^+$=419.2

341b) (1-(5-(4-Cyclopropylpyridin-2-yl)pyrimidin-2-yl)-3-(methylthio)-1H-indol-6-yl)(pyrrolidin-1-yl)methanone Bis(pinacolato)diboron (0.584 g, 2.3 mmol) and potassium acetate (0.421 g, 4.29 mmol) were added at room temperature to a solution of 341a) (0.6 g, 1.43 mmol) in dry dioxane (35 mL). The reaction apparatus was flushed with argon, PdCl2 (dppf) (58 mg, 0.071 mmol) was added and the resulting mixture was stirred for 1 h at 110° C. (complete consumption of starting material). 2-bromo-4-cyclopropyl-pyridine (0.328 g, 2.14 mmol), potassium carbonate (2M, 2.5 mL) and tetrakis(triphenylphosphine)palladium(0) (83 mg, 0.071 mmol) were added successively and the reaction mixture was stirred for 16 h at 100° C. The mixture was then cooled to ambient temperature and filtered through a sintered funnel. The filtrate was concentrated and the remnant was purified by flash column chromatography [silica; dichloromethane with 2% methanol]. White solid. Yield: 0.28 g (43% of theory)
HPLC-MS (method 5): R$_t$=4.06 min; m/z [M+H]$^+$=456.0

341c) (1-(5-(4-Cyclopropylpyridin-2-yl)pyrimidin-2-yl)-3-(methylsulfinyl)-1H-indol-6-yl)(pyrrolidin-1-yl)methanone m-Chloroperoxybenzoic acid (77%, 79 mg, 0.35 mmol) was added to an ice cooled solution of 341b) (0.2 g, 0.43 mmol) in dichloromethane (30 mL). The mixture was stirred at room temperature for 1 h and then diluted with dichloromethane (25 mL). The organic phase was washed successively with saturated sodium hydrogen solution (2×15 mL) and brine (1×15 mL), dried over sodium sulfate and evaporated. The residue was purified by flash column chromatography [silica; dichloromethane with 0-2% methanol]. White solid. Yield: 0.08 g (39% of theory)

HPLC-MS (method 5): $R_t$=3.06 min; m/z [M+H]$^+$=472.0

1H NMR (400 MHz, DMSO-d6, δ ppm): 9.57 (s, 2H), 9.06 (s, 1H), 8.79 (s, 1H), 8.53 (d, 1H, J=4.8 Hz), 8.01 (d, 1H, J=8.4 Hz), 7.85 (s, 1H), 7.53 (d, 1H, J=8.0 Hz), 7.19 (d, 1H, J=4.0 Hz), 3.54-3.48 (m, 4H), 3.08 (s, 3H), 2.03 (bs, 1H), 1.91-1.83 (m, 4H), 1.22 (bs, 2H), 0.98 (bs, 2H).

EXAMPLE 342

(1-(5-(4-Methoxypyridin-2-yl)pyrimidin-2-yl)-3-(methylsulfinyl)-1H-indol-6-yl)(pyrrolidin-1-yl)methanone Synthesized analogously to example 341. White solid. Yield: 0.11 g HPLC-MS: m/z [M+H]$^+$=462.2

1H NMR (400 MHz, DMSO-d6, δ ppm): 9.59 (s, 2H), 9.05 (s, 1H), 8.79 (s, 1H), 8.55 (d, 1H, J=5.6 Hz), 8.01 (d, 1H, J=8.1 Hz), 7.77 (s, 1H), 7.53 (d, 1H, J=8.0 Hz), 7.07 (bs, 1H), 3.95 (s, 3H), 3.53-3.48 (m, 4H), 3.08 (s, 3H), 1.91-1.83 (m, 4H).

EXAMPLE 343

(1-(5-(4-Ethoxypyridin-2-yl)pyrimidin-2-yl)-3-(methylsulfinyl)-1H-indol-6-yl)(pyrrolidin-1-yl)methanone Synthesized analogously to example 341. White solid. Yield: 0.11 g HPLC-MS (method 5): $R_t$=2.99 min; m/z [M+H]$^+$=476.0

1H NMR (400 MHz, DMSO-d6, δ ppm): 9.58 (s, 2H), 9.05 (s, 1H), 8.79 (s, 1H), 8.54 (d, 1H, J=5.3 Hz), 8.01 (d, 1H, J=8.2 Hz), 7.75 (s, 1H), 7.53 (d, 1H, J=8.5 Hz), 7.04 (bs, 1H), 4.26-4.24 (m, 2H), 3.54-3.48 (m, 4H), 3.08 (s, 3H), 1.91-1.83 (m, 4H), 1.39 (t, 3H, J=6.8 Hz).

EXAMPLE 344 and 345

(1-(5-(2-Fluoro-5-(1-hydroxyethyl)phenyl)pyrimidin-2-yl)-3-(methylsulfonyl)-1H-indol-6-yl)(morpholino)methanone one (faster and slower eluting enantiomer)

(1-(5-(2-Fluoro-5-(1-hydroxyethyl)phenyl)pyrimidin-2-yl)-3-(methylsulfonyl)-1H-indol-6-yl)(morpholino)methanone (racemate, 0.30 g) was prepared from methyl 1-(5-bromopyrimidin-2-yl)-3-(methylthio)-1H-indole-6-carboxylate and 1-(3-bromo-4-fluorophenyl)ethanol adopting the synthesis strategy described for example 300. The single enantiomers were obtained from this racemate via preparative chiral HPLC column and the enantiomeric excess of the isolated enantiomers was measured with the following analytical method: column: Chiralpak IA 4.6×250 mm, 5 µm; injection volume: 2 µL; mobile phase: hexane/ethyl acetate/ethanol/diethylamine=50/25/25/0.1; flow rate: 1.0 mL/min.

Faster eluting enantiomer (example 344):

White solid. Yield: 80 mg

HPLC-MS (method 5): $R_t$=2.94 min; m/z [M+H]$^+$=524.8

1H NMR (400 MHz, DMSO-d6, δ ppm): 9.22 (s, 2H), 8.94 (d, 2H, J=12.1 Hz), 8.02 (d, 1H, J=8.2 Hz), 7.71 (d, 1H, J=7.5 Hz), 7.54-7.50 (m, 2H), 7.41-7.36 (m, 1H), 5.33 (d, 1H, J=4.3 Hz), 4.84-4.81 (m, 1H), 3.64 (m, 8H), 3.39 (s, 3H), 1.40 (d, 1H, J=6.4 Hz).

Specific optical rotation: [α]$_{589}^{25}$=+11.3° (c. 0.4, chloroform)

Enantiomeric excess determined by analytical chiral HPLC method: 100% ($R_t$=13.56 min)

Slower eluting enantiomer (example 345):

White solid. Yield: 80 mg

HPLC-MS (method 5): $R_t$=2.95 min; m/z [M+H]$^+$=525.0

Enantiomeric excess determined by analytical chiral HPLC method: 95.3% ($R_t$=15.54 min)

1H NMR (400 MHz, DMSO-d6, δ ppm): 9.22 (s, 2H), 8.94 (d, 2H, J=12.5 Hz), 8.02 (d, 1H, J=8.1 Hz), 7.71 (d, 1H, J=7.2 Hz), 7.52 (d, 2H, J=8.1 Hz), 7.41 (t, 1H, J=9.5 Hz), 5.34 (d, 1H, J=4.2 Hz), 4.84-4.81 (m, 1H), 3.66 (m, 8H), 3.39 (s, 3H), 1.40 (d, 1H, J=6.3 Hz).

Specific optical rotation: [α]$_{589}^{25}$=−11.9° (c. 0.46, chloroform).

Synthesis examples 346 to 348 were prepared from 1-(5-(2-fluorophenyl)pyrimidin-2-yl)-3-(methylsulfinyl)-1H-indole-6-carboxylic acid (51e) and the appropriate partially BOC-protected amines in analogy to the procedure of synthesis example 52.

EXAMPLE 346

1-(5-(2-Fluorophenyl)pyrimidin-2-yl)-N-methyl-N-(2-(methylamino)ethyl)-3-(methylsulfinyl)-1H-indole-6-carboxamide White solid: Yield: 95 mg, HPLC-MS (method 12): $R_t$=4.90 min; m/z [M+H]$^+$=466.3

Melting range: 122-126° C.

1H NMR (400 MHz, DMSO-d6, δ ppm): 9.18 (d, J=1.6 Hz, 2H), 8.90 (s, 1H), 8.77 (s, 1H), 8.02 (d, J=8.0 Hz, 1H), 7.80-7.76 (m, 1H), 7.57-7.55 (m, 1H), 7.46-7.39 (m, 3H), 3.68-3.40 (m, 2H), 3.08 (s, 3H), 3.00-2.66 (m, 6H), 2.45-2.32 (m, 1H), 2.25-2.12 (m, 2H).

EXAMPLE 347

2,5-Diazabicyclo[2.2.2]octan-2-yl(1-(5-(2-fluorophenyl)pyrimidin-2-yl)-3-(methylsulfinyl)-1H-indol-6-yl)methanone Pale brown solid. Yield: 95 mg HPLC-MS (method 12): $R_t$=4.90 min; m/z [M+H]$^+$=490.2

Melting range: 141-144° C.

1H NMR (400 MHz, DMSO-d6, 90° C., δ ppm): 9.14 (s, 2H), 8.94 (s, 1H), 8.74 (s, 1H), 8.03 (d, J=8.0 Hz, 1H), 7.78-7.74 (m, 1H), 7.56-7.52 (m, 1H), 7.42-7.38 (m, 3H), 3.80-3.31 (m, 4H), 3.32-3.12 (m, 3H), 3.07 (s, 3H), 2.10-1.79 (m, 4H).

EXAMPLE 348

3,8-Diazabicyclo[3.2.1]octan-8-yl(1-(5-(2-fluorophenyl)pyrimidin-2-yl)-3-(methylsulfinyl)-1H-indol-6-yl)methanone White solid. Yield: 69 mg HPLC-MS (method 12): $R_t$=5.05 min; m/z [M+H]$^+$=490.2

Melting range: 237-240° C.

1H NMR (400 MHz, DMSO-d6, δ ppm): 9.19 (s, 2H), 9.02 (s, 1H), 8.79 (s, 1H), 8.03 (d, J=8.4 Hz, 1H), 7.81-7.76 (m, 1H), 7.58-7.39 (m, 4H), 4.62-4.50 (m, 1H), 4.05-3.95 (m, 1H), 3.08 (s, 3H), 2.98-2.80 (m, 2H), 2.75-2.55 (m, 2H), 1.95-1.75 (m, 4H).

EXAMPLE 349

(1R,4R)-2-Oxa-5-azabicyclo[2.2.1]heptan-5-yl(1-(5-(2-fluorophenyl)pyrimidin-2-yl)-3-(methylsulfonyl)-1H-indol-6-yl)methanone White solid. Yield: 65 mg
HPLC-MS (method 5): $R_t$=3.15 min; m/z [M+H]$^+$=493.0
$[\alpha]_{589}^{25}$=−35.9° (c. 0.51, chloroform)

EXAMPLE 350

(1-(5-(2-Fluoro-5-methylphenyl)pyrimidin-2-yl)-3-(methylsulfonyl)-1H-indol-6-yl)(morpholino)methanone Prepared from (1-(5-bromopyrimidin-2-yl)-3-(methylthio)-1H-indol-6-yl)(morpholino)methanone in two steps namely a Suzuki reaction with (AtaPhos)2PdCl2 as catalyst and an oxidation with m-chloroperoxybenzoic acid. Light yellow solid. Yield: 0.15 g
HPLC-MS (method 5): $R_t$=3.35 min; m/z [M+H]$^+$=495.2 (MW calc. 494.54)
1H NMR (400 MHz, DMSO-d6, δ ppm): 9.21 (s, 2H), 8.93 (s, 1H), 8.9 (s, 1H), 7.99 (d, 1H, J=8.1 Hz), 7.59 (d, 1H, J=7.3 Hz), 7.5 (d, 1H, J=8.3 Hz), 7.34-7.29 (m, 2H), 3.63 (bs, 8H), 3.38 (s, 3H), 2.39 (s, 3H).

EXAMPLES 351 AND 352

(1-(5-(4-Methylpyridin-2-yl)pyrimidin-2-yl)-3-(methylsulfinyl)-1H-indol-6-yl)(morpholino)methanone (faster and slower eluting enantiomer)

The single enantiomers were obtained from the racemic synthesis example 142 via preparative chiral HPLC and the enantiomeric excess of the isolated enantiomers was measured with the following analytical method: column: Chiralpak IC 4.6×250 mm, 5 μm; injection volume: 2 μL; mobile phase: dichloromethane/isopropyl alcohol/diethylamine=90/10/0.1; flow rate: 1.0 mL/min.

Faster eluting enantiomer (example 351):
White solid. Yield: 0.45 g
HPLC-MS (method 5): $R_t$=2.60 min; m/z [M+H]$^+$=462.1 (MW calc. 461.54)
1H NMR (400 MHz, DMSO-d6, δ ppm): 9.57 (s, 2H), 8.95 (s, 1H), 8.79 (s, 1H), 8.6 (d, 1H, J=4.9 Hz), 8.05-8.03 (m, 2H), 7.42 (d, 1H, J=8.7 Hz), 7.31 (d, 1H, J=4.8 Hz), 3.65 (bs, 8H), 3.08 (s, 3H), 2.44 (s, 3H).
Specific optical rotation: $[\alpha]_{589}^{25}$=+63.6° (c. 0.502, chloroform)
Enantiomeric excess determined by analytical chiral HPLC method: 100% ($R_t$=21.95 min)
Slower eluting enantiomer (example 352):
White solid. Yield: 0.43 g
HPLC-MS (method 5): $R_t$=2.59 min; m/z [M+H]$^+$=462.3 (MW calc. 461.54)
Specific optical rotation: $[\alpha]_{589}^{25}$=−61.4° (c. 0.51, chloroform)
Enantiomeric excess determined by analytical chiral HPLC method: 100% ($R_t$=39.47 min)

EXAMPLE 353

(1-(5-(4-Methylpyridin-2-yl)pyrimidin-2-yl)-3-(methylsulfonyl)-1H-indol-6-yl)(morpholino)methanone (1-(5-Bromopyrimidin-2-yl)-3-(methylthio)-1H-indol-6-yl)(morpholino)methanone was oxidized with m-chloroperoxybenzoic acid to the corresponding sulfone which was then submitted to a Suzuki reaction in analogy to procedure 244a). White solid. Yield: 0.12 g
HPLC-MS (method 5): $R_t$=2.99 min; m/z [M+H]$^+$=478.3 (MW calc. 477.54)
1H NMR (400 MHz, DMSO-d6, 100° C., δ ppm): 9.57 (s, 2H), 8.94 (s, 1H), 8.92 (s, 1H), 8.61 (d, 1H, J=4.8 Hz), 8.03-8.01 (m, 2H), 7.49 (d, 1H, J=8.0 Hz), 7.31 (d, 1H, J=4.8 Hz), 3.68-3.66 (m, 4H), 3.59-3.58 (m, 4H), 3.35 (s, 3H), 2.46 (s, 3H)

EXAMPLE 354

(3-Cyclopropyl-1-(5-(2-fluorophenyl)pyrimidin-2-yl)-1H-indol-6-yl)(morpholino) methanone

354a) (3-Iodo-1H-indol-6-yl)(morpholino)methanone

Potassium hydroxide (422 mg, 7.543 mmol, 3.47 eq), iodine (1.103 g, 4.347 mmol, 2.0 eq) and (1H-indol-6-yl)(morpholino)methanone (500 mg, 2.173 mmol, 1.0 eq) in DMF (10 mL) were stirred at room temperature for 5 h. The reaction mixture was diluted with water (20 mL) and extracted with ethyl acetate (2×15 mL). The combined organic phase was washed with brine (20 mL), dried over anhydrous sodium sulfate and evaporated in vacuo. White solid. Yield: 600 mg (77% of theory)
1H NMR (400 MHz, DMSO-d6, δ ppm): 11.73 (d, J=3.0 Hz, 1H), 7.67 (d, J=2.5 Hz, 1H), 7.46 (s, 1H), 7.32 (d, J=8.1 Hz, 1H), 7.15 (dd, J=8.3, 1.4 Hz, 1H), 3.71-3.41 (m, 8H).

354b) (1-(5-(2-Fluorophenyl)pyrimidin-2-yl)-3-iodo-1H-indol-6-yl)(morpholino)methanone Potassium tert-butoxide (236 mg, 2.106 mmol, 1.5 eq), compound 354a) (500 mg, 1.404 mmol, 1.0 eq) and 2-chloro-5-(2-fluorophenyl)pyrimidine (292 mg, 1.404 mmol, 1.0 eq) in DMF (10 mL) were stirred at 120° C. for 5 h. The reaction mixture was cooled to room temperature, diluted with water (15 mL), and extracted with ethyl acetate (2×20 mL). The combined organic layers were washed with brine (30 mL), dried over sodium sulfate and concentrated. The residue was purified by silica gel column chromatography [100-200 mesh silica; ethyl acetate/pet ether=7:3]. Yield: 400 mg (53% of theory).
1H NMR (400 MHz, DMSO-d6, δ ppm): 9.14 (s, 2H), 8.86 (s, 1H), 8.58 (s, 1H), 7.81-7.72 (m, 1H), 7.59-7.51 (m, 1H), 7.49-7.45 (m, 1H), 7.44-7.37 (m, 3H), 3.74-3.52 (m, 8H).

354c) (3-Cyclopropyl-1-(5-(2-fluorophenyl)pyrimidin-2-yl)-1H-indol-6-yl)(morpholino)methanone Lithium chloride (79.5 mg, 1.893 mmol, 3.0 eq) and tetrakis(triphenylphosphine)palladium(0) (109.3 g, 0.094 mmol, 0.1 eq) were added to a solution of 354b) (500 mg, 0.946 mmol, 1.0 eq) and tributyl(cyclopropyl)stannane (376 mg, 1.136 mmol, 1.2 eq) in DMF (10 mL) that was kept under an argon atmosphere at room temperature. The mixture was then stirred at 160° C. under microwave irradiation for 1 h, cooled to room temperature and diluted with ethyl acetate (10 mL). The organic phase was separated, washed with water (10 mL), and dried (sodium sulfate). The solvents were distilled off under reduced pressure and the residue was purified by preparative HPLC. White solid. Yield: 70 mg (16% of theory)

Melting range: 177-181° C.

HPLC-MS (method 6): $R_f$=12.29 min; m/z [M+H]$^+$=443.2

1H NMR (400 MHz, DMSO-d6, δ ppm): 9.09 (s, 2H), 8.84 (s, 1H), 8.07 (s, 1H), 7.80-7.73 (m, 2H), 7.55-7.51 (m, 1H), 7.46-7.34 (m, 2H), 7.33-7.31 (m, 1H), 3.71-3.41 (m, 8H), 2.08-2.02 (m, 1H), 1.05-0.92 (m, 2H), 0.81-0.71 (m, 2H).

The examples in table 4 were synthesized according to the following general procedure:

1-Hydroxybenzotriazole monohydrate (60 μmol) and N,N-diisopropylethylamine (400 μmol) in dichloromethane (2 mL) were added to 1-(5-(2-fluorophenyl)pyrimidin-2-yl)-3-(methylsulfinyl)-1H-indole-6-carboxylic acid (100 μmol) and N,N-diisopropylethylamine (180 μmol) in dichloromethane (1 mL). EDCxHCl (150 μmol) in dichloromethane (1 mL) was added and the mixture was agitated for 15 min in a shaking device. The appropriate amine (125 μmol) in dichloromethane (1 mL) was then added and the reaction mixture was agitated for 16 h at room temperature. The reaction was quenched by addition of saturated sodium hydrogen carbonate solution (2.5 mL) and shaking was continued for further 30 min. The aqueous layer was separated and extracted with dichloromethane (2×3 mL). The organic layers were combined, the solvent was removed under reduced pressure, and the raw product was purified by preparative HPLC.

TABLE 4

| Example no. | Name | Mass peak [M + H]$^+$ |
|---|---|---|
| 355 | Azetidin-1-yl(1-(5-(2-fluorophenyl)pyrimidin-2-yl)-3-(methylsulfinyl)-1H-indol-6-yl)methanone | 435.1 |
| 356 | N-Ethyl-1-(5-(2-fluorophenyl)pyrimidin-2-yl)-N-methyl-3-(methylsulfinyl)-1H-indole-6-carboxamide | 437.1 |
| 357 | N,N-Diethyl-1-(5-(2-fluorophenyl)pyrimidin-2-yl)-3-(methylsulfinyl)-1H-indole-6-carboxamide | 451.2 |
| 358 | (1-(5-(2-Fluorophenyl)pyrimidin-2-yl)-3-(methylsulfinyl)-1H-indol-6-yl)(piperidin-1-yl)methanone | 463.2 |
| 359 | (1-(5-(2-Fluorophenyl)pyrimidin-2-yl)-3-(methylsulfinyl)-1H-indol-6-yl)(2-methylpyrrolidin-1-yl)methanone | 463.2 |
| 360 | N-(Cyclopropylmethyl)-1-(5-(2-fluorophenyl)pyrimidin-2-yl)-N-methyl-3-(methylsulfinyl)-1H-indole-6-carboxamide | 463.2 |
| 361 | (1-(5-(2-Fluorophenyl)pyrimidin-2-yl)-3-(methylsulfinyl)-1H-indol-6-yl)(2-methylpiperidin-1-yl)methanone | 477.2 |
| 362 | (1-(5-(2-Fluorophenyl)pyrimidin-2-yl)-3-(methylsulfinyl)-1H-indol-6-yl)(3-methylpiperidin-1-yl)methanone | 477.2 |
| 363 | (1-(5-(2-Fluorophenyl)pyrimidin-2-yl)-3-(methylsulfinyl)-1H-indol-6-yl)(4-methylpiperidin-1-yl)methanone | 477.2 |
| 364 | Azepan-1-yl(1-(5-(2-fluorophenyl)pyrimidin-2-yl)-3-(methylsulfinyl)-1H-indol-6-yl)methanone | 477.2 |
| 365 | (1-(5-(2-Fluorophenyl)pyrimidin-2-yl)-3-(methylsulfinyl)-1H-indol-6-yl)(4-methylpiperazin-1-yl)methanone | 478.2 |
| 366 | 1-(5-(2-Fluorophenyl)pyrimidin-2-yl)-N,N-diisopropyl-3-(methylsulfinyl)-1H-indole-6-carboxamide | 479.2 |
| 367 | N-(2-(Dimethylamino)ethyl)-1-(5-(2-fluorophenyl)pyrimidin-2-yl)-N-methyl-3-(methylsulfinyl)-1H-indole-6-carboxamide | 480.2 |
| 368 | (1-(5-(2-Fluorophenyl)pyrimidin-2-yl)-3-(methylsulfinyl)-1H-indol-6-yl)(thiomorpholino)methanone | 481.1 |
| 369 | 3-(1-(5-(2-Fluorophenyl)pyrimidin-2-yl)-N-methyl-3-(methylsulfinyl)-1H-indole-6-carboxamido)propanoic acid | 481.1 |
| 370 | (1-(5-(2-Fluorophenyl)pyrimidin-2-yl)-3-(methylsulfinyl)-1H-indol-6-yl)(2-oxa-6-azaspiro[3.4]octan-6-yl)methanone | 491.2 |
| 371 | (2-Ehylpiperidin-1-yl)(1-(5-(2-fluorophenyl)pyrimidin-2-yl)-3-(methylsulfinyl)-1H-indol-6-yl)methanone | 491.2 |
| 372 | (3,5-Dimethylpiperidin-1-yl)(1-(5-(2-fluorophenyl)pyrimidin-2-yl)-3-(methylsulfinyl)-1H-indol-6-yl)methanone (diastereomer 1) | 491.2 |
| 373 | (3,5-Dimethylpiperidin-1-yl)(1-(5-(2-fluorophenyl)pyrimidin-2-yl)-3-(methylsulfinyl)-1H-indol-6-yl)methanone (diastereomer 2) | 491.2 |
| 374 | ((R)-3-(Dimethylamino)pyrrolidin-1-yl)(1-(5-(2-fluorophenyl)-pyrimidin-2-yl)-3-(methylsulfinyl)-1H-indol-6-yl)methanone | 492.2 |
| 375 | (4-Ethylpiperazin-1-yl)(1-(5-(2-fluorophenyl)pyrimidin-2-yl)-3-(methylsulfinyl)-1H-indol-6-yl)methanone | 492.2 |
| 376 | (1-(5-(2-Fluorophenyl)pyrimidin-2-yl)-3-(methylsulfinyl)-1H-indol-6-yl)(4-methyl-1,4-diazepan-1-yl)methanone | 492.2 |
| 377 | (2,6-Dimethylmorpholino)(1-(5-(2-fluorophenyl)pyrimidin-2-yl)-3-(methylsulfinyl)-1H-indol-6-yl)methanone (diastereomer 1) | 493.2 |
| 378 | (2,6-Dimethylmorpholino)(1-(5-(2-fluorophenyl)pyrimidin-2-yl)-3-(methylsulfinyl)-1H-indol-6-yl)methanone (diastereomer 2) | 493.2 |
| 379 | (1-(5-(2-Fluorophenyl)pyrimidin-2-yl)-3-(methylsulfinyl)-1H-indol-6-yl)(2-(hydroxymethyl)piperidin-1-yl)methanone | 493.2 |
| 380 | (1-(5-(2-Fluorophenyl)pyrimidin-2-yl)-3-(methylsulfinyl)-1H-indol-6-yl)(4-(hydroxymethyl)piperidin-1-yl)methanone | 493.2 |
| 381 | (1-(5-(2-Fluorophenyl)pyrimidin-2-yl)-3-(methylsulfinyl)-1H-indol-6-yl)(4-methoxypiperidin-1-yl)methanone | 493.2 |
| 382 | 1-(5-(2-Fluorophenyl)pyrimidin-2-yl)-N-methyl-3-(methylsulfinyl)-N-(tetrahydro-2H-pyran-4-yl)-1H-indole-6-carboxamide | 493.2 |

TABLE 4-continued

| Example no. | Name | Mass peak [M + H]+ |
|---|---|---|
| 383 | (2,2-Dimethylmorpholino)(1-(5-(2-fluorophenyl)pyrimidin-2-yl)-3-(methylsulfinyl)-1H-indol-6-yl)methanone | 493.2 |
| 384 | (1-(5-(2-Fluorophenyl)pyrimidin-2-yl)-3-(methylsulfinyl)-1H-indol-6-yl)(2-oxa-7-azaspiro[3.5]nonan-7-yl)methanone | 505.2 |
| 385 | 1-(4-(1-(5-(2-Fluorophenyl)pyrimidin-2-yl)-3-(methyl sulfinyl)-1H-indole-6-carbonyl)piperazin-1-yl)ethanone | 506.2 |
| 386 | (1-(5-(2-Fluorophenyl)pyrimidin-2-yl)-3-(methylsulfinyl)-1H-indol-6-yl)(4-isopropylpiperazin-1-yl)methanone | 506.2 |
| 387 | (4-(Dimethylamino)piperidin-1-yl)(1-(5-(2-fluorophenyl)pyrimidin-2-yl)-3-(methylsulfinyl)-1H-indol-6-yl)methanone | 506.2 |
| 388 | Methyl 1-(1-(5-(2-fluorophenyl)pyrimidin-2-yl)-3-(methylsulfinyl)-1H-indole-6-carbonyl)pyrrolidine-3-carboxylate | 507.1 |
| 389 | (1-(5-(2-Fluorophenyl)pyrimidin-2-yl)-3-(methylsulfinyl)-1H-indol-6-yl)(4-(2-hydroxyethyl)piperazin-1-yl)methanone | 508.2 |
| 390 | (1,1-Dioxidothiomorpholino)(1-(5-(2-fluorophenyl)pyrimidin-2-yl)-3-(methylsulfinyl)-1H-indol-6-yl)methanone | 513.1 |
| 391 | 3-(4-(1-(5-(2-Fluorophenyl)pyrimidin-2-yl)-3-(methyl sulfinyl)-1H-indole-6-carbonyl)piperazin-1-yl)propanenitrile | 517.2 |
| 392 | (1-(5-(2-Fluorophenyl)pyrimidin-2-yl)-3-(methylsulfinyl)-1H-indol-6-yl)(4-(2-methoxyethyl)piperazin-1-yl)methanone | 522.2 |
| 393 | Ethyl 1-(1-(5-(2-fluorophenyl)pyrimidin-2-yl)-3-(methylsulfinyl)-1H-indole-6-carbonyl)piperidine-4-carboxylate | 535.2 |
| 394 | Ethyl 4-(1-(5-(2-fluorophenyl)pyrimidin-2-yl)-3-(methylsulfinyl)-1H-indole-6-carbonyl)piperazine-1-carboxylat | 536.2 |
| 395 | 2-(4-(1-(5-(2-Fluorophenyl)pyrimidin-2-yl)-3-(methylsulfinyl)-1H-indole-6-carbonyl)piperazin-1-yl)-N,N-dimethylacetamide | 549.2 |

Biological Testing cAMP HTRF® Assay to Determine the Activity of hPDE4B1

The inhibiting effect of the compounds on the enzyme activity of human PDE4B1 was measured by the quantification of 5'-adenosine monophosphate (5'-AMP), which is formed from 3',5'-cyclic adenosine monophosphate (cAMP). Human recombinant enzyme, expressed in Sf9 cells, and the HTRF (homogeneous time-resolved fluorescence) detection method were used in the assay.

The test compound or water (control) was mixed with the human recombinant PDE4B1 enzyme (4.8 U) in a buffer consisting of 44.4 mM tris-HCl, 5.28 mM MgCl2, 2.64 mM DTT and 0.044% Tween 20 (pH 7.8). After adding the cAMP enzyme substrate (final concentration 40 nM), the mixture was incubated for 30 minutes at room temperature. Then a fluorescence acceptor (Dye2 marked with cAMP), a fluorescence donor (anti-cAMP antibody marked with a europium cryptate) and the non-specific phosphodiesterase inhibitor IBMX (3-isobutyl-1-methylxanthine; final concentration 1 mM) were added. After 60 minutes the fluorescence transfer, which correlates with the amount of remaining cAMP, was measured with a microplate reader (Rubystar, BMG) at λex=337 nm, λem=620 nm and λem=665 nm. The enzyme activity was calculated from the quotient formed from the measured signal at 665 nm and that at 620 nm. The result was expressed as the percentage inhibition of enzyme activity of the control (without PDE4 inhibitor). The enzyme was omitted for measurement of the basal control. IC50 values (IC50=concentration causing a half-maximal inhibition of control specific activity) were derived from dose response measurements with eight different concentrations (n=2; N=1-3).

Literature: N. Saldou et al., Comparison of recombinant human PDE4 isoforms: interaction with substrate and inhibitors, Cell. Signal. Vol. 10, No. 6, 427-440, 1998

The compounds according to the invention were tested with above mentioned assay and the results are given below TR-FRET Assay Using the LANCE® Ultra cAMP Kit to Determine the Activity of hPDE4B1

The effects of the compounds on the activity of the human PDE4B1 was quantified by measuring the production of 5'AMP from cAMP using a human recombinant enzyme expressed in Sf9 cells and the LANCE® Ultra cAMP kit, a TR-FRET detection method from PerkinElmer. The human PDE4B1 enzyme was purchased from SignalChem Lifesciences (Catalog# P92-31BG, Lot# H296-2).

The test compound, reference compound or water (control) was mixed with the enzyme (0.96 U) in a reaction buffer containing 50 mM Tris-HCl, 50 mM MgCl2 and 5 mM DTT (pH 8.5). Thereafter, the reaction was initiated by addition of 500 nM cAMP (substrate) and the mixture was incubated for 30 minutes at room temperature. For control basal measurements, the enzyme was omitted from the reaction mixture. After 30 minutes, the reaction was stopped and diluted by a factor of 100 with the reaction buffer supplemented with 500 µM IBMX. The fluorescence donor (europium chelate-labeled cAMP) and the fluorescence acceptor (anti-cAMP antibody labeled with the ULight™ dye) were then added together with 500 µM IBMX to a 10 µl aliquot. After 60 minutes, the fluorescence transfer corresponding to the amount of residual cAMP was measured at λex=337 nm, λem=620 nm and λem=665 nm using a microplate reader (PHERAstar, BMG). The enzyme activity was determined by dividing the signal measured at 665 nm by that measured at 620 nm (ratio) multiplied by 10000. The results were expressed as percent inhibition of the control enzyme activity. IC50 values (IC50=concentration causing a half-maximal inhibition of control specific activity) were derived from dose response measurements with ten different concentrations (n=3; N=1-3).

Table 5 shows the inhibition of PDE4B at a test substrate concentration of 1 µM in [%] as determined by the cAMP HTRF® assay:

TABLE 5

| Cpd. No. | Inhibition in % |
|---|---|
| 1 | 104 |
| 2 | 98 |
| 3 | 98 |
| 4 | 82 |
| 5 | 72 |
| 6 | 88 |
| 7 | 88 |
| 8 | 50 |
| 9 | 78 |
| 10 | 74 |
| 11 | 109 |
| 12 | 33 |
| 13 | 51 |
| 14 | 38 |
| 15 | 44 |
| 17 | 41 |
| 18 | 91 |
| 19 | 94 |
| 20 | 74 |
| 21 | 32 |
| 24 | 41 |
| 26 | 41 |
| 27 | 79 |
| 28 | 98 |
| 29 | 57 |
| 30 | 106 |
| 31 | 75 |
| 32 | 80 |
| 33 | 88 |
| 34 | 90 |
| 35 | 67 |
| 36 | 90 |
| 37 | 103 |
| 38 | 102 |
| 39 | 105 |
| 40 | 93 |
| 41 | 100 |
| 42 | 86 |
| 43 | 83 |
| 44 | 82 |
| 45 | 115 |
| 46 | 102 |
| 47 | 61 |
| 48 | 63 |
| 49 | 72 |
| 50 | 91 |
| 51 | 86 |
| 52 | 91 |
| 54 | 46 |
| 55 | 40 |
| 56 | 86 |
| 58 | 90 |
| 60 | 79 |
| 61 | 77 |
| 63 | 37 |
| 64 | 67 |
| 65 | 40 |
| 66 | 97 |
| 67 | 47 |
| 68 | 108 |
| 69 | 95 |
| 70 | 84 |
| 71 | 63 |
| 72 | 33 |
| 73 | 78 |
| 74 | 63 |
| 75 | 47 |
| 76 | 58 |
| 77 | 67 |
| 78 | 70 |
| 79 | 103 |
| 80 | 96 |
| 81 | 63 |
| 82 | 71 |
| 83 | 67 |
| 84 | 106 |
| 85 | 115 |
| 86 | 99 |
| 141 | 115 |
| 142 | 110 |
| 143 | 65 |
| 144 | 47 |
| 145 | 83 |
| 146 | 118 |
| 147 | 67 |
| 148 | 46 |
| 149 | 87 |
| 150 | 49 |
| 151 | 91 |
| 152 | 90 |
| 153 | 76 |
| 154 | 98 |
| 155 | 97 |
| 156 | 58 |
| 157 | 81 |
| 158 | 104 |
| 159 | 98 |
| 160 | 107 |
| 161 | 109 |
| 162 | 95 |
| 163 | 104 |
| 164 | 92 |
| 165 | 105 |
| 166 | 93 |
| 167 | 87 |
| 168 | 43 |
| 170 | 54 |
| 171 | 38 |
| 172 | 46 |
| 173 | 70 |
| 174 | 105 |
| 175 | 114 |
| 177 | 39 |
| 178 | 88 |
| 179 | 90 |
| 180 | 99 |
| 181 | 96 |
| 182 | 95 |
| 183 | 60 |
| 184 | 86 |
| 185 | 97 |
| 186 | 74 |
| 187 | 56 |
| 188 | 104 |
| 189 | 109 |
| 190 | 90 |
| 191 | 85 |
| 192 | 112 |
| 193 | 91 |
| 194 | 92 |
| 198 | 114 |
| 199 | 99 |
| 200 | 87 |
| 201 | 81 |
| 202 | 94 |
| 209 | 101 |
| 210 | 96 |
| 211 | 85 |
| 212 | 33 |
| 213 | 106 |
| 214 | 92 |
| 215 | 110 |
| 216 | 94 |
| 217 | 109 |
| 218 | 98 |
| 223 | 89 |
| 224 | 102 |
| 225 | 92 |
| 226 | 99 |
| 227 | 108 |
| 228 | 104 |
| 229 | 106 |
| 230 | 110 |
| 231 | 121 |
| 232 | 57 |
| 233 | 103 |

TABLE 5-continued

| Cpd. No. | Inhibition in % |
|---|---|
| 234 | 91 |
| 236 | 85 |
| 237 | 36 |
| 238 | 32 |
| 239 | 78 |
| 240 | 101 |
| 242 | 66 |
| 243 | 64 |
| 244 | 102 |
| 250 | 30 |
| 251 | 45 |
| 252 | 97 |
| 253 | 120 |
| 254 | 95 |
| 255 | 95 |
| 355 | 77 |
| 356 | 96 |
| 357 | 107 |
| 358 | 98 |
| 359 | 90 |
| 360 | 75 |
| 361 | 40 |
| 362 | 78 |
| 363 | 41 |
| 364 | 73 |
| 365 | 54 |
| 366 | 30 |
| 367 | 40 |
| 368 | 103 |
| 369 | 87 |
| 370 | 23 |
| 371 | 32 |
| 372 | 40 |
| 373 | 36 |
| 374 | 47 |
| 375 | 66 |
| 376 | 31 |
| 377 | 70 |
| 378 | 31 |
| 379 | 50 |
| 380 | 9 |
| 381 | 12 |
| 382 | 0 |
| 383 | 68 |
| 384 | 3 |
| 385 | 0 |
| 386 | 6 |
| 387 | 8 |
| 388 | 45 |
| 389 | 52 |
| 390 | 6 |
| 391 | 31 |
| 392 | 0 |
| 393 | 10 |
| 394 | 0 |
| 395 | 0 |

Table 6 shows the inhibition of PDE4B at a test substrate concentration of 1 μM (10 μM) in [%] as determined by the TR-FRET assay using the LANCE® Ultra cAMP kit:

TABLE 6

| Cpd. No. | Inhibition in % |
|---|---|
| 195 | 95 |
| 196 | 96 |
| 197 | 96 |
| 203 | 67 |
| 204 | 82 |
| 205 | 93 |
| 206 | 85 |
| 208 | 82 |
| 219 | 87 |
| 220 | 93 |
| 221 | 94 |
| 222 | 73 |
| 245 | 86 |
| 246 | 96 |
| 247 | 90 |
| 248 | 97 |
| 249 | 93 |
| 256 | 96 |
| 257 | 93 |
| 258 | 92 |
| 259 | 95 |
| 260 | 95 |
| 261 | 55 |
| 262 | 70 |
| 263 | 97 |
| 264 | 94 |
| 265 | 98 |
| 266 | 98 |
| 267 | 94 |
| 268 | 95 |
| 269 | 97 |
| 270 | 102 |
| 271 | 97 |
| 272 | 93 |
| 273 | 91 |
| 274 | 104 |
| 275 | 113 |
| 276 | 106 |
| 277 | 93 |
| 278 | 92 |
| 279 | 97 |
| 280 | 93 |
| 281 | 97 |
| 282 | 90 |
| 283 | 92 |
| 284 | 104 |
| 285 | 91 |
| 286 | 101 (10 μM) |
| 287 | 93 |
| 288 | 92 |
| 289 | 93 |
| 290 | 97 (10 μM) |
| 291 | 90 |
| 292 | 91 (10 μM) |
| 293 | 94 |
| 294 | 98 (10 μM) |
| 295 | 98 (10 μM) |
| 296 | 97 |
| 297 | 93 |
| 298 | 119 |
| 299 | 94 |
| 300 | 93 |
| 301 | 99 (10 μM) |
| 302 | 103 (10 μM) |
| 303 | 99 (10 μM) |
| 304 | 115 (10 μM) |
| 305 | 85 (10 μM) |
| 306 | 80 |
| 307 | 82 |
| 308 | 101 (10 μM) |
| 309 | 97 (10 μM) |
| 310 | 91 (10 μM) |
| 311 | 98 (10 μM) |
| 312 | 93 (10 μM) |
| 313 | 92 |
| 314 | 98 (10 μM) |
| 315 | 97 (10 μM) |
| 316 | 98 (10 μM) |
| 317 | 87 (10 μM) |
| 318 | 96 (10 μM) |
| 319 | 99 (10 μM) |
| 320 | 109 (10 μM) |
| 321 | 143 (10 μM) |
| 322 | 100 (10 μM) |
| 323 | 103 (10 μM) |
| 324 | 76 |
| 325 | 91 (10 μM) |
| 326 | 98 |
| 327 | 90 (10 μM) |

TABLE 6-continued

| Cpd. No. | Inhibition in % |
|---|---|
| 328 | 89 (10 μM) |
| 331 | 109 (10 μM) |
| 332 | 82 (10 μM) |
| 333 | 87 (10 μM) |
| 334 | 99 (10 μM) |
| 335 | 100 (10 μM) |
| 336 | 64 (10 μM) |
| 337 | 102 (10 μM) |
| 338 | 99 (10 μM) |
| 339 | 105 (10 μM) |
| 340 | 100 (10 μM) |
| 341 | 108 (10 μM) |
| 342 | 113 (10 μM) |
| 343 | 100 (10 μM) |
| 344 | 96 (10 μM) |
| 345 | 95 (10 μM) |
| 346 | 87 |
| 347 | 97 (10 μM) |
| 348 | 99 |
| 349 | 92 (10 μM) |
| 350 | 93 |
| 351 | 93 |
| 352 | 95 |
| 353 | 54 |
| 354 | 71 |
| 1d | 89 |
| 142a | 90 |

The invention claimed is:

1. A 2,5-substituted pyrimidine having the following general formula (I)

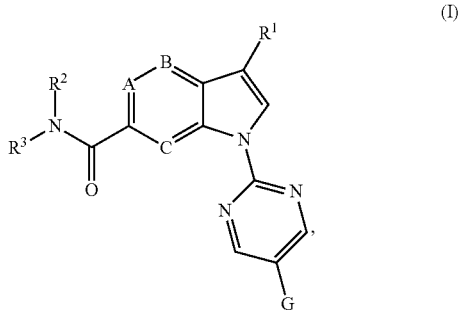

(I)

wherein

A, B, C each independently of each other stands for N or CH;

$R^1$ stands for $(C_1\text{-}C_6)$-alkyl, $(C_1\text{-}C_6)$-hydroxyalkyl, $(C_3\text{-}C_6)$-cycloalkyl, or $SO_x\text{---}(C_1\text{-}C_6)$-alkyl;

x is 0, 1 or 2;

G is an optionally with at least one substituent Y substituted phenyl or 5- or 6-membered heteroaryl which comprises at least one oxygen, sulfur or nitrogen atom, whereas the nitrogen atoms present in the heteroaryl can be substituted with $R^4$;

$R^4$ is hydrogen, $(C_1\text{-}C_6)$-alkyl, $(C_1\text{-}C_6)$-haloalkyl, CO—$(C_1\text{-}C_6)$-alkyl, SO$(C_1\text{-}C_6)$-alkyl, SO$_2(C_1\text{-}C_6)$-alkyl;

Y is OH, CN, SH, $(C_1\text{-}C_6)$-alkyl, $(C_2\text{-}C_6)$-alkenyl, $(C_2\text{-}C_6)$-alkinyl, $(C_3\text{-}C_6)$-cycloalkyl, $(C_1\text{-}C_6)$-alkoxy, $(C_1\text{-}C_6)$-thioalkyl, $(C_1\text{-}C_6)$-haloalkyl, $(C_1\text{-}C_6)$-thiohaloalkyl, $(C_1\text{-}C_6)$-haloalkoxy, CO$_2$H, CO$_2(C_1\text{-}C_6)$-alkyl, CHO, CO$(C_1\text{-}C_6)$-alkyl, OCO$(C_1\text{-}C_6)$-alkyl, CONH$_2$, CONH—$(C_1\text{-}C_6)$-alkyl, CON$((C_1\text{-}C_6)$-alkyl$)_2$, OCO—NH$(C_1\text{-}C_6)$-alkyl, OCO—N$((C_1\text{-}C_6)$-alkyl$)_2$, NH$_2$, NH$(C_1\text{-}C_6)$-alkyl, N$((C_1\text{-}C_6)$-alkyl$)_2$, N-pyrrolidinyl, N-piperidinyl, N-morpholinyl, NH—CO—$(C_1\text{-}C_6)$-alkyl, NH—CO$_2$ $(C_1\text{-}C_6)$-alkyl, N$(C_1\text{-}C_6)$-alkyl-CO$_2$ $(C_1\text{-}C_6)$-alkyl, NH—CO—NH$_2$, NH—CO—NH$(C_1\text{-}C_6)$-alkyl, NH—CO—N$((C_1\text{-}C_6)$-alkyl$)_2$, N$(C_1\text{-}C_6)$-alkyl-CO—NH$_2$, N$(C_1\text{-}C_6)$alkyl-CO—NH$(C_1\text{-}C_6)$-alkyl, N$(C_1\text{-}C_6)$-alkyl-CO—N$((C_1\text{-}C_6)$-alkyl$)_2$, NH—SO$_2$—$(C_1\text{-}C_6)$-alkyl, N$(C_1\text{-}C_6)$alkyl-SO$_2$—$(C_1\text{-}C_6)$-alkyl, S—$(C_1\text{-}C_6)$-alkyl, SO$(C_1\text{-}C_6)$-alkyl, SO$_2$—$(C_1\text{-}C_6)$-alkyl, SO$_2$H, SO$_2$OH, SO$_2$NH$_2$, SO$_2$NH$(C_1\text{-}C_6)$-alkyl, SO$_2$N$((C_1\text{-}C_6)$-alkyl$)_2$, C(=N)—NH, NHC(=N)—NH$_2$, —N=C=O, or —S—CN, wherein the aforementioned alkyl chains may be substituted with at least one of the following substituents OH, CN, $(C_3\text{-}C_6)$-cycloalkyl, $(C_1\text{-}C_6)$-alkoxy, CO$_2$H, CO$_2(C_1\text{-}C_6)$-alkyl or —NH$_2$;

$R^2$ and $R^{3'}$ independently of one another stand for hydrogen or optionally substituted $(C_1\text{-}C_6)$-alkyl, $(C_1\text{-}C_6)$-haloalkyl, $(C_1\text{-}C_6)$-hydroxyalkyl, $(C_1\text{-}C_6)$-alkoxy$(C_1\text{-}C_6)$-alkylen, $(C_1\text{-}C_6)$-alkylen-CO$_2$H, $(C_1\text{-}C_6)$-alkylen-CO$_2(C_1\text{-}C_6)$-alkyl, $(C_1\text{-}C_6)$-alkylen-CONH$_2$, $(C_1\text{-}C_6)$-alkylen-CONH$(C_1\text{-}C_6)$-alkyl, $(C_1\text{-}C_6)$-alkylen-CON$((C_1\text{-}C_6)$-alkyl$)_2$, $(C_1\text{-}C_6)$-alkylen-$(C_3\text{-}C_6)$-cycloalkyl, $(C_1\text{-}C_6)$-hydroxyalkyl-$(C_3\text{-}C_6)$-cycloalkylen, a group $L^1V$, a group $L^2W$, or together with the nitrogen atom to which they are attached form an optionally with at least one substituent $X^Q$ substituted 3- to 12-membered mono- or bicyclic heteroaliphatic residue Q which may additionally contain at least one oxygen, sulfur or further nitrogen atom, whereas these one or more additional nitrogen atoms are substituted with $R^5$;

$X^Q$ independently of each other stand for =O(carbonyl), halogen, OH, CN, SH, $(C_1\text{-}C_6)$-alkyl, $(C_1\text{-}C_6)$-hydroxyalkyl, $(C_1\text{-}C_6)$-cyanoalkyl, $(C_2\text{-}C_6)$-alkenyl, $(C_2\text{-}C_6)$-alkinyl, $(C_3\text{-}C_6)$-cycloalkyl, $(C_1\text{-}C_6)$-alkoxy, $(C_1\text{-}C_6)$-alkoxy$(C_1\text{-}C_6)$-alkylen, $(C_1\text{-}C_6)$-thioalkyl, $(C_1\text{-}C_6)$-haloalkyl, $(C_1\text{-}C_6)$-thiohaloalkyl, $(C_1\text{-}C_6)$-haloalkoxy, —NH$_2$, NH$(C_1\text{-}C_6)$-alkyl, N$((C_1\text{-}C_6)$-alkyl$)_2$, $(C_1\text{-}C_6)$-alkylen-NH$(C_1\text{-}C_6)$-alkyl, $(C_1\text{-}C_6)$-alkylen-N$((C_1\text{-}C_6)$-alkyl$)_2$ NH—CHO, NH—CO$(C_1\text{-}C_6)$-alkyl, N$(C_1\text{-}C_6)$-alkyl-CO$(C_1\text{-}C_6)$-alkyl, NH—CO—O$(C_1\text{-}C_6)$-alkyl, N$(C_1\text{-}C_6)$-alkyl-CO—O$(C_1\text{-}C_6)$-alkyl, NH—CO—NH$_2$, NH—CO—NH$(C_1\text{-}C_6)$-alkyl, NH—CO—N$((C_1\text{-}C_6)$-alkyl$)_2$, N$(C_1\text{-}C_6)$-alkyl-CO—NH$_2$, N$(C_1\text{-}C_6)$-alkyl-CO—NH$(C_1\text{-}C_6)$-alkyl, N$(C_1\text{-}C_6)$-alkyl-CO—N$((C_1\text{-}C_6)$-alkyl$)_2$, NH—SO$_2$—$(C_1\text{-}C_6)$-alkyl, N$(C_1\text{-}C_6)$-alkyl-SO$_2$—$(C_1\text{-}C_6)$-alkyl, CO$_2$H, CO$_2(C_1\text{-}C_6)$-alkyl, CHO, CO$(C_1\text{-}C_6)$-alkyl, O—CO$(C_1\text{-}C_6)$-alkyl, CO—NH$_2$, CO—NH$(C_1\text{-}C_6)$-alkyl, CO—N$((C_1\text{-}C_6)$-alkyl$)_2$, O—CO—NH$(C_1\text{-}C_6)$-alkyl, O—CO—N$((C_1\text{-}C_6)$-alkyl$)_2$, S—$(C_1\text{-}C_6)$-alkyl, SO$(C_1\text{-}C_6)$-alkyl, SO$_2$—$(C_1\text{-}C_6)$-alkyl, SOOH, SO$_2$OH, SO$_2$NH$_2$, SO$_2$NH$(C_1\text{-}C_6)$-alkyl, SO$_2$N$((C_1\text{-}C_6)$-alkyl$)_2$, C(=N)—NH, NHC(=N)—NH$_2$, —N=C=O, or —S—CN, wherein the aforementioned alkyl chains may be substituted with at least one of the following substituents OH, CN, $(C_3\text{-}C_6)$-cycloalkyl, $(C_r\text{-}C_6)$-alkoxy, CO$_2$H, CO$_2(C_1\text{-}C_6)$-alkyl or —NH$_2$;

$R^5$ is hydrogen, $(C_1\text{-}C_6)$-alkyl, $(C_1\text{-}C_6)$-haloalkyl, CO—$(C_1\text{-}C_6)$-alkyl, SO—$(C_1\text{-}C_6)$-alkyl, SO$_2$—$(C_1\text{-}C_6)$-alkyl;

$L^1$ is a bond or a branched or straight-chain optionally substituted $(C_1\text{-}C_6)$-alkylene group connected to the amide nitrogen;

V is an optionally with at least one substituent $X^V$ substituted 3- to 12-membered mono- or bicyclic aliphatic or heteroaliphatic residue, whereas if one or more nitrogen atoms are present in the mono- or bicyclic heteroaliphatic residue, then at least one of these nitrogen atoms is substituted with $R^6$;

$X^V$ independently of each other stand for =O (carbonyl), halogen, OH, CN, SH, $(C_1-C_6)$-alkyl, $(C_1-C_6)$-hydroxyalkyl, $(C_1-C_6)$-cyanoalkyl, $(C_2-C_6)$-alkenyl, $(C_2-C_6)$-alkinyl, $(C_3-C_6)$-cycloalkyl, $(C_1-C_6)$-alkoxy, $(C_1-C_6)$-alkoxy$(C_1-C_6)$-alkylen, $(C_1-C_6)$-thioalkyl, $(C_1-C_6)$-haloalkyl, $(C_1-C_6)$-thiohaloalkyl, $(C_1-C_6)$-haloalkoxy, —$NH_2$, $NH(C_1-C_6)$-alkyl, $N((C_1-C_6)$-alkyl$)_2$, $(C_1-C_6)$-alkylen-$NH(C_1-C_6)$-alkyl, $(C_1-C_6)$-alkylen-$N((C_1-C_6)$-alkyl$)_2$ NH—CHO, NH—CO$(C_1-C_6)$-alkyl, $N(C_1-C_6)$-alkyl-CO$(C_1-C_6)$-alkyl, NH—CO—O$(C_1-C_6)$-alkyl, $N(C_1-C_6)$-alkyl-CO—O$(C_1-C_6)$-alkyl, NH—CO—$NH_2$, NH—CO—$NH(C_1-C_6)$-alkyl, NH—CO—$N((C_1-C_6)$-alkyl$)_2$, $N(C_1-C_6)$-alkyl-CO—$NH_2$, $N(CO—NH(C_1-C_6)$-alkyl, $N(C_1-C_6)$-alkyl-CO—$N((C_1-C_6)$-alkyl$)_2$, NH—$SO_2$—$(C_1-C_6)$-alkyl, $N(C_1-C_6)$-alkyl-$SO_2$—$(C_1-C_6)$-alkyl, $CO_2H$, $CO_2(C_1-C_6)$-alkyl, CHO, $CO(C_1-C_6)$-alkyl, O—$CO(C_1-C_6)$-alkyl, CO—$NH_2$, CO—$NH(C_1-C_6)$-alkyl, CO—$N((C_1-C_6)$-alkyl$)_2$, O—CO—$NH(C_1-C_6)$-alkyl, O—CO—$N((C_1-C_6)$-alkyl$)_2$, S—$(C_1-C_6)$-alkyl, $SO(C_1-C_6)$-alkyl, $SO_2$—$(C_1-C_6)$-alkyl, SOOH, $SO_2OH$, $SO_2NH_2$, $SO_2NH(C_1-C_6)$-alkyl, $SO_2N((C_1-C_6)$-alkyl$)_2$, C(=N)—NH, NHC(=N)—$NH_2$, —N=C=O, or —S—CN, wherein the aforementioned alkyl chains may be substituted with at least one of the following substituents OH, CN, $(C_3-C_6)$-cycloalkyl, $(C_1-C_6)$-alkoxy, $CO_2H$, $CO_2(C_1-C_6)$-alkyl or —$NH_2$;

$R^6$ is hydrogen, $(C_1-C_6)$-alkyl, $(C_1-C_6)$-haloalkyl, CO—$(C_1-C_6)$-alkyl, $SO(C_1-C_6)$-alkyl, or $SO_2(C_1-C_6)$-alkyl;

$L^2$ is a bond or a branched or straight-chain optionally substituted $(C_1-C_6)$-alkylene group connected to the amide nitrogen;

W is an optionally with at least one substituent Z substituted phenyl or 5- or 6-membered heteroaryl which comprises at least one oxygen, sulfur or nitrogen atom; and Z independently of each other stand for halogen, OH, CN, SH, $(C_1-C_6)$-alkyl, $(C_2-C_6)$-alkenyl, $(C_2-C_6)$-alkinyl, $(C_3-C_6)$-cycloalkyl, $(C_1-C_6)$-alkoxy, $(C_1-C_6)$-thioalkyl, $(C_1-C_6)$-haloalkyl $(C_1-C_6)$-thiohaloalkyl, $(C_1-C_6)$-haloalkoxy, —$NH_2$, $NH(C_1-C_6)$-alkyl, $N((C_1-C_6)$-alkyl$)_2$, N-pyrrolidinyl, N-piperidinyl, N-morpholinyl, NH—CHO, NH—CO$(C_1-C_6)$-alkyl, $N(C_1-C_6)$-alkyl-CO$(C_1-C_6)$-alkyl, NH—$CO_2(C_1-C_6)$-alkyl, $N(C_1-C_6)$-alkyl-$CO_2(C_1-C_6)$-alkyl, NH—CO—$NH_2$, NH—CO—$NH(C_1-C_6)$-alkyl, NH—CO—$N((C_1-C_6)$-alkyl$)_2$, $N(C_1-C_6)$-alkyl-CO—$NH_2$, $N(C_1-C_6)$-alkyl-CO—NH$(C_1-C_6)$-alkyl, $N(C_1-C_6)$-alkyl-CO—$N((C_1-C_6)$-alkyl$)_2$, NH—$SO_2$—$(C_1-C_6)$-alkyl, $N(C_1-C_6)$-alkyl-$SO_2$—$(C_1-C_6)$-alkyl, $CO_2H$, $CO_2(C_1-C_6)$-alkyl, CHO, $CO(C_1-C_6)$-alkyl, O—$CO(C_1-C_6)$-alkyl, CO—$NH_2$, CO—$NH(C_1-C_6)$-alkyl, CO—$N((C_1-C_6)$-alkyl$)_2$, O—CO—$NH(C_1-C_6)$-alkyl, O—CO—$N((C_1-C_6)$-alkyl$)_2$, S—$(C_1-C_6)$-alkyl, $SO(C_1-C_6)$-alkyl, $SO_2$—$(C_1-C_6)$-alkyl, $SO_2H$, $SO_2OH$, $SO_2NH_2$, $SO_2NH(C_1-C_6)$-alkyl, $SO_2N((C_1-C_6)$ alkyl$)_2$, C(=N)—NH, NHC(=N)—$NH_2$, —N=C=O, or —S—CN, wherein the aforementioned alkyl chains may be substituted with at least one of the following substituents OH, CN, $(C_3-C_6)$-cycloalkyl, $(C_1-C_6)$-alkoxy, $CO_2H$, $CO_2(C_1-C_6)$-alkyl or —$NH_2$.

2. The 2,5-substituted pyrimidine according to claim 1, wherein

G stands for optionally with at least one substituent Y substituted phenyl, pyridyl, pyrimidyl, furyl, thiophenyl, oxazolyl, thiazolyl or for one of the following groups G1 to G45:

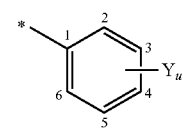

G1

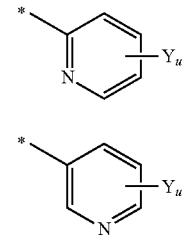

G2

G3

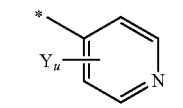

G4

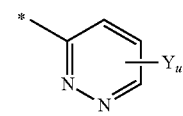

G5

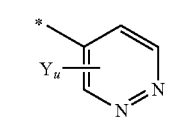

G6

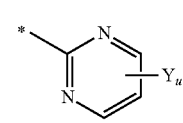

G7

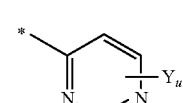

G8

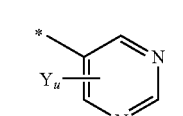

G9

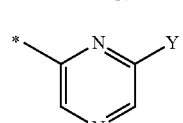

G10

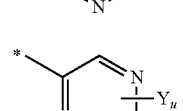

G11

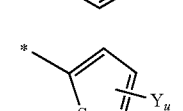

G12

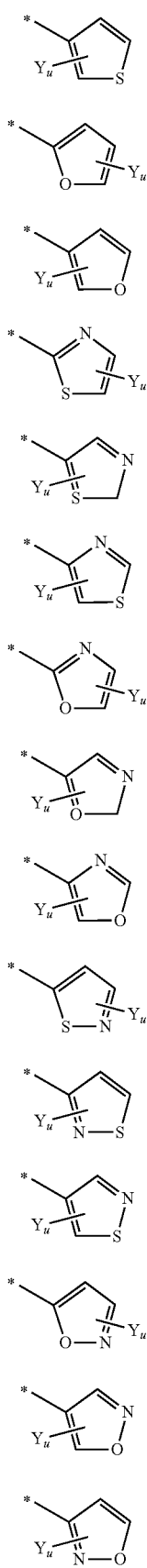
G13
G14
G15
G16
G17
G18
G19
G20
G21
G22
G23
G24
G25
G26
G27
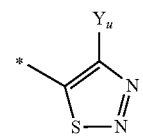 G28
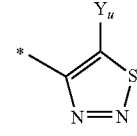 G29
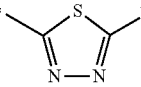 G30
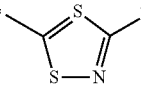 G31
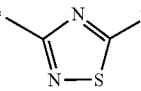 G32
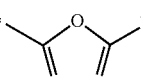 G33
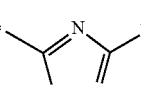 G34
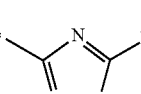 G35
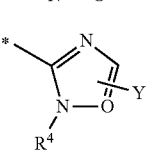 G36
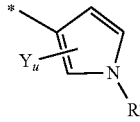 G37
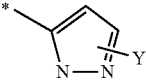 G38
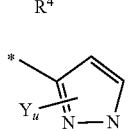 G39
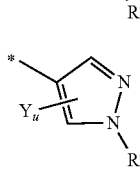 G40

405

-continued

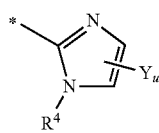

G41

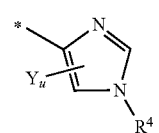

G42

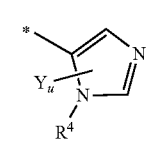

G43

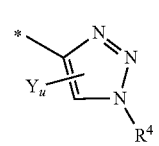

G44

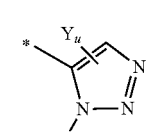

G45 wherein the site marked with an asterisk (*) indicates the binding site to the position 4 of the pyrimidine ring; and u is 0, 1, 2, 3 or 4.

3. The 2,5-substituted pyrimidine according to claim 1, wherein $R^2$ and $R^3$ independently of one another stand for hydrogen, $(C_1\text{-}C_4)$-alkyl, $(C_1\text{-}C_4)$-hydroxyalkyl, $(C_1\text{-}C_4)$-alkoxy$(C_1\text{-}C_4)$-alkylen, $(C_1\text{-}C_4)$-alkylen-$CO_2H$, $(C_1\text{-}C_4)$-alkylen-$CO_2(C_1\text{-}C_4)$-alkyl, $(C_1\text{-}C_4)$-alkylen-$CONH_2$, $(C_1\text{-}C_4)$-alkylen-$CONH(C_1\text{-}C_2)$-alkyl), $(C_1\text{-}C_4)$-alkylen-$CON((C_1\text{-}C_2)$-alkyl)$_2$, $(C_1\text{-}C_4)$-alkylen-$(C_3\text{-}C_6)$-cycloalkyl, $(C_1\text{-}C_4)$-hydroxyalkyl-$(C_3\text{-}C_6)$-cycloalkylen, a group $L^1V$, or a group $L^2W$, wherein $L^1$ is a bond, or a branched or a straight-chain optionally substituted $(C_1\text{-}C_4)$-alkylene group;

V is one of the following groups V1 to V40:

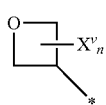

V1

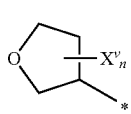

V2

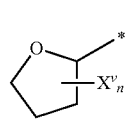

V3

406

-continued

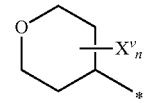

V4

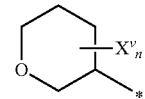

V5

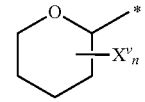

V6

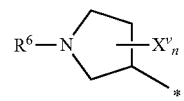

V7

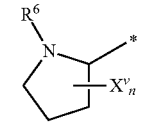

V8

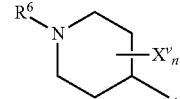

V9

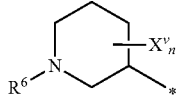

V10

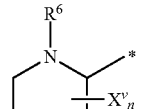

V11

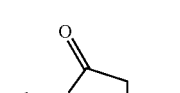

V12

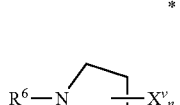

V13

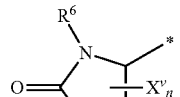

V14

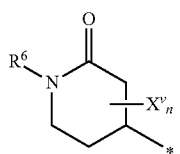 V15
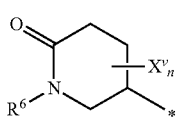 V16
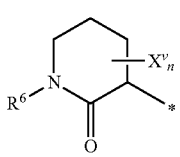 V17
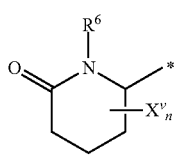 V18
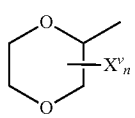 V19
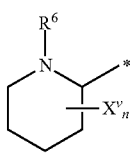 V20
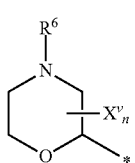 V21
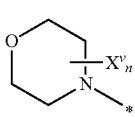 V22
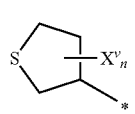 V23
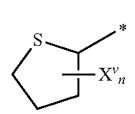 V24
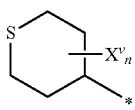 V25
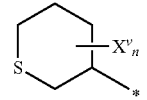 V26
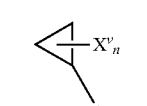 V27
V28
V29
V30
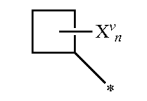 V31
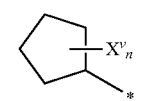 V32
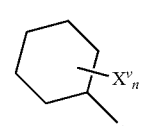 V33
 V34
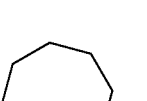 V35
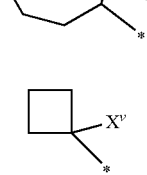 V36
 V37

-continued

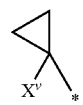 V38

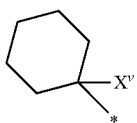 V39

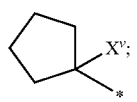 V40

L² is a bond, or a branched or straight-chain optionally substituted ($C_1$-$C_4$)-alkylene; and W stands for optionally with at least one substituent Z substituted phenyl, pyridyl, pyrimidyl, furyl.

4. The 2,5-substituted pyrimidine according to claim 1, wherein

R² and R³ independently of one another stand for hydrogen, ($C_1$-$C_4$)-alkyl, ($C_1$-$C_4$)-hydroxyalkyl, ($C_1$-$C_4$)-alkoxy($C_1$-$C_4$)-alkylen, ($C_1$-$C_4$)-alkylen-$CO_2H$, ($C_1$-$C_4$)-alkylen-$CO_2$($C_1$-$C_4$)-alkyl, ($C_1$-$C_4$)-alkylen-$CONH_2$, ($C_1$-$C_4$)-alkylen-CONH($C_1$-$C_2$)-alkyl), ($C_1$-$C_4$)-alkylen-CON(($C_1$-$C_2$)-alkyl)$_2$, ($C_1$-$C_4$)-alkylen-($C_3$-$C_6$)-cycloalkyl, ($C_1$-$C_4$)-hydroxyalkyl-($C_3$-$C_6$)-cycloalkylen, or a group L¹V, wherein L¹ is bond or methylene or ethylene; and V is one of the following groups V1, V2, V4, V5, V7, V9, V10, V12, V13, V15 to V17, V23, V25, V26, V31 to V36, V38:

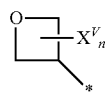 V1

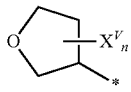 V2

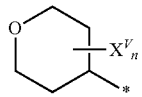 V4

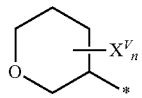 V5

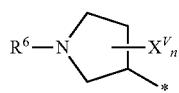 V7

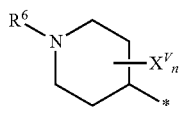 V9

-continued

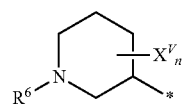 V10

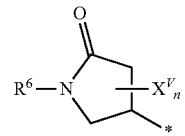 V12

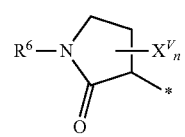 V13

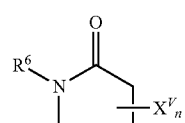 V15

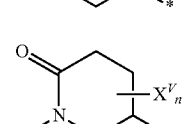 V16

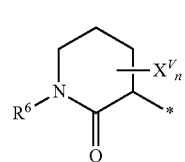 V17

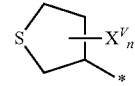 V23

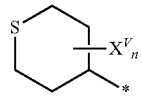 V25

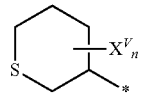 V26

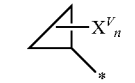 V31

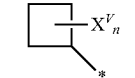 V32

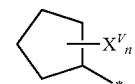 V33

V34

411
-continued
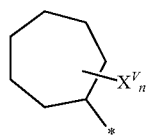 V35
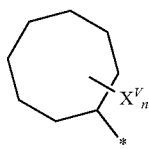 V36
 V38
5. The 2,5-substituted pyrimidine according to claim 1, wherein
R² and R³ together with the nitrogen atom to which they are attached form an optionally with at least one substituent $X^Q$ substituted 3- to 12-membered mono- or bicyclic heteroaliphatic residue Q selected from the groups Q1 to Q27:
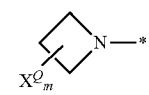 Q1
 Q2
 Q3
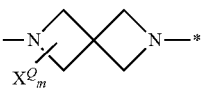 Q4
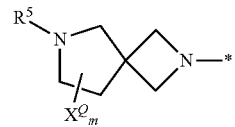 Q5
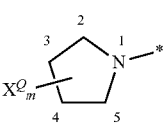 Q6
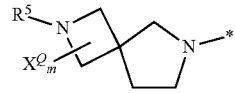 Q7
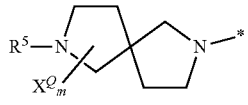 Q8
412
-continued
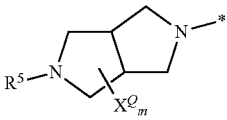 Q9
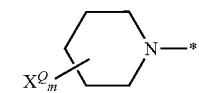 Q10
 Q11
 Q12
 Q12a
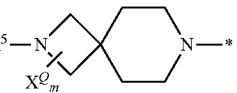 Q13
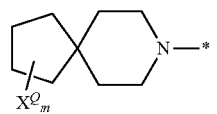 Q14
 Q15
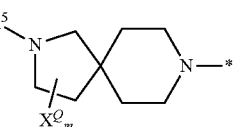 Q16
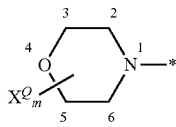 Q17
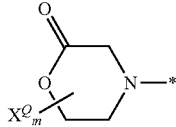 Q18
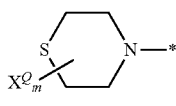 Q19
Q20

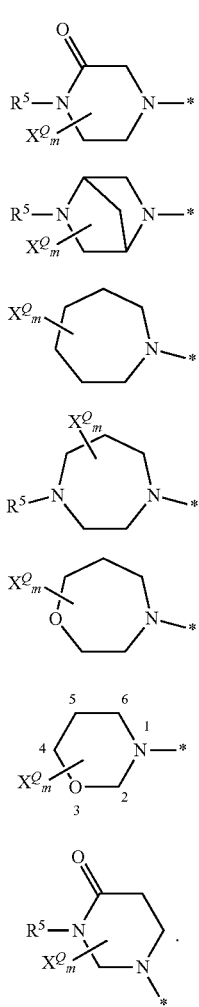

6. The 2,5-substituted pyrimidine according to claim 1 wherein

R¹ stands for methyl, ethyl, propyl, i-propyl, n-butyl, hydroxymethyl, hydroxyethyl, hydroxypropyl, cyclopropyl, SOCH₃ or SO₂CH₃.

7. The 2,5-substituted pyrimidine according to claim 1 wherein
R¹ stands for methyl.

8. The 2,5-substituted pyrimidine according to claim 1 wherein
R¹ stands for SOCH₃ or SO₂CH₃.

9. The 2,5-substituted pyrimidine according to claim 1 wherein
R¹ stands for 1-hydroxyethyl, 2-hydroxypropan-2-yl.

10. The 2,5-substituted pyrimidine according to claim 1 wherein A, B, and C each stand for CH.

11. The 2,5-substituted pyrimidine according to claim 2 wherein
G stands for optionally with at least one substituent Y substituted group G1, G2, G3, G4, G5, G12, G13, G16, or G17; and
Y independently of one another is halogen, CN, OH, NH₂, N((C₁-C₄)-alkyl)₂, CONH₂, (C₁-C₄)-alkyl, (C₁-C₄)-alkoxy, or (C₃-C₆)-cycloalkyl.

12. A medicament comprising a 2,5-substituted pyrimidine of claim 1.

13. A method of treating a condition or disease in a subject comprising administering to the subject the 2,5-substituted pyrimidine of claim 1 in its presented form, or in its acid or base form, or in the form of a physiologically tolerable salt, or in its solvate form, or in the form of its racemates, pure stereoisomers, enantiomers or diastereomers, or in the form of mixtures of stereoisomers, enantiomers or diastereomers, in any mixing ratio, wherein the condition or disease is selected from the group consisting of rheumatoid arthritis, psoriatic arthritis, ankylosing spondylitis, gout, osteoarthritis, psoriasis, atopic dermatitis, uveitis, Crohn's disease, ulcerative colitis, acute and chronic inflammations of the gall bladder and bile ducts, systemic lupus erythematosus, lupus nephritis, chronic prostatitis, interstitial cystitis, chronic obstructive pulmonary disease, asthma, allergic and non-allergic rhinitis, pulmonary arterial hypertension, schizophrenia, depression, bipolar or manic depression, generalized anxiety disorder, and Alzheimer's disease.

* * * * *